US010329297B2

(12) United States Patent
Sherer

(10) Patent No.: US 10,329,297 B2
(45) Date of Patent: *Jun. 25, 2019

(54) COMPOUNDS FOR THE INHIBITION OF INDOLEAMINE-2,3-DIOXYGENASE

(71) Applicant: Merck Patent GmbH, Darmstadt (DE)

(72) Inventor: Brian A. Sherer, Nashua, NH (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/680,683

(22) Filed: Aug. 18, 2017

(65) Prior Publication Data

US 2017/0355703 A1    Dec. 14, 2017

Related U.S. Application Data

(63) Continuation of application No. 14/845,428, filed on Sep. 4, 2015, now Pat. No. 9,771,370.

(60) Provisional application No. 62/151,011, filed on Apr. 22, 2015, provisional application No. 62/046,242, filed on Sep. 5, 2014.

(51) Int. Cl.
*C07D 471/14* (2006.01)
*C07D 487/04* (2006.01)
*C07D 471/12* (2006.01)
*A61K 31/4188* (2006.01)
*A61K 31/437* (2006.01)
*A61K 31/454* (2006.01)
*A61K 31/4545* (2006.01)
*A61K 31/519* (2006.01)
*A61K 45/06* (2006.01)
*C07D 487/14* (2006.01)

(52) U.S. Cl.
CPC ........ *C07D 487/04* (2013.01); *A61K 31/4188* (2013.01); *A61K 31/437* (2013.01); *A61K 31/454* (2013.01); *A61K 31/4545* (2013.01); *A61K 31/519* (2013.01); *A61K 45/06* (2013.01); *C07D 471/12* (2013.01); *C07D 471/14* (2013.01); *C07D 487/14* (2013.01)

(58) Field of Classification Search
CPC ............................ C07D 471/14; C07D 487/04
See application file for complete search history.

(56) References Cited

U.S. PATENT DOCUMENTS 9,771,370 B2 * 9/2017 Sherer ............... C07D 471/12
2011/0212941 A1 * 9/2011 Manley ............... C07D 487/04
514/210.18

FOREIGN PATENT DOCUMENTS

WO        200209706 A1    2/2002
WO       2012142237 A1   10/2012
WO       2014159248 A1   10/2014
WO    WO-2016/059412 A1 * 4/2016 ........... C07D 487/14

OTHER PUBLICATIONS

Balachandran et al., Imatinib potentiates antitumor T cell responses in gastrointestinal stromal tumor through the inhibition of Ido, Nat Med., 2011; 17(9):1094-1100.
S. M. Berge et al., Pharmaceutical Salts, J. Pharmaceutical Sciences, 1977, 66:1-19.
Brandacher et al., Prognostic Value of Indoleamine 2,3-Dioxygenase Expression in Colorectal Cancer: Effect on Tumor-Infiltrating T Cells, Clin. Cancer Res., 2006; 12(4):1144-1151.
Foster, Deuterium Isotope Effects in the Metabolism of Drugs and Xenobiotics: Implications for Drug Design, Adv. Drug Res., 1985, 14:1-40.
Gillette et al., Theory for the Observed Isotope Effects on the Formation of Multiple Products by Different Kinetic Mechanisms of Cytochrome P450 Enzymes, Biochemistry, 1994, 33(10):2927-2937.
Hanzlik et al., Active Site Dynamics of Toluene Hydroxylation by Cytochrome P-450, J. Org. Chem., 1990, 55:3992-3997.
Hou et al., Inhibition of Indoleamine 2,3-Dioxygenase in Dendritic Cells by Stereoisomers of 1-Methyl-Tryptophan Correlates with Antitumor Responses, Cancer Res., 2007; 67(2):792-801.
Ino et al., Inverse Correlation between Tumoral Indoleamine 2,3-Dioxygenase Expression and Tumor-Infiltrating Lymphocytes in Endometrial Cancer: Its Association with Disease Progression and Survival, Clin. Cancer Res., 2008; 14(8):2310-2317.
Jarman, The deuterium isotope effect for the a-hydroxylation of tamoxifen by rat liver microsomes accounts for the reduced genotoxicity of [D5-ethyl] tamoxifen, Carcinogenesis, 1995, 16(4):683-688.
Johnson and Munn, Host Indoleamine 2,3-Dioxygenase: Contribution to Systemic Acquired Tumor Tolerance, Immunol Invest 2012; 41(6-7): 765-797.
Koblish et al., Hydroxyamidine Inhibitors of Indoleamine-2,3-dioxygenase Potently Suppress Systemic Tryptophan Catabolism and the Growth of IDO-Expressing Tumors, Mol Cancer Ther., 2010; 9(2):489-498.
Liu et al., Selective inhibition of IDO1 effectively regulates mediators of antitumor immunity, Blood., 2010; 115(17):3520-3530.
Mellor and Munn, IDO Expression by Dendritic Cells: Tolerance and Tryptophan Catabolism, Nat Rev Immunol, 2004; 4(10):762-774.
Muller et al, Inhibition of indoleamine 2,3-dioxygenase, an immunoregulatory target of the cancer suppression gene Bin1, potentiates cancer chemotherapy, Nat Med., 2005; 11(3):312-319.
Munn, Blocking IDO activity to enhance anti-tumor immunity, Front Biosci., 2012; 4:734-745.
(Continued)

*Primary Examiner* — Laura L Stockton
(74) *Attorney, Agent, or Firm* — Millen White Zelano and Branigan, PC; John Sopp

(57) ABSTRACT

The present invention relates to compounds, and pharmaceutically acceptable compositions thereof, useful as antagonists of IDO, and for the treatment of IDO-related disorders.

12 Claims, No Drawings

(56) References Cited

OTHER PUBLICATIONS

Pallotta et al., Indoleamine 2,3-dioxygenase is a signaling protein in long-term tolerance by dendritic cells, Nat Immunol., 2011; 12(9):870-878.
Schwarcz et al., Kynurenines in the mammalian brain: when physiology meets pathology, Nat Rev Neurosci., 2012; 13(7):465-477.
Sharma et al., Indoleamine 2,3-dioxygenase controls conversion of Foxp31 Tregs to TH17-like cells in tumor-draining lymph nodes, Blood., 2009;113(24):6102-6111.
Tnani and Bayard, Evidence for IRF-1-dependent gene expression deficiency in interferon unresponsive HepG2 cells, Biochim Biophys Acta., 1999; 1451(1):59-72.
Uyttenhove et al., Evidence for a tumoral immune resistance mechanism based on tryptophan degradation by Indoleamine 2,3-dioxygenase, Nat Med., 2003; 10:1269-1274.
Reider et al., Synthesis of (R)-Serine-2-d and Its Conversion to the Broad Spectrum Antibiotic Fludalanine, J. Org. Chem., 1987; 52:3326-3334.

* cited by examiner

COMPOUNDS FOR THE INHIBITION OF INDOLEAMINE-2,3-DIOXYGENASE

RELATED APPLICATIONS

This application is a Continuation application of U.S. patent application Ser. No. 14/845,428, filed on Sep. 4, 2015, which claims the benefit of U.S. provisional application 62/046,242, filed on Sep. 5, 2014, and U.S. provisional application 62/151,011, filed on Apr. 22, 2015. The entire contents of the aforementioned applications are hereby incorporated by reference in their emtireties.

TECHNICAL FIELD OF THE INVENTION

The present invention relates to indazoline compounds useful as antagonists of indoleamine-2,3-dioxygenase (IDO). The invention also provides pharmaceutically acceptable compositions comprising compounds of the present invention and methods of using said compositions in the treatment of various disorders.

BACKGROUND OF THE INVENTION

The oxygenase indoleamine 2,3-dioxygenase (IDO) is responsible for the extra-hepatic conversion of Trp to N-formyl-kynurenine as a rate-limiting first step of Trp metabolism. N-formyl-kynurenine is a precursor of a variety of bioactive molecules called kynurenines that have immunomodulatory properties (Schwarcz et al., Nat Rev Neurosci. 2012; 13(7):465-77).

IDO is an inducible enzyme that has a primary role in immune cell modulation. The reduction of Trp levels and increase in the pool of kynurenines cause inhibition of effector immune cells and promote adaptive immune suppression through induction and maintenance of regulatory T cells (Tregs; Munn, Front Biosci. 2012; 4:734-45).

Increased turnover of Trp to kynurenines by IDO has been observed in a number of disorders linked to activation of the immune system, e.g. infection, malignancy, autoimmune diseases, trauma and AIDS (Johnson and Munn, Immunol Invest 2012; 41(6-7): 765-97). Additional studies in these indications have shown that induction of IDO results in suppression of T-cell responses and promotion of tolerance. In cancer, for example, a large body of evidence suggests that IDO upregulation serves as a mechanism in tumor cells to escape immune surveillance. IDO is expressed widely in solid tumors (Uyttenhove et al., Nat Med. 2003; 10:1269-74) and has been observed in both primary and metastatic cancer cells. IDO is induced in tumors by proinflammatory cytokines, including type I and type II interferons that are produced by infiltrating lymphocytes (Tnani and Bayard, Biochim Biophys Acta. 1999; 1451(1):59-72; Mellor and Munn, Nat Rev Immunol 2004; 4(10):762-74; Munn, Front Biosci. 2012; 4:734-45) and TGF-Beta (Pallotta et al., Nat Immunol. 2011; 12(9):870-8). Certain oncogenic mutations can also lead to increased IDO expression, e.g., loss of the tumor suppressor Binl (Muller et al, Nat Med. 2005; 11(3): 312-9) or activating mutations in KIT (Balachandran et al., Nat Med. 2011; 17(9): 1094-1100). IDO expression has been correlated with immune anergy in some tumors (e.g. Ino et al., Clin Cancer Res. 2008 Apr. 15; 14(8):2310-7; Brandacher et al., Clin. Cancer Res. 2006 Feb. 15; 12(4):1144-51), and a recent report has shown that reduction of IDO expression in human gastrointestinal tumors goes along with an increased infiltration of tumors by effector T cells (Balachandran et al., Nat Med. 2011; 17(9): 1094-1100).

A significant amount of preclinical data has been published that further validates the role of IDO in the anti-tumor immune response. For example, forced IDO induction in cancer cells was shown to confer a survival advantage (Uyttenhove et al., Nat Med. 2003; 10:1269-74). Other in vivo studies showed that IDO inhibitors cause lymphocyte dependent reduction in tumour growth by lowering kynurenine levels (Liu et al., Blood. 2010; 115(17):3520-30). Preclinical studies also highlighted the scope for IDO inhibitors to work synergistically in combination with agents that promote tumour antigenicity like irradiation, chemotherapy or vaccines (Koblish et al., Mol Cancer Ther. 2010; 9(2): 489-98, Hou et al., Cancer Res. 2007; 67(2):792-801; Sharma et al., Blood. 2009; 113(24):6102-11).

SUMMARY OF THE INVENTION

It has now been found that compounds of this invention, and pharmaceutically acceptable compositions thereof, are effective as antagonists of IDO. Such compounds have general formula I:

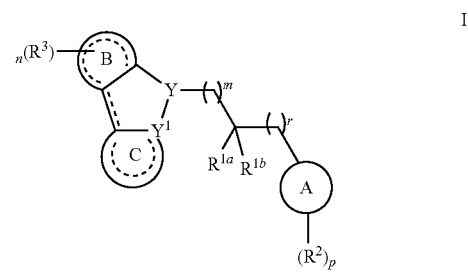

or a pharmaceutically acceptable salt thereof, wherein each of Ring A, Ring B, Ring C, Y, $Y^1$, $R^{1a}$, $R^{1b}$, $R^2$, $R^3$, m, n, p, and r, is as defined and described in embodiments herein.

Compounds of the present invention, and pharmaceutically acceptable compositions thereof, are useful for treating a variety of diseases, disorders or conditions, associated with IDO activity. Such diseases, disorders, or conditions include those described herein.

DETAILED DESCRIPTION OF CERTAIN EMBODIMENTS

1. General Description of Compounds of the Invention

In certain embodiments, the present invention provides antagonists of IDO. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group. The term "alkynylene" refers to a bivalent alkynyl group. A substituted alkynylene chain is a group containing at least one triple bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydropyranyl, tetrahydrothiophenyl pyrrolidinyl, piperidinyl, pyrrolinyl, morpholinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

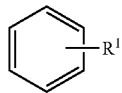

refers to at least

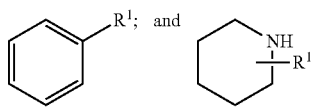

refers to at least

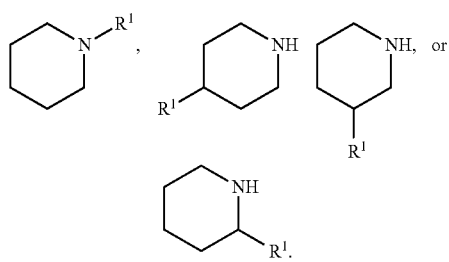

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which are optionally substituted with $R°$; —$(CH_2)_{0-4}O(CH_2)_{0-1}Ph$ which is optionally substituted with $R°$; —$CH=CHPh$, which is optionally substituted with $R°$; —$(CH_2)_{0-4}O(CH_2)_{0-1}$-pyridyl which is optionally substituted with $RO$; —$NO_2$; —$CN$; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ is optionally substituted as defined below and is independently hydrogen, $C_{1-6}$ aliphatic, —$CH_2Ph$, —$O(CH_2)_{0-1}Ph$, —$NH(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on $R°$ (or the ring formed by taking two independent occurrences of $R°$ together with their intervening atoms), are independently deuterium, halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —$CN$, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)O$R^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, —$O(C(R^*_2))_{2-3}O$—, or —$S(C(R^*_2))_{2-3}S$—, wherein each independent occurrence of R* is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,
—OH, protected hydroxy, alkoxy, oxo, thiooxo,
—NO$_2$, —CN, CF$_3$, N$_3$,
—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino,
—O— alkyl, —O— alkenyl, —O— alkynyl, —O— cycloalkyl, —O-aryl, —O-heteroaryl, —O-heterocyclic,
—C(O)— alkyl, —C(O)— alkenyl, —C(O)— alkynyl, —C(O)— carbocyclyl, —C(O)-aryl, —C(O)— heteroaryl, —C(O)-heterocyclyl,
—CONH$_2$, —CONH— alkyl, —CONH— alkenyl, —CONH— alkynyl, —CONH-carbocyclyl, —CONH-aryl, —CONH-heteroaryl, —CONH-heterocyclyl,
—OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl,
—NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH-alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl,
—C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl,
—S(O)— alkyl, —S(O)— alkenyl, —S(O)— alkynyl, —S(O)— carbocyclyl, —S(O)-aryl, —S(O)-heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl,
—NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,
—CH$_2$NH$_2$, —CH$_2$SO$_2$CH$_3$,
-mono-, di-, or tri-alkyl silyl,
-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, tautomers, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant. Compounds of the invention may be substituted by $^{18}F$, for use as PET imaging agents.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concen-tra-tion at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 μM. In certain embodiments, a modulator has an $IC_{50}$ and/or binding constant of less than about 5 μM. In certain embodiments, a modulator has an $IC_{50}$ and/or binding constant of between about 1 to about 5 μM. In certain embodiments, a modulator has an $IC_{50}$ and/or binding constant of less than about 1 μM. In certain embodiments, a modulator has an $IC_{50}$ and/or binding constant of between about 500 to about 1000 nM. In certain embodiments, a modulator has an $IC_{50}$ and/or binding constant of less than about 500 nM. In certain embodiments, a modulator has an $IC_{50}$ and/or binding constant of between about 100 to about 500 nM. In certain embodiments, a modulator has an $IC_{50}$ and/or binding constant of less than about 100 nM. In certain embodiments, a modulator has an $IC_{50}$ and/or binding constant of between about 10 to about 100 nM. In certain embodiments, a modulator has an $IC_{50}$ and/or binding constant of less than about 10 nM.

The terms "measurable affinity" and "measurably inhibit," as used herein, means a measurable change in IDO activity between a sample comprising a compound of the present invention, or composition thereof, and IDO, and an equivalent sample comprising IDO, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

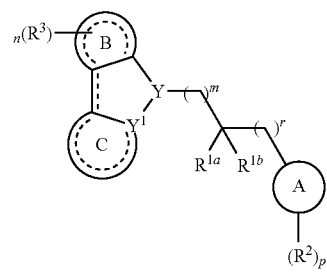

or a pharmaceutically acceptable salt thereof, wherein:
Y is CR or N;
$Y^1$ is C, CR, or N; wherein one of Y or $Y^1$ is N;
$R^{1a}$ is —R, halogen, -haloalkyl, -hydroxyalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;
$R^{1b}$ is —R, halogen, -haloalkyl, -hydroxyalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$; or
$R^{1a}$ and $R^{1b}$, together with the atom to which each is attached, may form a fused or spiro ring selected from $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
Ring A is $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur;
each $R^2$ is independently —R, halogen, -haloalkyl, -hydroxyalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;
Ring B is $C_{5-10}$ aryl, a 3-8 membered saturated or partially unsaturated carbocyclic ring, a 3-7 membered heterocylic ring having 1-3 heteroatoms independently selected from $X^1$, $X^2$, or $X^3$, selected from nitrogen, oxygen, or sulfur, or a 5-6 membered monocyclic heteroaryl ring having 1-3 heteroatoms independently selected from $X^1$, $X^2$, or $X^3$, each of which is selected from nitrogen, oxygen, or sulfur;
each $R^3$ is independently —R, halogen, -haloalkyl, -hydroxyalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;
Ring C is $C_{5-10}$ aryl, a 3-8 membered saturated or partially unsaturated carbocyclic ring, a 3-7 membered heterocylic ring having 1-4 heteroatoms independently selected from Z, $Z^1$, $Z^2$, $Z^3$, or $Z^4$, selected from nitrogen, oxygen, or sulfur, or a 5-6 membered monocyclic heteroaryl ring having 1-4 heteroatoms independently selected from Z, $Z^1$, $Z^2$, $Z^3$, or $Z^4$, each of which is selected from nitrogen, oxygen, or sulfur;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

m is 1 or 2;
n is 0, 1, 2, or 3;
p is 0, 1, 2, or 3; and
r is 0 or 1;

wherein when Ring A is non-fluoro substituted cyclohexyl, Ring B is benzo, and Ring C is

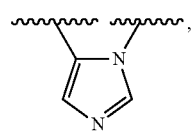 [SMILES: *c1cncn1*]

and $R^{1a}$ is H, then $R^{1b}$ cannot be OH.

In certain embodiments, Y is CR. In certain embodiments, Y is CH. In certain embodiments, Y is N.

In certain embodiments, $Y^1$ is CR. In certain embodiments, $Y^1$ is CH. In certain embodiments, $Y^1$ is C. In certain embodiments, $Y^1$ is N.

In certain embodiments, $R^{1a}$ is —R.
In certain embodiments, $R^{1a}$ is —H.
In certain embodiments, $R^{1a}$ is halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.
In certain embodiments, $R^{1a}$ is halogen, -haloalkyl, -hydroxyalkyl, —OR, —NRC(O)R, —NRC(O)N(R)$_2$, —NRSO$_2$R, or —N(R)$_2$.
In certain embodiments, $R^{1a}$ is halogen, —OR, —NRSO$_2$R, or —N(R)$_2$.
In certain embodiments, $R^{1a}$ is

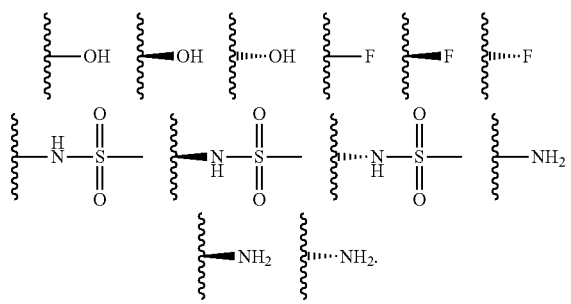

In certain embodiments, $R^{1b}$ is —R.
In certain embodiments, $R^{1b}$ is —H.
In certain embodiments, $R^{1b}$ is halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^{1b}$ is halogen, -haloalkyl, -hydroxyalkyl, —OR, —NRC(O)R, —NRC(O)N(R)$_2$, —NRSO$_2$R, or —N(R)$_2$.
In certain embodiments, $R^{1b}$ is halogen, —OR, —NRSO$_2$R, or —N(R)$_2$.
In certain embodiments, $R^{1b}$ is

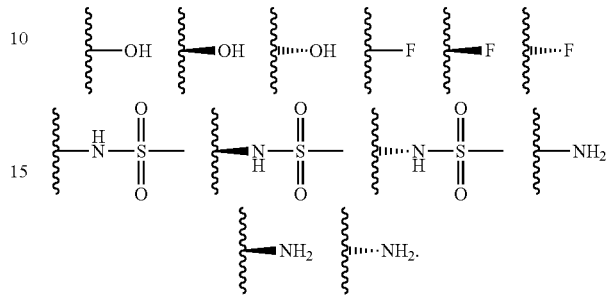

In certain embodiments, each $R^2$ is independently —R.
In certain embodiments, each $R^2$ is independently —H.
In certain embodiments, each $R^2$ is independently alkyl.
In certain embodiments, each $R^2$ is independently methyl, ethyl, propyl, i-propyl, n-butyl, s-butyl, t-butyl, straight chain or branched pentyl, or straight chain or branched hexyl.
In certain embodiments, each $R^2$ is independently halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.
In certain embodiments, each $R^2$ is independently halogen or —OR.
In certain embodiments, each $R^2$ is independently —F or —OH.
In certain embodiments, two $R^2$ groups are R, and each R on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted. In certain embodiments, the ring is cyclopropyl, cyclobutyl, cyclopentyl, or cyclohexyl. In certain embodiments, the ring is cyclopropyl.

In certain embodiments, Ring A is $C_{5-10}$ aryl. In certain embodiments, Ring A is a 3-8 membered saturated or partially unsaturated carbocyclic ring. In certain embodiments, Ring A is a 3-7 membered heterocyclic ring having 1-4 heteroatoms independently selected from nitrogen, oxygen, or sulphur. In certain embodiments, Ring A is a 5-6 membered monocyclic heteroaryl ring having 1-4 heteroatoms independently selected from nitrogen, oxygen, or sulphur.

In certain embodiments, Ring A is phenyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, oxetanyl, azetidinyl, or xanthenyl.

In certain embodiments, Ring A is $C_{5-10}$ aryl. In certain embodiments, Ring A is a 3-8 membered saturated or partially unsaturated carbocyclic ring.

In certain embodiments, Ring A is phenyl, piperidinyl, cycloheptyl, cyclohexyl, cyclopentyl, cyclobuty, or cyclopropyl. In certain embodiments, Ring A is phenyl, piperidinyl, tetrahydropyran, or cyclohexyl.

In certain embodiments, Ring A is

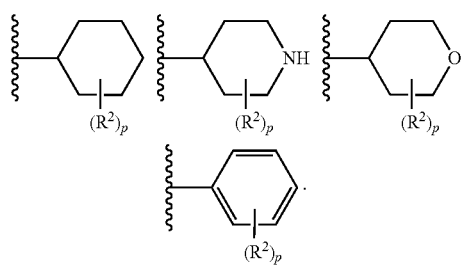

In certain embodiments, Ring A is

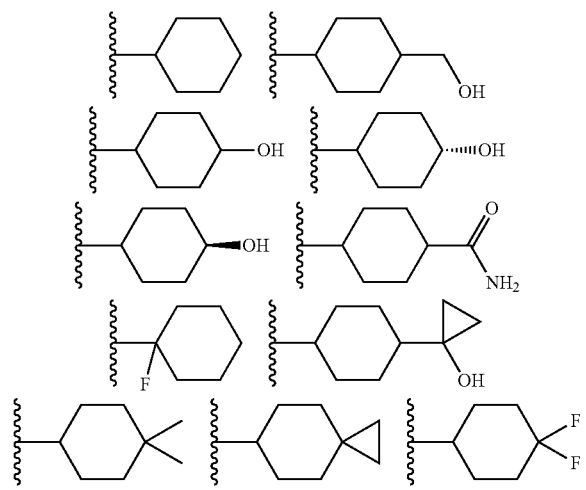

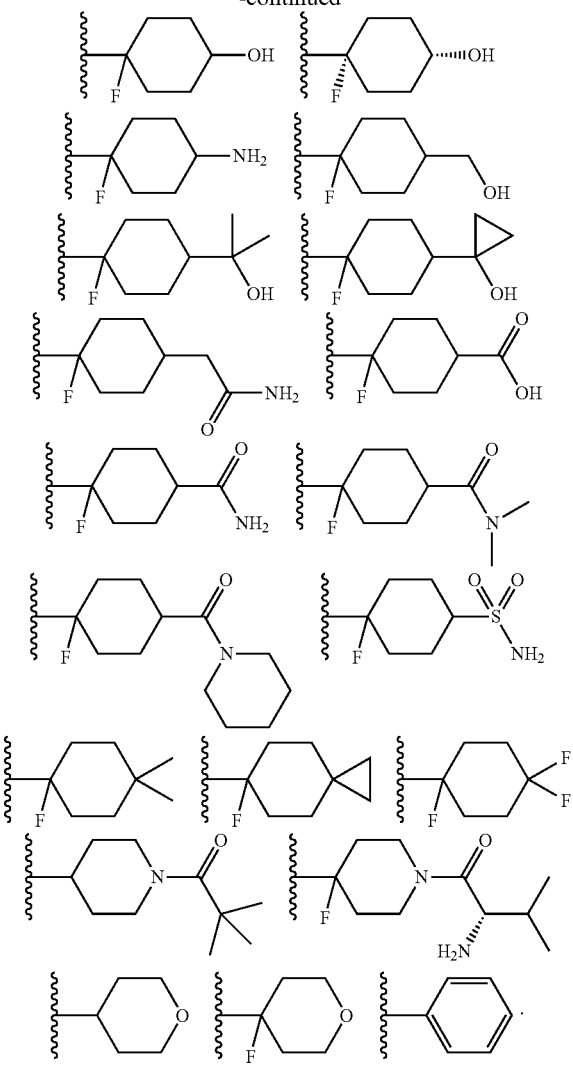

In certain embodiments, Ring B is $C_{5-10}$ aryl. In certain embodiments, Ring B is a 3-8 membered saturated or partially unsaturated carbocyclic ring. In certain embodiments, Ring B is a 3-7 membered heterocylic ring having 1-4 heteroatoms independently selected from nitrogen, oxygen, or sulphur. In certain embodiments, Ring B is a 5-6 membered monocyclic heteroaryl ring having 1-4 heteroatoms independently selected from nitrogen, oxygen, or sulphur.

In certain embodiments, Ring B is phenyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl.

In certain embodiments, Ring B is

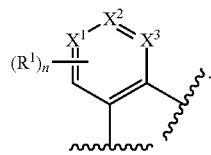

In certain embodiments, Ring B is phenyl, cycloheptyl, cyclohexyl, cyclopentyl, cyclobuty, cyclopropyl, cyclohexadiene, pyridinyl, pyrimidinyl.

In certain embodiments, Ring B is

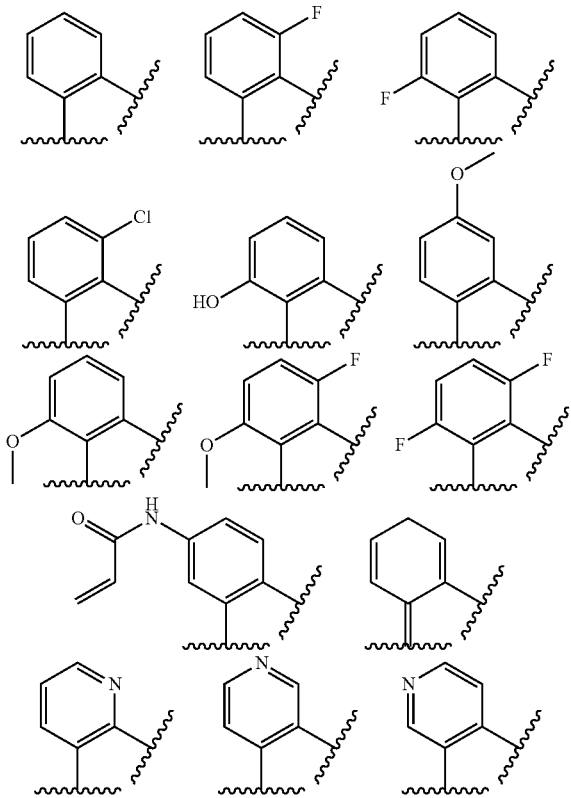

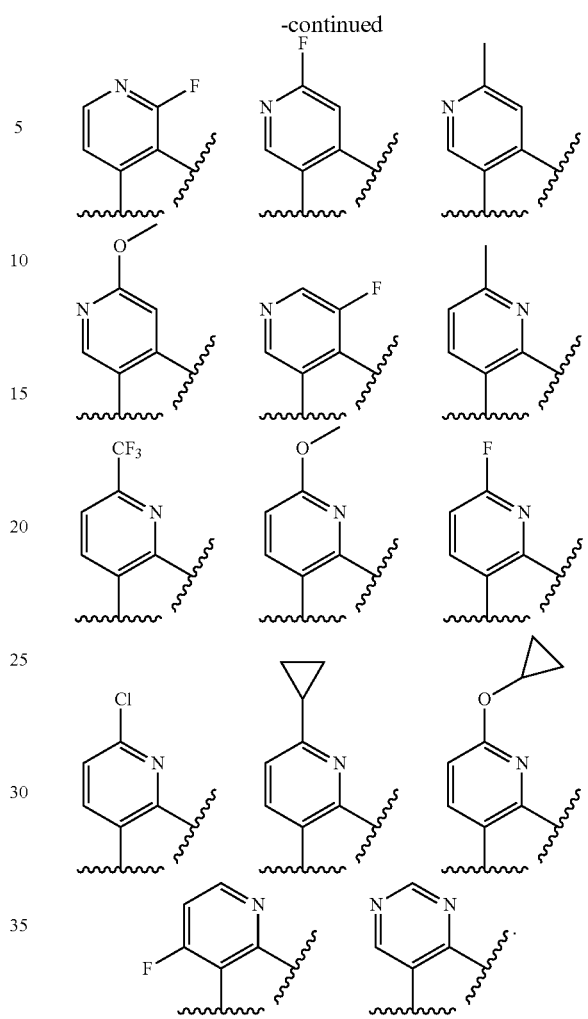

In certain embodiments, Ring C is $C_{5-10}$ aryl. In certain embodiments, Ring C is a 3-8 membered saturated or partially unsaturated carbocyclic ring. In certain embodiments, Ring C is a 3-7 membered heterocylic ring having 1-4 heteroatoms independently selected from nitrogen, oxygen, or sulphur. In certain embodiments, Ring C is a 5-6 membered monocyclic heteroaryl ring having 1-4 heteroatoms independently selected from nitrogen, oxygen, or sulphur.

In certain embodiments, Ring C is phenyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl.

In certain embodiments, Ring C is

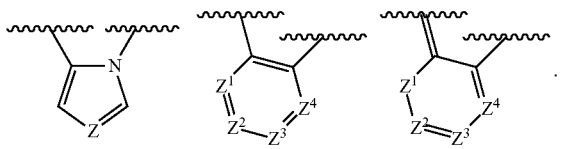

In certain embodiments, Ring C is phenyl, imidazole, pyrrole, pyridine, pyrimidine, pyrazine, pyridazine, dihydropyridine, dihydropyrimidine, dihydropyrazine, dihydropyridazine.

In certain embodiments, Ring C is

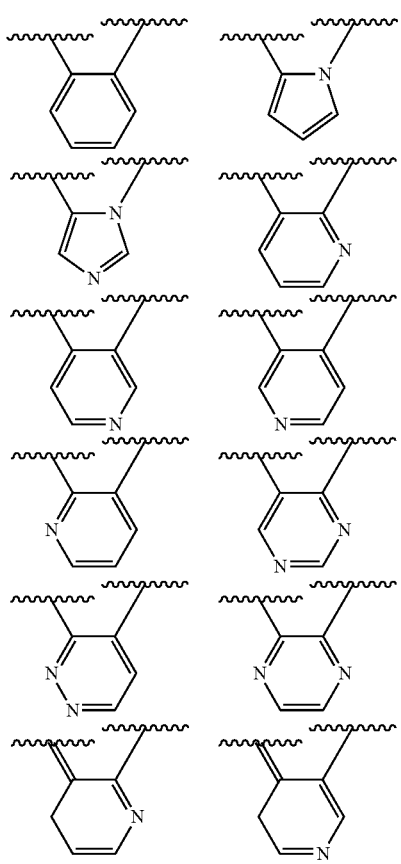

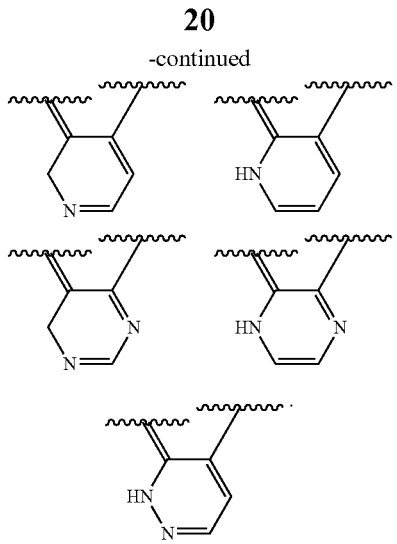

In certain embodiments, the present invention provides a compound of formula II,

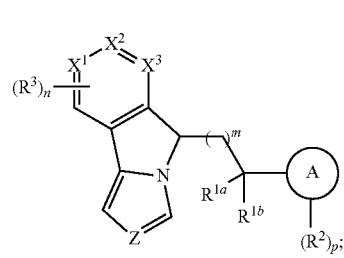

or a pharmaceutically acceptable salt thereof, wherein each of Ring A, $X^1$, $X^2$, $X^3$, Z, R, $R^{1a}$, $R^{1b}$, $R^2$, $R^3$, m, n, and p, is as defined above and described in embodiments, classes and subclasses above and herein, singly or in combination.

In certain embodiments, the present invention provides a compound of formula III:

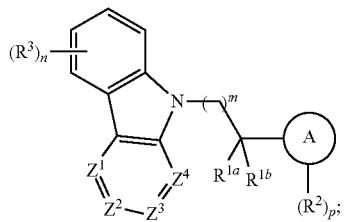

or a pharmaceutically acceptable salt thereof, wherein each of Ring A, $Z^1$, $Z^2$, $Z^3$, $Z^4$, R, $R^{1a}$, $R^{1b}$, $R^2$, $R^3$, m, n, and p, is as defined above and described in embodiments, classes and subclasses above and herein, singly or in combination.

In certain embodiments, the present invention provides a compound of formula IV:

IV

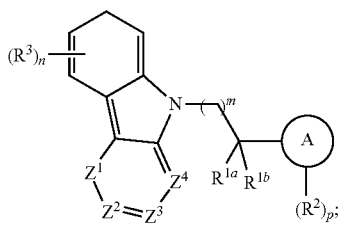

or a pharmaceutically acceptable salt thereof, wherein each of Ring A, $Z^1$, $Z^2$, $Z^3$, $Z^4$, R, $R^{1a}$, $R^{1b}$ $R^2$, $R^3$, m, n, and p, is as defined above and described in embodiments, classes and subclasses above and herein, singly or in combination.

In certain embodiments, the present invention provides a compound of any of the formulae presented below, or a pharmaceutically acceptable salt thereof, wherein each of Ring A, $X^1$, $X^2$, $X^3$, Z, $Z^1$, $Z^2$, $Z^3$, $Z^4$, R, $R^{1a}$, $R^{1b}$, $R^2$, $R^3$, m, n, and p, is as defined above and described in embodiments, classes and subclasses above and herein, singly or in combination.

II-a

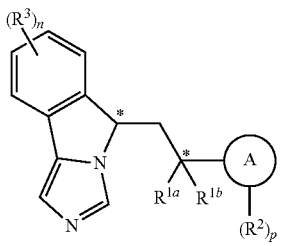

II-b

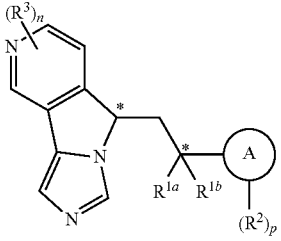

II-c

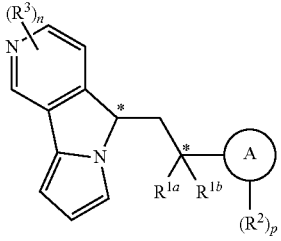

II-d

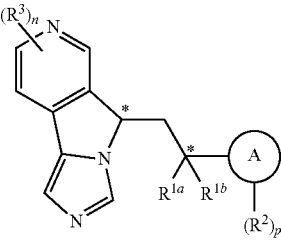

II-e

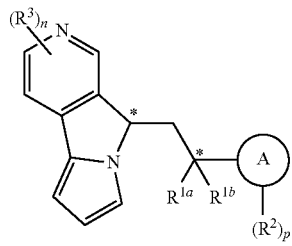

II-f

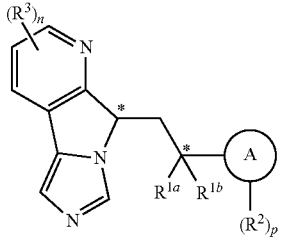

II-g

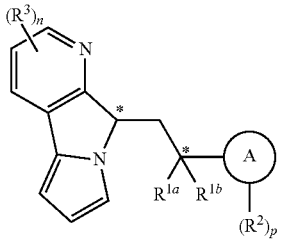

III-a

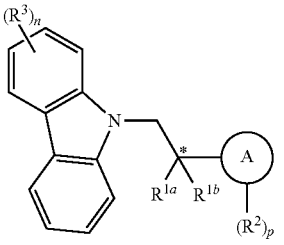

III-b

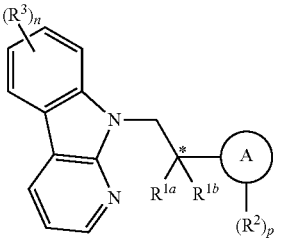

III-c

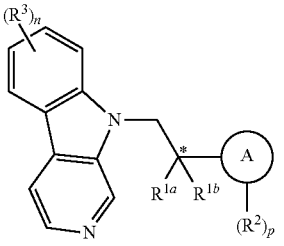

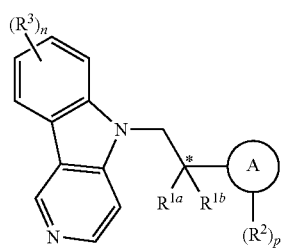 III-d
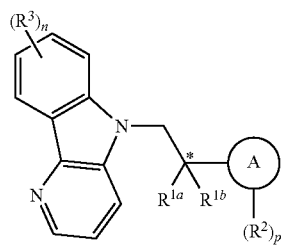 III-e
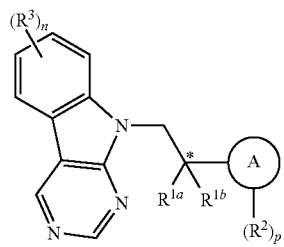 III-f
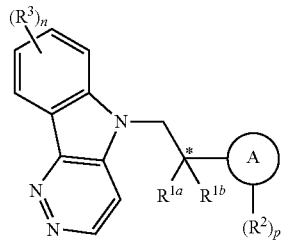 III-g
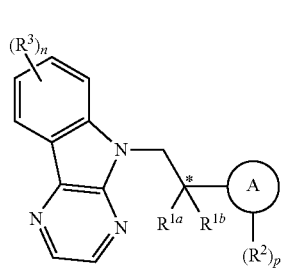 III-h
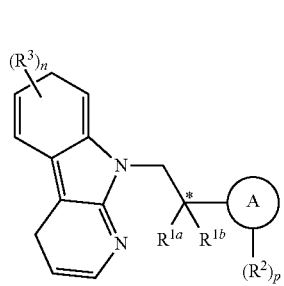 IV-a
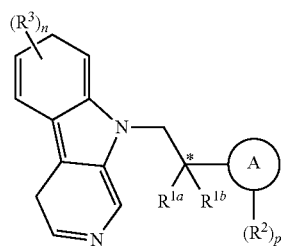 IV-b
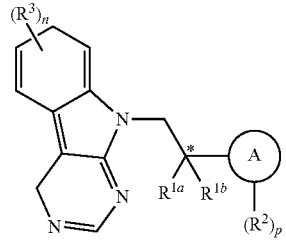 IV-c
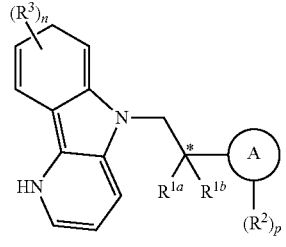 IV-d
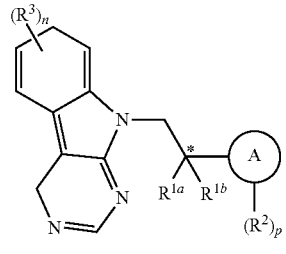 IV-e
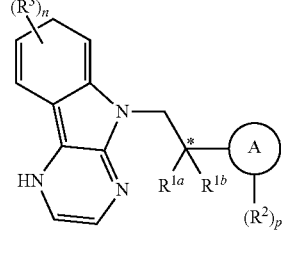 IV-f
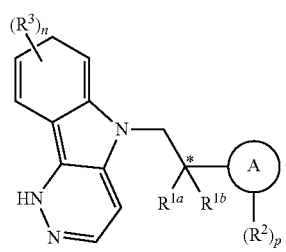 IV-g
In certain embodiments, the present invention provides a compound of formula V:

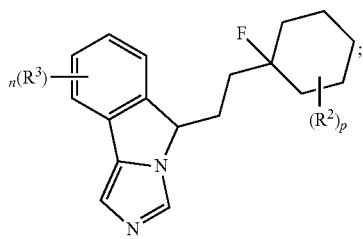

V or a pharmaceutically acceptable salt thereof, wherein each of $R^2$, $R^3$, n, and p, is as defined above and described in embodiments, classes and subclasses above and herein, singly or in combination.

In certain embodiments, the present invention provides a compound of formula VI:

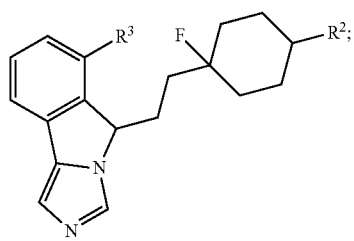

VI or a pharmaceutically acceptable salt thereof, wherein each of $R^2$ and $R^3$ is as defined above and described in embodiments, classes and subclasses above and herein, singly or in combination.

In certain embodiments, the compounds embodied by the invention include the racemate of *. In certain embodiments, the compounds embodied by the invention include the (R) enantiomer of *. In certain embodiments, the compounds embodied by the invention include the (S) enantiomer of *. In certain embodiments, each enantiomer is over 50% enantiopure. In certain embodiments, each enantiomer is over 75% enantiopure. In certain embodiments, each enantiomer is over 90% enantiopure. In certain embodiments, each enantiomer is over 50% enantiopure. In certain embodiments, each enantiomer is over 95% enantiopure. In certain embodiments, each enantiomer is over 97% enantiopure. In certain embodiments, each enantiomer is over 99% enantiopure.

In certain embodiments, when two stereocenters in a compound exist, the invention includes each diastereomer, and each enantiomer of each disatereomer (e.g., (R)(R), (R)(S), (S)(R), and (S)(S)).

In certain embodiments, when three stereocenters in a compound exist, the invention includes each diastereomer, and each enantiomer of each disatereomer (e.g., (R)(R)(R), (R)(S)(R), (R)(R)(S), (S)(R)(R), (S)(R)(S), (R)(S)(S), (S)(S)(R), and (S)(S)(S)).

In certain embodiments, the invention provides a compound of any of the formulae presented herein, wherein each of Ring A, Ring B, Ring C, Y, $Y^1$, $R^{1a}$, Rib, $R^2$, $R^3$, $X^1$, $X^2$, $X^3$, Z, $Z^1$, $Z^2$, $Z^3$, $Z^4$, R, m, n, and p, is as defined above and described in embodiments, classes and subclasses above and herein, singly or in combination.

In certain embodiments, the invention provides a compound selected from Table 1:

TABLE 1

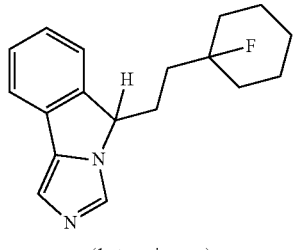

1a (1 stereoisomer)

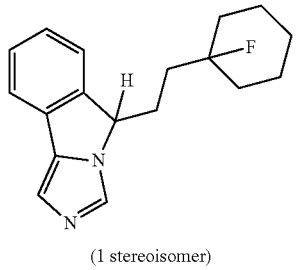

1b (1 stereoisomer)

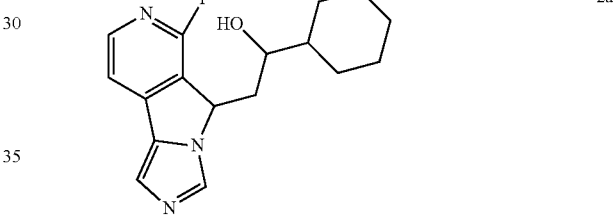

2a (2 stereoisomers)

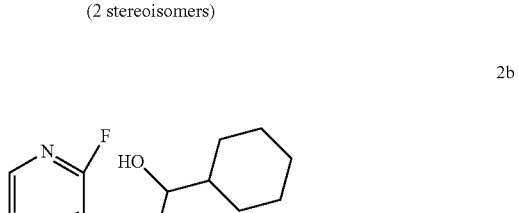

2b (2 stereoisomers)

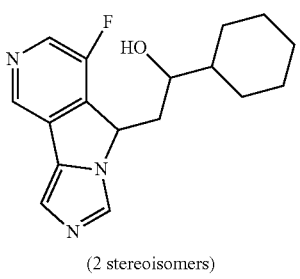 [SMILES: OC(CC1c2c(F)cncc2-c2cncn21)C1CCCCC1]

3a (2 stereoisomers)

TABLE 1-continued
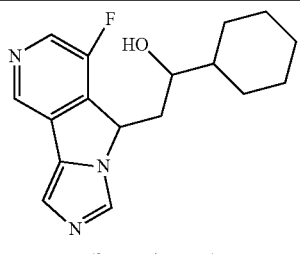
(2 stereoisomers)
3b
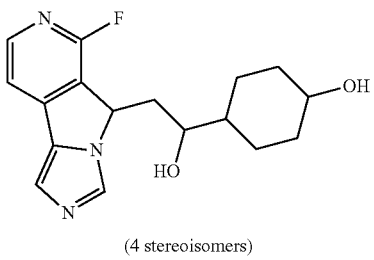 [SMILES: OC1CCC(C(O)CC2c3c(ccnc3F)-c3cncn32)CC1]
(4 stereoisomers)
4a
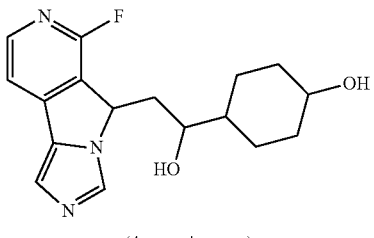
(4 stereoisomers)
4b
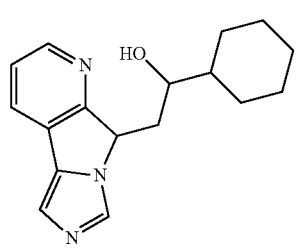
(2 stereoisomers)
5a
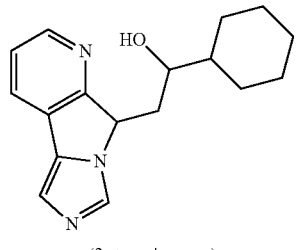
(2 stereoisomers)
5b
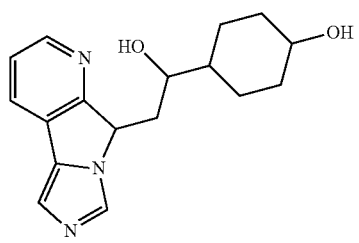
(2 stereoisomers)
6a
TABLE 1-continued
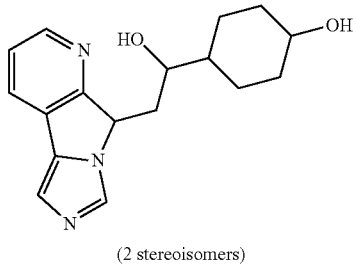 [SMILES: OC1CCC(C(O)CC2c3ncccc3-c3cncn32)CC1]
(2 stereoisomers)
6b
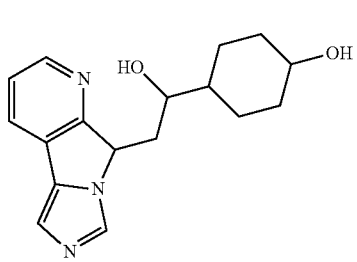
(2 stereoisomers)
6c
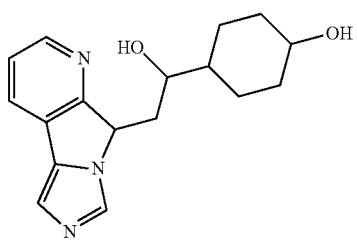
(2 stereoisomers)
6d
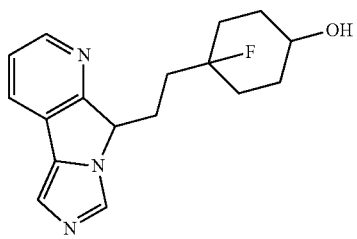
(2 stereoisomers)
7a
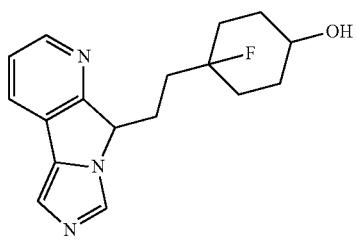
(2 stereoisomers)
7b TABLE 1-continued
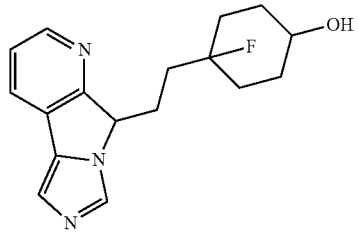
(1 stereoisomers) 8a
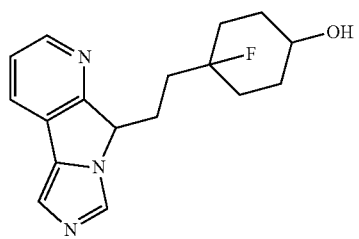
(1 stereoisomers) 8b
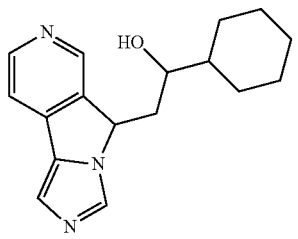
(2 stereoisomers) 9a
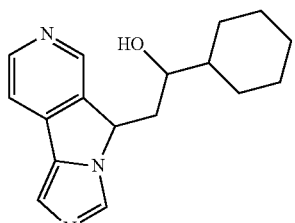
(2 stereoisomers) 9b
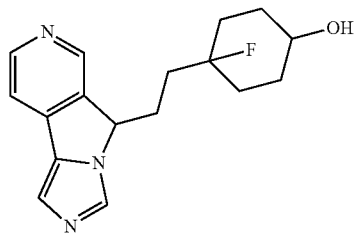
(1 stereoisomer) 10a
TABLE 1-continued
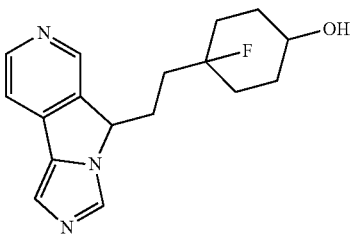
(1 stereoisomer) 10b
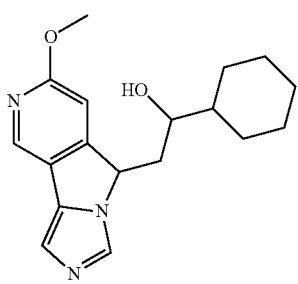
(2 stereoisomers) 11a
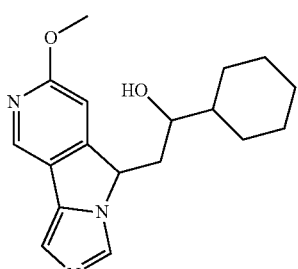
(2 stereoisomers) 11b
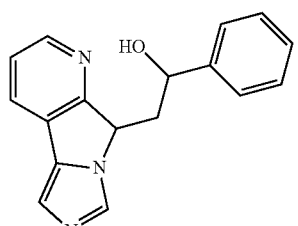
(2 stereoisomers) 12a
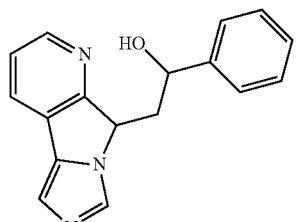
(2 stereoisomers) 12b TABLE 1-continued
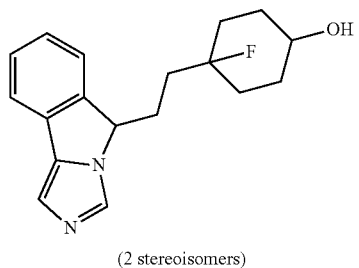
13a
(2 stereoisomers)
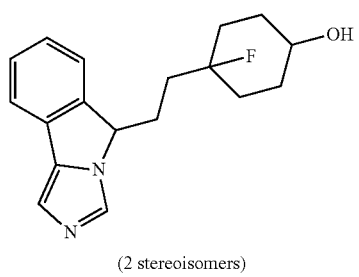
13b
(2 stereoisomers)
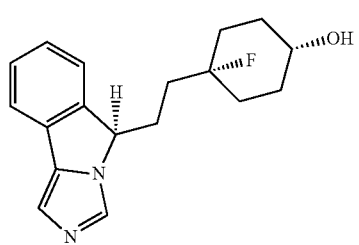
14a
(1 stereoisomer)
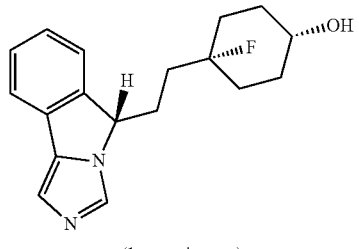
14b
(1 stereoisomer)
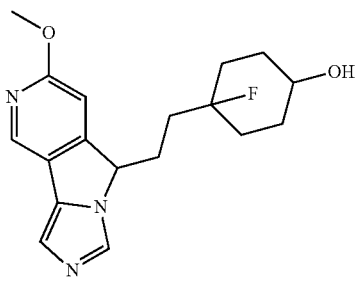
15a
(1 stereoisomer)
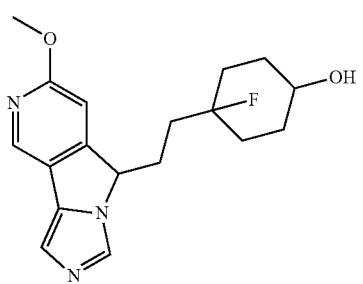
15b
(1 stereoisomer)
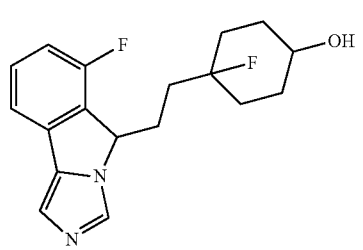
16a
(2 stereoisomers)
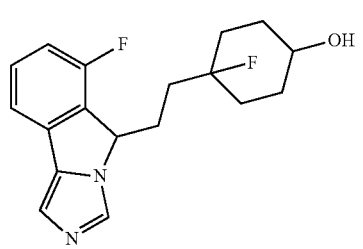
16b
(2 stereoisomers)
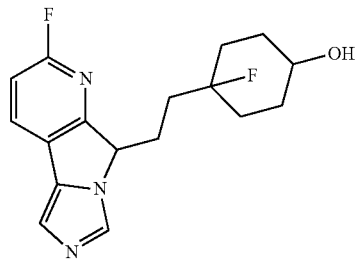
17
(1 stereoisomer)
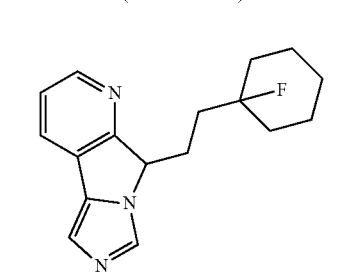
18a
(1 stereoisomer)

TABLE 1-continued
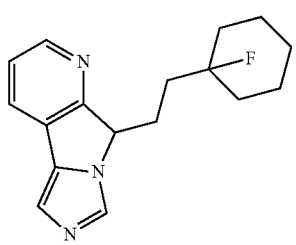
18b
(1 stereoisomer)
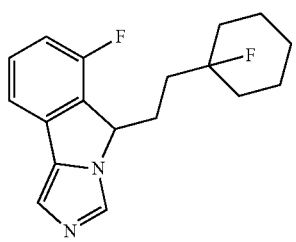
19a
(1 stereoisomer)
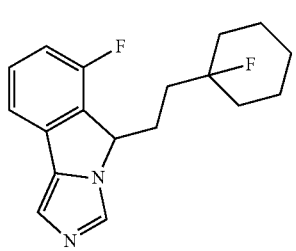
19b
(1 stereoisomer)
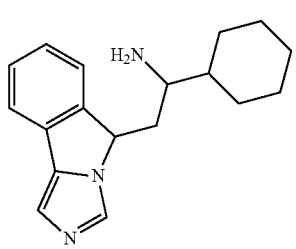
20a
(2 stereoisomers)
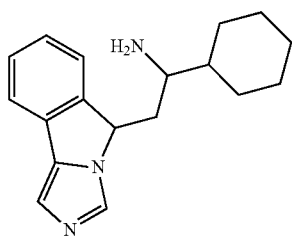
20b
(2 stereoisomers)
TABLE 1-continued
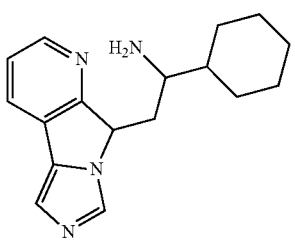
21a
(2 stereoisomers)
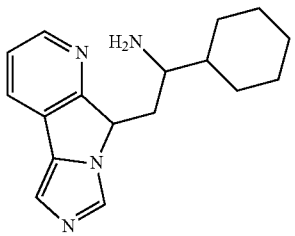
21b
(2 stereoisomers)
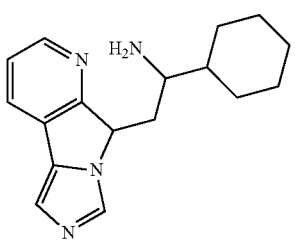
21c
(2 stereoisomers)
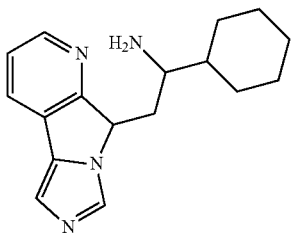
21d
(2 stereoisomers)
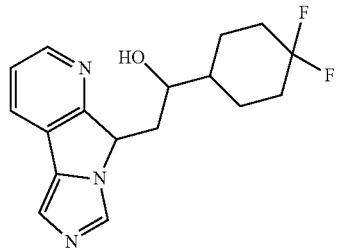
22a
(1 stereoisomer)

TABLE 1-continued
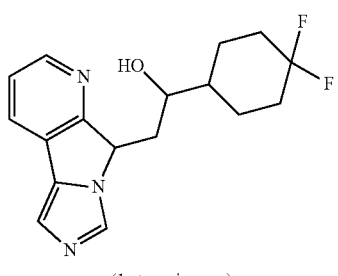
22b
(1 stereoisomer)
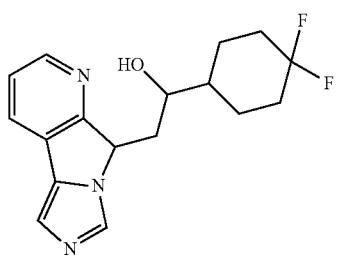
22c
(1 stereoisomer)
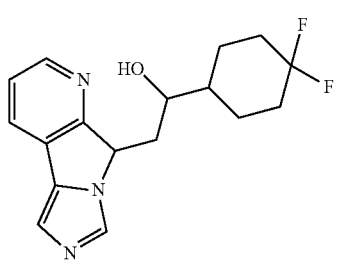
22d
(1 stereoisomer)
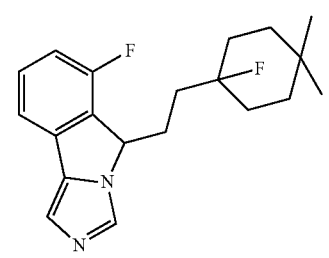
23a
(1 stereoisomer)
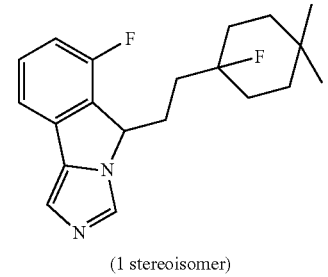
23b
(1 stereoisomer)
TABLE 1-continued
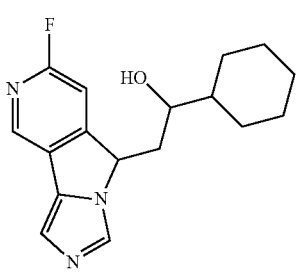
24a
(1 stereoisomer)
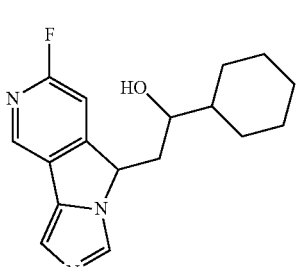
24b
(1 stereoisomer)
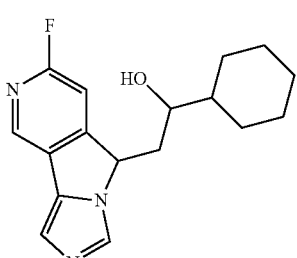
24c
(1 stereoisomer)
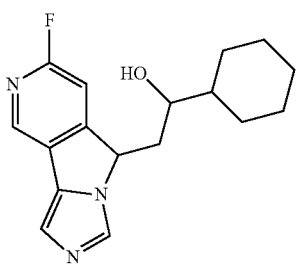
24d
(1 stereoisomer)
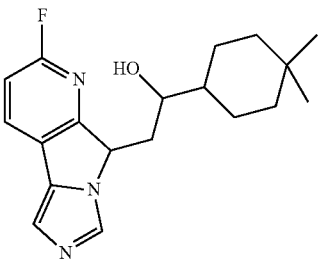
25a
(1 stereoisomer)

TABLE 1-continued
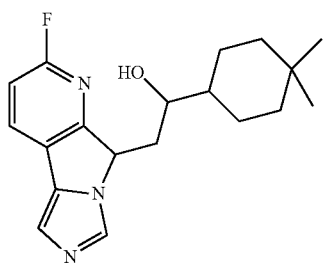
(1 stereoisomer)
25b
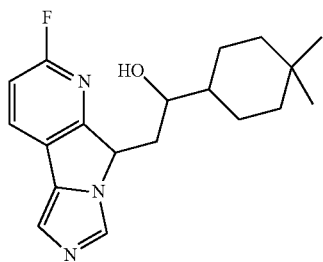
(1 stereoisomer)
25c
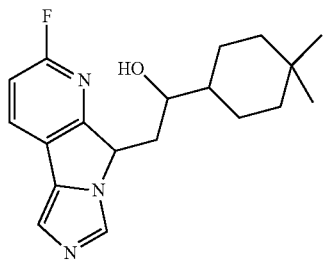
(1 stereoisomer)
25d
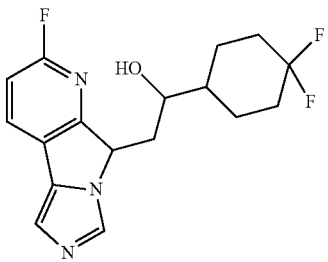
(2 stereoisomers)
26a
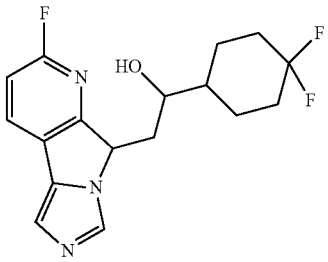
(2 stereoisomers)
26b
TABLE 1-continued
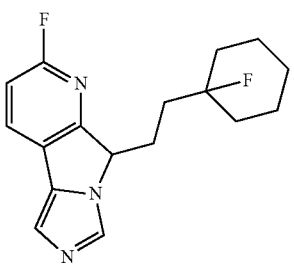
(1 stereoisomer)
27a
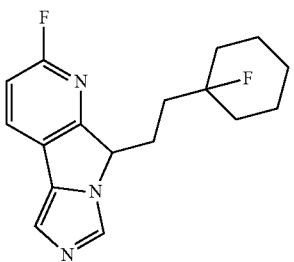
(1 stereoisomer)
27b
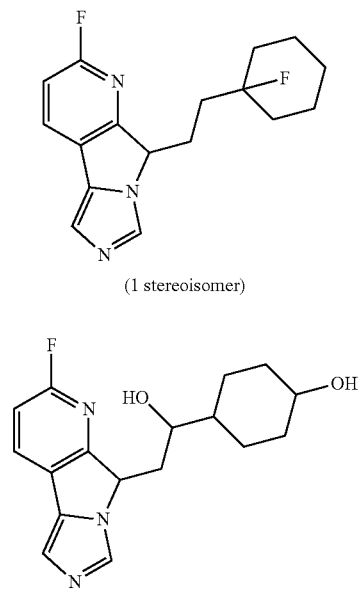
(2 stereoisomers)
28a
(2 stereoisomers)
28b
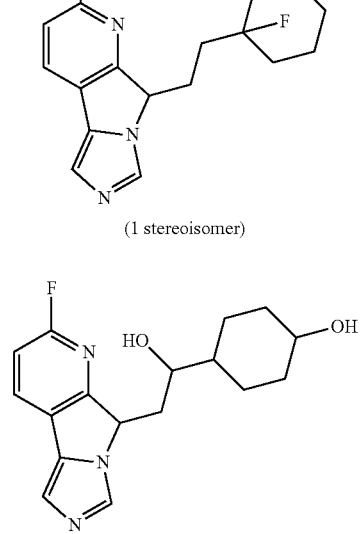
(2 stereoisomers)
28c TABLE 1-continued
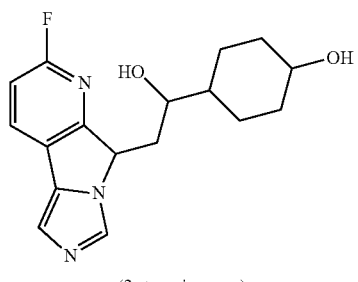
28d
(2 stereoisomers)
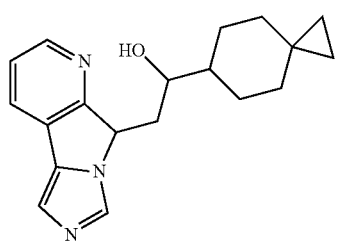
29a
(1 stereoisomer)
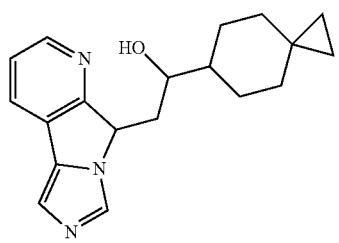
29b
(1 stereoisomer)
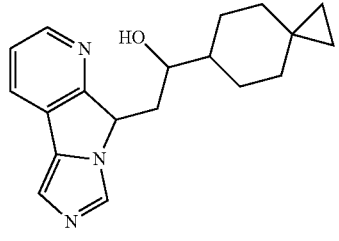
29c
(1 stereoisomer)
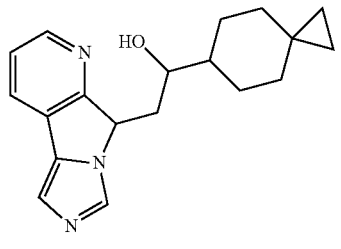
29d
(1 stereoisomer)
TABLE 1-continued
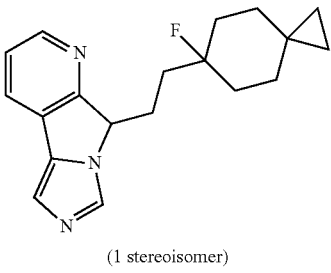 [SMILES: FC1(CCC2c3ncccc3-c3cncn32)CCC2(CC1)CC2]
30a
(1 stereoisomer)
30b
(1 stereoisomer)
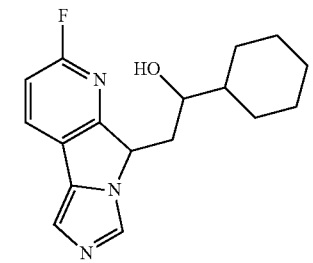
31a
(2 stereoisomers)
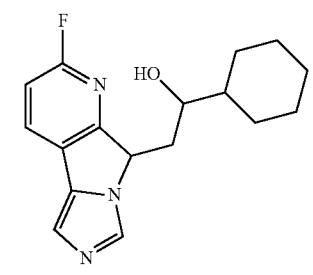
31b
(2 stereoisomers)
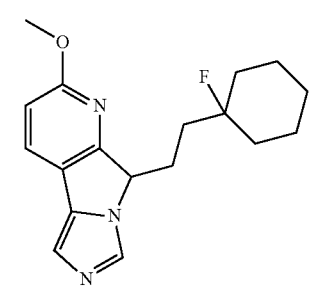
32b
(1 stereoisomer)

TABLE 1-continued
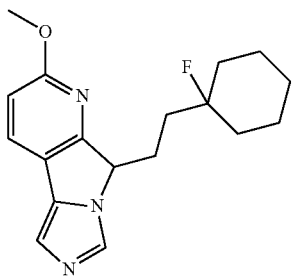
(1 stereoisomer)
32c
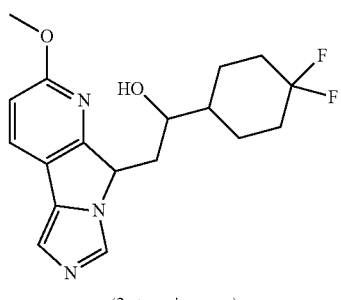
(2 stereoisomers)
33a
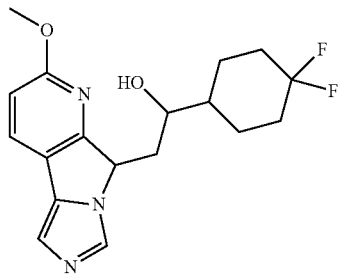
(2 stereoisomers)
33b
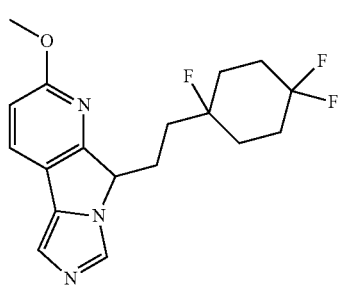
(1 stereoisomer)
34a
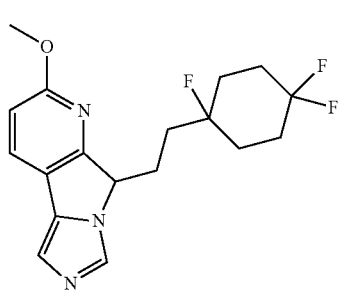
(1 stereoisomer)
34b
TABLE 1-continued
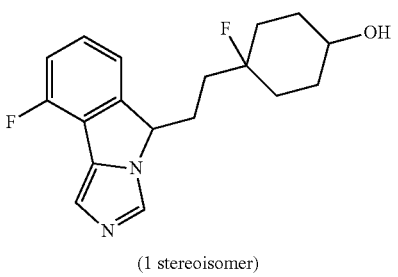 [SMILES: OC1CCC(F)(CCC2c3cccc(F)c3-c3cncn32)CC1]
(1 stereoisomer)
35a
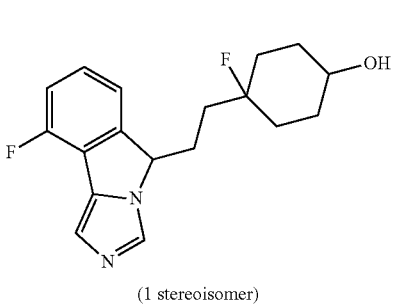 [SMILES: OC1CCC(F)(CCC2c3cccc(F)c3-c3cncn32)CC1]
(1 stereoisomer)
35b
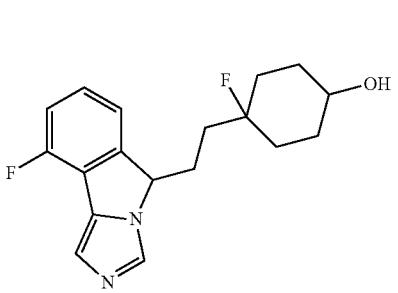
(1 stereoisomer)
35c
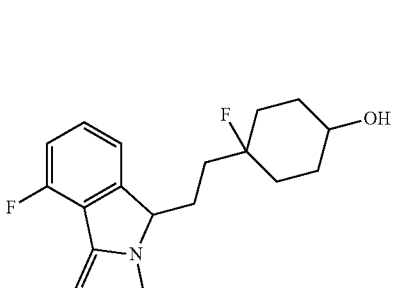
(1 stereoisomer)
35d
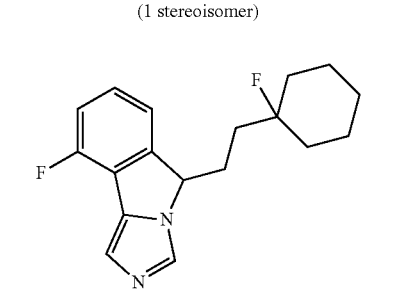
(1 stereoisomer)
36a TABLE 1-continued
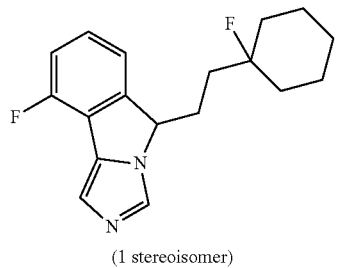 [SMILES: Fc1cccc2c1-c1cncn1C2CCC1(F)CCCCC1]
36b
(1 stereoisomer)
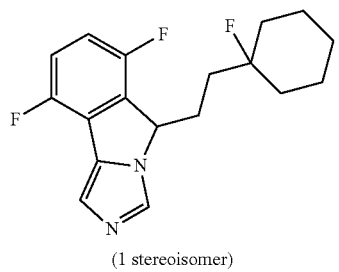 [SMILES: Fc1ccc(F)c2c1-c1cncn1C2CCC1(F)CCCCC1]
37a
(1 stereoisomer)
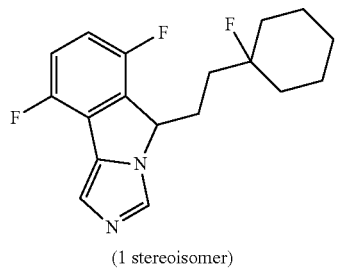 [SMILES: Fc1ccc(F)c2c1-c1cncn1C2CCC1(F)CCCCC1]
37b
(1 stereoisomer)
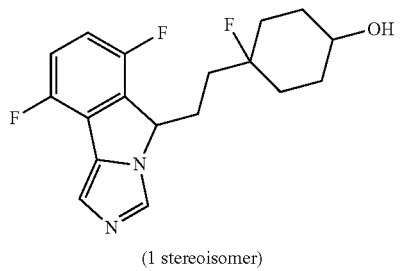 [SMILES: OC1CCC(F)(CCC2c3c(F)ccc(F)c3-c3cncn32)CC1]
38a
(1 stereoisomer)
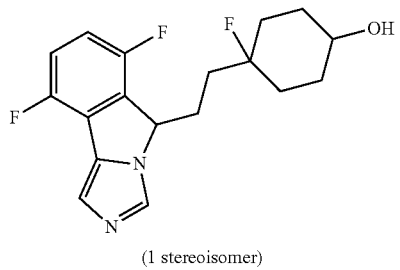 [SMILES: OC1CCC(F)(CCC2c3c(F)ccc(F)c3-c3cncn32)CC1]
38b
(1 stereoisomer)
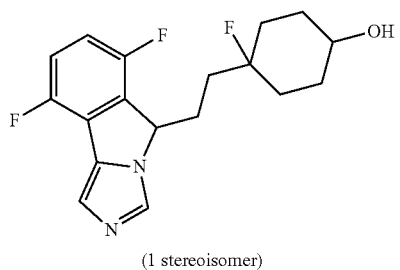 [SMILES: OC1CCC(F)(CCC2c3c(F)ccc(F)c3-c3cncn32)CC1]
38c
(1 stereoisomer)
TABLE 1-continued
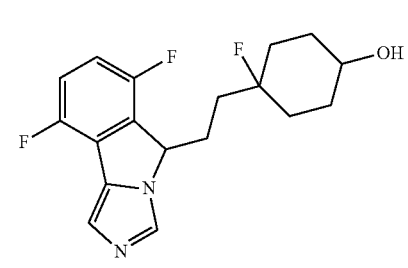
38d
(1 stereoisomer)
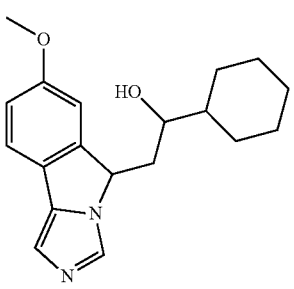
39a
(2 stereoisomers)
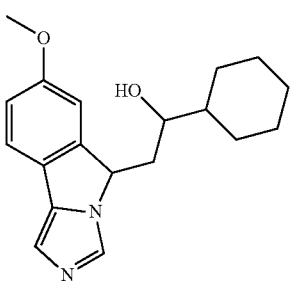
39b
(2 stereoisomers)
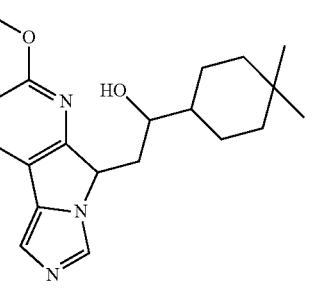
40a
(2 stereoisomers)
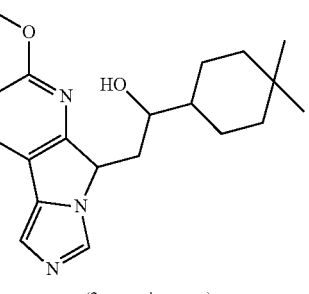
40b
(2 stereoisomers)

TABLE 1-continued
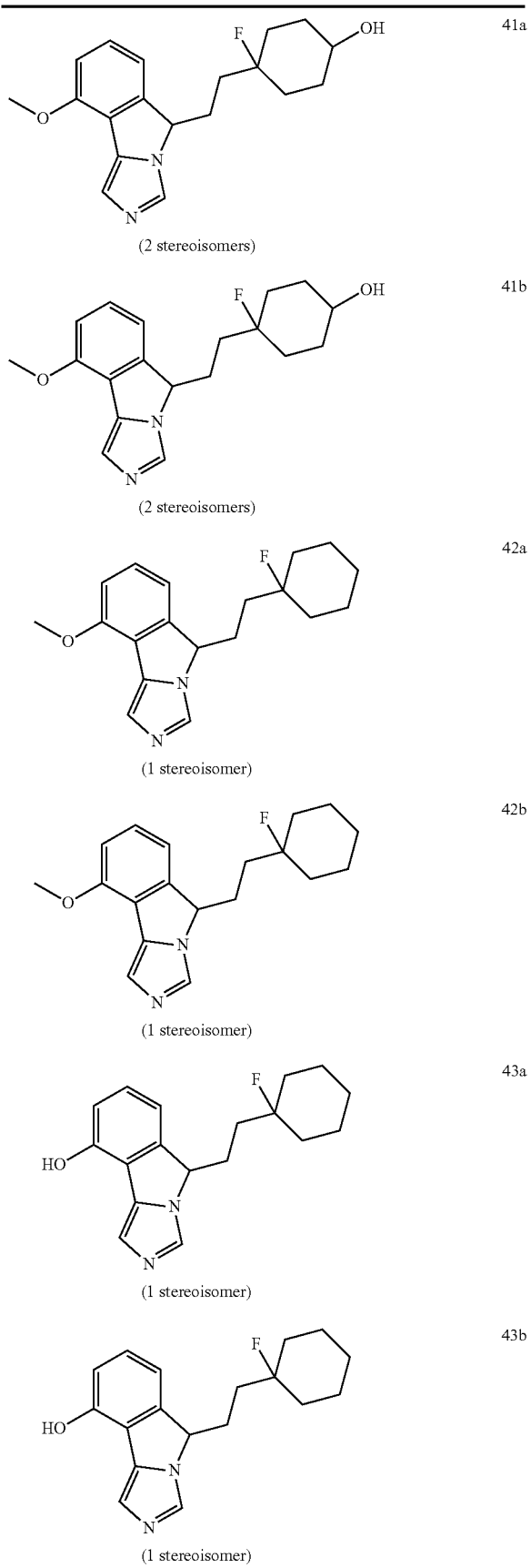
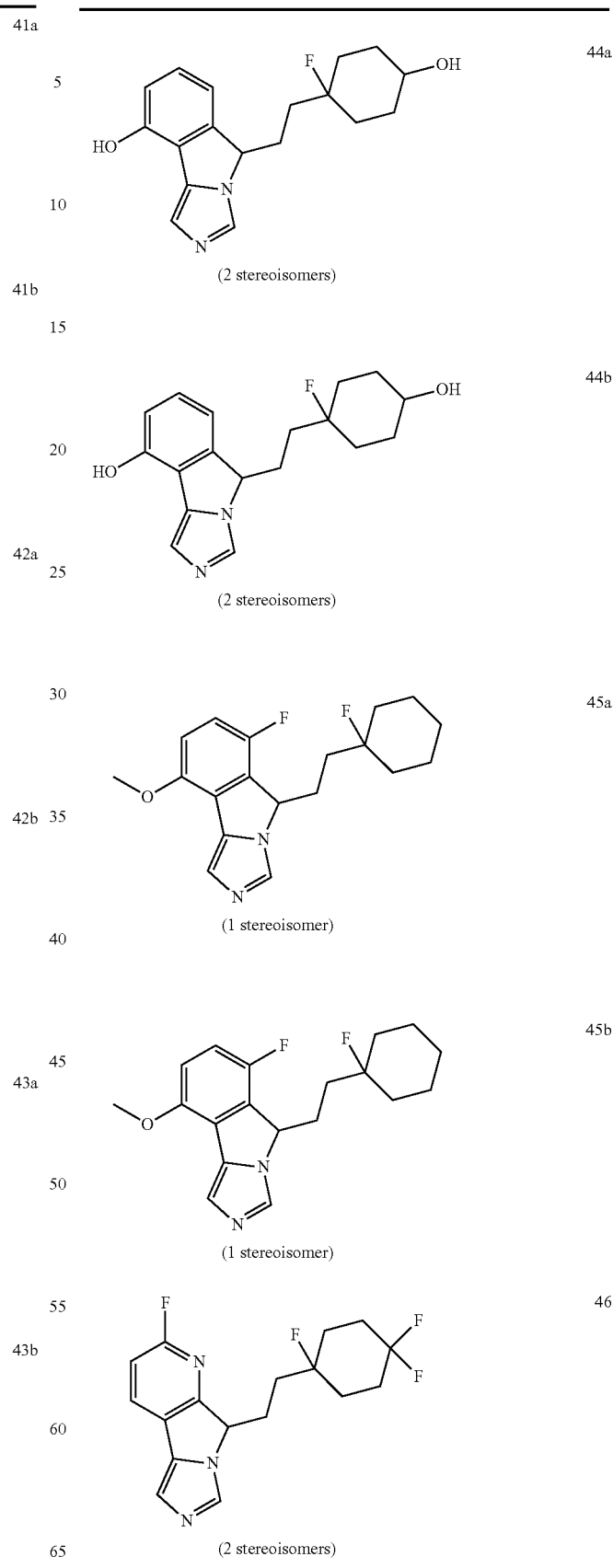

TABLE 1-continued
| | |
|---|---|
| 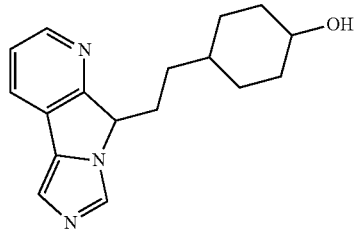<br>(1 stereoisomer) | 47 |
| 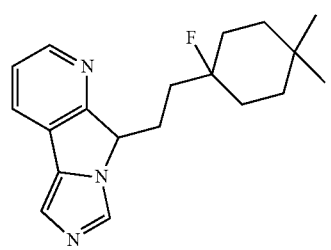<br>(1 stereoisomer) | 48a |
| 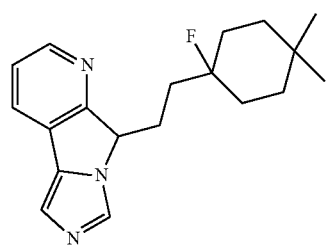<br>(1 stereoisomer) | 48b |
| 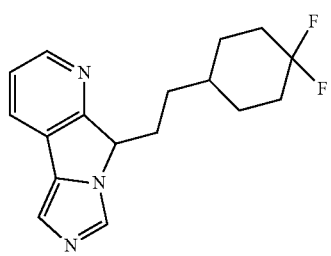<br>(2 stereoisomers) | 49 |
| 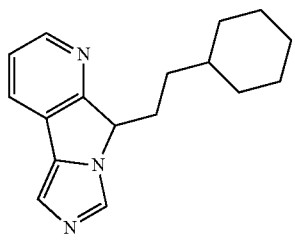<br>(2 stereoisomers) | 50 |
| 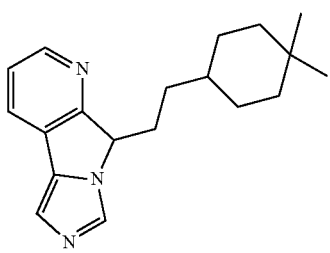<br>(2 stereoisomers) | 51 |
| 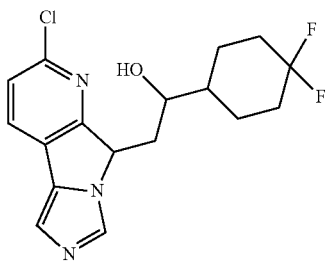<br>(1 stereoisomer) | 52a |
| 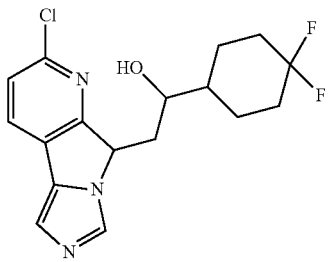<br>(2 stereoisomers) | 52b |
| 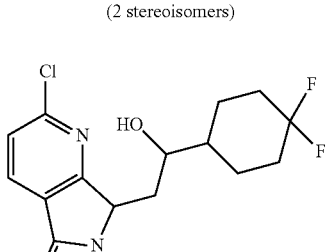<br>(1 stereoisomer) | 52c |
| 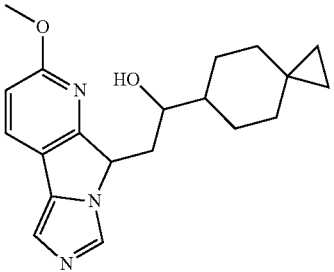<br>(2 stereoisomers) | 53a |

TABLE 1-continued
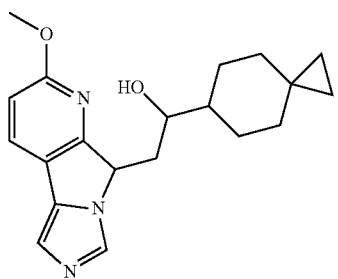
53b
(1 stereoisomer)
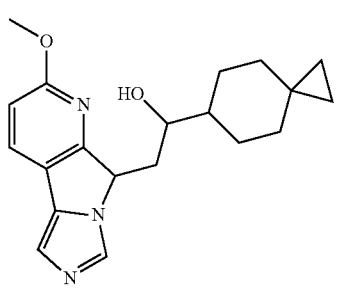
53c
(1 stereoisomer)
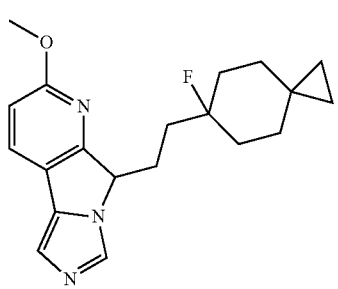
54a
(1 stereoisomer)
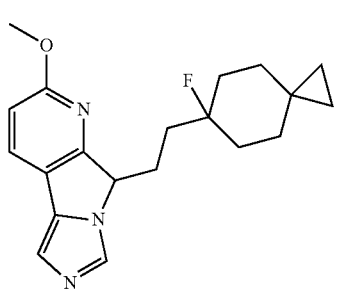
54b
(1 stereoisomer)
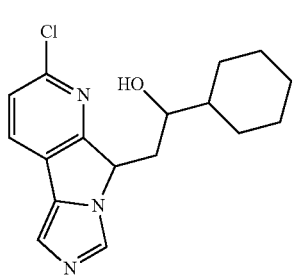
55a
(1 stereoisomer)
TABLE 1-continued
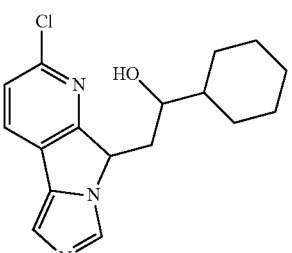
55b
(1 stereoisomer)
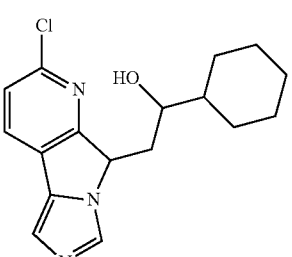
55c
(1 stereoisomer)
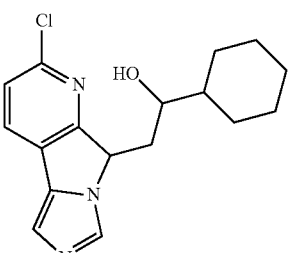
55d
(1 stereoisomer)
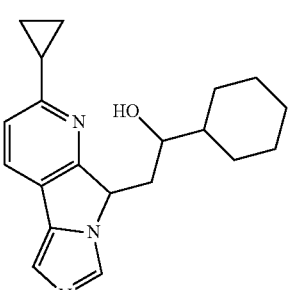
56a
(2 stereoisomers)
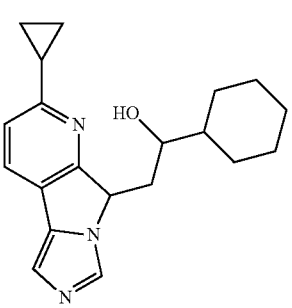
56b
(1 stereoisomer)

TABLE 1-continued
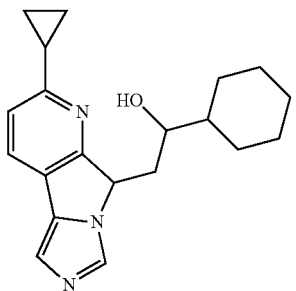
56c
(1 stereoisomer)
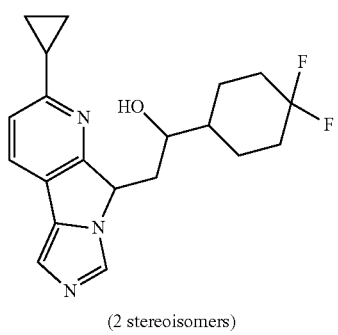 [SMILES: OC(CC1c2nc(C3CC3)ccc2-c2cncn21)C1CCC(F)(F)CC1]
57a
(2 stereoisomers)
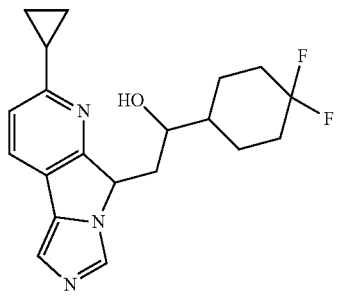
57b
(1 stereoisomer)
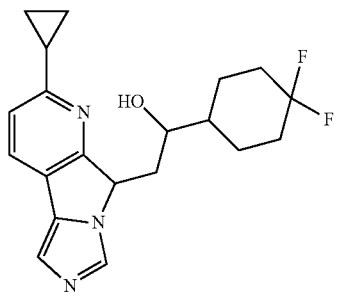
57c
(1 stereoisomer)
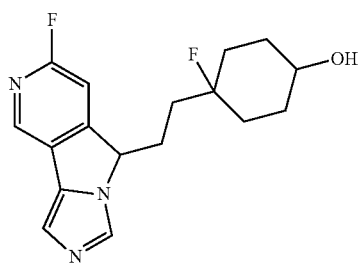
58a
(1 stereoisomer)
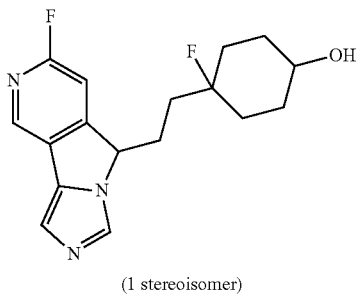 [SMILES: OC1CCC(F)(CCC2c3cc(F)ncc3-c3cncn32)CC1]
58b
(1 stereoisomer)
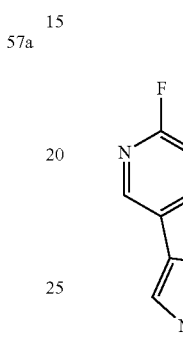
58c
(1 stereoisomer)
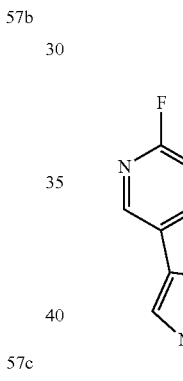
58d
(1 stereoisomer)
59a
(1 stereoisomer)
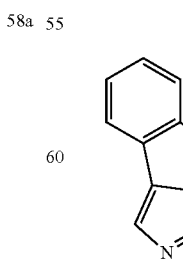
59b
(1 stereoisomer)

TABLE 1-continued
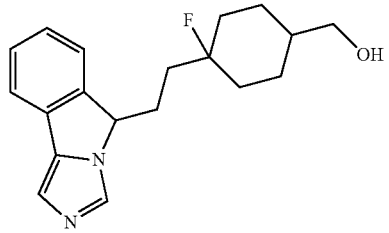
59c
(1 stereoisomer)
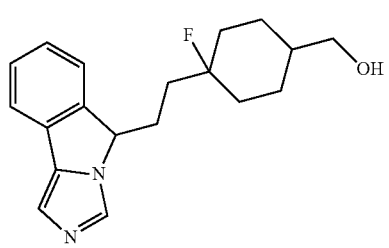
59d
(1 stereoisomer)
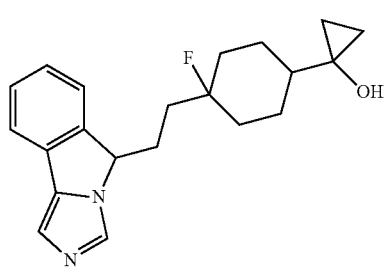
60a
(1 stereoisomer)
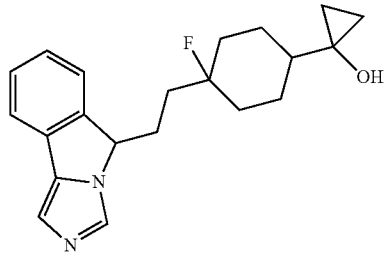
60b
(1 stereoisomer)
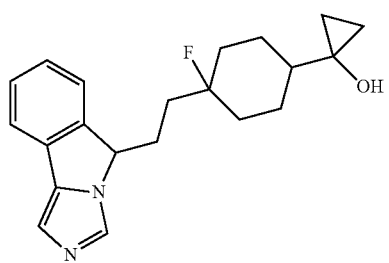
60c
(1 stereoisomer)
TABLE 1-continued
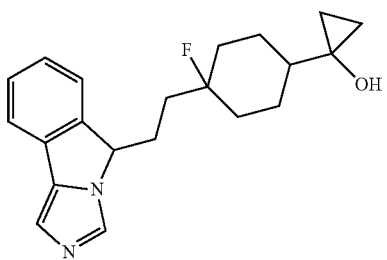
60d
(1 stereoisomer)
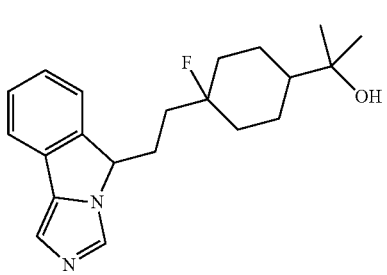
61a
(1 stereoisomer)
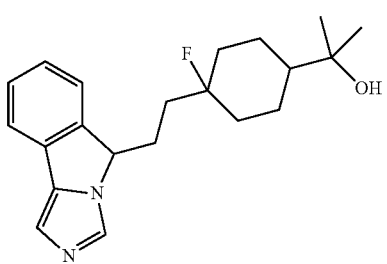
61b
(1 stereoisomer)
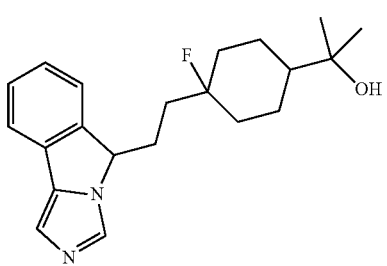
61c
(1 stereoisomer)
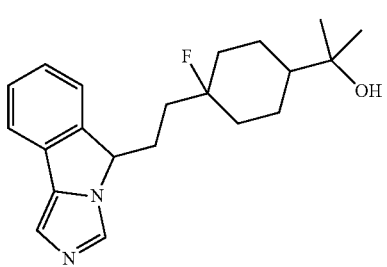
61d
(1 stereoisomer)

TABLE 1-continued
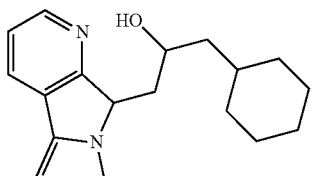
62a
(1 stereoisomer)
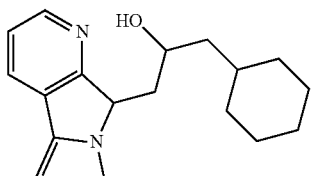
62b
(1 stereoisomer)
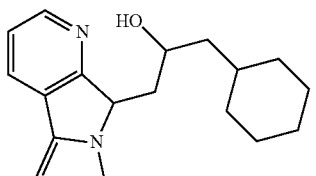
62c
(1 stereoisomer)
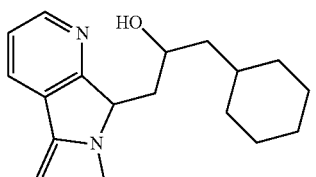
62d
(1 stereoisomer)
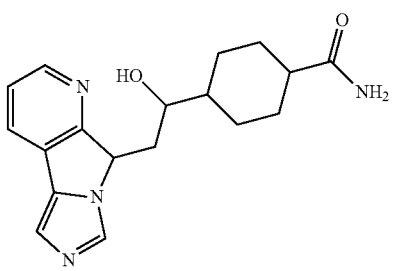
63a
(1 stereoisomer)
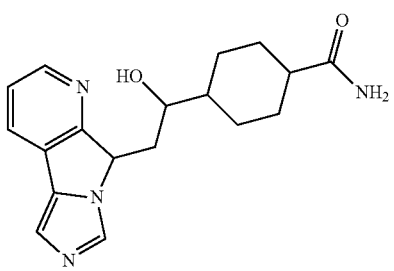
63b
(1 stereoisomer)
TABLE 1-continued
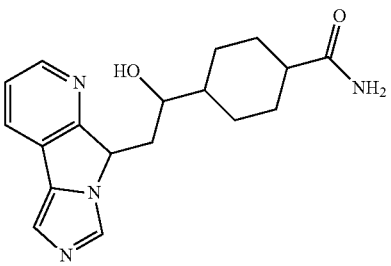
63c
(1 stereoisomer)
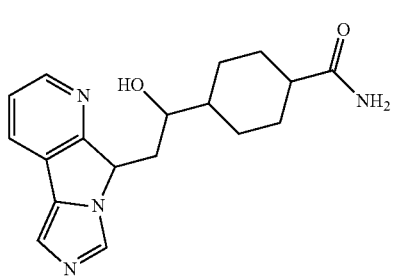
63d
(1 stereoisomer)
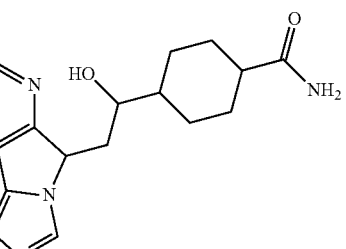
64
(2 stereoisomers)
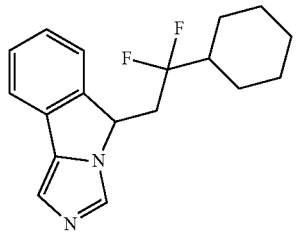
65
(2 stereoisomers)
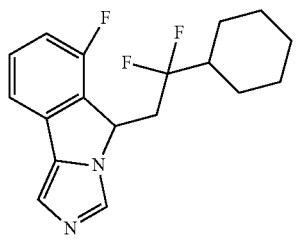
66a
(1 stereoisomer)
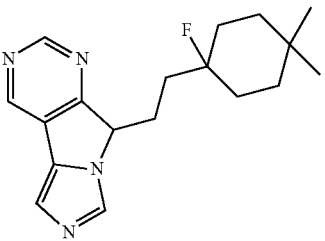

TABLE 1-continued
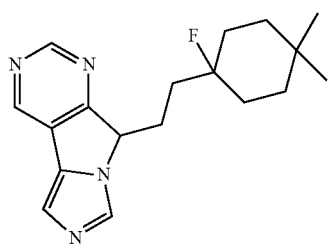
66b
(1 stereoisomer)
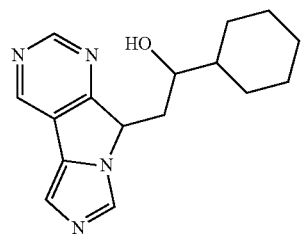
67a
(1 stereoisomer)
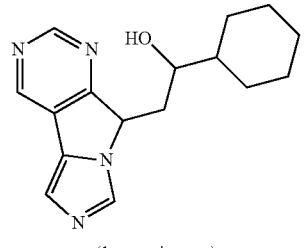
67b
(1 stereoisomer)
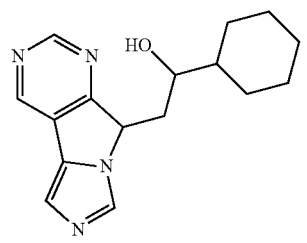
67c
(1 stereoisomer)
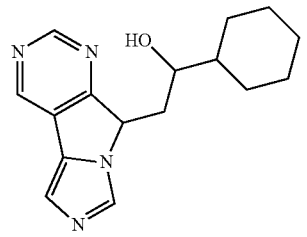
67d
(1 stereoisomer)
TABLE 1-continued
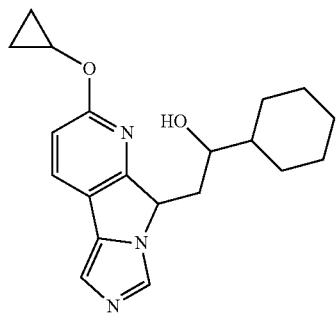
68a
(1 stereoisomer)
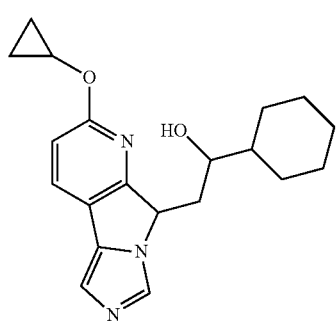
68b
(2 stereoisomers)
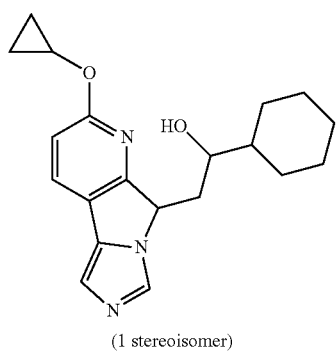 [SMILES: OC(CC1c2nc(OC3CC3)ccc2-c2cncn21)C1CCCCC1]
68c
(1 stereoisomer)
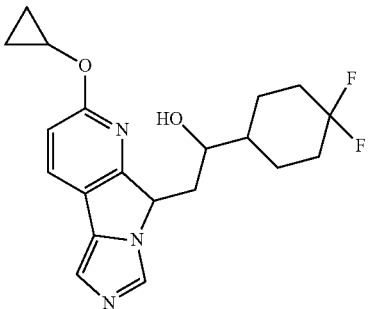
69a
(1 stereoisomer)

TABLE 1-continued
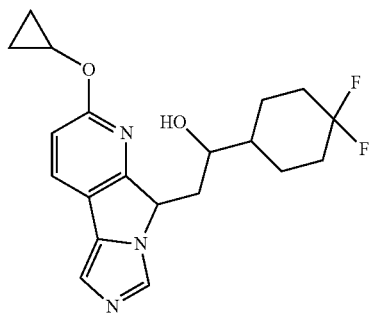
69b
(1 stereoisomer)
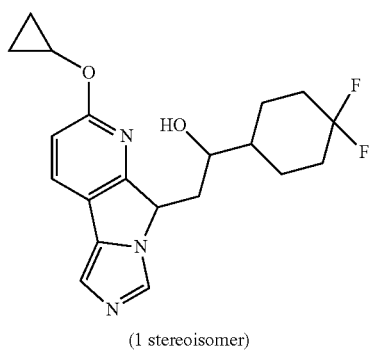
69c
(1 stereoisomer)
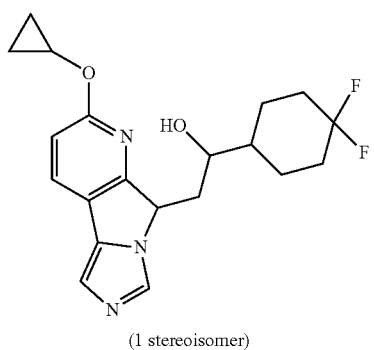 [SMILES: OC(CC1c2nc(OC3CC3)ccc2-c2cncn21)C1CCC(F)(F)CC1]
69d
(1 stereoisomer)
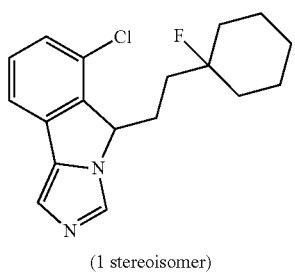 [SMILES: FC1(CCC2c3c(Cl)cccc3-c3cncn32)CCCCC1]
70a
(1 stereoisomer)
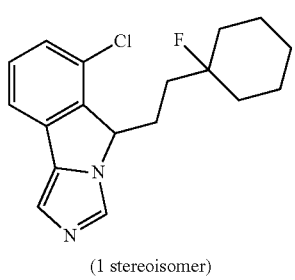 [SMILES: FC1(CCC2c3c(Cl)cccc3-c3cncn32)CCCCC1]
70b
(1 stereoisomer)
TABLE 1-continued
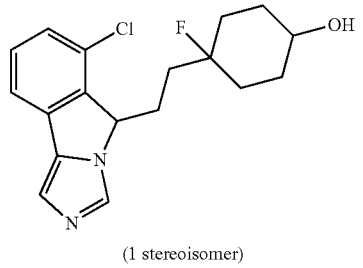 [SMILES: OC1CCC(F)(CCC2c3c(Cl)cccc3-c3cncn32)CC1]
71a
(1 stereoisomer)
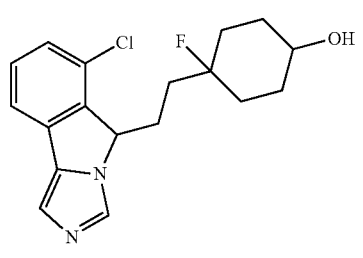
71b
(1 stereoisomer)
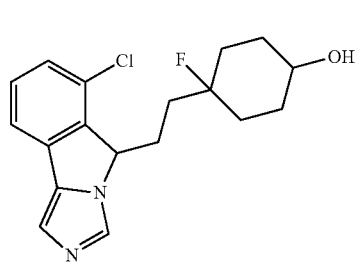
71c
(1 stereoisomer)
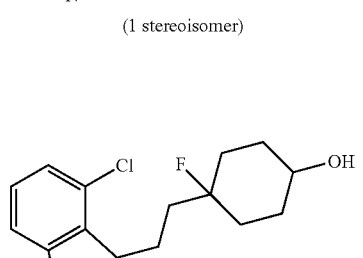
71d
(1 stereoisomer)
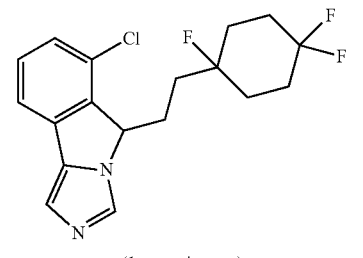
72a
(1 stereoisomer)

TABLE 1-continued
72b
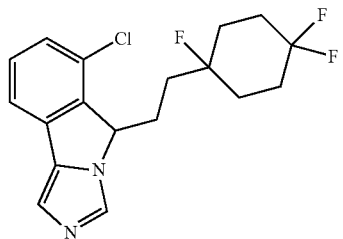
(1 stereoisomer)
73a
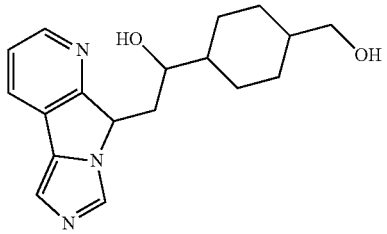
(1 stereoisomer)
73b
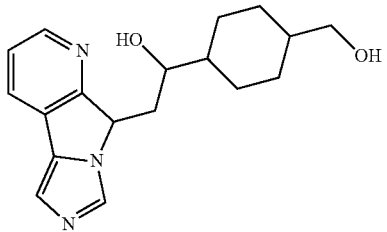
(1 stereoisomer)
73c
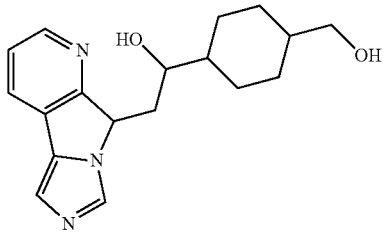
(1 stereoisomer)
73d
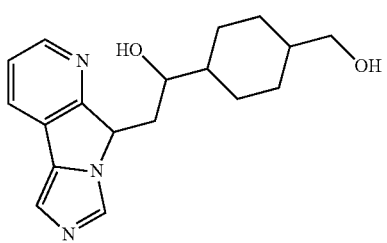
(1 stereoisomer)
TABLE 1-continued
74a
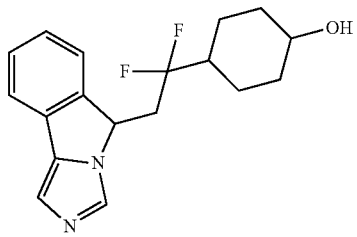
(2 stereoisomers)
74b
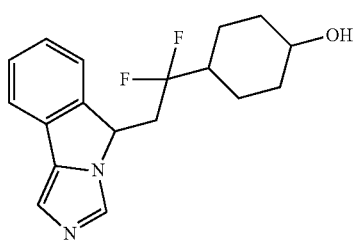
(2 stereoisomers)
75a
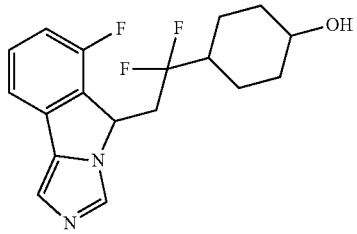
(2 stereoisomers)
75b
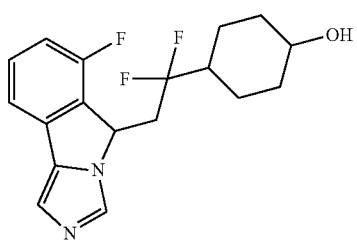
(2 stereoisomers)
76a
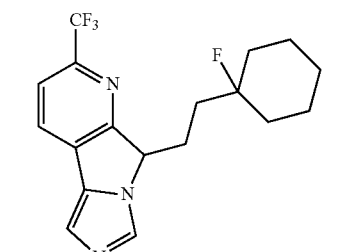
(1 stereoisomer)

TABLE 1-continued
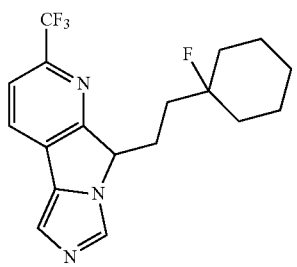
(1 stereoisomer) 76b
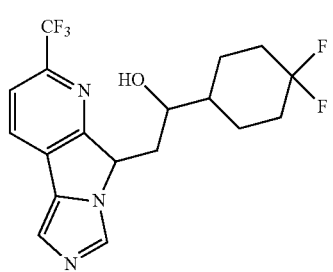
(1 stereoisomer) 77a
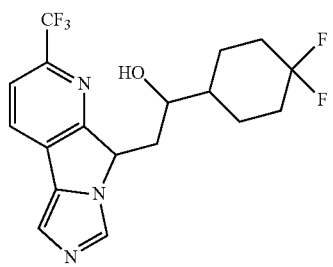
(1 stereoisomer) 77b
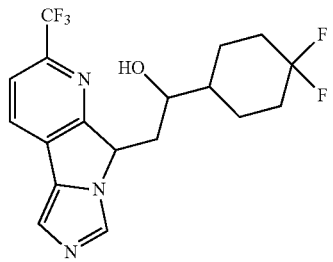
(1 stereoisomer) 77c
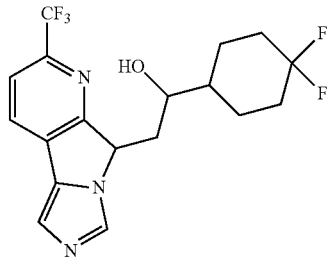
(1 stereoisomer) 77d
TABLE 1-continued
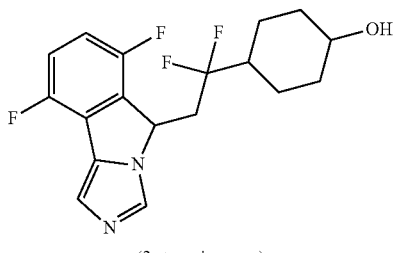
(2 stereoisomers) 78a
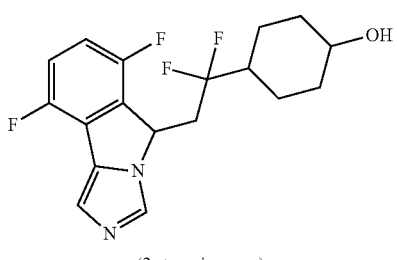
(2 stereoisomers) 78b
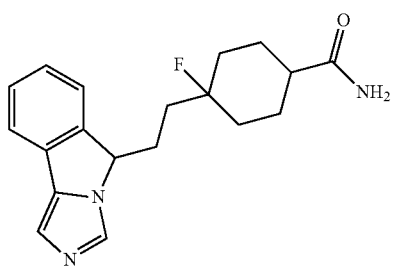
(1 stereoisomer) 79a
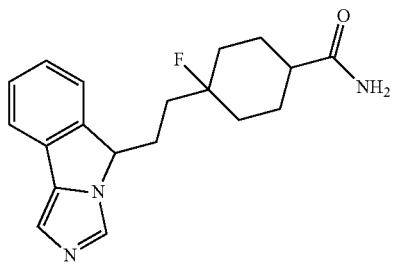
(1 stereoisomer) 79b
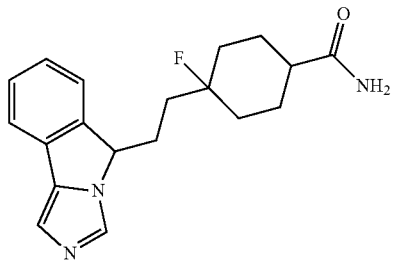
(1 stereoisomer) 79c TABLE 1-continued
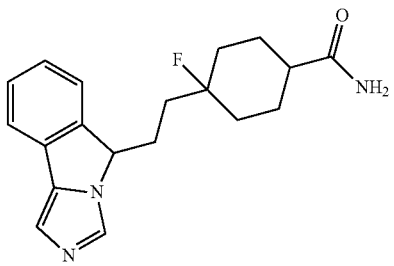
(1 stereoisomer)
79d
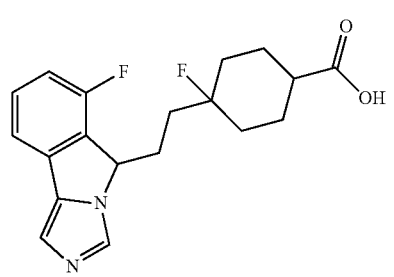
(2 stereoisomers)
80a
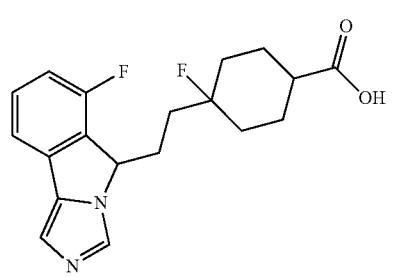
(2 stereoisomers)
80b
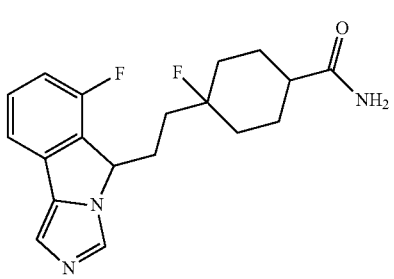
(1 stereoisomer)
81a
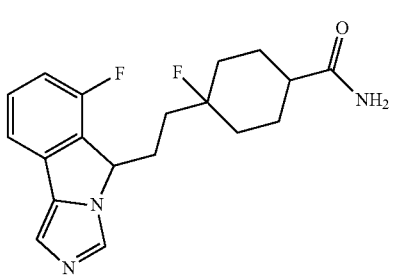
(1 stereoisomer)
81b
TABLE 1-continued
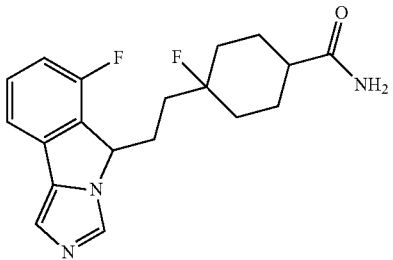
(1 stereoisomer)
81c
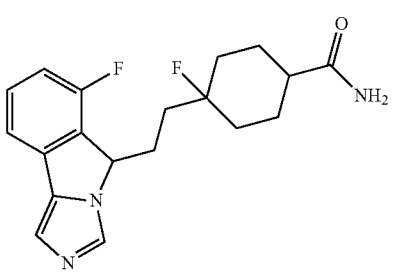
(1 stereoisomer)
81d
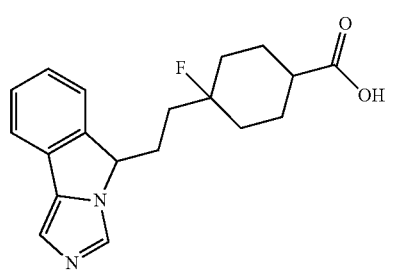
(2 stereoisomers)
82a
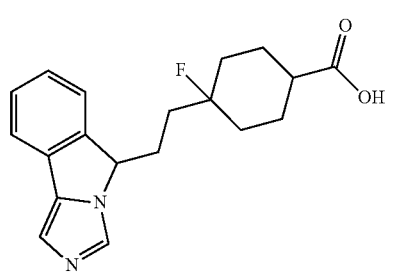
(2 stereoisomers)
82b
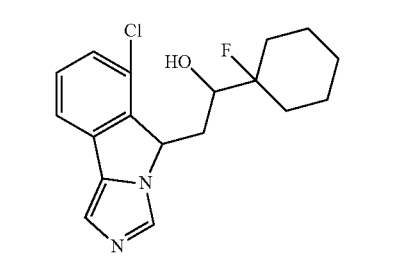
(1 stereoisomer)
83a TABLE 1-continued
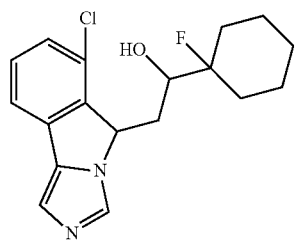
83b
(1 stereoisomer)
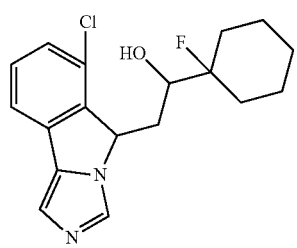
83c
(1 stereoisomer)
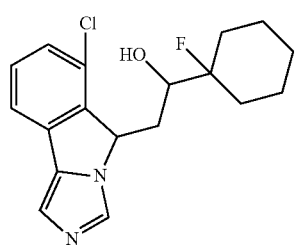
83d
(1 stereoisomer)
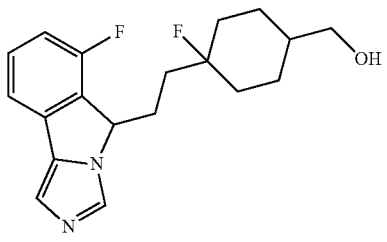
84a
(1 stereoisomer)
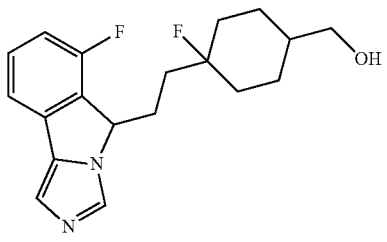
84b
(1 stereoisomer)
TABLE 1-continued
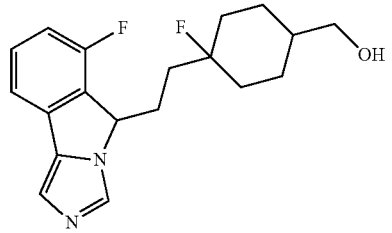
84c
(1 stereoisomer)
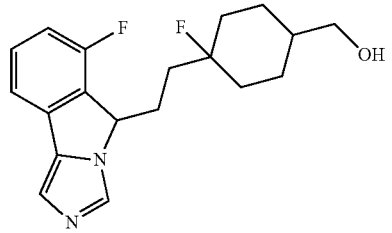
84d
(1 stereoisomer)
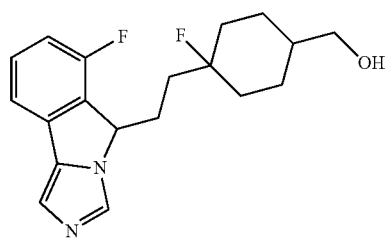
85a
(2 stereoisomers)
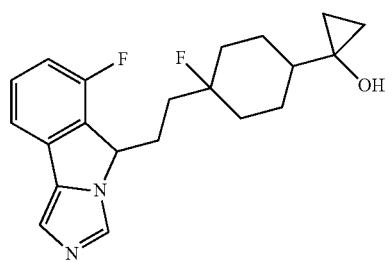
85b
(2 stereoisomers)
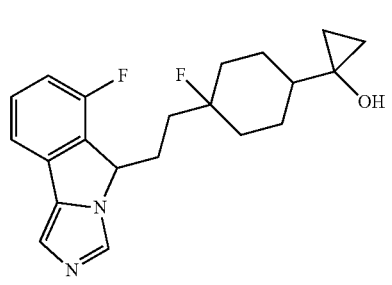
86a
(2 stereoisomers)

TABLE 1-continued
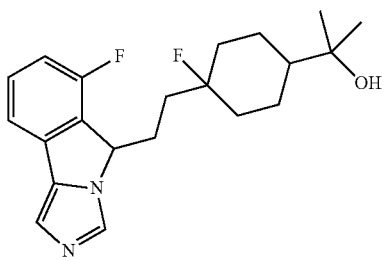
86b
(2 stereoisomers)
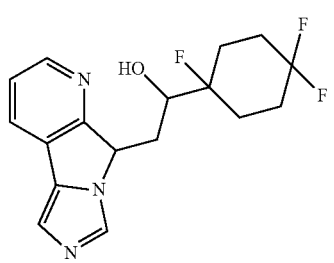
87a
(1 stereoisomer)
87b
(1 stereoisomer)
87c
(1 stereoisomer)
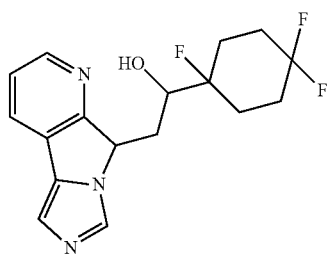
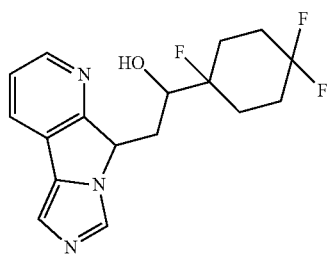
87d
(1 stereoisomer)
TABLE 1-continued
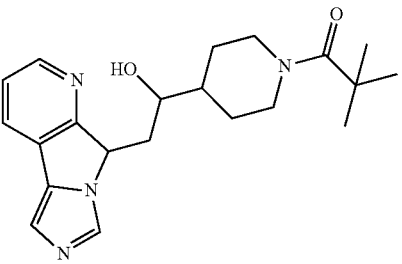
88a
(1 stereoisomer)
88b
(1 stereoisomer)
88c
(1 stereoisomer)
88d
(1 stereoisomer)
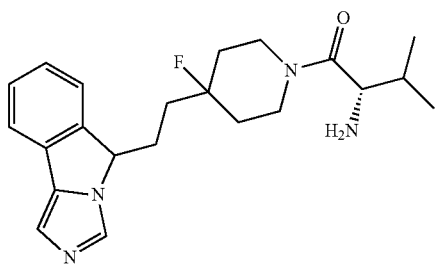
89a
(1 stereoisomer)

TABLE 1-continued
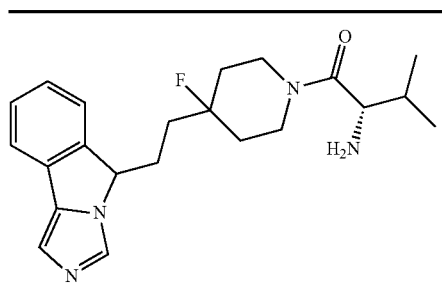
89b
(1 stereoisomer)
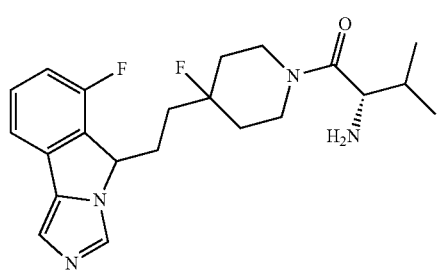
90a
(1 stereoisomer)
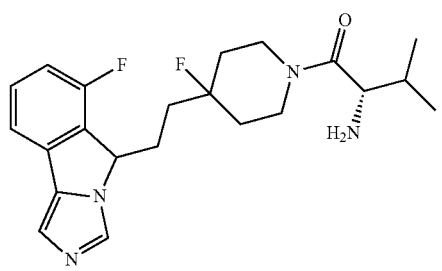
90b
(1 stereoisomer)
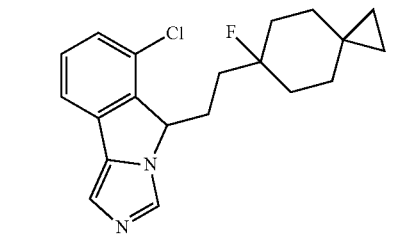
91a
(1 stereoisomer)
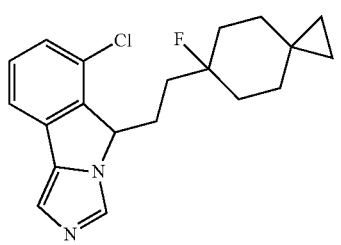
91b
(1 stereoisomer)
TABLE 1-continued
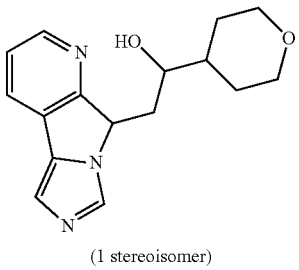 [SMILES: OC(CC1c2ncccc2-c2cncn21)C1CCOCC1]
92a
(1 stereoisomer)
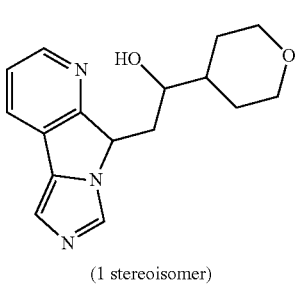 [SMILES: OC(CC1c2ncccc2-c2cncn21)C1CCOCC1]
92b
(1 stereoisomer)
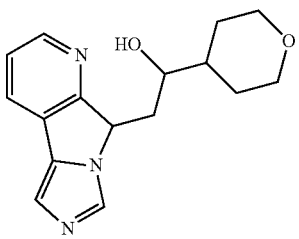
92c
(1 stereoisomer)
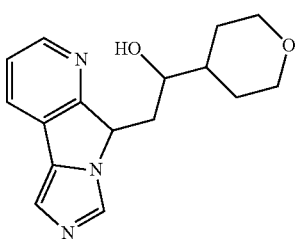
92d
(1 stereoisomer)
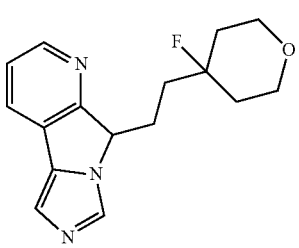
93a
(1 stereoisomer)
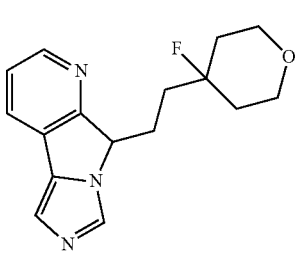
93b
(1 stereoisomer)

TABLE 1-continued
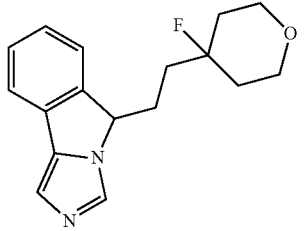
94a
(1 stereoisomer)
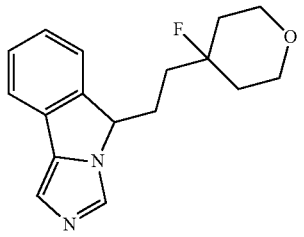
94b
(1 stereoisomer)
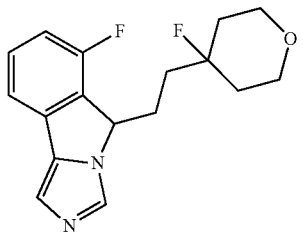
95a
(1 stereoisomer)
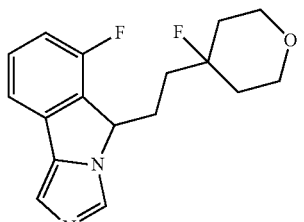
95b
(1 stereoisomer)
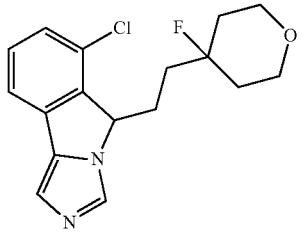
96a
(1 stereoisomer)
TABLE 1-continued
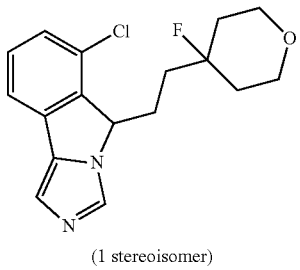 [SMILES: FC1(CCC2c3c(Cl)cccc3-c3cncn32)CCOCC1]
96b
(1 stereoisomer)
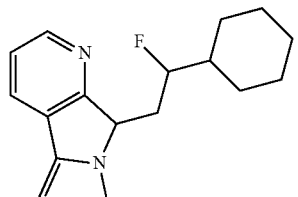
97a
(1 stereoisomer)
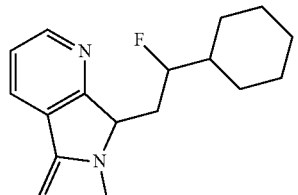
97b
(1 stereoisomer)
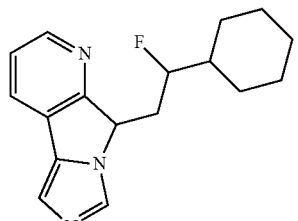
97c
(1 stereoisomer)
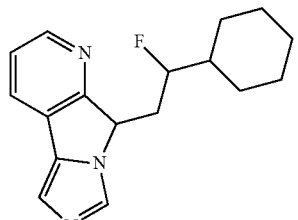
97d
(1 stereoisomer)
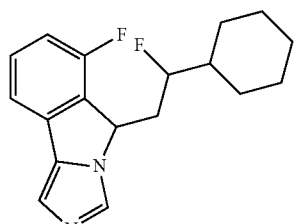
98a
(1 stereoisomer)

TABLE 1-continued
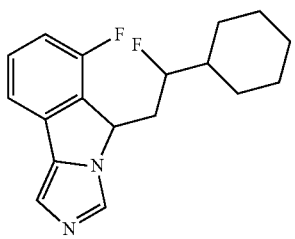
98b
(1 stereoisomer)
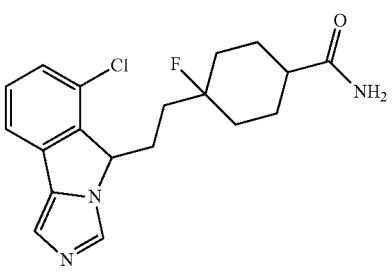
99a
(1 stereoisomer)
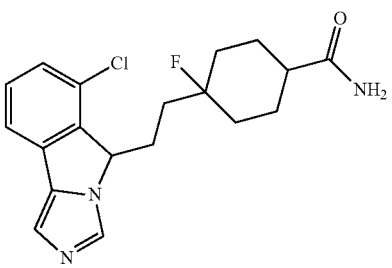
99b
(1 stereoisomer)
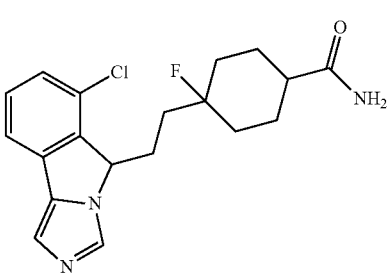
99c
(1 stereoisomer)
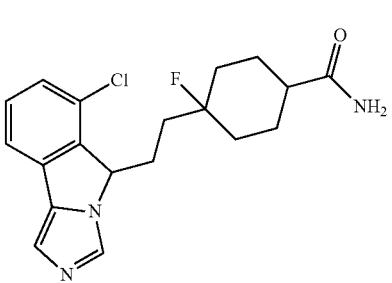
99d
(1 stereoisomer)
TABLE 1-continued
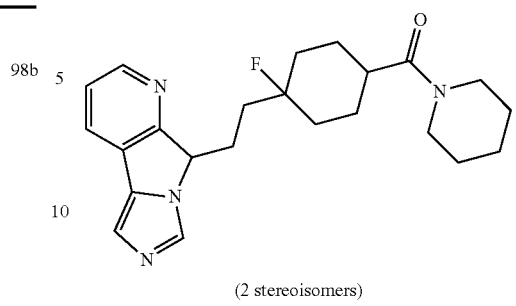
100a
(2 stereoisomers)
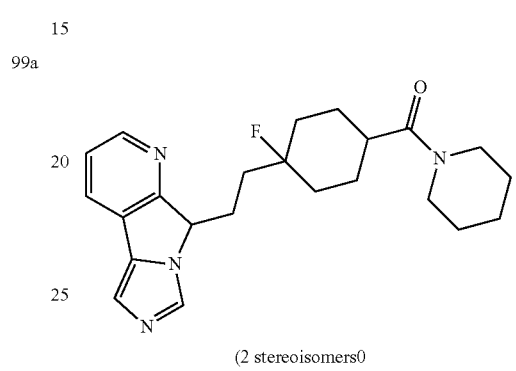
100b
(2 stereoisomers0
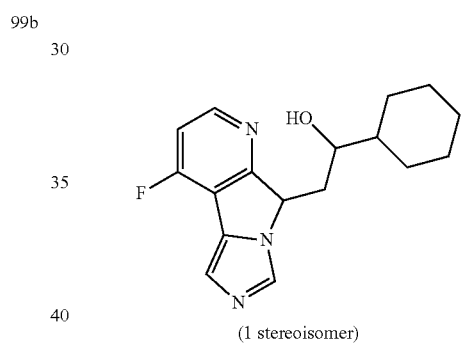
101a
(1 stereoisomer)
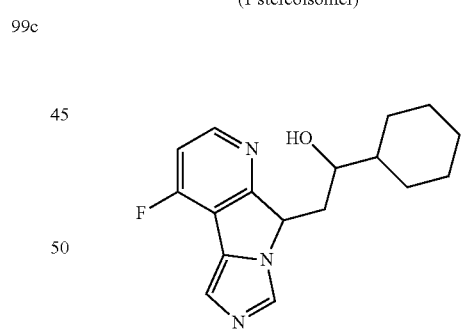
101b
(1 stereoisomer)
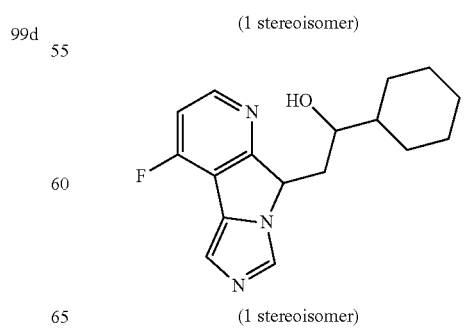
101c
(1 stereoisomer)

TABLE 1-continued
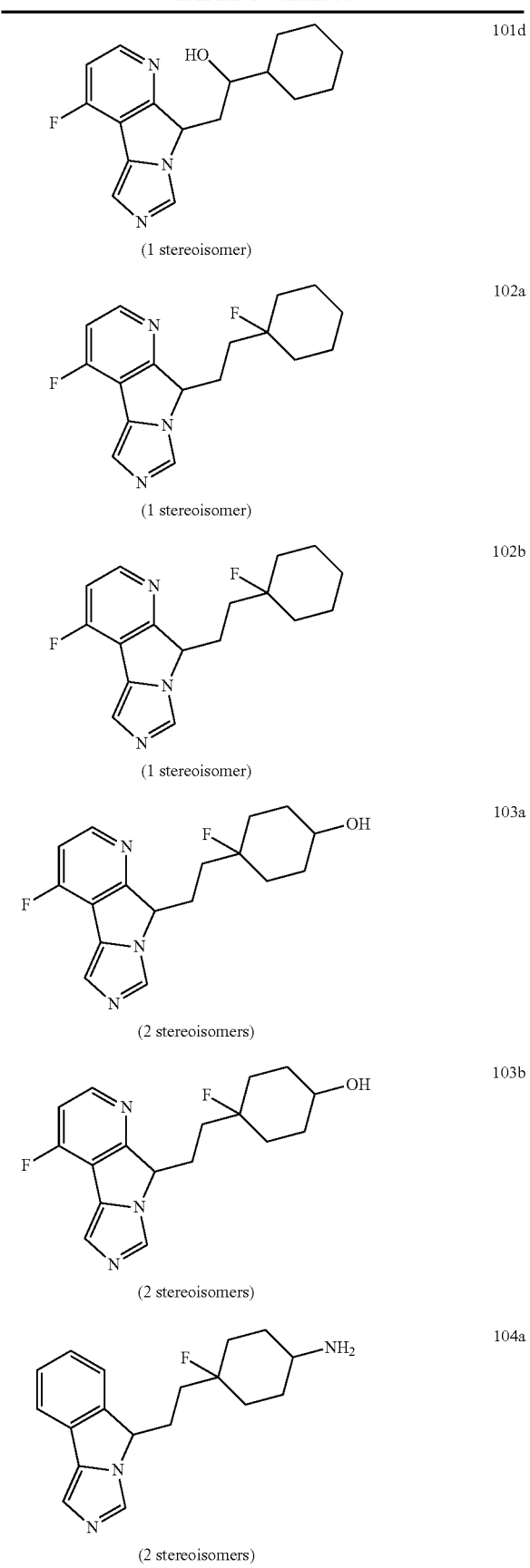
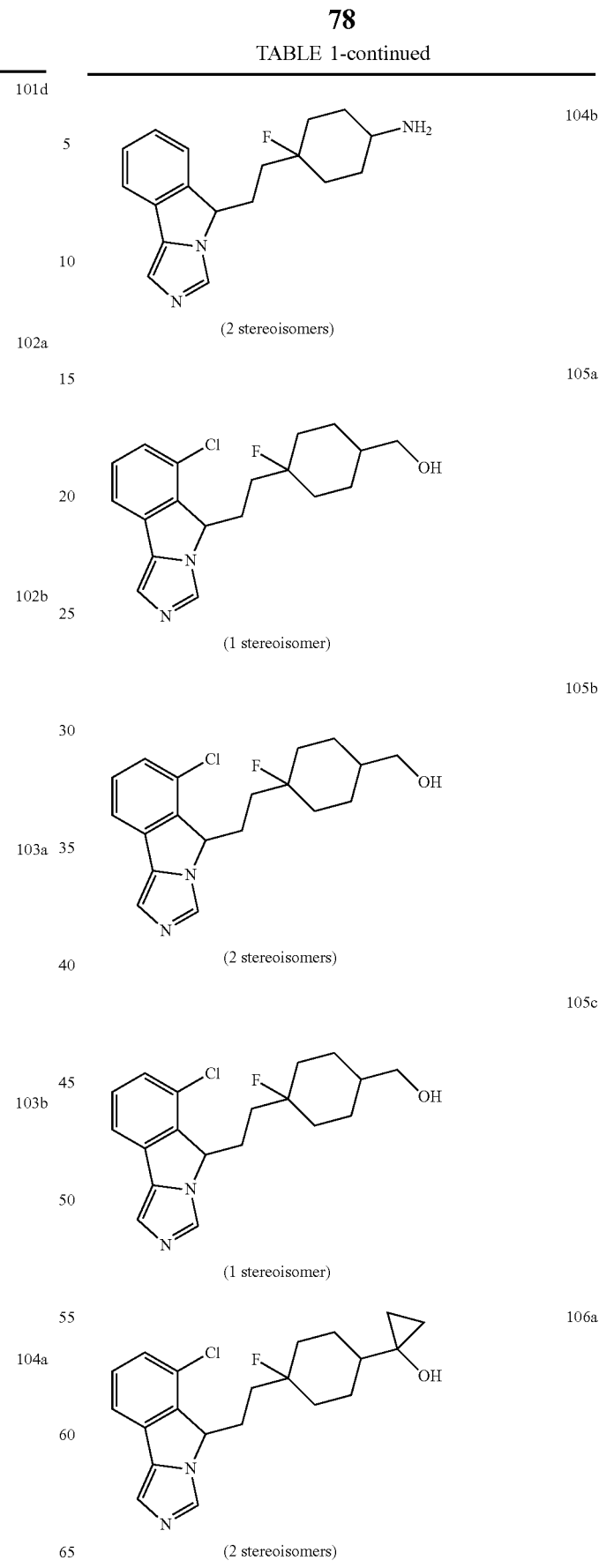

TABLE 1-continued
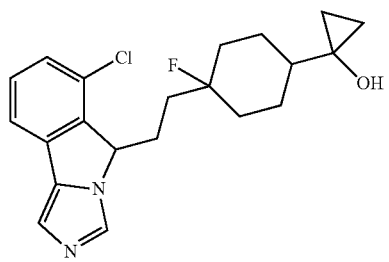
106b
(2 stereoisomers)
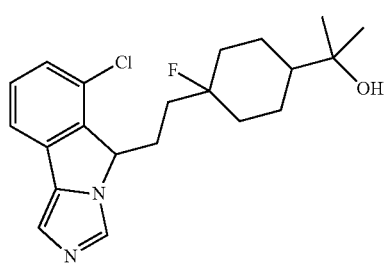
107a
(2 stereoisomers)
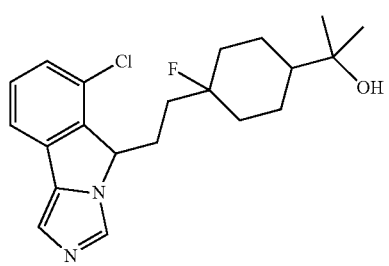
107b
(2 stereoisomers)
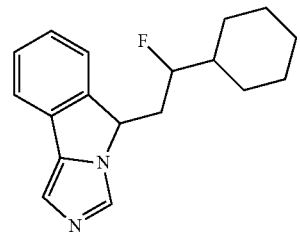
108a
(2 stereoisomers)
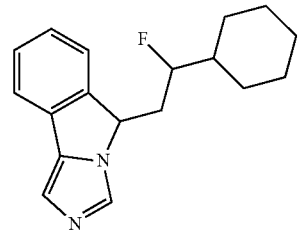
108b
(2 stereoisomers)
TABLE 1-continued
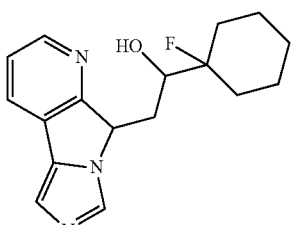
109a
(1 stereoisomer)
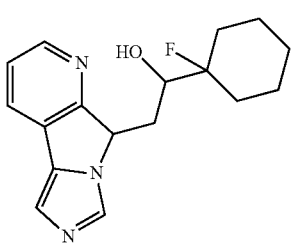
109b
(2 stereoisomers)
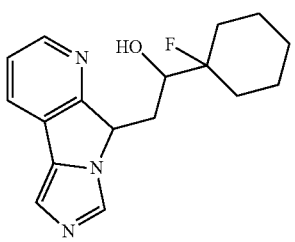
109c
(1 stereoisomer)
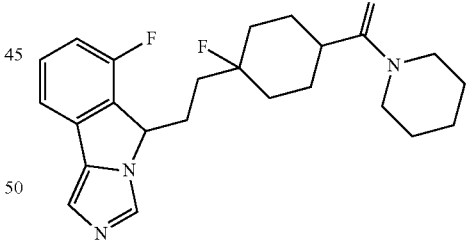
110a
(2 stereoisomers)
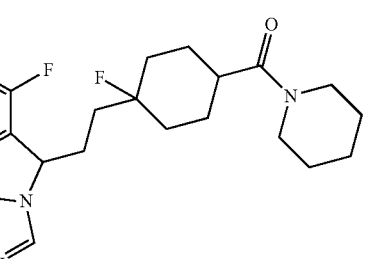
110b
(2 stereoisomers)

TABLE 1-continued
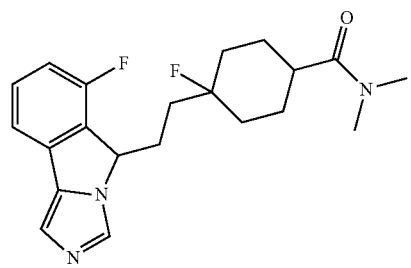
111a
(2 stereoisomers)
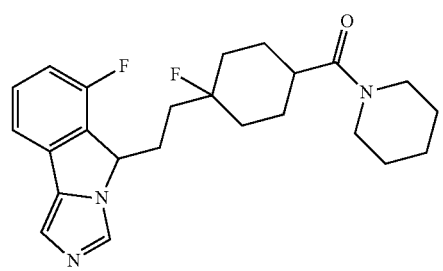
111b
(2 stereoisomers)
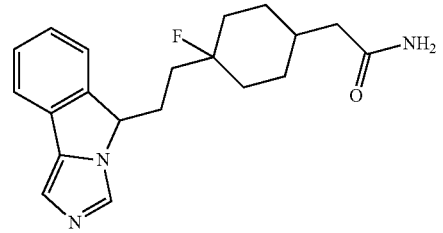
112a
(1 stereoisomer)
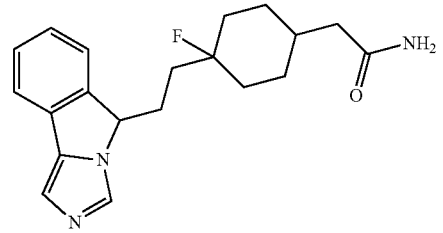
112b
(1 stereoisomer)
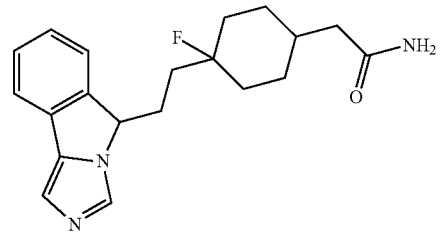
112c
(1 stereoisomer)
TABLE 1-continued
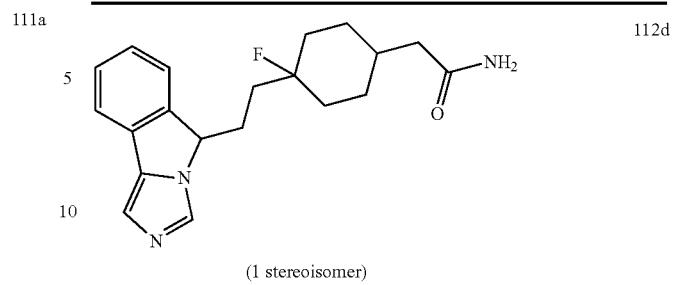
112d
(1 stereoisomer)
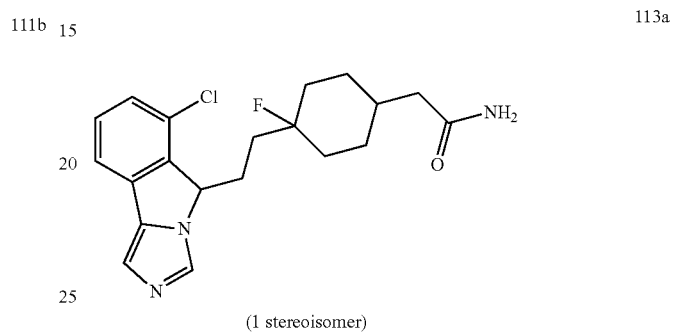
113a
(1 stereoisomer)
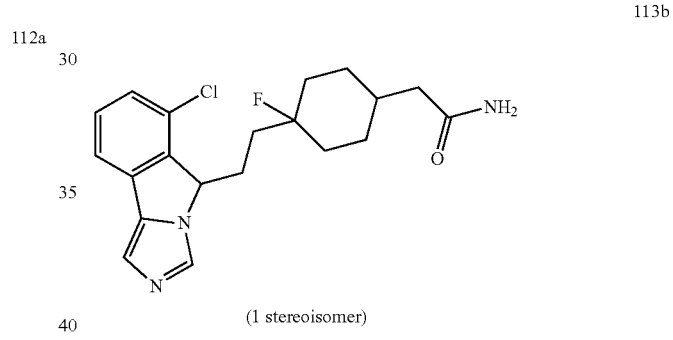
113b
(1 stereoisomer)
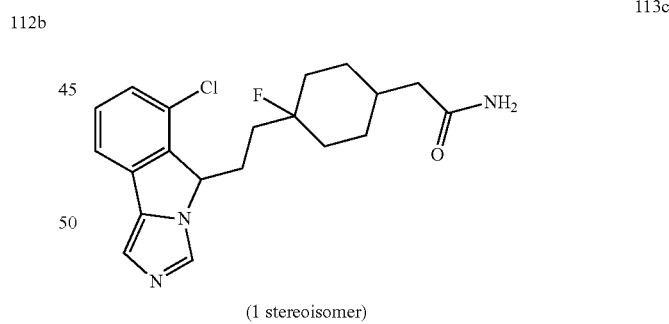
113c
(1 stereoisomer)
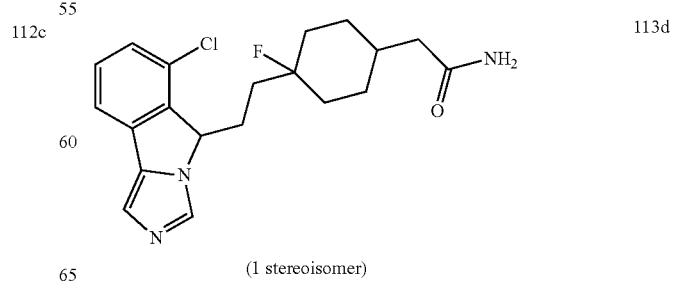
113d
(1 stereoisomer)

TABLE 1-continued
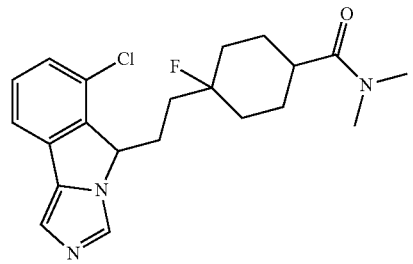
114a
(1 stereoisomer)
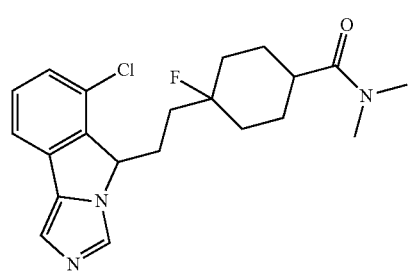
114b
(1 stereoisomer)
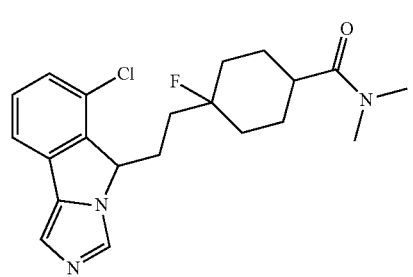
114c
(1 stereoisomer)
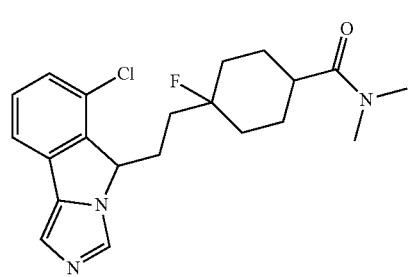
114d
(1 stereoisomer)
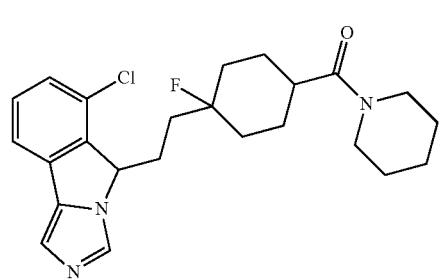
115a
(1 stereoisomer)
TABLE 1-continued
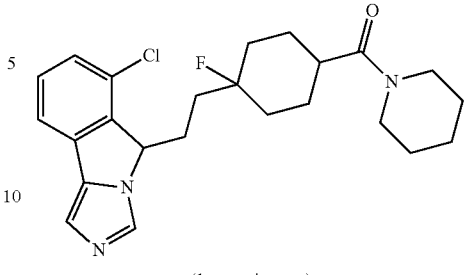
115b
(1 stereoisomer)
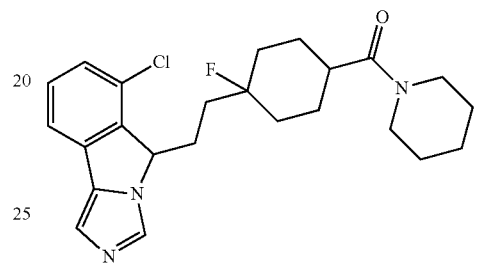
115c
(1 stereoisomer)
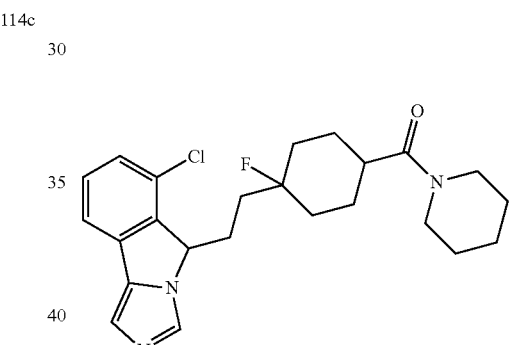
115d
(1 stereoisomer)
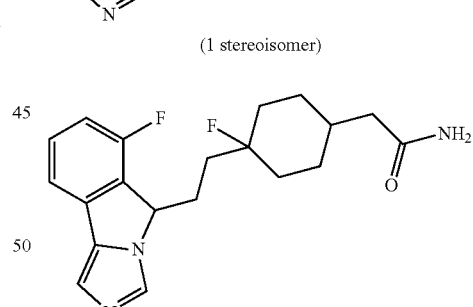
116a
(1 stereoisomer)
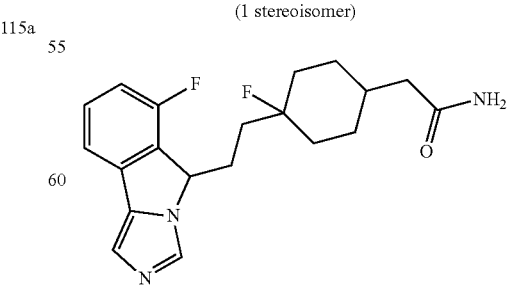
116b
(1 stereoisomer)

TABLE 1-continued
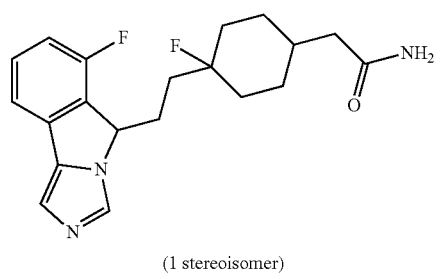 [SMILES: NC(=O)CC1CCC(F)(CCC2c3c(F)cccc3-c3cncn32)CC1]
116c
(1 stereoisomer)
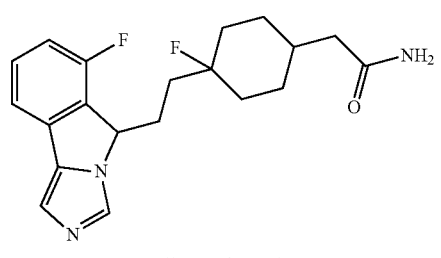
116d
(1 stereoisomer)
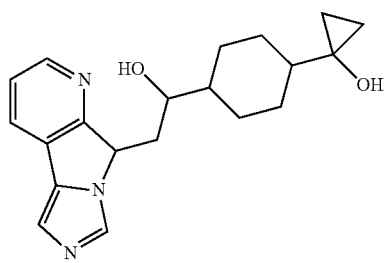
117a
(1 stereoisomer)
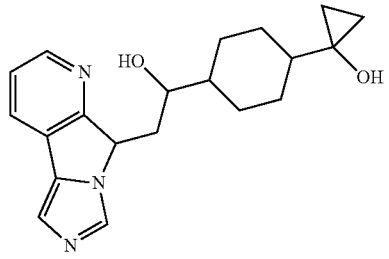
117b
(1 stereoisomer)
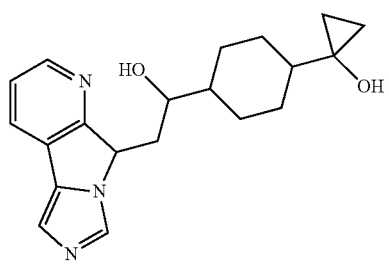
117c
(1 stereoisomer)
TABLE 1-continued
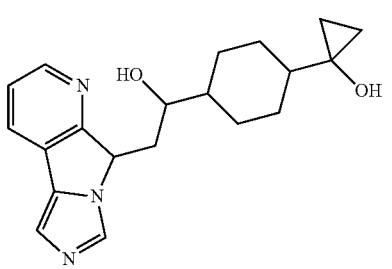
117d
(1 stereoisomer)
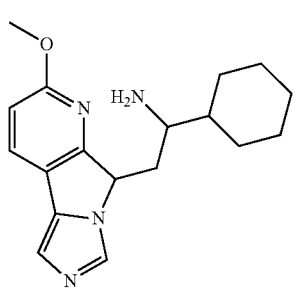
118a
(2 stereoisomers)
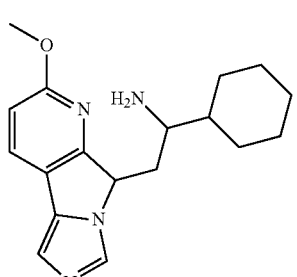
118b
(1 stereoisomer)
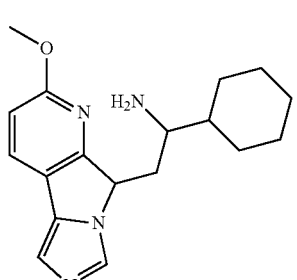
118c
(1 stereoisomer)
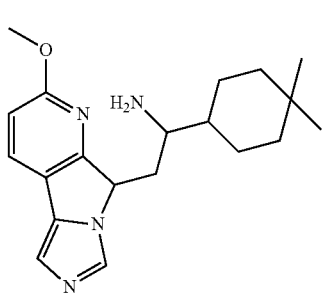
119a
(1 stereoisomer)

US 10,329,297 B2
TABLE 1-continued
TABLE 1-continued
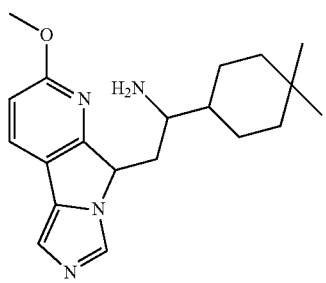
119b
(1 stereoisomer)
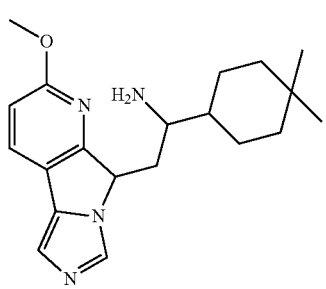
119c
(1 stereoisomer)
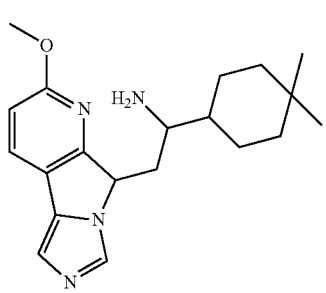
119d
(1 stereoisomer)
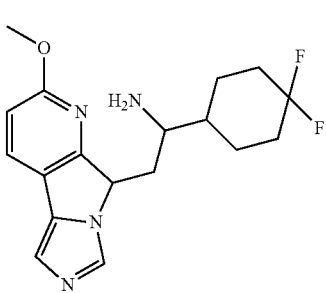
120a
(1 stereoisomer)
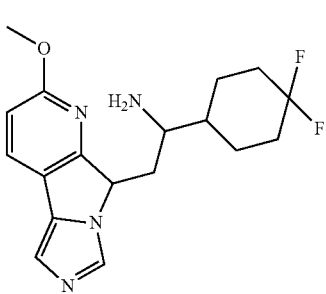
120b
(1 stereoisomer)
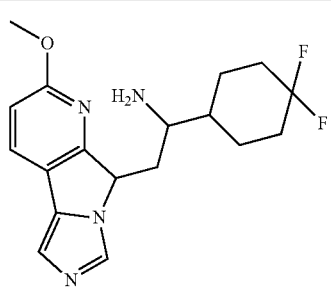
120c
(1 stereoisomer)
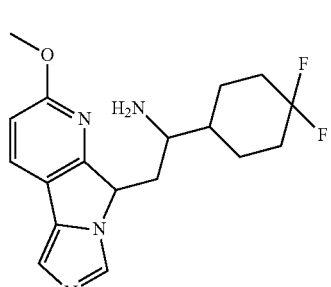
120d
(1 stereoisomer)
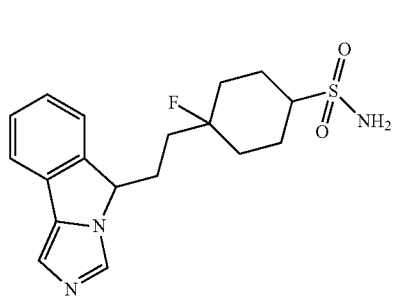
121a
(1 stereoisomer)
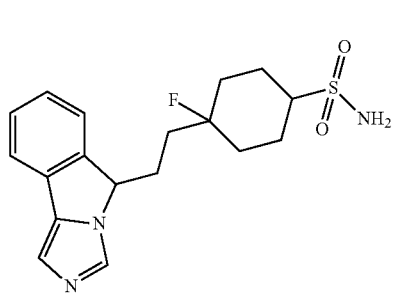
121b
(1 stereoisomer)
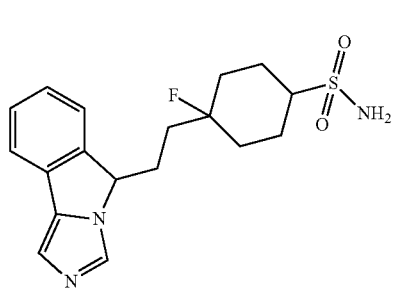
121c
(1 stereoisomer)

TABLE 1-continued

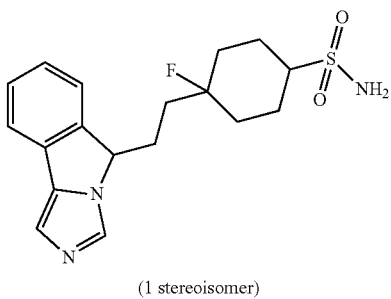 [SMILES: NS(=O)(=O)C1CCC(F)(CCC2c3ccccc3-c3cncn32)CC1]

121d (1 stereoisomer)

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

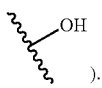
).

In certain embodiments, the compounds of the invention were synthesized in accordance with Schemes below. More specific examples of compounds made utilizing the Schemes are provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate IDO in a biological sample or in a patient. In certain embodiments, the amount of compound in compositions of this invention is such that is effective to measurably modulate IDO in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this aremineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for antagonizing IDO in a positive manner in a patient or in a biological sample comprising the step of administering to said patient or contacting said biological sample with a compound according to the invention.

In certain embodiments, the invention is directed to the use of compounds of the invention and/or physiologically acceptable salts thereof, for antagonizing IDO. The compounds are characterized by such a high affinity to IDO, which ensures a reliable binding and preferably antagonization of IDO. In certain embodiments, the substances are mono-specific in order to guarantee an exclusive and directed recognition with the single IDO target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In certain embodiments, the present invention relates to a method for antagonizing IDO with at least one compound of formula (I) according to the invention and/or physiologically acceptable salts thereof, under conditions such that said IDO receptor is antagonized. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for antagonizing IDO is performed in-vitro. The prior teaching of the present specification concerning the compounds of formula (I), including any embodiments thereof, is valid and applicable without restrictions to the compounds according to formula (I) and their salts when used in the method for antagonizing IDO. The prior teaching of the present specification concerning the compounds of formula (I), including any embodiments thereof, is valid and applicable without restrictions to the compounds according to formula (I) and their salts when used in the method for antagonizing IDO.

In certain embodiments, the compounds according to the invention exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect.

In certain embodiments, the invention provides a method for preventing, treating or ameliorating in a subject a disease, disorder, or condition that is causally related to the aberrant activity of IDO receptor, which comprises administering to the subject a therapeutically effective amount of a compound of any formulae herein, or a pharmaceutically acceptable salt thereof. In certain embodiments, the disease or disorder is an autoimmune, inflammatory or cardiovascular disease or disorder.

One aspect of this invention provides compounds or compositions that are inhibitors of indoleamine 2,3-dioxygenase (IDO), or pharmaceutically acceptable salts thereof, and thus are useful for treating or lessening the severity of a disease, condition, or disorder in a patient, wherein IDO is implicated in the disease, condition, or disorder. The terms, "disease", "disorder", and "condition" may be used interchangeably here to refer to an IDO mediated medical or pathological condition. The term "IDO mediated condition", as used herein, means any disease state or other deleterious condition in which IDO is known to play a role. The term "IDO mediated condition" or "disease" also means those diseases or conditions that are alleviated by treatment with an IDO inhibitor. Such conditions include cancer and sepsis. As used herein, the terms "subject" and "patient" are used interchangeably. The terms "subject" and "patient" refer to an animal, and more specifically a human. In one embodiment, the subject is a non-human animal such as a rat or dog. In a preferred embodiment, the subject is a human.

In one aspect, the present invention provides a method for treating or lessening the severity of a disease, condition, or disorder where IDO is implicated in the disease state. In another aspect, the present invention provides a method for treating or lessening the severity of an IDO mediated disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to IDO. Another aspect provides a method for treating or lessening the severity of an IDO mediated disease, condition, or disorder by inhibiting enzymatic activity of IDO with an IDO inhibitor.

In certain embodiments, the present invention provides a method for inhibiting IDO activity in a patient comprising administering to the patient a compound or composition of the present invention. In another embodiment, the present invention provides a method for inhibiting IDO activity in a biological sample comprising administering a compound or composition of the present invention.

In certain embodiments, the method is used to treat or prevent a condition selected from a proliferative or hyperproliferative disease, e.g., cancer. In another embodiment, the method is used to treat or prevent sepsis.

In certain embodiments the invention provides a method of treating, preventing, or lessening the severity of a disease or condition of a patient selected from cancer, proliferative disorder, viral disease, sepsis, pneumonia, bacteremia, trauma, tuberculosis, parasitic disease, neuroinflammation, schizophrenia, depression, neurodegenerative disease, and pain, by administering a compound or composition of the present invention.

In certain embodiments, the invention provides compounds that are useful for the treatment of diseases, disorders, and conditions, e.g, viral disease, pneumonia, bacteremia, trauma, tuberculosis, parasitic disease, neuroinflammation, schizophrenia, depression, neurodegenerative disease, and pain.

In certain embodiments, the neurodegenerative disease is selected from Alzheimer's disease, Parkinson's disease, Amyotrophic Lateral Sclerosis (ALS), Dementia, Multiple Sclerosis, and Huntington's disease.

In certain embodiments, the viral disease is selected from Human Immunodeficiency Virus (HIV), Hepatitis A-D, Human Papilloma Virus (HPV), and Herpes, including Herpes Simplex I and II, as well as the Epstein Barr Virus.

In certain embodiments, the disorder is sepsis.

In certain embodiments, the invention provides for the treatment of diseases, disorders, and conditions characterized by excessive or abnormal cell proliferation. Such diseases include a proliferative or hyperproliferative disease. Examples of proliferative and hyperproliferative diseases include cancer and myeloproliferative disorders.

In certain embodiments, the term "cancer" includes, but is not limited to the following cancers. Oral: head and neck, including buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: Non-small cell lung carcinoma including adenocarcinoma (acinar, bronchioloalveolar carcinoma [nonmucinous, mucinous, mixed], papillary, solid adenocarcionoma, clear cell, mucinous [colloid] adenocarcinoma, mucinous cystadenocarcinoma, signet ring, well-differentiated fetal), bronchioalveolar, squamous cell carcinoma (basaloid, clear cell, papillary, small cell), large cell (undifferentiated) carcinoma (giant cell, basaloid, clear cell, large cell [with rhabdoid phenotype], large cell neuroendocrine carcinoma [LCNEC], combined LCNEC); small cell lung cancer including small cell (oat cell) carcinoma, combined small cell; adenoid cystic carcinoma; hamartoma; lymphoma; neuroendocrine/carcinoid; sarcoma. Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Female/Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from head and neck, ovarian, melanoma cervical, endometrial, esophageal, or breast cancer.

In certain embodiments, the term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Combination Therapies

As used herein, the term "in combination" or "co-administration" can be used interchangeably to refer to the use of more than one therapy (e.g., one or more therapeutic agents). The use of the term does not restrict the order in which therapies (e.g., therapeutic agents) are administered to a subject.

In certain embodiments, the invention provides a method treatment, as described above, further comprising an additional step of administering to said patient an additional therapeutic agent selected from a chemotherapeutic or antiproliferative agent, an anti-inflammatory agent, an immunomodulatory or immunosuppressive agent, a neurotrophic factor, an agent for treating cardiovascular disease, an agent for treating destructive bone disorders, an anti-viral agent, an agent for treating blood disorders, or an agent for treating immunodeficiency disorders, wherein said additional therapeutic agent is appropriate for the disease being treated.

In certain embodiments, the additional therapeutic agent is administered together with the compound/composition of formula I as a single dosage form. In certain embodiments, the additional therapeutic agent is administered separately from the compound/composition of formula I as part of a multiple dosage form.

In certain embodiments, the invention is directed towards a method of treating cancer in a subject in need thereof, comprising administration of a compound/composition of formula I or a pharmaceutically acceptable salt thereof, and an additional therapeutic agent. In certain embodiments, the additional therapeutic agent is administered together with the compound/composition of formula I as a single dosage form. In certain embodiments, the additional therapeutic agent is administered separately from the compound/composition of formula I as part of a multiple dosage form.

In certain embodiments, the additional therapeutic agent is an anti-cancer agent, an anti-proliferative agent, or a chemotherapeutic agent.

In certain embodiments, the additional therapeutic agent is selected from cisplatin (Platino®), carboplatin (Paraplatin®), oxaliplatin (Eloxatin®), daunomycin (Daunorubicin®, DanuoXome®, Cerubidine®), doxorubicin (Adriamycin®, Rubex®), epirubicin (Ellence®), idarubicin (Idamycin®), valrubicin (Valstar®), mitoxantrone (Novantrone®), paclitaxel (Taxol®), docetaxel (Taxotere®) and cyclophosphamide (Cytoxan®).

In other embodiments, the additional therapeutic agent is selected from anti-cancer antibody or immunoglobulin therapies or agents including, but not limited to, ipilimumab (Yervoy®), tremelimumab, antibodies or agents that target programmed death receptor 1 [PD-1] or programmed death ligand 1 [PD-L1], e.g., CT-011 (Curetech), BMS-936558 (Bristol-Myers Squibb), BMS-936559 (Bristol-Myers Squibb), AMP-224 (Amplimmune/Glaxo-Smithkline), pembrolizumab (Merck & Co.), MPDL3280A (Roche), MGA-271 (Macrogenics), dacarbazine, Lambrolizumab (MK-3475), MSB0010718C (MerckSerono), or MEDI-4736 (MedImmune).

In other embodiments, the additional therapeutic agent is selected from a CTLA4 agent (e.g., ipilimumab (BMS)); GITR agent (e.g., MK-4166 (MSD)); vaccines (e.g., Nanovacc (MerckSerono), Stimuvax (MerckSerono), Sipuleucel-T (Dendron); or a SOC agent (e.g., radiation, docetaxel, Temozolomide (MSD), Gemcitibine, or Paclitaxel). In other embodiments, the additional therapeutic agent is an immune enhancer such as a vaccine, immune-stimulating antibody, immunoglobulin, agent or adjuvant including, but not limited to, sipuleucel-t (Provenge®), BMS-663513 (Bristol-Myers Squibb), CP-870893 (Pfizer/VLST), anti-OX40 (AgonOX), or CDX-1127 (CellDex).

In certain embodiments, the additional therapeutic agent is an anti-PD-1 or anti-PD-L1 agent and is administered together with the compound/composition of formula I as a single dosage form. In certain embodiments, the additional therapeutic agent is an anti-PD-1 or anti-PD-L1 agent and is administered separately from the compound/composition of formula I as part of a multiple dosage form. In certain embodiments, the anti-PD-1 or anti-PD-L1 is administered as an intravenous infusion.

In certain embodiments, more than one additional therapeutic agents are used and are administered together with the compound/composition of formula I as a single dosage form. In certain embodiments, more than one additional therapeutic agents are used and are administered separately from the compound/composition of formula I as part of a multiple dosage form. In certain embodiments, the more than one additional therapeutic agents are anti-PD-1 or anti-PD-L1 agents. In certain embodiments, the anti-PD-1 or anti-PD-L1 agents are administered as an intravenous infusion.

Other cancer therapies or anticancer agents that may be used in combination with the inventive agents of the present invention include surgery, radiotherapy (e.g., gamma-radiation, neutron beam radiotherapy, electron beam radiotherapy, proton therapy, brachytherapy, low-dose radiotherapy, and systemic radioactive isotopes), immune response modifiers such as chemokine receptor antagonists, chemokines and cytokines (e.g., interferons, interleukins, tumour necrosis factor (TNF), and GM-CSF)), hyperthermia and cryotherapy, agents to attenuate any adverse effects (e.g. antimetics, steroids, anti-inflammatory agents), and other approved chemotherapeutic drugs.

A compound of the instant invention may also be useful for treating cancer in combination with or in addition to any of the following standard of care (SOC) therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In certain embodiments, the additional therapeutic agent is selected from an antibiotic, a vasopressor, a steroid, an inotrope, an anti-thrombotic agent, a sedative, opioids, or an anesthetic.

In certain embodiments, the additional therapeutic agent is selected from cephalosporins, macrolides, penams, beta-lactamase inhibitors, aminoglycoside antibiotics, fluoroquinolone antibiotics, glycopeptide antibiotics, penems, monobactams, carbapenmems, nitroimidazole antibiotics, lincosamide antibiotics, vasopressors, positive inotropic agents, steroids, benzodiazepines, phenol, alpha2-adrenergic receptor agonists, GABA-A receptor modulators, anti-thrombotic agents, anesthetics, or opiods.

In certain embodiments, the additional therapeutic agent is Alatrofloxacin, Amifloxacin, Balofloxacin, Besifloxacin, Ciprofloxacin, Clinafloxacin, Danofloxacin, Delafloxacin, Difloxacin, Enoxacin, Enrofloxacin, Fleroxacin, Garenoxacin, Gatifloxacin, Gemifloxacin, Grepafloxacin, Levofloxacin, Lomefloxacin, Marbofloxacin, Moxifloxacin, Nadifloxacin, Norfloxacin, Ofloxacin, Orbifloxacin, Pazufloxacin, Pefloxacin, Prulifloxacin, Rufloxacin, Sitafloxacin, Sparfloxacin, Temafloxacin, Tosufloxacin, Trovafloxacin, Vancomycin, Teicoplanin, Telavancin, Bleomycin, Ramoplanin, Decaplanin, Azanidazole, Dimetridazole, Metronidazole, Nimorazole, Ornidazole, Propenidazole, Secnidazole, Tinidazole, Linomycin, Clindamycin, Cefazolin, Cefacetril(e), Cefadroxil, Cefalexin, Cefaloglycin, Cefalonium, Cefaloridin(e), Cefaoltin, Cefapirin, Cefatrizin(e), Cefazedon(e), Cefazaflur, Cefradin(e), Cefroxadin(e), Ceftezol(e), Cefaclor, Cefamandole, Cefminox, Cefonicid, Ceforanide, Cefotiam, Cefprozil, Cefbuperazone, Cefuroxime, Cefuzonam, Cephamycin (Cefoxitin, Cefotetan, Cefmetazole), Carbacephem (Loracarbef), Cefixime, Ceftriaxome, Ceftazidime, Cefoperazone, Cefcapene, Cefdaloxime, Cefdinir, Cefditoren, Cafatamet, Cefmenoxime, Cefodizime, Cefotaxime, Cefpimizole, Cefpiramide, Cefpodoxime, Cefsulodin, Cefteram, Cefrtibuten, Ceftiolene, Ceftizoxime, Oxacephem, Cefepime, Cefozopran, Cefpirome, Cefquinome, Ceftobiprole, Ceftaroline fosamil, Amoxicillin, Ampicillin, Epicillin, Carbenicillin, e.g., Carindacillin, Ticarcillin, Temocillin, Azlocillin, Piperacillin, Mezlocillin, Mecillinam, Sulbenicillin, Benzylpenicillin, Clometocillin, Benzathine benylpenecillin, Procaine benylpenecillin, Azidocillin, Penamecillin, Phenoxymethylpenecillin, Propicillin, Benzathine phenoxymthylpenecillin, Pheneticillin, Cloxacillin, Oxacillin, Meticillin, Nafcillin, Faropenem, Aztreonam, Tigemonam, Carumonam, Nocardicin A, Biapenem, Ertapenem, Antipseudomonal, Panipenem, Penam, Clavam, Azithromycin, Clarithromycin, Dirithromycin, Erythromycin, Kitasamycin, Midecamycin, Roxithromycin, Troleandomycin, Ansamycin, Carbomycin, Cethromycin, Oleandomycin, Solithromycin, Spiramycin, Telithromycin, Tylosin, Amikacin, Arbekcacin, Gentamicin, Kanamycin, Neomycin, Netilmicin, Paromycin, Rhodostreptomycin, Streptomycin, Tobramycin, Apramycin, Norepinephrine, Epinephrine, Phenylepinephrine, Dopamine, Vasopressin, Berberine, Calcium, Omecamtiv, Dobutamine, Dopexamine, Isoprenaline, Phenylepinephrine, Dogoxin, Prostaglandins, Enoximone, Milrinone, Amrinone, Theophylline, Digitalis, Glucagon, Hydrocortisone, Cortisone, Fluorocortisone, Heparin, Diazepam, Lorazepam, Midazolam, Propofol, Dexmedetomidine, Etomidate, Fentanyl, Hydromorphone, Morphine, Meperidine, Remifentanil, or Ketamine.

In other embodiments, the invention provides compounds of the invention for use as a pharmaceutical especially in the treatment or prevention of the aforementioned conditions and diseases. Also provided herein is the use of the present compounds in the manufacture of a medicament for the treatment or prevention of one of the aforementioned conditions and diseases. The present invention also provides the use of a compound of the invention or a pharmaceutically acceptable salt thereof for the manufacture of a medicament for the treatment of conditions or diseases selected from IDO receptor mediated conditions or diseases.

When used to prevent the onset of an IDO related disease/disorder, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to antagonize IDO activity, usually between about one hour and one week. In-vitro treatment can be carried out using cultivated cells from a biopsy sample or cell line.

The host or subject can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, suitable models or model systems have been developed, for example cell culture models and models of transgenic animals. For the determination of certain stages in the signal transduction cascade, interacting compounds can be utilized in order to modulate the signal. The compounds according to the invention can also be used as reagents for testing IDO-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. In certain embodiments, the in-vitro use is preferably applied to samples of humans suffering from IDO-related disorders. Testing of several specific compounds and/or derivatives thereof makes the selection of that active ingredient possible that is best suited for the treatment of the human subject. The in-vivo dose rate of the chosen derivative is advantageously pre-adjusted to the IDO susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the antagonism of IDO activity if expedient.

The invention also relates to the use of compounds according to formula (I) and/or physiologically acceptable salts thereof for the prophylactic or therapeutic treatment and/or monitoring of diseases that are caused, mediated and/or propagated by IDO activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by IDO activity. In certain embodiments, the invention provides the use of a compound according to formula I or physiologically acceptable salts thereof, for the production of a medicament for the prophylactic or therapeutic treatment of an IDO-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The methods of the invention can also be used to reducing the likelihood of developing a disorder or even prevent the initiation of disorders associated with IDO activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously passed disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with IDO activity, in such a way that a pathogenic modification of their overall condition or of the condition of particular regions of the organism could establish at least temporarily.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be utilized as commercial research reagents for various medical research and diagnostic uses. Such uses can include but are not limited to: use as a calibration standard for quantifying the activities of candidate IDO antagonists in a variety of functional assays; use as blocking reagents in random compound screening, i.e. in looking for new families of IDO receptor ligands, the compounds can be used to block recovery of the presently claimed IDO compounds; use in the co-crystallization with IDO receptor, i.e. the compounds of the present invention will allow formation of crystals of the compound bound to IDO, enabling the determination of receptor/compound structure by x-ray crystallography; other research and diagnostic applications, etc.; use in assays as probes for determining the expression of IDO on the surface of cells; and developing assays for detecting compounds which bind to the same site as the IDO binding ligands.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Antagonism of IDO activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth supra.
General Conditions and Analytical Methods All solvents used were commercially available and were used without further purification. Reactions were typically run using anhydrous solvents under an inert atmosphere of nitrogen.

All NMR experiments were recorded on a Bruker Mercury Plus 400 NMR Spectrometer equipped with a Bruker 400 BBFO probe at 400 MHz for proton NMR. All deuterated solvents contained typically 0.03% to 0.05% v/v tetramethylsilane, which was used as the reference signal (set at $\delta$ 0.00 for both $^1$H and $^{13}$C).

LC-MS analyses were performed on a SHIMADZU LC-MS machine consisting of an UFLC 20-AD system and LCMS 2020 MS detector. The column used was a Shimpack XR-ODS, 2.2 μm, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array Detector was scanned from 200-400 nm. The mass spectrometer was equipped with an electro spray ion source (ES) operated in a positive or negative mode. The mass spectrometer was scanned between m/z 90-900 with a scan time of 0.6 s.

Measurement of human IDO-1 inhibition is performed in 384 well format using the Bridge-IT® tryptophan Fluorescence Assay (Mediomics, LLC, St. Louis, Mo., U.S.A.). The assay was adapted from published protocol; Meininger et al., *Biochimica et Biophysica Acta* 2011.

Recombinant human IDO in assay buffer (50 mM potassium phosphate buffer pH 6.5, 20 mM Ascorbic acid (Sigma), 10 mM Methylen Blue (Sigma) and 0.1 ug/ml catalase (Sigma)) was added to a range of compounds concentration previously serial diluted in DMSO (range of concentrations from 10 μM to 38 pM) or controls (1% DMSO). The concentration of enzyme in all the reaction wells was 7.5 nM. The reaction is initiated by the addition of L-Tryptophan (Sigma) at a final concentration of 100 μM in assay buffer. After 90 minutes of incubation at 37° C., the reaction is stopped by transferring 1 μl of the reaction mixture to 9 μl of Bridge-IT assay solution A. After 30 min of incubation at 30° C., the fluorescence intensity was measured at $\lambda_{ex}$=485 nm and $\lambda_{em}$=665 nm using Perkin Elmer Envision® Multilabel Reader.

Intermediate A:
4-(tributylstannyl)-1-trityl-1H-imidazole

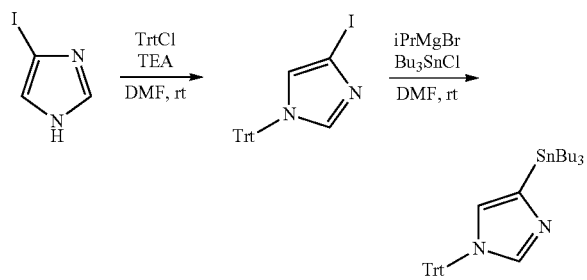

4-iodo-1-(triphenylmethyl)-1H-imidazole

At 0° C., to a solution of 4-iodo-1H-imidazole (5 g, 25.8 mmol) in DMF (100 mL) was added triethylamine (3.13 g, 30.9 mmol) slowly. After stirring for additional 10 min at 0° C., the reaction mixture was added by TrtCl (7.17 g, 25.7 mmol). The resulting solution was then stirred at room temperature for 16 h. The reaction mixture was poured into 1 L water. A white solid precipitated out and were collected by filtration. The solid was rinsed with MeOH (50 mL×2) and Et₂O (50 mL×3), and then dried in vacuo to yield 4-iodo-1-(triphenylmethyl)-1H-imidazole as white solid (10.4 g, 92%).

4-(tributylstannyl)-1-trityl-1H-imidazole

To a solution of 4-iodo-1-(triphenylmethyl)-1H-imidazole (5 g, 11.47 mmol) in dichloromethane (75 mL) was added iPrMgBr solution (1 M in THF, 17.2 mL, 17.2 mmol) dropwise at room temperature. After stirring for additional 1 h, the reaction mixture was added by Bu₃SnCl (4.49 g, 13.76 mmol) slowly. The resulting mixture was then stirred at room temperature for 16 h. The reaction mixture was quenched by the addition of water (100 mL) carefully and the mixture was extracted with DCM (100 mL×2). The organic phases were combined, washed with brine and dried over Na₂SO₄. The solvent was removed under reduced pressure to yield 4-(tributylstannyl)-1-trityl-1H-imidazole as light yellow solid (6.6 g, 96% crude yield) which was used in next step without further purification. MS: m/z=601.3 [M+H]⁺.

Intermediate B: Dimethyl 2-(4-(tert-butyldimethylsilyloxy)cyclohexyl)-2-oxoethylphosphonate

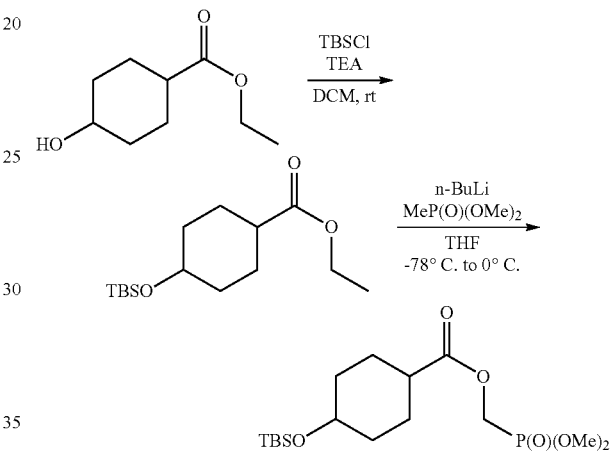

Ethyl 4-[(tert-butyldimethylsilyl)oxy]cyclohexane-1-carboxylate

To a solution of ethyl 4-hydroxycyclohexane-1-carboxylate (10 g, 58.06 mmol) in dichloromethane (25 mL) was added triethylamine (13 g, 128.47 mmol) slowly at room temperature. After stirring for additional 20 min, TBDMSCl (24.9 g, 87.09 mmol) was slowly added. The resulting reaction mixture was then stirred at room temperature for 40 h. The reaction mixture was quenched by the addition of water (100 mL) and extracted with dichloromethane (100 mL×2). The organic phases were combined, washed with brine and dried over Na₂SO₄. The solvent was removed under reduced pressure and the residue was purified by flash chromatography eluting with EtOAc in hexane (1% to 10% gradient) to yield ethyl 4-[(tert-butyldimethylsilyl)oxy]cyclohexane-1-carboxylate as yellow oil (7.5 g, 45%).

2-(4-(tert-butyldimethylsilyloxy)cyclohexyl)-2-oxoethylphosphonat

At −78° C., to a solution of MeP(O)(OMe)₂ (4.96 g, 40 mmol) in THF (50 mL) was added n-BuLi (2.5 M, 16.8 mL, 42 mmol) dropwise. After stirring for additional 30 min at −78° C., the reaction mixture was added by a solution of 4-[(tert-butyldimethylsilyl)oxy]cyclohexane-1-carboxylate (5.72 g, 20 mmol) in THF (5 mL) slowly. The resulting reaction mixture was kept stirring at −78° C. for 30 min and then slowly warmed up to 0° C. in 1 h. The reaction mixture was quenched by the addition of water (80 mL) carefully and the mixture was extracted with EtOAc (100 mL×2). The organic phases were combined, washed with brine and dried over Na$_2$SO$_4$. The solvent was removed under reduced pressure and the residue was purified by flash chromatography eluting with EtOAc in petroleum ether (50% to 100% gradient) to yield 2-(4-(tert-butyldimethylsilyloxy)cyclohexyl)-2-oxoethylphosphonate as light yellow oil (5.68 g, 78%). $^{31}$P NMR (162 MHz, CDCl$_3$) δ=22.91 (s).

Intermediate C: Dimethyl 2-cyclohexyl-2-oxoethylphosphonate

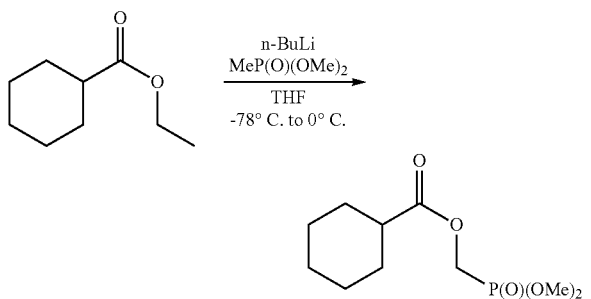

Dimethyl 2-cyclohexyl-2-oxoethylphosphonate

At −78° C., to a solution of MeP(O)(OMe)$_2$ (4.96 g, 40 mmol) in THF (50 mL) was added n-BuLi solution (2.5 M in THF, 16.8 mL, 42 mmol) dropwise. After stirring for additional 30 min at −78° C., the mixture was added by a solution of ethyl cyclohexanecarboxylate (3.12 g, 20 mmol) in THF (5 mL) slowly. The resulting reaction mixture was kept stirring at −78° C. for 30 min and then allowed to slowly warm to 0° C. in 1 h. The reaction was quenched by the addition of water (80 mL) carefully and the mixture was extracted with ethyl acetate (100 mL×2). The organic phases were combined, washed with brine and dried over Na$_2$SO$_4$. The solvent was removed under reduced pressure and the residue was purified by flash chromatography eluting with methanol in dicholromethane (1% to 8% gradient) to yield dimethyl 2-cyclohexyl-2-oxoethylphosphonate as clear oil (3.89 g, 83%). $^{31}$P NMR (162 MHz, CDCl$_3$) δ=23.18 (s).

Intermediate D: Dimethyl [2-(4,4-difluorocyclohexyl)-2-oxoethyl]phosphonate

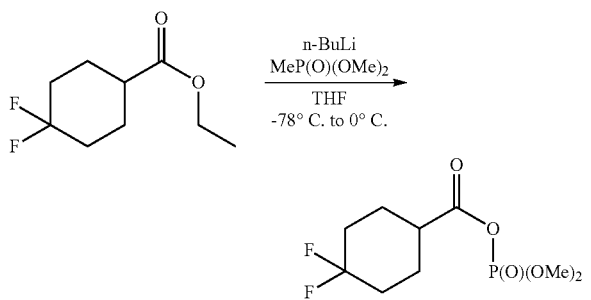

Dimethyl [2-(4,4-difluorocyclohexyl)-2-oxoethyl]phosphonate

At −78° C., to a solution of MeP(O)(OMe)$_2$ (5 g, 40.3 mmol) in THF (50 mL) was added n-BuLi solution (2.5 M in THF, 16.9 mL, 42.3 mmol) dropwise. After stirring for additional 30 min at −78° C., ethyl 4,4-difluorocyclohexane-1-carboxylate (3.88 g, 20.2 mmol) in THF (5 mL) was added to the reaction mixture slowly. The resulting reaction mixture was kept stirring at −78° C. for 30 min and then allowed to slowly warm to 0° C. in 1 h. The reaction mixture was quenched by the addition of water (80 mL) carefully and the mixture was extracted with ethyl acetate (100 mL×2). The organic phases were combined, washed with brine and dried over Na$_2$SO$_4$. The solvent was removed under reduced pressure and the residue was purified by flash chromatography eluting with methanol in dichloromethane (1% to 5% gradient) to yield dimethyl [2-(4,4-difluorocyclohexyl)-2-oxoethyl]phosphonate as clear oil (4 g, 73%). $^{31}$P NMR (162 MHz, CDCl$_3$) δ=22.28 (s).\

Intermediate E: Dimethyl [2-(4,4-dimethylcyclohexyl)-2-oxoethyl]phosphonate

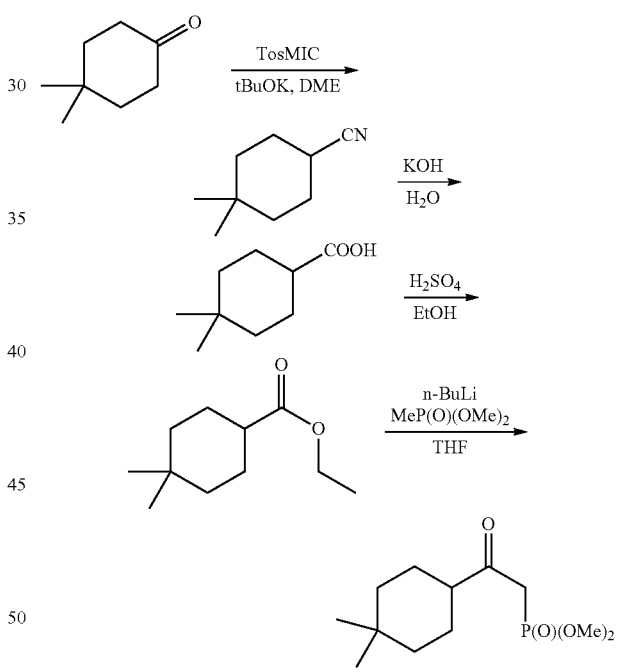

4,4-Dimethylcyclohexane-1-carbonitrile

At 0° C., to a solution of 4,4-dimethylcyclohexan-1-one (6.4 g, 50.71 mmol) in dimethoxyethane 100 mL) was added t-BuOK (11.4 g, 101.42 mmol) and 1-(isocyanomethane) sulfonyl-4-methylbenzene (9.9 g, 50.71 mmol) successively. The resulting mixture was then stirred at room temperature for 2 h. The reaction mixture was filtered to remove insoluble solid, which was rinsed with DME (40 mL×3). The solvent was removed under reduced pressure and the residue was purified by flash chromatography eluting with 100% petroleum ether to yield 4,4-dimethylcyclohexane-1-carbonitrile as clear oil (4 g, 57%).

4,4-Dimethylcyclohexane-1-carboxylic acid

A mixture of 4,4-dimethylcyclohexane-1-carbonitrile (1 g, 7.29 mmol) in aqueous potassium hydroxide solution (5 M, 30 mL) was stirred at 100° C. for 24 h. The reaction mixture was washed with ethyl acetate (30 mL×2) and the aqueous phase was neutralized with aq. HCl solution (2M) carefully. The resulting solution was extracted with ethyl acetate (80 mL×4) and the combined organic phase was washed with brine and dried over $Na_2SO_4$. The solvent was removed under reduced pressure to yield 4,4-dimethylcyclohexane-1-carboxylic acid as yellow oil (500 mg, 44%, crude yield) which was used in next step without further purification.

Ethyl 4,4-dimethylcyclohexane-1-carboxylate

To a solution of 4,4-dimethylcyclohexane-1-carboxylic acid (1 g, 6.40 mmol) in ethanol (40 mL) was added catalytic amount of $H_2SO_4$ carefully at room temperature. The resulting reaction mixture was then stirred at 70° C. for 2 h. The solvent was removed under reduced pressure to yield ethyl 4,4-dimethylcyclohexane-1-carboxylate as yellow oil (800 mg, 68%, crude yield) which was used in next step without further purification.

Dimethyl [2-(4,4-dimethylcyclohexyl)-2-oxoethyl]phosphonate

At −78° C., to a solution of MeP(O)(OMe)$_2$ (942 mg, 7.60 mmol) in THF (20 mL) was added n-BuLi solution (2.5 M in THF, 3.2 mL, 7.98 mmol) dropwise. After stirring for additional 30 min at −78° C., to the reaction mixture was added a solution of ethyl 4,4-dimethylcyclohexane-1-carboxylate (700 mg, 3.80 mmol) in THF (5 mL) slowly. The resulting reaction mixture was kept stirring at −78° C. for 30 min and then allowed to slowly warm to 0° C. in 1 h. The reaction was quenched by the addition of water (50 mL) carefully and the mixture was extracted with ethyl acetate (80 mL×2). The organic phases were combined, washed with brine and dried over $Na_2SO_4$. The solvent was removed under reduced pressure and the residue was purified by flash chromatography eluting with petroleum ether:EtOAc (5:1 to 2:1 gradient) to yield dimethyl [2-(4,4-dimethylcyclohexyl)-2-oxoethyl]phosphonate as light yellow oil (700 mg, 70%). $^{31}$P NMR (162 MHz, CDCl$_3$) δ=23.15 (s).

Intermediate F: Intermediate 6: Synthesis of dimethyl (3-cyclohexyl-2-oxopropyl)phosphonate

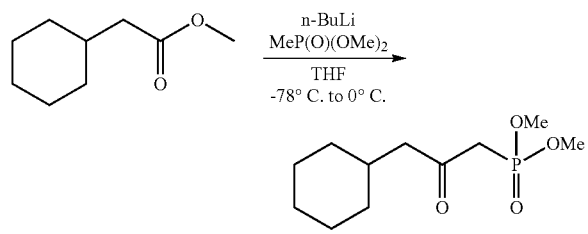

Dimethyl (3-cyclohexyl-2-oxopropyl)phosphonate

At −78° C., to a solution of dimethyl methylphosphonate (5 g, 40.3 mmol) in THF (50 mL) was added n-BuLi solution (2.5 M in THF, 16.9 mL, 42.3 mmol) dropwise. After stirring for 30 min at −78° C., the reaction mixture was added by a solution of methyl 2-cyclohexylacetate (3.15 g, 20.2 mmol) in THF (10 mL) slowly. The resulting reaction mixture was kept stirring at −78° C. for 30 min, and then slowly warmed up to 0° C. over 1 h period. Then the reaction was quenched by the addition of water (80 mL) carefully and the mixture was extracted with ethyl acetate (100 mL×2). The organic phases were combined, washed with brine and dried over sodium sulfate. The solvent was removed under reduced pressure and the residue was purified by flash chromatography eluting with ethyl acetate in petroleum ether (20% to 100% gradient) to yield dimethyl (3-cyclohexyl-2-oxopropyl)phosphonate as light yellow oil (3.15 g, 66%). $^1$H NMR (400 MHz, CDCl$_3$, ppm) δ=3.78 (s, 3H), 3.76 (s, 3H), 3.05 (d, J=22.8 Hz, 2H), 2.47 (d, J=6.8 Hz, 2H), 1.86-1.79 (m, 1H), 1.68-1.59 (m, 5H), 1.31-1.04 (m, 3H), 0.96-0.87 (m, 2H). $^{31}$P NMR (162 MHz, CDCl$_3$, ppm) δ=22.75 (s).

Intermediate G: Synthesis of dimethyl [2-(oxan-4-yl)-2-oxoethyl]phosphonate

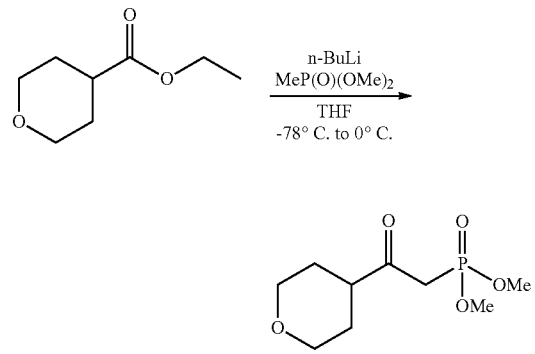

Dimethyl [2-(oxan-4-yl)-2-oxoethyl]phosphonate

At −78° C., to a solution of dimethyl methylphosphonate (5 g, 40.3 mmol) in THF (50 mL) was added n-BuLi solution (2.5 M in THF, 16.9 mL, 42.3 mmol) dropwise. After stirring for 30 min at −78° C., the reaction mixture was added by a solution of ethyl tetrahydro-2H-pyran-4-carboxylate (3.2 g, 20.2 mmol) in THF (10 mL) slowly. The resulting mixture was kept stirring at −78° C. for 30 min, and then slowly warmed up to 0° C. in 1 h period. Then the reaction was quenched by the addition of water (80 mL) carefully and the mixture was extracted with ethyl acetate (100 mL×2). The organic phases were combined, washed with brine and dried over sodium sulfate. The solvent was removed under reduced pressure and the residue was purified by flash chromatography eluting with ethyl acetate in petroleum ether (20% to 100% gradient) to yield dimethyl [2-(oxan-4-yl)-2-oxoethyl]phosphonate as light yellow oil (3.73 g, 78%). $^1$H NMR (300 MHz, CDCl$_3$, ppm) δ=4.02-3.97 (m, 2H), 3.78 (s, 3H), 3.76 (s, 3H), 3.46-3.39 (m, 2H), 3.15 (d, J=22.5 Hz, 2H), 2.83-2.76 (m, 1H), 1.82-1.61 (m, 4H).

Intermediate H: Synthesis of dimethyl (2-[1,4-dioxaspiro[4.5]decan-8-yl]-2-oxoethyl)phosphonate

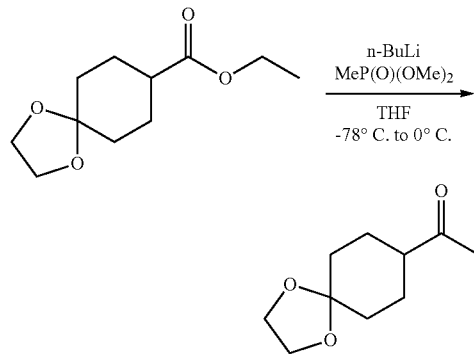

Dimethyl (2-[1,4-dioxaspiro[4.5]decan-8-yl]-2-oxoethyl)phosphonate

At −78° C., to a solution of dimethyl methylphosphonate (5 g, 40.3 mmol) in THF (50 mL) was added n-BuLi solution (2.5 M in THF, 16.9 mL, 42.3 mmol) dropwise. After stirring for 30 min at −78° C., the reaction mixture was added by a solution of ethyl 1,4-dioxaspiro[4.5]decane-8-carboxylate (4.33 g, 20.2 mmol) in THF (10 mL) slowly. The resulting mixture was kept stirring at −78° C. for 30 min and then slowly warmed up to 0° C. in 1 h period. Then the reaction was quenched by the addition of water (80 mL) carefully and the mixture was extracted with ethyl acetate (100 mL×2). The organic phases were combined, washed with brine and dried over sodium sulfate. The solvent was removed under reduced pressure and the residue was purified by flash chromatography eluting with ethyl acetate in petroleum ether (20% to 100% gradient) to yield dimethyl (2-[1,4-dioxaspiro[4.5]decan-8-yl]-2-oxoethyl)phosphonate as light yellow oil (3.85 g, 62%). $^1$H NMR (400 MHz, CDCl$_3$, ppm): δ=3.93-3.90 (m, 4H), 3.79 (s, 3H), 3.77 (s, 3H), 3.13 (d, J=22.8 Hz, 2H), 2.60-2.55 (m, 1H), 1.92-1.87 (m, 2H), 1.80-1.63 (m, 4H), 1.58-1.47 (m, 2H).

Intermediate I: Synthesis of methyl 4-[2-(dimethoxyphosphoryl)acetyl]cyclohexane-1-carboxylate

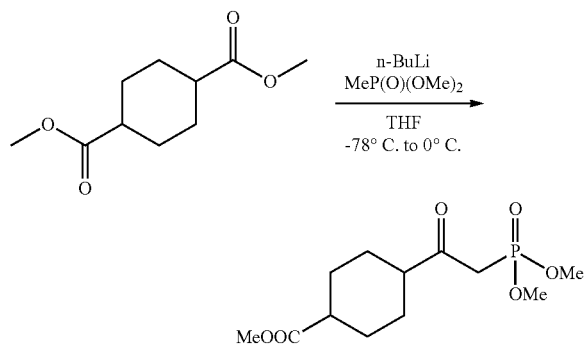

Methyl 4-[2-(dimethoxyphosphoryl)acetyl]cyclohexane-1-carboxylate

At −78° C., to a solution of dimethyl methylphosphonate (5 g, 40.3 mmol) in THF (50 mL) was added n-BuLi solution (2.5 M in THF, 16.9 mL, 42.3 mmol) dropwise. After stirring for 30 min at −78° C., the reaction mixture was added by a solution of 1,4-dimethyl cyclohexane-1,4-dicarboxylate (4 g, 20.2 mmol) in THF (10 mL) slowly. The resulting mixture was kept stirring at −78° C. for 30 min, and then slowly warmed up to 0° C. in 1 h period. Then the reaction was quenched by the addition of water (80 mL) carefully and the mixture was extracted with ethyl acetate (100 mL×2). The organic phases were combined, washed with brine and dried over sodium sulfate. The solvent was removed under reduced pressure and the residue was purified by flash chromatography eluting with ethyl acetate in petroleum ether (20% to 100% gradient) to yield methyl 4-[2-(dimethoxyphosphoryl)acetyl]cyclohexane-1-carboxylate as light yellow oil (3.76 g, 68%). $^1$H NMR (400 MHz, CDCl$_3$, ppm) δ=3.81 (s, 3H), 3.78 (s, 3H), 3.68 (s, 3H), 3.13 (d, J=22.4 Hz, 2H), 2.69-2.53 (m, 2H), 2.28-1.98 (m, 3H), 1.74-1.61 (m, 3H), 1.52-1.24 (m, 2H). $^{31}$P NMR (162 MHz, CDCl$_3$, ppm) δ=22.97 & 22.74 (s). MS: m/z=314.95 [M+Na]$^+$.

Intermediate J: Synthesis of dimethyl [2-(1-fluorocyclohexyl)-2-oxoethyl]phosphonate

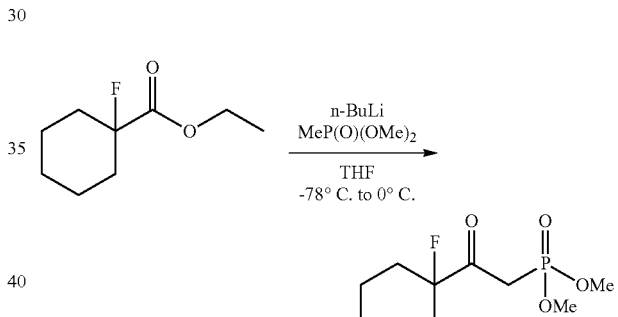

Dimethyl [2-(1-fluorocyclohexyl)-2-oxoethyl]phosphonate

At −78° C., to a solution of dimethyl methylphosphonate (2.5 g, 20.2 mmol) in THF (30 mL) was added n-BuLi solution (2.5 M in THF, 8.5 mL, 21.3 mmol) dropwise. After stirring for 30 min at −78° C., the reaction mixture was added by a solution of ethyl 1-fluorocyclohexanecarboxylate (1.76 g, 10.1 mmol) in THF (5 mL) slowly. The resulting mixture was kept stirring at −78° C. for 30 min, and then slowly warmed up to 0° C. in 1 h period. Then the reaction was quenched by the addition of water (50 mL) carefully and the mixture was extracted with EtOAc (80 mL×2). The organic phases were combined, washed with brine and dried over Na$_2$SO$_4$. The solvent was removed under reduced pressure and the residue was purified by flash chromatography eluting with EtOAc in petroleum ether (20% to 100% gradient) to yield dimethyl [2-(1-fluorocyclohexyl)-2-oxoethyl]phosphonate as clear oil (1.28 g, 57%). $^1$H NMR (400 MHz, CDCl$_3$, ppm) δ=3.81 (s, 3H), 3.78 (s, 3H), 3.32 (d, J=22.0 Hz, 2H), 1.89-1.84 (m, 2H), 1.75-1.53 (m, 7H), 1.32-1.23 (m, 1H).

Intermediate K: Synthesis of dimethyl (2-oxo-2-[spiro[2.5]octan-6-yl]ethyl)phosphonate

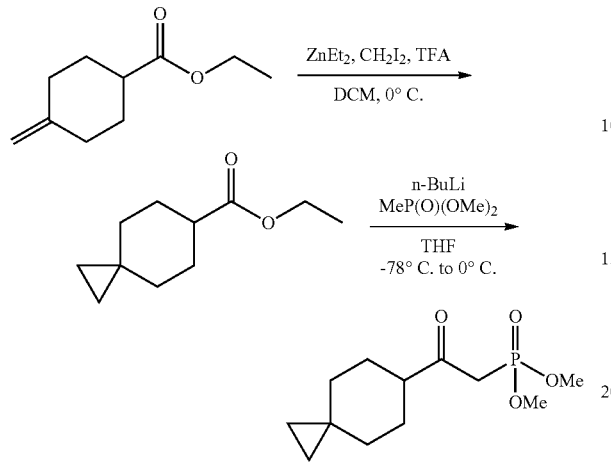

Ethyl spiro[2.5]octane-6-carboxylate

At 0° C., trifluoroacetic acid (2.2 mL, 32.7 mmol) was added dropwise to a solution of diethylzinc (1 M in hexane, 33 mL) in DCM (50 mL). The mixture was stirred for 1 h at 0° C., and then was added by diiodomethane (2.64 mL, 32.7 mmol) slowly. The resulting mixture was stirred for another 40 min at 0° C., and then was added by a solution of ethyl 4-methylidenecyclohexane-1-carboxylate (2.20 g, 13.08 mmol) in DCM (5 mL) dropwise. The reaction mixture was kept stirring at 0° C. for 2 h. Then the reaction was quenched by the addition of water (50 mL) and the mixture was extracted with DCM (50 mL×2). The organic phases were combined, washed with brine and dried over $Na_2SO_4$. The solvent was removed under reduced pressure and the residue was purified by flash chromatography eluting with EtOAc in petroleum ether (1% to 8% gradient) to yield ethyl spiro[2.5]octane-6-carboxylate as light yellow oil (2 g, 84%). $^1$H NMR (300 MHz, $CDCl_3$, ppm) δ=4.11 (q, J=7.2 Hz, 2H), 2.32-2.24 (m, 1H), 1.87-1.83 (m, 2H), 1.69-1.52 (m, 4H), 1.23 (t, J=7.2 Hz, 3H), 0.97-0.93 (m, 2H), 0.26-0.15 (m, 4H).

Dimethyl (2-oxo-2-[spiro[2.5]octan-6-yl]ethyl)phosphonate

At −78° C., to a solution of dimethyl methylphosphonate (2.72 g, 21.92 mmol) in THF (30 mL) was added n-BuLi solution (2.5 M in THF, 8.8 mL, 22.0 mmol) dropwise. After stirring for 30 min at −78° C., the mixture was added by a solution of ethyl spiro[2.5]octane-6-carboxylate (2 g, 10.97 mmol) in THF (6 mL) slowly. The resulting mixture was kept stirring at −78° C. for 30 min, and then slowly warmed up to 0° C. in 1 h period. Then the reaction was quenched by the addition of water (60 mL) and the mixture was extracted with EtOAc (80 mL×2). The organic phases were combined, washed with brine and dried over $Na_2SO_4$. The solvent was removed under reduced pressure and the residue was purified by flash chromatography eluting with EtOAc in petroleum ether (20% to 100% gradient) to yield dimethyl (2-oxo-2-[spiro[2.5]octan-6-yl]ethyl)phosphonate as light yellow oil (2.2 g, 77%). $^{31}$P NMR (162 MHz, $CDCl_3$, ppm) δ=23.12 (s).

Intermediate L: Synthesis of dimethyl [2-oxo-2-(1,4,4-trifluorocyclohexyl)ethyl]phosphonate

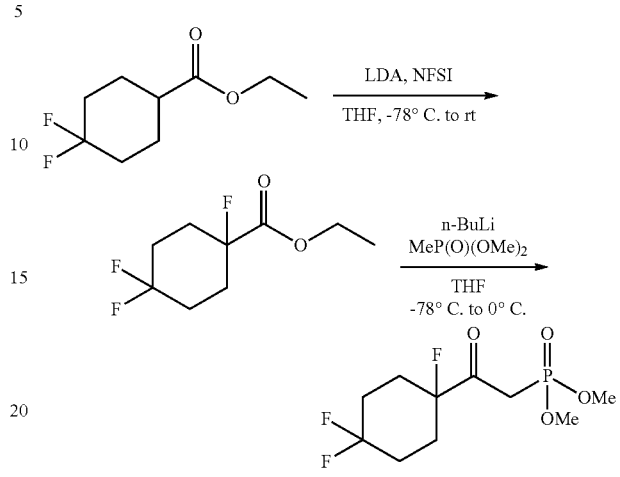

Ethyl 1,4,4-trifluorocyclohexane-1-carboxylate

To a solution of ethyl 4,4-difluorocyclohexane-1-carboxylate (3.5 g, 18.23 mmol) in THF (70 mL) was added LDA (2 M in THF, 13.7 mL, 27.4 mmol) dropwise at −78° C. After stirring for 1 h at −78° C., the mixture was added by N-(benzenesulfonyl)-S-phenylfluoranesulfonamido (6.89 g, 21.88 mmol) slowly. The resulting mixture was warmed up to room temperature and stirred for 16 h. Then the reaction was quenched by the addition of saturated ammonium chloride solution (50 mL) carefully and the mixture was extracted with EtOAc (80 mL×2). The organic phases were combined, washed with brine and dried over $Na_2SO_4$. The solvent was removed under reduced pressure and the residue was purified by flash chromatography eluting with EtOAc in petroleum ether (0% to 3% gradient) to yield ethyl 1,4,4-trifluorocyclohexane-1-carboxylate as light yellow oil (580 mg, 16%). $^1$H NMR (300 MHz, $CDCl_3$, ppm) δ=4.11 (q, J=7.2 Hz, 2H), 2.32-2.24 (m, 1H), 1.87-1.83 (m, 2H), 1.69-1.52 (m, 4H), 1.23 (t, J=7.2 Hz, 3H), 0.97-0.93 (m, 2H), 0.26-0.15 (m, 4H).

Dimethyl [2-oxo-2-(1,4,4-trifluorocyclohexyl)ethyl]phosphonate

At −78° C., to a solution of dimethyl methylphosphonate (680 mg, 5.48 mmol) in THF (10 mL) was added n-BuLi solution (2.5 M in THF, 2.2 mL, 5.5 mmol) dropwise. After stirring for 30 min at −78° C., the mixture was added by a solution of ethyl 1,4,4-trifluorocyclohexane-1-carboxylate (580 mg, 2.76 mmol) in THF (3 mL) slowly. The resulting mixture was kept stirring at −78° C. for 30 min, and then slowly warmed up to 0° C. in 1 h period. Then the reaction was quenched by the addition of water (30 mL) carefully and the mixture was extracted with EtOAc (50 mL×2). The organic phases were combined, washed with brine and dried over $Na_2SO_4$. The solvent was removed under reduced pressure and the residue was purified by flash chromatography eluting with EtOAc in petroleum ether (20% to 100% gradient) to yield dimethyl [2-oxo-2-(1,4,4-trifluorocyclohexyl)ethyl]phosphonate as light yellow oil (445 mg, 56%).

Intermediate M: Synthesis of dimethyl [2-(4-[[(tert-butyldimethylsilyl)oxy]methyl]cyclohexyl)-2-oxoethyl]phosphonate

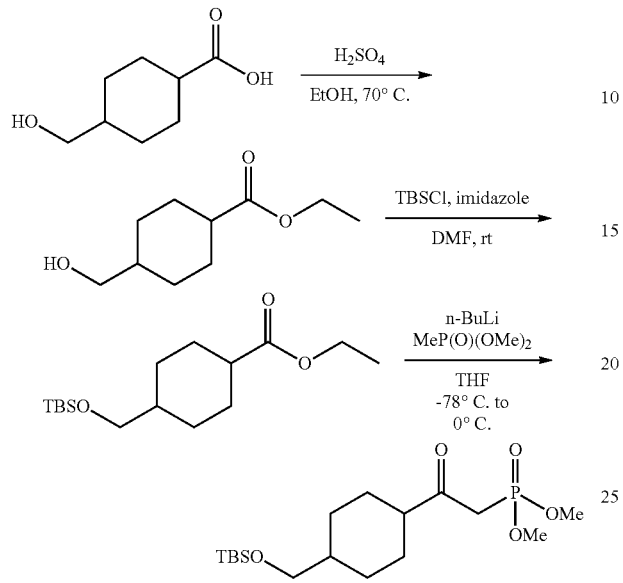

Ethyl 4-(hydroxymethyl)cyclohexane-1-carboxylate

To a solution of 4-(hydroxymethyl)cyclohexane-1-carboxylic acid (5 g, 30.03 mmol) in ethanol (50 mL) was added sulfuric acid (0.25 mL, 4.60 mmol) at room temperature. The resulting mixture was stirred at 70° C. for 16 h. Then the reaction mixture was diluted with water (100 mL) and extracted with EtOAc (150 mL×2). The organic phases were combined, washed with brine and dried over $Na_2SO_4$. The solvent was removed under reduced pressure to yield ethyl 4-(hydroxymethyl)cyclohexane-1-carboxylate as clear oil (5.2 g, 93%) which was used in the next step without further purification.

Ethyl 4-[[(tert-butyldimethylsilyl)oxy]methyl]cyclohexane-1-carboxylate

At room temperature, to a solution of ethyl 4-(hydroxymethyl)cyclohexane-1-carboxylate (5.2 g, 27.9 mmol) in DMF (60 mL) was added imidazole (3.8 g, 55.8 mmol) and TBSCl (5.45 g, 36.2 mmol) successively. The resulting mixture was stirred at room temperature for 16 h. Then the reaction was quenched by the addition of water (150 mL) and the mixture was extracted with EtOAc (150 mL×2). The organic phases were combined, washed with brine and dried over $Na_2SO_4$. The solvent was removed under reduced pressure and the residue was purified by flash chromatography eluting with EtOAc in petroleum ether (1% to 10% gradient) to yield ethyl 4-[[(tert-butyldimethylsilyl)oxy]methyl]cyclohexane-1-carboxylate as light yellow oil (7.5 g, 89%).

Dimethyl [2-(4-[[(tert-butyldimethylsilyl)oxy]methyl]cyclohexyl)-2-oxoethyl]phosphonate At −78° C., to a solution of dimethyl methylphosphonate (5 g, 40.3 mmol) in THF (50 mL) was added n-BuLi solution (2.5 M in THF, 16.9 mL, 42.3 mmol) dropwise. After stirring for 30 min at −78° C., the mixture was added by a solution of ethyl 4-[[(tert-butyldimethylsilyl)oxy]methyl]cyclohexane-1-carboxylate (6.1 g, 20.2 mmol) in THF (10 mL) slowly. The resulting mixture was kept stirring at −78° C. for 30 min, and then slowly warmed up to 0° C. in 1 h period. Then the reaction was quenched by the addition of water (80 mL) carefully and the mixture was extracted with EtOAc (150 mL×2). The organic phases were combined, washed with brine and dried over $Na_2SO_4$. The solvent was removed under reduced pressure and the residue was purified by flash chromatography eluting with EtOAc in petroleum ether (20% to 100% gradient) to yield dimethyl [2-(4-[[(tert-butyldimethylsilyl)oxy]methyl]cyclohexyl)-2-oxoethyl]phosphonate as light yellow oil (5.76 g, 75%). $^1$H NMR (300 MHz, $CDCl_3$, ppm) δ=3.77 (s, 3H), 3.74 (s, 3H), 3.39-3.37 (m, 2H), 3.10 (d, J=22.5 Hz, 2H), 2.71-2.42 (m, 1H), 1.95-1.80 (m, 3H), 1.62-1.50 (m, 3H), 1.34-1.20 (m, 2H), 1.02-0.90 (m, 1H), 0.85 (s, 9H), −0.01 (s, 6H). $^{31}$P NMR (162 MHz, $CDCl_3$, ppm) δ=23.29 (s).

EXAMPLES

Example 1: Synthesis of 5-(2-(1-fluorocyclohexyl)ethyl)-5H-imidazo[5,1-a]isoindole (1a and 1b)

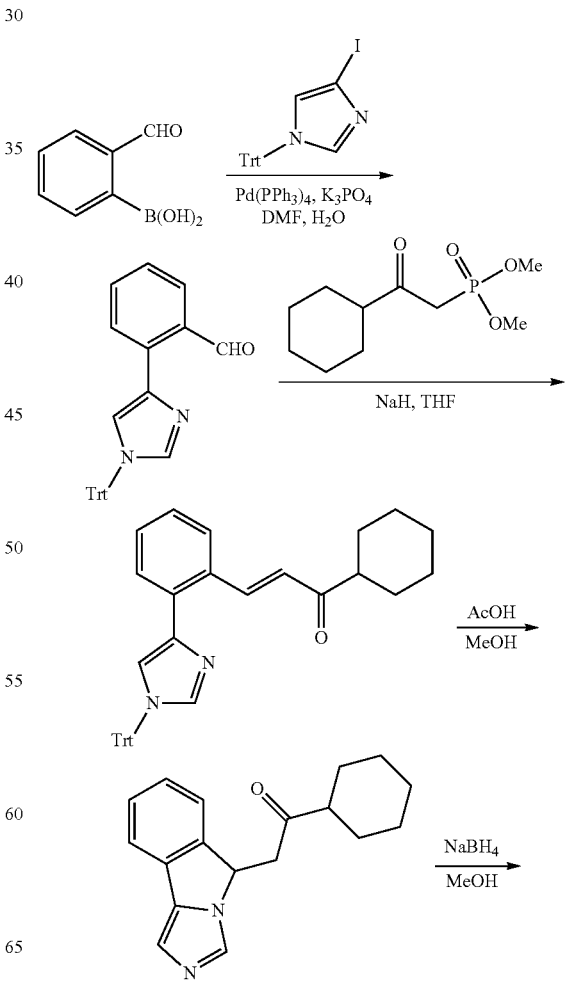

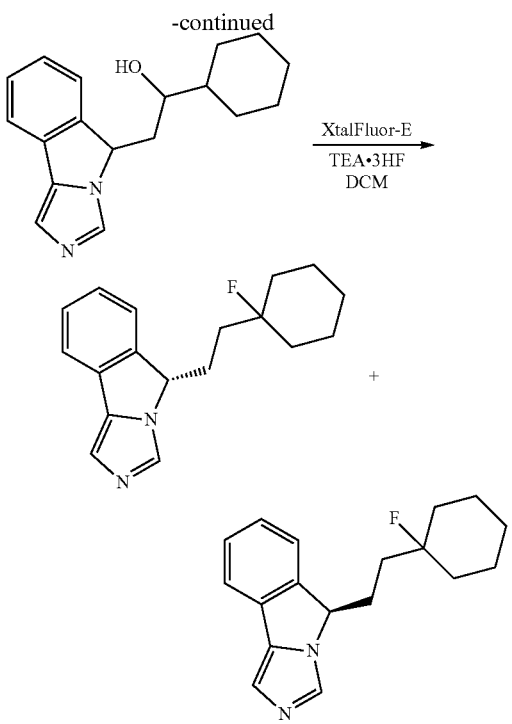

2-(1-Trityl-1H-imidazol-4-yl)benzaldehyde

A mixture of 4-iodo-1-(triphenylmethyl)-1H-imidazole (Intermediate A, 4.36 g, 9.99 mmol), (2-formylphenyl)boronic acid (1.65 g, 11.00 mmol), Pd(PPh$_3$)$_4$ (1.16 g, 1.0 mmol) and K$_3$PO$_4$ (4.25 g, 20.02 mmol) in DMF (40 mL) and water (8 mL) was stirred at 100° C. for 16 h under N$_2$ atmosphere. The reaction mixture was diluted with water (100 mL) and extracted with ethyl acetate (150 mL×2). The organic phases were combined, washed with brine and dried over Na$_2$SO$_4$. The solvent was removed under reduced pressure and the residue was purified by flash chromatography eluting with EtOAc in hexane (1% to 25% gradient) to yield 2-(1-trityl-1H-imidazol-4-yl)benzaldehyde as yellow solid (3 g, 72%). MS: m/z=415.1 [M+H]$^+$.

1-cyclohexyl-3-(2-(1-trityl-1H-imidazol-4-yl)phenyl)prop-2-en-1-one

At 0° C., to a suspension of sodium hydride (60%, 348 mg, 8.7 mmol) in THF (40 mL) was added a solution of dimethyl (2-cyclohexyl-2-oxoethyl)phosphonate (1.87 g, 7.98 mmol) in THF (10 mL) slowly. After stirring for additional 15 min at 0° C., the reaction mixture was treated with a solution of 2-[1-(triphenylmethyl)-1H-imidazol-4-yl] benzaldehyde (3 g, 7.24 mmol) in THF (15 mL). The resulting mixture was then stirred at room temperature for 2.5 h. The reaction was then quenched by water (100 mL) and the mixture was extracted with ethyl acetate (150 mL×2). The organic phases were combined, washed with brine, and dried over Na$_2$SO$_4$. The solvent was removed under reduced pressure to yield 1-cyclohexyl-3-(2-(1-trityl-1H-imidazol-4-yl)phenyl)prop-2-en-1-one as light yellow solid (3.5 g, 93% crude yield) which was used in next step without further purification. MS: m/z=523.2 [M+H]$^+$.

1-Cyclohexyl-2-(5H-imidazo[5,1-a]isoindol-5-yl)ethanone

To a suspension of 1-cyclohexyl-3-[2-[1-(triphenylmethyl)-1H-imidazol-4-yl]phenyl]prop-2-en-1-one (3.5 g, 6.70 mmol) in methanol (30 mL) was added acetic acid (10 mL) slowly at room temperature. The resulting reaction mixture was stirred at 90° C. for 2 h. The solvent was removed under reduced pressure and the residue was dissolved in ethyl acetate (100 mL). The diluted solution was washed with sat. NaHCO$_3$ solution (40 mL×2) and brine, and then dried over Na$_2$SO$_4$. The solvent was removed under reduced pressure and the residue was purified by flash chromatography eluting with methanol in dicholormethane (1% to 6% gradient) to yield 1-cyclohexyl-2-[5H-imidazo[4,3-a]isoindol-5-yl]ethan-1-one as yellow oil (1.6 g, 78.8% over two steps). MS: m/z=281.0 [M+H]$^+$.

1-cyclohexyl-2-(5H-imidazo[5,1-a]isoindol-5-yl)ethanol

At 0° C., to a solution of 1-cyclohexyl-2-[5H-imidazo[4,3-a]isoindol-5-yl]ethan-1-one (300 mg, 1.07 mmol) in methanol (5 mL) was added sodium borohydride (81 mg, 2.14 mmol) slowly. The resulting reaction mixture was kept stirring at 0° C. for 30 min. The reaction mixture was then quenched by water (30 mL) and the mixture was extracted with ethyl acetate (50 mL×2). The organic phases were combined, washed with brine, and dried over Na$_2$SO$_4$. The solvent was removed under reduced pressure and the residue was purified by flash chromatography eluting with methanol in dichloromethane (1% to 6% gradient) to yield 1-cyclohexyl-2-(5H-imidazo[5,1-a]isoindol-5-yl)ethanol as clear oil (250 mg, 83%). MS: m/z=283.1 [M+H]$^+$.

5-(2-(1-Fluorocyclohexyl)ethyl)-5H-imidazo[5,1-a]isoindole (Ent 1a & 1b)

At 0° C., to a suspension of XtalFluor-E (144 mg, 0.64 mmol) in DCM (6 mL) was added a solution of 1-cyclohexyl-2-[5H-imidazo[4,3-a]isoindol-5-yl]ethan-1-ol (120 mg, 0.44 mmol) in dichloromethane (2 mL), and triethylamine-hydrogen fluoride (104 mg, 0.64 mmol) successively. The resulting reaction mixture was stirred at room temperature for 1 h. The reaction mixture was then quenched by water (30 mL) and the mixture was extracted with dichloromethane (40 mL×2). The organic phases were combined, washed with brine, and dried over Na$_2$SO$_4$. The solvent was removed under reduced pressure and the residue was first purified by prep-HPLC under the following conditions: XBridge Prep C18 OBD Column, 19×150 mm, 5 μm; acetonitrile in water (with 0.05% trifluoroacetic acid), 15% to 40% gradient in 20 min. Then the two enantiomers were separated by chiral prep-HPLC under the following conditions: CHIRALCEL OJ-H, 2×25 cm; mobile phase, ethanol in hexane; 5% isocratic in 29 min; Detector, UV 254/220 nm.

Compound 1a:

(20 mg, 16.7%, light yellow oil, containing 1 stereoisomer) HPLC: 92.7% purity, RT=1.70 min. MS: m/z=285.0 [M+H]$^+$. $^1$H NMR (300 MHz, CDCl$_3$, ppm) δ=7.78 (s, 1H), 7.59-7.50 (m, 1H), 7.42-7.18 (m, 4H), 5.32-5.21 (t, J=5.1 Hz, 1H), 2.34-2.24 (m, 1H), 2.18-2.04 (m, 1H), 1.80-1.71 (m, 2H), 1.60-1.10 (m, 10H);

Compound 1b (21 mg, 17.5%, light yellow oil, containing 1 stereoisomer) HPLC: 95.7% purity, RT=2.76 min. MS: m/z=285.0 [M+H]$^+$. $^1$H NMR (300 MHz, CDCl$_3$, ppm) δ=7.78 (s, 1H), 7.58-7.51 (m, 1H), 7.42-7.18 (m, 4H), 5.32-5.21 (t, J=5.1 Hz, 1H), 2.38-2.24 (m, 1H), 2.18-2.08 (m, 1H), 1.80-1.71 (m, 2H), 1.60-1.10 (m, 10H).

Example 2: 1-Cyclohexyl-2-[9-fluoro-4,6,10-triazatricyclo[6.4.0.0^[2,6]]dodeca-1(8),2,4,9,11-pentaen-7-yl]ethan-1-ol (2a and 2b)

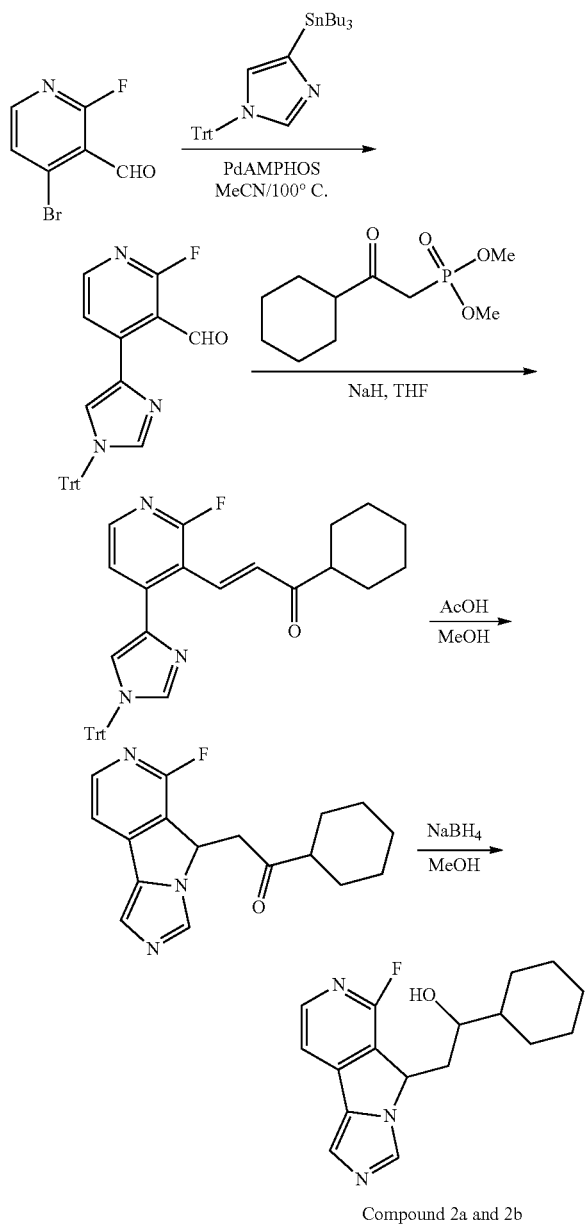

Compound 2a and 2b

2-Fluoro-4-[1-(triphenylmethyl)-1H-imidazol-4-yl]pyridine-3-carbaldehyde

A mixture of 4-bromo-2-fluoropyridine-3-carbaldehyde (101 mg, 0.5 mmol), 4-(tributylstannyl)-1-(triphenylmethyl)-1H-imidazole (Intermediate A, 450 mg, 0.75 mmol) and PdAMPHOS (35 mg, 0.05 mmol) in acetonitrile (3 mL) was stirred at 100° C. for 5 h under $N_2$ atmosphere. Then the reaction mixture was diluted with water (30 mL) and extracted with ethyl acetate (50 mL×2). The organic phases were combined, washed with brine, and dried over $Na_2SO_4$. The solvent was removed under reduced pressure and the residue was purified by flash chromatography eluting with ethyl acetate in hexane (10% to 30% gradient) to yield 2-fluoro-4-[1-(triphenylmethyl)-1H-imidazol-4-yl]pyridine-3-carbaldehyde (70 mg, 33%) as light yellow oil.

1-Cyclohexyl-3-[2-fluoro-4-[1-(triphenylmethyl)-1H-imidazol-4-yl]pyridin-3-yl]prop-2-en-1-one To a suspension of sodium hydride (60%, 29 mg, 0.73 mmol) in THF (6 mL) was added a solution of dimethyl (2-cyclohexyl-2-oxoethyl)phosphonate (Intermediate C, 155 mg, 0.66 mmol) in THF (2 mL) slowly at 0° C. After stirring for additional 15 min at 0° C., the reaction mixture was added by a solution of 2-fluoro-4-[1-(triphenylmethyl)-1H-imidazol-4-yl]pyridine-3-carbaldehyde (260 mg, 0.6 mmol) in THF (2 mL). The resulting reaction mixture was then stirred at room temperature for 1.5 h. The reaction mixture was quenched by water (30 mL) and the mixture was extracted with ethyl acetate (50 mL×2). The organic phases were combined, washed with brine, and dried over $Na_2SO_4$. The solvent was removed under reduced pressure to yield 1-cyclohexyl-3-[2-fluoro-4-[1-(triphenylmethyl)-1H-imidazol-4-yl]pyridin-3-yl]prop-2-en-1-one (260 mg, 80% crude yield) as yellow oil, which was used in next step without further purification. MS: m/z=542.2 [M+H]$^+$.

1-Cyclohexyl-2-[9-fluoro-4,6,10-triazatricyclo[6.4.0.0^[2,6]]dodeca-1(8),2,4,9,11-pentaen-7-yl]ethan-1-one To a solution of 1-cyclohexyl-3-[2-fluoro-4-[1-(triphenylmethyl)-1H-imidazol-4-yl]pyridin-3-yl]prop-2-en-1-one (260 mg, 0.48 mmol) in methanol (6 mL) was added acetic acid (2 mL) slowly at room temperature. The resulting reaction mixture was stirred at 90° C. for 1 h. The solvent was removed under reduced pressure and the residue was dissolved in ethyl acetate (60 mL). The solution was washed with sat. $NaHCO_3$ solution (20 mL×2) and brine, and then dried over $Na_2SO_4$. The solvent was removed under reduced pressure and the residue was purified by flash chromatography eluting with methanol in dichloromethane (1% to 10% gradient) to yield 1-cyclohexyl-2-[9-fluoro-4,6,10-triazatricyclo[6.4.0.0^[2,6]]dodeca-1(8),2,4,9,11-pentaen-7-yl]ethan-1-one (130 mg, 72% over two steps) as yellow oil.

1-Cyclohexyl-2-[9-fluoro-4,6,10-triazatricyclo[6.4.0.0^[2,6]]dodeca-1(8),2,4,9,11-pentaen-7-yl]ethan-1-ol To a solution of 1-cyclohexyl-2-[9-fluoro-4,6,10-triazatricyclo[6.4.0.0^[2,6]]dodeca-1 (8),2,4,9,11-pentaen-7-yl]ethan-1-one (120 mg, 0.40 mmol) in methanol (8 mL) was added sodium borohydride (30.4 mg, 0.80 mmol) slowly at 0° C. The resulting reaction mixture was kept stirring at 0° C. for 30 min. The reaction mixture was quenched by water (30 mL) and extracted with EtOAc (45 mL×2). The organic phases were combined, washed with brine and dried over $Na_2SO_4$. The solvent was removed under reduced pressure and the residue was purified by prep-HPLC under the following conditions: Gemini-NX C18 Column, 21.2×150 mm, 5 μm; MeCN in water (with 10 mM $NH_4HCO_3$), 15% to 43% gradient in 12 min.

Compound 2a:

(35 mg, 29%, white solid, containing 2 stereoisomers) HPLC: 100% purity, RT=1.46 min. MS: m/z=302.2 [M+H]$^+$. $^1$H NMR (300 MHz, $CD_3OD$, ppm) δ=8.13-8.03 (m, 1H), 8.00 (s, 1H), 7.48-7.39 (m, 1H), 7.29 (s, 1H), 5.53-5.49 (m, 1H), 3.22-3.17 (m, 1H), 2.43-2.32 (m, 1H), 2.08-1.93 (m, 1H), 1.70-1.52 (m, 5H), 1.20-0.82 (m, 7H);

Compound 2b:

(18 mg, 15%, white solid, containing 2 stereoisomers) HPLC: 99.7% purity, RT=2.47 min. MS: m/z=302.2 [M+H]$^+$. $^1$H NMR (300 MHz, CD$_3$OD, ppm) δ=8.18-8.13 (m, 1H), 7.95 (s, 1H), 7.50-7.42 (m, 1H), 7.31 (s, 1H), 5.69-5.62 (m, 1H), 3.52-3.42 (m, 1H), 2.38-2.25 (m, 1H), 1.85-1.52 (m, 6H), 1.30-0.82 (m, 6H).

Example 3: 1-cyclohexyl-2-[9-fluoro-4,6,11-triazatricyclo[6.4.0.0ˆ[2,6]]dodeca-1(8),2,4,9,11-pentaen-7-yl]ethan-1-ol (3a and 3b)

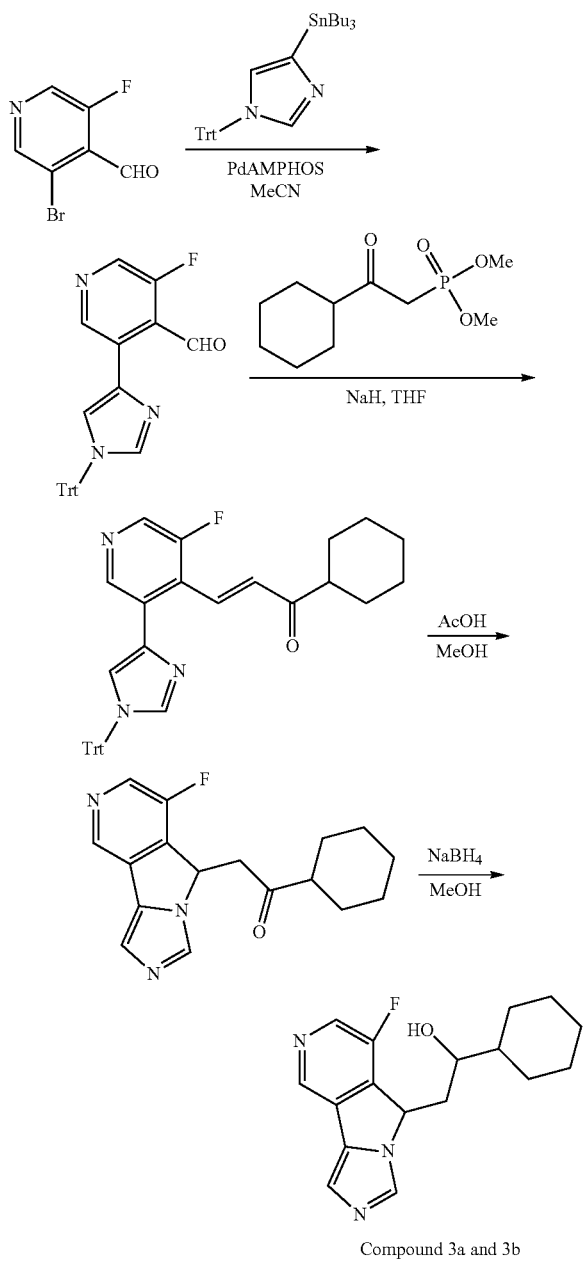

Compound 3a and 3b

3-Fluoro-5-[1-(triphenylmethyl)-1H-imidazol-4-yl]pyridine-4-carbaldehyde

A mixture of 3-bromo-5-fluoropyridine-4-carbaldehyde (406 mg, 1.99 mmol), 4-(tributylstannyl)-1-(triphenylmethyl)-1H-imidazole (Intermediate A, 1.8 g, 3.0 mmol) and PdAMPHOS (142 mg, 0.20 mmol) in acetonitrile (12 mL) was stirred at 100° C. for 4 h under N$_2$ atmosphere. Then the reaction mixture was diluted with water (50 mL) and extracted with ethyl acetate (80 mL×2). The combined organic phase was washed with brine and dried over Na$_2$SO$_4$. The solvent was removed under reduced pressure and the residue was purified by flash chromatography eluting with ethyl acetate in hexane (10% to 30% gradient) to yield 3-fluoro-5-[1-(triphenylmethyl)-1H-imidazol-4-yl]pyridine-4-carbaldehyde (610 mg, 71%) as light yellow oil.

1-Cyclohexyl-3-[3-fluoro-5-[1-(triphenylmethyl)-1H-imidazol-4-yl]pyridin-4-yl]prop-2-en-1-one To a suspension of sodium hydride (60% in oil, 20 mg, 0.50 mmol) in THF (5 mL) was added a solution of dimethyl (2-cyclohexyl-2-oxoethyl)phosphonate (Intermediate C, 107 mg, 0.46 mmol) in THF (2 mL) slowly at 0° C. After stirring for additional 15 min at 0° C., the reaction mixture was added by a solution of 2-fluoro-4-[1-(triphenylmethyl)-1H-imidazol-4-yl]pyridine-3-carbaldehyde (180 mg, 0.42 mmol) in THF (2 mL) carefully. The resulting reaction mixture was then stirred at room temperature for 1 h. The reaction mixture was quenched by the addition of water (25 mL) carefully and the mixture was extracted with ethyl acetate (40 mL×2). The combined organic phase was washed with brine and dried over Na$_2$SO$_4$. The solvent was removed under reduced pressure to yield 1-cyclohexyl-3-[3-fluoro-5-[1-(triphenylmethyl)-1H-imidazol-4-yl]pyridin-4-yl]prop-2-en-1-one (180 mg, 80% crude yield) as yellow oil which was used in next step without further purification.

1-Cyclohexyl-2-[9-fluoro-4,6,11-triazatricyclo[6.4.0.0ˆ[2,6]]dodeca-1(8),2,4,9,11-pentaen-7-yl]ethan-1-one To a solution of 1-cyclohexyl-3-[3-fluoro-5-[1-(triphenylmethyl)-1H-imidazol-4-yl]pyridin-4-yl]prop-2-en-1-one (200 mg, 0.37 mmol) in methanol (6 mL) was added acetic acid (2 mL) slowly at room temperature. The resulting reaction mixture was stirred at 90° C. for 1 h. The solvent was removed under reduced pressure and the residue was dissolved in ethyl acetate (70 mL). The solution was washed with sat. NaHCO$_3$ solution (20 mL×2) and brine, then dried over Na$_2$SO$_4$. The solvent was removed under reduced pressure and the residue was purified by flash chromatography eluting with methanol in dichloromethane (1% to 10% gradient) to yield 1-cyclohexyl-2-[9-fluoro-4,6,10-triazatricyclo[6.4.0.0ˆ[2,6]]dodeca-1(8),2,4,9,11-pentaen-7-yl]ethan-1-one (50 mg, 40% over two steps) as yellow solid. MS: m/z=300.0 [M+H]$^+$.

1-Cyclohexyl-2-[9-fluoro-4,6,11triazatricyclo[6.4.0.0ˆ[2,6]]dodeca-1(8),2,4,9,11-pentaen-7-yl]ethan-1-ol To a solution of 1-cyclohexyl-2-[9-fluoro-4,6,10-triazatricyclo[6.4.0.0ˆ[2,6]]dodeca-1 (8),2,4,9,11-pentaen-7-yl] ethan-1-one (120 mg, 0.40 mmol) in methanol (8 mL) was added sodium borohydride (30.4 mg, 0.80 mmol) slowly at 0° C. The resulting solution was kept stirring at 0° C. for 30 min. The reaction mixture was quenched by water (30 mL) and extracted with ethyl acetate (45 mL×2). The organic phases were combined, washed with brine and dried over Na$_2$SO$_4$. The solvent was removed under reduced pressure and the residue was purified by prep-HPLC under the following conditions: Gemini-NX C18 Column, 21.2×150 mm, 5 μm; acetonitrile in water (with 10 mmol NH$_4$HCO$_3$), 28% isocratic in 20 min.

Compound 3a:

(31 mg, 25.8%, white solid, containing 2 stereoisomers). HPLC: 99.1% purity, RT=0.79 min. MS: m/z=302.1 [M+H]$^+$. $^1$H NMR (300 MHz, CD$_3$OD) δ=8.69 (s, 1H), 8.40 (s, 1H), 8.07 (s, 1H), 7.33 (s, 1H), 5.75 (t, J=4.8 Hz, 1H), 3.30 (s, 1H), 2.58-2.47 (m, 1H), 2.22-2.18 (m, 1H), 1.81-1.60 (m, 5H), 1.31-0.92 (m, 6H).

Compound 3b:

(14 mg, 11.7%, white solid, containing 2 stereoisomers). HPLC: 99.1% purity, RT=0.81 min. MS: m/z=302.1 [M+H]$^+$. $^1$H NMR (300 MHz, CD$_3$OD) δ=8.61 (s, 1H), 8.29 (s, 1H), 7.92 (s, 1H), 7.23 (s, 1H), 5.72-5.68 (m, 1H), 3.51-3.42 (m, 1H), 2.38-2.27 (m, 1H), 1.85-1.50 (m, 6H), 1.33-0.82 (m, 6H).

Example 4: 4-(2-[9-fluoro-4,6,10-triazatricyclo[6.4.0.0^[2,6]]dodeca-1(8),2,4,9,11-pentaen-7-yl]-1-hydroxyethyl)cyclohexan-1-ol (4a and 4b)

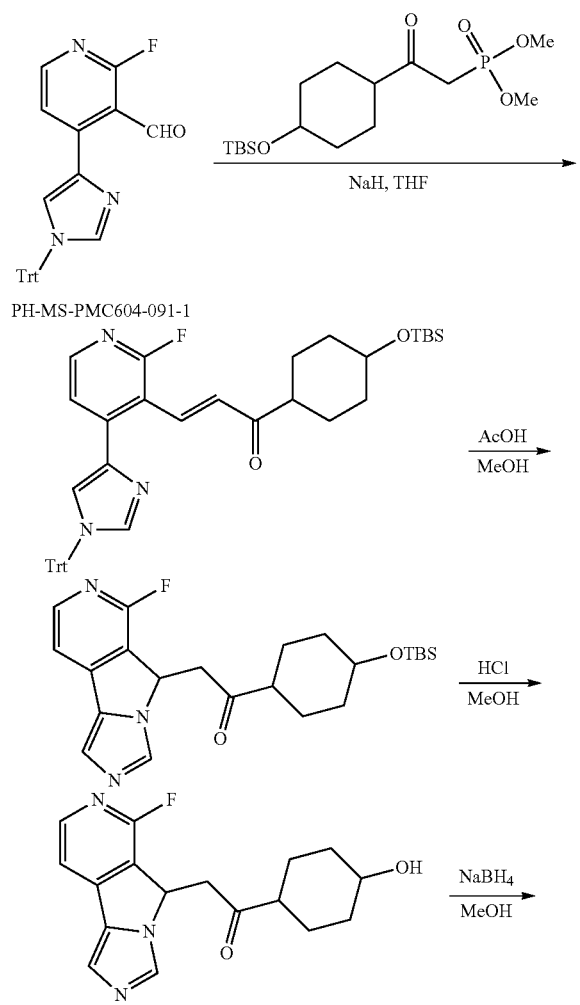

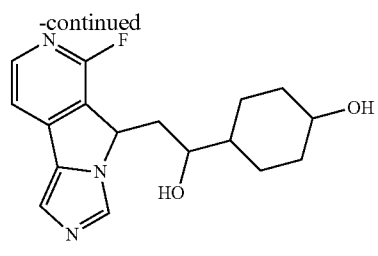

Compound 4a and 4b

1-[4-[(tert-butyldimethylsilyl)oxy]cyclohexyl]-3-[2-fluoro-4-[1-(triphenylmethyl)-1H-imidazol-4-yl]pyridin-3-yl]prop-2-en-1-one To a suspension of sodium hydride (60%, 40 mg, 1.0 mmol) in THF (8 mL) was added a solution of dimethyl (2-[4-[(tert-butyldimethylsilyl)oxy]cyclohexyl]-2-oxoethyl)phosphonate (Intermediate B, 333 mg, 0.91 mmol) in THF (2 mL) slowly at 0° C. After stirring for additional 15 min at 0° C., the reaction mixture was added by a solution of 2-fluoro-4-[1-(triphenylmethyl)-1H-imidazol-4-yl]pyridine-3-carbaldehyde (360 mg, 0.83 mmol) in THF (2 mL). The resulting mixture was then stirred at room temperature for 1 h. The reaction mixture was quenched by water (40 mL) and the mixture was extracted with ethyl acetate (50 mL×2). The combined organic phase was washed with brine and dried over Na$_2$SO$_4$. The solvent was removed under reduced pressure to yield 1-[4-[(tert-butyldimethylsilyl)oxy]cyclohexyl]-3-[2-fluoro-4-[1-(triphenylmethyl)-1H-imidazol-4-yl]pyridin-3-yl]prop-2-en-1-one (430 mg, 77% crude yield) as yellow oil which was used in next step without further purification. MS: m/z=672.4 [M+H]$^+$.

1-[4-[(tert-butyldimethylsilyl)oxy]cyclohexyl]-2-[9-fluoro-4,6,10-triazatricyclo[6.4.0.0^[2,6]]dodeca-1(8),2,4,9,11-pentaen-7-yl]ethan-1-one To a solution of 1-[4-[(tert-butyldimethylsilyl)oxy]cyclohexyl]-3-[2-fluoro-4-[1-(triphenylmethyl)-1H-imidazol-4-yl]pyridin-3-yl]prop-2-en-1-one (430 mg, 0.64 mmol) in methanol (6 mL) was added acetic acid (2 mL) slowly at room temperature. The resulting reaction mixture was stirred at 90° C. for 1 h. The solvent was removed under reduced pressure and the residue was dissolved in ethyl acetate (70 mL). The organic phase was washed with sat. NaHCO$_3$ solution (20 mL×2) and brine, and then dried over Na$_2$SO$_4$. The solvent was removed under reduced pressure and the residue was purified by flash chromatography eluting with methanol in dichloromethane (1% to 5% gradient) to yield 1-[4-[(tert-butyldimethylsilyl)oxy]cyclohexyl]-2-[9-fluoro-4,6,10-triazatricyclo[6.4.0.0^[2,6]]-dodeca-1(8),2,4,9,11-pentaen-7-yl]ethan-1-one (253 mg, 71% over two steps) as yellow oil. MS: m/z=430.2 [M+H]$^+$.

2-[9-fluoro-4,6,10-triazatricyclo[6.4.0.0^[2,6]]dodeca-1(8),2,4,9,11-pentaen-7-yl]-1-(4-hydroxycyclohexyl)ethan-1-one To a solution of 1-[4-[(tert-butyldimethylsilyl)oxy]cyclohexyl]-2-[9-fluoro-4,6,10-triazatricyclo[6.4.0.0^[2,6]]dodeca-1(8),2,4,9,11-pentaen-7-yl]ethan-1-one (250 mg, 0.59 mmol) in methanol (6 mL) was added hydrochloric acid (6 M in water, 2 mL, 12 mmol) slowly. The resulting reaction mixture was stirred at 50° C. for 20 min. The solvent was removed under reduced pressure and the residue was dissolved in ethyl acetate (80 mL). The organic phase was washed with sat. NaHCO₃ solution (20 mL×2) and brine, and then dried over Na₂SO₄. The solvent was removed under reduced pressure and the residue was purified by flash chromatography eluting with methanol in dichloromethane (1% to 8% gradient) to yield 2-[9-fluoro-4,6,10-triazatricyclo[6.4.0.0^[2,6]]dodeca-1(8),2,4,9,11-pentaen-7-yl]-1-(4-hydroxycyclohexyl)ethan-1-one (100 mg, 54%) as yellow oil. MS: m/z=316.0 [M+H]⁺.

4-(2-[9-fluoro-4,6,10-triazatricyclo[6.4.0.0^[2,6]]dodeca-1(8),2,4,9,11-pentaen-7-yl]-1-hydroxyethyl)cyclohexan-1-ol To a solution of 2-[9-fluoro-4,6,10-triazatricyclo[6.4.0.0^[2,6]]dodeca-1(8),2,4,9,11-pentaen-7-yl]-1-(4-hydroxycyclohexyl)ethan-1-one (100 mg, 0.32 mmol) in methanol (5 mL) was added sodium borohydride (24 mg, 0.64 mmol) slowly at 0° C. The resulting mixture was kept stirring at 0° C. for 30 min. The reaction was quenched by water (20 mL) and the mixture was extracted with ethyl acetate (35 mL×5). The combined organic phase was washed with brine and dried over Na₂SO₄. The solvent was removed under reduced pressure and the residue was purified by prep-HPLC to separate the cis- and trans-configuration isomers under the following conditions: Gemini-NX C18 Column, 21.2×150 mm, 5 μm; MeCN in water (with 0.05% TFA), 3% to 10% gradient in 10 min.

Compound 4a:

(19 mg, 19%, white solid, containing 4 stereoisomers) HPLC: 70.9% and 26.2% purity for each pair of enantiomeric products respectively, RT=1.28 and 1.30 min. MS: m/z=318.0 [M+H]⁺. ¹H NMR (300 MHz, CD₃OD) δ=9.32-9.22 (m, 1H), 8.39-8.35 (m, 1H), 8.01 (s, 1H), 7.78-7.74 (m, 1H), 5.98-5.96 (m, 1H), 3.58-3.30 (m, 2H), 2.59-2.52 (m, 1H), 2.14-1.68 (m, 5H), 1.52-1.06 (m, 5H);

Compound 4b:

(17 mg, 17%, white solid, containing 4 stereoisomers) HPLC: 99.3% purity, RT=1.17 min. MS: m/z=318.0 [M+H]⁺. ¹H NMR (300 MHz, CD₃OD) δ=9.28-9.12 (m, 1H), 8.37-8.32 (m, 1H), 7.97 (s, 1H), 7.79-7.73 (m, 1H), 6.08-5.95 (m, 1H), 3.90 (br s s, 1H), 3.59-3.27 (m, 1H), 2.65-2.50 (m, 1H), 2.28-2.04 (m, 1H), 1.80-1.65 (m, 2H), 1.58-1.30 (m, 7H).

Example 5: 1-cyclohexyl-2-[4,6,9-triazatricyclo[6.4.0.0^[2,6]]dodeca-1(8),2,4,9,11-pentaen-7-yl]ethan-1-ol (5a and 5b)

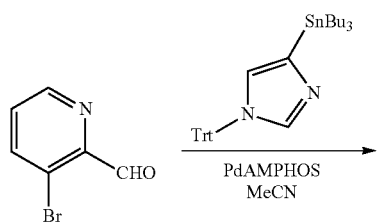

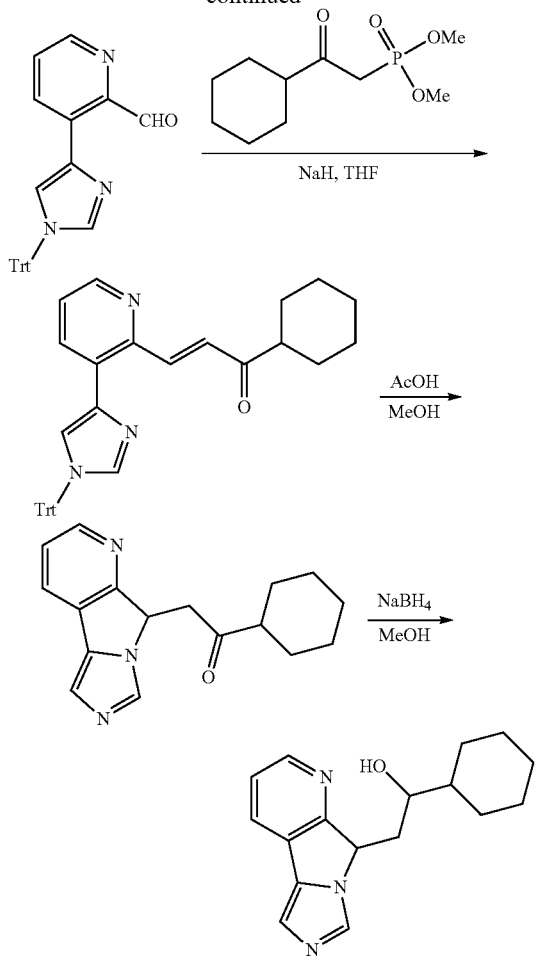

Compound 5a and 5b

3-[1-(Triphenylmethyl)-1H-imidazol-4-yl]pyridine-2-carbaldehyde

A mixture of 3-bromopyridine-2-carbaldehyde (93 mg, 0.50 mmol), 4-(tributylstannyl)-1-(triphenylmethyl)-1H-imidazole (Intermediate A, 360 mg, 0.60 mmol) and PdAMPHOS (35 mg, 0.05 mmol) in acetonitrile (5 mL) was stirred at 100° C. for 4 h under N₂ atmosphere. The resulting reaction mixture was diluted with water (25 mL) and extracted with ethyl acetate (45 mL×2). The combined organic phase was washed with brine and dried over Na₂SO₄. The solvent was removed under reduced pressure and the residue was purified by flash chromatography eluting with ethyl acetate in hexane (10% to 60% gradient) to yield 3-[1-(triphenylmethyl)-1H-imidazol-4-yl]pyridine-2-carbaldehyde (150 mg, 72%) as light yellow oil. MS: m/z=416.0 [M+H]⁺.

1-Cyclohexyl-3-[3-[1-(triphenylmethyl)-1H-imidazol-4-yl]pyridin-2-yl]prop-2-en-1-one To a suspension of sodium hydride (60% in oil, 15 mg, 0.38 mmol) in THF (5 mL) was added a solution of dimethyl (2-cyclohexyl-2-oxoethyl)phosphonate (Intermediate C, 80 mg, 0.34 mmol) in THF (1 mL) slowly at 0° C. After stirring for additional 15 min at 0° C., the reaction mixture was added by a solution of 3-[1-(triphenylmethyl)-1H-imidazol-4-yl]pyridine-2-carbaldehyde (130 mg, 0.31 mmol) in THF (1 mL) slowly. The resulting solution was then stirred at room temperature for 1 h. The reaction was quenched by water (25 mL) and the mixture was extracted with ethyl acetate (40 mL×2). The organic phases were combined, washed with brine and dried over $Na_2SO_4$. The solvent was removed under reduced pressure to yield 1-cyclohexyl-3-[3-[1-(triphenylmethyl)-1H-imidazol-4-yl]pyridin-2-yl]prop-2-en-1-one (150 mg, 92% crude yield) as yellow oil which was used in next step without further purification. MS: m/z=524.2 [M+H]$^+$.

1-Cyclohexyl-2-[4,6,9-triazatricyclo[6.4.0.0^[2,6]]dodeca-1(8),2,4,9,11-pentaen-7-yl]ethan-1-one To a solution of 1-cyclohexyl-3-[3-[1-(triphenylmethyl)-1H-imidazol-4-yl]pyridin-2-yl]prop-2-en-1-one (150 mg, 0.29 mmol) in methanol (3 mL) was added acetic acid (1 mL) slowly at room temperature. The resulting reaction mixture was stirred at 90° C. for 1 h. The solvent was removed under reduced pressure and the residue was dissolved in ethyl acetate (60 mL). The organic phase was washed with sat. $NaHCO_3$ solution (20 mL×2) and brine, and then dried over $Na_2SO_4$. The solvent was removed under reduced pressure and the residue was purified by flash chromatography eluting methanol in dichloromethane (1% to 10% gradient) to yield 1-cyclohexyl-2-[4,6,9-triazatricyclo[6.4.0.0^[2,6]]dodeca-1(8),2,4,9,11-pentaen-7-yl]ethan-1-one (70 mg, 73% over two steps) as yellow oil. MS: m/z=282.1 [M+H]$^+$.

1-Cyclohexyl-2-[4,6,9-triazatricyclo[6.4.0.0^[2,6]]dodeca-1(8),2,4,9,11-pentaen-7-yl]ethan-1-ol To a solution of 1-cyclohexyl-2-[4,6,9-triazatricyclo[6.4.0.0^[2,6]]dodeca-1(8),2,4,9,11-pentaen-7-yl]ethan-1-one (120 mg, 0.42 mmol) in methanol (8 mL) was added sodium borohydride (32 mg, 0.84 mmol) slowly at 0° C. The resulting reaction mixture was kept stirring at 0° C. for 30 min. The reaction mixture was then quenched by water (40 mL) and the mixture was extracted with ethyl acetate (50 mL×2). The combined organic phase was washed with brine and dried over $Na_2SO_4$. The solvent was removed under reduced pressure and the residue was purified by prep-HPLC under the following conditions: XBridge Prep C18 OBD Column, 19×150 mm, 5 μm; acetonitrile in water (with 0.05% TFA), 30% to 80% gradient in 8 min.

Compound 5a:

(25 mg, 20.8%, white solid, containing 2 stereoisomers) HPLC: 90.5% purity, RT=1.29 min. MS: m/z=284.1 [M+H]$^+$. $^1$H NMR (300 MHz, $CD_3OD$) δ=8.29 (m, 1H), 7.98-7.88 (m, 2H), 7.34-7.29 (m, 1H), 7.21-7.18 (m, 1H), 5.39-5.25 (m, 1H), 3.59-3.53 (m, 1H), 2.37-2.28 (m, 1H), 1.83-1.56 (m, 6H), 1.30-1.08 (m, 4H), 1.01-0.80 (m, 2H);

Compound 5b:

(12 mg, 10%, white solid, containing 2 stereoisomers) HPLC: 92.3% purity, RT=1.42 min. MS: m/z=284.1 [M+H]$^+$. $^1$H NMR (300 MHz, $CD_3OD$) δ=8.29 (m, 1H), 7.99 (s, 1H), 7.92-7.89 (m, 1H), 7.32-7.29 (m, 1H), 7.27-7.21 (m, 1H), 5.27-5.23 (m, 1H), 3.74-3.71 (m, 1H), 2.31-2.24 (m, 1H), 2.00-1.90 (m, 1H), 1.79-1.59 (m, 5H), 1.29-1.09 (m, 4H), 1.04-0.89 (m, 2H).

Example 6: 4-[1-hydroxy-2-[4,6,9-triazatricyclo[6.4.0.0^[2,6]]dodeca-1(8),2,4,9,11-pentaen-7-yl]ethyl]cyclohexan-1-ol (6a, 6b, 6c, 6d)

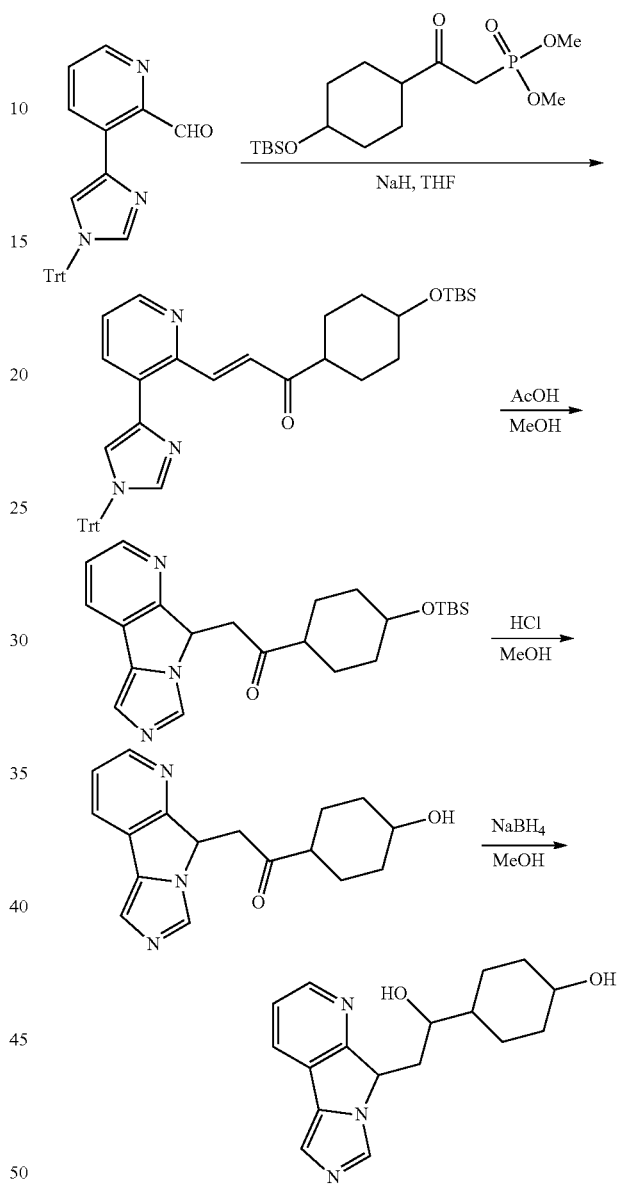

Compound 6a, 6b, 6c, 6d

1-[4-[(Tert-butyldimethylsilyl)oxy]cyclohexyl]-3-[3-[1-(triphenylmethyl)-1H-imidazol-4-yl]pyridin-2-yl]prop-2-en-1-one To a suspension of sodium hydride (60%, 63 mg, 1.58 mmol) in THF (10 mL) was added a solution of dimethyl (2-[4-[(tert-butyldimethylsilyl)oxy]cyclohexyl]-2-oxoethyl)phosphonate (Intermediate B, 531 mg, 1.46 mmol) in THF (2 mL) slowly at 0° C. After stirring for additional 15 min at 0° C., the reaction mixture was added by a solution of 3-[1-(triphenylmethyl)-1H-imidazol-4-yl]pyridine-2-carbaldehyde (550 mg, 1.32 mmol) in THF (2 mL). The resulting solution was then stirred at room temperature for 1 h. The reaction mixture was quenched by water (40 mL) and the mixture was extracted with ethylacetate (60 mL×2). The combined organic phase was washed with brine and dried over $Na_2SO_4$. The solvent was removed under reduced pressure to yield 1-[4-[(tert-butyldimethylsilyl)oxy]cyclohexyl]-3-[3-[1-(triphenylmethyl)-1H-imidazol-4-yl]pyridin-2-yl]prop-2-en-1-one (793 mg, 92% crude yield) as yellow oil which was used in next step without further purification.: m/z=654.2 $[M+H]^+$.

1-[4-[(Tert-butyldimethylsilyl)oxy]cyclohexyl]-2-[4, 6,9-triazatricyclo[6.4.0.0^[2,6]]dodeca-1(8),2,4,9,11-pentaen-7-yl]ethan-1-one To a solution of 1-[4-[(tert-butyldimethylsilyl)oxy]cyclohexyl]-3-[3-[1-(triphenylmethyl)-1H-imidazol-4-yl]pyridin-2-yl]prop-2-en-1-one (793 mg, 1.21 mmol) in methanol (6 mL) was added acetic acid (2 mL) slowly at room temperature. The resulting reaction mixture was stirred at 90° C. for 1.5 h. The solvent was removed under reduced pressure and the residue was dissolved in ethyl acetate (80 mL). The organic phase was washed with sat. $NaHCO_3$ solution (20 mL×2) and brine, and then dried over $Na_2SO_4$. The solvent was removed under reduced pressure and the residue was purified by flash chromatography eluting with methanol in dichloromethane (1% to 7% gradient) to yield 1-[4-[(tert-butyldimethylsilyl)oxy]cyclohexyl]-2-[4,6,9-triazatricyclo[6.4.0.0^[2,6]]dodeca-1(8),2,4,9,11-pentaen-7-yl]ethan-1-one (370 mg, 68% over two steps) as yellow oil. MS: m/z=412.2 $[M+H]^+$.

1-(4-Hydroxycyclohexyl)-2-[4,6,9-triazatricyclo[6.4.0.0^[2,6]]dodeca-1(8),2,4,9,11-pentaen-7-yl]ethan-1-one To a solution of 1-[4-[(tert-butyldimethylsilyl)oxy]cyclohexyl]-2-[4,6,9-triazatricyclo[6.4.0.0^[2,6]]dodeca-1(8),2,4,9,11-pentaen-7-yl]ethan-1-one (370 mg, 0.90 mmol) in methanol (6 mL) was added hydrochloric acid (6 M in water, 2 mL, 12 mmol) slowly. The resulting reaction mixture was stirred at 50° C. for 20 min. The solvent was removed under reduced pressure and the resulting residue was dissolved in ethyl acetate (120 mL). The organic phase was washed with sat. $NaHCO_3$ solution (20 mL×2) and brine, and then dried over $Na_2SO_4$. The solvent was removed under reduced pressure and the residue was purified by flash chromatography eluting with methanol in dichlromethane (1% to 8% gradient) to yield 1-(4-hydroxycyclohexyl)-2-[4,6,9-triazatricyclo[6.4.0.0^[2,6]]dodeca-1(8),2,4,9,11-pentaen-7-yl]ethan-1-one (220 mg, 80%) as yellow solid. MS: m/z=298.0 $[M+H]^+$.

4-[1-hydroxy-2-[4,6,9-triazatricyclo[6.4.0.0^[2,6]]dodeca-1(8),2,4,9,11-pentaen-7-yl]ethyl]cyclohexan-1-ol To a solution of 1-[4-hydroxycyclohexyl]-2-[4,6,9-triazatricyclo[6.4.0.0^[2,6]]dodeca-1(8),2,4,9,11-pentaen-7-yl]ethan-1-one (150 mg, 0.50 mmol) in methanol (8 mL) at 0° C. was added sodium borohydride (37.8 mg, 1.0 mmol) slowly. The resulting reaction mixture was kept stirring at 0° C. for 30 min. The reaction mixture was then quenched by the addition of water (15 mL) carefully and the mixture was extracted with ethyl acetate (40 mL×5). The combined organic phase was washed with brine and dried over $Na_2SO_4$. The solvent was removed under reduced pressure and the residue was purified by prep-HPLC under the following conditions: XBridge Prep C18 OBD Column, 19×150 mm, 5 μm; acetonitrile in water (with 0.05% TFA), 5% to 25% gradient in 10 min.

Compound 6a:

(13 mg, 8.7%, white solid, containing 2 stereoisomers) HPLC: 76.4% purity RT=3.61 min. MS: m/z=300.2 $[M+H]^+$. $^1$H NMR (300 MHz, $CD_3OD$) δ=9.11 (s, 1H), 8.60-8.59 (d, J=4.8 Hz, 1H), 8.24-8.19 (m, 1H), 7.83 (s, 1H), 7.54-7.51 (m, 1H), 5.76-5.63 (m, 1H), 3.43-3.40 (m, 2H), 2.59-2.50 (m, 1H), 2.21-2.06 (m, 1H), 1.94-1.87 (m, 3H), 1.72-1.59 (m, 1H), 1.41-0.97 (m, 5H);

Compound 6b:

(13 mg, 8.7%, white solid, containing 2 stereoisomers) HPLC: 83.6% purity RT=4.32 min. MS: m/z=300.2 $[M+H]^+$. $^1$H NMR (300 MHz, $CD_3OD$) δ=9.18 (s, 1H), 8.61-8.58 (m, 1H), 8.22-8.19 (m, 1H), 7.83 (s, 1H), 7.54-7.49 (m, 1H), 5.65-5.61 (m, 1H), 3.94-3.90 (m, 1H), 3.43-3.40 (m, 1H), 2.56-2.48 (m, 1H), 2.05-1.88 (m, 4H), 1.75-1.72 (m, 1H), 1.32-1.10 (m, 5H);

Compound 6c:

(8 mg, 5.3%, white solid, containing 2 stereoisomers) HPLC: 82.7% purity RT=3.96 min. MS: m/z=300.2 $[M+H]^+$. $^1$H NMR (300 MHz, $CD_3OD$) δ=9.18 (s, 1H), 8.66-8.65 (d, J=4.2 Hz, 1H), 8.29-8.25 (m, 1H), 7.89 (s, 1H), 7.60-7.56 (m, 1H), 5.83-5.69 (m, 1H), 3.94 (br s, 1H), 3.49-3.32 (m, 1H), 2.64-2.54 (m, 1H), 2.31-2.10 (m, 1H), 1.83-1.72 (m, 2H), 1.62-1.31 (m, 7H);

Compound 6d:

(12 mg, 8%, white solid, containing 2 stereoisomers) HPLC: 49.0% purity, RT=0.45 min. MS: m/z=300.1 $[M+H]^+$. $^1$H NMR (300 MHz, $CD_3OD$) δ=9.20 (s, 0.5H), 9.13 (s, 0.5H), 8.61-8.59 (m, 1H), 8.24-8.20 (m, 1H), 7.84 (s, 1H), 7.55-7.49 (m, 1H), 5.80-5.77 (m, 0.5H), 5.67-5.63 (m, 0.5H), 4.85-3.90 (m, 1.5H), 3.41-3.38 (m, 0.5H), 2.60-2.49 (m, 1H), 2.26-2.20 (m, 0.5H), 2.07-2.00 (m, 0.5H), 1.99-1.68 (m, 2H), 1.58-1.26 (m, 7H).

Example 7: Synthesis of 4-fluoro-4-(2-{4,6,9-triazatricyclo[6.4.0.0^[2,6]]dodeca-1(8),2,4,9,11-pentaen-7-yl}ethyl)cyclohexan-1-ol (7a and 7b)

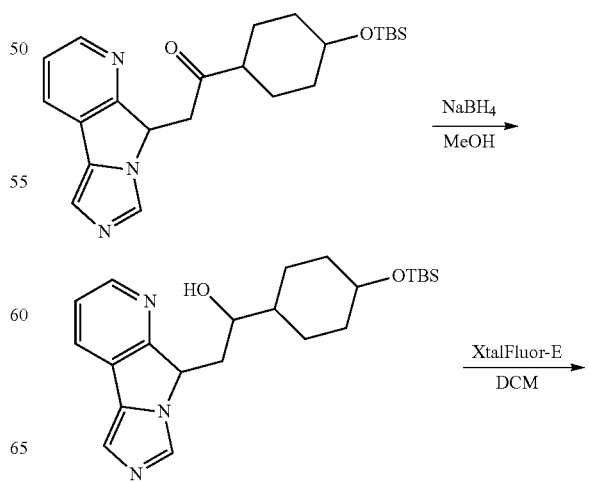

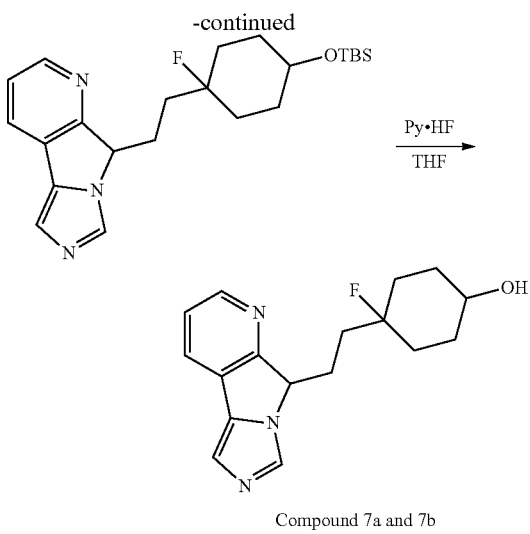

Compound 7a and 7b

1-[4-[(Tert-butyldimethylsilyl)oxy]cyclohexyl]-2-[4,6,9-triazatricyclo[6.4.0.0^[2,6]]dodeca-1(8),2,4,9,11-pentaen-7-yl]ethan-1-ol To a solution of 1-[4-[(tert-butyldimethylsilyl)oxy]cyclohexyl]-2-[4,6,9-triazatricyclo[6.4.0.0^[2,6]]dodeca-1(8),2,4,9,11-pentaen-7-yl]ethan-1-one (see Example 6 prep, 370 mg, 0.90 mmol) in methanol (10 mL) was added sodium borohydride (68 mg, 1.8 mmol) slowly at 0° C. The resulting solution was kept stirring at 0° C. for 30 min. The reaction mixture was then quenched by the addition of water (30 mL) carefully and the reaction mixture was extracted with ethyl acetate (50 mL×3). The combined organic phase was washed with brine and dried over $Na_2SO_4$. The solvent was removed under reduced pressure and the residue was purified by flash chromatography eluting with methanol in dichlromethane (1% to 7% gradient) to yield 1-[4-[(tert-butyldimethylsilyl)oxy]cyclohexyl]-2-[4,6,9-triazatricyclo[6.4.0.0^[2,6]]dodeca-1(8),2,4,9,11-pentaen-7-yl]ethan-1-ol (300 mg, 81%) as colorless foam. MS: m/z=414.1 [M+H]$^+$.

7-(2-{4-[(tert-Butyldimethylsilyl)oxy]-1-fluorocyclohexyl}ethyl)-4,6,9-triazatricyclo[6.4.0.0^[2,6]]dodeca-1(8),2,4,9,11-pentaene At −10° C., to a suspension of XtalFluor-E (249 mg, 1.09 mmol) in dichloromethane (8 mL) was added a solution of 1-[4-[(tert-butyldimethylsilyl)oxy]cyclohexyl]-2-[4,6,9-triazatricyclo[6.4.0.0^[2,6]]dodeca-1(8),2,4,9,11-pentaen-7-yl]ethan-1-ol (300 mg, 0.73 mmol) in dichloromethane (5 mL) slowly. The resulting solution was stirred at −10° C. for 1 h. The reaction mixture was quenched by water (30 mL) and the reaction mixture was extracted with dichloromethane (40 mL×2). The combined organic phase was washed with brine and dried over $Na_2SO_4$. The solvent was removed under reduced pressure and the residue was purified by flash chromatography eluting with methanol in dichloromethane (1% to 5% gradient) to yield 7-(2-{4-[(tert-butyldimethylsilyl)oxy]-1-fluorocyclohexyl}ethyl)-4,6,9-triazatricyclo[6.4.0.0^[2,6]]dodeca-1(8),2,4,9,11-pentaene 7-(2-[4-[(tert-butyldimethylsilyl)oxy]cyclohexyl]-2-fluoroethyl)-4,6,9-triazatricyclo[6.4.0.0^[2,6]]dodeca-1(8),2,4,9,11-pentaene (210 mg, 70%) as colorless oil. MS: m/z=416.3 [M+H]$^+$.

4-Fluoro-4-(2-{4,6,9-triazatricyclo[6.4.0.0^[2,6]]dodeca-1(8),2,4,9,11-pentaen-7-yl}ethyl)cyclohexan-1-ol 4-(1-Fluoro-2-[4,6,9-triazatricyclo[6.4.0.0^[2,6]]dodeca-1(8),2,4,9,11-pentaen-7-yl]ethyl)cyclohexan-1-ol To a solution of 7-(2-{4-[(tert-butyldimethylsilyl)oxy]-1-fluorocyclohexyl}ethyl)-4,6,9-triazatricyclo[6.4.0.0^[2,6]]dodeca-1(8),2,4,9,11-pentaene (180 mg, 0.43 mmol) in anhydrous THF (5 mL) was added Py.HF (0.5 mL, 5.55 mmol) slowly at 0° C. The resulting solution was stirred at room temperature for 2 h. The reaction mixture was quenched by sat. $NaHCO_3$ solution (20 mL) and then extracted with ethyl acetate (40 mL×3). The combined organic phase was washed with brine and dried over $Na_2SO_4$. The solvent was removed under reduced pressure and the resulting residue was purified by prep-HPLC to separate the cis and trans isomers under the following conditions: Gemini-NX C18 Column, 21.2×150 mm, 5 μm; acetonitrile in water (with 10 mmol $NH_4HCO_3$), 5% to 30% gradient in 10 min.

Compound 7a:

(46 mg, 35%, clear oil, containing 2 stereoisomers) HPLC: 99.2% purity, RT=0.96 min. MS: m/z=302.2 [M+H]$^+$. $^1$H NMR (300 MHz, $CD_3OD$, ppm) δ=8.38 (d, J=3.6 Hz, 1H), 8.37-8.00 (m, 2H), 7.39 (m, 1H), 7.28 (s, 1H), 5.37 (t, J=4.8 Hz, 1H), 3.49 (m, 1H), 2.42 (m, 1H), 2.25 (m, 1H), 1.83-1.68 (m, 4H), 1.59-1.21 (m, 6H);

Compound 7b:

(39 mg, 30%, clear oil, containing 2 stereoisomers) HPLC: 99.0% purity, RT=2.27 min. MS: m/z=302.3 [M+H]$^+$. $^1$H NMR (300 MHz, $CD_3OD$, ppm) δ=8.38 (d, J=3.6 Hz, 1H), 8.01-7.98 (m, 2H), 7.39 (m, 1H), 7.29 (s, 1H), 5.35 (t, J=4.8 Hz, 1H), 3.85 (m, 1H), 2.44-2.43 (m, 1H), 2.25 (m, 1H), 1.80-1.21 (m, 10H).

Example 8: 4-[1-hydroxy-2-[4,6,9-triazatricyclo[6.4.0.0^[2,6]]dodeca-1(8),2,4,9,11-pentaen-7-yl]ethyl]cyclohexan-1-ol (8a and 8b)

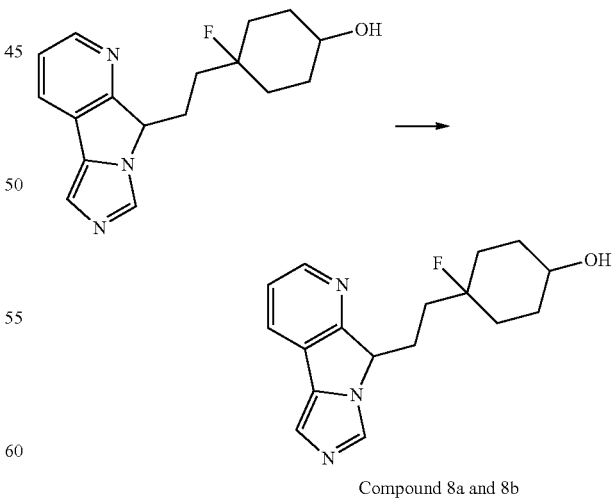

Compound 8a and 8b

Compound 7a was subjected to chiral SFC purification Whelk 01 column, 45% ethanol/0.5% diethylamine, 8 mL/min provide to single enantiomers compound 7a and compound 7b.

Compound 8a:

Retention time 3.98 min; MS: m/z=302.2 [M+H]$^+$. $^1$H NMR (300 MHz, CD$_3$OD) δ=8.38 (d, J=3.6 Hz, 1H), 8.37-8.00 (m, 2H), 7.39 (m, 1H), 7.28 (s, 1H), 5.37 (t, J=4.8 Hz, 1H), 3.49 (m, 1H), 2.42 (m, 1H), 2.25 (m, 1H), 1.83-1.19 (m, 9H);

Compound 8b:

Retention time under chiral purification 4.26 min; MS: m/z=302.2 [M+H]$^+$. $^1$H NMR (300 MHz, CD$_3$OD) δ=8.38 (d, J=3.6 Hz, 1H), 8.37-8.00 (m, 2H), 7.39 (m, 1H), 7.28 (s, 1H), 5.37 (t, J=4.8 Hz, 1H), 3.49 (m, 1H), 2.42 (m, 1H), 2.25 (m, 1H), 1.83-1.19 (m, 9H);

Example 9: 1-Cyclohexyl-2-[4,6,10-triazatricyclo[6.4.0.0ˆ[2,6]]dodeca-1(8),2,4,9,11-pentaen-7-yl]ethan-1-ol (9a and 9b)

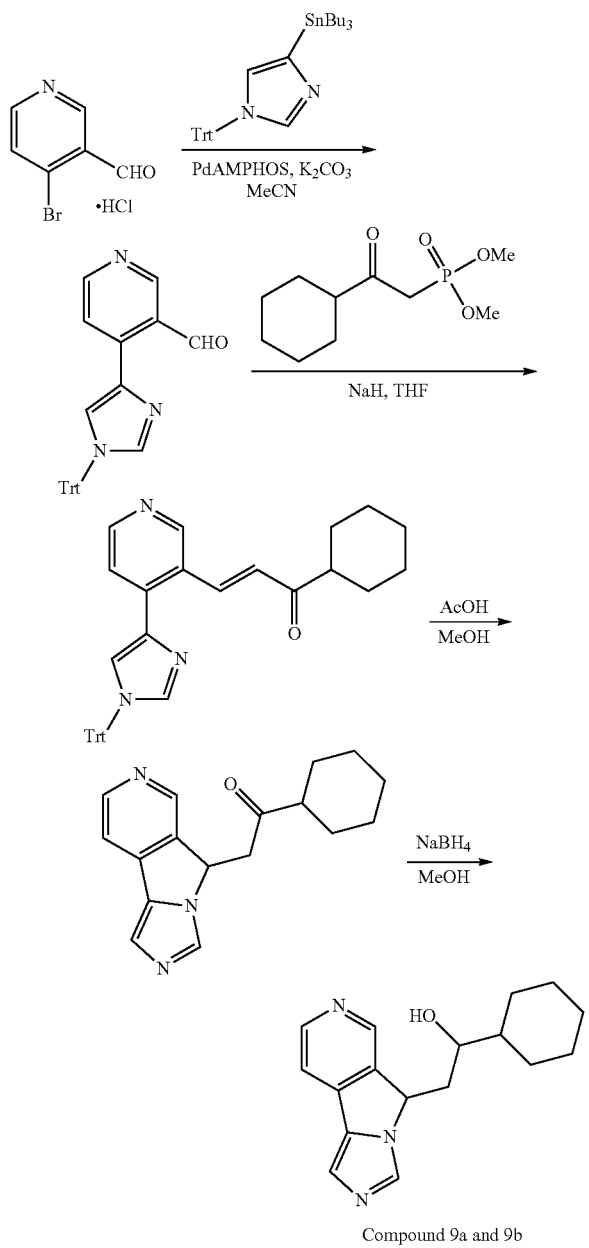

Compound 9a and 9b

4-[1-(Triphenylmethyl)-1H-imidazol-4-yl]pyridine-3-carbaldehyde

A mixture of 4-bromopyridine-3-carbaldehyde hydrochloride (331 mg, 1.49 mmol), 4-(tributylstannyl)-1-(triphenylmethyl)-1H-imidazole (Intermediate A, 1080 mg, 1.80 mmol), K$_2$CO$_3$ (207 mg, 1.50 mmol) and PdAMPHOS (106 mg, 0.15 mmol) in acetonitrile (40 mL) was stirred at 100° C. for 8 h under N$_2$ atmosphere. The resulting reaction mixture was diluted with water (60 mL) and extracted with ethyl acetate (120 mL×2). The combined organic phase was washed with brine and dried over Na$_2$SO$_4$. The solvent was removed under reduced pressure and the residue was purified by flash chromatography eluting with petroleum ether:ethyl acetate (1:1) to yield 4-[1-(triphenylmethyl)-1H-imidazol-4-yl]pyridine-3-carbaldehyde (240 mg, 39%) as light yellow oil. MS: m/z=416.0 [M+H]$^+$.

1-Cyclohexyl-3-[4-[1-(triphenylmethyl)-1H-imidazol-4-yl]pyridin-3-yl]prop-2-en-1-one At 0° C., to a suspension of sodium hydride (60%, 28 mg, 0.70 mmol) in THF (8 mL) was added a solution of dimethyl (2-cyclohexyl-2-oxoethyl)phosphonate (Intermediate C, 149 mg, 0.64 mmol) in THF (2 mL) slowly. After stirring for additional 15 min at 0° C., the reaction mixture was added by a solution of 4-[1-(triphenylmethyl)-1H-imidazol-4-yl]pyridine-3-carbaldehyde (240 mg, 0.58 mmol) in THF (2 mL). The resulting solution was then stirred at room temperature for 1 h. The reaction mixture was quenched by the addition of water (30 mL) carefully and the mixture was extracted with ethyl acetate (60 mL×2). The combined organic phase was washed with brine and dried over Na$_2$SO$_4$. The solvent was removed under reduced pressure to yield 1-cyclohexyl-3-[4-[1-(triphenylmethyl)-1H-imidazol-4-yl]pyridin-3-yl]prop-2-en-1-one (210 mg, 69% crude yield) as yellow oil which was used in next step without further purification. MS: m/z=524.3 [M+H]$^+$.

1-Cyclohexyl-2-[4,6,10-triazatricyclo[6.4.0.0ˆ[2,6]]dodeca-1(8),2,4,9,11-pentaen-7-yl]ethan-1-one To a solution of 1-cyclohexyl-3-[4-[1-(triphenylmethyl)-1H-imidazol-4-yl]pyridin-3-yl]prop-2-en-1-one (200 mg, 0.38 mmol) in methanol (6 mL) was added acetic acid (2 mL) slowly. The resulting reaction mixture was stirred at 90° C. for 1 h. The solvent was removed under reduced pressure and the resulting residue was dissolved in ethyl acetate (80 mL). The organic phase was washed with sat. NaHCO$_3$ solution (20 mL×2) and brine, and then dried over Na$_2$SO$_4$. The solvent was removed under reduced pressure and the residue was purified by flash chromatography eluting with methanol in dichloromethane (1% to 5% gradient) to yield 1-cyclohexyl-2-[4,6,10-triazatricyclo[6.4.0.0ˆ[2,6]]dodeca-1(8),2,4,9,11-pentaen-7-yl]ethan-1-one (100 mg, 64% over two steps) as light yellow oil. MS: m/z=282.0 [M+H]$^+$.

1-Cyclohexyl-2-[4,6,10-triazatricyclo[6.4.0.0ˆ[2,6]]dodeca-1(8),2,4,9,11-pentaen-7-yl]ethan-1-ol To a solution of 1-cyclohexyl-2-[4,6,10-triazatricyclo[6.4.0.0ˆ[2,6]]dodeca-1(8),2,4,9,11-pentaen-7-yl]ethan-1-one (100 mg, 0.36 mmol) in methanol (8 mL) was added sodium borohydride (21 mg, 0.72 mmol) slowly at 0° C. The resulting solution was kept stirring at 0° C. for 30 min. The reaction was then quenched by the addition of water (30 mL) carefully and the reaction mixture was extracted with ethyl acetate (50 mL×2). The combined organic phase was washed with brine and dried over Na$_2$SO$_4$. The solvent was removed under reduced pressure and the residue was purified by Phenomenex Lux Column, 21.2×250 mm, 5 μm; mobile phase, iPrOH (with 0.1% DEA) in hexane; 20% iPrOH isocratic in 33 min.

Compound 9a:

(25 mg, 20.8%, yellow solid, containing two stereoisomers) HPLC: 96.7% purity, RT=1.34 min. MS: m/z=284.2 [M+H]$^+$. $^1$H NMR (300 MHz, DMSO-d$_6$) δ=8.72 (s, 1H), 8.53 (d, J=5.1 Hz, 1H), 8.04 (s, 1H), 7.62 (d, J=8.1 Hz, 1H), 7.38 (s, 1H), 5.57 (m, 1H), 4.99 (m, 1H), 3.61 (m, 1H), 2.82 (m, 1H), 2.20 (m, 1H), 1.83-1.58 (m, 6H), 1.32-0.93 (m, 5H);

Compound 9b:

(12 mg, 10%, yellow solid, containing two stereoisomers) HPLC: 98.4% purity, RT=0.64 min. MS: m/z=284.1 [M+H]$^+$. $^1$H NMR (300 MHz, DMSO-d$_6$) δ=8.72 (s, 1H), 8.53 (d, J=5.1 Hz, 1H), 8.04 (s, 1H), 7.62 (d, J=8.1 Hz, 1H), 7.38 (s, 1H), 5.52 (m, 1H), 4.92 (m, 1H), 3.55 (m, 1H), 2.90 (m, 1H), 2.15 (m, 1H), 1.83-1.58 (m, 6H), 1.32-0.93 (m, 5H).

Example 10: Synthesis of 7-[2-(1-fluorocyclohexyl)ethyl]-4,6,10-triazatricyclo[6.4.0.0^[2,6]]dodeca-1(8),2,4,9,11-pentaene (10a and 10b)

cratic in 15 min. Then the two enantiomers were separated by chiral prep-HPLC under the following conditions: CHIRALPAK IC, 2×25 cm, 5 μm; mobile phase, ethanol in hexane; 30% ethanol isocratic in 25 min; Detector, UV 254/220 nm.

Compound 10a:

(28 mg, 23.3%, yellow oil, containing one stereoisomer) HPLC: 100% purity, RT=1.91 min. MS: m/z=286.1 [M+H]$^+$. $^1$H NMR (300 MHz, CD$_3$OD, ppm) δ=8.59 (s, 1H), 8.44 (d, J=5.1 Hz, 1H), 7.96 (s, 1H), 7.57 (d, J=5.1 Hz, 1H), 7.32 (s, 1H), 5.49 (m, 1H), 2.30-2.28 (m, 1H), 2.16-2.09 (m, 1H), 1.69-1.60 (m, 2H), 1.50-1.10 (m, 10H);

Compound 10b:

(33 mg, 27.5%, yellow oil, containing one stereoisomer) HPLC: 100% purity, RT=1.24 min. MS: m/z=286.1 [M+H]$^+$. $^1$H NMR (300 MHz, CD$_3$OD, ppm) δ=8.55 (s, 1H), 8.43 (d, J=5.1 Hz, 1H), 7.96 (s, 1H), 7.56 (d, J=5.1 Hz, 1H), 7.30 (s, 1H), 5.47 (m, 1H), 2.33-2.25 (m, 1H), 2.17-2.09 (m, 1H), 1.69-1.60 (m, 2H), 1.50-1.10 (m, 10H).

Example 11: 1-cyclohexyl-2-[10-methoxy-4,6,11-triazatricyclo[6.4.0.0^[2,6]]dodeca-1(8),2,4,9,11-pentaen-7-yl]ethan-1-ol (11a and 11b)

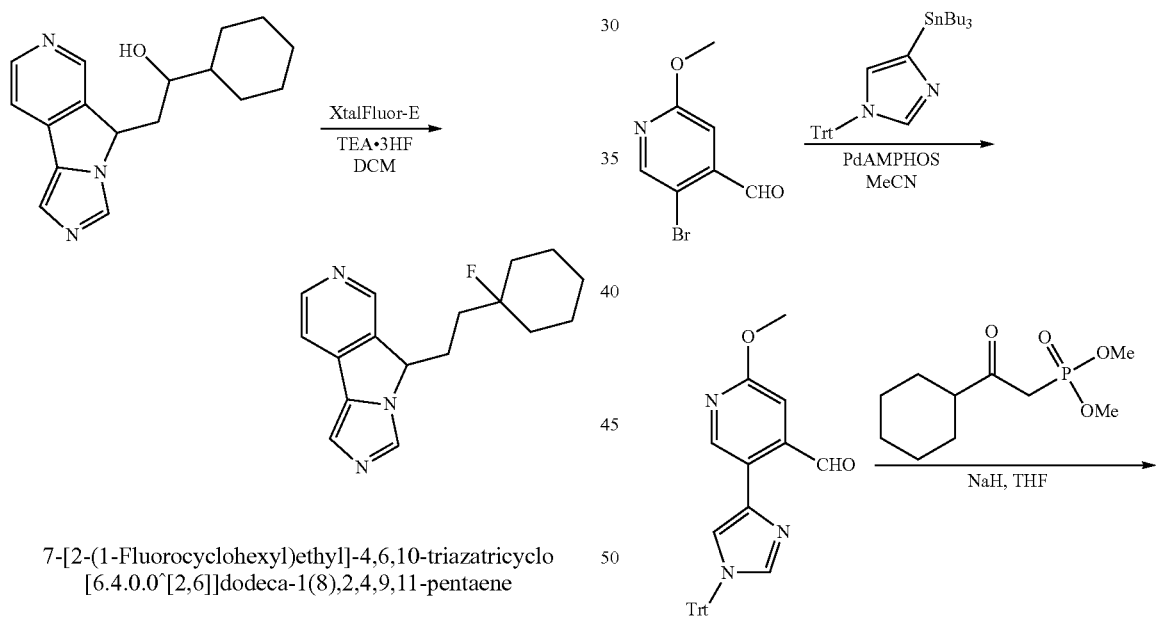

7-[2-(1-Fluorocyclohexyl)ethyl]-4,6,10-triazatricyclo[6.4.0.0^[2,6]]dodeca-1(8),2,4,9,11-pentaene At −10° C., to a suspension of XtalFluor-E (144 mg, 0.64 mmol) in dichloromethane (6 mL) was added a solution of 1-cyclohexyl-2-[4,6,10-triazatricyclo[6.4.0.0^[2,6]]dodeca-1(8),2,4,9,11-pentaen-7-yl]ethan-1-ol (Compound 9a, 120 mg, 0.42 mmol) in dichloromethane (2 mL) and triethylamine hydrogen fluoride (104 mg, 0.64 mmol) successively. The resulting solution was stirred at −10° C. for 2 h. The reaction mixture was then quenched by the addition of water (30 mL) carefully and the reaction mixture was extracted with dichloromethane (40 mL×2). The combined organic phase was washed with brine, and dried over Na$_2$SO$_4$. The solvent was removed under reduced pressure and the residue was first purified by prep-HPLC under the following conditions: Gemini-NX C18 Column, 21.2×150 mm, 5 μm; acetonitrile in water (with 10 mM NH$_4$HCO$_3$), 30% acetonitrile iso-

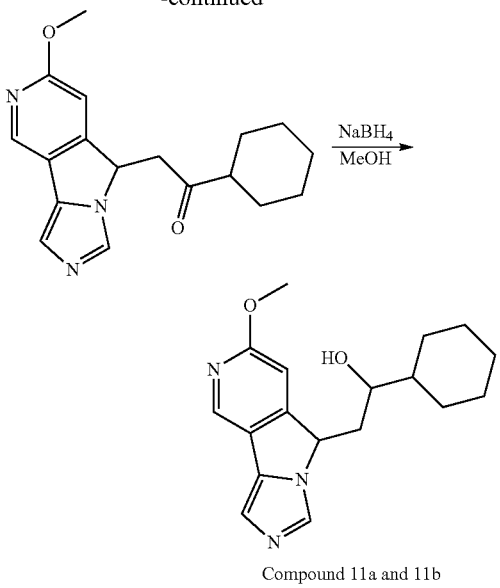

Compound 11a and 11b

2-Methoxy-5-[1-(triphenylmethyl)-1H-imidazol-4-yl]pyridine-4-carbaldehyde

A mixture of 5-bromo-2-methoxypyridine-4-carbaldehyde (430 mg, 1.99 mmol), 4-(tributylstannyl)-1-(triphenylmethyl)-1H-imidazole (Intermediate A, 1800 mg, 3.0 mmol) and PdAMPHOS (142 mg, 0.20 mmol) in acetonitrile (20 mL) was stirred at 100° C. for 8 h under $N_2$ atmosphere. The resulting reaction mixture was diluted with water (40 mL) and extracted with ethyl acetate (80 mL×2). The combined organic phase was washed with brine, and dried over $Na_2SO_4$. The solvent was removed under reduced pressure and the residue was purified by flash chromatography eluting with petroleum ether:ethyl acetate (7:3) to yield 2-methoxy-5-[1-(triphenylmethyl)-1H-imidazol-4-yl]pyridine-4-carbaldehyde (630 mg, 71%) as yellow solid. MS: m/z=446.0 [M+H]$^+$.

1-Cyclohexyl-3-[2-methoxy-5-[1-(triphenylmethyl)-1H-imidazol-4-yl]pyridin-4-yl]prop-2-en-1-one At 0° C., to a suspension of sodium borohydride (60%, 42 mg, 1.05 mmol) in THF (10 mL) was added a solution of dimethyl (2-cyclohexyl-2-oxoethyl)phosphonate (226 mg, 0.96 mmol) in THF (2 mL) slowly. After stirring for additional 15 min at 0° C., the reaction mixture was added by a solution of 2-methoxy-5-[1-(triphenylmethyl)-1H-imidazol-4-yl]pyridine-4-carbaldehyde (390 mg, 0.88 mmol) in THF (3 mL). The resulting solution was then stirred at room temperature for 1 h. The reaction mixture was quenched by water (30 mL) and extracted with ethyl acetate (60 mL×2). The combined organic phase was washed with brine and dried over $Na_2SO_4$. The solvent was removed under reduced pressure to yield 1-cyclohexyl-3-[2-methoxy-5-[1-(triphenylmethyl)-1H-imidazol-4-yl]pyridin-4-yl]prop-2-en-1-one (410 mg, 85% crude yield) as yellow oil which was used in next step without further purification. MS: m/z=554.2 [M+H]$^+$.

1-Cyclohexyl-2-[10-methoxy-4,6,11-triazatricyclo[6.4.0.0^[2,6]]dodeca-1(8),2,4,9,11-pentaen-7-yl]ethan-1-one To a solution of 1-cyclohexyl-3-[2-methoxy-5-[1-(triphenylmethyl)-1H-imidazol-4-yl]pyridin-4-yl]prop-2-en-1-one (400 mg, 0.72 mmol) in methanol (6 mL) was added acetic acid (2 mL) slowly at room temperature. The resulting reaction mixture was stirred at 90° C. for 1 h. The solvent was removed under reduced pressure and the residue was dissolved in ethyl acetate (80 mL). The organic phase was washed with sat. $NaHCO_3$ solution (20 mL×2) and brine, and then dried over $Na_2SO_4$. The solvent was removed under reduced pressure and the residue was purified by flash chromatography eluting with methanol in dichloromethane (1% to 7% gradient) to yield 1-cyclohexyl-2-[10-methoxy-4,6,11-triazatricyclo[6.4.0.0^[2,6]]dodeca-1(8),2,4,9,11-pentaen-7-yl]ethan-1-one (170 mg, 65% over two steps) as light yellow solid. MS: m/z=312.0 [M+H]$^+$.

1-Cyclohexyl-2-[10-methoxy-4,6,11-triazatricyclo[6.4.0.0^[2,6]]dodeca-1(8),2,4,9,11-pentaen-7-yl]ethan-1-ol At 0° C., to a solution of 1-cyclohexyl-2-[10-methoxy-4,6,11-triazatricyclo[6.4.0.0^[2,6]]dodeca-1(8),2,4,9,11-pentaen-7-yl]ethan-1-one (170 mg, 0.54 mmol) in methanol (10 mL) was added sodium borohydride (40.8 mg, 1.08 mmol) slowly. The resulting solution was kept stirring at 0° C. for 30 min. The reaction mixture was quenched by water (30 mL) and extracted with ethyl acetate (50 mL×2). The combined organic phase was washed with brine and dried over $Na_2SO_4$. The solvent was removed under reduced pressure and the residue was purified by Phenomenex Lux Column, 21.2×250 mm, 5 μm; iPrOH in hexane, 20% iPrOH isocratic in 43 min.

Compound 11a:

(19 mg, 11.2%, white solid, containing 2 stereoisomers) HPLC: 93.9% purity, RT=0.89 min. MS: m/z=314.1 [M+H]$^+$. $^1$H NMR (300 MHz, DMSO-$d_6$) δ=8.40 (s, 1H), 7.87 (s, 1H), 7.09 (s, 1H), 7.03 (s, 1H), 5.43 (m, 1H), 4.98 (d, J=6.0 Hz, 1H), 3.88 (s, 3H), 3.58 (m, 1H), 2.17 (m, 1H), 1.86-1.51 (m, 6H), 1.31-0.95 (m, 6H);

Compound 11b:

(83 mg, 48.8%, white solid, containing 2 stereoisomers) HPLC: 95.1% purity, RT=0.87 min. MS: m/z=314.1 [M+H]$^+$. $^1$H NMR (300 MHz, DMSO-$d_6$) δ=8.40 (s, 1H), 7.92 (s, 1H), 7.07 (s, 1H), 7.04 (s, 1H), 5.43 (m, 1H), 4.81 (d, J=6.3 Hz, 1H), 3.89 (s, 3H), 3.51 (m, 1H), 2.12 (m, 1H), 1.88 (m, 1H), 1.78-1.54 (m, 6H), 1.29-0.91 (m, 6H).

Example 12: 1-cyclohexyl-2-[10-methoxy-4,6,11-triazatricyclo[6.4.0.0^[2,6]]dodeca-1(8),2,4,9,11-pentaen-7-yl]ethan-1-ol (12a and 12b)

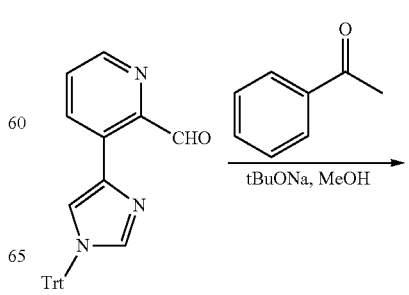

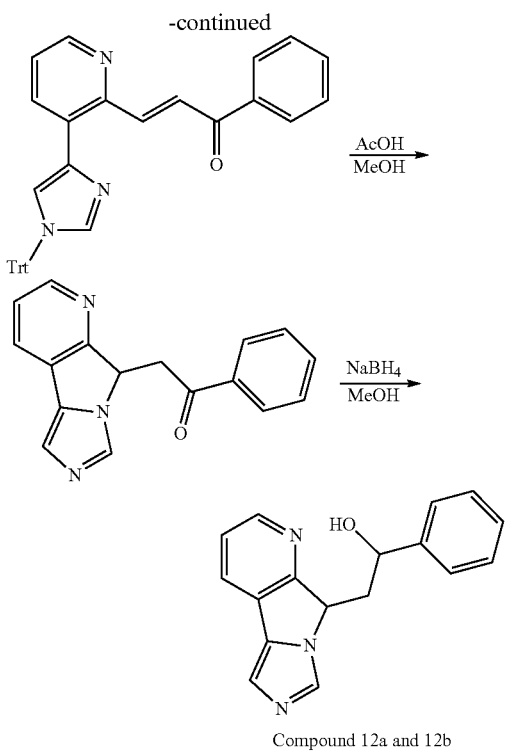

Compound 12a and 12b

1-Phenyl-3-[3-[1-(triphenylmethyl)-1H-imidazol-4-yl]pyridin-2-yl]prop-2-en-1-one At room temperature, to a solution of 3-[1-(triphenylmethyl)-1H-imidazol-4-yl]pyridine-2-carbaldehyde (240 mg, 0.58 mmol) and 1-phenylethan-1-one (76 mg, 0.63 mmol) in methanol (15 mL) was added t-BuONa (67 mg, 0.70 mmol) carefully. The resulting mixture was then stirred 65° C. for 3 h. The reaction mixture was quenched by the addition of water (45 mL) carefully and the mixture was extracted with ethyl acetate (80 mL×2). The combined organic phase was washed with brine and dried over $Na_2SO_4$. The solvent was removed under reduced pressure to yield 1-phenyl-3-[3-[1-(triphenylmethyl)-1H-imidazol-4-yl]pyridin-2-yl]prop-2-en-1-one (234 mg, 78% crude yield) as yellow oil which was used in next step without further purification. MS: m/z=518.1 $[M+H]^+$.

1-Phenyl-2-[4,6,9-triazatricyclo[6.4.0.0^[2,6]]dodeca-1(8),2,4,9,11-pentaen-7-yl]ethan-1-one To a solution of 1-phenyl-3-[3-[1-(triphenylmethyl)-1H-imidazol-4-yl]pyridin-2-yl]prop-2-en-1-one (234 mg, 0.46 mmol) in methanol (6 mL) was added acetic acid (2 mL) slowly at room temperature. The resulting reaction mixture was stirred at 90° C. for 1 h. The solvent was removed under reduced pressure and the residue was dissolved in ethyl acetate (80 mL). The organic phase was washed with sat. $NaHCO_3$ solution (20 mL×2) and brine, and then dried over $Na_2SO_4$. The solvent was removed under reduced pressure and the residue was purified by flash chromatography eluting with methanol in dichloromethane (1% to 8% gradient) to yield 1-phenyl-2-[4,6,9-triazatricyclo[6.4.0.0^[2,6]]dodeca-1(8),2,4,9,111-pentaen-7-yl]ethan-1-one (120 mg, 75% over two steps) as yellow solid. MS: m/z=276.0 $[M+H]^+$.

1-Phenyl-2-[4,6,9-triazatricyclo[6.4.0.0^[2,6]]dodeca-1(8),2,4,9,11-pentaen-7-yl]ethan-1-ol To a solution of 1-phenyl-2-[4,6,9-triazatricyclo[6.4.0.0^[2,6]]dodeca-1(8),2,4,9,11-pentaen-7-yl]ethan-1-one (120 mg, 0.43 mmol) in methanol (10 mL) was added sodium borohydride (34 mg, 0.86 mmol) slowly at 0° C. The resulting solution was kept stirring at 0° C. for 30 min. The reaction was then quenched by the addition of water (30 mL) carefully and the mixture was extracted with ethyl acetate (50 mL×2). The organic phase was washed with brine and dried over $Na_2SO_4$. The solvent was removed under reduced pressure and the residue was purified by prep-HPLC under the following conditions: Shim-pack XR-ODS, 3.0×50 mm, 2.2 μm; acetonitrile in water (with 0.05% TFA), 5% to 100% gradient in 3.6 min.

Compound 12a:

(48 mg, 40%, white solid, containing 2 stereoisomers) HPLC: 99.8% purity, RT=1.37 min. MS: m/z=278.2 $[M+H]^+$. $^1$H NMR (300 MHz, DMSO-$d_6$) δ=8.42 (d, J=5.1 Hz, 1H), 8.01-7.96 (m, 2H), 7.43-7.22 (m, 7H), 5.64-5.62 (d, J=5.7 Hz, 1H), 5.34-5.32 (m, 1H), 5.18-5.12 (m, 1H), 2.35 (m, 1H), 2.25 (m, 1H);

Compound 12b:

(29 mg, 24%, white solid, containing 2 stereoisomers) HPLC: 99.4% purity, RT=1.21 min. MS: m/z=278.1 $[M+H]^+$. $^1$H NMR (300 MHz, DMSO-$d_6$) δ=8.38 (d, J=5.1 Hz, 1H), 8.02-7.98 (m, 2H), 7.43-7.23 (m, 7H), 5.81 (d, J=5.7 Hz, 1H), 5.41-5.38 (m, 1H), 5.08-5.03 (m, 1H), 2.58 (m, 1H), 1.88 (m, 1H).

Example 13: Synthesis of 4-(2-(5H-imidazo[5,1-a]isoindol-5-yl)ethyl)-4-fluorocyclohexanol (13a and 13b)

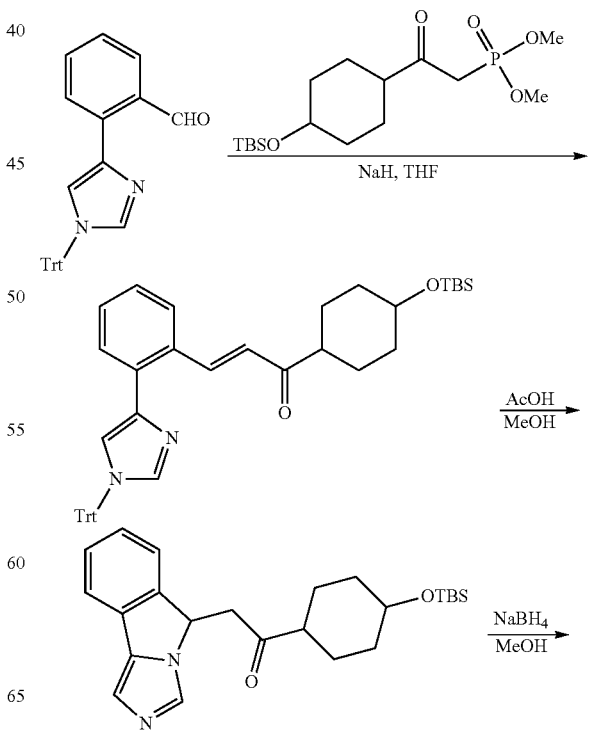

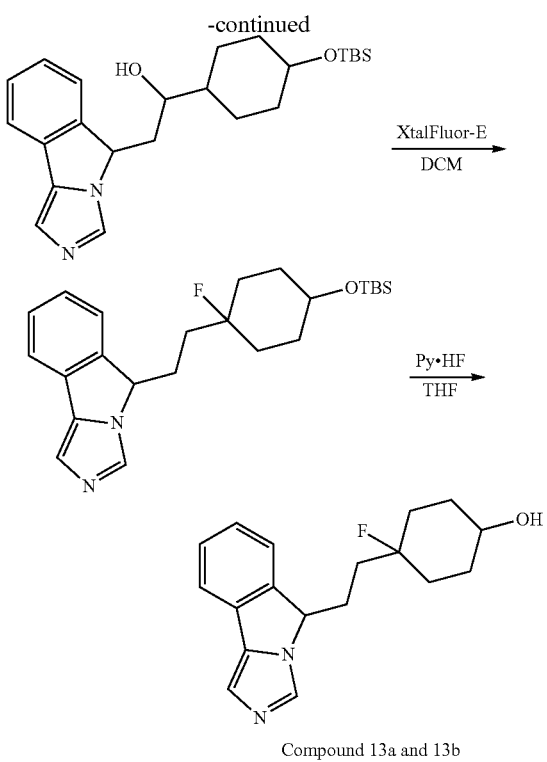

Compound 13a and 13b

1-[4-[(Tert-butyldimethylsilyl)oxy]cyclohexyl]-3-[2-[1-(triphenylmethyl)-1H-imidazol-4-yl]phenyl]prop-2-en-1-one At 0° C., to a suspension of sodium hydride (60% in oil, 116 mg, 2.90 mmol) in THF (10 mL) was added a solution of dimethyl (2-[4-[(tert-butyldimethylsilyl)oxy]cyclohexyl]-2-oxoethyl)phosphonate (Intermediate B, 967 mg, 2.65 mmol) in THF (5 mL) slowly. After stirring for additional 15 min at 0° C., the reaction mixture was added by a solution of 2-[1-(triphenylmethyl)-1H-imidazol-4-yl]benzaldehyde (1 g, 2.41 mmol) in THF (5 mL). The resulting reaction mixture was then stirred at room temperature for 2 h. The reaction was quenched by the addition of water (40 mL) carefully and the resulting mixture was extracted with ethyl acetate (80 mL×3). The combined organic phase was washed with brine and dried over Na$_2$SO$_4$. The solvent was removed under reduced pressure to yield 1-[4-[(tert-butyldimethylsilyl)oxy]cyclohexyl]-3-[2-[1-(triphenylmethyl)-1H-imidazol-4-yl]phenyl] prop-2-en-1-one (1.4 g, 89% crude yield) as yellow oil which was used in next step without further purification. MS: m/z=653.3 [M+H]$^+$.

1-[4-[(Tert-butyldimethylsilyl)oxy]cyclohexyl]-2-[5H-imidazo[4,3-a]isoindol-5-yl]ethan-1-one To a suspension of 1-[4-[(tert-butyldimethylsilyl)oxy]cyclohexyl]-3-[2-[1-(triphenylmethyl)-1H-imidazol-4-yl]phenyl]prop-2-en-1-one (1.4 g, 2.14 mmol) in methanol (12 mL) was added acetic acid (4 mL) slowly at room temperature. The resulting reaction mixture was stirred at 90° C. for 2 h. The solvent was removed under reduced pressure and the residue was dissolved in ethyl acetate (100 mL). The organic phase was washed with sat. NaHCO$_3$ solution (20 mL×2) and brine, and then dried over Na$_2$SO$_4$. The solvent was removed under reduced pressure and the residue was purified by flash chromatography eluting with methanol in dichloromethane (2% to 8% gradient) to yield 1-[4-[(tert-butyldimethylsilyl)oxy]cyclohexyl]-2-[5H-imidazo[4,3-a]isoindol-5-yl]ethan-1-one (410 mg, 34% over two steps) as yellow oil. MS: m/z=411.0 [M+H]$^+$.

1-[4-[(Tert-butyldimethylsilyl)oxy]cyclohexyl]-2-[5H-imidazo[4,3-a]isoindol-5-yl]ethan-1-ol To a solution of 1-[4-[(tert-butyldimethylsilyl)oxy]cyclohexyl]-2-[5H-imidazo[4,3-a]isoindol-5-yl]ethan-1-one (540 mg, 1.32 mmol) in methanol (15 mL) was added sodium borohydride (75 mg, 1.98 mmol) at 0° C. The resulting reaction mixture was kept stirring at 0° C. for 30 min. The reaction was then quenched by the addition of water (45 mL) carefully and the mixture was extracted with ethyl acetate (60 mL×3). The organic phases were combined, washed with brine and dried over Na$_2$SO$_4$. The solvent was removed under reduced pressure and the residue was purified by flash chromatography eluting with methanol in dichloromethane (1% to 5% gradient) to yield 1-[4-[(tert-butyldimethylsilyl)oxy]cyclohexyl]-2-[5H-imidazo[4,3-a]isoindol-5-yl]ethan-1-ol (465 mg, 86%) as yellow oil. MS: m/z=413.2 [M+H]$^+$.

5-(2-{4-[(tert-Butyldimethylsilyl)oxy]-1-fluorocyclohexyl}ethyl)-5H-imidazo[4,3-a]isoindole At −10° C., to a suspension of XtalFluor-E (445 mg, 1.94 mmol) in dichloromethane (10 mL) was added a solution of 1-[4-[(tert-butyldimethylsilyl)oxy]cyclohexyl]-2-[5H-imidazo[4,3-a]isoindol-5-yl]ethan-1-ol (535 mg, 1.30 mmol) in dichloromethane (5 mL). The resulting reaction mixture was stirred at −10° C. for 1 h. The reaction was then quenched by the addition of water (35 mL) carefully and the resulting mixture was extracted with dichloromethane (50 mL×2). The combined organic phase was washed with brine and dried over Na$_2$SO$_4$. The solvent was removed under reduced pressure and the residue was purified by flash chromatography eluting with methanol in dichloromethane (1% to 5% gradient) to yield 5-(2-{4-[(tert-butyldimethylsilyl)oxy]-1-fluorocyclohexyl}ethyl)-5H-imidazo[4,3-a]isoindole (300 mg, 56%) as yellow oil. MS: m/z=415.1 [M+H]$^+$.

4-(2-(5H-imidazo[5,1-a]isoindol-5-yl)ethyl)-4-fluorocyclohexanol

To a solution of 5-(2-{4-[(tert-butyldimethylsilyl)oxy]-1-fluorocyclohexyl}ethyl)-5H-imidazo[4,3-a]isoindole (200 mg, 0.49 mmol) in anhydrous THF (10 mL) was added Py.HF (1 mL, 11.1 mmol) slowly at 0° C. The resulting reaction mixture was then stirred at room temperature for 2 h. The reaction was quenched by sat. NaHCO$_3$ solution (20 mL), and then extracted with ethyl acetate (50 mL×3). The combined organic phase was washed with brine, and dried over Na$_2$SO$_4$. The solvent was removed under reduced pressure and the residue was purified by prep-HPLC under the following conditions: XBridge RP18 OBD Column, 19×150 mm, 5 μm; acetonitrile in water (with 0.05% TFA), 15% to 19% gradient in 11 min.

Compound 13a:

(26 mg, 18%, clear oil, containing 2 stereoisomers) HPLC: 98.0% purity, RT=1.15 min. MS: m/z=301.3 [M+H]$^+$. $^1$H NMR (300 MHz, CD$_3$OD, ppm) δ=9.19 (s, 1H), 7.82 (dd, J=4.2, 3.0 Hz, 1H), 7.75 (s, 1H), 7.63 (m, 1H), 7.54-7.52 (m, 2H), 5.78 (t, J=4.8 Hz, 1H), 3.49 (m, 1H), 2.45 (m, 1H), 2.34 (m, 1H), 1.85-1.68 (m, 4H), 1.56-1.25 (m, 6H);

Compound 13b:

(22 mg, 15%, clear oil, containing 2 stereoisomers) HPLC: 98.4% purity, RT=1.50 min. MS: m/z=301.0 [M+H]+. 1H NMR (300 MHz, CD3OD, ppm) δ=9.21 (s, 1H), 7.82 (m, 1H), 7.75 (s, 1H), 7.62 (m, 1H), 7.55-7.52 (m, 2H), 5.79 (t, J=5.1 Hz, 1H), 3.88 (m, 1H), 2.46 (m, 1H), 2.35 (m, 1H), 1.78-1.25 (m, 10H).

Example 14: (1R,4s)-4-(2-((R)-5H-imidazo[5,1-a]isoindol-5-yl)ethyl)-4-fluorocyclohexan-1-ol (14a) and (1S,4s)-4-(2-((S)-5H-imidazo[5,1-a]isoindol-5-yl)ethyl)-4-fluorocyclohexan-1-ol (14b)

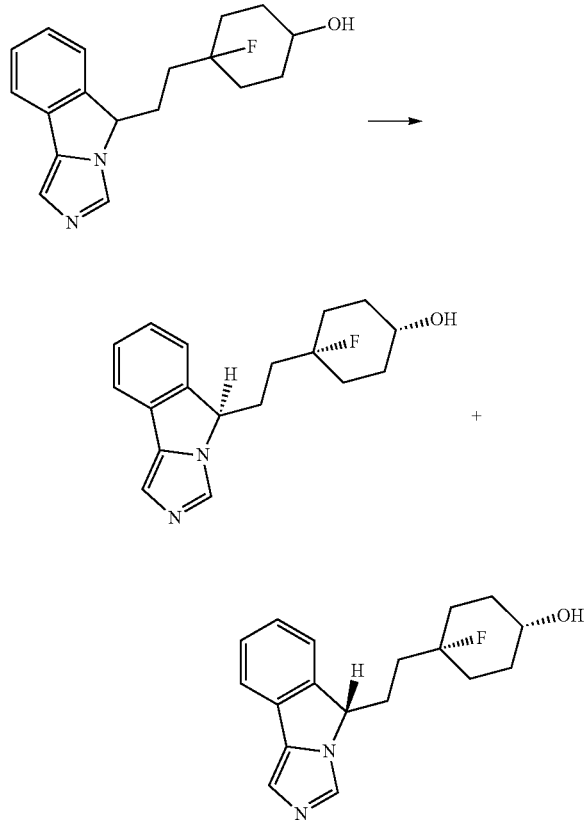

Compound 13a was subjected to chiral SFC under the following conditions IF/S4 chiral prep SFC, isocratic 45% ethanol with 0.1% dimethylamine, 8 mL/min to give two products.

Compound 14a:

retention time 4.2 min; MS: m/z=301.0 [M+H]+. 1H NMR (300 MHz, CD3OD) δ=9.21 (s, 1H), 7.82 (m, 1H), 7.75 (s, 1H), 7.60 (m, 1H), 7.55-7.52 (m, 2H), 5.79 (t, J=5.1 Hz, 1H), 3.88 (m, 1H), 2.46 (m, 1H), 2.35 (m, 1H), 1.78-1.25 (m, 9H).

Compound 14b:

retention time 4.6 min; MS: m/z=301.0 [M+H]+. 1H NMR (300 MHz, CD3OD) δ=9.21 (s, 1H), 7.82 (m, 1H), 7.75 (s, 1H), 7.62 (m, 1H), 7.55-7.52 (m, 2H), 5.79 (t, J=5.1 Hz, 1H), 3.88 (m, 1H), 2.46 (m, 1H), 2.35 (m, 1H), 1.78-1.25 (m, 9H).

Example 15: Synthesis of 7-[2-(1-fluorocyclohexyl)ethyl]-10-methoxy-4,6,11-triazatricyclo[6.4.0.0^[2,6]]dodeca-1(8),2,4,9,11-pentaene (15a and 15b)

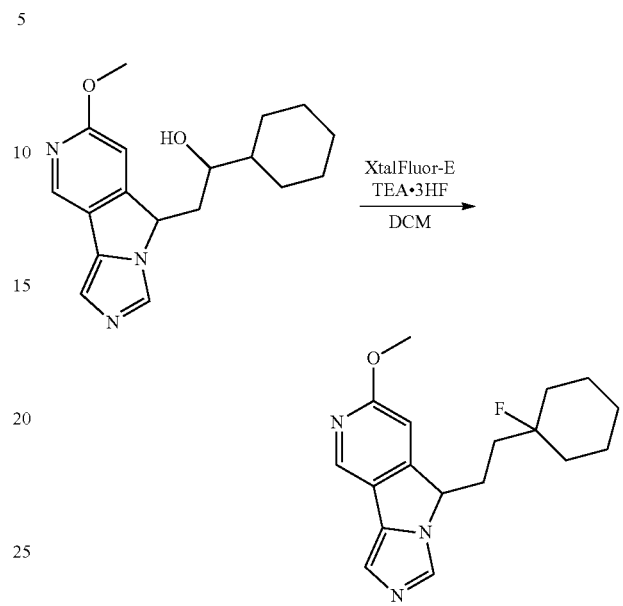

7-[2-(1-Fluorocyclohexyl)ethyl]-10-methoxy-4,6,11-triazatricyclo[6.4.0.0^[2,6]]dodeca-1(8),2,4,9,11-pentaene To a suspension of XtalFluor-E (338 mg, 1.5 mmol) in dichloromethane (10 mL) at −10° C. was added a solution of 1-cyclohexyl-2-[10-methoxy-4,6,11-triazatricyclo[6.4.0.0^[2,6]]dodeca-1(8),2,4,9,11-pentaen-7-yl]ethan-1-ol (Compound 11a, 300 mg, 1.0 mmol) in dichloromethane (5 mL) and triethylamine-hydrogen fluoride (244 mg, 1.5 mmol) successively. The resulting mixture was stirred at −10° C. for 2 h. The reaction was then quenched by the addition of water (40 mL) carefully and the mixture was extracted with dichloromethane (60 mL×2). The combined organic phase was washed with brine and dried over Na2SO4. The solvent was removed under reduced pressure and the residue was purified by prep-HPLC under the following conditions: XBridge RP18 OBD Column, 19×150 mm, 5 μm; acetonitrile in water (with 10 mmol NH4HCO3), 42% to 47% in 8 min. The products were separated by chiral prep-HPLC under the following conditions: Phenomenex Lux, 21.2×250 mm, 5 μm; mobile phase, iPrOH (with 0.1% DEA) in hexane, 30% isocratic in 26 min; Detector, UV 254/220 nm.

Compound 15a:

(45 mg, 15%, yellow oil, containing one stereoisomer) HPLC: 92.5% purity, RT=2.77 min. MS: m/z=316.1 [M+H]+. 1H NMR (300 MHz, CDCl3, ppm) δ=8.32 (s, 1H), 7.79 (s, 1H), 7.17 (s, 1H), 6.76 (s, 1H), 5.27 (t, J=5.4 Hz, 1H), 3.98 (s, 3H), 2.29 (m, 1H), 2.10 (m, 1H), 1.80-1.71 (m, 2H), 1.62-1.18 (m, 10H);

Compound 15b:

(44 mg, 14.7%, yellow oil, containing one stereoisomer) HPLC: 91.6% purity, RT=2.79 min. MS: m/z=316.2 [M+H]+. 1H NMR (300 MHz, CDCl3, ppm) δ=8.32 (s, 1H), 7.76 (s, 1H), 7.17 (br s, 1H), 6.76 (s, 1H), 5.26 (t, J=5.4 Hz, 1H), 3.98 (s, 3H), 2.29 (m, 1H), 2.10 (m, 1H), 1.80-1.71 (m, 2H), 1.62-1.18 (m, 10H).

Example 16: Synthesis of 4-fluoro-4-(2-(6-fluoro-5H-imidazo[5,1-a]isoindol-5-yl)ethyl)cyclohexanol (16a and 16b)

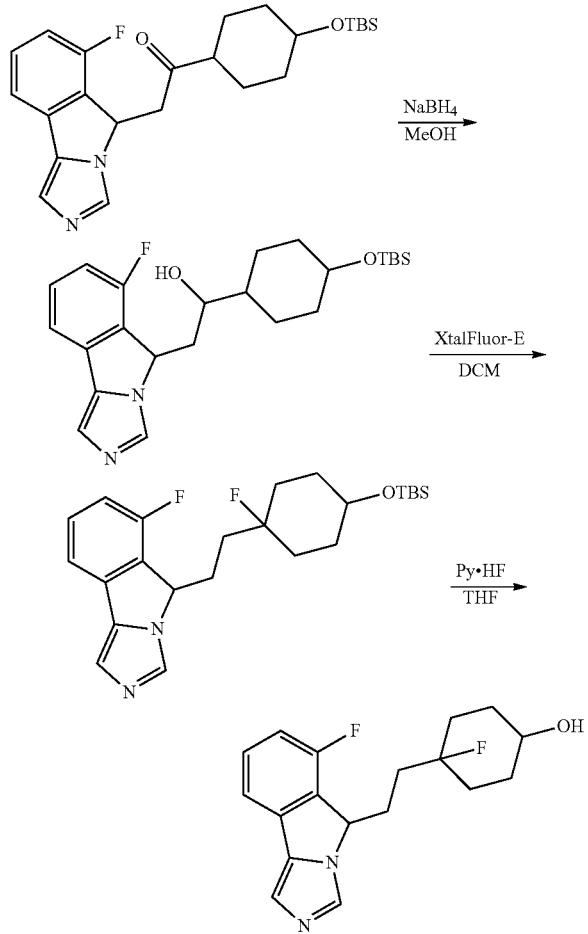

1-[4-[(tert-Butyldimethylsilyl)oxy]cyclohexyl]-2-[6-fluoro-5H-imidazo[4,3-a]isoindol-5-yl]ethan-1-ol To a solution of 1-[4-[(tert-butyldimethylsilyl)oxy]cyclohexyl]-2-[6-fluoro-5H-imidazo[4,3-a]isoindol-5-yl]ethan-1-one (310 mg, 0.72 mmol) in methanol (10 mL) was added sodium borohydride (23 mg, 1.42 mmol) slowly at 0° C. The resulting reaction mixture was kept stirring at 0° C. for 30 min. The reaction mixture was then quenched by the addition of water (30 mL) carefully and the mixture was extracted with ethyl acetate (50 mL×3). The combined organic phase was washed with brine and dried over $Na_2SO_4$. The solvent was removed under reduced pressure and the residue was purified by flash chromatography eluting with methanol in dichloromethane (2% to 5% gradient) to yield 1-[4-[(tert-butyldimethylsilyl)oxy]cyclohexyl]-2-[6-fluoro-5H-imidazo[4,3-a]isoindol-5-yl]ethan-1-ol (290 mg, 93%) as yellow oil. MS: m/z=431.2 [M+H]$^+$.

5-(2-{4-[(tert-Butyldimethylsilyl)oxy]-1-fluorocyclohexyl}ethyl)-6-fluoro-5H-imidazo[4,3-a]isoindole At 0° C., to a suspension of XtalFluor-E (232 mg, 1.01 mmol) in dichloromethane (5 mL) was added a solution of 1-[4-[(tert-butyldimethylsilyl)oxy]cyclohexyl]-2-[6-fluoro-5H-imidazo[4,3-a]isoindol-5-yl]ethan-1-ol (290 mg, 0.67 mmol) in dichloromethane (2 mL) slowly. The resulting reaction mixture was stirred at room temperature for 10 h. The reaction mixture was then quenched by water (25 mL) and the mixture was extracted with dichloromethane (40 mL×2). The combined organic phase was washed with brine and dried over $Na_2SO_4$. The solvent was removed under reduced pressure and the residue was purified by flash chromatography eluting with methanol in dichloromethane (2% to 5% gradient) to yield 5-(2-{4-[(tert-butyldimethylsilyl)oxy]-1-fluorocyclohexyl}ethyl)-6-fluoro-5H-imidazo[4,3-a]isoindole 5 (68 mg, 23%) as yellow oil. MS: m/z=433.2 [M+H]$^+$.

4-Fluoro-4-(2-(6-fluoro-5H-imidazo[5,1-a]isoindol-5-yl)ethyl)cyclohexanol

To a solution of 5-(2-{4-[(tert-butyldimethylsilyl)oxy]-1-fluorocyclohexyl}ethyl)-6-fluoro-5H-imidazo[4,3-a]isoindole (210 mg, 0.49 mmol) in anhydrous THF (10 mL) was added Py·HF (1 mL, 11.1 mmol) slowly at 0° C. The resulting reaction mixture was then stirred at room temperature for 2 h. The reaction was quenched by sat. $NaHCO_3$ solution (20 mL) and then extracted with ethyl acetate (50 mL×3). The combined organic phase was washed with brine, and dried over $Na_2SO_4$. The solvent was removed under reduced pressure and the resulting residue was purified by prep-HPLC under the following conditions: XBridge RP18 OBD Column, 19×150 mm, 5 μm; acetonitrile in water (with 0.05% TFA), 18% to 28% gradient in 9 min.

Compound 16a:

(12 mg, 7.8%, clear oil, containing 2 stereoisomers) HPLC: 96.1% purity, RT=1.77 min. MS: m/z=319.0 [M+H]$^+$. $^1$H NMR (300 MHz, $CD_3OD$, ppm) δ=9.14 (s, 1H), 7.77 (s, 1H), 7.66-7.55 (m, 2H), 7.29-7.23 (t, J=9.0 Hz, 1H), 5.97 (m, 1H), 3.48 (m, 1H), 2.55 (m, 1H), 2.37 (m, 1H), 1.86-1.69 (m, 3H), 1.60-1.40 (m, 3H), 1.35-1.21 (m, 4H).

Compound 16b:

(18 mg, 11.7%, clear oil, containing 2 stereoisomers) HPLC: 96.0% purity, RT=1.55 min. MS: m/z=319.0 [M+H]$^+$. $^1$H NMR (300 MHz, $CD_3OD$, ppm) δ=9.19 (s, 1H), 7.79 (s, 1H), 7.67-7.55 (m, 2H), 7.27 (t, J=9.0 Hz, 1H), 6.01 (m, 1H), 3.87 (m, 1H), 2.55 (m, 1H), 2.38 (m, 1H), 1.80-1.45 (m, 8H), 1.39-1.22 (m, 2H).

Example 17: Synthesis of 10-fluoro-7-[2-(1-fluorocyclohexyl)ethyl]-4,6,9-triazatricyclo[6.4.0.0^[2,6]]dodeca-1(8),2,4,9,11-pentaene

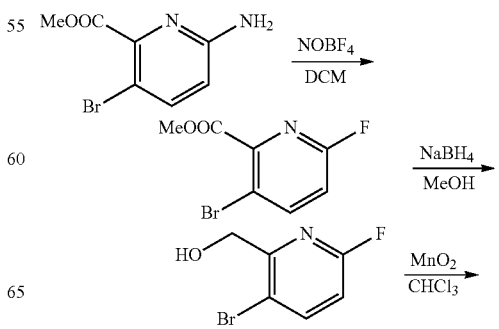

147

-continued

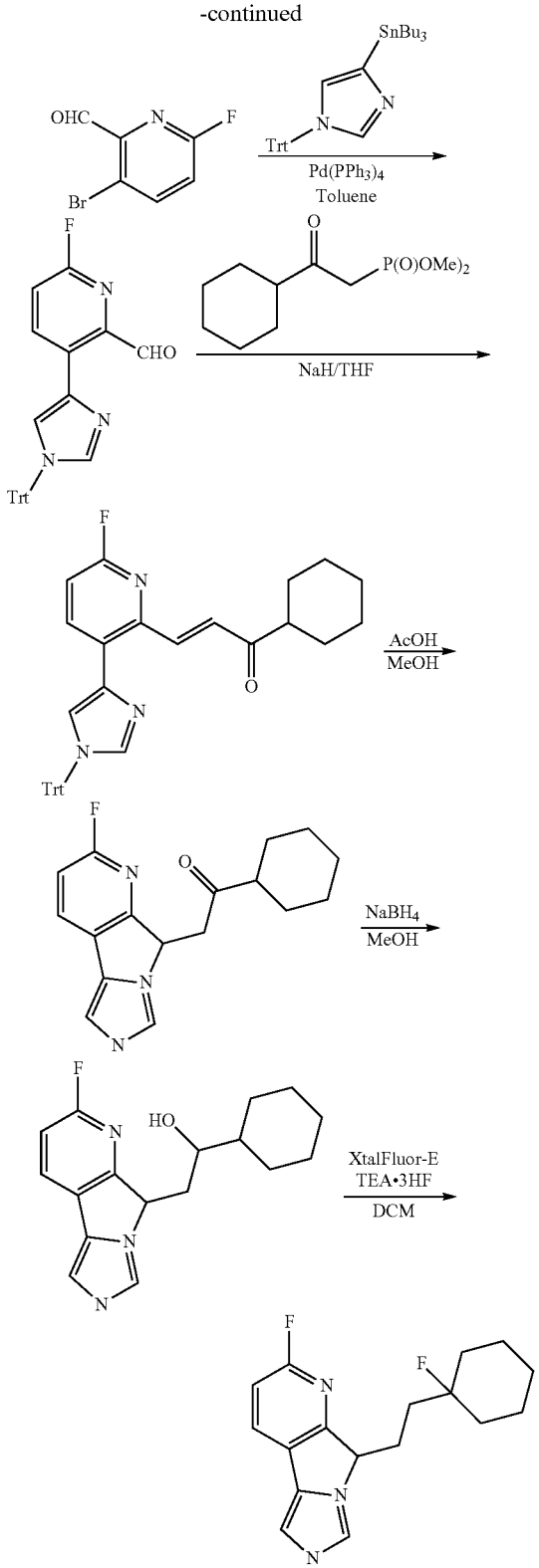

Methyl 3-bromo-6-fluoropyridine-2-carboxylate

At 0° C., to a solution of NOBF₄ (2.28 g, 19.52 mmol) in dichloromethane (60 mL) was added a solution of methyl 6-amino-3-bromopyridine-2-carboxylate (3.45 g, 14.93 mmol) in dichloromethane (15 mL) slowly. The resulting solution was stirred at room temperature for 16 h. The reaction mixture was then quenched by water (100 mL) and extracted with dichloromethane (120 mL×2). The combined organic phase was washed with brine and dried over Na₂SO₄. The solvent was removed under reduced pressure and the residue was purified by flash chromatography eluting with petroleum ether:ethyl acetate (10:1 to 7:3 gradient) to yield methyl 3-bromo-6-fluoropyridine-2-carboxylate (2.4 g, 69%) as light yellow oil. MS: m/z=233.8 [M+H]⁺.

(3-Bromo-6-fluoropyridin-2-yl)methanol

At 0° C., to a solution of methyl 3-bromo-6-fluoropyridine-2-carboxylate (2.4 g, 10.26 mmol) in methanol (40 mL) was added sodium borohydride (1.95 g, 51.54 mmol). The resulting reaction mixture was stirred at room temperature for 5 h. The reaction mixture was then quenched by the addition of water (100 mL) carefully and extracted with ethyl acetate (150 mL×2). The combined organic phase was washed with brine and dried over Na₂SO₄. The solvent was removed under reduced pressure and the residue was purified by flash chromatography eluting with petroleum ether:ethyl acetate (10:1 to 4:1 gradient) to yield (3-bromo-6-fluoropyridin-2-yl)methanol (1.7 g, 80%) as light yellow solid. MS: m/z=205.8 [M+H]⁺.

3-Bromo-6-fluoropyridine-2-carbaldehyde

To a solution of (3-bromo-6-fluoropyridin-2-yl)methanol (2 g, 9.71 mmol) in chloroform (60 mL) was added MnO₂ (8.5 g, 97.77 mmol) at room temperature. The resulting reaction mixture was stirred at 65° C. for 24 h. The reaction mixture was filtered to and the solid was rinsed with chloroform (30 mL×3). The filtrate was combined and concentrated under reduced pressure to yield 3-bromo-6-fluoropyridine-2-carbaldehyde (1.8 g, 91% crude yield) as light yellow solid, which was used in next step without further purification.

6-Fluoro-3-[1-(triphenylmethyl)-1H-imidazol-4-yl] pyridine-2-carbaldehyde

A mixture of 3-bromo-6-fluoropyridine-2-carbaldehyde (406 mg, 1.99 mmol), 4-(tributylstannyl)-1-(triphenylmethyl)-1H-imidazole (Intermediate A, 1.8 g, 3.0 mmol) and Pd(PPh₃)₄(231 mg, 0.20 mmol) in toluene (12 mL) was stirred at 100° C. for 16 h under N₂ atmosphere. The reaction mixture was diluted with water (50 mL) and extracted with ethyl acetate (80 mL×2). The combined organic phase was washed with brine and dried over Na₂SO₄. The solvent was removed under reduced pressure and the residue was purified by flash chromatography eluting with petroleum ether:ethyl acetate (10:1 to 7:3 gradient) to yield 6-fluoro-3-[1-(triphenylmethyl)-1H-imidazol-4-yl]pyridine-2-carbaldehyde (490 mg, 57%) as yellow solid. MS: m/z=434.1 [M+H]⁺.

1-Cyclohexyl-3-[6-fluoro-3-[1-(triphenylmethyl)-1H-imidazol-4-yl]pyridin-2-yl]prop-2-en-1-one At 0° C., to a suspension of sodium hydride (60%, 56 mg, 1.41 mmol) in THF (8 mL) was added a solution of dimethyl (2-cyclohexyl-2-oxoethyl)phosphonate (Intermediate C, 303 mg, 1.29 mmol) in THF (3 mL) slowly. After stirring for additional 15 min at 0° C., the reaction mixture was added by a solution of 6-fluoro-3-[1-(triphenylmethyl)-1H-imidazol-4-yl]pyridine-2-carbaldehyde (510 mg, 1.18 mmol) in THF (3 mL) carefully. The resulting reaction mixture was then stirred at room temperature for 1 h. The reaction was quenched by the addition of water (50 mL) carefully and the mixture was extracted with ethyl acetate (60 mL×2). The combined organic phase was washed with brine and dried over Na$_2$SO$_4$. The solvent was removed under reduced pressure to yield 1-cyclohexyl-3-[6-fluoro-3-[1-(triphenylmethyl)-1H-imidazol-4-yl]pyridin-2-yl]prop-2-en-1-one (540 mg, 85% crude yield) as yellow oil which was used in next step without further purification. MS: m/z=542.3 [M+H]$^+$.

1-Cyclohexyl-2-[10-fluoro-4,6,9-triazatricyclo[6.4.0.0ˆ[2,6]]dodeca-1(8),2,4,9,11-pentaen-7-yl]ethan-1-one To a solution of 1-cyclohexyl-3-[6-fluoro-3-[1-(triphenylmethyl)-1H-imidazol-4-yl]pyridin-2-yl]prop-2-en-1-one (541 mg, 1.0 mmol) in methanol (9 mL) was added acetic acid (3 mL) slowly at room temperature. The resulting reaction mixture was stirred at 90° C. for 2 h. The solvent was removed under reduced pressure and the resulting residue was dissolved in ethyl acetate (80 mL). The organic phase was washed with sat. NaHCO$_3$ solution (20 mL×2) and brine, and then dried over Na$_2$SO$_4$. The solvent was removed under reduced pressure and the residue was purified by flash chromatography eluting with methanol in dichloromethane (50:1 to 95:5 gradient) to yield 1-cyclohexyl-2-[10-fluoro-4,6,9-triazatricyclo[6.4.0.0ˆ[2,6]]dodeca-1(8),2,4,9,11-pentaen-7-yl]ethan-1-one (220 mg, 73% over two steps) as light yellow oil. MS: m/z=300.0 [M+H]$^+$.

1-Cyclohexyl-2-[10-fluoro-4,6,9-triazatricyclo[6.4.0.0ˆ[2,6]]dodeca-1(8),2,4,9,11-pentaen-7-yl]ethan-1-ol To a solution of 1-cyclohexyl-2-[10-fluoro-4,6,9-triazatricyclo[6.4.0.0ˆ[2,6]]dodeca-1 (8),2,4,9,11-pentaen-7-yl]ethan-1-one (110 mg, 0.37 mmol) in methanol (8 mL) was added sodium borohydride (28 mg, 0.74 mmol) slowly at 0° C. The resulting reaction mixture was kept stirring at 0° C. for 30 min. The reaction was then quenched by the addition of water (20 mL) carefully and the mixture was extracted with ethyl acetate (40 mL×2). The combined organic phase was washed with brine and dried over Na$_2$SO$_4$. The solvent was removed under reduced pressure and the residue was purified by flash chromatography eluting with methanol in dichloromethane (50:1 to 93:7 gradient) to yield 1-cyclohexyl-2-[10-fluoro-4,6,9-triazatricyclo[6.4.0.0ˆ[2,6]]dodeca-1(8),2,4,9,11-pentaen-7-yl]ethan-1-ol (90 mg, 82%) as light yellow solid. MS: m/z=302.0 [M+H]$^+$.

10-Fluoro-7-[2-(1-fluorocyclohexyl)ethyl]-4,6,9-triazatricyclo[6.4.0.0ˆ[2,6]]dodeca-1(8),2,4,9,11-pentaene At 0° C., to a suspension of XtalFluor-E (103 mg, 0.45 mmol) in dichlromethane (5 mL) was added a solution of 1-cyclohexyl-2-[10-fluoro-4,6,9-triazatricyclo[6.4.0.0ˆ[2,6]]dodeca-1(8),2,4,9,11-pentaen-7-yl]ethan-1-ol (90 mg, 0.30 mmol) in dichloromethane (1 mL) and TEA.3HF (72 mg, 0.45 mmol) successively. The resulting reaction mixture was stirred at 0° C. for 1 h. The reaction was then quenched by the addition of water (30 mL) carefully and the mixture was extracted with dichloromethane (40 mL×2). The combined organic phase was washed with brine and dried over Na$_2$SO$_4$. The solvent was removed under reduced pressure and the residue was purified by prep-HPLC to under the following conditions: Gemini-NX C18 Column, 21.2×150 mm, 5 µm; MeCN in water (with 0.05% TFA), 5% to 30% in 10 min. 7-[2-cyclohexyl-2-fluoroethyl]-10-fluoro-4,6,9-triazatricyclo[6.4.0.0ˆ[2,6]]dodeca-1(8),2,4,9,11-pentaene (17), 541 nM 28 mg, 31%, clear oil, containing 2 stereoisomers) HPLC: 86.6% purity, RT=2.27 min. MS: m/z=304.1 [M+H]$^+$. $^1$H NMR (300 MHz, CD$_3$OD, ppm) δ=9.22 (s, 1H), 8.35 (t, J=7.5 Hz, 1H), 7.80 (s, 1H), 7.23 (d, J=8.4 Hz, 1H), 5.62 (t, J=6.0 Hz, 1H), 2.47-2.32 (m, 2H), 1.88-1.67 (m, 2H), 1.58-1.19 (m, 10H).

Example 18: Synthesis of 7-[2-(1-fluorocyclohexyl)ethyl]-4,6,9-triazatricyclo[6.4.0.0ˆ[2,6]]dodeca-1(8),2,4,9,11-pentaene (18a and 18b)

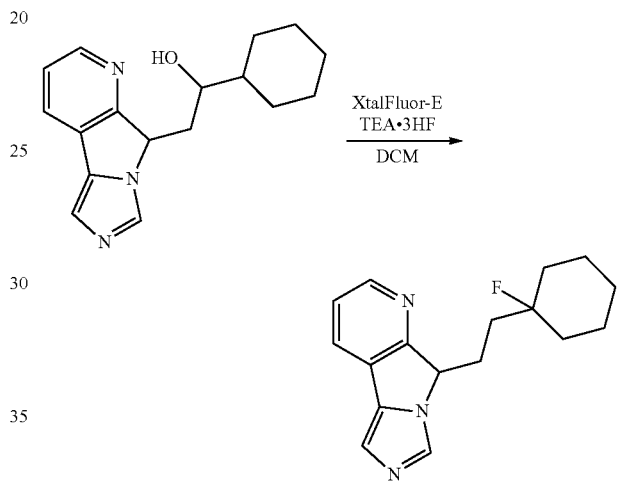

Compound 18a and 18b

7-[2-(1-Fluorocyclohexyl)ethyl]-4,6,9-triazatricyclo[6.4.0.0ˆ[2,6]]dodeca-1(8),2,4,9,11-pentaene At 0° C., to a suspension of XtalFluor-E (449 mg, 1.96 mmol) in dichloromethane (10 mL) was added a solution of 1-cyclohexyl-2-[4,6,9-triazatricyclo[6.4.0.0ˆ[2,6]]dodeca-1(12),2,4,8,10-pentaen-7-yl]ethan-1-ol (see Example 5, 370 mg, 1.31 mmol) in dichloromethane (5 mL) and TEA.3HF (316 mg, 1.96 mmol) successively. The resulting reaction mixture was stirred at 0° C. for 1 h. The reaction was then quenched by the addition of water (30 mL) carefully and the mixture was extracted with dichloromethane (50 mL×2). The combined organic phase was washed with brine and dried over Na$_2$SO$_4$. The solvent was removed under reduced pressure and the residue was purified by prep-HPLC under the following conditions: XBridge RP18 OBD Column, 19×150 mm, 5 µm; acetonitrile in water (with 10 mmol NH$_4$HCO$_3$), 25% to 63% in 10 min. Then two enantiomers were separated by chiral prep-HPLC oil under the following conditions: Chiralpak IC, 20×250 mm, 5 µm; mobile phase, EtOH in hexane, 30% isocratic in 25 min; Detector, UV 254/220 nm.

Compound 18a:
(46 mg, 12.4%, clear oil, containing 1 stereoisomer) HPLC: 97.8% purity, RT=0.95 min. MS: m/z=286.1 [M+H]$^+$. $^1$H NMR (300 MHz, CDCl$_3$, ppm) δ=8.41 (dd, J=5.1, 1.5 Hz, 1H), 7.82-7.79 (m, 2H), 7.31-7.26 (m, 2H), 5.20 (t, J=5.7 Hz, 1H), 2.39 (m, 1H), 2.22 (m, 1H), 1.85-1.75 (m, 2H), 1.61-1.17 (m, 10H).

Compound 18b (44 mg, 11.9%, clear oil, containing 1 stereoisomer) HPLC: 97.7% purity, RT=0.96 min. MS: m/z=286.0 [M+H]$^+$. $^1$H NMR (300 MHz, CDCl$_3$, ppm) δ=8.41 (dd, J=5.1, 1.5 Hz, 1H), 7.82-7.79 (m, 2H), 7.31-7.26 (m, 2H), 5.20 (t, J=5.4 Hz, 1H), 2.39 (m, 1H), 2.22 (m, 1H), 1.85-1.75 (m, 2H), 1.61-1.17 (m, 10H).

Example 19: Synthesis of 6-fluoro-5-(2-(1-fluorocyclohexyl)ethyl)-5H-imidazo[5,1-a]isoindole (19a and 19b)

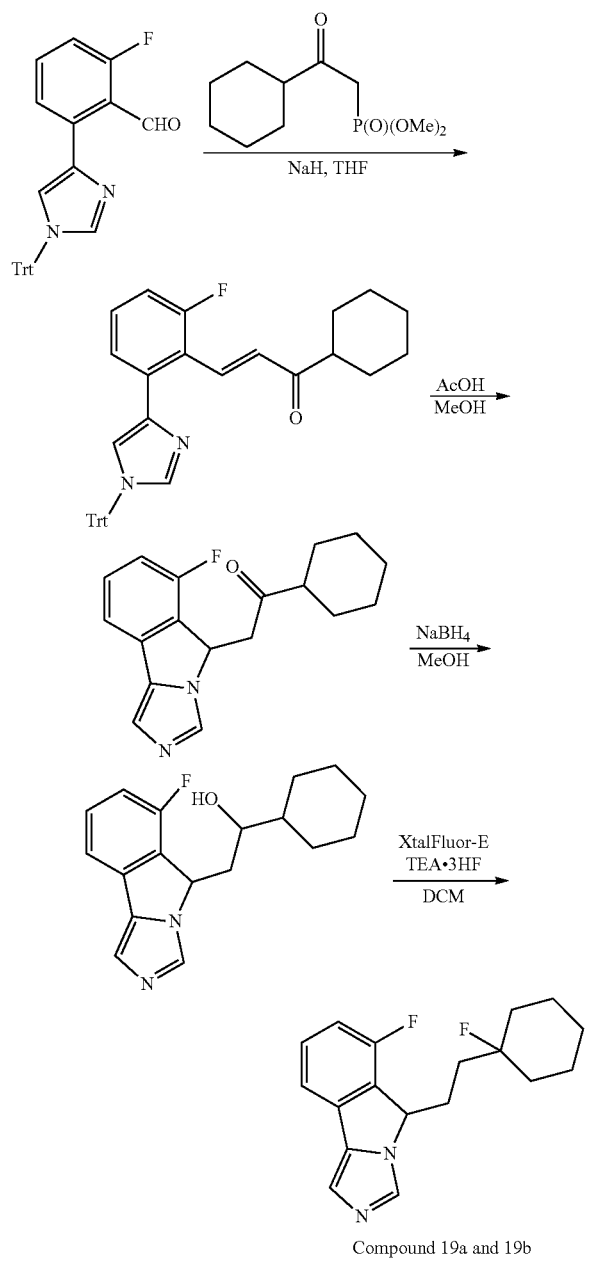

Compound 19a and 19b

1-Cyclohexyl-3-[2-fluoro-6-[1-(triphenylmethyl)-1H-imidazol-4-yl]phenyl]prop-2-en-1-one At 0° C., to a suspension of sodium hydride (60%, 33 mg, 0.83 mmol) in THF (5 mL) was added a solution of dimethyl (2-cyclohexyl-2-oxoethyl)phosphonate (Intermediate C, 179 mg, 0.76 mmol) in THF (2 mL) slowly. After stirring for additional 15 min at 0° C., a solution of 2-fluoro-6-[1-(triphenylmethyl)-1H-imidazol-4-yl]benzaldehyde (300 mg, 0.69 mmol) in THF (3 mL) was added carefully. The resulting reaction mixture was then stirred at room temperature for 1 h. The reaction mixture was quenched by the addition of water (30 mL) carefully and the mixture was extracted with ethyl acetate (50 mL×2). The combined organic phase was washed with brine and dried over Na$_2$SO$_4$. The solvent was removed under reduced pressure and dried in vacuo to yield 1-cyclohexyl-3-[2-fluoro-6-[1-(triphenylmethyl)-1H-imidazol-4-yl]phenyl]prop-2-en-1-one as yellow oil (350 mg, 93%, crude yield) which was used in next step without further purification. MS: m/z=541.3 [M+H]$^+$.

1-Cyclohexyl-2-[6-fluoro-5H-imidazo[4,3-a]isoindol-5-yl]ethan-1-one

To a solution of 1-cyclohexyl-3-[2-fluoro-6-[1-(triphenylmethyl)-1H-imidazol-4-yl]phenyl]prop-2-en-1-one (400 mg, 0.74 mmol) in methanol (9 mL) was added acetic acid (3 mL) slowly at room temperature. The resulting reaction mixture was stirred at 90° C. for 1 h. The solvent was removed under reduced pressure and the resulting residue was dissolved in ethyl acetate (80 mL). The organic phase was washed with sat. NaHCO$_3$ solution (20 mL×2) and brine, and then dried over Na$_2$SO$_4$. The solvent was removed under reduced pressure and the residue was purified by flash chromatography eluting with methanol in dichloromethane (2% to 5% gradient) to yield 1-cyclohexyl-2-[6-fluoro-5H-imidazo[4,3-a]isoindol-5-yl]ethan-1-one as yellow oil (150 mg, 73% over two steps). MS: m/z=299.0 [M+H]$^+$.

1-Cyclohexyl-2-[6-fluoro-5H-imidazo[4,3-a]isoindol-5-yl]ethan-1-ol

At 0° C., to a solution of 1-cyclohexyl-2-[6-fluoro-5H-imidazo[4,3-a]isoindol-5-yl]ethan-1-one (200 mg, 0.67 mmol) in methanol (8 mL) was added sodium borohydride (38 mg, 1.0 mmol) slowly. The resulting reaction mixture was kept stirring at 0° C. for 30 min. The reaction mixture was then quenched by the addition of water (30 mL) carefully and the mixture was extracted with ethyl acetate (50 mL×2). The combined organic phase was washed with brine and dried over Na$_2$SO$_4$. The solvent was removed under reduced pressure and the residue was purified by flash chromatography eluting with methanol in dichloromethane (2% to 6% gradient) to yield 1-cyclohexyl-2-[6-fluoro-5H-imidazo[4,3-a]isoindol-5-yl]ethan-1-ol as yellow oil (180 mg, 89%). MS: m/z=301.0 [M+H]$^+$.

6-Fluoro-5-(2-(1-fluorocyclohexyl)ethyl)-5H-imidazo[5,1-a]isoindole

At −10° C., to a suspension of XtalFluor-E (172 mg, 0.75 mmol) in dichloromethane (5 mL) was added a solution of 1-cyclohexyl-2-[6-fluoro-5H-imidazo[4,3-a]isoindol-5-yl]ethan-1-ol (150 mg, 0.50 mmol) in dichloromethane (2 mL) and TEA.3HF (121 mg, 0.75 mmol) successively. The resulting reaction mixture was stirred at −10° C. for 1 h. The reaction mixture was then quenched by water (25 mL) and the mixture was extracted with dichloromethane (30 mL×2). The combined organic phase was washed with brine and dried over Na$_2$SO$_4$. The solvent was removed under reduced pressure and the residue was purified by prep-HPLC under the following conditions: XBridge RP18 OBD Column, 19×150 mm, 5 μm; acetonitrile in water (with 10 mM NH$_4$HCO$_3$), 46% to 58% in 10 min. Then the two products were separated by chiral prep-HPLC under the following conditions: CHIRALCEL OJ-H, 20×250 mm, 5 μm; mobile phase, iPrOH in hexane, 30% isocratic in 11 min; Detector, UV 254/220 nm.

Compound 19a (33 mg, 22%, clear oil, containing 1 stereoisomer) HPLC: 99.9% purity, RT=1.17 min. MS: m/z=303.0 [M+H]$^+$. $^1$H NMR (300 MHz, CDCl$_3$, ppm) δ=7.93 (s, 1H), 7.43-7.40 (m, 2H), 7.17 (s, 1H), 7.02 (m, 1H), 5.62 (t, J=4.5 Hz, 1H), 2.41 (m, 1H), 2.22 (m, 1H), 1.70-1.61 (m, 2H), 1.56-1.37 (m, 6H), 1.30-1.09 (m, 4H).

Compound 19b:

(31 mg, 20.7%, clear oil, containing 1 stereoisomer) HPLC: 99.9% purity, RT=1.16 min. MS: m/z=303.0 [M+H]$^+$. $^1$H NMR (300 MHz, CDCl$_3$, ppm) δ=7.93 (s, 1H), 7.43-7.40 (m, 2H), 7.17 (s, 1H), 7.04-7.00 (m, 1H), 5.62 (t, J=4.5 Hz, 1H), 2.41 (m, 1H), 2.23 (m, 1H), 1.70-1.61 (m, 2H), 1.56-1.37 (m, 6H), 1.30-1.09 (m, 4H).

Example 20: 1-cyclohexyl-2-[5H-imidazo[4,3-a]isoindol-5-yl]ethan-1-amine (20a and 20b)

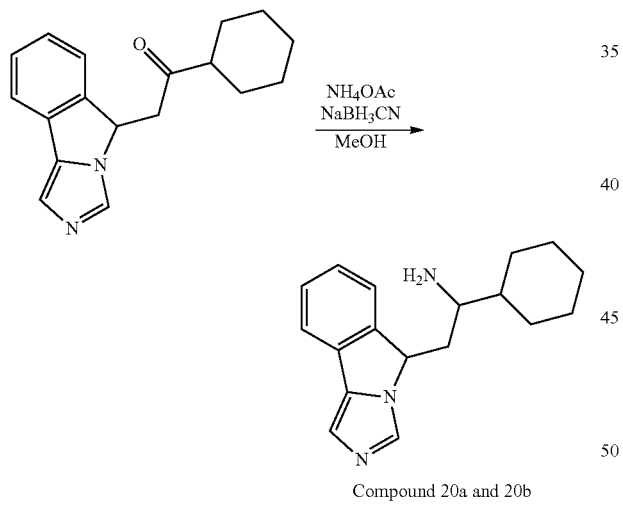

Compound 20a and 20b

1-Cyclohexyl-2-[5H-imidazo[4,3-a]isoindol-5-yl]ethan-1-amine

To a solution of 1-cyclohexyl-2-[5H-imidazo[4,3-a]isoindol-5-yl]ethan-1-one (315 mg, 1.12 mmol) in methanol (10 mL) was added ammonium acetate (867 mg, 11.25 mmol) and sodium cyanoborhydride (106 mg, 1.69 mmol) successively at room temperature. The resulting reaction mixture was stirred at 60° C. for 3 d in a sealed tube. The reaction mixture was then quenched by the addition of water (15 mL) carefully and the mixture was extracted with ethyl acetate (40 mL×5). The combined organic phases was washed with brine and dried over Na$_2$SO$_4$. The solvent was removed under reduced pressure and the residue was purified by prep-HPLC under the following conditions: Gemini-NX C18 Column, 21.2×150 mm, 5 μm; MeCN in water (with 0.05% TFA), 5% to 28% gradient in 10 min.

Compound 20a:

(28 mg, 8.8%, white solid, containing 2 stereoisomers), HPLC: 95.0% purity, RT=4.24 min. MS: m/z=282.1 [M+H]$^+$. $^1$H NMR (400 MHz, CD$_3$OD) δ=9.10 (s, 1H), 7.78 (d, J=6.8 Hz, 1H), 7.69 (s, 1H), 7.62 (d, J=7.2 Hz, 1H), 7.52-7.44 (m, 2H), 5.76 (br s, 1H), 3.38 (m, 1H), 2.44 (m, 1H), 2.30 (m, 1H), 1.76-1.53 (m, 5H), 1.41 (m, 1H), 1.17-0.93 (m, 5H);

Compound 20b:

(25 mg, 7.8%, white solid, containing 2 stereoisomers) HPLC: 98.4% purity, RT=2.37 min. MS: m/z=282.2 [M+H]$^+$. $^1$H NMR (300 MHz, CD$_3$OD) δ=9.31 (s, 1H), 7.88 (m, 1H), 7.81 (m, 1H), 7.68-7.55 (m, 3H), 5.88 (m, 1H), 3.55 (m, 1H), 2.52 (m, 1H), 2.31 (m, 1H), 1.80-1.55 (m, 6H), 1.29-1.06 (m, 5H).

Example 21: 1-cyclohexyl-2-[4,6,9-triazatricyclo[6.4.0.0^[2,6]]dodeca-1(8),2,4,9,11-pentaen-7-yl]ethan-1-amine (21a, 21b, 21c, 21d)

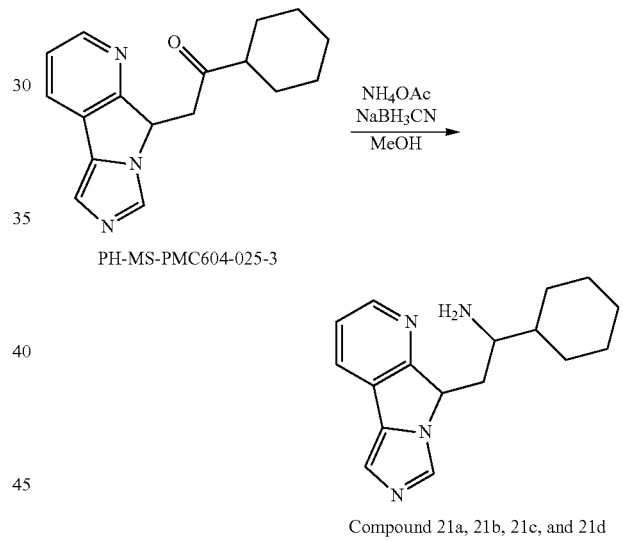

Compound 21a, 21b, 21c, and 21d

1-Cyclohexyl-2-[4,6,9-triazatricyclo[6.4.0.0^[2,6]]dodeca-1(8),2,4,9,11-pentaen-7-yl]ethan-1-amine To a solution of 1-cyclohexyl-2-[4,6,9-triazatricyclo[6.4.0.0^[2,6]]dodeca-1(8),2,4,9,11-pentaen-7-yl]ethan-1-one (201 mg, 0.71 mmol) in methanol (8 mL) was added ammonium acetate (555 mg, 7.20 mmol) and sodium cyanoborhydride (68 mg, 1.08 mmol) successively at room temperature. The resulting reaction mixture was stirred at 60° C. for 3 d in a sealed tube. The reaction was then quenched by the addition of water (15 mL) carefully and the mixture was extracted with ethyl acetate (40 mL×5). The combined organic phases was washed with brine and dried over Na$_2$SO$_4$. The solvent was removed under reduced pressure and the residue was purified by chiral prep-HPLC under the following conditions: Gemini-NX C18 Column, 21.2×150 mm, 5 μm; ethanol in hexane (with 0.2% diethylamine), 30% isocratic in 17 min.

Compound 21a:

(6 mg, 3%, clear oil, containing 2 stereoisomers), HPLC: 83.7% purity, RT=0.83 min. MS: m/z=283.1 [M+H]+. $^1$H NMR (300 MHz, CD$_3$OD) δ=8.42 (dd, J=5.1, 1.2 Hz, 1H), 8.07-8.00 (m, 2H), 7.42 (m, 1H), 7.31 (s, 1H), 5.43 (m, 1H), 3.08 (m, 1H), 2.22-2.13 (m, 2H), 1.78-1.63 (m, 4H), 1.33-1.02 (m, 7H);

Compound 21b:

(7 mg, 3.5%, clear oil, containing 2 stereoisomers) HPLC: 86.7% purity, RT=0.78 min. MS: m/z=283.1 [M+H]+. $^1$H NMR (300 MHz, CD$_3$OD) δ=8.42 (dd, J=5.1, 1.5 Hz, 1H), 8.07-8.02 (m, 2H), 7.43 (dd, J=7.8, 5.1 Hz, 1H), 7.33 (s, 1H), 5.50 (dd, J=9.0, 4.5 Hz, 1H), 2.98 (m, 1H), 2.22 (m, 1H), 1.90 (m, 1H), 1.77-1.68 (m, 5H), 1.37-1.04 (m, 6H);

Compound 21c:

(6 mg, 3%, clear oil, containing 2 stereoisomers), HPLC: 89.5% purity, RT=0.78 min. MS: m/z=283.1 [M+H]+. $^1$H NMR (300 MHz, CD$_3$OD) δ=8.42 (dd, J=5.1, 1.2 Hz, 1H), 8.06-8.02 (m, 2H), 7.43 (dd, J=7.8, 5.1 Hz, 1H), 7.33 (s, 1H), 5.50 (dd, J=9.0, 4.5 Hz, 1H), 2.98 (m, 1H), 2.22 (m, 1H), 1.89 (m, 1H), 1.77-1.68 (m, 5H), 1.36-1.05 (m, 6H);

Compound 21d:

(6 mg, 3%, clear oil, containing 2 stereoisomers) HPLC: 83.3% purity, RT=0.83 min. MS: m/z=283.1 [M+H]+. $^1$H NMR (300 MHz, CD$_3$OD) δ=8.42 (dd, J=5.1, 1.2 Hz, 1H), 8.07-8.02 (m, 2H), 7.42 (m, 1H), 7.31 (s, 1H), 5.43 (m, 1H), 3.08 (m, 1H), 2.22-2.13 (m, 2H), 1.78-1.63 (m, 4H), 1.34-1.03 (m, 7H).

Example 22: 1-(4,4-difluorocyclohexyl)-2-[4,6,9-triazatricyclo[6.4.0.0^[2,6]]dodeca-1(8),2,4,9,11-pentaen-7-yl]ethan-1-ol (22a, 22b, 22c, 22d)

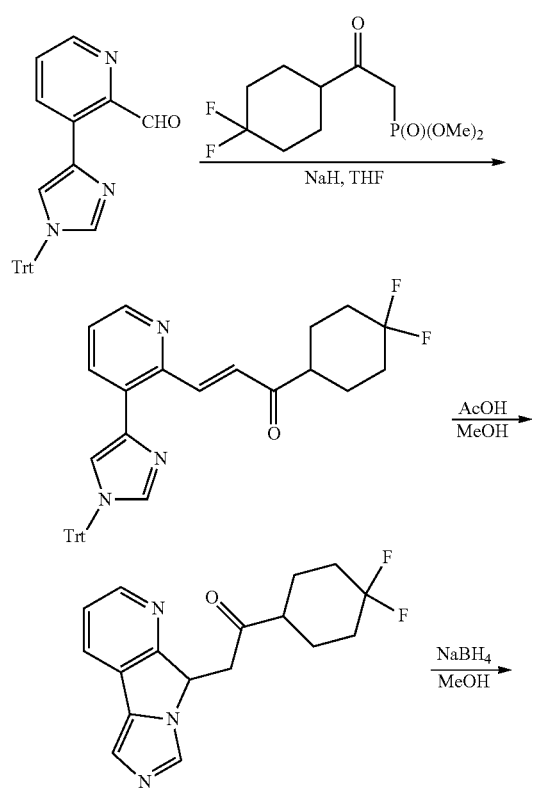

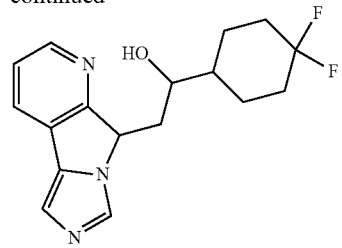

Compound 22a, 22b, 22c, and 22d 1-(4,4-Difluorocyclohexyl)-3-[3-[1-(triphenylmethyl)-1H-imidazol-4-yl]pyridin-2-yl]prop-2-en-1-one To a suspension of sodium hydride (60%, 116 mg, 2.90 mmol) in THF (10 mL) was added a solution of dimethyl [2-(4,4-difluorocyclohexyl)-2-oxoethyl]phosphonate (Intermediate D, 715 mg, 2.65 mmol) in THF (5 mL) slowly at 0° C. After stirring for additional 15 min at 0° C., the reaction mixture was added by a solution of 3-[1-(triphenylmethyl)-1H-imidazol-4-yl]pyridine-2-carbaldehyde (1 g, 2.41 mmol) in THF (8 mL) carefully. The resulting reaction mixture was then stirred at room temperature for 2 h. The reaction mixture was quenched by water (50 mL) and extracted with ethyl acetate (80 mL×2). The combined organic phase was washed with brine and dried over Na$_2$SO$_4$. The solvent was removed under reduced pressure to yield 1-(4,4-difluorocyclohexyl)-3-[3-[1-(triphenylmethyl)-1H-imidazol-4-yl]pyridin-2-yl]prop-2-en-1-one as yellow oil (1.3 g, 97%, crude yield) which was used in next step without further purification. MS: m/z=318.0 [M+H]+.

1-(4,4-Difluorocyclohexyl)-2-[4,6,9-triazatricyclo [6.4.0.0^[2,6]]dodeca-1(8),2,4,9,11-pentaen-7-yl] ethan-1-one To a solution of 1-(4,4-difluorocyclohexyl)-3-[3-[1-(triphenylmethyl)-1H-imidazol-4-yl]pyridin-2-yl]prop-2-en-1-one (1.30 g, 2.32 mmol) in methanol (15 mL) was added acetic acid (5 mL) slowly. The resulting reaction mixture was stirred at 90° C. for 2 h. The solvent was removed under reduced pressure and the resulting residue was dissolved in ethyl acetate (150 mL). The organic phase was washed with sat. NaHCO$_3$ solution (20 mL×2) and brine, and then dried over Na$_2$SO$_4$. The solvent was removed under reduced pressure and the residue was purified by flash chromatography eluting with methanol in dichloromethane (1% to 5% gradient) to yield 1-(4,4-difluorocyclohexyl)-2-[4,6,9-triazatricyclo[6.4.0.0^[2,6]]dodeca-1(8),2,4,9,11-pentaen-7-yl]ethan-1-one as yellow solid (400 mg, 53% over two steps). MS: m/z=318.0 [M+H]+.

1-(4,4-Difluorocyclohexyl)-2-[4,6,9-triazatricyclo [6.4.0.0^[2,6]]dodeca-1(8),2,4,9,11-pentaen-7-yl] ethan-1-ol To a solution of 1-(4,4-difluorocyclohexyl)-2-[4,6,9-triazatricyclo[6.4.0.0^[2,6]]dodeca-1 (8),2,4,9,11-pentaen-7-yl]ethan-1-one (100 mg, 0.32 mmol) in methanol (5 mL) was added sodium borohydride (24 mg, 0.63 mmol) slowly at 0° C. The resulting reaction mixture was kept stirring at 0° C. for 30 min. The reaction was then quenched by the addition of water (30 mL) carefully and the mixture was extracted with ethyl acetate (50 mL×3). The combined organic phase was washed with brine and dried over Na₂SO₄. The solvent was removed under reduced pressure and the residue was purified by chiral prep-HPLC under the following conditions: Phenomenex Lux, 21.2×150 mm, 5 μm; EtOH in hexane, 30% isocratic in 27 min.

Compound 22a:

(15 mg, 15%, white solid, single stereoisomer), HPLC: 98.1% purity, RT=0.80 min. MS: m/z=320.0 [M+H]⁺. ¹H NMR (300 MHz, CDCl₃) δ=8.38 (d, J=5.1 Hz, 1H), 7.89 (s, 1H), 7.84 (d, J=7.8 Hz, 1H), 7.34-7.29 (m, 2H), 5.36 (t, J=7.1 Hz, 1H), 3.97 (m, 1H), 3.81 (br s, 1H), 2.37 (m, 1H), 2.16-2.01 (m, 4H), 1.77-1.36 (m, 6H);

Compound 22b:

(9 mg, 9%, white solid, single stereoisomer) HPLC: 95.6% purity, RT=1.52 min. MS: m/z=320.0 [M+H]⁺. ¹H NMR (300 MHz, CDCl₃) δ=8.37 (d, J=4.2 Hz, 1H), 7.96 (br s, 1H), 7.86 (d, J=7.2 Hz, 1H), 7.35-7.31 (m, 2H), 5.32 (t, J=6.6 Hz, 1H), 4.12 (br s, 1H), 4.03 (m, 1H), 2.21-2.16 (m, 4H), 1.96 (m, 1H), 1.78-1.54 (m, 6H);

Compound 22c:

(9 mg, 9%, white solid, single stereoisomer), HPLC: 99.1% purity, RT=0.79 min. MS: m/z=320.0 [M+H]⁺. ¹H NMR (300 MHz, CDCl₃) δ=8.37 (d, J=4.5 Hz, 1H), 7.92 (br s, 1H), 7.86 (d, J=7.5 Hz, 1H), 7.35-7.31 (m, 2H), 5.31 (t, J=6.6 Hz, 1H), 4.12 (br s, 1H), 4.04 (m, 1H), 2.20-2.17 (m, 4H), 1.96 (m, 1H), 1.81-1.54 (m, 6H);

Compound 22d:

(17 mg, 17%, white solid, single stereoisomer), HPLC: 99.8% purity, RT=0.81 min. MS: m/z=312.0 [M+H]⁺. ¹H NMR (300 MHz, CDCl₃) δ=8.38 (d, J=4.8 Hz, 1H), 7.90 (s, 1H), 7.84 (d, J=7.8 Hz, 1H), 7.34-7.29 (m, 2H), 5.37 (t, J=7.2 Hz, 1H), 3.97 (m, 1H), 3.87 (br s, 1H), 2.37 (m, 1H), 2.16-2.01 (m, 4H), 1.77-1.36 (m, 6H).

Example 23: Synthesis of 6-fluoro-5-(2-(1-fluoro-4,4-dimethylcyclohexyl)ethyl)-5H-imidazo[5,1-a]isoindole (23a and 23b)

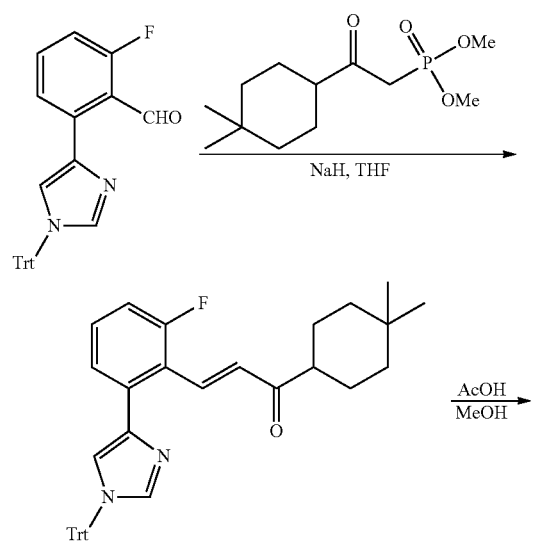

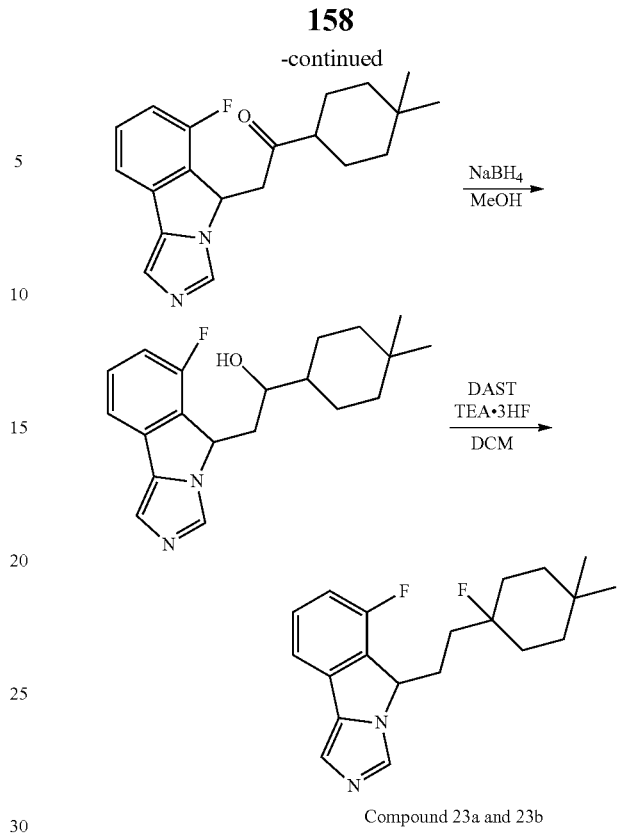

Compound 23a and 23b 1-(4,4-Dimethylcyclohexyl)-3-[2-fluoro-6-[1-(triphenylmethyl)-1H-imidazol-4-yl]phenyl]prop-2-en-1-one To a suspension of sodium hydride (60%, 110 mg, 2.77 mmol) in THF (10 mL) was added a solution of dimethyl [2-(4,4-dimethylcyclohexyl)-2-oxoethyl]phosphonate (Intermediate E, 668 mg, 2.54 mmol) in THF (5 mL) slowly at 0° C. After stirring for additional 15 min at 0° C., the reaction mixture was added by a solution of 2-fluoro-6-[1-(triphenylmethyl)-1H-imidazol-4-yl]benzaldehyde (1 g, 2.31 mmol) in THF (8 mL) carefully. The resulting reaction mixture was then stirred at room temperature for 2 h. The reaction mixture was quenched by water (40 mL) and extracted with ethyl acetate (80 mL×2). The combined organic phase was washed with brine and dried over Na₂SO₄. The solvent was removed under reduced pressure to yield 1-(4,4-dimethylcyclohexyl)-3-[2-fluoro-6-[1-(triphenylmethyl)-1H-imidazol-4-yl]phenyl]prop-2-en-1-one as yellow oil (1.2 g, 91%, crude yield) which was used in next step without further purification. MS: m/z=569.3 [M+H]⁺.

1-(4,4-Dimethylcyclohexyl)-2-[6-fluoro-5H-imidazo[4,3-a]isoindol-5-yl]ethan-1-one To a solution of 1-(4,4-dimethylcyclohexyl)-3-[2-fluoro-6-[1-(triphenylmethyl)-1H-imidazol-4-yl]phenyl]prop-2-en-1-one (1.2 g, 2.11 mmol) in methanol (15 mL) was added acetic acid (5 mL) slowly. The resulting reaction mixture was stirred at 90° C. for 2 h. The solvent was removed under reduced pressure and the residue was dissolved in ethyl acetate (150 mL). The organic phase was washed with sat. NaHCO₃ solution (20 mL×2) and brine, and then dried over Na₂SO₄. The solvent was removed under reduced pressure and the residue was purified by flash chromatography eluting with methanol in dichloromethane (1% to 5% gradient) to yield 1-(4,4-dimethylcyclohexyl)-2-[6-fluoro-5H-imidazo[4,3-a]isoindol-5-yl]ethan-1-one as yellow oil (300 mg, 40% over two steps).). MS: m/z=327.3[M+H].

1-(4,4-Dimethylcyclohexyl)-2-[6-fluoro-5H-imidazo[4,3-a]isoindol-5-yl]ethan-1-ol To a solution of 1-(4,4-dimethylcyclohexyl)-2-[6-fluoro-5H-imidazo[4,3-a]isoindol-5-yl]ethan-1-one (300 mg, 0.92 mmol) in methanol (8 mL) was added sodium borohydride (70 mg, 1.84 mmol) slowly at 0° C. The resulting reaction mixture was kept stirring at 0° C. for 30 min. The reaction was then quenched by the addition of water (30 mL) carefully and the mixture was extracted with ethyl acetate (50 mL×3). The combined organic phase was washed with brine and dried over Na$_2$SO$_4$. The solvent was removed under reduced pressure and the residue was purified by flash chromatography eluting with methanol in dichloromethane (1% to 7% gradient) to yield 1-(4,4-dimethylcyclohexyl)-2-[6-fluoro-5H-imidazo[4,3-a]isoindol-5-yl]ethan-1-ol as yellow solid (350 mg, 83%). MS: m/z=329.1 [M+H]$^+$.

6-Fluoro-5-(2-(1-fluoro-4,4-dimethylcyclohexyl)ethyl)-5H-imidazo[5,1-a]isoindole At 0° C., to a solution of 1-(4,4-dimethylcyclohexyl)-2-[6-fluoro-5H-imidazo[4,3-a]isoindol-5-yl]ethan-1-ol (200 mg, 0.61 mmol) in dichloromethane (8 mL) was added DAST (147 mg, 0.91 mmol) and TEA.3HF (147 mg, 0.91 mmol) successively. The resulting reaction mixture was kept stirring at 0° C. for 3 h. The reaction was then quenched by the addition of water (20 mL) carefully and the mixture was extracted with dichloromethane (30 mL×2). The combined organic phase was washed with brine and dried over Na$_2$SO$_4$. The solvent was removed under reduced pressure and the residue was purified prep-HPLC under the following conditions: Gemini-NX C18 Column, 21.2×150 mm, 5 μm; acetonitrile in water (with 10 mM NH$_4$HCO$_3$), 10% to 50% gradient in 10 min. Then the two products were separated by chiral prep-HPLC under the following conditions: Gemini-NX C18 Column, 20×250 mm, 5 μm; mobile phase, EtOH in hexane; 20% isocratic in 15 min; Detector, UV 254/220 nm.

Compound 23a:

(25 mg, 12.5%, light yellow oil, single stereoisomer), HPLC: 98.0% purity, RT=1.85 min. MS: m/z=331.2 [M+H]$^+$. $^1$H NMR (300 MHz, CDCl$_3$, ppm) δ=7.75 (s, 1H), 7.39-7.31 (m, 2H), 7.22 (s, 1H), 6.95 (m, 1H), 5.46 (t, J=4.8 Hz, 1H), 2.41 (m, 1H), 2.22 (m, 1H), 1.69-1.65 (m, 2H), 1.53-1.14 (m, 8H), 0.92 (s, 3H), 0.83 (s, 3H);

Compound 23b:

(26 mg, 13%, light yellow oil, single stereoisomer) HPLC: 99.5% purity, RT=3.55 min. MS: m/z=331.2 [M+H]$^+$. $^1$H NMR (300 MHz, CDCl$_3$, ppm) δ=7.74 (s, 1H), 7.38-7.31 (m, 2H), 7.22 (s, 1H), 6.95 (m, 1H), 5.46 (t, J=4.8 Hz, 1H), 2.41 (m, 1H), 2.22 (m, 1H), 1.69-1.65 (m, 2H), 1.53-1.14 (m, 8H), 0.92 (s, 3H), 0.83 (s, 3H).

Example 24: Synthesis of 1-cyclohexyl-2-[10-fluoro-4,6,11-triazatricyclo[6.4.0.0^[2,6]]dodeca-1(8),2,4,9,11-pentaen-7-yl]ethan-1-ol (24a, 24b, 24c, 24d)

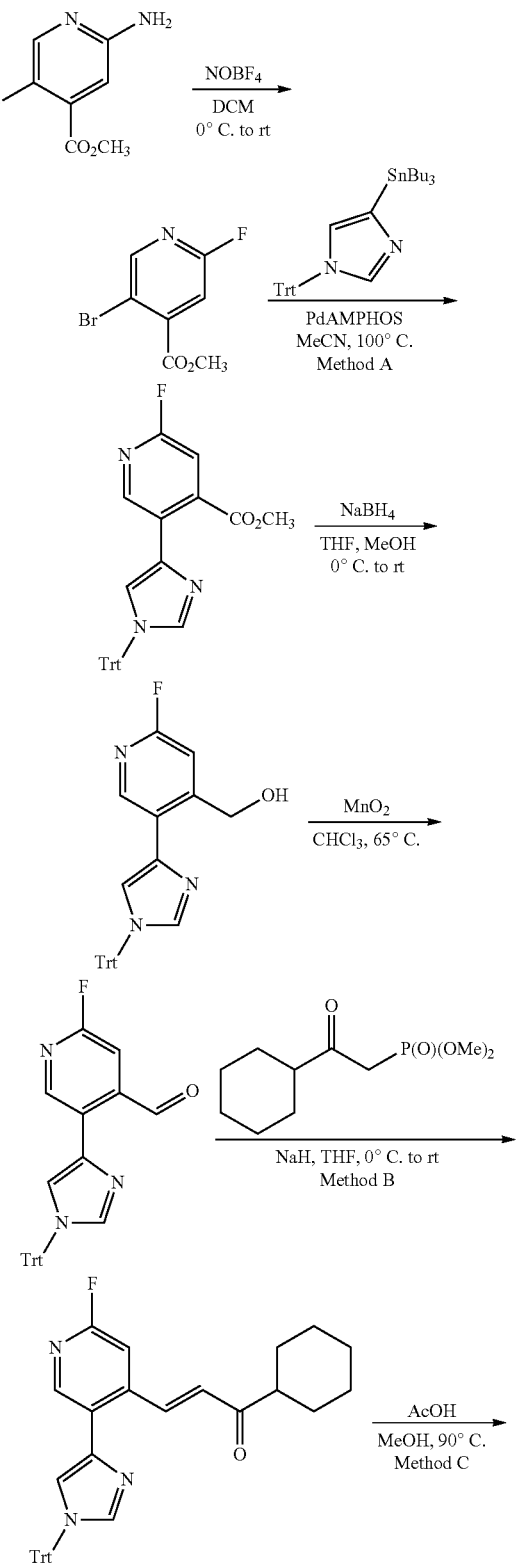

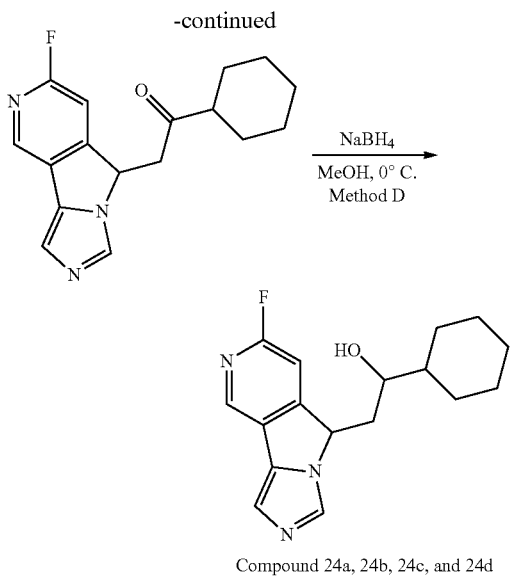

Compound 24a, 24b, 24c, and 24d

Methyl 5-bromo-2-fluoropyridine-4-carboxylate

To a solution of NOBF$_4$ (1.3 g, 11.13 mmol) in DCM (30 mL) at 0° C. was added methyl 2-amino-5-bromopyridine-4-carboxylate (2 g, 8.66 mmol) slowly. The resulting reaction mixture was stirred at room temperature for 16 h. The reaction mixture was then quenched by the addition of water (60 mL) carefully and the mixture was extracted with dicholormethane (50 mL×2). The combined organic phase was washed with brine and dried over sodium sulfate. The solvent was concentrated under reduced pressure and the resulting residue was purified by flash chromatography eluting with EtOAc in petroleum ether (10% to 30% gradient) to yield methyl 5-bromo-2-fluoropyridine-4-carboxylate as yellow oil (1.3 g, 64%). MS: m/z=233.9 [M+H]$^+$.
Method A:

Methyl 2-fluoro-5-[1-(triphenylmethyl)-1H-imidazol-4-yl]pyridine-4-carboxylate A mixture of methyl 5-bromo-2-fluoropyridine-4-carboxylate (2.34 g, 10.0 mmol), 4-(tributylstannyl)-1-(triphenylmethyl)-1H-imidazole (Intermediate A, 8.9 g, 14.85 mmol) and PdAMPHOS (708 mg, 1.0 mmol) in MeCN (100 mL) was stirred at 100° C. for 16 h. The reaction mixture cooled to room temperature, diluted with water (150 mL) and extracted with EtOAc (250 mL×2). The organic phases were combined, washed with brine and dried over sodium sulfate. The solvent was removed under reduced pressure and the resulting residue was purified by flash chromatography eluting with EtOAc in petroleum ether (10% to 30% gradient) to yield methyl 2-fluoro-5-[1-(triphenylmethyl)-1H-imidazol-4-yl]pyridine-4-carboxylate (3.1 g, 67%) as light yellow solid.

[2-Fluoro-5-[1-(triphenylmethyl)-1H-imidazol-4-yl]pyridin-4-yl]methanol

To a solution of methyl 2-fluoro-5-[1-(triphenylmethyl)-1H-imidazol-4-yl]pyridine-4-carboxylate (2.00 g, 4.31 mmol) in THF (30 mL) and MeOH (20 mL) at 0° C. was added sodium borohydride (820 mg, 21.67 mmol) in portions. The resulting mixture was then stirred at room temperature for 2 h. The reaction mixture was quenched by the addition of water (80 mL) carefully and the mixture was extracted with EtOAc (150 mL×3). The combined organic phase was washed with brine and dried over sodium sulfate$_4$. The solvent was removed under reduced pressure and the resulting residue was purified by flash chromatography eluting with EtOAc in petroleum ether (10% to 50% gradient) to yield [2-fluoro-5-[1-(triphenylmethyl)-1H-imidazol-4-yl]pyridin-4-yl]methanol as light yellow solid (1.16 g, 62%).

2-Fluoro-5-[1-(triphenylmethyl)-1H-imidazol-4-yl]pyridine-4-carbaldehyde

To a solution of [2-fluoro-5-[1-(triphenylmethyl)-1H-imidazol-4-yl]pyridin-4-yl]methanol (620 mg, 1.42 mmol) in chloroform (10 mL) was added manganese dioxide (1.2 g, 13.80 mmol) slowly. The resulting reaction mixture was then stirred 60° C. for 16 h. The reaction mixture was cooled to room temperature, filtered through a celite pad, and rinsed with chloroform (70 mL×3). The filtrate was concentrated under reduced pressure and the resulting residue was purified by flash chromatography eluting with EtOAc in petroleum ether (10% to 25% gradient) to yield 2-fluoro-5-[1-(triphenylmethyl)-1H-imidazol-4-yl]pyridine-4-carbaldehyde as yellow oil (272 mg, 44%).
Method B:

1-Cyclohexyl-3-[2-fluoro-5-[1-(triphenylmethyl)-1H-imidazol-4-yl]pyridin-4-yl]prop-2-en-1-one At 0° C., to a suspension of sodium hydride (60% in oil, 55 mg, 1.38 mmol) in THF (10 mL) was added a solution of dimethyl cyclohexanecarbonylphosphonate (Intermediate C, 275 mg, 1.25 mmol) in THF (5 mL) slowly. After stirring for 15 min at 0° C., the reaction mixture was added to a solution of 2-fluoro-5-[1-(triphenylmethyl)-1H-imidazol-4-yl]pyridine-4-carbaldehyde (500 mg, 1.15 mmol) in THF (5 mL) carefully. The resulting reaction mixture was then stirred at room temperature for 1 h. The reaction mixture was quenched by water (40 mL) and extracted with EtOAc (80 mL×2). The combined organic phase was washed with brine and dried over sodium sulfate. The solvent was removed under reduced pressure to yield 1-cyclohexyl-3-[2-fluoro-5-[1-(triphenylmethyl)-1H-imidazol-4-yl]pyridin-4-yl]prop-2-en-1-one as yellow oil (590 mg, 93%, crude yield), which was used in next step without further purification.
Method C:

1-Cyclohexyl-2-[10-fluoro-4,6,11-triazatricyclo[6.4.0.0^[2,6]]dodeca-1(8),2,4,9,11-pentaen-7-yl]ethan-1-one To a solution of 1-cyclohexyl-3-[2-fluoro-5-[1-(triphenylmethyl)-1H-imidazol-4-yl]pyridin-4-yl]prop-2-en-1-one (590 mg, 1.09 mmol) in MeOH (9 mL) was added AcOH (3 mL) slowly. The resulting reaction mixture was stirred at 90° C. for 1 h. The reaction mixture was cooled to room temperature, concentrated under reduced pressure and the residue was dissolved in EtOAc (100 mL). The resulting mixture was washed with saturated NaHCO$_3$ solution (20 mL×2) and brine, and then dried over sodium sulfate. The solvent was removed under reduced pressure and the resulting residue was purified by flash chromatography eluting with MeOH in DCM (1% to 6% gradient) to yield 1-cyclohexyl-2-[10-fluoro-4,6,11-triazatricyclo[6.4.0.0^[2,6]]dodeca-1(8),2,4,9,11-pentaen-7-yl]ethan-1-one as yellow oil (220 mg, 64% over two steps). MS: m/z=300.2 [M+H]⁺.
Method D:

1-Cyclohexyl-2-[10-fluoro-4,6,11-triazatricyclo
[6.4.0.0^[2,6]]dodeca-1(8),2,4,9,11-pentaen-7-yl]
ethan-1-ol To a solution of 1-cyclohexyl-2-[10-fluoro-4,6,11-triazatricyclo[6.4.0.0^[2,6]]dodeca-1 (8),2,4,9,11-pentaen-7-yl]ethan-1-one (100 mg, 0.34 mmol) in MeOH (8 mL) was added sodium borohydride (18 mg, 0.47 mmol) slowly at 0° C. The resulting reaction mixture was kept stirring at 0° C. for 30 min. The reaction mixture was then quenched by the addition of water (30 mL) carefully and the mixture was extracted with ethyl acetate (50 mL×3). The combined organic phase was washed with brine and dried over sodium sulfate. The solvent was removed under reduced pressure and the resulting residue was purified by chiral prep-HPLC to obtain four enantiomers under the following conditions: Chiralpak AD-H, 20×250 mm, 5 μm; iPrOH in hexane (0.2% DEA), 15% isocratic in 21 min; Detector, UV 254/220 nm.

Compound 24a:
(19 mg, 19%, white solid, single stereoisomer), HPLC: 99.4% purity, RT=0.73 min. MS: m/z=301.9 [M+H]⁺. ¹H NMR (300 MHz, CD₃OD, ppm) δ=8.45 (s, 1H), 7.98 (s, 1H), 7.29-7.27 (m, 2H), 5.63 (dd, J=10.2, 3.3 Hz, 1H), 3.71-3.65 (m, 1H), 2.32-2.21 (m, 1H), 1.97-1.68 (m, 6H), 1.47-1.01 (m, 6H);

Compound 24b:
(9 mg, 9%, white solid, single stereoisomer) HPLC: 99.2% purity, RT=0.73 min. MS: m/z=302.0 [M+H]⁺. ¹H NMR (300 MHz, CD₃OD, ppm) δ=8.41 (s, 1H), 7.98 (s, 1H), 7.25 (s, 1H), 7.20 (s, 1H), 5.54 (t, J=6.0 Hz, 1H), 3.49-3.42 (m, 1H), 2.18-2.16 (m, 2H), 1.82-1.61 (m, 5H), 1.31-0.97 (m, 6H);

Compound 24c:
(17 mg, 17%, white solid, single stereoisomer), HPLC: 98.7% purity, RT=0.74 min. MS: m/z=302.0 [M+H]⁺. ¹H NMR (300 MHz, CD₃OD, ppm) δ=8.42 (s, 1H), 7.94 (s, 1H), 7.25-7.23 (m, 2H), 5.58 (dd, J=10.2, 3.3 Hz, 1H), 3.66-3.59 (m, 1H), 2.29-2.19 (m, 1H), 1.90-1.63 (m, 6H), 1.37-0.98 (m, 6H);

Compound 24d:
(8 mg, 8%, white solid, single stereoisomer) HPLC: 99.9% purity, RT=1.14 min. MS: m/z=302.2 [M+H]⁺. ¹H NMR (300 MHz, CD₃OD, ppm) δ=8.40 (s, 1H), 7.99 (s, 1H), 7.25 (s, 1H), 7.20 (s, 1H), 5.54 (t, J=6.0 Hz, 1H), 3.49-3.42 (m, 1H), 2.18-2.16 (m, 2H), 1.82-1.61 (m, 5H), 1.31-0.95 (m, 6H).

Example 25: Synthesis of 1-(4,4-dimethylcyclohexyl)-2-[10-fluoro-4,6,9-triazatricyclo[6.4.0.0^[2,6]]dodeca-1(8),2,4,9,11-pentaen-7-yl]ethan-1-ol (25a, 25b, 25c, 25d)

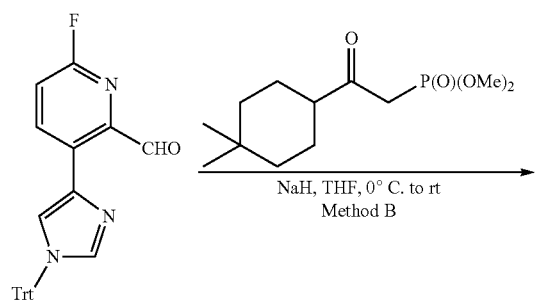

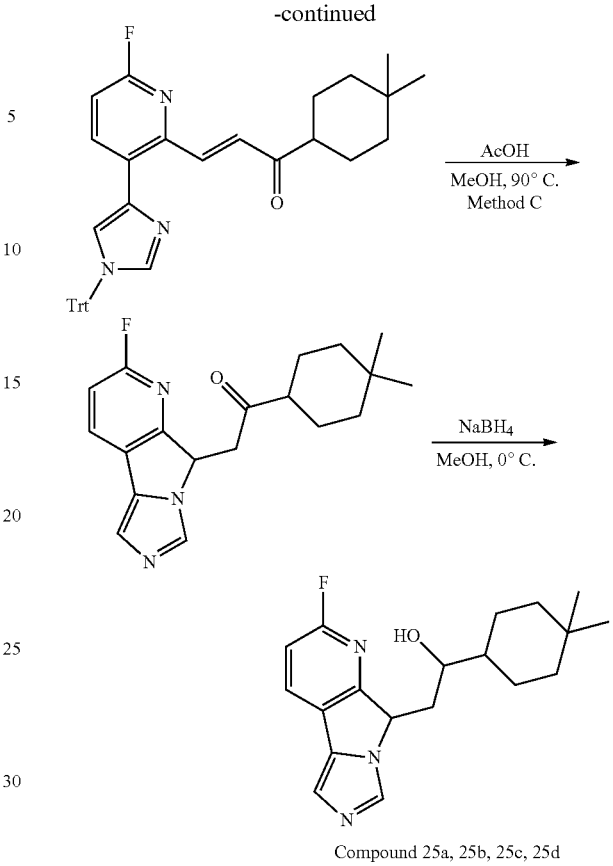

Compound 25a, 25b, 25c, 25d

The compounds were prepared according to the methods described previously.

1-(4,4-Dimethylcyclohexyl)-2-[10-fluoro-4,6,9-triazatricyclo[6.4.0.0^[2,6]]dodeca-1(8),2,4,9,11-pentaen-7-yl]ethan-1-ol 1-(4,4-Dimethylcyclohexyl)-2-[10-fluoro-4,6,9-triazatricyclo[6.4.0.0^[2,6]]dodeca-1 (8),2,4,9,11-pentaen-7-yl]ethan-1-ol was prepared from 6-fluoro-3-[1-(triphenylmethyl)-1H-imidazol-4-yl]pyridine-2-carbaldehyde and dimethyl [2-(4,4-dimethylcyclohexyl)-2-oxoethyl]phosphonate using Method B, C, and D. Four enantiomeric products were obtained by the separation on chiral prep-HPLC under the following conditions: Phenomenex Lux 5u Cellulose-4, AXIA Packed, 21.2×250 mm, 5 μm; EtOH in hexane (0.2% DEA), 10% isocratic in 40 min; Detector, UV 254/220 nm.

Compound 25a:
(15 mg, 8% for three steps, white solid, single stereoisomer), HPLC: 97.9% purity, RT=3.17 min. MS: m/z=330.2 [M+H]⁺. ¹H NMR (300 MHz, CD₃OD, ppm) δ=8.13-8.08 (m, 1H), 7.97 (s, 1H), 7.22 (s, 1H), 7.05 (dd, J=8.4, 0.9 Hz, 1H), 5.40 (dd, J=10.2, 3.0 Hz, 1H), 3.68-3.64 (m, 1H), 2.42-2.33 (m, 1H), 1.78-1.69 (m, 2H), 1.44-1.12 (m, 8H), 0.87 (s, 6H);

Compound 25b:
(9 mg, 4.5% for three steps, white solid, single stereoisomer) HPLC: 89.9% purity, RT=3.26 min. MS: m/z=330.2 [M+H]⁺. ¹H NMR (300 MHz, CD₃OD, ppm) δ=8.11-8.05 (m, 1H), 8.02 (s, 1H), 7.19 (s, 1H), 7.03 (dd, J=8.4, 0.9 Hz, 1H), 5.30 (t, J=6.0 Hz, 1H), 3.80-3.76 (m, 1H), 2.34-2.26 (m, 1H), 2.10-2.00 (m, 1H), 1.64-1.61 (m, 1H), 1.46-1.14 (m, 8H), 0.86 (s, 6H);

Compound 25c:

(17 mg, 9% for three steps, white solid, single stereoisomer), HPLC: 96.6% purity, RT=3.16 min. MS: m/z=330.2 [M+H]$^+$. $^1$H NMR (300 MHz, CD$_3$OD, ppm) δ=8.14-8.08 (m, 1H), 7.99 (s, 1H), 7.22 (s, 1H), 7.06-7.03 (m, 1H), 5.41 (dd, J=10.2, 3.3 Hz, 1H), 3.68-3.64 (m, 1H), 2.42-2.33 (m, 1H), 1.79-1.69 (m, 2H), 1.44-1.14 (m, 8H), 0.87 (s, 6H);

Compound 25d:

(9 mg, 4.5% for three steps, white solid, single stereoisomer) HPLC: 100% purity, RT=1.73 min. MS: m/z=330.2 [M+H]$^+$. $^1$H NMR (300 MHz, CD$_3$OD, ppm) δ=8.11-8.05 (m, 1H), 8.02 (s, 1H), 7.19 (s, 1H), 7.03 (dd, J=8.4, 0.9 Hz, 1H), 5.30 (t, J=6.0 Hz, 1H), 3.80-3.76 (m, 1H), 2.34-2.26 (m, 1H), 2.10-2.00 (m, 1H), 1.64-1.61 (m, 1H), 1.46-1.14 (m, 8H), 0.86 (s, 6H).

Example 26: Synthesis of 1-(4,4-difluorocyclohexyl)-2-[10-fluoro-4,6,9-triazatricyclo[6.4.0.0^[2,6]]dodeca-1(8),2,4,9,11-pentaen-7-yl]ethan-1-ol (26a and 26b)

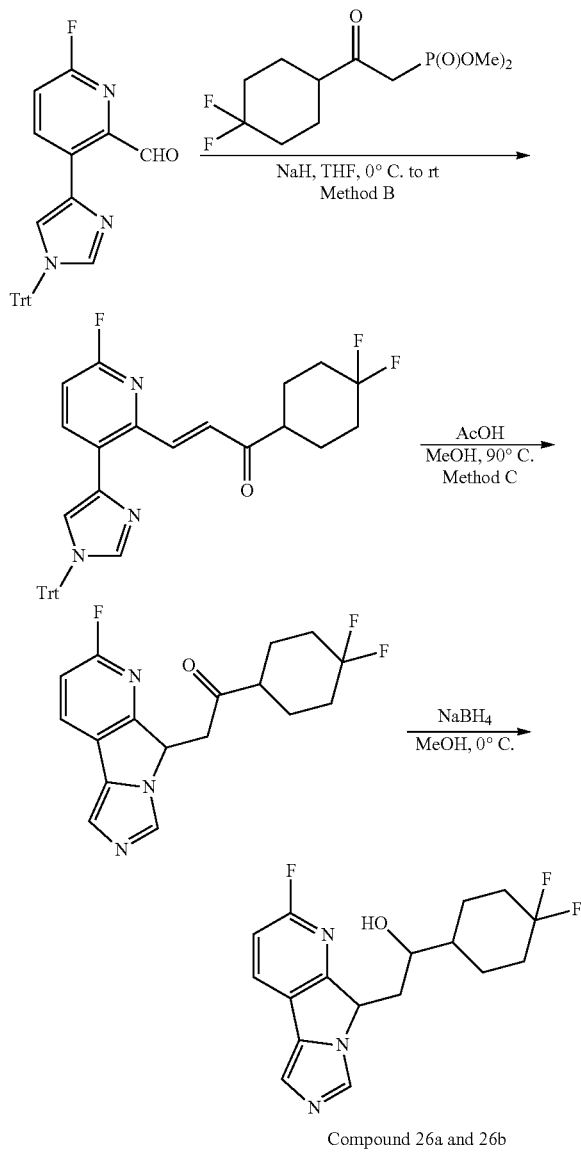

Compound 26a and 26b

The following compounds were prepared according to procedures described previously.

1-(4,4-Difluorocyclohexyl)-2-[10-fluoro-4,6,9-triazatricyclo[6.4.0.0^[2,6]]dodeca-1(8),2,4,9,11-pentaen-7-yl]ethan-1-ol 1-(4,4-Difluorocyclohexyl)-2-[10-fluoro-4,6,9-triazatricyclo[6.4.0.0^[2,6]]dodeca-1(8),2,4,9,11-pentaen-7-yl]ethan-1-ol was prepared from 6-fluoro-3-[1-(triphenylmethyl)-1H-imidazol-4-yl]pyridine-2-carbaldehyde and dimethyl [2-(4,4-difluorocyclohexyl)-2-oxoethyl]phosphonate using Method B, C, and D. Two pairs of enantiomeric products were obtained by the separation on chiral prep-HPLC under the following conditions: Chiralpak IB, 20×250 mm, 5 μm; iPrOH in hexane, 20% isocratic in 18 min; Detector, UV 254/220 nm.

Compound 26a:

(28 mg, 15% for three steps, white solid, containing two stereoisomers), HPLC: 92.0% purity, RT=0.74 min. MS: m/z=338.1 [M+H]$^+$. $^1$H NMR (300 MHz, CD$_3$OD, ppm) δ=8.12 (dd, J=8.1, 7.5 Hz, 1H), 7.98 (s, 1H), 7.22 (s, 1H), 7.06 (dd, J=8.4, 0.9 Hz, 1H), 5.41 (dd, J=10.2, 3.0 Hz, 1H), 3.73-3.68 (m, 1H), 2.44-2.35 (m, 1H), 2.06-1.95 (m, 3H), 1.78-1.64 (m, 4H), 1.43-1.26 (m, 3H);

Compound 26b:

(16 mg, 8.6% for three steps, white solid, containing two stereoisomers) HPLC: 95.2% purity, RT=0.72 min. MS: m/z=338.1 [M+H]$^+$. $^1$H NMR (300 MHz, CD$_3$OD, ppm) δ=9.07 (s, 1H), 8.34-8.29 (m, 1H), 7.72 (s, 1H), 7.20 (dd, J=8.7, 1.1 Hz, 1H), 5.61 (t, J=5.7 Hz, 1H), 3.97-3.91 (m, 1H), 2.49-2.42 (m, 1H), 2.16-1.99 (m, 3H), 1.90-1.65 (m, 4H), 1.45-1.35 (m, 3H).

Example 27: Synthesis of 10-fluoro-7-[2-(1-fluorocyclohexyl)ethyl]-4,6,11-triazatricyclo[6.4.0.0^[2,6]]dodeca-1(8),2,4,9,11-pentaene (27a and 27b)

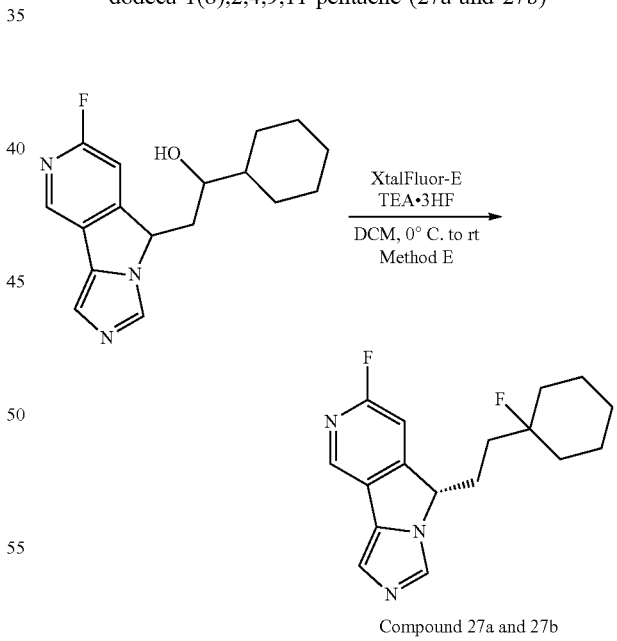

Compound 27a and 27b

Method E:

10-Fluoro-7-[2-(1-fluorocyclohexyl)ethyl]-4,6,11-triazatricyclo[6.4.0.0^[2,6]]dodeca-1(8),2,4,9,11-pentaene At 0° C., to a suspension of XtalFluor-E (180 mg, 0.80 mmol) in dichloromethane (6 mL) was added a solution of 1-cyclohexyl-2-[10-fluoro-4,6,11-triazatricyclo[6.4.0.0^[2,6]]dodeca-1(8),2,4,9,11-pentaen-7-yl]ethan-1-ol (160 mg, 0.53 mmol) in dichloromethane (2 mL) and TEA.3HF (130 mg, 0.80 mmol) successively. The resulting solution was stirred at room temperature for 1 h. The reaction mixture was then quenched by the addition of water (30 mL) carefully and the mixture was extracted with dichloromethane (40 mL×2). The combined organic phase was washed with brine, and dried over sodium sulfate. The solvent was removed under reduced pressure and the resulting residue was purified by chiral prep-HPLC to obtain two enantiomeric products under the following conditions: CHIRALPAK AD-H, 2×25 cm, 5 μm; mobile phase, EtOH in hexane, 30% isocratic in 21 min; Detector, UV 254/220 nm.

Compound 27a:
(22 mg, 13.8%, yellow oil, single stereoisomer) HPLC: 99.9% purity, RT=1.58 min. MS: m/z=304.0 [M+H]$^+$. $^1$H NMR (300 MHz, CD$_3$OD, ppm) δ=8.47 (s, 1H), 8.00 (s, 1H), 7.304-7.297 (m, 1H), 7.27 (s, 1H), 5.58 (t, J=5.1 Hz, 1H), 2.50-2.38 (m, 1H), 2.29-2.17 (m, 1H), 1.79-1.72 (m, 2H), 1.60-1.21 (m, 10H);

Compound 27b:
(20 mg, 12.5%, yellow oil, single stereoisomer) HPLC: 99.8% purity, RT=1.56 min. MS: m/z=304.0 [M+H]$^+$. $^1$H NMR (300 MHz, CD$_3$OD, ppm) δ=8.47 (s, 1H), 8.00 (s, 1H), 7.303-7.297 (m, 1H), 7.27 (s, 1H), 5.58 (t, J=5.1 Hz, 1H), 2.50-2.38 (m, 1H), 2.29-2.17 (m, 1H), 1.79-1.72 (m, 2H), 1.60-1.21 (m, 10H).

Example 28: Synthesis of 4-[2-[10-fluoro-4,6,11-triazatricyclo[6.4.0.0^[2,6]]dodeca-1(8),2,4,9,11-pentaen-7-yl]-1-hydroxyethyl]cyclohexan-1-ol (28a, 28b, 28c, 28d)

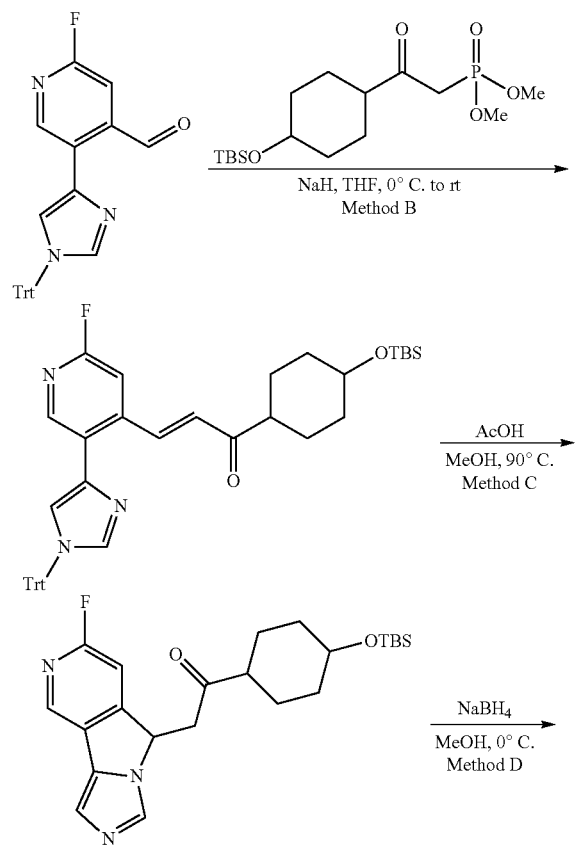

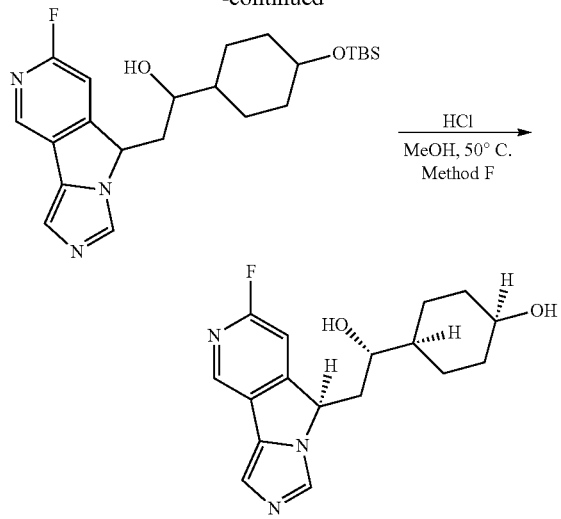

Compound 28a, 28b, 28c, and 28d

1-[4-[(tert-Butyldimethylsilyl)oxy]cyclohexyl]-2-[10-fluoro-4,6,11-triazatricyclo[6.4.0.0^[2,6]]dodeca-1(8),2,4,9,11-pentaen-7-yl]ethan-1-ol The compound was prepared from 2-fluoro-5-[1-(triphenylmethyl)-1H-imidazol-4-yl]pyridine-4-carbaldehyde and dimethyl (2-[4-[(tert-butyldimethylsilyl)oxy]cyclohexyl]-2-oxoethyl)phosphonate using Method B, C, and D. The compound was purified by flash chromatography eluting with methanol in dichloromethane (1% to 6% gradient) to yield 1-[4-[(tert-butyldimethylsilyl)oxy]cyclohexyl]-2-[10-fluoro-4,6,11-triazatricyclo[6.4.0.0^[2,6]]dodeca-1(8),2,4,9,11-pentaen-7-yl]ethan-1-ol as yellow solid (56% for three steps). MS: m/z=432.1 [M+H]$^+$.

Method F:

4-[2-[10-Fluoro-4,6,11-triazatricyclo[6.4.0.0^[2,6]]dodeca-1(8),2,4,9,11-pentaen-7-yl]-1-hydroxyethyl]cyclohexan-1-ol To a solution of 1-[4-[(tert-butyldimethylsilyl)oxy]cyclohexyl]-2-[10-fluoro-4,6,11-triazatricyclo[6.4.0.0^[2,6]]dodeca-1(8),2,4,9,11-pentaen-7-yl]ethan-1-ol (200 mg, 0.46 mmol) in methanol (6 mL) was added hydrochloric acid (6 M in water, 2 mL, 12 mmol) slowly. The resulting reaction mixture was stirred at 50° C. for 20 min. The reaction mixture was concentrated under reduced pressure and the residue was dissolved in ethyl acetate (80 mL). The reaction mixture was washed with sat. NaHCO$_3$ solution (20 mL×2) and brine, and then dried over sodium sulfate. The solvent was removed under reduced pressure and the residue was purified by prep-HPLC to obtain four pairs of enantiomeric products under the following conditions: Gemini-NX C18, 21.2×150 mm, 5 μm; mobile phase, MeCN in water (with 10 mM NH$_4$HCO$_3$), 20% to 30% gradient in 10 min; Detector, UV 254/220 nm.

Compound 28a:
(22 mg, 15%, white solid, containing two stereoisomers) HPLC: 99.9% purity, RT=1.06 min. MS: m/z=318.1 [M+H]$^+$. $^1$H NMR (300 MHz, CD$_3$OD, ppm) δ=8.44 (s, 1H), 8.03 (s, 1H), 7.30-7.29 (m, 1H), 7.24 (s, 1H), 5.58 (t, J=6.0 Hz, 1H), 3.55-3.42 (m, 2H), 2.25-2.17 (m, 2H), 1.98-1.86 (m, 3H), 1.72-1.68 (m, 1H), 1.30-1.05 (m, 5H);

Compound 28b:

(12 mg, 8.2%, white solid, containing two stereoisomers) HPLC: 95.0% purity, RT=0.59 min. MS: m/z=318.1 [M+H]⁺. ¹H NMR (300 MHz, CD$_3$OD, ppm) δ=8.45 (s, 1H), 7.98 (s, 1H), 7.29-7.24 (m, 2H), 5.63 (dd, J=10.2, 3.3 Hz, 1H), 3.71-3.65 (m, 1H), 3.47-3.43 (m, 1H), 2.34-2.24 (m, 1H), 2.04-1.95 (m, 3H), 1.87-1.69 (m, 2H), 1.36-1.12 (m, 5H);

Compound 28c:

(20 mg, 13.6%, white solid, containing two stereoisomers) HPLC: 98.7% purity, RT=1.14 min. MS: m/z=318.1 [M+H]⁺. ¹H NMR (300 MHz, CD$_3$OD, ppm) δ=8.44 (s, 1H), 8.13 (s, 1H), 7.31-7.30 (m, 1H), 7.27 (s, 1H), 5.59 (t, J=6.0 Hz, 1H), 3.93 (br s, 1H), 3.59-3.53 (m, 1H), 2.26-2.21 (m, 2H), 1.78-1.74 (m, 2H), 1.58-1.47 (m, 7H);

Compound 28d:

(13 mg, 8.9%, white solid, containing two stereoisomers) HPLC: 100% purity, RT=1.00 min. MS: m/z=318.1 [M+H]⁺. ¹H NMR (300 MHz, CD$_3$OD, ppm) δ=8.46 (s, 1H), 8.03 (br s, 1H), 7.29 (br s, 2H), 5.66-5.63 (m, 1H), 3.94 (br s, 1H), 3.74-3.70 (m, 1H), 2.33-2.24 (m, 1H), 1.88-1.65 (m, 3H), 1.58-1.45 (m, 7H).

Example 29: Synthesis of 1-[spiro[2.5]octan-6-yl]-2-[4,6,9-triazatricyclo[6.4.0.0ˆ[2,6]]dodeca-1(8),2,4,9,11-pentaen-7-yl]ethan-1-ol (29a, 29b, 29c, 29d)

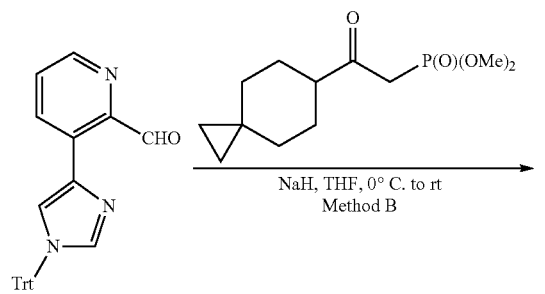

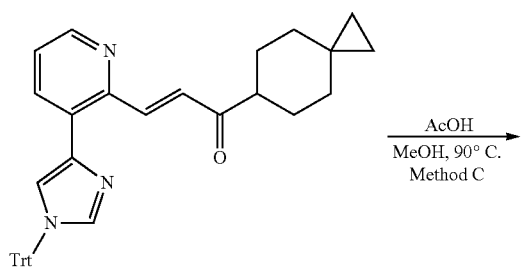

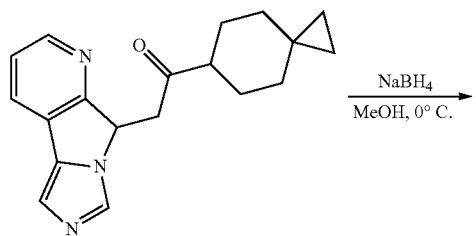

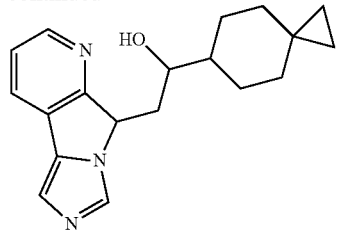

Compound 29a, 29b, 29c, 29d

1-[Spiro[2.5]octan-6-yl]-2-[4,6,9-triazatricyclo [6.4.0.0ˆ[2,6]]dodeca-1(8),2,4,9,11-pentaen-7-yl] ethan-1-ol 1-[Spiro[2.5]octan-6-yl]-2-[4,6,9-triazatricyclo[6.4.0.0ˆ[2,6]]dodeca-1(8),2,4,9,11-pentaen-7-yl]ethan-1-ol was prepared from 3-[1-(triphenylmethyl)-1H-imidazol-4-yl]pyridine-2-carbaldehyde and dimethyl (2-oxo-2-[spiro[2.5]octan-6-yl]ethyl)phosphonate using Method B, C, and D. The crude product was first purified by prep-HPLC to get two pairs of enantiomeric products under the following conditions: Gemini-NX C18, 21.2×150 mm, 5 μm; mobile phase, MeCN in water with 0.05% TFA; 5% to 30% MeCN gradient in 12 min; Detector, UV 254/220 nm. Four enantiomeric products were obtained by the separation on chiral prep-HPLC under the following conditions: CHIRALCEL OJ-H, 2×25 cm, 5 μm; EtOH in hexane (0.2% TEA), 10% isocratic in 17 min; Detector, UV 254/220 nm.

Compound 29a:

(17 mg, 8.3% for three steps, white solid, single stereoisomer), HPLC: 98.9% purity, RT=2.42 min. MS: m/z=310.1 [M+H]⁺. ¹H NMR (300 MHz, CD$_3$OD, ppm) δ=8.41 (dd, J=5.1, 0.9 Hz, 1H), 8.05-8.02 (m, 2H), 7.42 (dd, J=7.8, 5.1 Hz, 1H), 7.32 (s, 1H), 5.49 (dd, J=9.9, 3.6 Hz, 1H), 3.76-3.72 (m, 1H), 2.50-2.41 (m, 1H), 1.90-1.64 (m, 5H), 1.47-1.21 (m, 3H), 0.96-0.88 (m, 2H), 0.28-0.18 (m, 4H);

Compound 29b:

(10 mg, 4.9% for three steps, white solid, single stereoisomer) HPLC: 98.1% purity, RT=1.59 min. MS: m/z=310.1 [M+H]⁺. ¹H NMR (300 MHz, CD$_3$OD, ppm) δ=8.40 (dd, J=5.1, 1.2 Hz, 1H), 8.09 (s, 1H), 8.01 (dd, J=7.8, 1.2 Hz, 1H), 7.40 (dd, J=7.8, 5.1 Hz, 1H), 7.28 (s, 1H), 5.37 (t, J=5.7 Hz, 1H), 3.91-3.87 (m, 1H), 2.42-2.36 (m, 1H), 2.11-2.03 (m, 1H), 1.86-1.65 (m, 4H), 1.41-1.21 (m, 3H), 0.95-0.90 (m, 2H), 0.28-0.18 (m, 4H);

Compound 29c:

(9 mg, 4.4% for three steps, white solid, single stereoisomer), HPLC: 97.7% purity, RT=1.60 min. MS: m/z=310.1 [M+H]⁺. ¹H NMR (300 MHz, CD$_3$OD, ppm) δ=8.40 (dd, J=5.1, 1.2 Hz, 1H), 8.09 (s, 1H), 8.01 (dd, J=7.8, 1.2 Hz, 1H), 7.40 (dd, J=7.8, 5.1 Hz, 1H), 7.28 (s, 1H), 5.37 (t, J=5.7 Hz, 1H), 3.91-3.87 (m, 1H), 2.42-2.36 (m, 1H), 2.11-2.03 (m, 1H), 1.86-1.65 (m, 4H), 1.41-1.21 (m, 3H), 0.95-0.90 (m, 2H), 0.28-0.18 (m, 4H);

Compound 29d:

(15 mg, 7.3% for three steps, white solid, single stereoisomer) HPLC: 96.4% purity, RT=2.63 min. MS: m/z=310.1 [M+H]⁺. ¹H NMR (300 MHz, CD$_3$OD, ppm) δ=8.41 (dd, J=5.1, 0.9 Hz, 1H), 8.05-8.02 (m, 2H), 7.42 (dd, J=7.8, 5.1 Hz, 1H), 7.32 (s, 1H), 5.49 (dd, J=9.9, 3.6 Hz, 1H), 3.76-3.72 (m, 1H), 2.50-2.41 (m, 1H), 1.90-1.64 (m, 5H), 1.47-1.21 (m, 3H), 0.96-0.88 (m, 2H), 0.28-0.18 (m, 4H).

Example 30: Synthesis of 7-(2-{6-fluorospiro[2.5]octan-6-yl}ethyl)-4,6,9-triazatricyclo[6.4.0.0^[2,6]]dodeca-1(8),2,4,9,11-pentaene (30a and 30b)

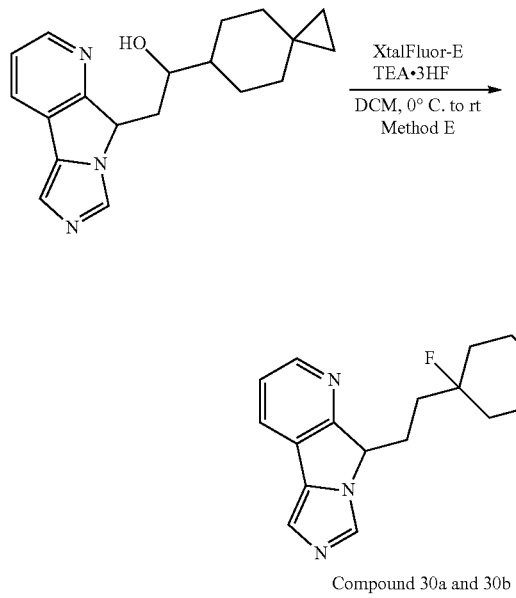

Compound 30a and 30b

7-(2-{6-Fluorospiro[2.5]octan-6-yl}ethyl)-4,6,9-triazatricyclo[6.4.0.0^[2,6]]dodeca-1(8),2,4,9,11-pentaene 7-(2-{6-Fluorospiro[2.5]octan-6-yl}ethyl)-4,6,9-triazatricyclo[6.4.0.0^[2,6]]dodeca-1(8),2,4,9,11-pentaene was prepared from 1-[spiro[2.5]octan-6-yl]-2-[4,6,9-triazatricyclo[6.4.0.0^[2,6]]dodeca-1 (8),2,4,9,11-pentaen-7-yl]ethan-1-ol using Method E. Two enantiomeric products were obtained by the separation on chiral prep-HPLC under the following conditions: Chiralpak IC, 2×25 cm, 5 μm; mobile phase, EtOH in hexane (with 0.2% IPA), 30% isocratic in 30 min; Detector, UV 254/220 nm.

Compound 30a:

(16 mg, 15%, yellow oil, single stereoisomer) HPLC: 97.0% purity, RT=1.64 min. MS: m/z=312.1 [M+H]$^+$. $^1$H NMR (400 MHz, CD$_3$OD, ppm) δ=8.44-8.43 (m, 1H), 8.05-8.03 (m, 2H), 7.45-7.42 (m, 1H), 7.33 (s, 1H), 5.39 (t, J=5.2 Hz, 1H), 2.51-2.45 (m, 1H), 2.31-2.25 (m, 1H), 1.86-1.75 (m, 4H), 1.59-1.29 (m, 4H), 1.86-1.81 (m, 2H), 0.29-0.18 (m, 4H);

Compound 30b:

(15 mg, 14%, yellow oil, single stereoisomer) HPLC: 97.2% purity, RT=1.64 min. MS: m/z=312.1 [M+H]$^+$. $^1$H NMR (400 MHz, CD$_3$OD, ppm) δ=8.44-8.43 (m, 1H), 8.05-8.03 (m, 2H), 7.45-7.42 (m, 1H), 7.33 (s, 1H), 5.39 (t, J=5.2 Hz, 1H), 2.51-2.45 (m, 1H), 2.31-2.25 (m, 1H), 1.86-1.75 (m, 4H), 1.59-1.29 (m, 4H), 1.86-1.81 (m, 2H), 0.29-0.18 (m, 4H).

Example 31: Synthesis of 1-cyclohexyl-2-[10-fluoro-4,6,9-triazatricyclo[6.4.0.0^[2,6]]dodeca-1(8),2,4,9,11-pentaen-7-yl]ethan-1-ol (31a and 31b)

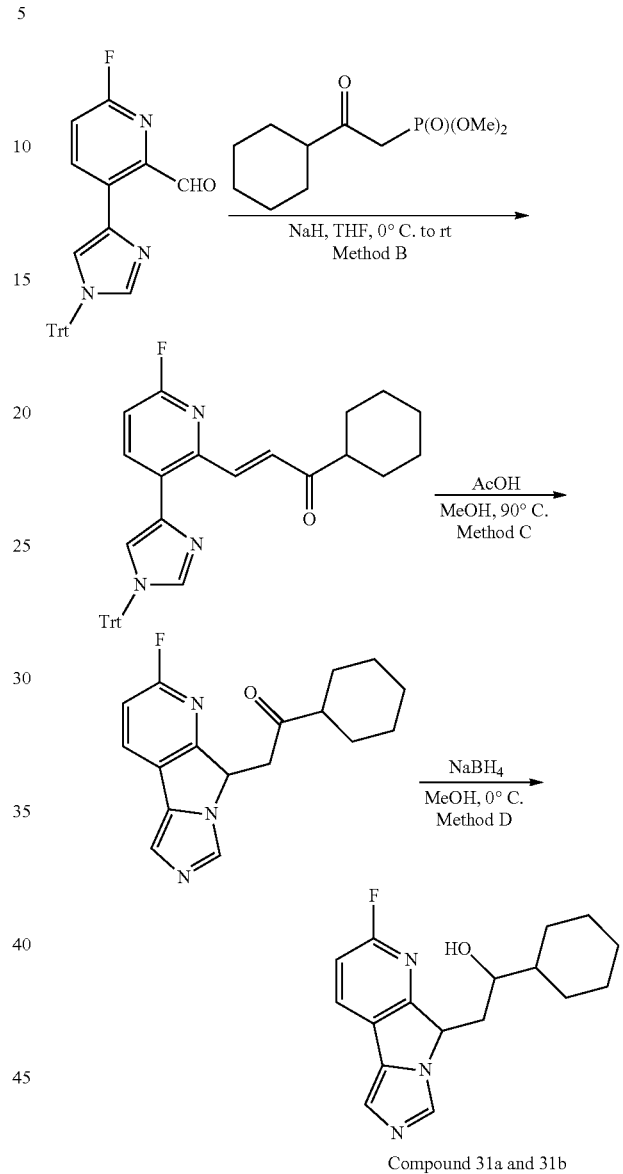

Compound 31a and 31b

1-Cyclohexyl-2-[10-fluoro-4,6,9-triazatricyclo[6.4.0.0^[2,6]]dodeca-1(8),2,4,9,11-pentaen-7-yl]ethan-1-ol 1-Cyclohexyl-2-[10-fluoro-4,6,9-triazatricyclo[6.4.0.0^[2,6]]dodeca-1(8),2,4,9,11-pentaen-7-yl]ethan-1-ol was prepared from 6-fluoro-3-[1-(triphenylmethyl)-1H-imidazol-4-yl]pyridine-2-carbaldehyde and dimethyl [2-(4,4-difluorocyclohexyl)-2-oxoethyl]phosphonate using Method B, C, and D. Two pairs of enantiomeric products were obtained by the separation on prep-HPLC under the following conditions: Gemini-NX C18, 21.2×150 mm, 5 μm; MeCN in water (with 0.05% TFA); 15% to 30% gradient in 10 min; Detector, UV 254/220 nm.

Compound 31a:

(18 mg, 15% for three steps, white solid, containing two stereoisomers), HPLC: 93.1% purity, RT=2.67 min. MS:

m/z=302.1 [M+H]⁺. ¹H NMR (300 MHz, CD₃OD, ppm) δ=8.40 (s, 1H), 8.20 (dd, J=8.4, 7.5 Hz, 1H), 7.43 (s, 1H), 7.11 (dd, J=8.4, 0.6 Hz, 1H), 5.52 (dd, J=9.6, 3.0 Hz, 1H), 3.55-3.50 (m, 1H), 2.46-2.37 (m, 1H), 1.93-1.84 (m, 2H), 1.73-1.64 (m, 4H), 1.39-0.98 (m, 6H);

Compound 31b:

(12 mg, 10% for three steps, white solid, containing two stereoisomers) HPLC: 94.3% purity, RT=2.72 min. MS: m/z=302.1 [M+H]⁺. ¹H NMR (300 MHz, CD₃OD, ppm) δ=8.61 (s, 1H), 8.21 (dd, J=8.1, 7.2 Hz, 1H), 7.48 (s, 1H), 7.12 (dd, J=8.4, 0.9 Hz, 1H), 5.46 (t, J=5.7 Hz, 1H), 3.80-3.77 (m, 1H), 2.41-2.34 (m, 1H), 2.10-2.04 (m, 1H), 1.80-1.67 (m, 5H), 1.34-1.01 (m, 6H).

Example 32: Synthesis of 7-[2-(1-fluorocyclohexyl)ethyl]-10-methoxy-4,6,9-triazatricyclo[6.4.0.0^[2,6]]dodeca-1(8),2,4,9,11-pentaene (32a and 32b)

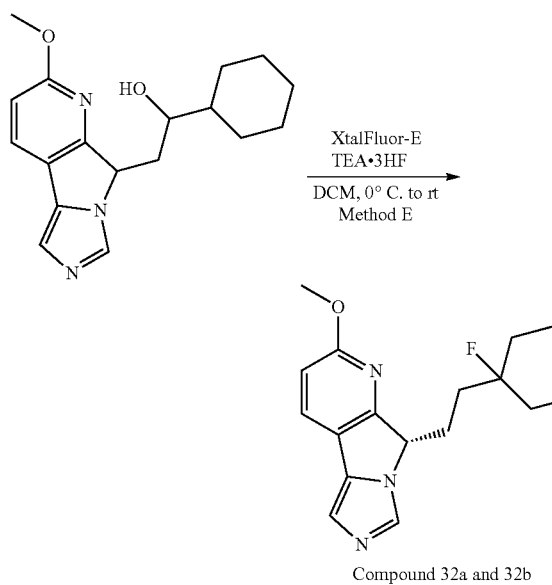

Compound 32a and 32b

7-[2-(1-Fluorocyclohexyl)ethyl]-10-methoxy-4,6,9-triazatricyclo[6.4.0.0^[2,6]]dodeca-1(8),2,4,9,11-pentaene 7-[2-(1-Fluorocyclohexyl)ethyl]-10-methoxy-4,6,9-triazatricyclo[6.4.0.0^[2,6]]dodeca-1(8),2,4,9,11-pentaene was prepared from 1-cyclohexyl-2-[10-methoxy-4,6,9-triazatricyclo[6.4.0.0^[2,6]]dodeca-1(8),2,4,9,11-pentaen-7-yl]ethan-1-ol using Method E. Two enantiomeric products were obtained by the separation on chiral prep-HPLC under the following conditions: CHIRALPAK AD-H, 21.2×150 mm, 5 μm; mobile phase, EtOH in hexane (with 0.2% DEA); 20% isocratic in 6 min; Detector, UV 254/220 nm.

Compound 32a:

(17 mg, 15%, yellow oil, single stereoisomer), HPLC: 94.1% purity, RT=2.66 min. MS: m/z=316.0 [M+H]⁺. ¹H NMR (300 MHz, CD₃OD, ppm) δ=8.07 (br s, 1H), 7.92 (d, J=8.7 Hz, 1H), 7.17 (br s, 1H), 6.83 (d, J=8.4 Hz, 1H), 5.27 (t, J=5.1 Hz, 1H), 3.98 (s, 3H), 2.42-2.22 (m, 2H), 1.75 (br s, 2H), 1.57-1.25 (m, 10H);

Compound 32b:

(15 mg, 13%, yellow oil, single stereoisomer) HPLC: 91.2% purity, RT=1.85 min. MS: m/z=316.1 [M+H]⁺. ¹H NMR (300 MHz, CD₃OD, ppm) δ=8.08 (br s, 1H), 7.92 (d, J=8.7 Hz, 1H), 7.17 (br s, 1H), 6.83 (d, J=8.4 Hz, 1H), 5.27 (t, J=5.1 Hz, 1H), 3.98 (s, 3H), 2.42-2.22 (m, 2H), 1.75 (br s, 2H), 1.57-1.25 (m, 10H).

Example 33: Synthesis of 1-(4,4-difluorocyclohexyl)-2-[10-methoxy-4,6,9-triazatricyclo[6.4.0.0^[2,6]]dodeca-1(8),2,4,9,11-pentaen-7-yl]ethan-1-ol (33a and 33b)

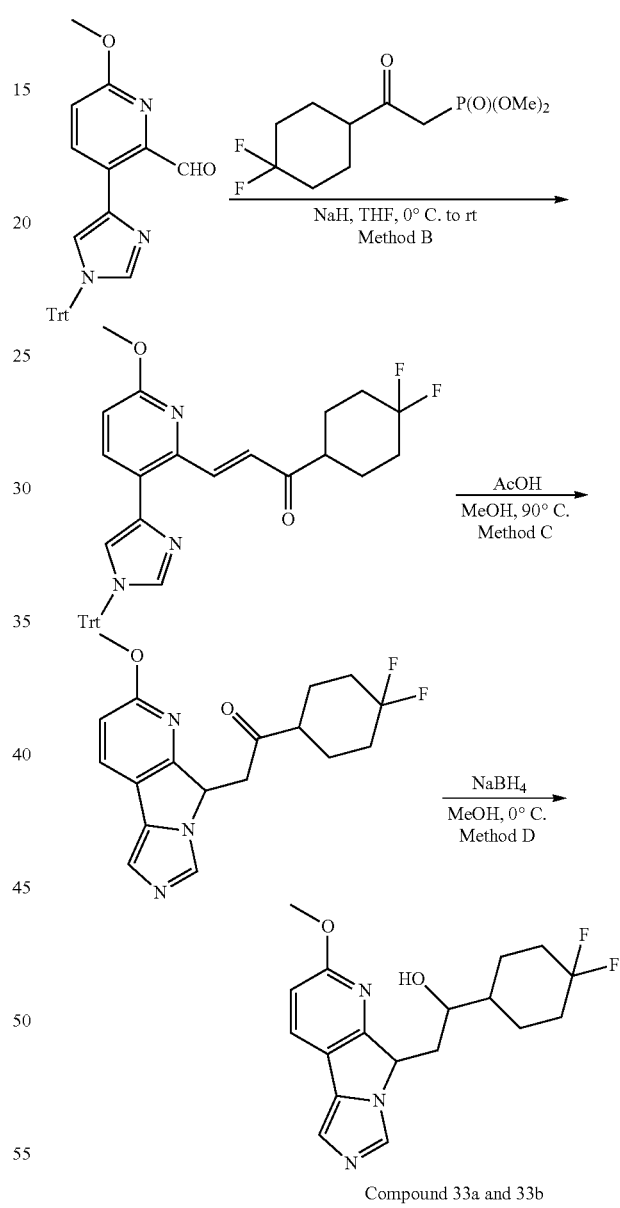

Compound 33a and 33b 1-(4,4-Difluorocyclohexyl)-2-[10-methoxy-4,6,9-triazatricyclo[6.4.0.0^[2,6]]dodeca-1(8),2,4,9,11-pentaen-7-yl]ethan-1-ol 1-(4,4-Difluorocyclohexyl)-2-[10-methoxy-4,6,9-triazatricyclo[6.4.0.0^[2,6]]dodeca-1(8),2,4,9,11-pentaen-7-yl]ethan-1-ol was prepared from 6-methoxy-3-[1-(triphenylmethyl)-1H-imidazol-4-yl]pyridine-2-carbaldehyde and dimethyl [2-(4,4-difluorocyclohexyl)-2-oxoethyl](methyl-idene)phosphonite using Method B, C, and D. Two pairs of enantiomeric products were obtained by the separation on chiral prep-HPLC under the following conditions: Chiralpak IB, 20×250 mm, 5 μm; mobile phase, iPrOH in hexane; 20% isocratic in 15 min; Detector, UV 254/220 nm.

Compound 33a:

(26 mg, 18% for three steps, white solid, containing two stereoisomers), HPLC: 96.4% purity, RT=2.68 min. MS: m/z=350.2 [M+H]$^+$. $^1$H NMR (300 MHz, CD$_3$OD, ppm) δ=7.99 (s, 1H), 7.89 (d, J=8.4 Hz, 1H), 7.09 (s, 1H), 6.81 (d, J=8.4 Hz, 1H), 5.27 (t, J=6.3 Hz, 1H), 4.15-4.12 (m, 1H), 3.97 (s, 3H), 2.29-1.92 (m, 5H), 1.80-1.63 (m, 3H), 1.49-1.41 (m, 3H);

Compound 33b:

(10 mg, 6.9% for three steps, white solid, containing two stereoisomers) HPLC: 99.3% purity, RT=1.56 min. MS: m/z=350.1 [M+H]$^+$. $^1$H NMR (300 MHz, CD$_3$OD, ppm) δ=7.98 (s, 1H), 7.91 (d, J=8.7 Hz, 1H), 7.11 (s, 1H), 6.81 (d, J=8.7 Hz, 1H), 5.35 (dd, J=5.7, 4.2 Hz, 1H), 3.97 (s, 3H), 3.82-3.76 (m, 1H), 2.47-2.38 (m, 1H), 2.10-1.98 (m, 3H), 1.88-1.63 (m, 4H), 1.50-1.38 (m, 3H).

Example 34: Synthesis of 10-methoxy-7-[2-(1,4,4-trifluorocyclohexyl)ethyl]-4,6,9-triazatricyclo[6.4.0.0^[2,6]]dodeca-1(8),2,4,9,11-pentaene (34a and 34b)

obtained by the separation on chiral prep-HPLC under the following conditions: Phenomenex Lux 5u Cellulose-4, AXIA Packed, 21.2×250 mm, 5 μm; mobile phase, iPrOH in hexane; 30% isocratic in 33 min; Detector, UV 254/220 nm.

Compound 34a:

(17 mg, 12%, yellow oil, single stereoisomer) HPLC: 99.4% purity, RT=1.66 min. MS: m/z=352.1 [M+H]$^+$. $^1$H NMR (300 MHz, CD$_3$OD, ppm) δ=7.95 (s, 1H), 7.90 (d, J=8.4 Hz, 1H), 7.11 (s, 1H), 6.82 (d, J=8.7 Hz, 1H), 5.24 (t, J=5.4 Hz, 1H), 3.97 (s, 3H), 2.42-2.24 (m, 2H), 2.10-1.92 (m, 6H), 1.78-1.42 (m, 4H);

Compound 34b:

(15 mg, 10.6%, yellow oil, single stereoisomer) HPLC: 99.1% purity, RT=1.67 min. MS: m/z=352.0 [M+H]$^+$. $^1$H NMR (300 MHz, CD$_3$OD, ppm) δ=7.99 (s, 1H), 7.91 (d, J=8.4 Hz, 1H), 7.13 (s, 1H), 6.82 (d, J=8.7 Hz, 1H), 5.25 (t, J=5.4 Hz, 1H), 3.97 (s, 3H), 2.42-2.24 (m, 2H), 2.10-1.92 (m, 6H), 1.78-1.42 (m, 4H).

Example 35: Synthesis of 4-fluoro-4-(2-(9-fluoro-5H-imidazo[5,1-a]isoindol-5-yl)ethyl)cyclohexanol (35a, 35b, 35c, 35d)

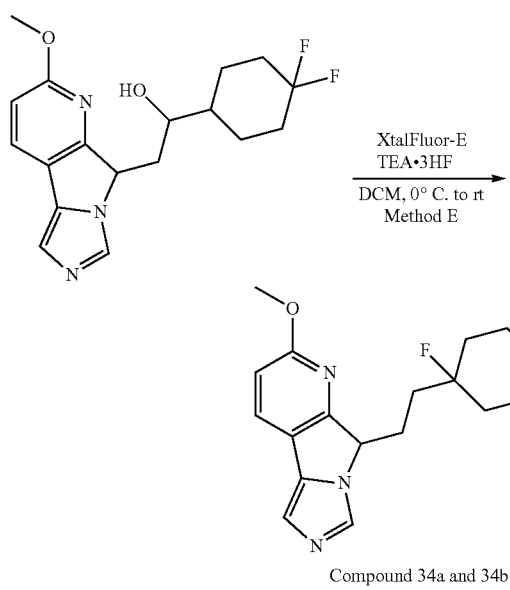

Compound 34a and 34b

10-Methoxy-7-[2-(1,4,4-trifluorocyclohexyl)ethyl]-4,6,9-triazatricyclo[6.4.0.0^[2,6]]dodeca-1(8),2,4,9,11-pentaene 10-Methoxy-7-[2-(1,4,4-trifluorocyclohexyl)ethyl]-4,6,9-triazatricyclo[6.4.0.0^[2,6]]dodeca-1(8),2,4,9,11-pentaene was prepared from 1-(4,4-difluorocyclohexyl)-2-[10-methoxy-4,6,9-triazatricyclo[6.4.0.0^[2,6]]dodeca-1(8),2,4,9,11-pentaen-7-yl]ethan-1-ol using Method E. The crude product was first purified by prep-HPLC under the following conditions: Atlantis prep T3 OBD column, 19×150 mm, 5 μm; MeCN in water (with 0.05% TFA); 10% to 25% gradient in 10 min. Two enantiomeric products were

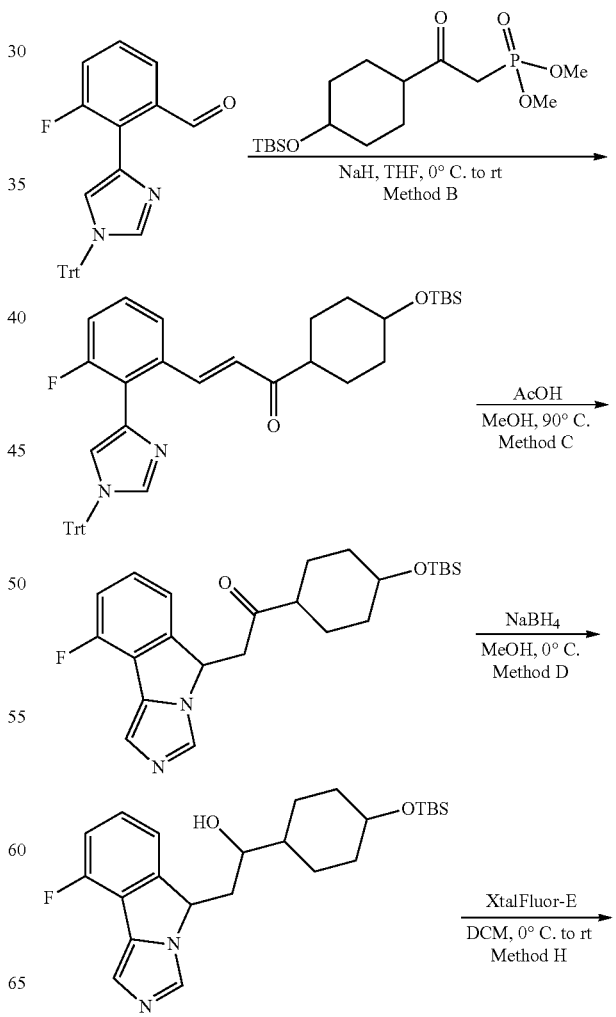

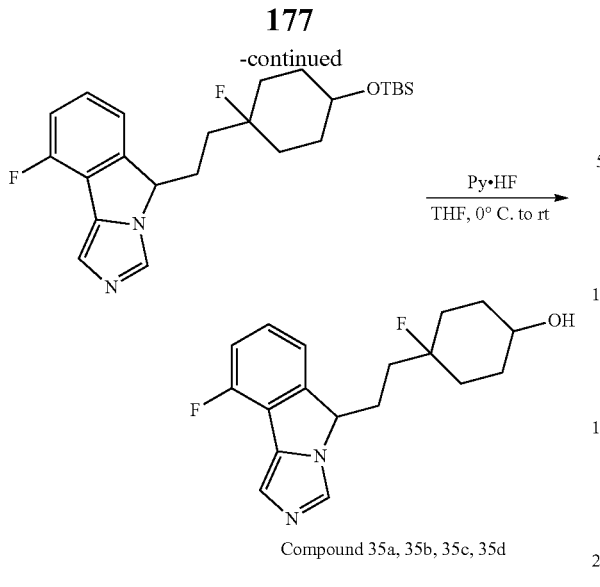

Compound 35a, 35b, 35c, 35d

4-Fluoro-4-(2-(9-fluoro-5H-imidazo[5,1-a]isoindol-5-yl)ethyl)cyclohexanol

4-Fluoro-4-(2-(9-fluoro-5H-imidazo[5,1-a]isoindol-5-yl)ethyl)cyclohexanol was prepared from 3-fluoro-2-[1-(triphenylmethyl)-1H-imidazol-4-yl]benzaldehyde and dimethyl (2-[4-[(tert-butyldimethylsilyl)oxy]cyclohexyl]-2-oxoethyl) phosphonate using Method B, C, D, and H. The four enantiomeric products were obtained by the separation on chiral prep-HPLC under the following conditions: Phenomenex Lux 5u Cellulose-4, AXIA Packed, 21.2×250 mm, 5 μm; EtOH in hexane, 20% isocratic in 39 min; Detector, UV 254/220 nm.

Compound 35a:

(18 mg, 6% for five steps, white solid, single stereoisomer) HPLC: 99.2% purity, RT=1.01 min. MS: m/z=319.2 [M+H]+. 1H NMR (300 MHz, CD3OD, ppm) δ=7.99 (s, 1H), 7.41-7.32 (m, 2H), 7.22-7.18 (m, 1H), 7.15 (s, 1H), 5.53 (t, J=4.8 Hz, 1H), 3.89 (br s, 1H), 2.47-2.38 (m, 1H), 2.28-2.16 (m, 1H), 1.80-1.47 (m, 6H), 1.35-1.21 (m, 4H);

Compound 35b:

(17 mg, 5.7% for five steps, white solid, single stereoisomer) HPLC: 99.4% purity, RT=1.00 min. MS: m/z=319.2 [M+H]+. 1H NMR (300 MHz, CD3OD, ppm) δ=7.99 (s, 1H), 7.41-7.32 (m, 2H), 7.22-7.18 (m, 1H), 7.15 (s, 1H), 5.53 (t, J=4.8 Hz, 1H), 3.89 (br s, 1H), 2.47-2.38 (m, 1H), 2.28-2.16 (m, 1H), 1.80-1.47 (m, 6H), 1.35-1.21 (m, 4H);

Compound 35c:

(9 mg, 3% for five steps, white solid, single stereoisomer) HPLC: 99.4% purity, RT=0.93 min. MS: m/z=319.2 [M+H]+. 1H NMR (300 MHz, CD3OD, ppm) δ=7.99 (s, 1H), 7.41-7.32 (m, 2H), 7.21-7.18 (m, 1H), 7.15 (s, 1H), 5.52 (t, J=5.1 Hz, 1H), 3.55-3.47 (m, 1H), 2.47-2.38 (m, 1H), 2.27-2.16 (m, 1H), 1.86-1.73 (m, 4H), 1.59-1.41 (m, 3H), 1.38-1.20 (m, 3H);

Compound 35d:

(9 mg, 3% for five steps, white solid, single stereoisomer) HPLC: 99.5% purity, RT=0.94 min. MS: m/z=319.2 [M+H]+. 1H NMR (300 MHz, CD3OD, ppm) δ=7.99 (s, 1H), 7.41-7.32 (m, 2H), 7.21-7.18 (m, 1H), 7.15 (s, 1H), 5.52 (t, J=5.1 Hz, 1H), 3.55-3.47 (m, 1H), 2.47-2.38 (m, 1H), 2.27-2.16 (m, 1H), 1.86-1.73 (m, 4H), 1.59-1.41 (m, 3H), 1.38-1.20 (m, 3H).

Example 36: Synthesis of 9-fluoro-5-(2-(1-fluorocyclohexyl)ethyl)-5H-imidazo[5,1-a]isoindole (36a and 36b)

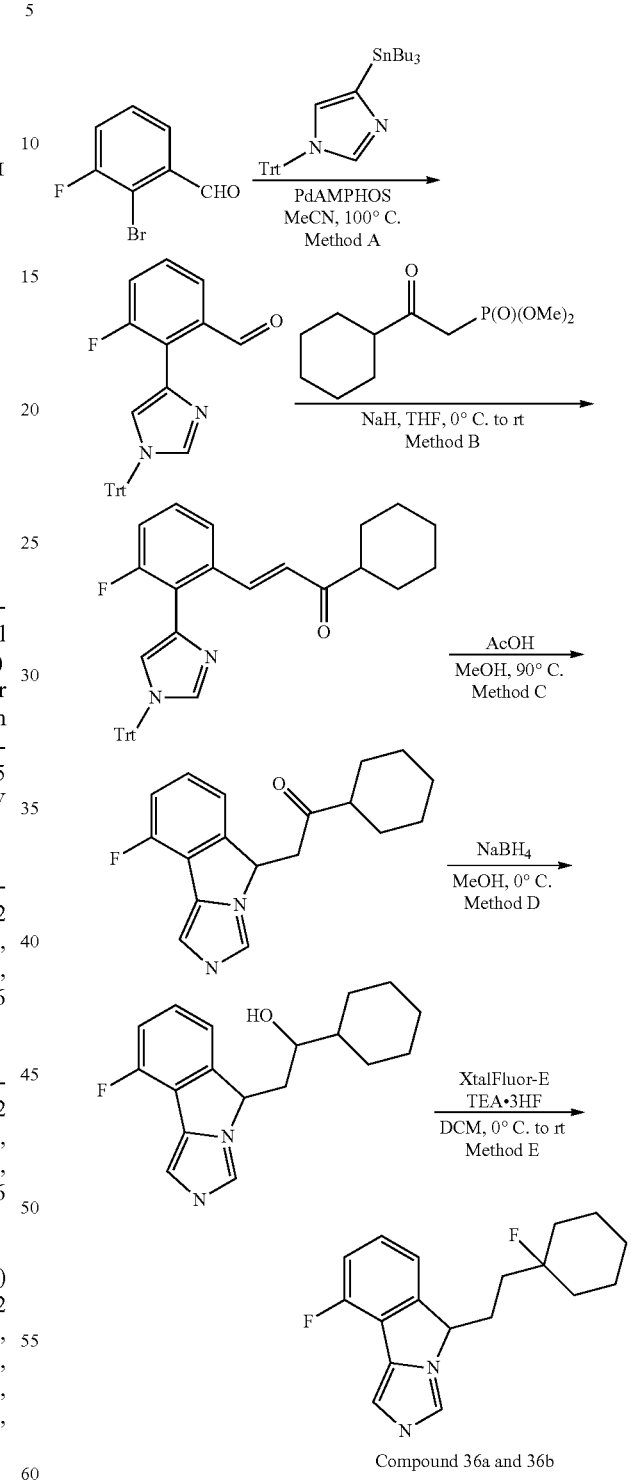

Compound 36a and 36b

9-Fluoro-5-(2-(1-fluorocyclohexyl)ethyl)-5H-imidazo[5,1-a]isoindole

9-Fluoro-5-(2-(1-fluorocyclohexyl)ethyl)-5H-imidazo[5,1-a]isoindole was prepared from 2-bromo-3-fluorobenzaldehyde, 4-(tributylstannyl)-1-(triphenylmethyl)-1H-imidazole, and dimethyl (2-cyclohexyl-2-oxoethyl)phosphonate using Method A, B, C, D, and E. Two enantiomeric products were obtained by the separation on chiral prep-HPLC under the following conditions: Chiralpak IA, 20×250 mm, 5 µm; EtOH in hexane (with 0.2% IPA), 5% EtOH isocratic in 30 min; Detector, UV 254/220 nm.

Compound 36a:

(18 mg, 8.3% for five steps, light yellow oil, single stereoisomer) HPLC: 95.3% purity, RT=1.31 min. MS: m/z=303.2 [M+H]+. 1H NMR (300 MHz, CD3OD, ppm) δ=7.97 (s, 1H), 7.40-7.31 (m, 2H), 7.21-7.17 (m, 1H), 7.14 (s, 1H), 5.51 (t, J=4.8 Hz, 1H), 2.45-2.37 (m, 1H), 2.24-2.16 (m, 1H), 1.77-1.67 (m, 2H), 1.58-1.41 (m, 6H), 1.37-1.16 (m, 4H);

Compound 36b:

(17 mg, 7.8% for five steps, light yellow oil, single stereoisomer) HPLC: 91.8% purity, RT=1.86 min. MS: m/z=303.2 [M+H]+. 1H NMR (300 MHz, CD3OD, ppm) δ=7.97 (s, 1H), 7.40-7.31 (m, 2H), 7.21-7.17 (m, 1H), 7.14 (s, 1H), 5.51 (t, J=5.1 Hz, 1H), 2.45-2.37 (m, 1H), 2.24-2.16 (m, 1H), 1.77-1.67 (m, 2H), 1.58-1.41 (m, 6H), 1.37-1.16 (m, 4H).

Example 37: Synthesis of 6,9-difluoro-5-(2-(1-fluorocyclohexyl)ethyl)-5H-imidazo[5,1-a]isoindole (37a and 37b)

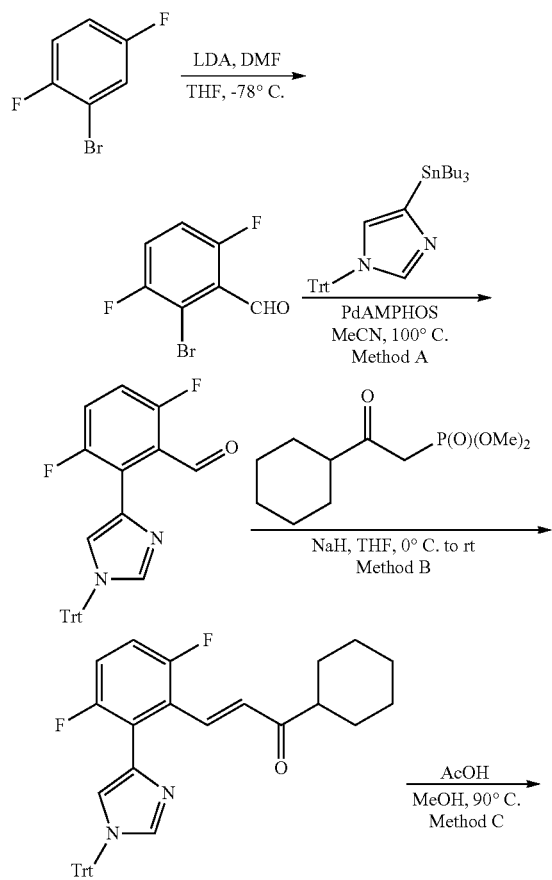

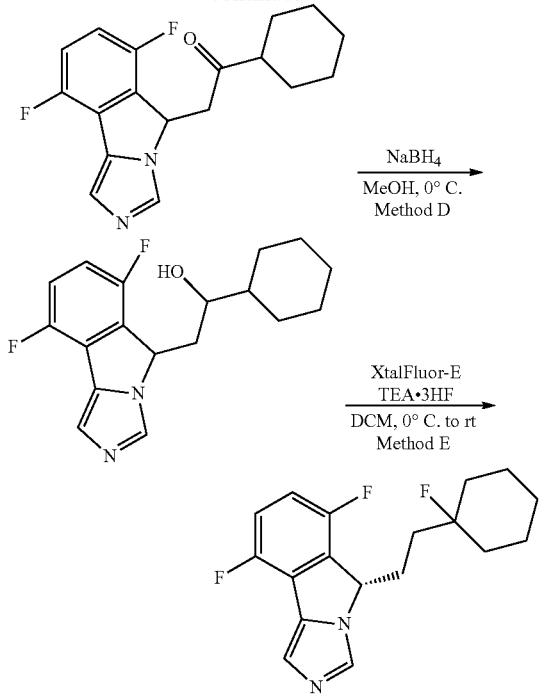

Compound 37a and 37b

2-Bromo-3,6-difluorobenzaldehyde

To a solution of 2-bromo-1,4-difluorobenzene (1 g, 5.18 mmol) in THF (25 mL) was added LDA solution (2 M in THF, 2.9 mL, 5.8 mmol) dropwise at −78° C. After stirring for 1 h at −78° C., DMF (0.441 mL, 6.03 mmol) was added dropwise and the resulting reaction mixture was stirred at −78° C. for additional 30 min. The reaction was quenched by sat. NH4Cl solution (40 mL) carefully and the mixture was extracted with EtOAc (80 mL×2). The combined organic phase was washed with brine and dried over sodium sulfate. The solvent was removed under reduced pressure to yield 2-bromo-3,6-difluorobenzaldehyde as light brown solid (1.05 g, 92%, crude yield) which was used in next step without further purification.

6,9-Difluoro-5-(2-(1-fluorocyclohexyl)ethyl)-5H-imidazo[5,1-a]isoindole 6,9-Difluoro-5-(2-(1-fluorocyclohexyl)ethyl)-5H-imidazo[5,1-a]isoindole was prepared from 2-bromo-3,6-difluorobenzaldehyde, 4-(tributylstannyl)-1-(triphenylmethyl)-1H-imidazole, and dimethyl (2-cyclohexyl-2-oxoethyl) phosphonate using Method A, B, C, D, and E. Two enantiomeric products were obtained by the separation on chiral prep-HPLC under the following conditions: Phenomenex Lux 5u Cellulose-4, AXIA Packed, 21.2×250 mm, 5 µm; EtOH in hexane, 10% isocratic in 17 min; Detector, UV 254/220 nm.

Compound 37a:

(13 mg, 4.2% for five steps, yellow oil, single stereoisomer) HPLC: 90.7% purity, RT=2.39 min. MS: m/z=321.1 [M+H]+. 1H NMR (300 MHz, CD3OD, ppm) δ=7.98 (s, 1H), 7.22-7.15 (m, 1H), 7.15 (s, 1H), 7.09-7.02 (m, 1H), 5.69 (t, J=4.8 Hz, 1H), 2.50-2.40 (m, 1H), 2.29-2.18 (m, 1H), 1.71-1.64 (m, 2H), 1.55-1.36 (m, 6H), 1.29-1.11 (m, 4H);

Compound 37b:

(11 mg, 3.5% for five steps, yellow oil, single stereoisomer) HPLC: 99.3% purity, RT=1.68 min. MS: m/z=321.1 [M+H]+. 1H NMR (300 MHz, CD3OD, ppm) δ=7.98 (s, 1H), 7.22-7.15 (m, 1H), 7.15 (s, 1H), 7.09-7.02 (m, 1H), 5.69 (t, J=4.8 Hz, 1H), 2.50-2.40 (m, 1H), 2.29-2.18 (m, 1H), 1.71-1.64 (m, 2H), 1.55-1.36 (m, 6H), 1.29-1.11 (m, 4H).

Example 38: Synthesis of 4-(2-(6,9-difluoro-5H-imidazo[5,1-a]isoindol-5-yl)ethyl)-4-fluorocyclohexanol (38a, 38b, 38c, 38d)

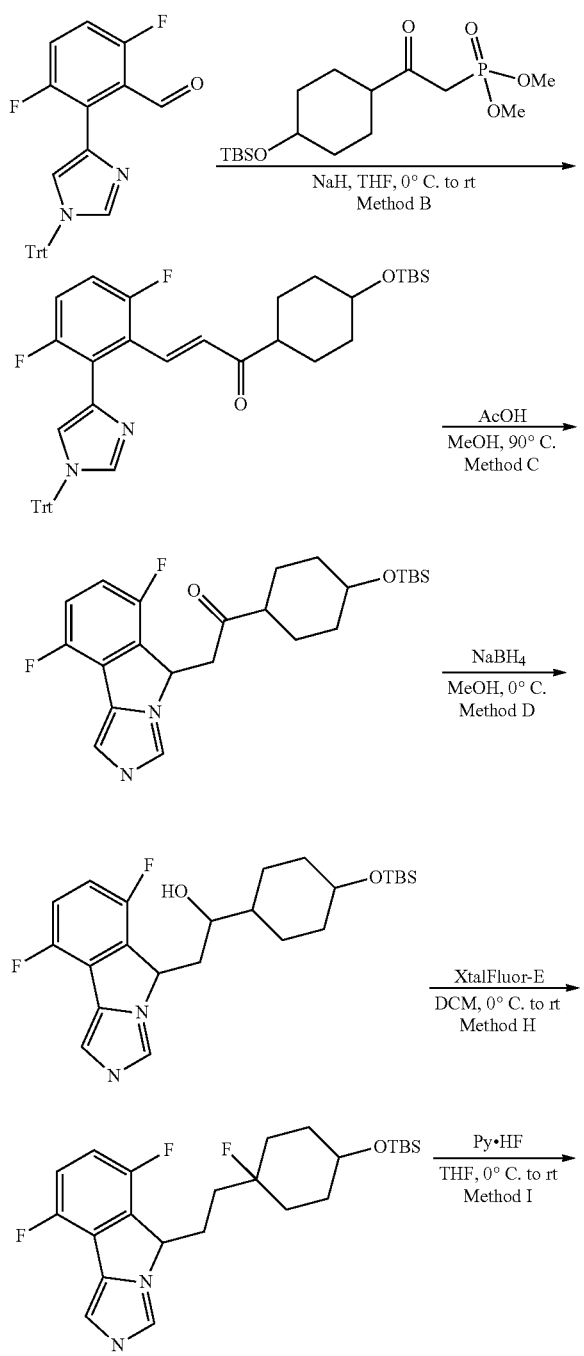

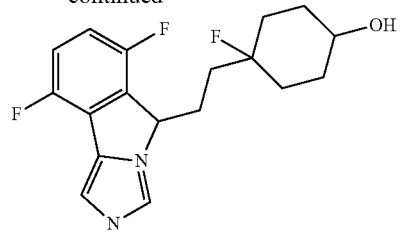

4-(2-(6,9-Difluoro-5H-imidazo[5,1-a]isoindol-5-yl)ethyl)-4-fluorocyclohexanol 4-(2-(6,9-Difluoro-5H-imidazo[5,1-a]isoindol-5-yl)ethyl)-4-fluorocyclohexanol was prepared from 3,6-difluoro-2-[1-(triphenylmethyl)-1H-imidazol-4-yl]benzaldehyde and dimethyl (2-[4-[(tert-butyldimethylsilyl)oxy]cyclohexyl]-2-oxoethyl)phosphonate using Method B, C, D, H, and I. Four enantiomeric products were obtained by the separation chiral prep-HPLC under the following conditions: Phenomenex Lux 5u Cellulose-4, AXIA Packed, 21.2×250 mm, 5 μm; iPrOH in hexane (with 0.2% DEA), 40% isocratic in 20 min; Detector, UV 254/220 nm.

Compound 38a:

(16 mg, 5% for five steps, white solid, single stereoisomer) HPLC: 99.9% purity, RT=0.89 min. MS: m/z=337.1 [M+H]+. 1H NMR (300 MHz, CD3OD, ppm) δ=7.99 (s, 1H), 7.23-7.16 (m, 1H), 7.15 (s, 1H), 7.10-7.03 (m, 1H), 5.71 (t, J=4.5 Hz, 1H), 3.86 (br s, 1H), 2.52-2.43 (m, 1H), 2.30-2.21 (m, 1H), 1.78-1.67 (m, 3H), 1.61-1.42 (m, 5H), 1.30-1.11 (m, 2H);

Compound 38b:

(15 mg, 4.7% for five steps, white solid, single stereoisomer) HPLC: 99.7% purity, RT=0.90 min. MS: m/z=337.1 [M+H]+. 1H NMR (300 MHz, CD3OD, ppm) δ=7.99 (s, 1H), 7.23-7.16 (m, 1H), 7.15 (s, 1H), 7.10-7.03 (m, 1H), 5.71 (t, J=4.5 Hz, 1H), 3.85 (br s, 1H), 2.52-2.43 (m, 1H), 2.30-2.21 (m, 1H), 1.78-1.67 (m, 3H), 1.61-1.42 (m, 5H), 1.30-1.11 (m, 2H);

Compound 38c:

(10 mg, 3.1% for five steps, white solid, single stereoisomer) HPLC: 99.1% purity, RT=0.86 min. MS: m/z=337.1 [M+H]+. 1H NMR (300 MHz, CD3OD, ppm) δ=7.99 (s, 1H), 7.22-7.16 (m, 1H), 7.15 (s, 1H), 7.09-7.02 (m, 1H), 5.70 (t, J=4.5 Hz, 1H), 3.51-3.47 (m, 1H), 2.50-2.41 (m, 1H), 2.30-2.20 (m, 1H), 1.82-1.66 (m, 4H), 1.54-1.36 (m, 3H), 1.25-1.12 (m, 3H);

Compound 38d:

(11 mg, 3.4% for five steps, white solid, single stereoisomer) HPLC: 99.0% purity, RT=0.83 min. MS: m/z=337.1 [M+H]+. 1H NMR (300 MHz, CD3OD, ppm) δ=7.99 (s, 1H), 7.22-7.16 (m, 1H), 7.15 (s, 1H), 7.09-7.02 (m, 1H), 5.70 (t, J=4.5 Hz, 1H), 3.51-3.47 (m, 1H), 2.50-2.41 (m, 1H), 2.30-2.20 (m, 1H), 1.82-1.66 (m, 4H), 1.54-1.36 (m, 3H), 1.25-1.12 (m, 3H).

Example 39: Synthesis of 1-cyclohexyl-2-[10-methoxy-4,6,9-triazatricyclo[6.4.0.0^[2,6]]dodeca-1(8),2,4,9,11-pentaen-7-yl]ethan-1-ol (39a and 39b)

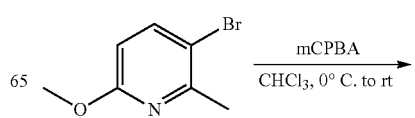

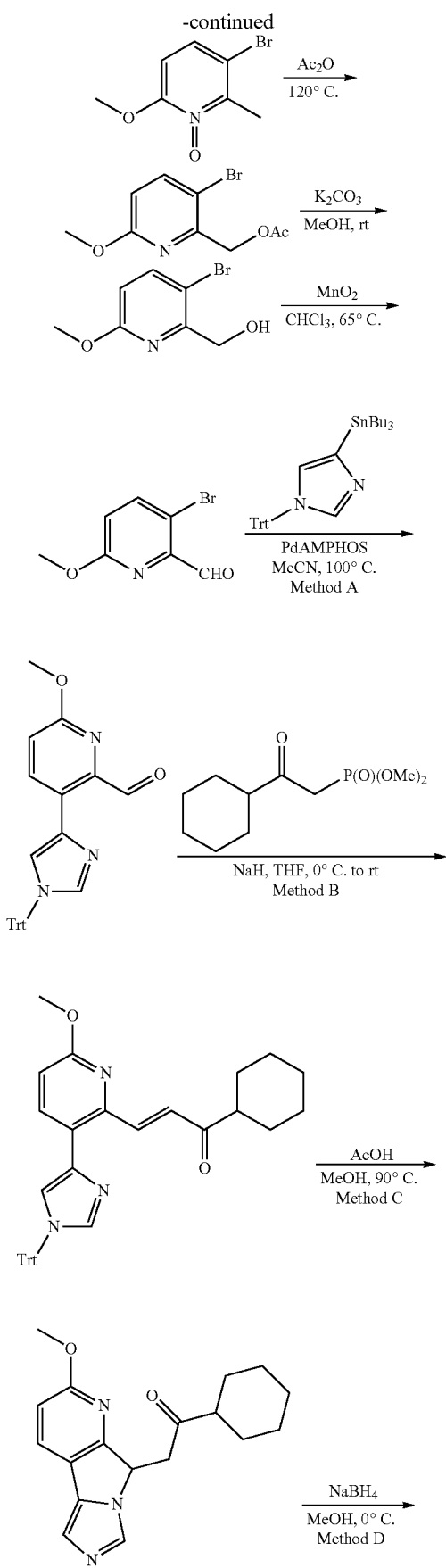

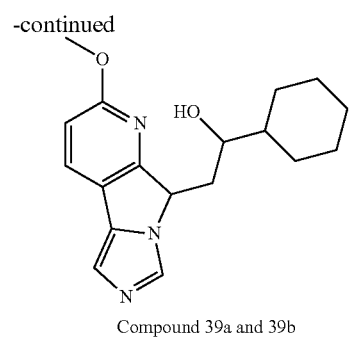

Compound 39a and 39b

3-Bromo-6-methoxy-2-methylpyridine 1-oxide

To a solution of 3-bromo-6-methoxy-2-methylpyridine (5 g, 24.75 mmol) in chloroform (100 mL) was added mCPBA (8.52 g, 49.37 mmol) in portions at 0° C. The resulting mixture was stirred at room temperature for 2 d. The reaction mixture was then diluted with sat. NaHCO$_3$ solution (200 mL) and was extracted with dichloromethane (250 mL×2). The combined organic phase was washed with brine and dried over sodium sulfate. The solvent was removed under reduced pressure and the residue was purified by flash chromatography eluting with methanol in dichloromethane (1% to 5% gradient) to yield 3-bromo-6-methoxy-2-methylpyridine 1-oxide as yellow solid (2.8 g, 52%). MS: m/z=217.9 [M+H]$^+$.

(3-Bromo-6-methoxypyridin-2-yl)methyl acetate

A mixture of 3-bromo-6-methoxy-2-methylpyridine 1-oxide (2.8 g, 12.84 mmol) in acetic anhydride (20 mL) was stirred at 120° C. for 3 h. The reaction mixture was concentrated under reduced pressure and the residue was purified by flash chromatography eluting with ethyl acetate in petroleum ether (1% to 5% gradient) to yield (3-bromo-6-methoxypyridin-2-yl)methyl acetate as yellow oil (2.03 g, 61%). MS: m/z=259.9 [M+H]$^+$.

(3-Bromo-6-methoxypyridin-2-yl)methanol

To a solution of (3-bromo-6-methoxypyridin-2-yl)methyl acetate (3.1 g, 11.92 mmol) in methanol (30 mL) was added potassium carbonate (2.47 g, 17.88 mmol) slowly. The resulting mixture was then stirred at room temperature for 16 h. The reaction mixture was diluted with water (150 mL) and extracted with dichloromethane (250 mL×2). The combined organic phase was washed with brine and dried over sodium sulfate. The solvent was removed under reduced pressure to yield (3-bromo-6-methoxypyridin-2-yl)methanol as yellow oil (2.35 g, 90%, crude yield) which was used in the next step without further purification. MS: m/z=217.8 [M+H]$^+$.

3-Bromo-6-methoxypyridine-2-carbaldehyde

To a solution of (3-bromo-6-methoxypyridin-2-yl)methanol (500 mg, 2.29 mmol) in chloroform (15 mL) was added manganese dioxide (1.4 g, 16.10 mmol) slowly. The resulting mixture was stirred at 65° C. for 16 h. The reaction was filtered through celite and washed with dichloromethane (50 mL×4). The combined organic phase was concentrated under reduced pressure to yield 3-bromo-6-methoxypyridine-2-carbaldehyde as yellow solid (460 mg, 93%, crude 1-Cyclohexyl-2-[10-methoxy-4,6,9-triazatricyclo[6.4.0.0^[2,6]]dodeca-1(8),2,4,9,11-pentaen-7-yl]ethan-1-ol 1-Cyclohexyl-2-[10-methoxy-4,6,9-triazatricyclo[6.4.0.0^[2,6]]dodeca-1(8),2,4,9,11-pentaen-7-yl]ethan-1-ol was prepared from 3-bromo-6-methoxypyridine-2-carbaldehyde, 4-(tributylstannyl)-1-(triphenylmethyl)-1H-imidazole, and dimethyl (2-cyclohexyl-2-oxoethyl)phosphonate using Method A, B, C, and D. Two pairs of enantiomeric products were obtained by the separation on chiral prep-HPLC under the following conditions: Chiralpak IB, 20×250 mm, 5 μm; mobile phase, iPrOH in hexane; 10% isocratic in 20 min; Detector, UV 254/220 nm.

Compound 39a:

(26 mg, 9.2% for four steps, white solid, containing two stereoisomers), HPLC: 98.8% purity, RT=2.93 min. MS: m/z=314.2 [M+H]$^+$. $^1$H NMR (400 MHz, CD$_3$OD, ppm) δ=8.00 (br s, 1H), 7.89 (d, J=8.4 Hz, 1H), 7.10 (br s, 1H), 6.81 (d, J=8.4 Hz, 1H), 5.26 (t, J=6.2 Hz, 1H), 4.07-4.03 (m, 1H), 3.98 (s, 3H), 2.27-2.21 (m, 1H), 2.11-2.05 (m, 1H), 1.91-1.88 (m, 1H), 1.78-1.68 (m, 4H), 1.41-1.07 (m, 6H);

Compound 39b:

(9 mg, 3.8% for four steps, white solid, containing two stereoisomers) HPLC: 96.6% purity, RT=2.88 min. MS: m/z=314.2 [M+H]$^+$. $^1$H NMR (300 MHz, CD$_3$OD, ppm) δ=7.93 (s, 1H), 7.90 (d, J=8.7 Hz, 1H), 7.11 (s, 1H), 6.81 (d, J=8.4 Hz, 1H), 5.34 (dd, J=9.6, 3.9 Hz, 1H), 3.97 (s, 3H), 3.72-3.66 (m, 1H), 2.43-2.35 (m, 1H), 1.95-1.90 (m, 1H), 1.82-1.65 (m, 5H), 1.42-1.01 (m, 6H).

Example 40: Synthesis of 1-(4,4-dimethylcyclohexyl)-2-[10-methoxy-4,6,9-triazatricyclo[6.4.0.0^[2,6]]dodeca-1(8),2,4,9,11-pentaen-7-yl]ethan-1-ol (40a and 40b)

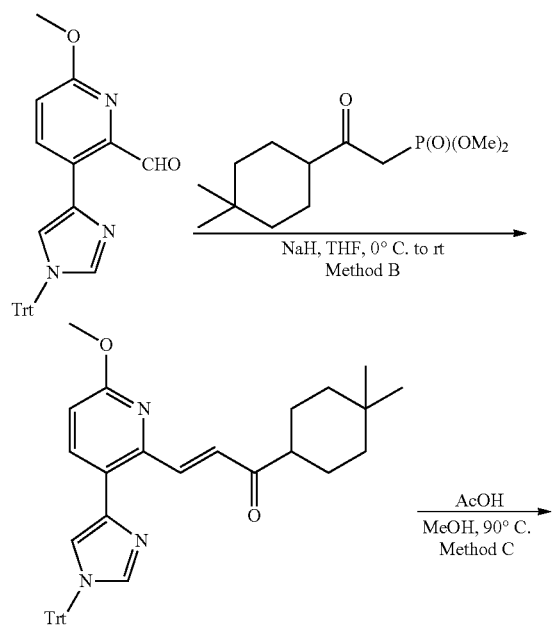

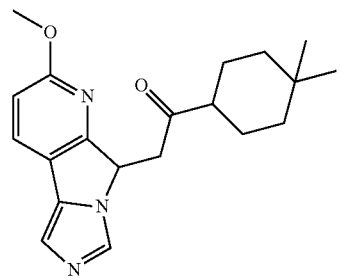

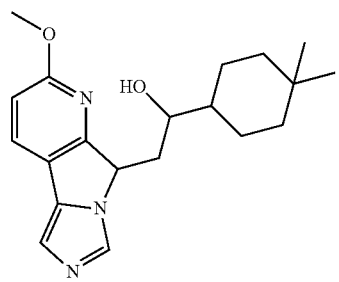

Compound 40a and 40b 1-(4,4-Dimethylcyclohexyl)-2-[10-methoxy-4,6,9-triazatricyclo[6.4.0.0^[2,6]]dodeca-1(8),2,4,9,11-pentaen-7-yl]ethan-1-ol 1-(4,4-Dimethylcyclohexyl)-2-[10-methoxy-4,6,9-triazatricyclo[6.4.0.0^[2,6]]dodeca-1(8),2,4,9,11-pentaen-7-yl]ethan-1-ol was prepared from 6-methoxy-3-[1-(triphenylmethyl)-1H-imidazol-4-yl]pyridine-2-carbaldehyde and dimethyl [2-(4,4-dimethylcyclohexyl)-2-oxoethyl]phosphonate using Method B, C, and D. Two pairs of enantiomeric products were obtained by the separation on prep-HPLC under the following conditions: Gemini-NX C18, 21.2×150 mm, 5 μm; MeCN in water (with 0.05% TFA); 25% to 35% gradient in 15 min.

Compound 40a:

(19 mg, 11% for three steps, white solid, containing two stereoisomers), HPLC: 99.6% purity, RT=1.79 min. MS: m/z=342.2 [M+H]$^+$. $^1$H NMR (400 MHz, CD$_3$OD, ppm) δ=9.07 (br s, 1H), 8.10 (d, J=8.4 Hz, 1H), 7.66 (s, 1H), 6.95 (d, J=8.8 Hz, 1H), 5.69-5.67 (m, 1H), 4.03 (s, 3H), 3.49-3.47 (m, 1H), 2.59-2.53 (m, 1H), 2.20-2.16 (m, 1H), 1.73-1.71 (m, 1H), 1.56-1.54 (m, 1H), 1.47-1.43 (m, 2H), 1.31-1.20 (m, 5H), 0.91 (s, 3H), 0.89 (s, 3H);

Compound 40b:

(13 mg, 7.5% for three steps, white solid, containing two stereoisomers) HPLC: 98.7% purity, RT=3.47 min. MS: m/z=342.2 [M+H]$^+$. $^1$H NMR (400 MHz, CD$_3$OD, ppm) δ=9.12 (s, 1H), 8.09 (d, J=8.4 Hz, 1H), 7.64 (s, 1H), 6.95 (d, J=8.4 Hz, 1H), 5.59-5.56 (m, 1H), 4.10-4.06 (m, 1H), 4.03 (s, 3H), 2.50-2.48 (m, 1H), 2.12-2.04 (m, 1H), 1.72-1.71 (m, 1H), 1.57-1.55 (m, 1H), 1.46-1.44 (m, 2H), 1.38-1.31 (m, 3H), 1.27-1.24 (m, 2H), 0.92 (s, 6H).

Example 41: Synthesis of 4-fluoro-4-(2-(9-methoxy-5H-imidazo[5,1-a]isoindol-5-yl)ethyl)cyclohexanol (41a and 41b)

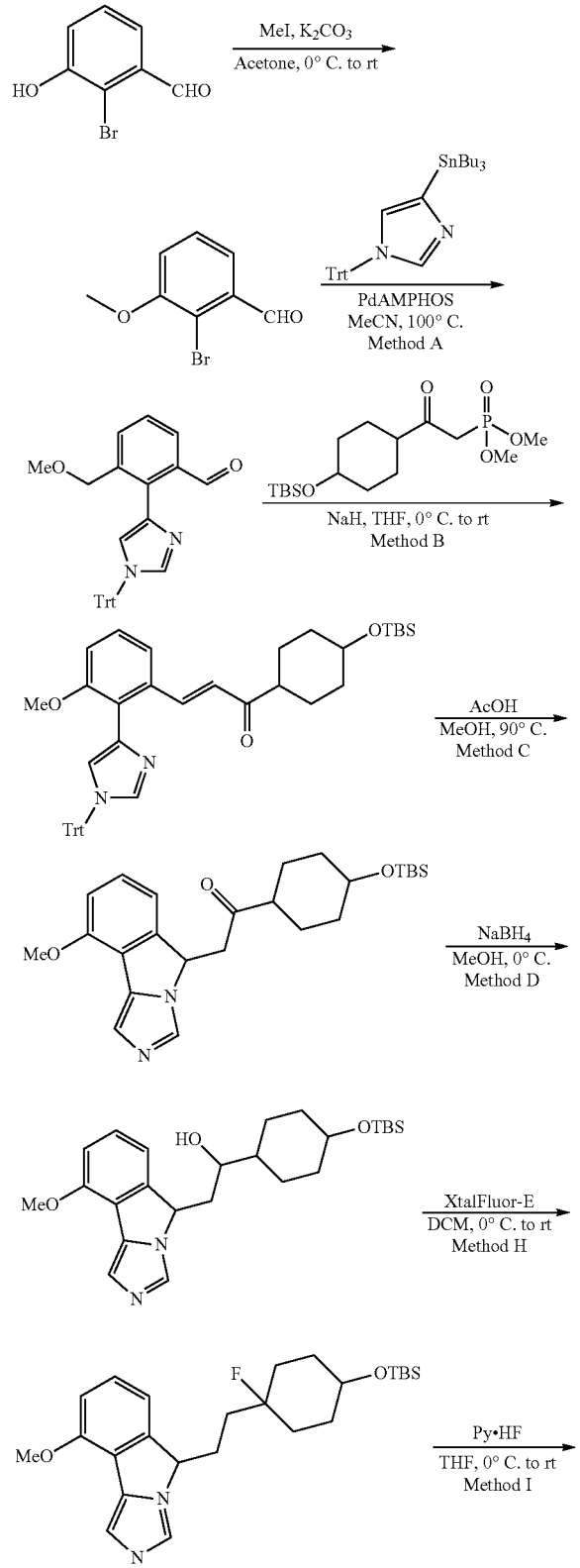

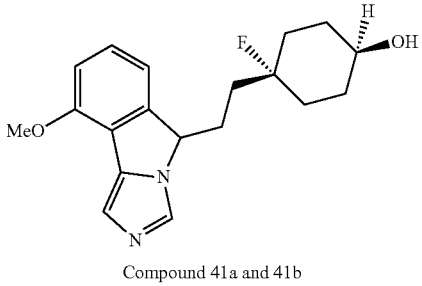 [SMILES: COc1cccc2c1-c1cncn1C2CC[C@]1(F)CC[C@H](O)CC1]

Compound 41a and 41b

2-Bromo-3-methoxybenzaldehyde

To a solution of 2-bromo-3-hydroxybenzaldehyde (1.5 g, 7.46 mmol) in acetone (20 mL) was added potassium carbonate (2.01 g, 14.54 mmol) at 0° C., followed by the addition of methyl iodide (0.7 mL, 11.24 mmol) carefully. The resulting mixture was then stirred at room temperature for 16 h. The reaction mixture was then diluted with water (150 mL) and extracted with EtOAc (150 mL×3). The combined organic phase was washed with brine and dried over sodium sulfate. The solvent was removed under reduced pressure to yield 2-bromo-3-methoxybenzaldehyde as yellow solid (1.5 g, 93%, crude yield) which was used in next step without further purification. MS: m/z=214.8 [M+H]$^+$.

4-Fluoro-4-(2-(9-methoxy-5H-imidazo[5,1-a]isoindol-5-yl)ethyl)cyclohexanol

4-Fluoro-4-(2-(9-methoxy-5H-imidazo[5,1-a]isoindol-5-yl)ethyl)cyclohexanol was prepared from 2-bromo-3-methoxybenzaldehyde, 4-(tributylstannyl)-1-(triphenylmethyl)-1H-imidazole and dimethyl (2-[4-[(tert-butyldimethylsilyl)oxy] cyclohexyl]-2-oxoethyl) phosphonate using Method A, B, C, D, H, and I. Two pairs of enantiomeric products were obtained by the separation on prep-HPLC under the following conditions: XBridge C18 OBD Prep Column, 19×250 mm, 5 μm; MeCN in water (with 10 mM NH$_4$HCO$_3$), 30% to 45% gradient in 10 min; Detector, UV 254/220 nm.

Compound 41a:

(17 mg, 7.2% for six steps, white solid, containing two stereoisomers), HPLC: 99.95% purity, RT=1.22 min. MS: m/z=331.1 [M+H]$^+$. $^1$H NMR (300 MHz, CD$_3$OD, ppm) δ=7.84 (s, 1H), 7.28 (dd, J=8.1, 7.8 Hz, 1H), 7.04-6.98 (m, 2H), 6.97 (s, 1H), 5.38 (t, J=4.8 Hz, 1H), 3.94 (s, 3H), 3.50-3.42 (m, 1H), 2.38-2.29 (m, 1H), 2.18-2.08 (m, 1H), 1.82-1.66 (m, 4H), 1.53-1.37 (m, 3H), 1.31-1.12 (m, 3H);

Compound 41b:

(10 mg, 4.2% for six steps, white solid, containing two stereoisomers) HPLC: 99.9% purity, RT=1.28 min. MS: m/z=331.1 [M+H]$^+$. $^1$H NMR (300 MHz, CD$_3$OD, ppm) δ=7.85 (s, 1H), 7.29 (t, J=7.8 Hz, 1H), 7.05-6.98 (m, 3H), 5.39 (t, J=4.8 Hz, 1H), 3.95 (s, 3H), 3.84 (br s, 1H), 2.39-2.29 (m, 1H), 2.19-2.10 (m, 1H), 1.77-1.63 (m, 4H), 1.59-1.44 (m, 4H), 1.30-1.13 (m, 2H).

Example 42: Synthesis of 5-(2-(1-fluorocyclohexyl)ethyl)-9-methoxy-5H-imidazo[5,1-a]isoindole (42a and 42b)

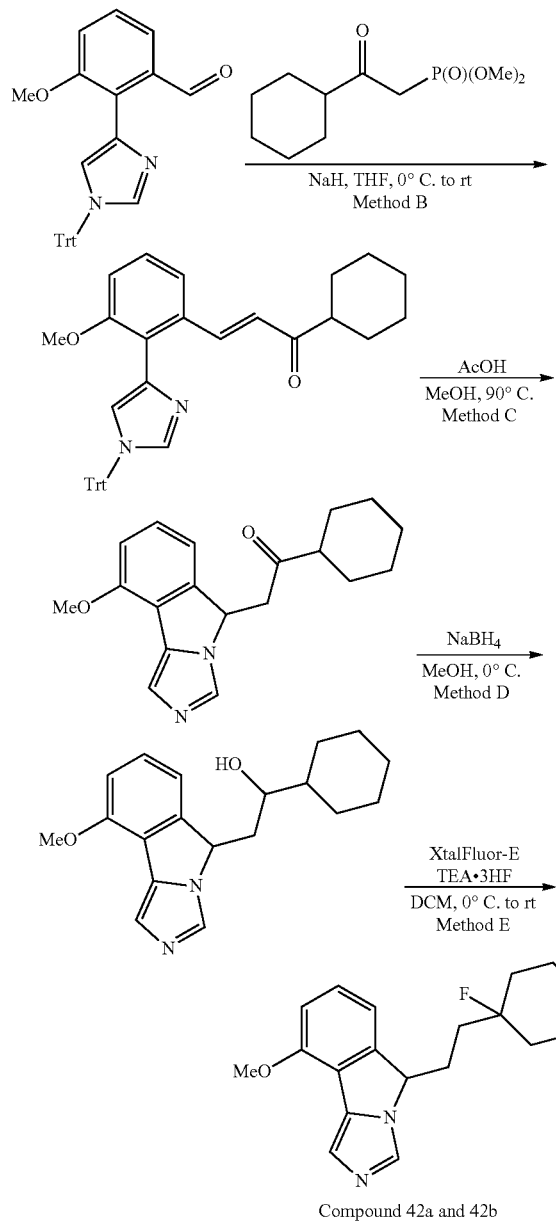

Compound 42a and 42b 5-(2-(1-Fluorocyclohexyl)ethyl)-9-methoxy-5H-imidazo[5,1-a]isoindole 5-(2-(1-Fluorocyclohexyl)ethyl)-9-methoxy-5H-imidazo[5,1-a]isoindole was prepared from 3-methoxy-2-[1-(triphenylmethyl)-1H-imidazol-4-yl]benzaldehyde and dimethyl (2-cyclohexyl-2-oxoethyl)phosphonate using Method B, C, D, and E. Two enantiomeric products were obtained by the separation on chiral prep-HPLC under the following conditions: Phenomenex Lux 5u Cellulose-4, AXIA Packed, 21.2×250 mm, 5 µm; mobile phase, iPrOH in hexane (with 0.2% DEA), 15% isocratic in 32 min; Detector, UV 254/220 nm.

Compound 42a:

(13 mg, 5.5% for four steps, off-white solid, single stereoisomer), HPLC: 98.7% purity, RT=1.36 min. MS: m/z=315.2 [M+H]$^+$. $^1$H NMR (300 MHz, CD$_3$OD, ppm) δ=7.84 (s, 1H), 7.31-7.25 (m, 1H), 7.03-6.97 (m, 3H), 5.39-5.37 (m, 1H), 3.94 (s, 3H), 2.39-2.29 (m, 1H), 2.16-2.08 (m, 1H), 1.72-1.64 (m, 2H), 1.57-1.33 (m, 6H), 1.30-1.11 (m, 4H);

Compound 42b:

(13 mg, 5.5% for four steps, off-white solid, single stereoisomer) HPLC: 99.4% purity, RT=1.37 min. MS: m/z=315.2 [M+H]$^+$. $^1$H NMR (300 MHz, CD$_3$OD, ppm) δ=7.84 (s, 1H), 7.31-7.25 (m, 1H), 7.03-6.97 (m, 3H), 5.39-5.37 (m, 1H), 3.94 (s, 3H), 2.39-2.29 (m, 1H), 2.16-2.08 (m, 1H), 1.72-1.64 (m, 2H), 1.57-1.33 (m, 6H), 1.30-1.11 (m, 4H).

Example 43: Synthesis of 5-(2-(1-fluorocyclohexyl)ethyl)-5H-imidazo[5,1-a]isoindol-9-ol (43a and 43b)

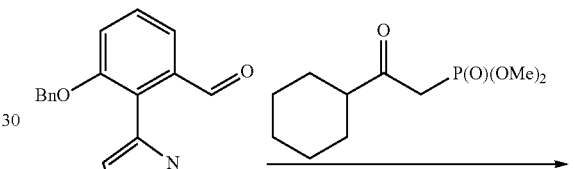

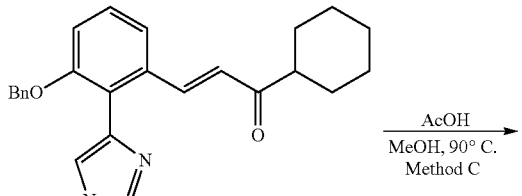

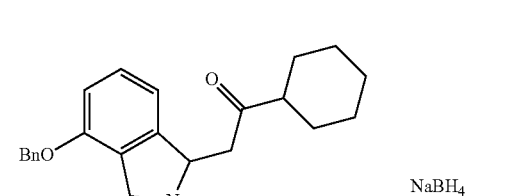

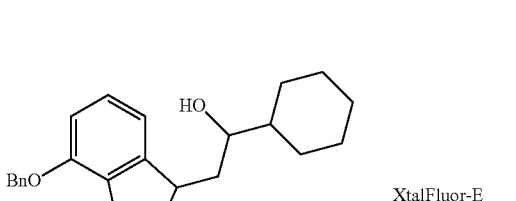

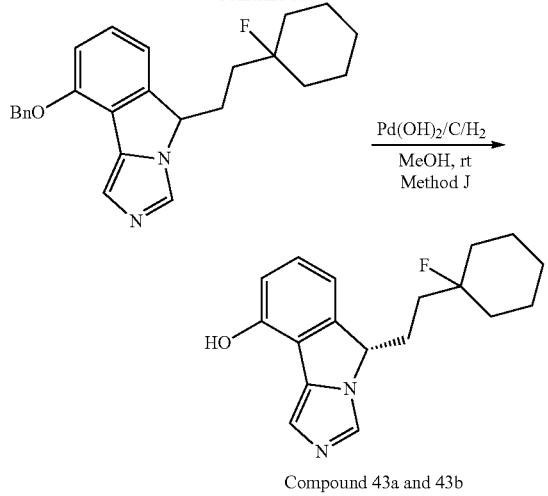

Compound 43a and 43b

5-(2-(1-Fluorocyclohexyl)ethyl)-5H-imidazo[5,1-a]isoindol-9-ol 5-(2-(1-Fluorocyclohexyl)ethyl)-5H-imidazo[5,1-a]isoindol-9-ol was prepared from 3-(benzyloxy)-2-[1-(triphenylmethyl)-1H-imidazol-4-yl]benzaldehyde and dimethyl (2-cyclohexyl-2-oxoethyl)phosphonate using Method B, C, D, E, and J. Two enantiomeric products were obtained by the separation on chiral prep-HPLC under the following conditions: Chiralpak AD-H, 20×250 mm, 5 μm; mobile phase, EtOH in hexane, 15% isocratic in 25 min; Detector, UV 254/220 nm.

Compound 43a:

(16 mg, 2.6% for five steps, white solid, single stereoisomer), HPLC: 99.9% purity, RT=1.65 min. MS: m/z=301.0 [M+H]$^+$. $^1$H NMR (300 MHz, CD$_3$OD, ppm) δ=7.81 (s, 1H), 7.13 (dd, J=8.1, 7.8 Hz, 1H), 6.99 (s, 1H), 6.90 (d, J=7.5 Hz, 1H), 6.80 (d, J=8.1 Hz, 1H), 5.35 (t, J=4.8 Hz, 1H), 2.36-2.28 (m, 1H), 2.15-2.07 (m, 1H), 1.72-1.67 (m, 2H), 1.53-1.38 (m, 6H), 1.28-1.12 (m, 4H);

Compound 43b:

(14 mg, 2.3% for five steps, white solid, single stereoisomer) HPLC: 99.9% purity, RT=1.63 min. MS: m/z=301.0 [M+H]$^+$. $^1$H NMR (300 MHz, CD$_3$OD, ppm) δ=7.81 (s, 1H), 7.13 (dd, J=8.1, 7.8 Hz, 1H), 6.99 (s, 1H), 6.90 (d, J=7.5 Hz, 1H), 6.80 (d, J=8.1 Hz, 1H), 5.35 (t, J=4.8 Hz, 1H), 2.36-2.28 (m, 1H), 2.15-2.07 (m, 1H), 1.72-1.67 (m, 2H), 1.53-1.38 (m, 6H), 1.28-1.12 (m, 4H).

Example 44: Synthesis of 5-(2-(1-fluoro-4-hydroxycyclohexyl)ethyl)-5H-imidazo[5,1-a]isoindol-9-ol (44a and 44b)

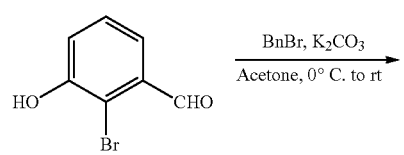

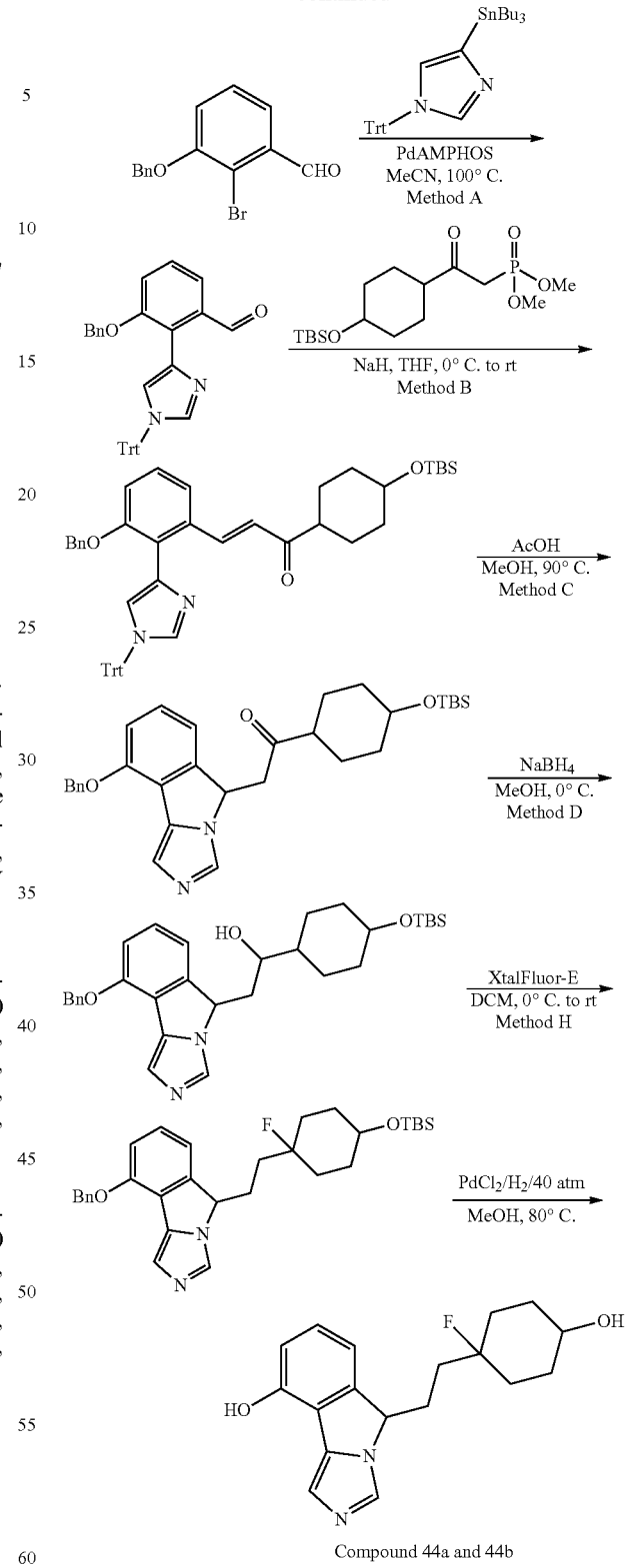

Compound 44a and 44b

3-(Benzyloxy)-2-bromobenzaldehyde

To a solution of 2-bromo-3-hydroxybenzaldehyde (1 g, 4.97 mmol) in acetone (20 mL) was added potassium carbonate (1.38 g, 9.99 mmol) at 0° C., followed by the addition of benzylbromide (1.02 g, 5.96 mmol) carefully. The resulting mixture was then stirred at room temperature for 16 h. The reaction mixture was diluted with water (150 mL) and extracted with ethyl acetate (150 mL×3). The combined organic phase was washed with brine and dried over sodium sulfate. The solvent was removed under reduced pressure and the residue was purified by flash chromatography eluting with ethyl acetate in petroleum ether (5% to 15% gradient) to yield 3-(benzyloxy)-2-bromobenzaldehyde as white solid (1.3 g, 90%).

9-(Benzyloxy)-5-(2-{4-[(tert-butyldimethylsilyl)oxy]-1-fluorocyclohexyl}ethyl)-5H-imidazo[4,3-a]isoindole 9-(Benzyloxy)-5-(2-{4-[(tert-butyldimethylsilyl)oxy]-1-fluorocyclohexyl}ethyl)-5H-imidazo[4,3-a]isoindole was prepared from 3-(benzyloxy)-2-bromobenzaldehyde, 4-(tributylstannyl)-1-(triphenylmethyl)-1H-imidazole, and dimethyl (2-[4-[(tert-butyldimethylsilyl)oxy] cyclohexyl]-2-oxoethyl)phosphonate using Method A, B, C, D, and H. The crude product was purified by flash chromatography eluting with MeOH in DCM (0% to 4% gradient) to yield 9-(Benzyloxy)-5-(2-[4-[(tert-butyldimethylsilyl)oxy]cyclohexyl]-2-fluoroethyl)-5H-imidazo[4,3-a]isoindole as yellow oil (1.5 g, 23% for five steps). MS: m/z=521.4 [M+H]$^+$.

5-(2-(1-Fluoro-4-hydroxycyclohexyl)ethyl)-5H-imidazo[5,1-a]isoindol-9-ol

To a solution of 9-(benzyloxy)-5-(2-{4-[(tert-butyldimethylsilyl)oxy]-1-fluorocyclohexyl}ethyl)-5H-imidazo[4,3-a]isoindole (400 mg, 0.75 mmol) in methanol (30 mL) in a pressure tank was added PdCl$_2$(200 mg, 1.15 mmol) under N$_2$ atmosphere. The pressure tank was vacuumed and flushed with H$_2$. The mixture was then stirred at 80° C. under H$_2$ atmosphere (40 atm) for 3 d. When the reaction was done, the reaction suspension was filtered through a celite pad, which was rinseded with EtOAc (50 mL×3). The combined filtrate was concentrated under reduced pressure and the residue was first purified by flash chromatography eluting with methanol in dichloromethane (5% to 15% gradient), and then the cis- and trans-product mixtures were obtained by the separation on prep-HPLC under the following conditions: Gemini-NX 5u C18, 110A, AXIA Packed, 21.2×150 mm, 5 μm; MeCN in water (with 10 mM NH$_4$HCO$_3$), 20% to 40% gradient in 12 min; Detector, UV 254/220 nm.

Compound 44a:

(15 mg, 6.2%, white solid, containing two stereoisomers), HPLC: 99.8% purity, RT=1.18 min. MS: m/z=317.1 [M+H]$^+$. $^1$H NMR (300 MHz, CD$_3$OD, ppm) δ=7.84 (br s, 1H), 7.13 (t, J=7.8 Hz, 1H), 7.00 (br s, 1H), 6.90 (d, J=7.5 Hz, 1H), 6.80 (d, J=8.1 Hz, 1H), 5.35 (t, J=4.8 Hz, 1H), 3.50-3.43 (m, 1H), 2.37-2.28 (m, 1H), 2.18-2.09 (m, 1H), 1.83-1.66 (m, 4H), 1.55-1.38 (m, 3H), 1.30-1.16 (m, 3H);

Compound 44b:

(12 mg, 5%, white solid, containing two stereoisomers) HPLC: 99.4% purity, RT=1.27 min. MS: m/z=317.1 [M+H]$^+$. $^1$H NMR (300 MHz, CD$_3$OD, ppm) δ=7.88 (br s, 1H), 7.13 (d, J=7.8 Hz, 1H), 7.01 (br s, 1H), 6.91 (d, J=7.5 Hz, 1H), 6.80 (d, J=8.1 Hz, 1H), 5.37 (t, J=4.8 Hz, 1H), 3.84 (br s, 1H), 2.39-2.29 (m, 1H), 2.18-2.09 (m, 1H), 1.78-1.67 (m, 3H), 1.60-1.44 (m, 5H), 1.30-1.15 (m, 2H).

Example 45: Synthesis of 6-fluoro-5-(2-(1-fluorocyclohexyl)ethyl)-9-methoxy-5H-imidazo[5,1-a]isoindole (45a and 45b)

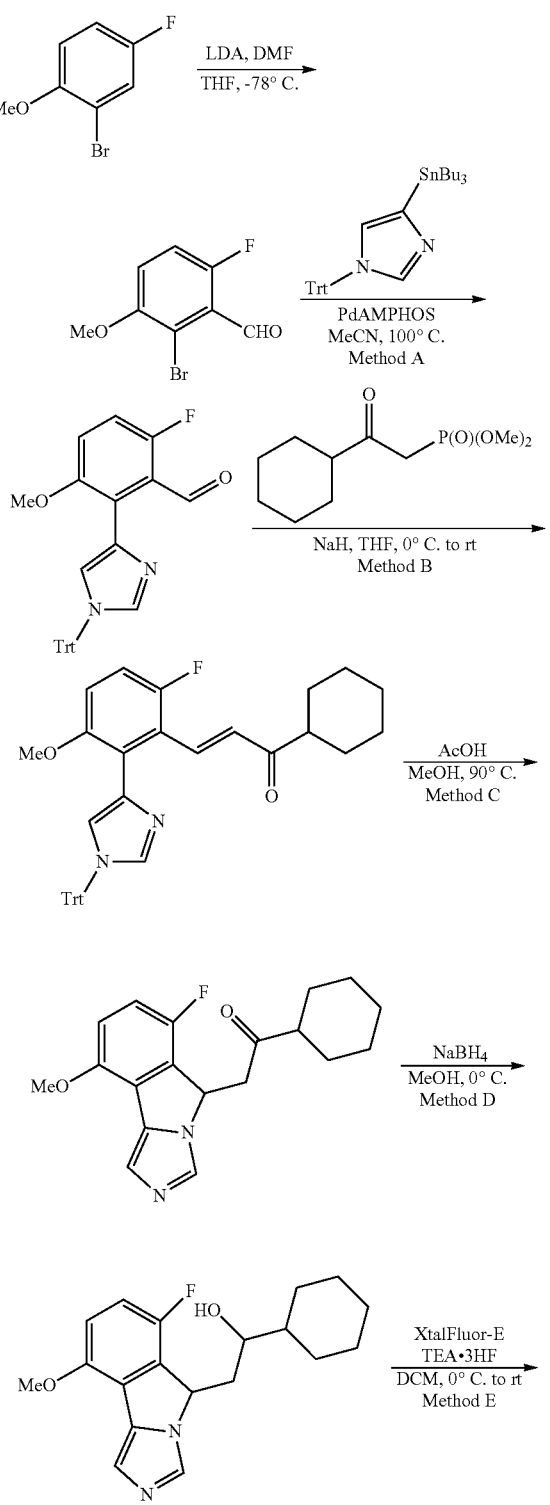

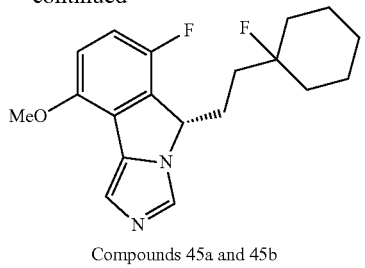

Compounds 45a and 45b

2-Bromo-6-fluoro-3-methoxybenzaldehyde

To a solution of 2-bromo-4-fluoro-1-methoxybenzene (4 g, 19.51 mmol) in THF (80 mL) was added LDA solution (2 M in THF, 10.7 mL, 21.4 mmol) slowly at −78° C. After stirring for 15 min at −78° C., anhydrous DMF (4.5 mL, 58.15 mmol) was added dropwise over 10 min period and the resulting reaction mixture was stirred for additional 1 h at −20° C. The reaction mixture was quenched by sat. ammonium chloride solution (80 mL) carefully and was extracted with ethyl acetate (120 mL×3). The combined organic phase was washed with brine and dried over sodium sulfate. The solvent was removed under reduced pressure to yield 2-bromo-6-fluoro-3-methoxybenzaldehyde as light yellow solid (4.27 g, 94%, crude yield) which was used in next step without further purification.

6-Fluoro-5-(2-(1-fluorocyclohexyl)ethyl)-9-methoxy-5H-imidazo[5,1-a]isoindole 6-Fluoro-5-(2-(1-fluorocyclohexyl)ethyl)-9-methoxy-5H-imidazo[5,1-a]isoindole was prepared from 2-bromo-6-fluoro-3-methoxybenzaldehyde, 4-(tributylstannyl)-1-(triphenylmethyl)-1H-imidazole, and dimethyl (2-cyclohexyl-2-oxoethyl)phosphonate using Method A, B, C, D, and E. Two enantiomeric products were obtained by the separation on chiral prep-HPLC under the following conditions: Phenomenex Lux 5u Cellulose-4, AXIA Packed, 21.2×250 mm, 5 μm; EtOH in hexane (with 0.2% DEA), 15% EtOH isocratic in 16 min; Detector, UV 254/220 nm.

Compound 45a:

(15 mg, 4.5% for five steps, white solid, single stereoisomer) HPLC: 99.3% purity, RT=1.72 min. MS: m/z=333.2 [M+H]$^+$. $^1$H NMR (300 MHz, CD$_3$OD, ppm) δ=7.92 (s, 1H), 7.07-7.02 (m, 3H), 5.66-5.65 (m, 1H), 3.97 (s, 3H), 2.48-2.38 (m, 1H), 2.30-2.21 (m, 1H), 1.74-1.68 (m, 2H), 1.58-1.40 (m, 6H), 1.32-1.10 (m, 4H);

Compound 45b:

(12 mg, 3.6% for five steps, white solid, single stereoisomer) HPLC: 99.99% purity, RT=1.73 min. MS: m/z=333.1 [M+H]$^+$. $^1$H NMR (300 MHz, CD$_3$OD, ppm) δ=7.92 (s, 1H), 7.07-7.02 (m, 3H), 5.65 (t, J=4.2 Hz, 1H), 3.97 (s, 3H), 2.48-2.38 (m, 1H), 2.30-2.21 (m, 1H), 1.74-1.68 (m, 2H), 1.58-1.40 (m, 6H), 1.32-1.10 (m, 4H).

Example 46: Synthesis of 10-fluoro-7-[2-(1,4,4-trifluorocyclohexyl)ethyl]-4,6,9-triazatricyclo[6.4.0.0ˆ[2,6]]dodeca-1(8),2,4,9,11-pentaene

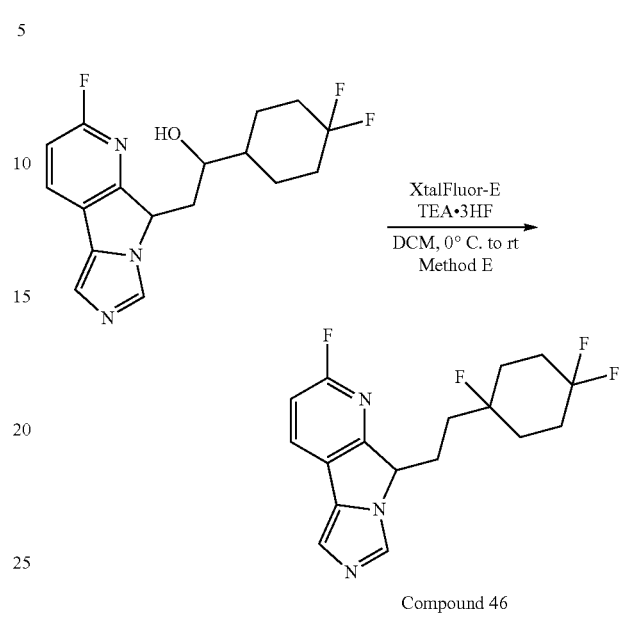

Compound 46

10-Fluoro-7-[2-(1,4,4-trifluorocyclohexyl)ethyl]-4,6,9-triazatricyclo[6.4.0.0ˆ[2,6]]dodeca-1(8),2,4,9,11-pentaene 10-Fluoro-7-[2-(1,4,4-trifluorocyclohexyl)ethyl]-4,6,9-triazatricyclo[6.4.0.0ˆ[2,6]]dodeca-1(8),2,4,9,11-pentaene was prepared from 1-(4,4-difluorocyclohexyl)-2-[10-fluoro-4,6,9-triazatricyclo[6.4.0.0ˆ[2,6]]dodeca-1(8),2,4,9,11-pentaen-7-yl]ethan-1-ol using Method E. One pair of enantiomeric products was obtained by the separation on prep-HPLC under the following conditions: Gemini-NX 5u C18, 110A, AXIA Packed, 21.2×150 mm, 5 μm; MeCN in water (with 0.05% TFA); 15% to 45% gradient in 10 min; Detector, UV 254/220 nm.

Compound 46:

(15 mg, 18%, white solid, containing two stereoisomers), HPLC: 99.7% purity, RT=1.73 min. MS: m/z=340.0 [M+H]$^+$. $^1$H NMR (300 MHz, CD$_3$OD, ppm) δ=9.21 (br s, 1H), 8.36 (dd, J=8.4, 7.5 Hz, 1H), 7.81 (br s, 1H), 7.24 (dd, J=8.4, 0.9 Hz, 1H), 5.63 (t, J=5.7 Hz, 1H), 2.46-2.32 (m, 2H), 2.06-1.90 (m, 6H), 1.79-1.56 (m, 4H).

Example 47: Synthesis of 4-(2-[4,6,9-triazatricyclo[6.4.0.0ˆ[2,6]]dodeca-1(8),2,4,9,11-pentaen-7-yl]ethyl)cyclohexan-1-ol

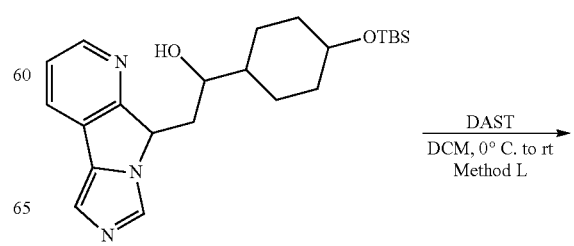

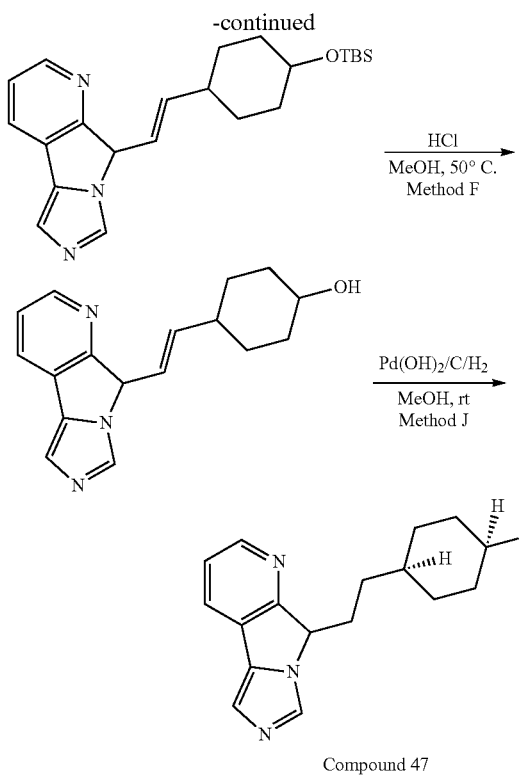

Compound 47

Method L:

7-[2-[4-[(tert-Butyldimethylsilyl)oxy]cyclohexyl]ethenyl]-4,6,9-triazatricyclo[6.4.0.0^[2,6]]dodeca-1(8),2,4,9,11-pentaene To a solution of 1-[4-[(tert-butyldimethylsilyl)oxy]cyclohexyl]-2-[4,6,9-triazatricyclo[6.4.0.0^[2,6]]dodeca-1(8),2,4,9,11-pentaen-7-yl]ethan-1-ol (360 mg, 0.87 mmol) in dichloromethane (10 mL) was added DAST (281 mg, 1.74 mmol) at 0° C. The resulting mixture was stirred at room temperature for 1 h. The reaction was then quenched with water (40 mL) and the mixture was extracted with dichloromethane (50 mL×2). The combined organic phase was washed with brine and dried over sodium sulfate. The solvent was removed under reduced pressure and the residue was purified by flash chromatography eluting with methanol in dichloromethane (1% to 5% gradient) to yield 7-[2-[4-[(tert-butyldimethylsilyl)oxy]cyclohexyl]ethenyl]-4,6,9-triazatricyclo[6.4.0.0^[2,6]]dodeca-1(8),2,4,9,11-pentaene as yellow solid (190 mg, 55%). MS: m/z=396.1 [M+H]+.

4-(2-[4,6,9-Triazatricyclo[6.4.0.0^[2,6]]dodeca-1(8),2,4,9,11-pentaen-7-yl]ethyl)cyclohexan-1-ol 4-(2-[4,6,9-Triazatricyclo[6.4.0.0^[2,6]]dodeca-1(8),2,4,9,11-pentaen-7-yl]ethyl)cyclohexan-1-ol was prepared from 7-[2-[4-[(tert-butyldimethylsilyl)oxy]cyclohexyl]ethenyl]-4,6,9-triazatricyclo[6.4.0.0^[2,6]]dodeca-1(8),2,4,9,11-pentaene using Method F and J. The cis- and trans-product mixtures were obtained by the separation on prep-HPLC under the following conditions: Gemini-NX C18, 21.2×150 mm, 5 μm; MeCN in water (with 0.05% TFA); 5% to 30% gradient in 10 min; Detector, UV 254/220 nm.

Compound 47:

(15 mg, 10% for two steps, colorless oil, containing two stereoisomers), HPLC: 94.6% purity, RT=0.48 min. MS: m/z=284.0 [M+H]+. 1H NMR (300 MHz, CD3OD, ppm) δ=8.42 (dd, J=4.8, 1.2 Hz, 1H), 8.03 (dd, J=7.8, 1.2 Hz, 1H), 8.01 (s, 1H), 7.42 (dd, J=7.8, 5.1 Hz, 1H), 7.31 (s, 1H), 5.35 (t, J=5.1 Hz, 1H), 3.44-3.35 (m, 1H), 2.39-2.31 (m, 1H), 2.23-2.14 (m, 1H), 1.87-1.85 (m, 2H), 1.72-1.67 (m, 2H), 1.22-1.05 (m, 3H), 0.98-0.83 (m, 4H);

Example 48: Synthesis of 7-[2-(1-fluoro-4,4-dimethylcyclohexyl)ethyl]-4,6,9-triazatricyclo[6.4.0.0^[2,6]]dodeca-1(8),2,4,9,11-pentaene (48a and 48b)

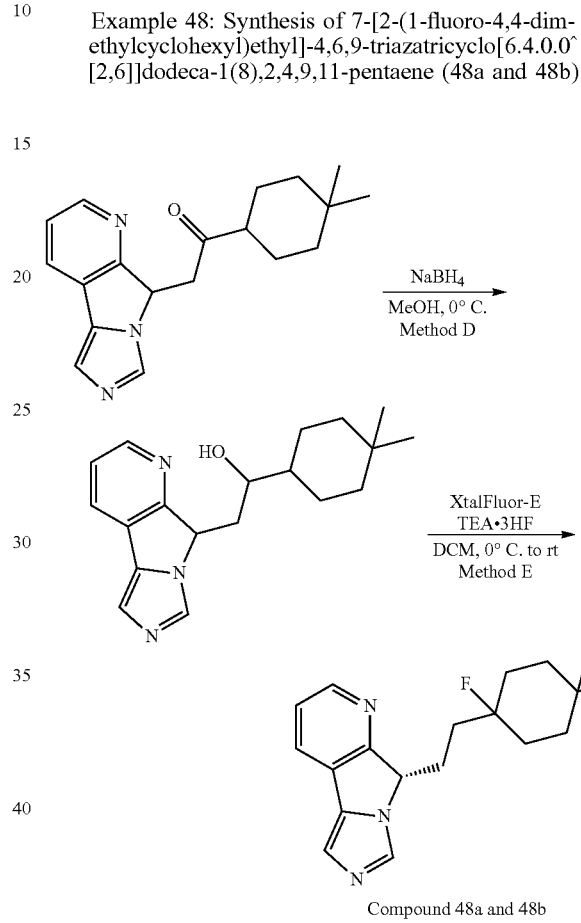

Compound 48a and 48b

7-[2-(1-Fluoro-4,4-dimethylcyclohexyl)ethyl]-4,6,9-triazatricyclo[6.4.0.0^[2,6]]dodeca-1(8),2,4,9,11-pentaene 7-[2-(1-Fluoro-4,4-dimethylcyclohexyl)ethyl]-4,6,9-triazatricyclo[6.4.0.0^[2,6]]dodeca-1(8),2,4,9,11-pentaene was prepared from 1-(4,4-dimethylcyclohexyl)-2-[4,6,9-triazatricyclo[6.4.0.0^[2,6]]dodeca-1(8),2,4,9,11-pentaen-7-yl]ethan-1-one using Method D and E. The crude product was first purified by prep-HPLC under the following conditions: Gemini-NX C18, 21.2×150 mm, 5 μm; mobile phase, MeCN in water (with 10 mM NH4HCO3), 20% to 25% gradient in 15 min. Two enantiomeric products were obtained by the separation on chiral prep-HPLC under the following conditions: CHIRALPAK AD-H, 21.2×150 mm, 5 μm; mobile phase, EtOH in hexane, 20% isocratic in 15 min; Detector, UV 254/220 nm.

Compound 48a:

(17 mg, 8.5% for two steps, light yellow oil, single stereoisomer), HPLC: 100% purity, RT=1.65 min. MS: m/z=314.1 [M+H]+. 1H NMR (400 MHz, CDCl3, ppm)

δ=8.43 (dd, J=5.2, 1.2 Hz, 1H), 7.83-7.81 (m, 2H), 7.32-7.29 (m, 2H), 5.21 (t, J=5.6 Hz, 1H), 2.43-2.35 (m, 1H), 2.25-2.17 (m, 1H), 1.76-1.68 (m, 2H), 1.60-1.40 (m, 6H), 1.19-1.16 (m, 2H), 0.93 (s, 3H), 0.84 (s, 3H);

Compound 48b:

(15 mg, 7.5% for two steps, light yellow oil, single stereoisomer) HPLC: 99.8% purity, RT=1.66 min. MS: m/z=314.1 [M+H]⁺. ¹H NMR (400 MHz, CDCl₃, ppm) δ=8.43 (dd, J=4.8, 0.8 Hz, 1H), 7.83-7.81 (m, 2H), 7.32-7.29 (m, 2H), 5.21 (t, J=5.2 Hz, 1H), 2.43-2.35 (m, 1H), 2.23 (br s, 2H), 1.76-1.68 (m, 2H), 1.60-1.40 (m, 6H), 1.19-1.16 (m, 2H), 0.93 (s, 3H), 0.84 (s, 3H).

Example 49: Synthesis of 7-[2-(4,4-difluorocyclohexyl)ethyl]-4,6,9-triazatricyclo[6.4.0.0^[2,6]]dodeca-1(8),2,4,9,11-pentaene (49)

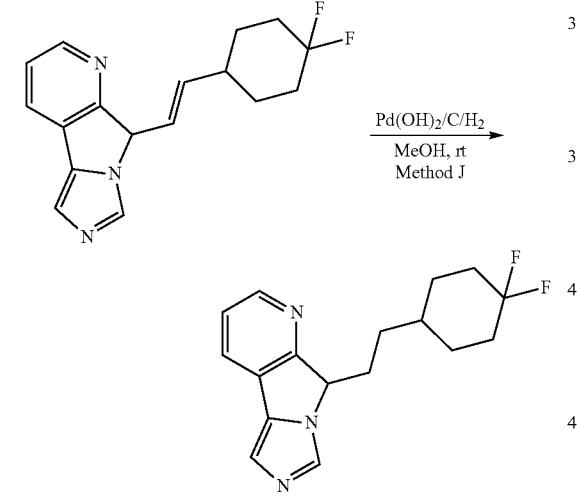

Compound 49

7-[2-(4,4-Difluorocyclohexyl)ethyl]-4,6,9-triazatricyclo[6.4.0.0^[2,6]]dodeca-1(8),2,4,9,11-pentaene 7-[2-(4,4-Difluorocyclohexyl)ethyl]-4,6,9-triazatricyclo[6.4.0.0^[2,6]]dodeca-1(8),2,4,9,11-pentaene was prepared from 1-(4,4-difluorocyclohexyl)-2-[4,6,9-triaazatricyclo[6.4.0.0^[2,6]] dodeca-1(8),2,4,9,11-pentaen-7-yl]ethan-1-ol using Method L and J. One pair of enantiomeric products was obtained by the separation on prep-HPLC under the following conditions: Gemini-NX C18, 21.2×150 mm, 5 µm; mobile phase, MeCN in water (with 0.05% TFA), 20% to 40% gradient in 10 min; Detector, UV 254/220 nm.

Compound 49:

(23 mg, 13.5% for two steps, white solid, containing two stereoisomers), HPLC: 97.4% purity, RT=1.51 min. MS: m/z=303.95 [M+H]⁺. ¹H NMR (400 MHz, CDCl₃, ppm) δ=8.92 (br s, 1H), 8.65 (dd, J=5.2, 1.6 Hz, 1H), 8.02 (dd, J=8.0, 1.6 Hz, 1H), 7.62 (s, 1H), 7.48 (dd, J=8.0, 5.2 Hz, 1H), 5.43 (t, J=5.6 Hz, 1H), 2.41-2.24 (m, 2H), 2.10-2.02 (m, 2H), 1.77-1.58 (m, 4H), 1.37-1.12 (m, 5H).

Example 50: Synthesis of 7-(2-cyclohexylethyl)-4,6,9-triazatricyclo[6.4.0.0^[2,6]]dodeca-1(8),2,4,9,11-pentaene (50)

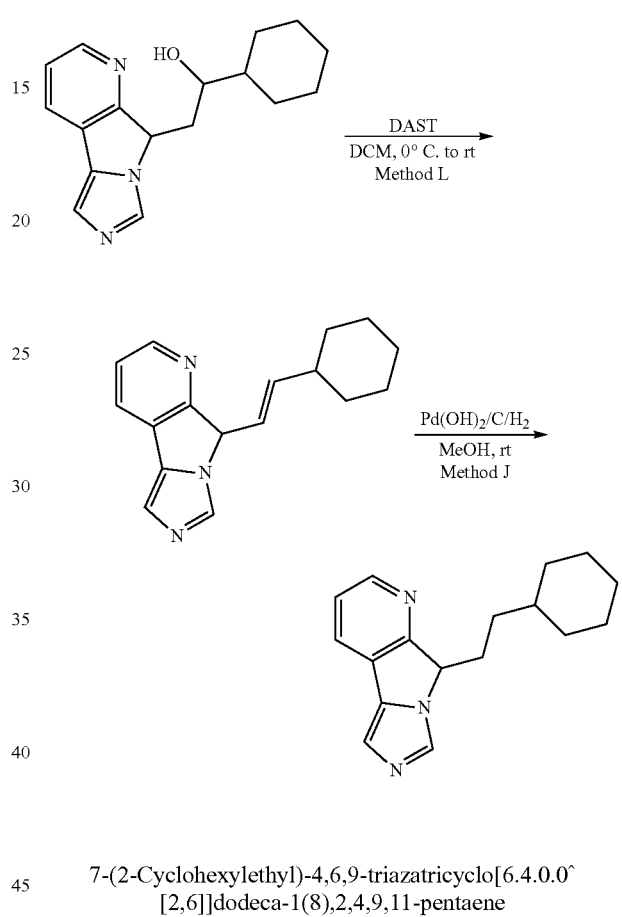

7-(2-Cyclohexylethyl)-4,6,9-triazatricyclo[6.4.0.0^[2,6]]dodeca-1(8),2,4,9,11-pentaene The compound was prepared from 1-cyclohexyl-2-[4,6,9-triazatricyclo[6.4.0.0^[2,6]]dodeca-1(8),2,4,9,11-pentaen-7-yl]ethan-1-ol using Method L and J. One pair of enantiomeric products was obtained by the separation on prep-HPLC under the following conditions: Atlantis Prep T3 OBD Column, 19×150 mm, 5 µm; mobile phase, MeCN in water (with 0.05% TFA), 18% to 40% gradient in 15 min; Detector, UV 254/220 nm.

Compound 50:

(18 mg, 12% for two steps, white solid, containing two stereoisomers), HPLC: 91.0% purity, RT=1.64 min. MS: m/z=268.0 [M+H]⁺. ¹H NMR (400 MHz, CDCl₃, ppm) δ=8.80 (br s, 1H), 8.65 (dd, J=4.8, 1.2 Hz, 1H), 8.01 (d, J=8.0 Hz, 1H), 7.61 (s, 1H), 7.46 (dd, J=7.6, 5.2 Hz, 1H), 5.40 (t, J=5.2 Hz, 1H), 2.43-2.34 (m, 1H), 2.23-2.17 (m, 1H), 1.70-1.61 (m, 5H), 1.28-1.09 (m, 6H), 0.90-0.81 (m, 2H).

Example 51: Synthesis of 7-[2-(4,4-dimethylcyclohexyl)ethyl]-4,6,9-triazatricyclo[6.4.0.0^[2,6]]dodeca-1(8),2,4,9,11-pentaene (51)

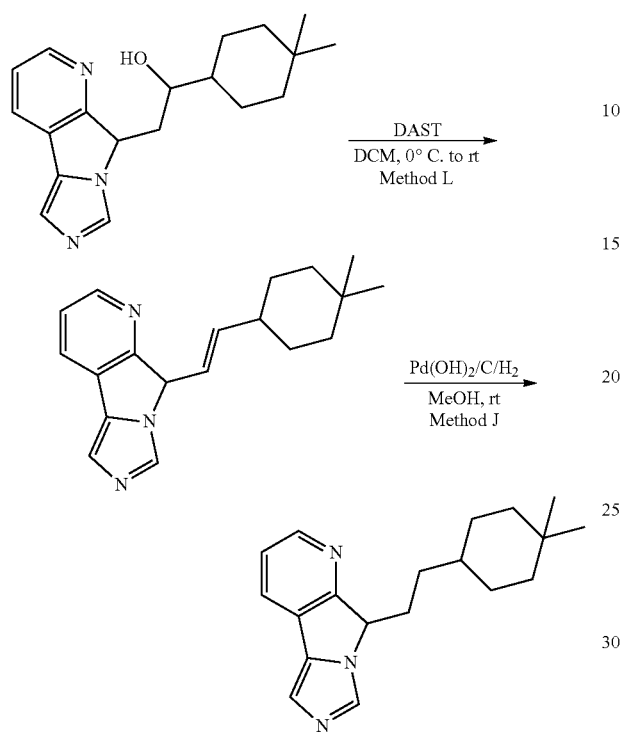

7-[2-(4,4-Dimethylcyclohexyl)ethyl]-4,6,9-triazatricyclo[6.4.0.0^[2,6]]dodeca-1(8),2,4,9,11-pentaene The compound was prepared from 1-(4,4-dimethylcyclohexyl)-2-[4,6,9-triazatricyclo[6.4.0.0^[2,6]]dodeca-1(8),2,4,9,11-pentaen-7-yl]ethan-1-ol using Method L and J. One pair of enantiomeric products was obtained by the separation on prep-HPLC under the following conditions: Atlantis Prep T3 OBD Column, 19×150 mm, 5 μm; mobile phase, MeCN in water (with 0.05% TFA), 10% to 30% gradient in 10 min; Detector, UV 254/220 nm.

Compound 51:

(20 mg, 14% for two steps, white solid, containing two stereoisomers), HPLC: 99.4% purity, RT=1.74 min. MS: m/z=296.1 [M+H]$^+$. $^1$H NMR (400 MHz, CDCl$_3$, ppm) δ=8.84 (br s, 1H), 8.64 (d, J=4.8 Hz, 1H), 8.01 (d, J=7.6 Hz, 1H), 7.62 (s, 1H), 7.46 (dd, J=7.2, 5.2 Hz, 1H), 5.41 (br s, 1H), 2.42-2.37 (m, 1H), 2.23-2.17 (m, 1H), 1.49 (br s, 2H), 1.36-1.32 (m, 2H), 1.20-1.01 (m, 7H), 0.87 (s, 3H), 0.83 (s, 3H).

Example 52: Synthesis of 2-[10-chloro-4,6,9-triazatricyclo[6.4.0.0^[2,6]]dodeca-1(8),2,4,9,11-pentaen-7-yl]-1-(4,4-difluorocyclohexyl)ethan-1-ol (52a, 52b, and 52c)

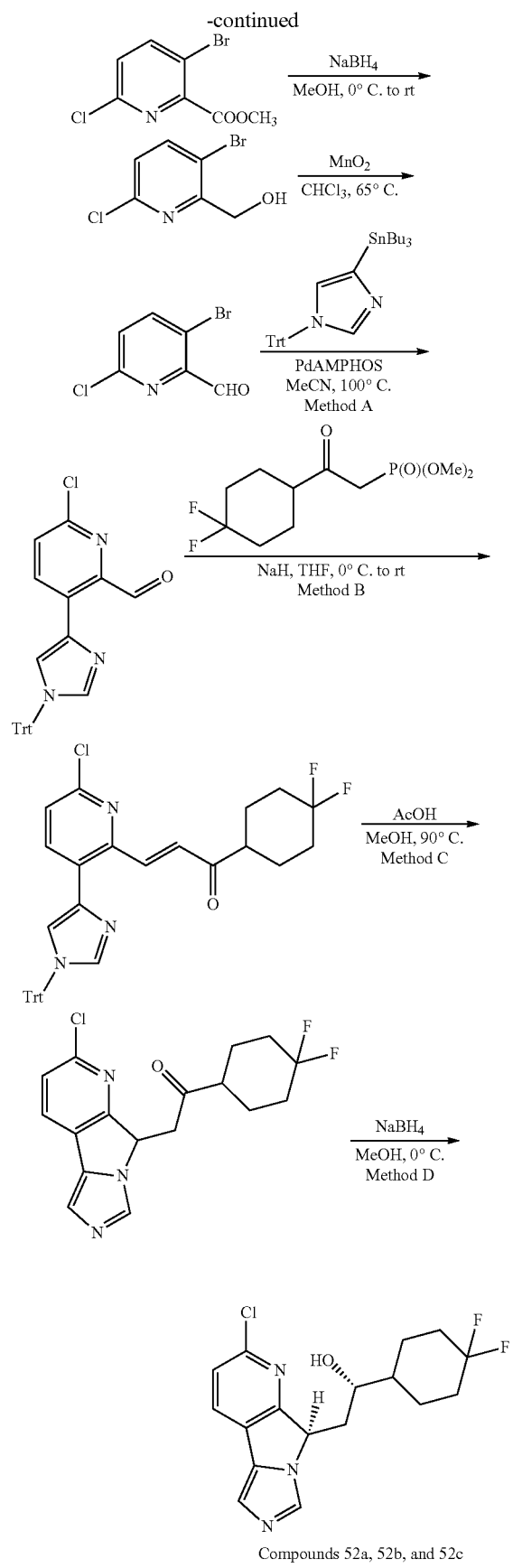

Compounds 52a, 52b, and 52c

Methyl 3-bromo-6-chloropyridine-2-carboxylate

To a solution of 3-bromo-6-chloropyridine-2-carboxylic acid (1 g, 4.23 mmol) in methanol (25 mL) was added one drop of concentrated $H_2SO_4$. The resulting mixture was then stirred at 70° C. for 16 h. The reaction mixture was diluted with water (80 mL) and extracted with ethyl acetate (80 mL×3). The combined organic phase was washed with brine, and dried over sodium sulfate. The solvent was removed under reduced pressure and the residue was purified by flash chromatography eluting with ethyl acetate in petroleum ether (5% to 30% gradient) to yield methyl 3-bromo-6-chloropyridine-2-carboxylate as light yellow solid (870 mg, 82%). MS: m/z=249.8 [M+H]$^+$.

(3-Bromo-6-chloropyridin-2-yl)methanol

At 0° C., to a solution of methyl 3-bromo-6-chloropyridine-2-carboxylate (700 mg, 2.81 mmol) in methanol (15 mL) was added sodium borohydride (534 mg, 14.06 mmol) in portions. The resulting mixture was then stirred room temperature for 4 h. The reaction was quenched with water (80 mL) carefully and the mixture was extracted with ethyl acetate (80 mL×3). The combined organic phase was washed with brine, and dried over sodium sulfate. The solvent was removed under reduced pressure and the residue was purified by flash chromatography eluting with ethyl acetate in petroleum ether (25% to 60% gradient) to yield (3-bromo-6-chloropyridin-2-yl)methanol as light yellow oil (395 mg, 64%). MS: m/z=221.8 [M+H]$^+$.

3-Bromo-6-chloropyridine-2-carbaldehyde

To a solution of (3-bromo-6-chloropyridin-2-yl)methanol (600 mg, 2.71 mmol) in chloroform (20 mL) was added manganese dioxide (2.36 g, 27.15 mmol) carefully at room temperature. The resulting mixture was then stirred at 65° C. for 16 h. The reaction was filtered through a celite pad, which was rinsed with dichloromethane (30 mL×4). The combined filtrate was concentrated under reduced pressure to yield 3-bromo-6-chloropyridine-2-carbaldehyde as light yellow solid (510 mg, 86%, crude yield) which was used in the next step without further purification.

2-[10-Chloro-4,6,9-triazatricyclo[6.4.0.0^[2,6]]dodeca-1(8),2,4,9,11-pentaen-7-yl]-1-(4,4-difluorocyclohexyl)ethan-1-ol 2-[10-Chloro-4,6,9-triazatricyclo[6.4.0.0^[2,6]]dodeca-1(8),2,4,9,11-pentaen-7-yl]-1-(4,4-difluorocyclohexyl)ethan-1-ol were prepared from 3-bromo-6-chloropyridine-2-carbaldehyde, 4-(tributylstannyl)-1-(triphenylmethyl)-1H-imidazole and dimethyl [2-(4,4-difluorocyclohexyl)-2-oxoethyl]phosphonate using Method A, B, C, and D. One pair of enantiomeric products and two enantiomeric products were obtained by the separation on chiral prep-HPLC under the following conditions: Chiralpak IC, 20×250 mm, 5 µm; mobile phase, EtOH in hexane (with 0.2% IPA), 30% isocratic in 15 min; Detector, UV 254/220 nm.

Compound 52a:

(20 mg, 6.5% for four steps, white solid, single stereoisomer) HPLC: 92.4% purity, RT=2.65 min. MS: m/z=353.95 [M+H]$^+$. $^1$H NMR (400 MHz, CDCl$_3$, ppm) δ=8.06 (s, 1H), 7.81 (d, J=8.0 Hz, 1H), 7.37 (d, J=8.0 Hz, 1H), 7.32 (s, 1H), 5.36 (t, J=6.4 Hz, 1H), 4.07-4.03 (m, 1H), 2.28-2.13 (m, 4H), 2.02-1.98 (m, 1H), 1.79-1.62 (m, 3H), 1.56-1.40 (m, 3H);

Compound 52b:

(9 mg, 2.9% for four steps, white solid, containing two stereoisomers) HPLC: 91.7% purity, RT=2.57 min. MS: m/z=353.95 [M+H]$^+$. $^1$H NMR (300 MHz, DMSO-d$_6$, ppm) δ=8.13-8.09 (m, 2H), 7.54 (d, J=7.8 Hz, 1H), 7.34 (s, 1H), 5.45 (dd, J=10.2, 2.4 Hz, 1H), 5.15 (d, J=6.6 Hz, 1H), 3.75-3.70 (m, 1H), 2.28-2.20 (m, 1H), 2.05-1.61 (m, 7H), 1.45-1.23 (m, 3H);

Compound 52c:

(20 mg, 6.5% for four steps, white solid, single stereoisomer) HPLC: 92.4% purity, RT=2.65 min. MS: m/z=354.0 [M+H]$^+$. $^1$H NMR (400 MHz, CDCl$_3$, ppm) δ=8.13 (s, 1H), 7.82 (d, J=8.4 Hz, 1H), 7.38 (d, J=8.0 Hz, 1H), 7.34 (s, 1H), 5.37 (t, J=6.8 Hz, 1H), 4.08-4.03 (m, 1H), 2.28-2.13 (m, 4H), 2.02-1.98 (m, 1H), 1.79-1.62 (m, 3H), 1.56-1.40 (m, 3H).

Example 53: Synthesis of 2-[10-methoxy-4,6,9-triazatricyclo[6.4.0.0^[2,6]]dodeca-1(8),2,4,9,11-pentaen-7-yl]-1-[spiro[2.5]octan-6-yl]ethan-1-ol (53a, 53b, 53c)

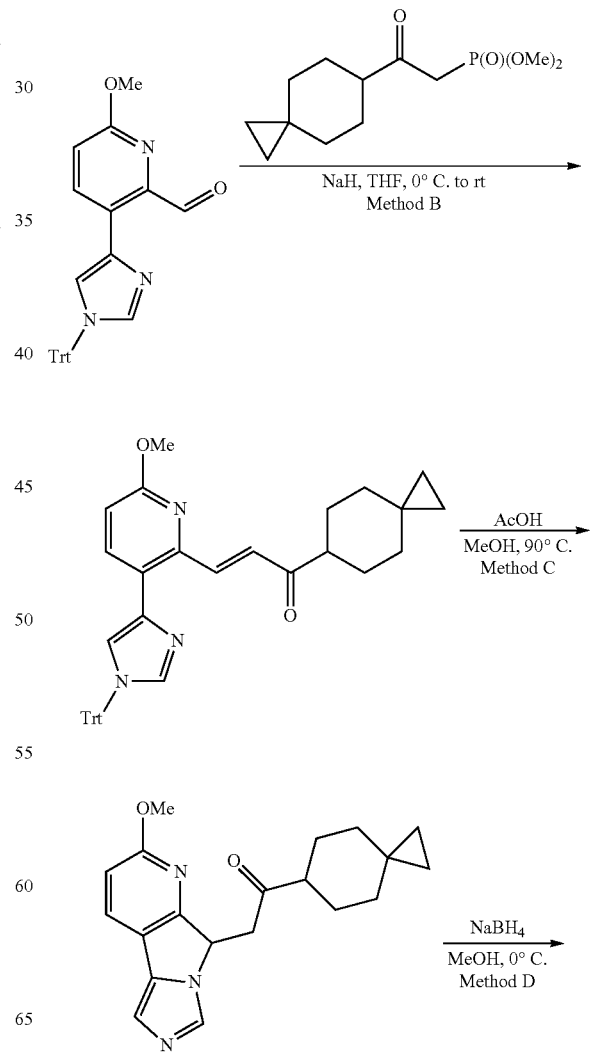

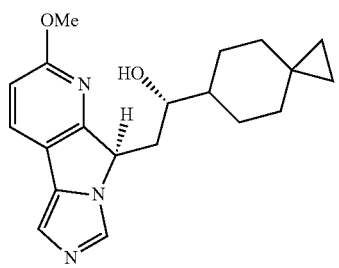

Compounds 53A, 53b, and 53c

2-[10-Methoxy-4,6,9-triazatricyclo[6.4.0.0^[2,6]]dodeca-1(8),2,4,9,11-pentaen-7-yl]-1-[spiro[2.5]octan-6-yl]ethan-1-ol 2-[10-Methoxy-4,6,9-triazatricyclo[6.4.0.0^[2,6]]dodeca-1(8),2,4,9,11-pentaen-7-yl]-1-[spiro[2.5]octan-6-yl]ethan-1-ol were prepared from 6-methoxy-3-[1-(triphenylmethyl)-1H-imidazol-4-yl]pyridine-2-carbaldehyde and dimethyl (2-oxo-2-[spiro[2.5]octan-6-yl]ethyl)phosphonate using Method B, C, and D. One pair of enantiomeric products and two enantiomeric products were obtained by the separation on chiral prep-HPLC under the following conditions: Chiralpak IC, 20×250 mm, 5 μm; mobile phase, iPrOH in hexane; 25% isocratic in 23 min; Detector, UV 254/220 nm.

Compound 53a:

(12 mg, 5.8% for three steps, white solid, containing two stereoisomers) HPLC: 97.2% purity, RT=1.35 min. MS: m/z=340.2 [M+H]$^+$. $^1$H NMR (400 MHz, CD$_3$OD, ppm) δ=7.96 (s, 1H), 7.91 (d, J=8.4 Hz, 1H), 7.12 (s, 1H), 6.82 (d, J=8.4 Hz, 1H), 5.36 (dd, J=9.6, 3.6 Hz, 1H), 3.98 (s, 3H), 3.79-3.75 (m, 1H), 2.46-2.38 (m, 1H), 1.91-1.67 (m, 5H), 1.47-1.41 (m, 1H), 1.31-1.25 (m, 2H), 0.96-0.89 (m, 2H), 0.27-0.19 (m, 4H);

Compound 53b:

(10 mg, 4.8% for three steps, white solid, single stereoisomer) HPLC: 96.7% purity, RT=1.34 min. MS: m/z=340.1 [M+H]$^+$. $^1$H NMR (300 MHz, CD$_3$OD, ppm) δ=7.99 (s, 1H), 7.89 (d, J=8.4 Hz, 1H), 7.09 (s, 1H), 6.81 (d, J=8.4 Hz, 1H), 5.27 (t, J=6.0 Hz, 1H), 4.12-4.08 (m, 1H), 3.98 (s, 3H), 2.30-2.22 (m, 1H), 2.13-2.04 (m, 1H), 1.87-1.65 (m, 4H), 1.42-1.25 (m, 3H), 0.97-0.90 (m, 2H), 0.29-0.18 (m, 4H);

Compound 53c:

(14 mg, 6.8% for three steps, white solid, single stereoisomer) HPLC: 94.0% purity, RT=1.77 min. MS: m/z=340.1 [M+H]$^+$. $^1$H NMR (400 MHz, CD$_3$OD, ppm) δ=7.99 (s, 1H), 7.90 (d, J=8.8 Hz, 1H), 7.09 (s, 1H), 6.81 (d, J=8.4 Hz, 1H), 5.28 (t, J=6.0 Hz, 1H), 4.12-4.08 (m, 1H), 3.98 (s, 3H), 2.30-2.22 (m, 1H), 2.13-2.04 (m, 1H), 1.86-1.83 (m, 1H), 1.77-1.67 (m, 3H), 1.42-1.25 (m, 3H), 0.97-0.90 (m, 2H), 0.29-0.18 (m, 4H).

Example 54: Synthesis of 7-(2-{6-fluorospiro[2.5]octan-6-yl}ethyl)-10-methoxy-4,6,9-triazatricyclo[6.4.0.0^[2,6]]dodeca-1(8),2,4,9,11-pentaene (54a and 54b)

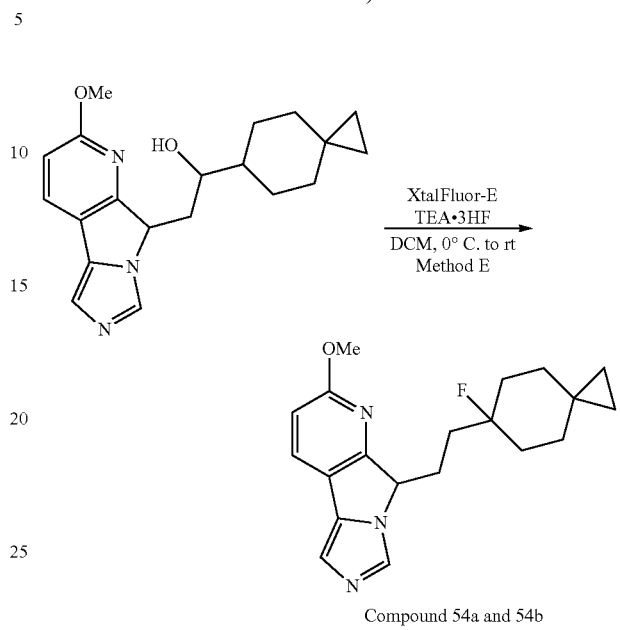

Compound 54a and 54b

7-(2-{6-Fluorospiro[2.5]octan-6-yl}ethyl)-10-methoxy-4,6,9-triazatricyclo[6.4.0.0^[2,6]]dodeca-1(8),2,4,9,11-pentaene 7-(2-{6-Fluorospiro[2.5]octan-6-yl}ethyl)-10-methoxy-4,6,9-triazatricyclo[6.4.0.0^[2,6]]dodeca-1(8),2,4,9,11-pentaene were prepared from 2-[10-methoxy-4,6,9-triazatricyclo[6.4.0.0[2,6]]dodeca-1(8),2,4,9,11-pentaen-7-yl]-1-[spiro[2.5]octan-6-yl]ethan-1-ol using Method E. Two enantiomeric products were obtained by the separation on chiral prep-HPLC under the following conditions: Phenomenex Lux 5u Cellulose-4, AXIA Packed, 21.2×250 mm, 5 μm; mobile phase, EtOH in hexane, 20% isocratic in 17 min; Detector, UV 254/220 nm.

Compound 54a:

(18 mg, 11%, colorless oil, single stereoisomer) HPLC: 99.8% purity, RT=1.84 min. MS: m/z=342.1 [M+H]$^+$. $^1$H NMR (400 MHz, CD$_3$OD, ppm) δ=7.96 (s, 1H), 7.91 (d, J=8.8 Hz, 1H), 7.12 (s, 1H), 6.83 (d, J=8.4 Hz, 1H), 5.26 (t, J=5.2 Hz, 1H), 3.99 (s, 3H), 2.42-2.25 (m, 2H), 1.87-1.76 (m, 4H), 1.61-1.36 (m, 4H), 0.88-0.83 (m, 2H), 0.31-0.20 (m, 4H);

Compound 54b:

(16 mg, 9.8%, colorless oil, single stereoisomer) HPLC: 99.8% purity, RT=1.83 min. MS: m/z=342.1 [M+H]$^+$. $^1$H NMR (400 MHz, CD$_3$OD, ppm) δ=7.96 (s, 1H), 7.91 (d, J=8.8 Hz, 1H), 7.12 (s, 1H), 6.83 (d, J=8.4 Hz, 1H), 5.26 (t, J=5.2 Hz, 1H), 3.99 (s, 3H), 2.42-2.25 (m, 2H), 1.87-1.76 (m, 4H), 1.61-1.36 (m, 4H), 0.88-0.83 (m, 2H), 0.31-0.20 (m, 4H).

Example 55: Synthesis of 2-[10-chloro-4,6,9-triazatricyclo[6.4.0.0^[2,6]]dodeca-1(8),2,4,9,11-pentaen-7-yl]-1-cyclohexylethan-1-ol (55a, 55b, 55c, and 55d)

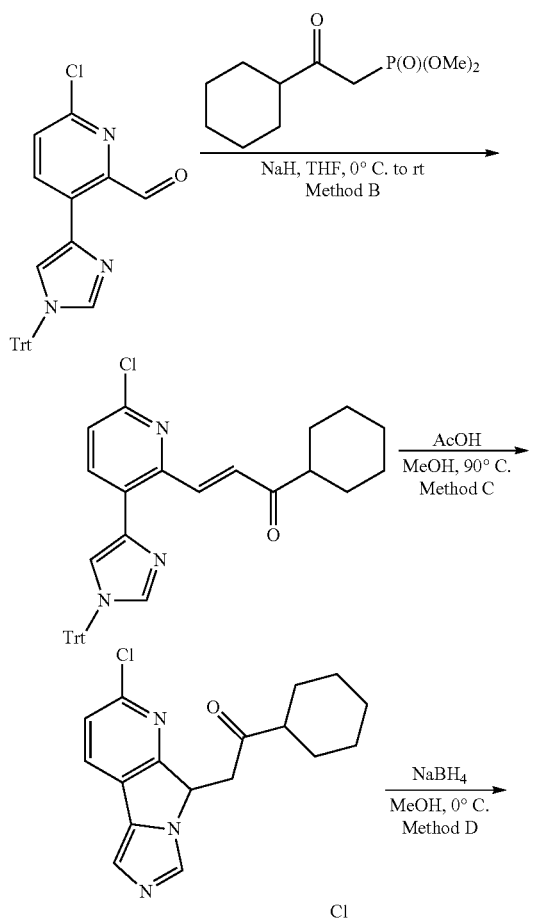

Compound 55a, 55b, 55c, and 55d

2-[10-Chloro-4,6,9-triazatricyclo[6.4.0.0^[2,6]]dodeca-1(8),2,4,9,11-pentaen-7-yl]-1-cyclohexylethan-1-ol 2-[10-Chloro-4,6,9-triazatricyclo[6.4.0.0^[2,6]]dodeca-1(8),2,4,9,11-pentaen-7-yl]-1-cyclohexylethan-1-ol were prepared from 6-chloro-3-[1-(triphenylmethyl)-1H-imidazol-4-yl]pyridine-2-carbaldehyde and dimethyl (2-cyclohexyl-2-oxoethyl)phosphonate using Method B, C, and D. Four enantiomeric products were obtained by the separation on chiral prep-HPLC under the following conditions: Phenomenex Lux 5u Cellulose-4, AXIA Packed, 21.2×250 mm, 5 µm; mobile phase, EtOH in hexane, 20% isocratic in 25 min; Detector, UV 254/220 nm.

Compound 55a:
(27 mg, 9.6% for three steps, white solid, single stereoisomer) HPLC: 98.6% purity, RT=2.64 min. MS: m/z=318.0 [M+H]+. 1H NMR (300 MHz, CD3OD, ppm) δ=8.08 (s, 1H), 7.98 (d, J=8.1 Hz, 1H), 7.43 (d, J=8.1 Hz, 1H), 7.28 (s, 1H), 5.36 (t, J=5.7 Hz, 1H), 3.81-3.77 (m, 1H), 2.38-2.31 (m, 1H), 2.12-2.01 (m, 1H), 1.88-1.65 (m, 5H), 1.37-1.19 (m, 4H), 1.17-1.04 (m, 2H);

Compound 55b:
(9 mg, 3.2% for three steps, white solid, single stereoisomer) HPLC: 97.2% purity, RT=2.58 min. MS: m/z=318.0 [M+H]+. 1H NMR (300 MHz, CD3OD, ppm) δ=8.02 (s, 1H), 8.01 (d, J=7.8 Hz, 1H), 7.46 (d, J=8.1 Hz, 1H), 7.31 (s, 1H), 5.46 (dd, J=10.2, 3.6 Hz, 1H), 3.68-3.61 (m, 1H), 2.46-2.38 (m, 1H), 1.95-1.88 (m, 1H), 1.81-1.67 (m, 5H), 1.40-1.32 (m, 1H), 1.30-1.20 (m, 3H), 1.12-1.05 (m, 2H);

Compound 55c:
(25 mg, 8.9% for three steps, white solid, single stereoisomer) HPLC: 99.7% purity, RT=1.65 min. MS: m/z=318.0 [M+H]+. 1H NMR (300 MHz, CD3OD, ppm) δ=8.08 (s, 1H), 7.98 (d, J=8.1 Hz, 1H), 7.43 (d, J=8.1 Hz, 1H), 7.28 (s, 1H), 5.35 (t, J=5.7 Hz, 1H), 3.81-3.77 (m, 1H), 2.38-2.31 (m, 1H), 2.12-2.01 (m, 1H), 1.88-1.65 (m, 5H), 1.37-1.19 (m, 4H), 1.17-1.04 (m, 2H);

Compound 55d:
(8 mg, 2.8% for three steps, white solid, single stereoisomer) HPLC: 99.5% purity, RT=1.63 min. MS: m/z=318.0 [M+H]+. 1H NMR (300 MHz, CD3OD, ppm) δ=8.02 (s, 1H), 8.01 (d, J=8.1 Hz, 1H), 7.46 (d, J=8.1 Hz, 1H), 7.31 (s, 1H), 5.46 (dd, J=10.2, 3.6 Hz, 1H), 3.68-3.61 (m, 1H), 2.46-2.38 (m, 1H), 1.95-1.88 (m, 1H), 1.81-1.67 (m, 5H), 1.40-1.32 (m, 1H), 1.30-1.20 (m, 3H), 1.12-1.05 (m, 2H).

Example 56: Synthesis of 1-cyclohexyl-2-[10-cyclopropyl-4,6,9-triazatricyclo[6.4.0.0^[2,6]]dodeca-1(8),2,4,9,11-pentaen-7-yl]ethan-1-ol (56a, 56b, 56c)

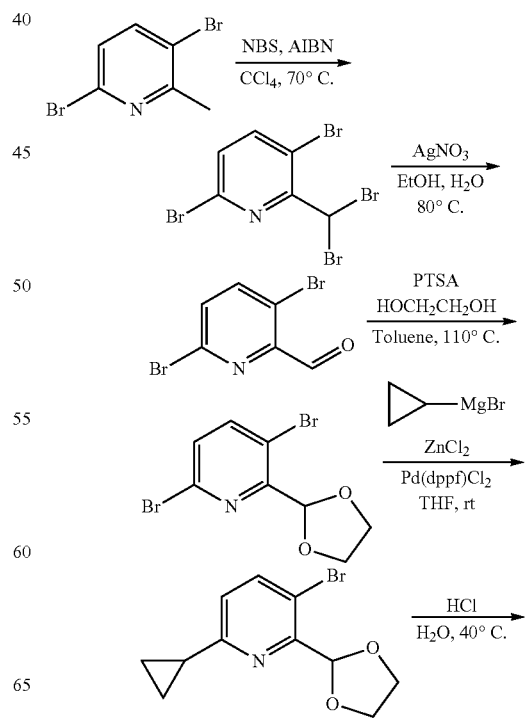

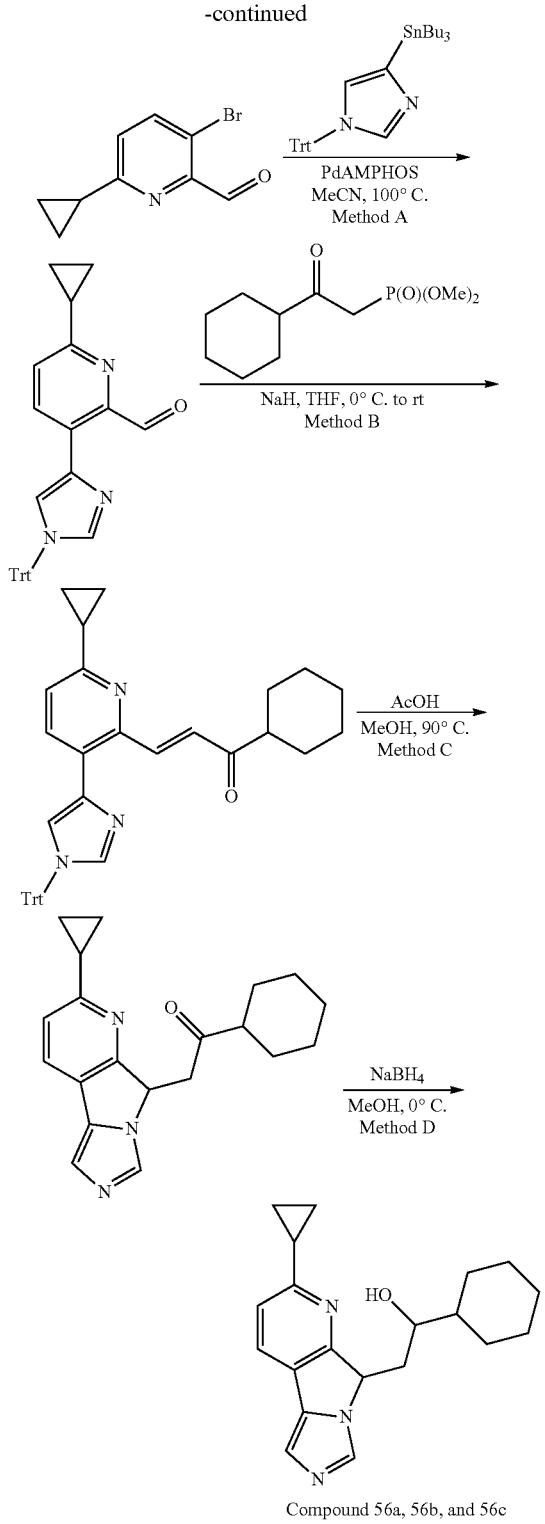

Compound 56a, 56b, and 56c

3,6-Dibromo-2-(dibromomethyl)pyridine

To a solution of 3,6-dibromo-2-methylpyridine (498 mg, 1.98 mmol) in carbon tetrachloride (10 mL) was added NBS (712 mg, 4.00 mmol), AIBN (66 mg, 0.40 mmol) successively at room temperature. The resulting mixture was then stirred at 70° C. for 16 h. The insoluable solids in the reaction mixture were removed by filtration and rinsed with dichloromethane (20 mL×3). The combined filtrate was concentrated under reduced pressure and the residue was purified by flash chromatography eluting with ethyl acetate in petroleum ether (5% to 15% gradient) to yield 3,6-dibromo-2-(dibromomethyl)pyridine as light yellow oil (610 mg, 75%). MS: m/z=409.6 [M+H]$^+$.

3,6-Dibromopyridine-2-carbaldehyde

To a solution of 3,6-dibromo-2-(dibromomethyl)pyridine (610 mg, 1.49 mmol mmol) in ethanol (7.5 mL) was added silver nitrate (640 mg, 3.77 mmol) and water (2 mL) at room temperature. The resulting mixture was then stirred at 80° C. for 5 h. The insoluable solids in the reaction mixture were removed by filtration. The filtrate was diluted with water (30 mL) and the mixture was extracted with ethyl acetate (40 mL×3). The combined organic phase was washed with brine and dried over sodium sulfate. The solvent was removed under reduced pressure and the residue was purified by flash chromatography eluting with ethyl acetate in petroleum ether (5% to 20% gradient) to yield 3,6-dibromopyridine-2-carbaldehyde as white solid (300 mg, 76%). MS: m/z=263.8 [M+H]$^+$.

3,6-Dibromo-2-(1,3-dioxolan-2-yl)pyridine

To a solution of 3,6-dibromopyridine-2-carbaldehyde (2.8 g, 10.57 mmol mmol) in toluene (50 mL) was added ethane-1,2-diol (1.65 g, 26.58 mmol) and PTSA (917 mg, 5.33 mmol) at room temperature. The resulting mixture was then stirred at 110° C. for 16 h. The reaction mixture was diluted with water (100 mL) and extracted with ethyl acetate (120 mL×3). The combined organic phase was washed with brine and dried over sodium sulfate. The solvent was removed under reduced pressure and the residue was purified by flash chromatography eluting with ethyl acetate in petroleum ether (10% to 25% gradient) to yield 3,6-dibromo-2-(1,3-dioxolan-2-yl)pyridine as light yellow oil (2.9 g, 89%). MS: m/z=307.9 [M+H]$^+$.

3-Bromo-6-cyclopropyl-2-(1,3-dioxolan-2-yl)pyridine

To a solution of zinc chloride (1 M, 4 mL, 4.0 mmol) in tetrahydrofuran (10 mL) was added bromo(cyclopropyl)magnesium (0.5 M, 10 mL, 5.0 mmol) dropwise at room temperature. After stirring at room temperature for 30 min, a solution of 3,6-dibromo-2-(1,3-dioxolan-2-yl)pyridine (1 g, 3.24 mmol) in THF (5 mL) and Pd(dppf)Cl$_2$.CH$_2$Cl$_2$ (135 mg, 0.17 mmol) were added successively. The resulting mixture was kept stirring for 16 h at room temperature. The reaction was then quenched with water (60 mL) and the mixture was extracted with ethyl acetate (80 mL×3). The combined organic phase was washed with brine, and dried over sodium sulfate. The solvent was removed under reduced pressure and the residue was purified by flash chromatography eluting with ethyl acetate in petroleum ether (3% to 10% gradient) to yield 3-bromo-6-cyclopropyl-2-(1,3-dioxolan-2-yl)pyridine as light yellow oil (600 mg, 69%). MS: m/z=269.9 [M+H]$^+$.

3-Bromo-6-cyclopropyl-2-(1,3-dioxolan-2-yl)pyridine

A mixture of 3-bromo-6-cyclopropyl-2-(1,3-dioxolan-2-yl)pyridine (700 mg, 2.59 mmol mmol) in aqueous solution of HCl (6 M, 7 mL) was stirred at 40° C. for 16 h. The reaction mixture was then neutralized with sat. sodium bicarbonate solution carefully and was extracted with ethyl acetate (60 mL×3). The combined organic phase was washed with brine and dried over sodium sulfate. The solvent was removed under reduced pressure and the residue was purified by flash chromatography eluting with ethyl cetate in petroleum ether (5% to 20% gradient) to yield 3-bromo-6-cyclopropylpyridine-2-carbaldehyde as light yellow solid (550 mg, 94%).

1-Cyclohexyl-2-[10-cyclopropyl-4,6,9-triazatricyclo[6.4.0.0^[2,6]]dodeca-1(8),2,4,9,11-pentaen-7-yl]ethan-1-ol 1-Cyclohexyl-2-[10-cyclopropyl-4,6,9-triazatricyclo[6.4.0.0^[2,6]]dodeca-1(8),2,4,9,11-pentaen-7-yl]ethan-1-ol was prepared from 3-bromo-6-cyclopropylpyridine-2-carbaldehyde, 4-(tributylstannyl)-1-(triphenylmethyl)-1H-imidazole, and dimethyl (2-cyclohexyl-2-oxoethyl)phosphonate using Method A, B, C, and D. One pair of enantiomeric products and two enantiomeric products were obtained by the separation on chiral prep-HPLC under the following conditions: Chiralpak IC, 20×250 mm, 5 μm; mobile phase, iPrOH in hexane, 20% isocratic in 36 min; Detector, UV 254/220 nm.

Compound 56a:

(12 mg, 5.6% for four steps, white solid, containing two stereoisomers) HPLC: 99.8% purity, RT=1.72 min. MS: m/z=324.1 [M+H]⁺. ¹H NMR (300 MHz, CDCl₃, ppm) δ=8.03 (s, 1H), 7.72 (d, J=8.1 Hz, 1H), 7.25 (s, 1H), 7.17 (d, J=8.1 Hz, 1H), 5.21 (t, J=6.9 Hz, 1H), 3.95-3.89 (m, 1H), 2.12-2.06 (m, 3H), 1.89-1.67 (m, 5H), 1.53-1.46 (m, 1H), 1.31-1.11 (m, 4H), 1.09-1.04 (m, 5H);

Compound 56b:

(9 mg, 4.2% for four steps, white solid, single stereoisomer) HPLC: 98.1% purity, RT=1.74 min. MS: m/z=324.1 [M+H]⁺. ¹H NMR (300 MHz, CDCl₃, ppm) δ=7.88 (s, 1H), 7.70 (d, J=8.1 Hz, 1H), 7.22 (s, 1H), 7.18 (d, J=7.8 Hz, 1H), 5.28 (dd, J=9.0, 6.3 Hz, 1H), 3.82-3.78 (m, 1H), 2.42-2.34 (m, 1H), 2.10-1.89 (m, 3H), 1.80-1.66 (m, 4H), 1.52-1.42 (m, 1H), 1.31-1.14 (m, 3H), 1.09-0.98 (m, 6H);

Compound 56c:

(9 mg, 4.2% for four steps, white solid, single stereoisomer) HPLC: 99.9% purity, RT=1.76 min. MS: m/z=324.1 [M+H]⁺. ¹H NMR (300 MHz, CDCl₃, ppm) δ=7.90 (s, 1H), 7.71 (d, J=8.1 Hz, 1H), 7.23 (s, 1H), 7.19 (d, J=8.1 Hz, 1H), 5.29 (dd, J=9.0, 6.3 Hz, 1H), 3.86-3.79 (m, 1H), 2.42-2.34 (m, 1H), 2.10-1.89 (m, 3H), 1.80-1.66 (m, 4H), 1.52-1.42 (m, 1H), 1.31-1.14 (m, 3H), 1.09-0.98 (m, 6H).

Example 57: Synthesis of 2-[10-cyclopropyl-4,6,9-triazatricyclo[6.4.0.0^[2,6]]dodeca-1(8),2,4,9,11-pentaen-7-yl]-1-(4,4-difluorocyclohexyl)ethan-1-ol (57a, 57b, 57c)

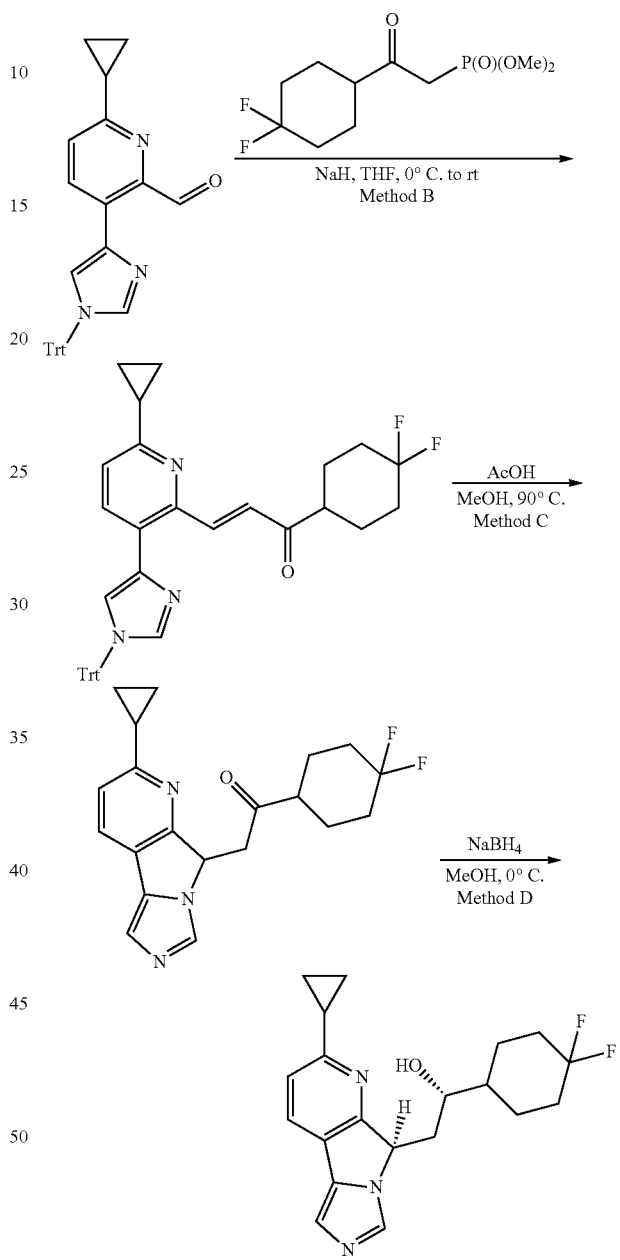

Compound 57a, 57b, and 57c

2-[10-Cyclopropyl-4,6,9-triazatricyclo[6.4.0.0^[2,6]]dodeca-1(8),2,4,9,11-pentaen-7-yl]-1-(4,4-difluorocyclohexyl)ethan-1-ol 2-[10-Cyclopropyl-4,6,9-triazatricyclo[6.4.0.0^[2,6]]dodeca-1(8),2,4,9,11-pentaen-7-yl]-1-(4,4-difluorocyclohexyl)ethan-1-ol was prepared from 6-cyclopropyl-3-[1-(triphenylmethyl)-1H-imidazol-4-yl]pyridine-2-carbaldehyde and dimethyl [2-(4,4-difluorocyclohexyl)-2-oxoethyl]phosphonate using Method B, C, and D. One pair of enantiomeric products and two enantiomeric products were obtained by the separation on chiral prep-HPLC under the following conditions: Chiralpak IC, 20×250 mm, 5 μm; mobile phase, iPrOH in hexane; 20% isocratic in 40 min; Detector, UV 254/220 nm.

Compound 57a:

(15 mg, 6.4% for three steps, white solid, containing two stereoisomers) HPLC: 99.2% purity, RT=1.68 min. MS: m/z=360.1 [M+H]$^+$. $^1$H NMR (300 MHz, CDCl$_3$, ppm) δ=8.05 (s, 1H), 7.73 (d, J=8.1 Hz, 1H), 7.25 (s, 1H), 7.20 (d, J=7.8 Hz, 1H), 5.20 (dd, J=8.7, 4.2 Hz, 1H), 4.06-4.02 (m, 1H), 2.25-1.93 (m, 6H), 1.78-1.49 (m, 6H), 1.07-1.04 (m, 4H);

Compound 57b:

(8 mg, 3.4% for three steps, white solid, single stereoisomer) HPLC: 99.5% purity, RT=1.70 min. MS: m/z=360.1 [M+H]$^+$. $^1$H NMR (300 MHz, CDCl$_3$, ppm) δ=7.89 (s, 1H), 7.73 (d, J=7.8 Hz, 1H), 7.23 (s, 1H), 7.21 (d, J=7.8 Hz, 1H), 5.32 (dd, J=9.0, 6.3 Hz, 1H), 3.90-3.83 (m, 1H), 2.49-2.40 (m, 1H), 2.17-2.05 (m, 4H), 1.91-1.84 (m, 1H), 1.78-1.53 (m, 4H), 1.47-1.38 (m, 2H), 1.06-0.94 (m, 4H);

Compound 57c:

(9 mg, 3.8% for three steps, white solid, single stereoisomer) HPLC: 99.7% purity, RT=1.70 min. MS: m/z=360.1 [M+H]$^+$. $^1$H NMR (300 MHz, CDCl$_3$, ppm) δ=7.83 (s, 1H), 7.73 (d, J=7.8 Hz, 1H), 7.23 (s, 1H), 7.21 (d, J=8.1 Hz, 1H), 5.31 (dd, J=9.6, 6.3 Hz, 1H), 3.88-3.82 (m, 1H), 2.49-2.40 (m, 1H), 2.17-2.05 (m, 4H), 1.91-1.84 (m, 1H), 1.78-1.53 (m, 4H), 1.47-1.38 (m, 2H), 1.06-0.94 (m, 4H).

Example 58: Synthesis of 4-fluoro-4-[2-[10-fluoro-4,6,11-triazatricyclo[6.4.0.0^[2,6]]dodeca-1(8),2,4,9,11-pentaen-7-yl]ethyl]cyclohexan-1-ol (58a, b, c, d)

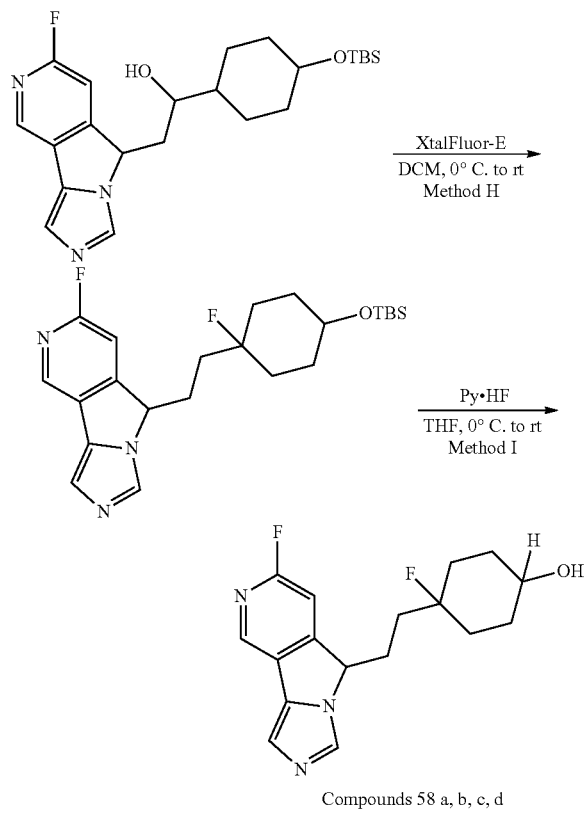

Compounds 58 a, b, c, d

4-Fluoro-4-[2-[10-fluoro-4,6,11-triazatricyclo[6.4.0.0^[2,6]]dodeca-1(8),2,4,9,11-pentaen-7-yl]ethyl] cyclohexan-1-ol 4-Fluoro-4-[2-[10-fluoro-4,6,11-triazatricyclo[6.4.0.0^[2,6]]dodeca-1(8),2,4,9,11-pentaen-7-yl]ethyl]cyclohexan-1-ol was prepared from 1-[4-[(tert-butyldimethylsilyl)oxy]cyclohexyl]-2-[10-fluoro-4,6,11-triazatricyclo[6.4.0.0^[2,6]]dodeca-1(8),2,4,9,11-pentaen-7-yl]ethan-1-ol using Method H and I. Four enantiomeric products were obtained by the separation on chiral prep-HPLC under the following conditions: Chiralpak IA, 20×250 mm, 5 μm; EtOH in hexane, 40% isocratic in 20 min; Detector, UV 254/220 nm.

Compound 58a:

(19 mg, 3.7% for two steps, white solid, single stereoisomer) HPLC: 97.7% purity, RT=1.14 min. MS: m/z=320.0 [M+H]$^+$. $^1$H NMR (300 MHz, CD$_3$OD, ppm) δ=8.45 (s, 1H), 7.98 (s, 1H), 7.29 (d, J=0.9 Hz, 1H), 7.25 (s, 1H), 5.56 (t, J=5.1 Hz, 1H), 3.54-3.47 (m, 1H), 2.48-2.36 (m, 1H), 2.28-2.16 (m, 1H), 1.88-1.81 (m, 2H), 1.75-1.69 (m, 2H), 1.59-1.42 (m, 3H), 1.38-1.23 (m, 3H);

Compound 58b:

(14 mg, 2.7% for two steps, white solid, single stereoisomer) HPLC: 99.97% purity, RT=1.14 min. MS: m/z=320.0 [M+H]$^+$. $^1$H NMR (300 MHz, CD$_3$OD, ppm) δ=8.45 (s, 1H), 7.98 (s, 1H), 7.29 (d, J=0.9 Hz, 1H), 7.25 (s, 1H), 5.56 (t, J=5.1 Hz, 1H), 3.54-3.47 (m, 1H), 2.48-2.36 (m, 1H), 2.28-2.16 (m, 1H), 1.88-1.81 (m, 2H), 1.75-1.69 (m, 2H), 1.59-1.42 (m, 3H), 1.38-1.23 (m, 3H);

Compound 58c:

(18.7 mg, 3.6% for two steps, white solid, single stereoisomer) HPLC: 99.9% purity, RT=1.23 min. MS: m/z=320.1 [M+H]$^+$. $^1$H NMR (300 MHz, CD$_3$OD, ppm) δ=8.45 (s, 1H), 8.00 (s, 1H), 7.30 (d, J=0.9 Hz, 1H), 7.26 (s, 1H), 5.57 (t, J=5.1 Hz, 1H), 3.89 (br s, 1H), 2.47-2.38 (m, 1H), 2.29-2.17 (m, 1H), 1.80-1.71 (m, 3H), 1.67-1.48 (m, 5H), 1.40-1.26 (m, 2H);

Compound 58d:

(21 mg, 4.1% for two steps, white solid, single stereoisomer) HPLC: 99.9% purity, RT=1.24 min. MS: m/z=320.0 [M+H]$^+$. $^1$H NMR (300 MHz, CD$_3$OD, ppm) δ=8.45 (s, 1H), 8.00 (s, 1H), 7.30 (d, J=0.9 Hz, 1H), 7.26 (s, 1H), 5.57 (t, J=5.1 Hz, 1H), 3.89 (br s, 1H), 2.47-2.38 (m, 1H), 2.29-2.17 (m, 1H), 1.80-1.71 (m, 3H), 1.67-1.48 (m, 5H), 1.40-1.26 (m, 2H).

Example 59: Synthesis of [4-fluoro-4-[2-[5H-imidazo[4,3-a]isoindol-5-yl]ethyl]cyclohexyl]methanol (Compound 59a, b, c, d)

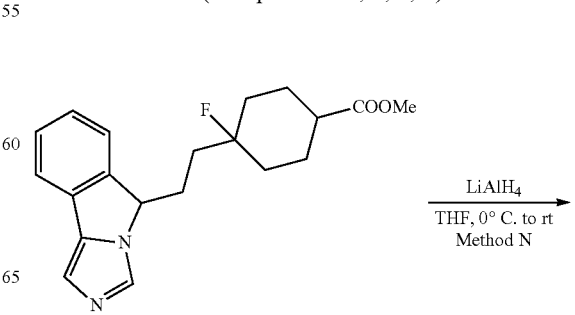

(m, 2H), 2.40-2.35 (m, 1H), 2.20-2.14 (m, 1H), 1.83-1.79 (m, 2H), 1.60-1.57 (m, 2H), 1.40-1.16 (m, 7H).

Example 60: Synthesis of 1-[4-fluoro-4-[2-[5H-imidazo[4,3-a]isoindol-5-yl]ethyl]cyclohexyl]cyclopropan-1-ol (60a, b, c, d)

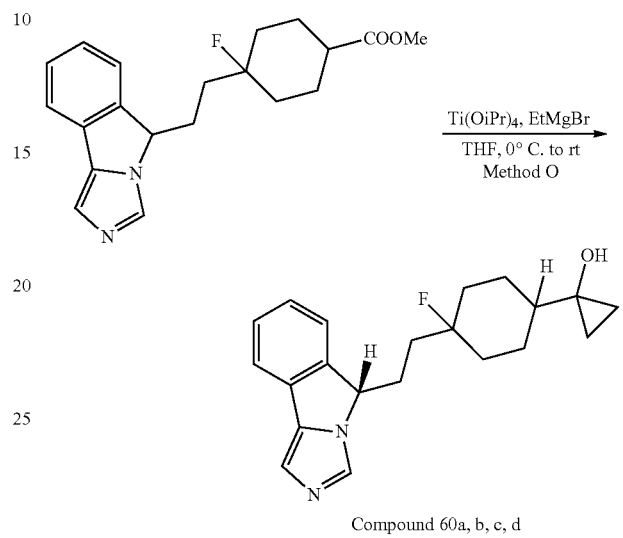

Method O:

1-[4-Fluoro-4-[2-[5H-imidazo[4,3-a]isoindol-5-yl]ethyl]cyclohexyl]cyclopropan-1-ol At 0° C., to a solution of methyl 4-fluoro-4-(2-[5H-imidazo[4,3-a]isoindol-5-yl]ethyl)cyclohexane-1-carboxylate (500 mg, 1.39 mmol) in THF (10 mL) was added Ti(OiPr)$_4$ (1.2 g, 4.01 mmol) slowly, followed by the dropwise addition of EtMgBr (1 M in THF, 8.3 mL, 8.3 mmol). The resulting mixture was then stirred at room temperature for 2 h. Then the reaction mixture was quenched with water (15 mL) and extracted with EtOAc (40 mL×4). The organic phases were combined, washed with brine and dried over Na$_2$SO$_4$. The solvent was removed under reduced pressure and the residue was purified by flash chromatography eluting with methanol in dichloromethane (2% to 5% gradient). Cis- and trans-isomers were separated on prep-HPLC under the following conditions: XBridge BEH C18 OBD Prep Column, 19×250 mm, 5 μm; mobile phase, acetonitrile in water (with 10 mM NH$_4$HCO$_3$), 40% to 45% gradient in 13 min; Detector, UV 254/220 nm. Four enantiomeric products were obtained by the further separation on chiral prep-HPLC under the following conditions: Phenomenex Lux 5μ Cellulose-4, AXIA Packed, 21.2×250 mm, 5 μm; iPrOH in hexane, 40% isocratic in 30 min; Detector, UV 254/220 nm.

Compound 60a:

(10.7 mg, 4.5%, white solid, single stereoisomer) HPLC: 97.9% purity, RT=1.04 min. MS: m/z=341.15 [M+H]$^+$. $^1$H NMR (300 MHz, CD$_3$OD, ppm) δ=8.11 (s, 1H), 7.64 (d, J=7.5 Hz, 1H), 7.50 (d, J=7.5 Hz, 1H), 7.45-7.33 (m, 2H), 7.24 (s, 1H), 5.48 (t, J=4.8 Hz, 1H), 2.46-2.35 (m, 1H), 2.24-2.15 (m, 1H), 1.90-1.81 (m, 2H), 1.70-1.57 (m, 4H), 1.39-1.17 (m, 4H), 0.98-0.86 (m, 1H), 0.61-0.58 (m, 2H), 0.42-0.38 (m, 2H);

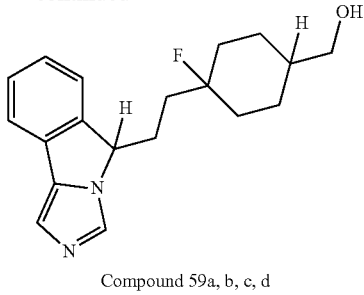

Compound 59a, b, c, d

Method N:

[4-Fluoro-4-[2-[5H-imidazo[4,3-a]isoindol-5-yl]ethyl]cyclohexyl]methanol

To a solution of methyl 4-fluoro-4-(2-[5H-imidazo[4,3-a]isoindol-5-yl]ethyl)cyclohexane-1-carboxylate (400 mg, 1.11 mmol) in THF (10 mL) was added LiAlH$_4$ (88.8 mg, 2.34 mmol) slowly at 0° C. The resulting mixture was stirred at room temperature for 2 h. Then the reaction mixture was quenched with water (15 mL) and extracted with EtOAc (40 mL×4). The organic phases were combined, washed with brine and dried over Na$_2$SO$_4$. The solvent was removed under reduced pressure and the residue was purified by flash chromatography eluting with methanol in dichloromethane (2% to 5% gradient). Four enantiomeric products were obtained by the separation on chiral prep-HPLC under the following conditions: Phenomenex Lux 5μ Cellulose-4, AXIA Packed, 21.2×250 mm, 5 μm; iPrOH in hexane, 40% isocratic in 30 min; Detector, UV 254/220 nm.

Compound 59a:

(14.8 mg, 3.9%, white solid, single stereoisomer) HPLC: 99.8% purity, RT=1.24 min. MS: m/z=315.1 [M+H]$^+$. $^1$H NMR (400 MHz, CD$_3$OD, ppm) δ=7.92 (s, 1H), 7.61 (d, J=7.6 Hz, 1H), 7.48 (d, J=7.6 Hz, 1H), 7.42-7.39 (m, 1H), 7.34-7.31 (m, 1H), 7.15 (s, 1H), 5.44 (t, J=4.4 Hz, 1H), 3.32-3.31 (m, 2H), 2.40-2.33 (m, 1H), 2.19-2.12 (m, 1H), 1.77-1.70 (m, 4H), 1.58-1.49 (m, 3H), 1.38-1.20 (m, 2H), 0.98-0.89 (m, 2H);

Compound 59b:

(11.1 mg, 2.9%, white solid, single stereoisomer) HPLC: 99.9% purity, RT=1.23 min. MS: m/z=315.1 [M+H]$^+$. $^1$H NMR (400 MHz, CD$_3$OD, ppm) δ=7.90 (s, 1H), 7.60 (d, J=7.6 Hz, 1H), 7.47 (d, J=7.6 Hz, 1H), 7.42-7.38 (m, 1H), 7.34-7.30 (m, 1H), 7.14 (s, 1H), 5.42 (br s, 1H), 3.32-3.31 (m, 2H), 2.40-2.35 (m, 1H), 2.20-2.14 (m, 1H), 1.83-1.79 (m, 2H), 1.60-1.57 (m, 2H), 1.40-1.16 (m, 7H);

Compound 59c:

(13.3 mg, 3.5%, white solid, single stereoisomer) HPLC: 99.8% purity, RT=1.24 min. MS: m/z=320.1 [M+H]$^+$. $^1$H NMR (400 MHz, CD$_3$OD, ppm) δ=7.92 (s, 1H), 7.61 (d, J=7.6 Hz, 1H), 7.48 (d, J=7.6 Hz, 1H), 7.42-7.39 (m, 1H), 7.34-7.31 (m, 1H), 7.15 (s, 1H), 5.44 (t, J=4.4 Hz, 1H), 3.32-3.31 (m, 2H), 2.40-2.33 (m, 1H), 2.19-2.12 (m, 1H), 1.77-1.70 (m, 4H), 1.58-1.49 (m, 3H), 1.38-1.20 (m, 2H), 0.98-0.89 (m, 2H);

Compound 59d:

(17.3 mg, 4.6%, white solid, single stereoisomer) HPLC: 99.7% purity, RT=1.23 min. MS: m/z=315.1 [M+H]$^+$. $^1$H NMR (400 MHz, CD$_3$OD, ppm) δ=7.90 (s, 1H), 7.60 (d, J=7.6 Hz, 1H), 7.47 (d, J=7.6 Hz, 1H), 7.42-7.38 (m, 1H), 7.34-7.30 (m, 1H), 7.14 (s, 1H), 5.42 (br s, 1H), 3.32-3.31

Compound 60b:

(12.6 mg, 5.3%, white solid, single stereoisomer) HPLC: 97.9% purity, RT=1.04 min. MS: m/z=341.15 [M+H]$^+$. $^1$H NMR (300 MHz, CD$_3$OD, ppm) δ=7.99 (s, 1H), 7.62 (d, J=7.5 Hz, 1H), 7.50 (d, J=7.5 Hz, 1H), 7.44-7.31 (m, 2H), 7.19 (s, 1H), 5.48 (t, J=4.8 Hz, 1H), 2.46-2.31 (m, 1H), 2.24-2.12 (m, 1H), 1.90-1.83 (m, 2H), 1.71-1.67 (m, 2H), 1.60-1.09 (m, 6H), 0.99-0.91 (m, 1H), 0.58-0.54 (m, 2H), 0.37-0.34 (m, 2H);

Compound 60c:

(13.1 mg, 5.5%, white solid, single stereoisomer) HPLC: 96.2% purity, RT=1.00 min. MS: m/z=341.15 [M+H]$^+$. $^1$H NMR (300 MHz, CD$_3$OD, ppm) δ=8.11 (s, 1H), 7.64 (d, J=7.5 Hz, 1H), 7.50 (d, J=7.5 Hz, 1H), 7.45-7.33 (m, 2H), 7.24 (s, 1H), 5.48 (t, J=4.8 Hz, 1H), 2.46-2.35 (m, 1H), 2.24-2.15 (m, 1H), 1.90-1.81 (m, 2H), 1.70-1.57 (m, 4H), 1.39-1.17 (m, 4H), 0.98-0.86 (m, 1H), 0.61-0.58 (m, 2H), 0.42-0.38 (m, 2H);

Compound 60d:

(15.3 mg, 6.4%, white solid, single stereoisomer) HPLC: 98.2% purity, RT=1.04 min. MS: m/z=341.15 [M+H]$^+$. $^1$H NMR (300 MHz, CD$_3$OD, ppm) δ=7.99 (s, 1H), 7.62 (d, J=7.5 Hz, 1H), 7.50 (d, J=7.5 Hz, 1H), 7.44-7.31 (m, 2H), 7.19 (s, 1H), 5.48 (t, J=4.8 Hz, 1H), 2.46-2.31 (m, 1H), 2.24-2.12 (m, 1H), 1.90-1.83 (m, 2H), 1.71-1.67 (m, 2H), 1.60-1.09 (m, 6H), 0.99-0.91 (m, 1H), 0.58-0.54 (m, 2H), 0.37-0.34 (m, 2H).

Example 61: Synthesis of 2-[4-fluoro-4-[2-[5H-imidazo[4,3-a]isoindol-5-yl]ethyl]cyclohexyl]propan-2-ol (61a, b, c, d)

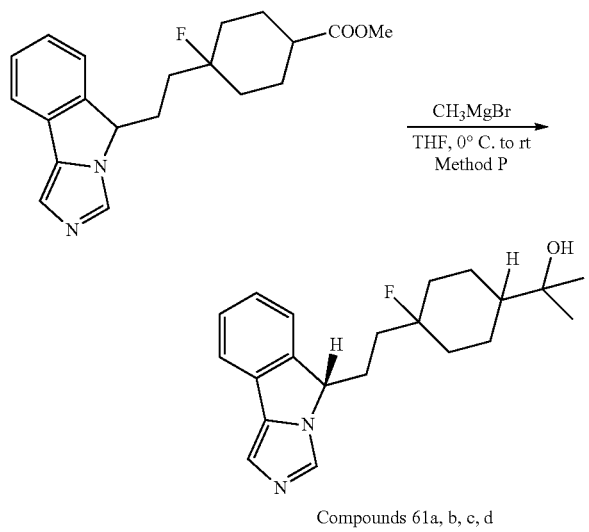

Compounds 61a, b, c, d

Method P:

2-[4-Fluoro-4-[2-[5H-imidazo[4,3-a]isoindol-5-yl]ethyl]cyclohexyl]propan-2-ol

At 0° C., to a solution of methyl 4-fluoro-4-(2-[5H-imidazo[4,3-a]isoindol-5-yl]ethyl)cyclohexane-1-carboxylate (360 mg, 1.01 mmol) in THF (10 mL) was added CH$_3$MgBr (1 M in THF, 10 mL, 10 mmol) slowly. The resulting mixture was stirred at room temperature for 2 h. Then the reaction mixture was quenched with saturated ammonium chloride solution (25 mL) and extracted with ethyl acetate (40 mL×4). The organic phases were combined, washed with brine and dried over sodium sulfate. The solvent was removed under reduced pressure and the residue was purified by flash chromatography eluting with methanol in dichloromethane (2% to 5% gradient). Then cis- and trans-isomers were separated on prep-HPLC under the following conditions: XBridge C18 OBD Prep Column, 19×250 mm, 5 μm; mobile phase, MeCN in water (with 10 mM NH$_4$HCO$_3$), 31% to 34% gradient in 14 min; Detector, UV 254/220 nm. Four enantiomeric products were obtained by the further separation on chiral prep-HPLC under the following conditions: Phenomenex Lux 5μ Cellulose-4, AXIA Packed, 21.2×250 mm, 5 μm; iPrOH in hexane, 40% isocratic in 30 min; Detector, UV 254/220 nm.

Compound 61a:

(19.1 mg, 5.3%, white solid, single stereoisomer) HPLC: 99.9% purity, RT=1.34 min. MS: m/z=343.1 [M+H]$^+$. $^1$H NMR (400 MHz, CD$_3$OD, ppm) δ=7.91 (s, 1H), 7.61 (d, J=7.6 Hz, 1H), 7.49 (d, J=7.6 Hz, 1H), 7.42-7.38 (m, 1H), 7.34-7.30 (m, 1H), 7.15 (s, 1H), 5.46 (t, J=4.4 Hz, 1H), 2.42-2.34 (m, 1H), 2.20-2.13 (m, 1H), 1.86-1.82 (m, 2H), 1.74-1.71 (m, 2H), 1.58-1.45 (m, 2H), 1.36-1.17 (m, 3H), 1.02 (s, 6H), 0.89-0.75 (m, 2H);

Compound 61b:

(13.7 mg, 3.8%, white solid, single stereoisomer) HPLC: 99.7% purity, RT=1.35 min. MS: m/z=343.1 [M+H]$^+$. $^1$H NMR (400 MHz, CD$_3$OD, ppm) δ=7.89 (s, 1H), 7.60 (d, J=7.2 Hz, 1H), 7.47 (d, J=7.6 Hz, 1H), 7.42-7.38 (m, 1H), 7.34-7.30 (m, 1H), 7.14 (s, 1H), 5.42 (t, J=4.8 Hz, 1H), 2.42-2.34 (m, 1H), 2.21-2.15 (m, 1H), 1.87-1.82 (m, 2H), 1.66-1.63 (m, 2H), 1.38-1.15 (m, 7H), 1.11 (s, 6H);

Compound 61c:

(12.3 mg, 3.4%, white solid, single stereoisomer) HPLC: 98.4% purity, RT=1.36 min. MS: m/z=343.1 [M+H]$^+$. $^1$H NMR (400 MHz, CD$_3$OD, ppm) δ=7.89 (s, 1H), 7.60 (d, J=7.2 Hz, 1H), 7.47 (d, J=7.6 Hz, 1H), 7.42-7.38 (m, 1H), 7.34-7.30 (m, 1H), 7.14 (s, 1H), 5.42 (t, J=4.8 Hz, 1H), 2.42-2.34 (m, 1H), 2.21-2.15 (m, 1H), 1.87-1.82 (m, 2H), 1.66-1.63 (m, 2H), 1.38-1.15 (m, 7H), 1.11 (s, 6H);

Compound 61d:

(25.1 mg, 7%, white solid, single stereoisomer) HPLC: 99.9% purity, RT=1.35 min. MS: m/z=343.1 [M+H]$^+$. $^1$H NMR (400 MHz, CD$_3$OD, ppm) δ=7.91 (s, 1H), 7.61 (d, J=7.6 Hz, 1H), 7.49 (d, J=7.6 Hz, 1H), 7.42-7.38 (m, 1H), 7.34-7.30 (m, 1H), 7.15 (s, 1H), 5.46 (t, J=4.4 Hz, 1H), 2.42-2.34 (m, 1H), 2.20-2.13 (m, 1H), 1.86-1.82 (m, 2H), 1.74-1.71 (m, 2H), 1.58-1.45 (m, 2H), 1.36-1.17 (m, 3H), 1.02 (s, 6H), 0.89-0.75 (m, 2H).

Example 62: Synthesis of 1-cyclohexyl-3-[4,6,9-triazatricyclo[6.4.0.0^[2,6]]dodeca-1(8),2,4,9,11-pentaen-7-yl]propan-2-ol (62a, b, c, d)

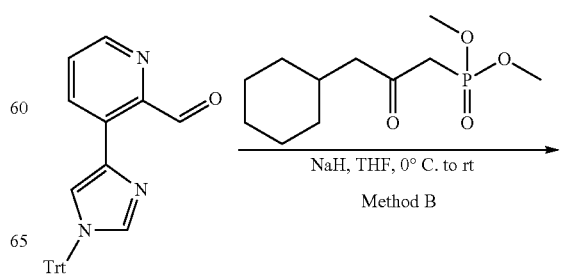

-continued

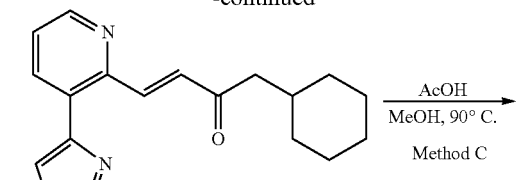

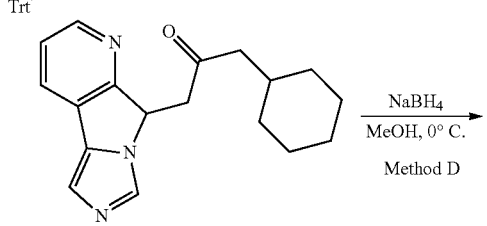

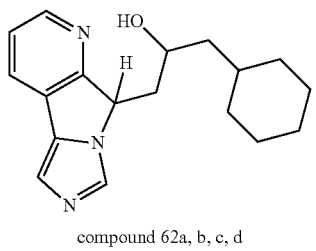

compound 62a, b, c, d

1-Cyclohexyl-3-[4,6,9-triazatricyclo[6.4.0.0^[2,6]] dodeca-1(8),2,4,9,11-pentaen-7-yl]propan-2-ol 1-Cyclohexyl-3-[4,6,9-triazatricyclo[6.4.0.0^[2,6]]dodeca-1(8),2,4,9,11-pentaen-7-yl]propan-2-ol was prepared from 3-[1-(triphenylmethyl)-1H-imidazol-4-yl]pyridine-2-carbaldehyde and dimethyl (3-cyclohexyl-2-oxopropyl) phosphonate using Method B, C, and D. Four enantiomeric products were obtained by the separation on chiral prep-HPLC under the following conditions: Phenomenex Lux 5μ Cellulose-4, AXIA Packed, 21.2×250 mm, 5 μm; iPrOH in hexane, 30% isocratic in 38 min; Detector, UV 254/220 nm.

Compound 62a:

(13.3 mg, 8% for three steps, white solid, single stereoisomer) HPLC: 99.8% purity, RT=1.41 min. MS: m/z=298.1 [M+H]$^+$. $^1$H NMR (400 MHz, CD$_3$OD, ppm) δ=8.39 (d, J=1.6 Hz, 1H), 8.07 (s, 1H), 8.01 (dd, J=8.0, 1.6 Hz, 1H), 7.39 (dd, J=8.0, 4.8 Hz, 1H), 7.28 (s, 1H), 5.37 (t, J=5.6 Hz, 1H), 4.15-4.10 (m, 1H), 2.32-2.27 (m, 1H), 2.08-2.02 (m, 1H), 1.80-1.75 (m, 1H), 1.69-1.64 (m, 4H), 1.51-1.39 (m, 2H), 1.30-1.15 (m, 4H), 0.99-0.82 (m, 2H);

Compound 62b:

(6 mg, 3.6% for three steps, white solid, single stereoisomer) HPLC: 99.5% purity, RT=1.37 min. MS: m/z=298.1 [M+H]$^+$. $^1$H NMR (400 MHz, CD$_3$OD, ppm) δ=8.39 (d, J=1.2 Hz, 1H), 8.04-8.02 (m, 2H), 7.41 (dd, J=7.6, 5.2 Hz, 1H), 7.31 (s, 1H), 5.46 (dd, J=9.2, 3.6 Hz, 1H), 4.03-3.98 (m, 1H), 2.39-2.31 (m, 1H), 1.82-1.75 (m, 2H), 1.69-1.63 (m, 4H), 1.51-1.46 (m, 2H), 1.30-1.15 (m, 4H), 0.98-0.81 (m, 2H);

Compound 62c:

(9.4 mg, 5.6% for three steps, white solid, single stereoisomer) HPLC: 99.1% purity, RT=1.42 min. MS: m/z=298.1 [M+H]$^+$. $^1$H NMR (400 MHz, CD$_3$OD, ppm) δ=8.39 (d, J=1.6 Hz, 1H), 8.07 (s, 1H), 8.01 (dd, J=8.0, 1.6 Hz, 1H), 7.39 (dd, J=8.0, 4.8 Hz, 1H), 7.28 (s, 1H), 5.37 (t, J=5.6 Hz, 1H), 4.15-4.10 (m, 1H), 2.32-2.27 (m, 1H), 2.08-2.02 (m, 1H), 1.80-1.75 (m, 1H), 1.69-1.64 (m, 4H), 1.51-1.39 (m, 2H), 1.30-1.15 (m, 4H), 0.99-0.82 (m, 2H);

Compound 62d:

(4.1 mg, 2.5% for three steps, white solid, single stereoisomer) HPLC: 99.6% purity, RT=1.38 min. MS: m/z=298.1 [M+H]$^+$. $^1$H NMR (400 MHz, CD$_3$OD, ppm) δ=8.39 (d, J=1.2 Hz, 1H), 8.04-8.02 (m, 2H), 7.41 (dd, J=7.6, 5.2 Hz, 1H), 7.31 (s, 1H), 5.46 (dd, J=9.2, 3.6 Hz, 1H), 4.03-3.98 (m, 1H), 2.39-2.31 (m, 1H), 1.82-1.75 (m, 2H), 1.69-1.63 (m, 4H), 1.51-1.46 (m, 2H), 1.30-1.15 (m, 4H), 0.98-0.81 (m, 2H).

Example 63: Synthesis of 4-[1-hydroxy-2-[4,6,9-triazatricyclo[6.4.0.0^[2,6]]dodeca-1(8),2,4,9,11-pentaen-7-yl]ethyl]cyclohexane-1-carboxamide (63a, b, c, d)

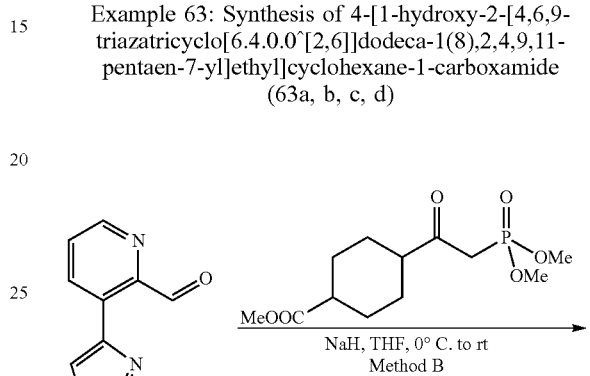

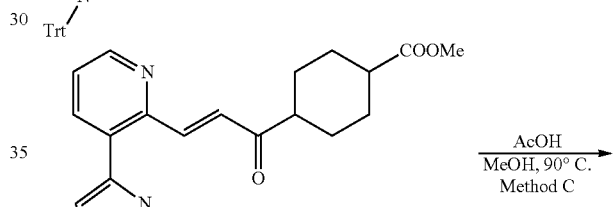

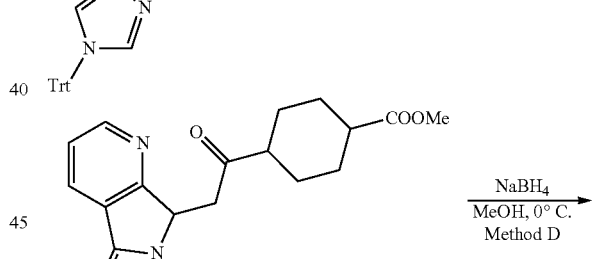

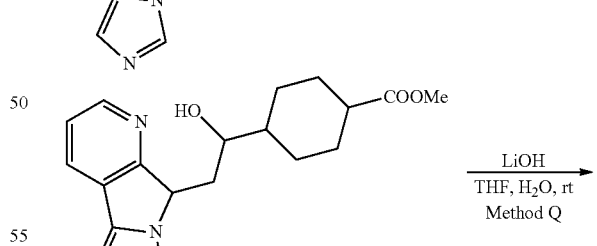

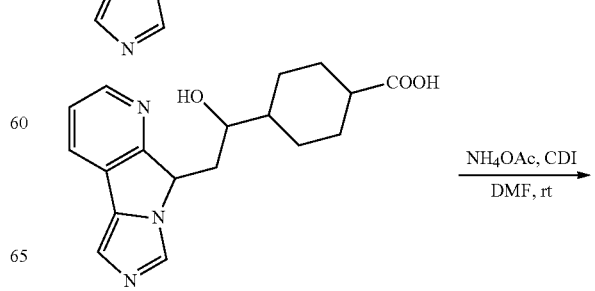

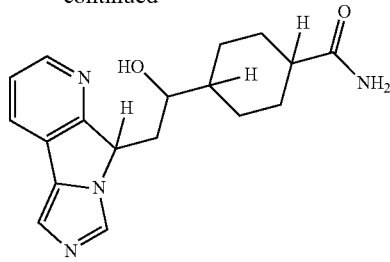

Compound 63a, b, c, d

Methyl 4-(1-hydroxy-2-[4,6,9-triazatricyclo[6.4.0.0^[2,6]]dodeca-1(8),2,4,9,11-pentaen-7-yl]ethyl)cyclohexane-1-carboxylate Methyl 4-(1-hydroxy-2-[4,6,9-triazatricyclo[6.4.0.0^[2,6]]dodeca-1(8),2,4,9,11-pentaen-7-yl]ethyl)cyclohexane-1-carboxylate (1.1 g, 81%) was prepared from 3-[1-(triphenylmethyl)-1H-imidazol-4-yl]pyridine-2-carbaldehyde and methyl 4-[2-(dimethoxyphosphoryl)acetyl]cyclohexane-1-carboxylate using Method B, C, and D. MS: m/z=342.1 [M+H]$^+$.

Method Q:

4-(1-Hydroxy-2-[4,6,9-triazatricyclo[6.4.0.0^[2,6]]dodeca-1(8),2,4,9,11-pentaen-7-yl]ethyl)cyclohexane-1-carboxylic acid At room temperature, to a solution of methyl 4-(1-hydroxy-2-[4,6,9-triazatricyclo[6.4.0.0^[2,6]]dodeca-1(8),2,4,9,11-pentaen-7-yl]ethyl)cyclohexane-1-carboxylate (1.1 g, 3.22 mmol) in THF (21 mL) and water (7 mL) was added lithium hydroxide (310 mg, 12.94 mmol) slowly. The resulting mixture was stirred at room temperature for 16 h. Then the reaction mixture was neutralized with hydrochloric acid solution (1 M) and the mixture was concentrated under reduced pressure. The residue was purified by flash chromatography eluting with methanol in dichloromethane (5% to 10% gradient) to yield 4-(1-hydroxy-2-[4,6,9-triazatricyclo[6.4.0.0^[2,6]]dodeca-1(8),2,4,9,11-pentaen-7-yl]ethyl)cyclohexane-1-carboxylic acid (950 mg, 90%) as light yellow oil. MS: m/z=328.1 [M+H]$^+$.

4-[1-Hydroxy-2-[4,6,9-triazatricyclo[6.4.0.0^[2,6]]dodeca-1(8),2,4,9,11-pentaen-7-yl]ethyl]cyclohexane-1-carboxamide At room temperature, to a solution of 4-(1-hydroxy-2-[4,6,9-triazatricyclo[6.4.0.0^[2,6]]dodeca-1(8),2,4,9,11-pentaen-7-yl]ethyl)cyclohexane-1-carboxylic acid (300 mg, 0.91 mmol) in DMF (8 mL) was added CDI (297 mg, 1.83 mmol) slowly. The mixture was stirred at room temperature for 2 h, and then was added by ammonium acetate (283 mg, 3.66 mmol) in one batch. The resulting mixture was kept stirring for another 16 h at room temperature. Then the reaction mixture was diluted with water (30 mL) and extracted with ethyl acetate (40 mL×4). The organic phases were combined, washed with brine and dried over sodium sulfate. The solvent was removed under reduced pressure and the residue was purified by flash chromatography eluting with methanol in dichloromethane (5% to 10% gradient). Four pairs of enantiomers were obtained by the separation on prep-HPLC under the following conditions: XBridge C18 OBD Prep Column, 19×250 mm, 5 µm; mobile phase, acetonitrile in water (with 10 mM NH$_4$HCO$_3$), 18% isocratic in 14 min; Detector, UV 254/220 nm.

Compound 63a:

(7.2 mg, 2.2%, white solid, mixture of two stereoisomers) HPLC: 98.4% purity, RT=0.66 min. MS: m/z=327.1 [M+H]$^+$. $^1$H NMR (400 MHz, CD$_3$OD, ppm) δ=8.40-8.39 (m, 1H), 8.08 (s, 1H), 8.00 (dd, J=8.0, 1.6 Hz, 1H), 7.39 (dd, J=8.0, 5.2 Hz, 1H), 7.28 (s, 1H), 5.36 (t, J=6.0 Hz, 1H), 3.85-3.82 (m, 1H), 2.39-2.34 (m, 1H), 2.18-2.02 (m, 2H), 1.99-1.84 (m, 3H), 1.80-1.76 (m, 1H), 1.48-1.34 (m, 3H), 1.22-1.13 (m, 2H);

Compound 63b:

(11.9 mg, 4%, white solid, mixture of two stereoisomers) HPLC: 99.5% purity, RT=0.58 min. MS: m/z=327.1 [M+H]$^+$. $^1$H NMR (400 MHz, CD$_3$OD, ppm) δ=8.41-8.40 (m, 1H), 8.04-8.02 (m, 2H), 7.42 (dd, J=8.0, 5.2 Hz, 1H), 7.31 (s, 1H), 5.47 (dd, J=9.6, 3.2 Hz, 1H), 3.70-3.67 (m, 1H), 2.47-2.39 (m, 1H), 2.18-2.12 (m, 1H), 2.03-1.98 (m, 1H), 1.91-1.76 (m, 4H), 1.49-1.38 (m, 3H), 1.20-1.11 (s, 2H);

Compound 63c:

(11.8 mg, 3.9%, white solid, mixture of two stereoisomers) HPLC: 98.4% purity, RT=0.66 min. MS: m/z=327.1 [M+H]$^+$. $^1$H NMR (400 MHz, CD$_3$OD, ppm) δ=8.40-8.39 (m, 1H), 8.09 (s, 1H), 7.99 (dd, J=8.0, 1.2 Hz, 1H), 7.39 (dd, J=7.6, 4.8 Hz, 1H), 7.27 (s, 1H), 5.37 (t, J=5.6 Hz, 1H), 4.06-4.01 (m, 1H), 2.43-2.38 (m, 2H), 2.04-1.88 (m, 3H), 1.66-1.63 (m, 2H), 1.69-1.48 (m, 7H);

Compound 63d:

(22.6 mg, 7.5%, white solid, mixture of two stereoisomers) HPLC: 99.5% purity, RT=0.92 min. MS: m/z=327.1 [M+H]$^+$. $^1$H NMR (400 MHz, CD$_3$OD, ppm) δ=8.40-8.39 (m, 1H), 8.05 (s, 1H), 8.02 (dd, J=7.6, 1.2 Hz, 1H), 7.41 (dd, J=7.6, 4.8 Hz, 1H), 7.31 (s, 1H), 5.48 (dd, J=10.0, 3.6 Hz, 1H), 3.86-3.84 (m, 1H), 2.43-2.34 (m, 2H), 1.98-1.49 (m, 10H).

Example 64: Synthesis of 5-(2-cyclohexyl-2,2-difluoroethyl)-5H-imidazo[4,3-a]isoindole

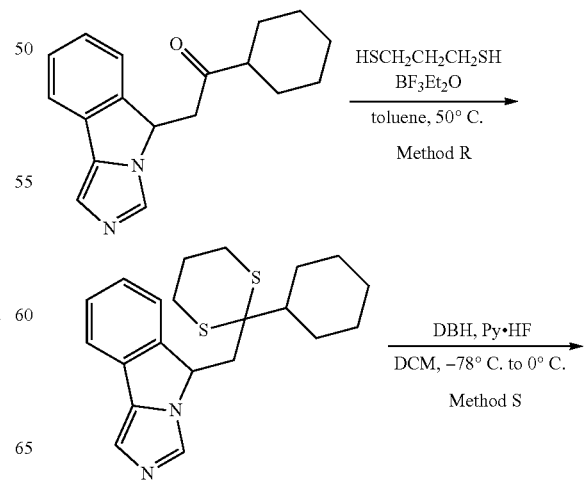

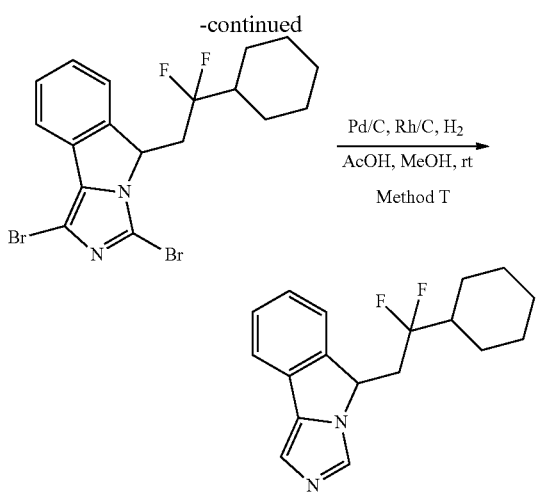

Method R:

5-[(2-Cyclohexyl-1,3-dithian-2-yl)methyl]-5H-imidazo[4,3-a]isoindole

To a solution of 1-cyclohexyl-2-[5H-imidazo[4,3-a]isoindol-5-yl]ethan-1-one (390 mg, 1.04 mmol) and propane-1,3-dithiol (592 mg, 5.20 mmol) in toluene (10 mL) was added BF$_3$·Et$_2$O (775 mg, 5.20 mmol) slowly at room temperature. The resulting mixture was stirred at 50° C. for 16 h. Then the reaction mixture was quenched with water (30 mL) and extracted with ethyl acetate (50 mL×2). The organic phases were combined, washed with brine and dried over sodium sulfate. The solvent was removed under reduced pressure and the residue was purified by flash chromatography eluting with MeOH in DCM (1% to 4% gradient) to yield 5-[(2-cyclohexyl-1,3-dithian-2-yl)methyl]-5H-imidazo[4,3-a]isoindole (270 mg, 70%) as yellow oil. MS: m/z=370.95 [M+H]$^+$.

Method S:

1,3-Dibromo-5-(2-cyclohexyl-2,2-difluoroethyl)-5H-imidazo[4,3-a]isoindole

At −78° C., to a suspension of 1,3-dibromo-5,5-dimethylimidazolidine-2,4-dione (625 mg, 2.08 mmol) in dichloromethane (6 mL) was added HF-pyridine (836 mg, 8.01 mmol) dropwise, followed by the addition of a solution of 5-[(2-cyclohexyl-1,3-dithian-2-yl)methyl]-5H-imidazo[4,3-a]isoindole (270 mg, 0.66 mmol) in dichloromethane (2 mL) slowly. The resulting mixture was kept stirring while slowly warmed up to 0° C. over 1 h period. Then the reaction mixture was neutralized with saturated sodium bicarbonate solution and extracted with dichloromethane (40 mL×2). The organic phases were combined, washed with brine and dried over sodium sulfate. The solvent was removed under reduced pressure and the residue was purified by flash chromatography eluting with EtOAc in petroleum ether (25% to 50% gradient) to yield 1,3-dibromo-5-(2-cyclohexyl-2,2-difluoroethyl)-5H-imidazo[4,3-a]isoindole (141 mg, 47%) as yellow oil. MS: m/z=458.8 [M+H]$^+$.

Method T:

5-(2-Cyclohexyl-2,2-difluoroethyl)-5H-imidazo[4,3-a]isoindole

At room temperature, to a solution of 1,3-dibromo-5-(2-cyclohexyl-2,2-difluoroethyl)-5H-imidazo[4,3-a]isoindole (141 mg, 0.30 mmol) in AcOH (6 mL) and MeOH (3 mL) was added Rh/C (5%, 56 mg) and Pd/C (10%, 56 mg) under N$_2$ atmosphere. The reaction flask was vacuumed and flushed with hydrogen, and then the reaction mixture was stirred at room temperature for 16 h under H$_2$ atmosphere using a hydrogen balloon. Then the reaction mixture was filtered through a celite pad, which was rinsed with EtOAc (20 mL×2). The combined filtrate was concentrated under reduced pressure and the residue was purified by prep-HPLC under the following conditions: XBridge C18 OBD Prep Column, 19×250 mm, 5 μm; mobile phase, MeCN in water (with 10 mM NH$_4$HCO$_3$), 45% to 75% gradient in 8 min; Detector, UV 254/220 nm. One pair of enantiomeric product was obtained.

Compound 64:

(18 mg, 19%, white solid, mixture of two stereoisomers) HPLC: 99.6% purity, RT=1.22 min. MS: m/z=303.1 [M+H]$^+$. $^1$H NMR (400 MHz, CD$_3$OD, ppm) δ=7.86 (s, 1H), 7.62 (d, J=7.6 Hz, 1H), 7.52 (d, J=7.6 Hz, 1H), 7.45-7.41 (m, 1H), 7.37-7.33 (m, 1H), 7.15 (s, 1H), 5.61 (dd, J=8.4, 2.4 Hz, 1H), 2.83-2.67 (m, 1H), 2.47-2.30 (m, 1H), 1.95-1.85 (m, 5H), 1.75-1.70 (m, 1H), 1.38-1.20 (m, 5H).

Example 65: Synthesis of 5-(2-cyclohexyl-2,2-difluoroethyl)-6-fluoro-5H-imidazo[4,3-a]isoindole

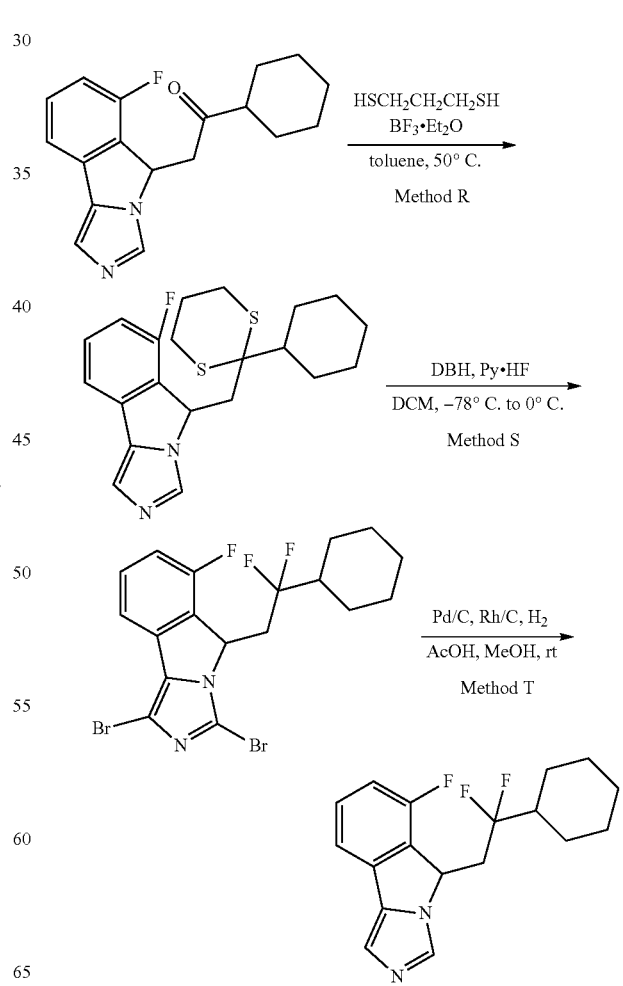

5-(2-Cyclohexyl-2,2-difluoroethyl)-6-fluoro-5H-imidazo[4,3-a]isoindole 5-(2-Cyclohexyl-2,2-difluoroethyl)-6-fluoro-5H-imidazo[4,3-a]isoindole was prepared from 1-cyclohexyl-2-[6-fluoro-5H-imidazo[4,3-a]isoindol-5-yl]ethan-1-one using Method R, S, and T. One pair of enantiomeric product was obtained by the separation on prep-HPLC under the following conditions: XBridge Shield RP18 OBD Column, 19×150 mm, 5 μm; mobile phase, MeCN in water (with 10 mM NH₄HCO₃), 45% to 75% gradient in 8 min; Detector, UV 254/220 nm.

Compound 65:
(24 mg, 16%, light yellow solid, mixture of two stereoisomers) HPLC: 99.96% purity, RT=1.24 min. MS: m/z=321.1 [M+H]⁺. ¹H NMR (400 MHz, CD₃OD, ppm) δ=7.88 (s, 1H), 7.51-7.45 (m, 2H), 7.20 (s, 1H), 7.09-7.06 (m, 1H), 5.82 (d, J=8.4 Hz, 1H), 3.02-2.90 (m, 1H), 2.44-2.32 (m, 1H), 1.93-1.83 (m, 5H), 1.74-1.70 (m, 1H), 1.37-1.21 (m, 5H).

Example 66: Synthesis of 7-[2-(1-fluoro-4,4-dimethylcyclohexyl)ethyl]-4,6,9,11-tetraazatricyclo[6.4.0.0ˆ[2,6]]dodeca-1(8),2,4,9,11-pentaene (66a, b)

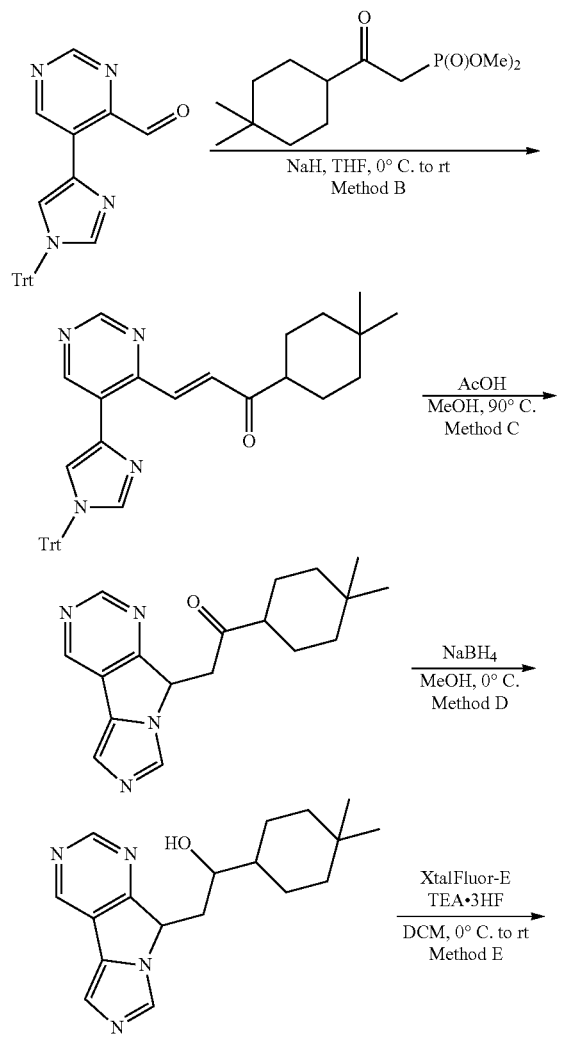

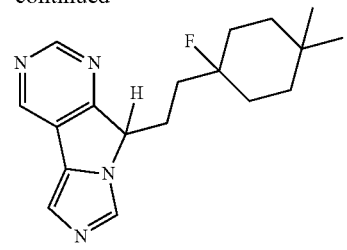

Compound 66a and 66b

7-[2-(1-Fluoro-4,4-dimethylcyclohexyl)ethyl]-4,6,9, 11-tetraazatricyclo[6.4.0.0ˆ[2,6]]dodeca-1(8),2,4,9, 11-pentaene 7-[2-(1-Fluoro-4,4-dimethylcyclohexyl)ethyl]-4,6,9,11-tetraazatricyclo[6.4.0.0ˆ[2,6]] dodeca-1(8),2,4,9,11-pentaene was prepared from 5-[1-(triphenylmethyl)-1H-imidazol-4-yl]pyrimidine-4-carbaldehyde and dimethyl [2-(4,4-dimethylcyclohexyl)-2-oxoethyl]phosphonate using Method B, C, D, and E. Two enantiomeric products were obtained by the separation on chiral prep-HPLC under the following conditions: Chiralpak IB, 20×250 mm, 5 μm; EtOH in hexane, 30% isocratic in 14 min; Detector, UV 254/220 nm.

Compound 66a:
(15 mg, 8%, light yellow solid, single stereoisomer) HPLC: 99.6% purity, RT=1.45 min. MS: m/z=315.1 [M+H]⁺. ¹H NMR (400 MHz, CD₃OD, ppm) δ=9.08 (s, 1H), 9.04 (s, 1H), 8.13 (s, 1H), 7.44 (s, 1H), 5.47 (t, J=5.6 Hz, 1H), 2.49-2.42 (m, 1H), 2.34-2.26 (m, 1H), 1.73-1.68 (m, 2H), 1.58-1.40 (m, 6H), 1.21-1.18 (m, 2H), 0.94 (s, 3H), 0.89 (s, 3H);

Compound 66b:
(14.2 mg, 7.6%, light yellow solid, single stereoisomer) HPLC: 99.7% purity, RT=1.45 min. MS: m/z=315.1 [M+H]⁺. ¹H NMR (400 MHz, CD₃OD, ppm) δ=9.08 (s, 1H), 9.04 (s, 1H), 8.13 (s, 1H), 7.44 (s, 1H), 5.47 (t, J=5.6 Hz, 1H), 2.49-2.42 (m, 1H), 2.34-2.26 (m, 1H), 1.73-1.68 (m, 2H), 1.58-1.40 (m, 6H), 1.21-1.18 (m, 2H), 0.94 (s, 3H), 0.89 (s, 3H).

Example 67: Synthesis of 1-cyclohexyl-2-[4,6,9,11-tetraazatricyclo[6.4.0.0ˆ[2,6]]dodeca-1(8),2,4,9,11-pentaen-7-yl]ethan-1-ol (67a, b, c, d)

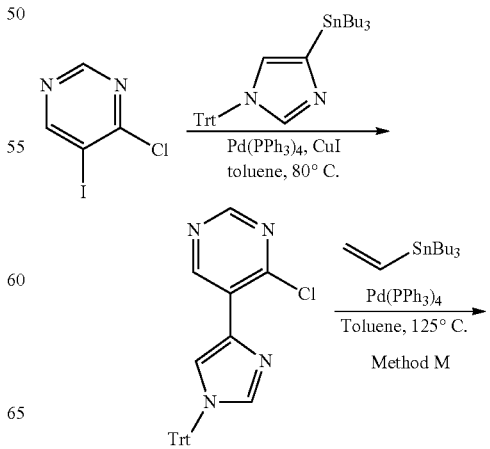

227
-continued

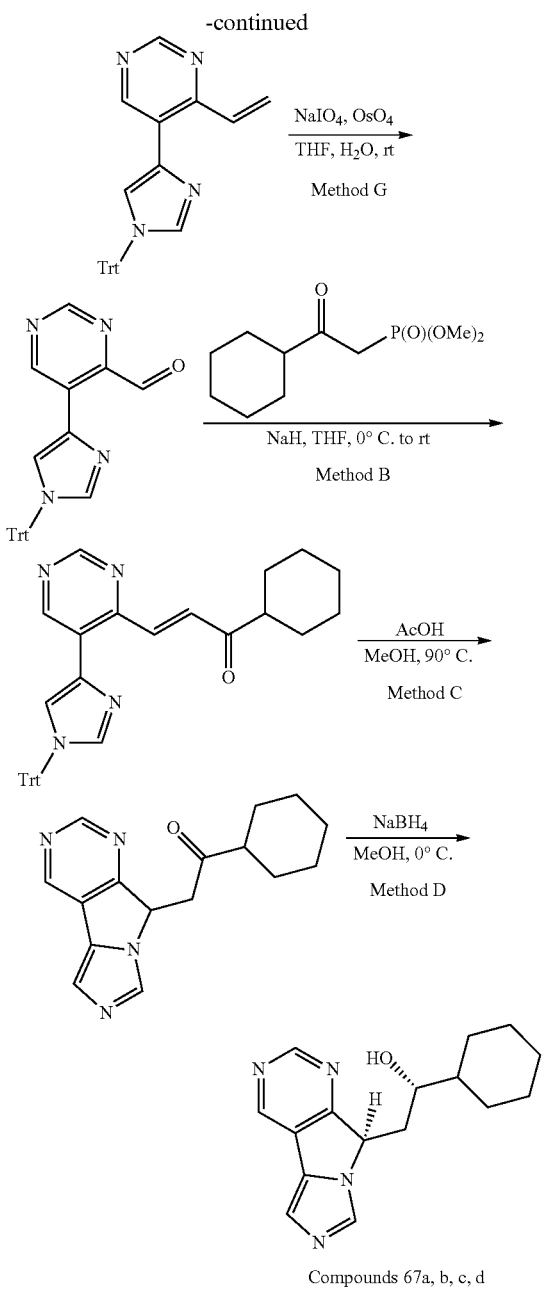

Compounds 67a, b, c, d

4-Chloro-5-[1-(triphenylmethyl)-1H-imidazol-4-yl]pyrimidine

At 80° C., a mixture of 4-chloro-5-iodopyrimidine (5.2 g, 21.63 mmol), 4-(tributylstannyl)-1-(triphenylmethyl)-1H-imidazole (19.47 g, 32.48 mmol), Pd(PPh$_3$)$_4$ (2.5 g, 2.16 mmol) and CuI (824.2 mg, 4.33 mmol) in toluene (120 mL) was stirred for 16 h under argon atmosphere. Then the reaction mixture was diluted with water (100 mL) and extracted with EtOAc (250 mL×2). The organic phases were combined, washed with brine and dried over Na$_2$SO$_4$. The solvent was removed under reduced pressure and the residue was purified by flash chromatography eluting with EtOAc in petroleum ether (20% to 50% gradient) to yield 4-chloro-5-[1-(triphenylmethyl)-1H-imidazol-4-yl]pyrimidine (6.6 g, 72%) as yellow solid. MS: m/z=370.95 [M+H]$^+$.

228

1-Cyclohexyl-2-[4,6,9,11-tetraazatricyclo[6.4.0.0^[2,6]]dodeca-1(8),2,4,9,11-pentaen-7-yl]ethan-1-ol 1-Cyclohexyl-2-[4,6,9,11-tetraazatricyclo[6.4.0.0^[2,6]]dodeca-1(8),2,4,9,11-pentaen-7-yl]ethan-1-ol was prepared from 4-chloro-5-[1-(triphenylmethyl)-1H-imidazol-4-yl]pyrimidine and dimethyl (2-cyclohexyl-2-oxoethyl)phosphonate using Method M, G, B, C, and D. Four enantiomeric products were obtained by the separation on chiral prep-HPLC under the following conditions: Chiralpak IA, 20×250 mm, 5 μm; EtOH in hexane, 10% isocratic in 32 min; Detector, UV 254/220 nm.

Compound 67a:

(28.3 mg, 5.6% for five steps, white solid, mixture of two stereoisomers, epimerization occurred) HPLC: 99.5% purity, RT=1.33 min. MS: m/z=285.0 [M+H]$^+$. $^1$H NMR (400 MHz, CD$_3$OD, ppm) δ=9.06-8.99 (m, 1H), 8.15-8.10 (m, 2H), 7.44-7.41 (m, 1H), 5.59-5.46 (m, 1H), 3.71-3.66 (m, 1H), 2.47-2.41 (m, 1H), 2.21-1.92 (m, 1H), 1.83-1.67 (m, 5H), 1.43-1.02 (m, 6H);

Compound 67b:

(33.9 mg, 6.7% for five steps, white solid, single stereoisomer) HPLC: 99.5% purity, RT=1.33 min. MS: m/z=285.1 [M+H]$^+$. $^1$H NMR (400 MHz, CD$_3$OD, ppm) δ=9.06 (s, 1H), 9.04 (s, 1H), 8.10 (s, 1H), 7.44 (s, 1H), 5.58 (dd, J=10.4, 3.2 Hz, 1H), 3.70-3.66 (m, 1H), 2.48-2.41 (m, 1H), 1.95-1.91 (m, 1H), 1.85-1.68 (m, 5H), 1.47-1.38 (m, 1H), 1.31-1.02 (m, 5H);

Compound 67c:

(5.9 mg, 1.2% for five steps, white solid, single stereoisomer) HPLC: 97.5% purity, RT=1.33 min. MS: m/z=285.1 [M+H]$^+$. $^1$H NMR (400 MHz, CD$_3$OD, ppm) δ=9.04 (s, 1H), 9.00 (s, 1H), 8.16 (s, 1H), 7.42 (s, 1H), 5.48 (t, J=5.6 Hz, 1H), 3.70-3.67 (m, 1H), 2.45-2.39 (m, 1H), 2.23-2.14 (m, 1H), 1.86-1.68 (m, 5H), 1.36-1.03 (m, 6H);

Compound 67d:

(8.1 mg, 1.6% for five steps, white solid, mixture of two stereoisomers, epimerization occurred) HPLC: 99.2% purity, RT=1.33 min. MS: m/z=285.1 [M+H]$^+$. $^1$H NMR (400 MHz, CD$_3$OD, ppm) δ=9.06-9.00 (m, 2H), 8.15-8.10 (m, 1H), 7.44-7.41 (m, 1H), 5.59-5.48 (m, 1H), 3.71-3.67 (m, 1H), 2.47-2.42 (m, 1H), 2.22-1.91 (m, 1H), 1.86-1.68 (m, 5H), 1.43-1.02 (m, 6H).

Example 68: Synthesis of 1-cyclohexyl-2-[10-cyclopropoxy-4,6,9-triazatricyclo[6.4.0.0^[2,6]]dodeca-1(8),2,4,9,11-pentaen-7-yl]ethan-1-ol (68a, b, c)

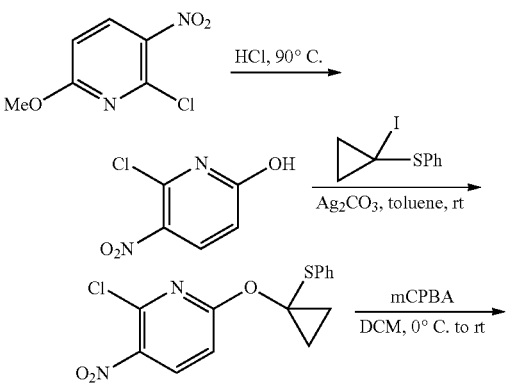

229
-continued

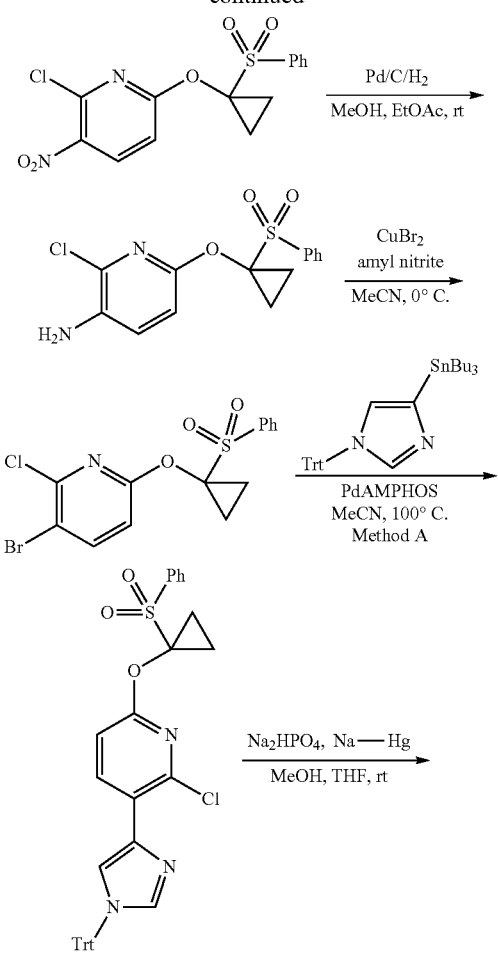

230
-continued

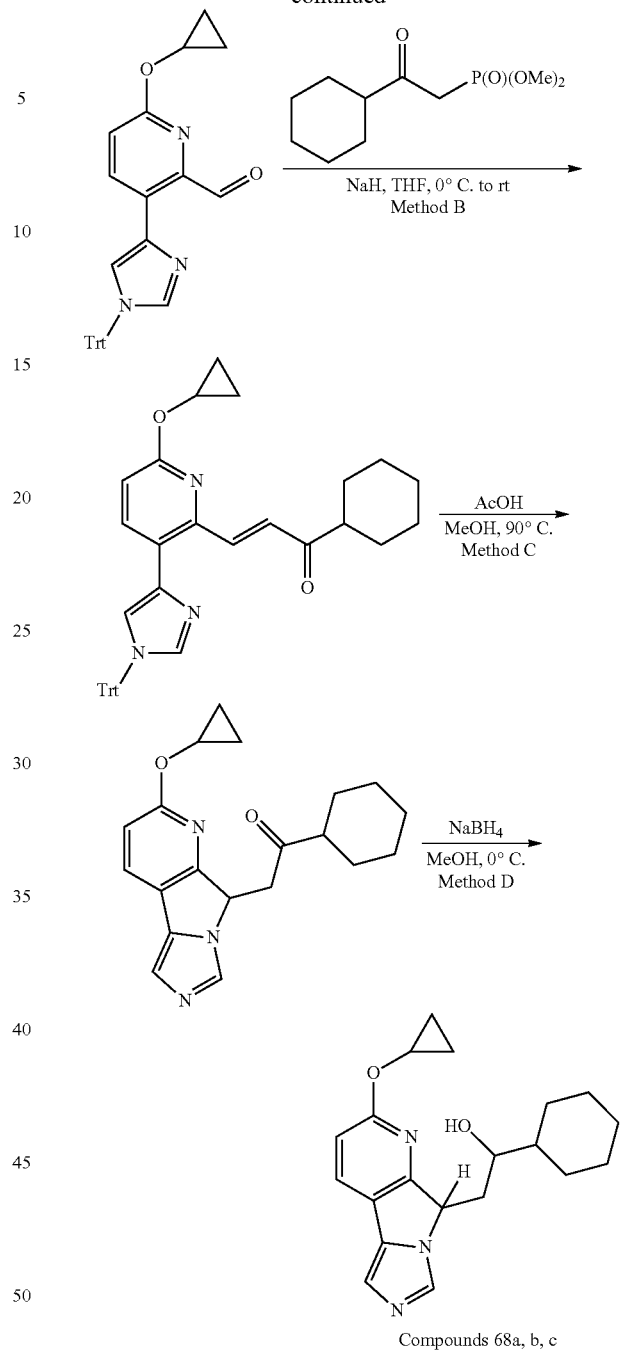

Compounds 68a, b, c

6-Chloro-5-nitropyridin-2-ol

A mixture of 2-chloro-6-methoxy-3-nitropyridine (5 g, 10.61 mmol) in HCl solution (12 M, 60 mL) was stirred at 90° C. for 16 h. Then the reaction mixture was neutralized with NaOH carefully and extracted with EtOAc (100 mL×2). The organic phases were combined, washed with brine and dried over $Na_2SO_4$. The solvent was removed under reduced pressure to yield 6-chloro-5-nitropyridin-2-ol (2.8 g, 60%) as red solid which was used in the following reaction without further purification. MS: m/z=197.1 $[M+Na]^+$.

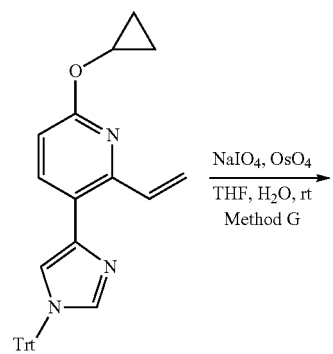

2-Chloro-3-nitro-6-[1-(phenylsulfanyl)cyclopropoxy]pyridine

To a solution of 6-chloro-5-nitropyridin-2-ol (2.1 g, 11.97 mmol) and [(1-iodocyclopropyl)sulfanyl]benzene (6.64 g, 24.15 mmol) in toluene (40 mL) was added silver carbonate (6.64 g, 24.15 mmol) at room temperature. The resulting mixture was stirred at room temperature for 16 h. Then the reaction mixture was filtered through a celite pad, which was rinsed with EtOAc (40 mL×3). The filtrate was concentrated under reduced pressure and the residue was purified by flash chromatography eluting with EtOAc in petroleum ether (1% to 4% gradient) to yield 2-chloro-3-nitro-6-[1-(phenylsulfanyl)cyclopropoxy]pyridine (3.36 g, 87%) as red oil. MS: m/z=323.0 [M+H]$^+$.

6-[1-(Benzenesulfonyl)cyclopropoxy]-2-chloro-3-nitropyridine

At 0° C., to a solution of 2-chloro-3-nitro-6-[1-(phenylsulfanyl)cyclopropoxy]pyridine (2.76 g, 8.55 mmol) in DCM (50 mL) was added mCPBA (6.33 g, 36.68 mmol) in portions. The resulting mixture was stirred at room temperature for 5 h. Then the reaction mixture was diluted with water (100 mL) and extracted with DCM (100 mL×2). The organic phases were combined, washed with brine and dried over Na$_2$SO$_4$. The solvent was removed under reduced pressure and the residue was purified by flash chromatography eluting with EtOAc in petroleum ether (5% to 30% gradient) to yield 6-[1-(benzenesulfonyl)cyclopropoxy]-2-chloro-3-nitropyridine (3 g, 99%) as yellow solid.

6-[1-(Benzenesulfonyl)cyclopropoxy]-2-chloropyridin-3-amine

To a solution of 6-[1-(benzenesulfonyl)cyclopropoxy]-2-chloro-3-nitropyridine (3 g, 8.46 mmol) in MeOH (40 mL) and EtOAc (40 mL) was added Pd/C (10%, 300 mg) carefully under N$_2$. The reaction flask was vacuumed and flushed with hydrogen, and then the reaction mixture was stirred at room temperature for 2 h under H$_2$ atmosphere using a hydrogen balloon. Then the reaction mixture was filtered through a celite pad which was rinsed with EtOAc (30 mL×3). The combined filtrate was concentrated under reduced pressure and the residue was purified by flash chromatography eluting with EtOAc in petroleum ether (10% to 40% gradient) to yield 6-[1-(benzenesulfonyl)cyclopropoxy]-2-chloropyridin-3-amine (1.3 g, 47%) as yellow solid. MS: m/z=324.8 [M+H]$^+$.

6-[1-(Benzenesulfonyl)cyclopropoxy]-3-bromo-2-chloropyridine

At 0° C., to a solution of 6-[1-(benzenesulfonyl)cyclopropoxy]-2-chloropyridin-3-amine (1.3 g, 4.0 mmol) in MeCN (25 mL) was added CuBr$_2$ (985 mg, 4.41 mmol) and pentyl nitrite (706 mg, 6.02 mmol) in sequence. The resulting mixture was stirred at 0° C. for 1.5 h. Then the reaction mixture was diluted with water (50 mL) and extracted with EtOAc (100 mL×2). The organic phases were combined, washed with brine and dried over Na$_2$SO$_4$. The solvent was removed under reduced pressure, and the residue was purified by flash chromatography eluting with EtOAc in DCM (5% to 15% gradient) to yield 6-[1-(benzenesulfonyl)cyclopropoxy]-3-bromo-2-chloropyridine (923 mg, 59%) as light yellow solid.

6-[1-(Benzenesulfonyl)cyclopropoxy]-2-chloro-3-[1-(triphenylmethyl)-1H-imidazol-4-yl]pyridine 6-[1-(Benzenesulfonyl)cyclopropoxy]-2-chloro-3-[1-(triphenylmethyl)-1H-imidazol-4-yl]pyridine (957 mg, 65%) was prepared from 6-[1-(benzenesulfonyl)cyclopropoxy]-3-bromo-2-chloropyridine and 4-(tributylstannyl)-1-(triphenylmethyl)-1H-imidazole using Method A. MS: m/z=640.15 [M+Na]$^+$.

2-Chloro-6-cyclopropoxy-3-[1-(triphenylmethyl)-1H-imidazol-4-yl]pyridine

At room temperature, to a solution of 6-[1-(benzenesulfonyl)cyclopropoxy]-2-chloro-3-[1-(triphenylmethyl)-1H-imidazol-4-yl]pyridine (476 mg, 0.77 mmol) in MeOH (10 mL) and THF (10 mL) were added Na$_2$HPO$_4$ (438 mg, 3.08 mmol) and Na—Hg (1.42 g, 6.35 mmol) in sequence. The resulting mixture was stirred at room temperature for 1.5 h. Then the reaction mixture was quenched with water (50 mL) and extracted with EtOAc (80 mL×2). The organic phases were combined, washed with brine and dried over Na$_2$SO$_4$. The solvent was removed under reduced pressure and the residue was purified by flash chromatography eluting with EtOAc in petroleum (5% to 25% gradient) to yield 2-chloro-6-cyclopropoxy-3-[1-(triphenylmethyl)-1H-imidazol-4-yl]pyridine (212 mg, 58%) as light yellow solid. MS: m/z=478.1 [M+H]$^+$.

1-Cyclohexyl-2-[10-cyclopropoxy-4,6,9-triazatricyclo[6.4.0.0ˆ[2,6]]dodeca-1(8),2,4,9,11-pentaen-7-yl]ethan-1-ol 1-Cyclohexyl-2-[10-cyclopropoxy-4,6,9-triazatricyclo[6.4.0.0ˆ[2,6]]dodeca-1(8),2,4,9,11-pentaen-7-yl]ethan-1-ol was prepared from 6-[1-(benzenesulfonyl)cyclopropoxy]-2-chloro-3-[1-(triphenylmethyl)-1H-imidazol-4-yl]pyridine and dimethyl (2-cyclohexyl-2-oxoethyl)phosphonate using Method M, G, B, C, and D. Three enantiomeric products were obtained by the separation on chiral prep-HPLC under the following conditions: Phenomenex Lux 5µ Cellulose-4, AXIA Packed, 21.2×250 mm, 5 µm; iPrOH in hexane, 50% isocratic in 23 min; Detector, UV 254/220 nm.

Compound 68a:
(25.7 mg, 6.8% for five steps, white solid, single stereoisomer) HPLC: 99.7% purity, RT=1.57 min. MS: m/z=340.15 [M+H]$^+$. $^1$H NMR (400 MHz, CDCl$_3$, ppm) δ=8.10 (s, 1H), 7.79 (d, J=8.4 Hz, 1H), 7.19 (s, 1H), 6.82 (d, J=8.4 Hz, 1H), 5.34 (t, J=7.2 Hz, 1H), 4.13-4.10 (m, 1H), 3.93-3.88 (m, 1H), 2.38-2.30 (m, 1H), 2.08-1.98 (m, 2H), 1.80-1.61 (m, 4H), 1.49-1.42 (m, 1H), 1.29-1.00 (m, 5H), 0.86-0.73 (m, 4H);

Compound 68b:
(13.9 mg, 3.7% for five steps, white solid, mixture of two stereoisomers) HPLC: 99.1% purity, RT=2.25 min. MS: m/z=340.15 [M+H]$^+$. $^1$H NMR (400 MHz, CDCl$_3$, ppm) δ=8.54 (br s, 1H), 7.80 (d, J=8.4 Hz, 1H), 7.23 (s, 1H), 6.83 (d, J=8.4 Hz, 1H), 5.38 (t, J=6.8 Hz, 1H), 4.19-4.17 (m, 1H), 3.87-3.84 (m, 1H), 2.36-2.29 (m, 1H), 2.06-2.01 (m, 1H), 1.92-1.88 (m, 1H), 1.80-1.61 (m, 4H), 1.50-1.44 (m, 1H), 1.28-1.07 (m, 5H), 0.84-0.79 (m, 4H);

Compound 68c:
(21.3 mg, 5.6% for five steps, white solid, single stereoisomer) HPLC: 99.0% purity, RT=3.01 min. MS: m/z=340.15 [M+H]$^+$. $^1$H NMR (400 MHz, CDCl$_3$, ppm) δ=8.13 (s, 1H), 7.79 (d, J=8.4 Hz, 1H), 7.19 (s, 1H), 6.82 (d, J=8.4 Hz, 1H), 5.34 (t, J=7.2 Hz, 1H), 4.13-4.10 (m, 1H), 3.93-3.88 (m, 1H), 2.38-2.30 (m, 1H), 2.08-1.98 (m, 2H), 1.80-1.61 (m, 4H), 1.49-1.42 (m, 1H), 1.29-1.00 (m, 5H), 0.86-0.73 (m, 4H).

Example 69: Synthesis of 2-[10-cyclopropoxy-4,6,9-triazatricyclo[6.4.0.0^[2,6]]dodeca-1(8),2,4,9,11-pentaen-7-yl]-1-(4,4-difluorocyclohexyl)ethan-1-ol (69 a, b, c, d)

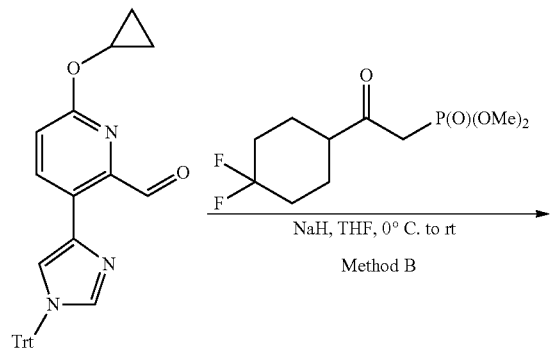

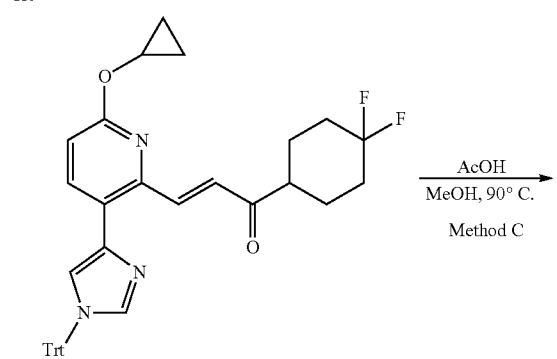

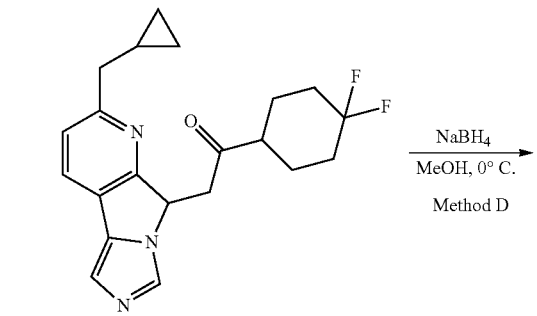

Compound 69a, b, c, d

2-[10-Cyclopropoxy-4,6,9-triazatricyclo[6.4.0.0^[2,6]]dodeca-1(8),2,4,9,11-pentaen-7-yl]-1-(4,4-difluorocyclohexyl)ethan-1-ol 2-[10-Cyclopropoxy-4,6,9-triazatricyclo[6.4.0.0^[2,6]]dodeca-1(8),2,4,9,11-pentaen-7-yl]-1-(4,4-difluorocyclohexyl)ethan-1-ol was prepared from 6-cyclopropoxy-3-[1-(triphenylmethyl)-1H-imidazol-4-yl]pyridine-2-carbaldehyde and dimethyl [2-(4,4-difluorocyclohexyl)-2-oxoethyl]phosphonate using Method B, C, and D. Four enantiomeric products were obtained by the separation on chiral prep-HPLC under the following conditions: Phenomenex Lux 5μ Cellulose-4, AXIA Packed, 21.2×250 mm, 5 μm; EtOH in hexane, 30% isocratic in 20 min; Detector, UV 254/220 nm.

Compound 69a:
(18.7 mg, 10.8% for three steps, white solid, single stereoisomer) HPLC: 99.9% purity, RT=1.46 min. MS: m/z=376.1 [M+H]⁺. ¹H NMR (400 MHz, CDCl₃, ppm) δ=7.94 (s, 1H), 7.80 (d, J=8.4 Hz, 1H), 7.17 (s, 1H), 6.82 (d, J=8.4 Hz, 1H), 5.34 (dd, J=8.8, 6.4 Hz, 1H), 4.09-4.07 (m, 1H), 3.99-3.96 (m, 1H), 2.48-2.41 (m, 1H), 2.17-2.12 (m, 3H), 1.97-1.92 (m, 1H), 2.79-2.62 (m, 3H), 1.59-1.53 (m, 1H), 0.89-0.73 (m, 4H);

Compound 69b:
(4.5 mg, 2.6% for three steps, white solid, single stereoisomer) HPLC: 99.1% purity, RT=1.45 min. MS: m/z=376.1 [M+H]⁺. ¹H NMR (400 MHz, CDCl₃, ppm) δ=8.63 (br s, 1H), 7.81 (d, J=8.4 Hz, 1H), 7.22 (s, 1H), 6.83 (d, J=8.4 Hz, 1H), 5.38 (t, J=6.8 Hz, 1H), 4.19-4.15 (m, 1H), 4.02-3.98 (m, 1H), 2.32-2.27 (m, 1H), 2.19-1.97 (m, 4H), 1.82-1.47 (m, 6H), 0.84-0.78 (m, 4H);

Compound 69c:
(17.2 mg, 9.9% for three steps, white solid, single stereoisomer) HPLC: 99.95% purity, RT=1.47 min. MS: m/z=376.1 [M+H]⁺. ¹H NMR (400 MHz, CDCl₃, ppm) δ=7.92 (s, 1H), 7.80 (d, J=8.4 Hz, 1H), 7.17 (s, 1H), 6.82 (d, J=8.4 Hz, 1H), 5.34 (dd, J=8.8, 6.4 Hz, 1H), 4.09-4.07 (m, 1H), 3.99-3.96 (m, 1H), 2.48-2.41 (m, 1H), 2.17-2.12 (m, 3H), 1.97-1.92 (m, 1H), 2.79-2.62 (m, 3H), 1.59-1.53 (m, 1H), 0.89-0.73 (m, 4H);

Compound 69d:
(4.1 mg, 2.4% for three steps, white solid, single stereoisomer) HPLC: 99.4% purity, RT=1.45 min. MS: m/z=376.1 [M+H]⁺. ¹H NMR (400 MHz, CDCl₃, ppm) δ=8.31 (br s, 1H), 7.80 (d, J=8.8 Hz, 1H), 7.19 (s, 1H), 6.83 (d, J=8.4 Hz, 1H), 5.29 (t, J=6.8 Hz, 1H), 4.17-4.13 (m, 1H), 4.02-3.98 (m, 1H), 2.24-1.95 (m, 5H), 1.82-1.47 (m, 6H), 0.84-0.78 (m, 4H).

Example 70: Synthesis of 6-chloro-5-[2-(1-fluorocyclohexyl)ethyl]-5H-imidazo[4,3-a]isoindole (70a and 70 b)

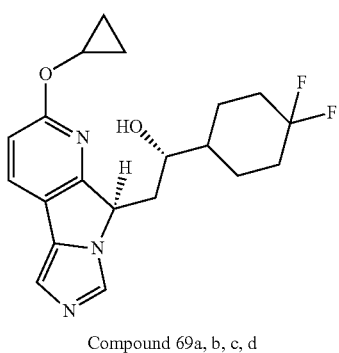

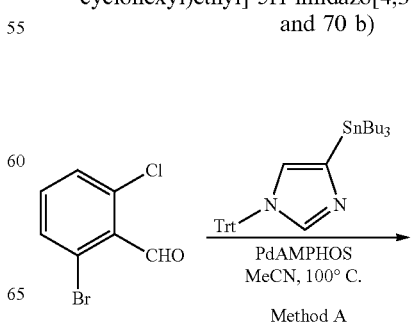

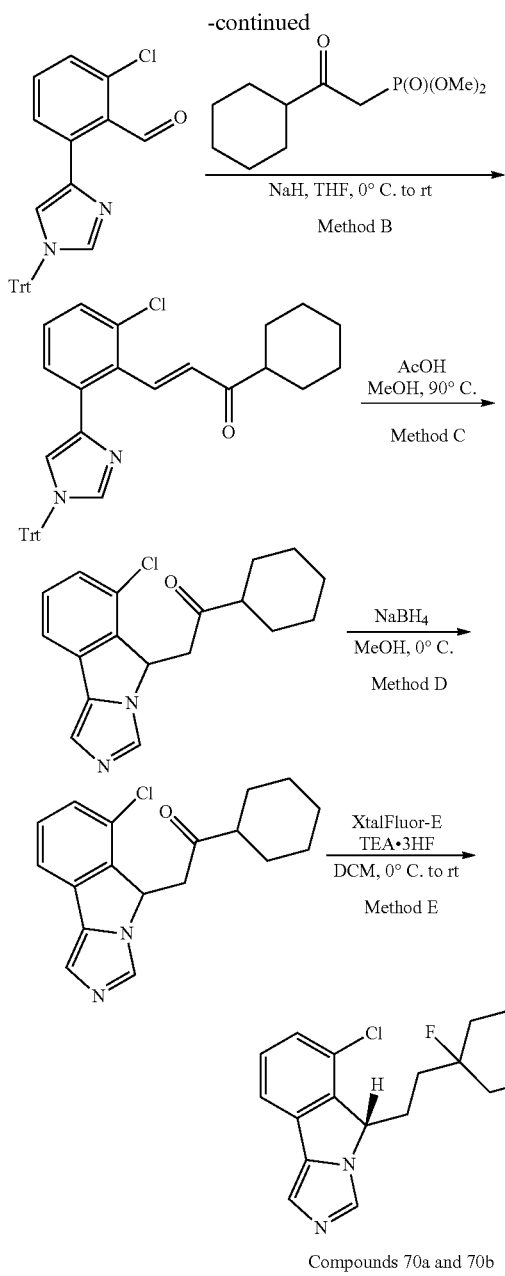

Compounds 70a and 70b

6-Chloro-5-[2-(1-fluorocyclohexyl)ethyl]-5H-imidazo[4,3-a]isoindole

6-Chloro-5-[2-(1-fluorocyclohexyl)ethyl]-5H-imidazo[4,3-a]isoindole was prepared from 2-bromo-6-chlorobenzaldehyde, 4-(tributylstannyl)-1-(triphenylmethyl)-1H-imidazole, and dimethyl (2-cyclohexyl-2-oxoethyl)phosphonate using Method A, B, C, D, and E. Two enantiomeric products were obtained by the separation on chiral prep-HPLC under the following conditions: Phenomenex Lux 5μ Cellulose-4, AXIA Packed, 21.2×250 mm, 5 μm; iPrOH in hexane, 30% isocratic in 18 min; Detector, UV 254/220 nm.

Compound 70a:

(18 mg, 4.8% for five steps, light yellow oil, single stereoisomer) HPLC: 99.9% purity, RT=1.58 min. MS: m/z=319.0 [M+H]+. 1H NMR (400 MHz, CD3OD, ppm) δ=7.98 (s, 1H), 7.59 (d, J=7.2 Hz, 1H), 7.44 (t, J=7.6 Hz, 1H), 7.32 (d, J=8.0 Hz, 1H), 7.23 (s, 1H), 5.62 (t, J=4.0 Hz, 1H), 2.59-2.48 (m, 2H), 1.69 (br s, 2H), 1.58-1.51 (m, 3H), 1.47-1.22 (m, 5H), 1.14-0.91 (m, 2H);

Compound 70b:

(20.1 mg, 5.3% for five steps, light yellow oil, single stereoisomer) HPLC: 99.97% purity, RT=1.58 min. MS: m/z=319.0 [M+H]+. 1H NMR (400 MHz, CD3OD, ppm) δ=7.99 (s, 1H), 7.59 (d, J=7.2 Hz, 1H), 7.44 (t, J=7.6 Hz, 1H), 7.32 (d, J=8.0 Hz, 1H), 7.24 (s, 1H), 5.62 (t, J=4.0 Hz, 1H), 2.59-2.48 (m, 2H), 1.69 (br s, 2H), 1.58-1.51 (m, 3H), 1.47-1.22 (m, 5H), 1.14-0.91 (m, 2H).

Example 71: Synthesis of 4-[2-[6-chloro-5H-imidazo[4,3-a]isoindol-5-yl]ethyl]-4-fluorocyclohexan-1-ol (71a, b, c, d)

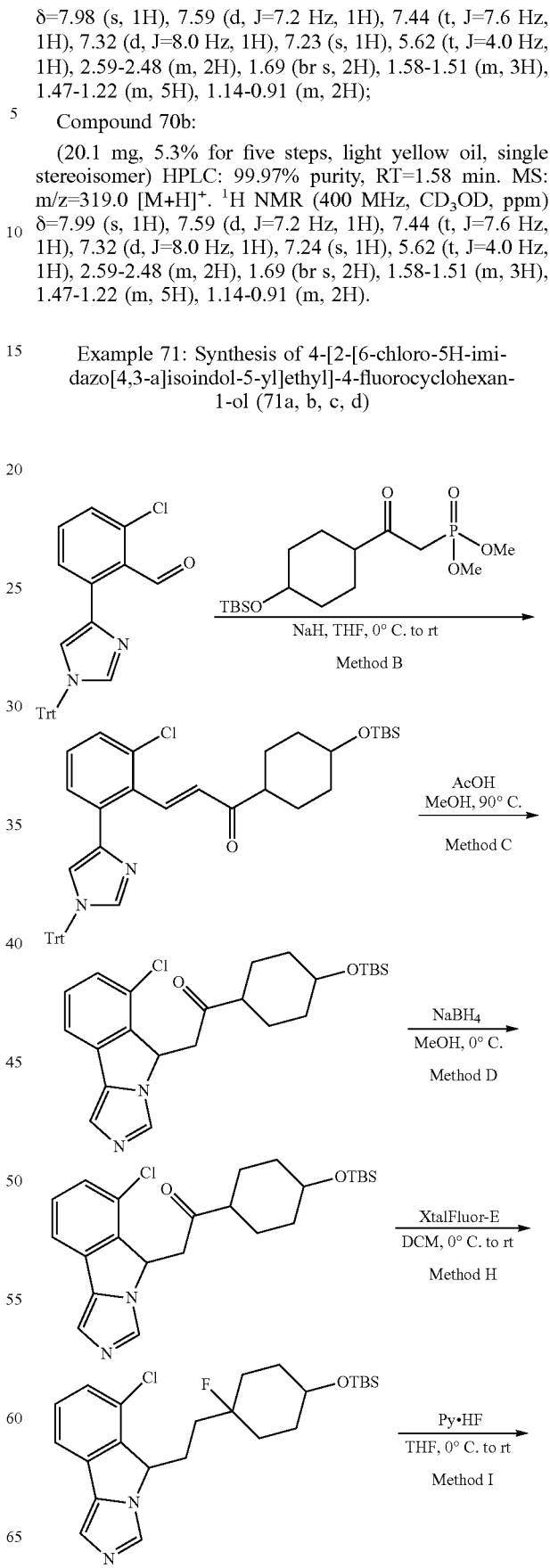

237

-continued

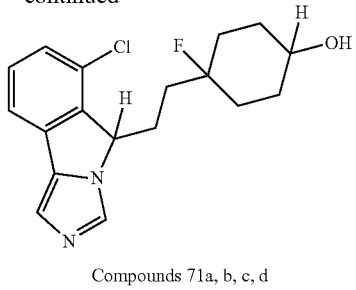

Compounds 71a, b, c, d

4-[2-[6-Chloro-5H-imidazo[4,3-a]isoindol-5-yl]ethyl]-4-fluorocyclohexan-1-ol

4-[2-[6-Chloro-5H-imidazo[4,3-a]isoindol-5-yl]ethyl]-4-fluorocyclohexan-1-ol was prepared from 2-chloro-6-[1-(triphenylmethyl)-1H-imidazol-4-yl]benzaldehyde and dimethyl (2-[4-[(tert-butyldimethylsilyl)oxy]cyclohexyl]-2-oxoethyl)phosphonate using Method B, C, D, H, and I. Four enantiomeric products were obtained by the separation on chiral prep-HPLC under the following conditions: Phenomenex Lux 5μ Cellulose-4, AXIA Packed, 21.2×250 mm, 5 μm; EtOH in hexane, 30% isocratic in 20 min; Detector, UV 254/220 nm.

Compound 71a:

(5.2 mg, 2.2% for five steps, white solid, single stereoisomer) HPLC: 99.98% purity, RT=1.28 min. MS: m/z=335.1 [M+H]+. 1H NMR (400 MHz, CD3OD, ppm) δ=8.09 (s, 1H), 7.62 (d, J=7.6 Hz, 1H), 7.46 (t, J=8.0 Hz, 1H), 7.35 (dd, J=8.0, 0.8 Hz, 1H), 7.28 (s, 1H), 5.67 (t, J=4.0 Hz, 1H), 3.89-3.87 (m, 1H), 2.61-2.50 (m, 2H), 1.80-1.48 (m, 8H), 1.20-0.98 (m, 2H);

Compound 71b:

(16 mg, 6.7% for five steps, white solid, single stereoisomer) HPLC: 99.9% purity, RT=1.29 min. MS: m/z=334.95 [M+H]+. 1H NMR (400 MHz, CD3OD, ppm) δ=8.11 (s, 1H), 7.62 (d, J=7.6 Hz, 1H), 7.46 (t, J=8.0 Hz, 1H), 7.35 (dd, J=8.0, 0.8 Hz, 1H), 7.30 (s, 1H), 5.68 (t, J=4.0 Hz, 1H), 3.89-3.87 (m, 1H), 2.61-2.50 (m, 2H), 1.80-1.48 (m, 8H), 1.20-0.98 (m, 2H);

Compound 71c:

(8.7 mg, 3.6% for five steps, white solid, single stereoisomer) HPLC: 96.4% purity, RT=1.21 min. MS: m/z=334.95 [M+H]+. 1H NMR (400 MHz, CD3OD, ppm) δ=8.33 (s, 1H), 7.66 (d, J=7.6 Hz, 1H), 7.49 (t, J=8.0 Hz, 1H), 7.40-7.38 (m, 2H), 5.73 (t, J=4.4 Hz, 1H), 3.55-3.48 (m, 1H), 2.62-2.51 (m, 2H), 1.87-1.70 (m, 4H), 1.58-1.28 (m, 4H), 1.18-0.99 (m, 2H);

Compound 71d:

(4.6 mg, 1.9% for five steps, white solid, single stereoisomer) HPLC: 99.6% purity, RT=1.21 min. MS: m/z=335.0 [M+H]+. 1H NMR (400 MHz, CD3OD, ppm) δ=8.31 (s, 1H), 7.66 (d, J=7.6 Hz, 1H), 7.49 (t, J=8.0 Hz, 1H), 7.40-7.38 (m, 2H), 5.72 (t, J=4.4 Hz, 1H), 3.55-3.48 (m, 1H), 2.62-2.51 (m, 2H), 1.87-1.70 (m, 4H), 1.58-1.28 (m, 4H), 1.18-0.99 (m, 2H).

238

Example 72: Synthesis of 6-chloro-5-[2-(1,4,4-trifluorocyclohexyl)ethyl]-5H-imidazo[4,3-a]isoindole (72a, b)

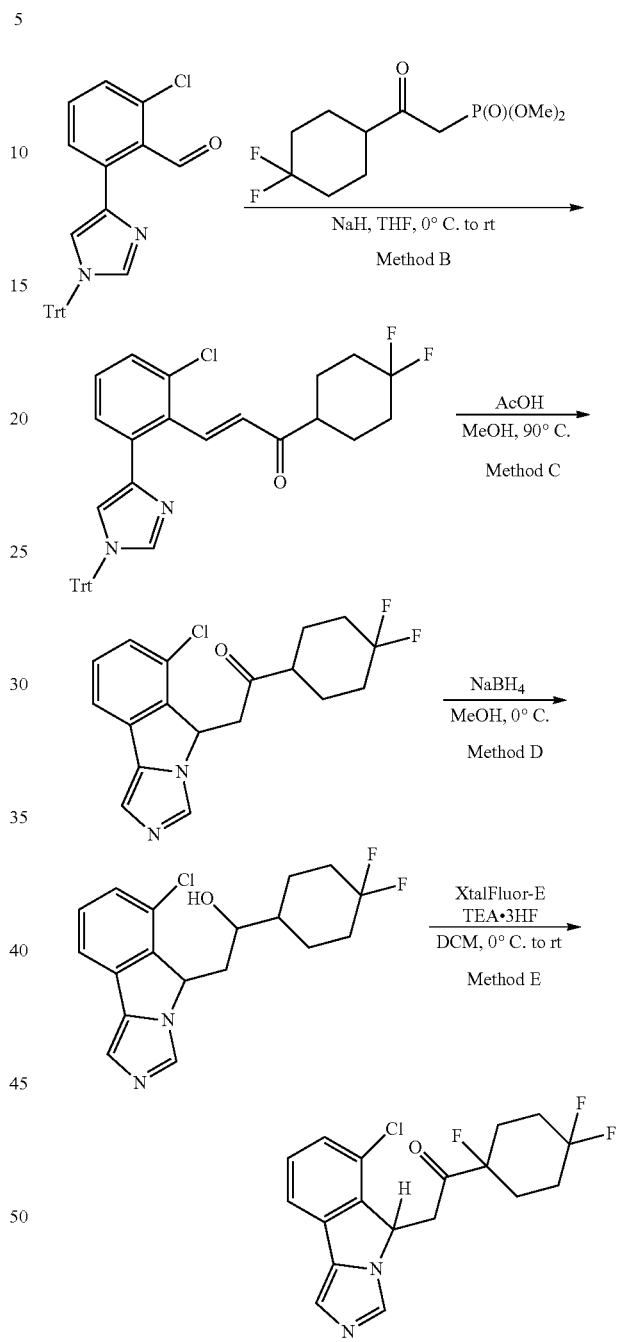

Compound 72a, and b

6-Chloro-5-[2-(1,4,4-trifluorocyclohexyl)ethyl]-5H-imidazo[4,3-a]isoindole

6-Chloro-5-[2-(1,4,4-trifluorocyclohexyl)ethyl]-5H-imidazo[4,3-a]isoindole was prepared from 2-chloro-6-[1-(triphenylmethyl)-1H-imidazol-4-yl]benzaldehyde and dimethyl [2-(4,4-difluorocyclohexyl)-2-oxoethyl]phosphonate using Method B, C, D, and E. Two enantiomeric products were obtained by the separation on chiral prep-HPLC under the following conditions: Chiralpak IA, 20×250 mm, 5 μm; EtOH in hexane, 20% isocratic in 12 min; Detector, UV 254/220 nm.

Compound 72a:

(16 mg, 6.4% for four steps, light yellow oil, single stereoisomer) HPLC: 99.99% purity, RT=1.16 min. MS: m/z=355.05 [M+H]$^+$. $^1$H NMR (400 MHz, CD$_3$OD, ppm) δ=7.99 (s, 1H), 7.60 (d, J=7.6 Hz, 1H), 7.45 (t, J=8.0 Hz, 1H), 7.33 (d, J=8.0 Hz, 1H), 7.24 (s, 1H), 5.64 (t, J=4.4 Hz, 1H), 2.60-2.50 (m, 2H), 2.08-1.88 (m, 6H), 1.68-1.51 (m, 2H), 1.23-1.02 (m, 2H);

Compound 72b:

(12 mg, 4.8% for four steps, light yellow oil, single stereoisomer) HPLC: 99.9% purity, RT=1.16 min. MS: m/z=355.05 [M+H]$^+$. $^1$H NMR (400 MHz, CD$_3$OD, ppm) δ=7.99 (s, 1H), 7.60 (d, J=7.6 Hz, 1H), 7.45 (t, J=8.0 Hz, 1H), 7.33 (d, J=8.0 Hz, 1H), 7.23 (s, 1H), 5.63 (t, J=4.4 Hz, 1H), 2.60-2.50 (m, 2H), 2.08-1.88 (m, 6H), 1.68-1.51 (m, 2H), 1.23-1.02 (m, 2H).

Example 73: Synthesis of 1-[4-(hydroxymethyl)cyclohexyl]-2-[4,6,9-triazatricyclo[6.4.0.0^[2,6]]dodeca-1(8),2,4,9,11-pentaen-7-yl]ethan-1-ol (73 a, b, c, d)

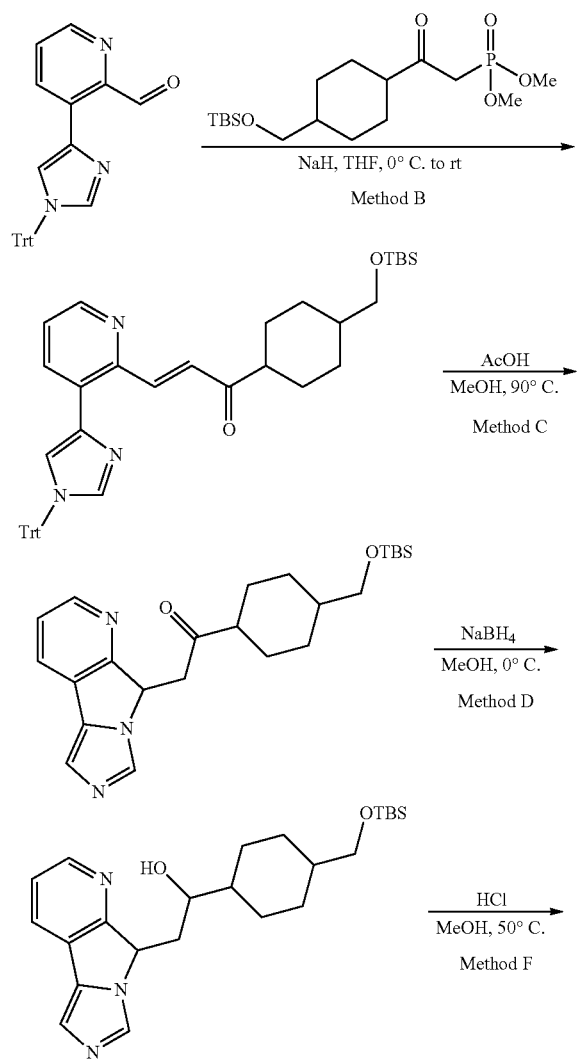

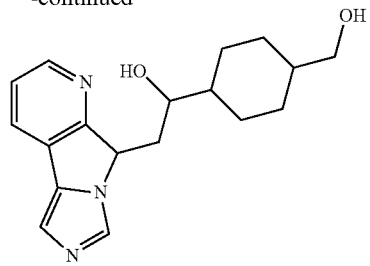

Compounds 73a, b, c, d

1-[4-(Hydroxymethyl)cyclohexyl]-2-[4,6,9-triazatricyclo[6.4.0.0^[2,6]]dodeca-1(8),2,4,9,11-pentaen-7-yl]ethan-1-ol 1-[4-(Hydroxymethyl)cyclohexyl]-2-[4,6,9-triazatricyclo[6.4.0.0^[2,6]]dodeca-1(8),2,4,9,11-pentaen-7-yl]ethan-1-ol was prepared from 3-[1-(triphenylmethyl)-1H-imidazol-4-yl]pyridine-2-carbaldehyde and dimethyl [2-(4-[[(tert-butyldimethylsilyl)oxy]methyl]cyclohexyl)-2-oxoethyl]phosphonate using Method B, C, D, and F. Four pairs of enantiomeric products were obtained by the separation on chiral prep-HPLC under the following conditions: CHIRALPAK-AD-H-SL001, 20×250 mm, 5 μm; EtOH in hexane, 40% isocratic in 13 min; Detector, UV 254/220 nm.

Compound 73a (30.8 mg, 5.6% for four steps, white solid, mixture of two stereoisomers) HPLC: 87.4% purity, RT=1.49 min. MS: m/z=314.1 [M+H]$^+$. $^1$H NMR (400 MHz, CD$_3$OD, ppm) δ=8.42 (dd, J=4.8, 1.2 Hz, 1H), 8.11 (s, 1H), 8.02 (dd, J=7.6, 1.2 Hz, 1H), 7.42 (dd, J=7.6, 5.2 Hz, 1H), 7.30 (s, 1H), 5.38 (t, J=6.0 Hz, 1H), 3.86-3.82 (m, 1H), 3.37-3.35 (m, 2H), 2.42-2.37 (m, 1H), 2.10-2.03 (m, 1H), 1.97-1.84 (m, 3H), 1.78-1.75 (m, 1H), 1.42-1.31 (m, 2H), 1.20-1.07 (m, 2H), 1.00-0.90 (m, 2H);

Compound 73b:

(29.1 mg, 5.3% for four steps, white solid, mixture of two stereoisomers) HPLC: 98.9% purity, RT=0.98 min. MS: m/z=314.1 [M+H]$^+$. $^1$H NMR (400 MHz, CD$_3$OD, ppm) δ=8.42 (dd, J=5.2, 1.2 Hz, 1H), 8.11 (s, 1H), 8.02 (dd, J=8.0, 1.2 Hz, 1H), 7.42 (dd, J=7.6, 5.2 Hz, 1H), 7.30 (s, 1H), 5.38 (t, J=6.0 Hz, 1H), 3.86-3.83 (m, 1H), 3.37-3.35 (m, 2H), 2.42-2.37 (m, 1H), 2.10-2.03 (m, 1H), 1.97-1.84 (m, 3H), 1.78-1.75 (m, 1H), 1.43-1.30 (m, 2H), 1.21-1.06 (m, 2H), 0.99-0.90 (m, 2H);

Compound 73c:

(21.8 mg, 4% for four steps, white solid, mixture of two stereoisomers) HPLC: 99.4% purity, RT=0.96 min. MS: m/z=314.1 [M+H]$^+$. $^1$H NMR (400 MHz, CD$_3$OD, ppm) δ=8.43 (dd, J=5.2, 1.2 Hz, 1H), 8.07-8.04 (m, 2H), 7.44 (dd, J=7.6, 5.2 Hz, 1H), 7.33 (s, 1H), 5.50 (dd, J=10.0, 3.6 Hz, 1H), 3.72-3.68 (m, 1H), 3.37-3.35 (m, 2H), 2.49-2.42 (m, 1H), 2.02-1.98 (m, 1H), 1.90-1.73 (m, 4H), 1.42-1.36 (m, 2H), 1.18-1.07 (m, 2H), 0.99-0.91 (m, 2H);

Compound 73d:

(19.5 mg, 3.5% for four steps, white solid, mixture of two stereoisomers) HPLC: 99.9% purity, RT=0.96 min. MS: m/z=314.1 [M+H]$^+$. $^1$H NMR (400 MHz, CD$_3$OD, ppm) δ=8.43 (dd, J=5.2, 1.2 Hz, 1H), 8.07-8.05 (m, 2H), 7.44 (dd, J=8.0, 5.2 Hz, 1H), 7.34 (s, 1H), 5.50 (dd, J=10.0, 3.6 Hz, 1H), 3.72-3.68 (m, 1H), 3.37-3.35 (m, 2H), 2.49-2.42 (m, 1H), 2.02-1.98 (m, 1H), 1.90-1.73 (m, 4H), 1.42-1.36 (m, 2H), 1.17-1.06 (m, 2H), 0.98-0.90 (m, 2H).

Example 74: Synthesis of 4-(1,1-difluoro-2-[5H-imidazo[4,3-a]isoindol-5-yl]ethyl)cyclohexan-1-ol (74a, b)

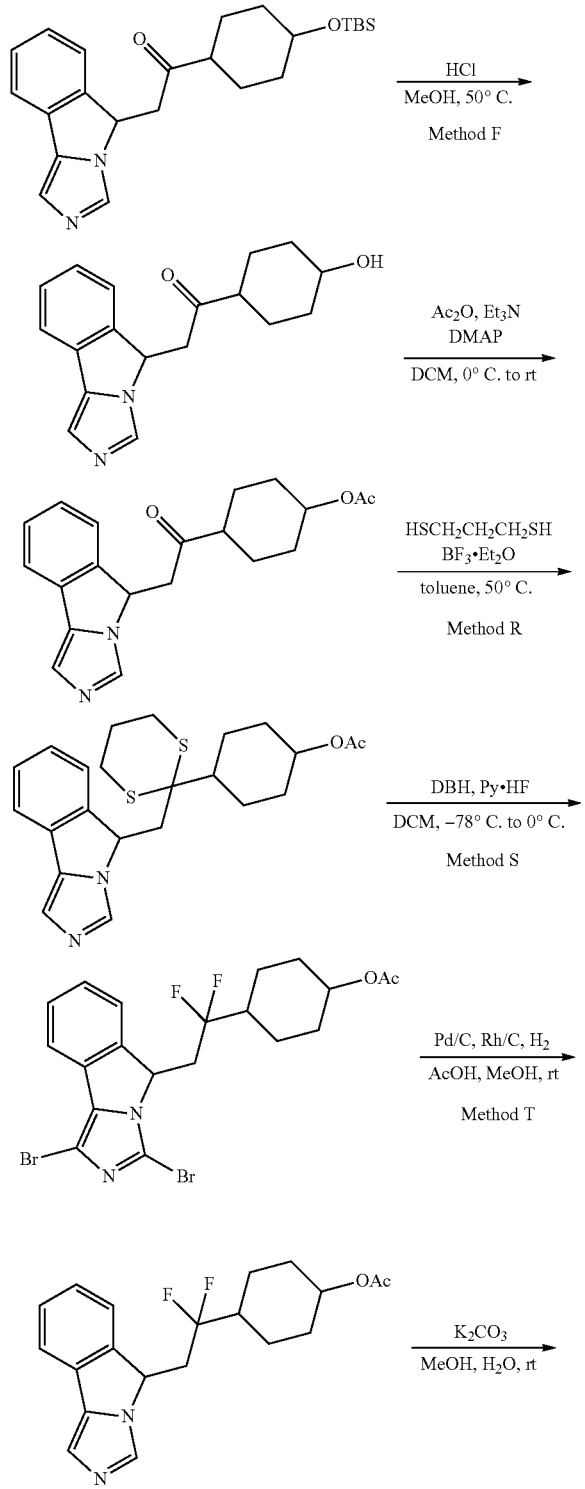

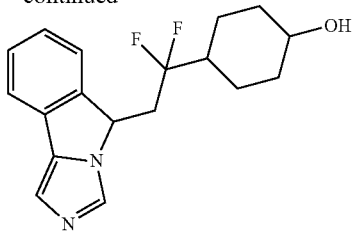

Compound 74a and 74b 1-(4-Hydroxycyclohexyl)-2-[5H-imidazo[4,3-a]isoindol-5-yl]ethan-1-one 1-(4-Hydroxycyclohexyl)-2-[5H-imidazo[4,3-a]isoindol-5-yl]ethan-1-one (820 mg, 83%) was prepared from 1-[4-[(tert-butyldimethylsilyl)oxy]cyclohexyl]-2-[5H-imidazo[4,3-a]isoindol-5-yl]ethan-1-one using Method F. MS: m/z=297.0 [M+H]$^+$.

4-(2-[5H-Imidazo[4,3-a]isoindol-5-yl]acetyl)cyclohexyl acetate

At room temperature, to a solution of 1-(4-hydroxycyclohexyl)-2-[5H-imidazo[4,3-a]isoindol-5-yl]ethan-1-one (820 mg, 2.62 mmol) in dichloromethane (15 mL) was added TEA (840 mg, 7.88 mmol), acetic anhydride (424 mg, 3.94 mmol), and 4-dimethylaminopyridine (68 mg, 0.52 mmol) in sequence. The resulting mixture was stirred at room temperature for 16 h. Then the reaction was quenched by the addition of water (50 mL) and the mixture was extracted with dichloromethane (50 mL×2). The organic phases were combined, washed with brine and dried over sodium sulfate. The solvent was removed under reduced pressure, and the residue was purified by flash chromatography eluting with methanol in dichloromethane (1% to 5% gradient) to yield 4-(2-[5H-imidazo[4,3-a]isoindol-5-yl]acetyl)cyclohexyl acetate (900 mg, 91%) as light yellow oil. MS: m/z=339.05 [M+H]$^+$.

4-(1,1-Difluoro-2-[5H-imidazo[4,3-a]isoindol-5-yl]ethyl)cyclohexyl acetate 4-(1,1-Difluoro-2-[5H-imidazo[4,3-a]isoindol-5-yl]ethyl)cyclohexyl acetate (125 mg, 13%) was prepared from 4-(2-[5H-imidazo[4,3-a]isoindol-5-yl]acetyl)cyclohexyl acetate using Method R, S, and T. MS: m/z=361.1 [M+H]$^+$.

4-(1,1-Difluoro-2-[5H-imidazo[4,3-a]isoindol-5-yl]ethyl)cyclohexan-1-ol

At room temperature, to a solution of 4-(1,1-difluoro-2-[5H-imidazo[4,3-a]isoindol-5-yl]ethyl)cyclohexyl acetate (100 mg, 0.25 mmol) in methanol (5 mL) and water (0.5 mL) was added potassium carbonate (57 mg, 0.39 mmol). The resulting mixture was stirred at room temperature for 16 h. Then the reaction mixture was neutralized with saturated ammonium chloride solution and extracted with ethyl acetate (40 mL×3). The organic phases were combined, washed with brine and dried over sodium sulfate. The solvent was removed under reduced pressure, and the residue was purified by flash chromatography eluting with methanol in dichloromethane (1% to 5% gradient). Two pairs of enantiomeric products were obtained by the separation on prep-HPLC under the following conditions: XBridge Prep C18 OBD Column, 19×150 mm, 5 μm; mobile phase, acetonitrile in water (with 10 mM $NH_4HCO_3$), 27% to 38% gradient in 10 min; Detector, UV 254/220 nm.

Compound 74a:

(18.6 mg, 21%, white solid, mixture of two stereoisomers) HPLC: 99.7% purity, RT=0.67 min. MS: m/z=319.1 [M+H]$^+$. $^1$H NMR (300 MHz, CD$_3$OD, ppm) δ=7.81 (s, 1H), 7.57 (d, J=7.5 Hz, 1H), 7.47 (d, J=7.8 Hz, 1H), 7.41-7.38 (m, 1H), 7.36-7.27 (m, 1H), 7.10 (s, 1H), 5.56 (dd, J=8.1, 2.1 Hz, 1H), 3.51-3.41 (m, 1H), 2.82-2.65 (m, 1H), 2.45-2.25 (m, 1H), 2.00-1.79 (m, 5H), 1.39-1.17 (m, 4H);

Compound 74b:

(15 mg, 17%, white solid, mixture of two stereoisomers) HPLC: 99.4% purity, RT=0.69 min. MS: m/z=319.1 [M+H]$^+$. $^1$H NMR (300 MHz, CD$_3$OD, ppm) δ=7.83 (s, 1H), 7.57 (d, J=7.5 Hz, 1H), 7.48 (d, J=7.5 Hz, 1H), 7.38-7.36 (m, 1H), 7.32-7.27 (m, 1H), 7.11 (s, 1H), 5.58-5.55 (m, 1H), 3.96-3.94 (m, 1H), 2.81-2.63 (m, 1H), 2.42-2.23 (m, 1H), 1.98-1.79 (m, 3H), 1.74-1.42 (m, 6H).

Example 75: Synthesis of 4-(1,1-difluoro-2-[6-fluoro-5H-imidazo[4,3-a]isoindol-5-yl]ethyl)cyclohexan-1-ol (75a, b)

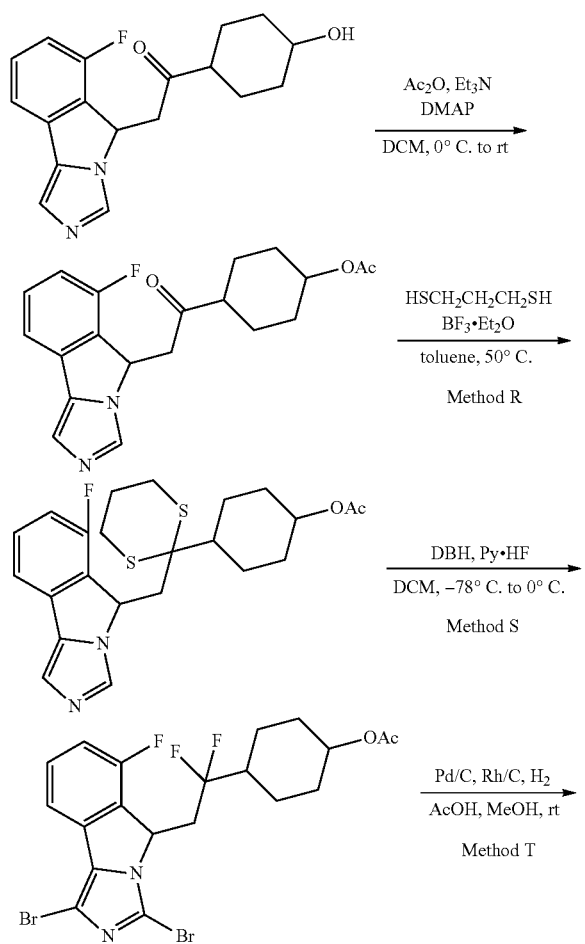

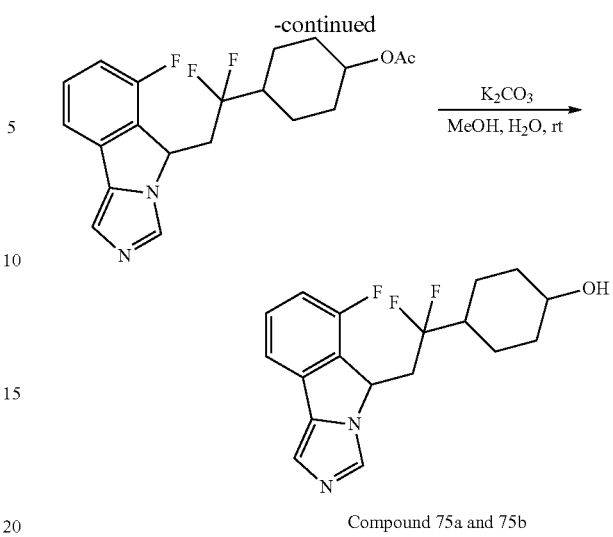

Compound 75a and 75b 4-(2-[6-Fluoro-5H-imidazo[4,3-a]isoindol-5-yl]acetyl)cyclohexyl acetate At room temperature, to a solution of 2-[6-fluoro-5H-imidazo[4,3-a]isoindol-5-yl]-1-(4-hydroxycyclohexyl)ethan-1-one (610 mg, 1.84 mmol) in DCM (15 mL) was added TEA (589 mg, 5.53 mmol), acetic anhydride (297 mg, 2.76 mmol) and 4-dimethylaminopyridine (47 mg, 0.37 mmol) in sequence. The resulting mixture was stirred at room temperature for 16 h. Then the reaction was quenched by the addition of water (50 mL) and the mixture was extracted with DCM (50 mL×2). The organic phases were combined, washed with brine and dried over Na$_2$SO$_4$. The solvent was removed under reduced pressure and the residue was purified by flash chromatography eluting with MeOH in DCM (1% to 5% gradient) to yield 4-(2-[6-fluoro-5H-imidazo[4,3-a]isoindol-5-yl]acetyl)cyclohexyl acetate (650 mg, 94%) as light yellow oil. MS: m/z=357.1 [M+H]$^+$.

4-(1,1-Difluoro-2-[6-fluoro-5H-imidazo[4,3-a]isoindol-5-yl]ethyl)cyclohexyl acetate 4-(1,1-Difluoro-2-[6-fluoro-5H-imidazo[4,3-a]isoindol-5-yl]ethyl)cyclohexyl acetate (100 mg, 14%) was prepared from 4-(2-[6-fluoro-5H-imidazo[4,3-a]isoindol-5-yl]acetyl)cyclohexyl acetate using Method R, S, and T. MS: m/z=379.05 [M+H]$^+$.

4-(1,1-Difluoro-2-[6-fluoro-5H-imidazo[4,3-a]isoindol-5-yl]ethyl)cyclohexan-1-ol At room temperature, to a solution of 4-(1,1-difluoro-2-[6-fluoro-5H-imidazo[4,3-a]isoindol-5-yl]ethyl)cyclohexyl acetate (100 mg, 0.24 mmol) in MeOH (5 mL) and H$_2$O (0.5 mL) was added potassium carbonate (55 mg, 0.38 mmol). The resulting mixture was stirred at room temperature for 16 h. Then the reaction mixture was neutralized with sat. NH$_4$Cl solution and extracted with EtOAc (40 mL×3). The organic phases were combined, washed with brine and dried over Na$_2$SO$_4$. The solvent was removed under reduced pressure and the residue was purified by flash chromatography eluting with MeOH in DCM (1% to 5% gradient). Two pairs of enantiomeric products were obtained by further separation on prep-HPLC under the following conditions:

XBridge Prep C18 OBD Column, 19×150 mm, 5 μm; mobile phase, MeCN in water (with 10 mM NH₄HCO₃), 20% to 50% gradient in 10 min; Detector, UV 254/220 nm.

Compound 75a:

(21.9 mg, 24%, white solid, mixture of two stereoisomers) HPLC: 99.2% purity, RT=0.88 min. MS: m/z=337.05 [M+H]⁺. ¹H NMR (300 MHz, CD₃OD, ppm) δ=7.83 (s, 1H), 7.46-7.39 (m, 2H), 7.14 (s, 1H), 7.03-6.99 (m, 1H), 5.76 (d, J=8.7 Hz, 1H), 3.49-3.39 (m, 1H), 3.01-2.82 (m, 1H), 2.44-2.23 (m, 1H), 1.98-1.73 (m, 5H), 1.35-1.13 (m, 4H);

Compound 75b:

(12.7 mg, 14%, white solid, mixture of two stereoisomers) HPLC: 99.1% purity, RT=1.26 min. MS: m/z=337.05 [M+H]⁺. ¹H NMR (300 MHz, CD₃OD, ppm) δ=7.84 (s, 1H), 7.44-7.41 (m, 2H), 7.13 (s, 1H), 7.06-7.00 (m, 1H), 5.77 (d, J=8.4 Hz, 1H), 3.95-3.94 (m, 1H), 3.05-2.84 (m, 1H), 2.44-2.25 (m, 1H), 1.95-1.80 (m, 3H), 1.73-1.44 (m, 6H).

Example 76: Synthesis of 7-[2-(1-fluorocyclohexyl)ethyl]-10-(trifluoromethyl)-4,6,9-triazatricyclo[6.4.0.0^[2,6]]dodeca-1(8),2,4,9,11-pentaene (76a, b)

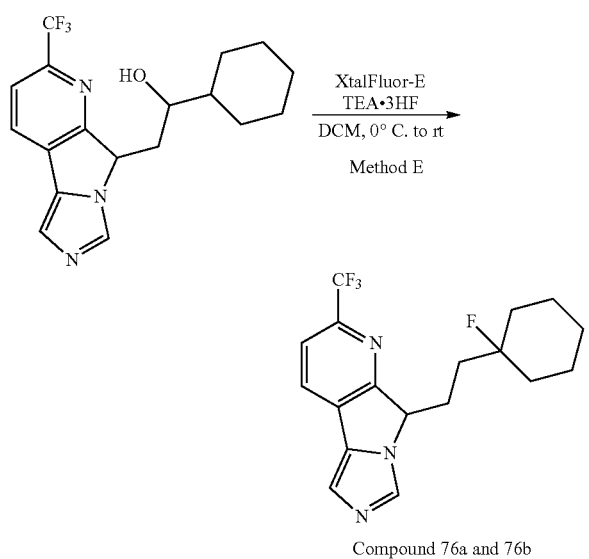

Compound 76a and 76b

7-[2-(1-Fluorocyclohexyl)ethyl]-10-(trifluoromethyl)-4,6,9-triazatricyclo[6.4.0.0^[2,6]]dodeca-1(8),2,4,9,11-pentaene 7-[2-(1-Fluorocyclohexyl)ethyl]-10-(trifluoromethyl)-4,6,9-triazatricyclo[6.4.0.0^[2,6]]dodeca-1(8),2,4,9,11-pentaene was prepared from 1-cyclohexyl-2-[10-(trifluoromethyl)-4,6,9-triazatricyclo[6.4.0.0^[2,6]]dodeca-1(8),2,4,9,11-pentaen-7-yl]ethan-1-ol using Method E. Two enantiomeric products were obtained by the separation on chiral prep-HPLC under the following conditions: Phenomenex Lux 5μ Cellulose-4, AXIA Packed, 21.2×250 mm, 5 μm; iPrOH in hexane, 50% isocratic in 16 min; Detector, UV 254/220 nm.

Compound 76a:

(19.9 mg, 6.8%, off-white solid, single stereoisomer) HPLC: 99.9% purity, RT=1.26 min. MS: m/z=354.15 [M+H]⁺. ¹H NMR (300 MHz, CD₃OD, ppm) δ=8.15 (d, J=8.1 Hz, 1H), 8.08 (s, 1H), 7.79 (d, J=8.1 Hz, 1H), 7.42 (s, 1H), 5.42 (t, J=5.1 Hz, 1H), 2.46-2.21 (m, 2H), 1.76-1.62 (m, 2H), 1.56-1.20 (m, 10H);

Compound 76b:

(18.7 mg, 6.4%, off-white solid, single stereoisomer) HPLC: 99.9% purity, RT=1.24 min. MS: m/z=354.1 [M+H]⁺. ¹H NMR (300 MHz, CD₃OD, ppm) δ=8.15 (d, J=8.1 Hz, 1H), 8.08 (s, 1H), 7.79 (d, J=8.1 Hz, 1H), 7.42 (s, 1H), 5.42 (t, J=5.1 Hz, 1H), 2.46-2.21 (m, 2H), 1.76-1.62 (m, 2H), 1.56-1.20 (m, 10H).

Example 77: Synthesis of 1-(4,4-difluorocyclohexyl)-2-[10-(trifluoromethyl)-4,6,9-triazatricyclo[6.4.0.0^[2,6]]dodeca-1(8),2,4,9,11-pentaen-7-yl]ethan-1-ol (77a, b)

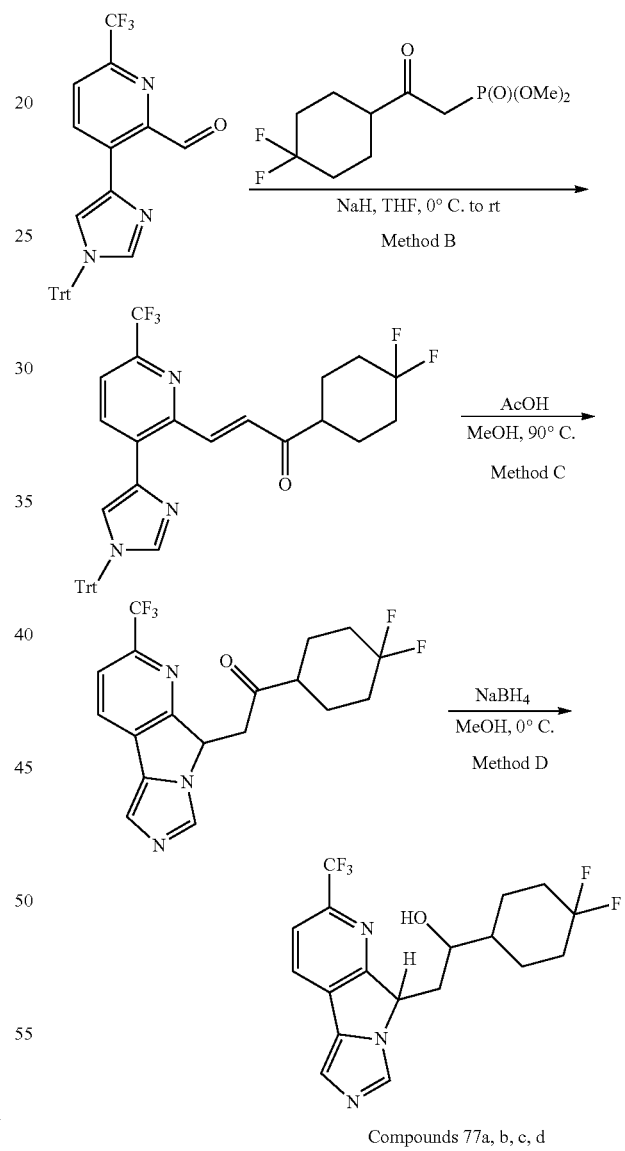

Compounds 77a, b, c, d 1-(4,4-Difluorocyclohexyl)-2-[10-(trifluoromethyl)-4,6,9-triazatricyclo[6.4.0.0^[2,6]]dodeca-1(8),2,4,9,11-pentaen-7-yl]ethan-1-ol 1-(4,4-Difluorocyclohexyl)-2-[10-(trifluoromethyl)-4,6,9-triazatricyclo[6.4.0.0^[2,6]]dodeca-1(8),2,4,9,11-pentaen- 7-yl]ethan-1-ol was prepared from 6-(trifluoromethyl)-3-[1-(triphenylmethyl)-1H-imidazol-4-yl]pyridine-2-carbaldehyde and dimethyl [2-(4,4-difluorocyclohexyl)-2-oxoethyl]phosphonate using Method B, C, and D. Four enantiomeric products were obtained by the separation on chiral prep-HPLC under the following conditions: Phenomenex Lux 5μ Cellulose-4, AXIA Packed, 21.2×250 mm, 5 μm; mobile phase, iPrOH in hexane (with 0.2% DEA), 30% isocratic in 20 min; Detector, UV 254/220 nm.

Compound 77a:

(5.5 mg, 4.8% for three steps, white solid, single stereoisomer), HPLC: 99.3% purity, RT=1.09 min. MS: m/z=388.05 [M+H]+. 1H NMR (300 MHz, CD3OD, ppm) δ=8.16 (d, J=8.1 Hz, 1H), 8.07 (s, 1H), 7.79 (d, J=8.1 Hz, 1H), 7.42 (s, 1H), 5.54 (dd, J=9.6, 3.0 Hz, 1H), 3.72-3.67 (m, 1H), 2.51-2.42 (m, 1H), 2.08-1.59 (m, 7H), 1.52-1.31 (m, 3H);

Compound 77b:

(8.3 mg, 7.2% for three steps, white solid, single stereoisomer) HPLC: 99.6% purity, RT=1.11 min. MS: m/z=388.1 [M+H]+. 1H NMR (300 MHz, CD3OD, ppm) δ=8.14-8.13 (m, 2H), 7.78 (d, J=8.1 Hz, 1H), 7.40 (s, 1H), 5.44 (t, J=5.7 Hz, 1H), 3.99-3.97 (m, 1H), 2.37-2.31 (m, 1H), 2.17-1.98 (m, 3H), 1.89-1.60 (m, 4H), 1.45-1.32 (m, 3H);

Compound 77c:

(5.8 mg, 5% for three steps, white solid, single stereoisomer), HPLC: 96.8% purity, RT=1.20 min. MS: m/z=388.1 [M+H]+. 1H NMR (400 MHz, CD3OD, ppm) δ=8.16 (d, J=8.1 Hz, 1H), 8.07 (s, 1H), 7.79 (d, J=8.1 Hz, 1H), 7.42 (s, 1H), 5.54 (dd, J=9.6, 3.0 Hz, 1H), 3.72-3.67 (m, 1H), 2.51-2.42 (m, 1H), 2.08-1.59 (m, 7H), 1.52-1.31 (m, 3H);

Compound 77d:

(8 mg, 7% for three steps, white solid, single stereoisomer) HPLC: 99.4% purity, RT=1.22 min. MS: m/z=388.05 [M+H]+. 1H NMR (300 MHz, CD3OD, ppm) δ=8.14-8.13 (m, 2H), 7.78 (d, J=8.1 Hz, 1H), 7.40 (s, 1H), 5.44 (t, J=5.7 Hz, 1H), 3.99-3.97 (m, 1H), 2.37-2.31 (m, 1H), 2.17-1.98 (m, 3H), 1.89-1.60 (m, 4H), 1.45-1.32 (m, 3H).

Example 78: Synthesis of 4-(2-[6,9-difluoro-5H-imidazo[4,3-a]isoindol-5-yl]-1,1-difluoroethyl)cyclohexan-1-ol (78a, b)

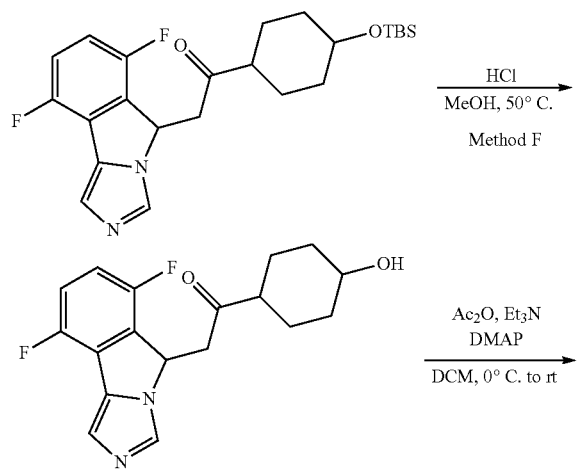

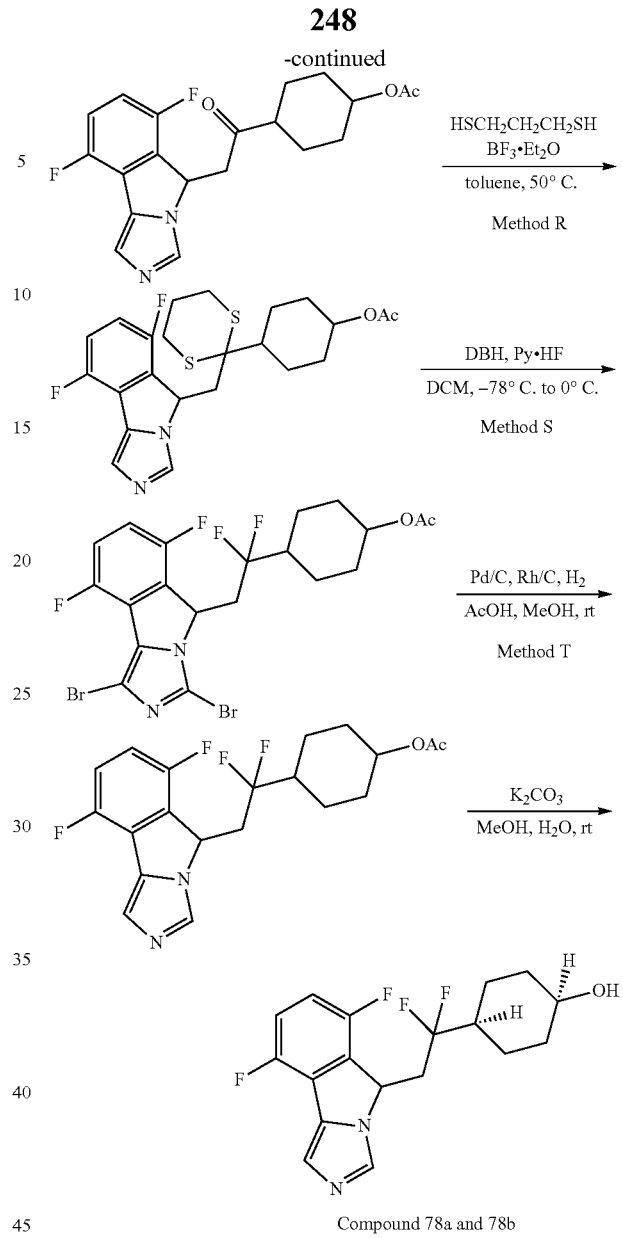

Compound 78a and 78b

2-[6,9-Difluoro-5H-imidazo[4,3-a]isoindol-5-yl]-1-(4-hydroxycyclohexyl)ethan-1-one 2-[6,9-Difluoro-5H-imidazo[4,3-a]isoindol-5-yl]-1-(4-hydroxycyclohexyl)ethan-1-one (750 mg, 83%) was prepared from 1-[4-[(tert-butyldimethylsilyl)oxy]cyclohexyl]-2-[6,9-difluoro-5H-imidazo[4,3-a]isoindol-5-yl]ethan-1-one using Method F.

4-(2-[6,9-Difluoro-5H-imidazo[4,3-a]isoindol-5-yl]acetyl)cyclohexyl acetate

At room temperature, to a solution of 2-[6,9-difluoro-5H-imidazo[4,3-a]isoindol-5-yl]-1-(4-hydroxycyclohexyl)ethan-1-one (620 mg, 1.77 mmol) in DCM (15 mL) was added TEA (567 mg, 5.32 mmol), acetic anhydride (286 mg, 2.66 mmol) and 4-dimethylaminopyridine (46 mg, 0.36 mmol) in sequence. The resulting mixture was stirred at room temperature for 16 h. Then the reaction was quenched by the addition of water (50 mL) and the mixture was extracted with DCM (50 mL×2). The organic phases were combined, washed with brine and dried over Na$_2$SO$_4$. The solvent was removed under reduced pressure and the residue was purified by flash chromatography eluting with MeOH in DCM (1% to 5% gradient) to yield 4-(2-[6,9-difluoro-5H-imidazo[4,3-a]isoindol-5-yl]acetyl)cyclohexyl acetate (630 mg, 90%) as light yellow solid. MS: m/z=375.1 [M+H]$^+$.

4-(2-[6,9-Difluoro-5H-imidazo[4,3-a]isoindol-5-yl]-1,1-difluoroethyl)cyclohexyl acetate 4-(2-[6,9-Difluoro-5H-imidazo[4,3-a]isoindol-5-yl]-1,1-difluoroethyl)cyclohexyl acetate (100 mg, 15%) was prepared from 4-(2-[6,9-difluoro-5H-imidazo[4,3-a]isoindol-5-yl]acetyl)cyclohexyl acetate using Method R, S, and T. MS: m/z=397.1 [M+H]$^+$.

4-(2-[6,9-Difluoro-5H-imidazo[4,3-a]isoindol-5-yl]-1,1-difluoroethyl)cyclohexan-1-ol At room temperature, to a solution of 4-(2-[6,9-difluoro-5H-imidazo[4,3-a]isoindol-5-yl]-1,1-difluoroethyl)cyclohexyl acetate (100 mg, 0.23 mmol) in MeOH (5 mL) and H$_2$O (0.5 mL) was added potassium carbonate (52 mg, 0.36 mmol). The resulting mixture was stirred at room temperature for 16 h. Then the reaction mixture was neutralized with sat. NH$_4$Cl solution and extracted with EtOAc (40 mL×3). The organic phases were combined, washed with brine and dried over Na$_2$SO$_4$. The solvent was removed under reduced pressure and the residue was purified by flash chromatography eluting with MeOH in DCM (1% to 5% gradient). Two pairs of enantiomeric products were obtained by the separation on prep-HPLC under the following conditions: XBridge Prep C18 OBD Column, 19×150 mm, 5 μm; mobile phase, MeCN in water (with 10 mM NH$_4$HCO$_3$), 20% to 40% gradient in 10 min; Detector, UV 254/220 nm.

Compound 78a:
(15 mg, 19%, white solid, mixture of two stereoisomers) HPLC: 99.5% purity, RT=0.88 min. MS: m/z=355.1 [M+H]$^+$. $^1$H NMR (300 MHz, CD$_3$OD, ppm) δ=7.88 (s, 1H), 7.22-7.16 (m, 1H), 7.13 (s, 1H), 7.09-7.02 (m, 1H), 5.83 (d, J=8.1 Hz, 1H), 3.51-3.40 (m, 1H), 3.02-2.83 (m, 1H), 2.53-2.34 (m, 1H), 2.00-1.77 (m, 5H), 1.38-1.16 (m, 4H);

Compound 78b:
(13 mg, 16%, white solid, mixture of two stereoisomers) HPLC: 97.0% purity, RT=0.92 min. MS: m/z=355.1 [M+H]$^+$. $^1$H NMR (300 MHz, CD$_3$OD, ppm) δ=7.89 (s, 1H), 7.22-7.16 (m, 1H), 7.13 (s, 1H), 7.08-7.02 (m, 1H), 5.84 (d, J=8.4 Hz, 1H), 3.92 (br s, 1H), 3.03-2.84 (m, 1H), 2.52-2.31 (m, 1H), 1.90-1.79 (m, 3H), 1.71-1.44 (m, 6H).

Example 79: Synthesis of 4-fluoro-4-[2-[5H-imidazo[4,3-a]isoindol-5-yl]ethyl]cyclohexane-1-carboxamide (79a, b)

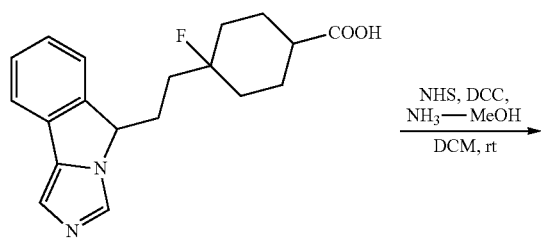

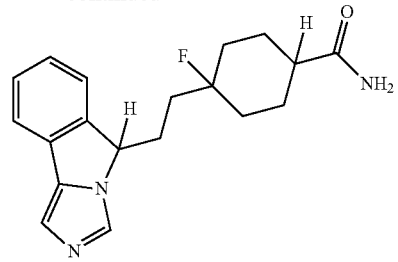

Compound 79a, b, c, d

4-Fluoro-4-[2-[5H-imidazo[4,3-a]isoindol-5-yl]ethyl]cyclohexane-1-carboxamide

At room temperature, to a solution of 4-fluoro-4-(2-[5H-imidazo[4,3-a]isoindol-5-yl]ethyl)cyclohexane-1-carboxylic acid (372 mg, 1.0 mmol) in DCM (7 mL) was added 1-hydroxypyrrolidine-2,5-dione (133 mg, 1.1 mmol) and DCC (237 mg, 1.1 mmol) slowly. The resulting mixture was stirred at room temperature for 30 min, and then was added by NH$_3$-MeOH (7 M, 1.4 mL). The reaction mixture was kept stirring for another 16 h at room temperature. Then the reaction mixture was diluted with H$_2$O (40 mL) and extracted with DCM (40 mL×4). The organic phases were combined, washed with brine and dried over Na$_2$SO$_4$. The solvent was removed under reduced pressure and the residue was purified by flash chromatography eluting with MeOH in DCM (5% to 10% gradient). Then cis- and trans-isomers were separated on prep-HPLC under the following conditions: XBridge BEH C18 OBD Prep Column, 19×250 mm, 5 μm; mobile phase, MeCN in water (with 10 mM NH$_4$HCO$_3$), 30% to 35% gradient in 11 min; Detector, UV 254/220 nm. Four enantiomers were obtained by the further separation on chiral prep-HPLC under the following conditions: Chiralpak IA, 20×250 mm, 5 μm; mobile phase, EtOH in hexane (with 0.1% DEA), 40% isocratic in 18 min; Detector, UV 254/220 nm.

Compound 79a:
(9.9 mg, 2.7%, white solid, single stereoisomer) HPLC: 100% purity, RT=1.17 min. MS: m/z=328.15 [M+H]$^+$. $^1$H NMR (300 MHz, CD$_3$OD, ppm) δ=7.89 (s, 1H), 7.58 (d, J=7.5 Hz, 1H), 7.45 (d, J=7.5 Hz, 1H), 7.40-7.27 (m, 2H), 7.13 (s, 1H), 5.41 (t, J=4.8 Hz, 1H), 2.42-2.32 (m, 1H), 2.20-2.10 (m, 2H), 1.89-1.78 (m, 2H), 1.72-1.63 (m, 4H), 1.41-1.10 (m, 4H);

Compound 79b:
(14.2 mg, 3.8%, white solid, single stereoisomer) HPLC: 99.9% purity, RT=1.22 min. MS: m/z=328.15 [M+H]$^+$. $^1$H NMR (300 MHz, CD$_3$OD, ppm) δ=7.90 (s, 1H), 7.58 (d, J=7.5 Hz, 1H), 7.46 (d, J=7.5 Hz, 1H), 7.40-7.27 (m, 2H), 7.12 (s, 1H), 5.42-5.38 (m, 1H), 2.40-2.28 (m, 2H), 2.18-2.08 (m, 1H), 1.83-1.72 (m, 4H), 1.62-1.25 (m, 6H);

Compound 79c:
(8.3 mg, 2.2%, white solid, single stereoisomer) HPLC: 99.9% purity, RT=1.17 min. MS: m/z=328.15 [M+H]$^+$. $^1$H NMR (300 MHz, CD$_3$OD, ppm) δ=7.89 (s, 1H), 7.58 (d, J=7.5 Hz, 1H), 7.45 (d, J=7.5 Hz, 1H), 7.40-7.27 (m, 2H), 7.13 (s, 1H), 5.41 (t, J=4.8 Hz, 1H), 2.42-2.32 (m, 1H), 2.20-2.10 (m, 2H), 1.89-1.78 (m, 2H), 1.72-1.63 (m, 4H), 1.41-1.10 (m, 4H);

Compound 79d:
(9.7 mg, 2.6%, white solid, single stereoisomer) HPLC: 99.9% purity, RT=1.22 min. MS: m/z=328.1 [M+H]$^+$. $^1$H NMR (300 MHz, CD₃OD, ppm) δ=7.90 (s, 1H), 7.58 (d, J=7.5 Hz, 1H), 7.46 (d, J=7.5 Hz, 1H), 7.40-7.27 (m, 2H), 7.12 (s, 1H), 5.42-5.38 (m, 1H), 2.40-2.28 (m, 2H), 2.18-2.08 (m, 1H), 1.83-1.72 (m, 4H), 1.62-1.25 (m, 6H).

Example 80: Synthesis of 4-fluoro-4-(2-[6-fluoro-5H-imidazo[4,3-a]isoindol-5-yl]ethyl)cyclohexane-1-carboxylic acid (80a, b)

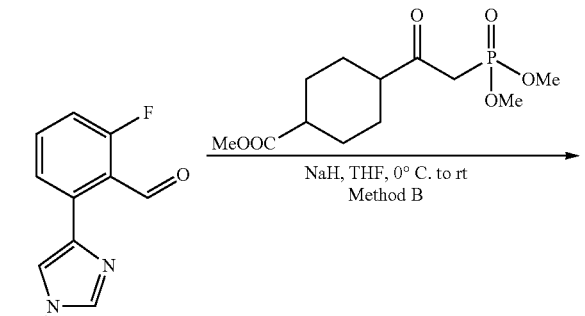

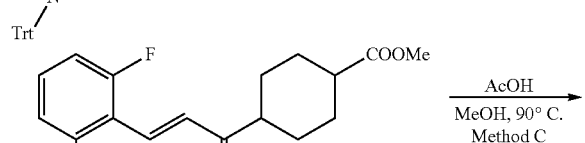

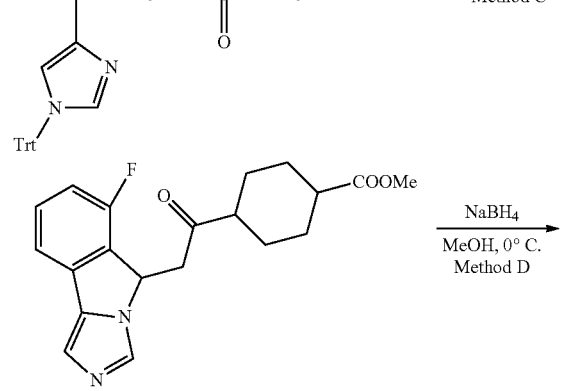

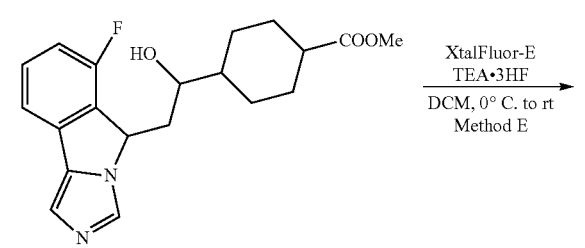

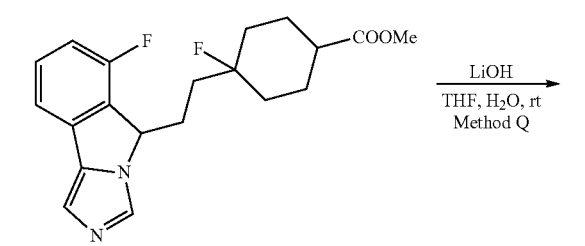

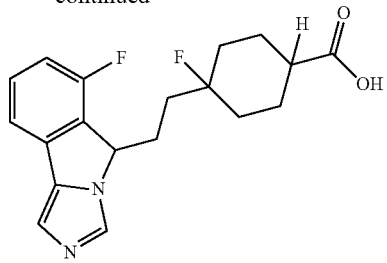

Compounds 80a and 80b

4-Fluoro-4-(2-[6-fluoro-5H-imidazo[4,3-a]isoindol-5-yl]ethyl)cyclohexane-1-carboxylic acid 4-Fluoro-4-(2-[6-fluoro-5H-imidazo[4,3-a]isoindol-5-yl]ethyl)cyclohexane-1-carboxylic acid was prepared from 2-fluoro-6-[1-(triphenylmethyl)-1H-imidazol-4-yl]benzaldehyde and methyl 4-[2-(dimethoxyphosphoryl)acetyl]cyclohexane-1-carboxylate using Method B, C, D, E, and Q. Two pairs of enantiomers were obtained by the separation on prep-HPLC under the following conditions: Gemini-NX 5μ C18, 110A, AXIA Packed, 19×150 mm, 5 μm; mobile phase, MeCN in water (with 10 mM NH₄HCO₃), 20% to 40% gradient in 12 min; Detector, UV 254/220 nm.

Compound 80a:

(16.7 mg, 5.1% for five steps, white solid, mixture of two stereoisomers) HPLC: 98.1% purity, RT=1.75 min. MS: m/z=347.1 [M+H]⁺. ¹H NMR (300 MHz, CD₃OD, ppm) δ=7.91 (s, 1H), 7.44-7.41 (m, 2H), 7.17 (s, 1H), 7.06-6.99 (m, 1H), 5.64 (t, J=4.5 Hz, 1H), 2.50-2.39 (m, 1H), 2.29-2.15 (m, 2H), 1.83-1.58 (m, 6H), 1.42-1.10 (m, 4H);

Compound 80b:

(11.5 mg, 3.5% for five steps, white solid, mixture of two stereoisomers) HPLC: 95.1% purity, RT=3.49 min. MS: m/z=347.05 [M+H]⁺. ¹H NMR (300 MHz, CD₃OD, ppm) δ=7.93 (s, 1H), 7.46-7.41 (m, 2H), 7.18 (s, 1H), 7.07-6.99 (m, 1H), 5.64 (t, J=4.5 Hz, 1H), 2.47-2.38 (m, 2H), 2.28-2.18 (m, 1H), 1.81-1.78 (m, 2H), 1.69-1.57 (m, 6H), 1.34-1.10 (m, 2H).

Example 81: Synthesis of 4-fluoro-4-[2-[6-fluoro-5H-imidazo[4,3-a]isoindol-5-yl]ethyl]cyclohexane-1-carboxamide (81a, b)

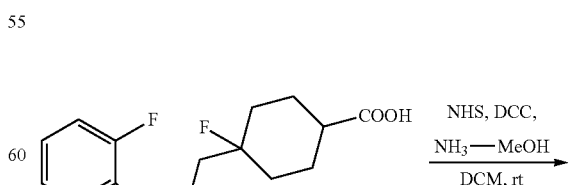

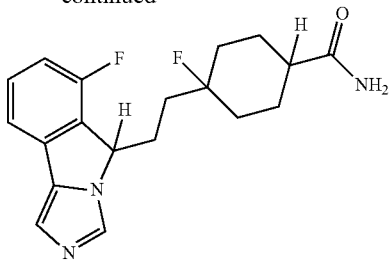

Compounds 81a, b, c, d

4-Fluoro-4-[2-[6-fluoro-5H-imidazo[4,3-a]isoindol-5-yl]ethyl] cyclohexane-1-carboxamide At room temperature, to a solution of 4-fluoro-4-(2-[6-fluoro-5H-imidazo[4,3-a]isoindol-5-yl]ethyl) cyclohexane-1-carboxylic acid (250 mg, 0.65 mmol) in DCM (5 mL) was added 1-hydroxypyrrolidine-2,5-dione (91 mg, 0.75 mmol) and DCC (164 mg, 0.76 mmol) slowly. The resulting mixture was stirred at room temperature for 30 min, and then was added by $NH_3$-MeOH (7 M, 1 mL). The reaction mixture was kept stirring for another 16 h at room temperature. Then the reaction mixture was diluted with $H_2O$ (40 mL) and extracted with DCM (40 mL×4). The organic phases were combined, washed with brine and dried over $Na_2SO_4$. The solvent was removed under reduced pressure and the residue was purified by flash chromatography eluting with MeOH in DCM (5% to 10% gradient). Then cis- and trans-isomers were separated on prep-HPLC under the following conditions: XBridge BEH C18 OBD Prep Column, 19×250 mm, 5 μm; mobile phase, MeCN in water (with 10 mM $NH_4HCO_3$), 31% to 39% gradient in 10 min; Detector, UV 254/220 nm. Four enantiomers were obtained by the further separation on chiral prep-HPLC under the following conditions: Chiralpak IA, 20×250 mm, 5 μm; mobile phase, EtOH in hexane (with 0.1% DEA), 30% isocratic in 18 min; Detector, UV 254/220 nm.

Compound 81a:
(7.7 mg, 3.1%, white solid, single stereoisomer) HPLC: 99.8% purity, RT=1.21 min. MS: m/z=346.15 [M+H]$^+$. $^1$H NMR (300 MHz, $CD_3OD$, ppm) δ=7.93 (s, 1H), 7.44-7.40 (m, 2H), 7.17 (s, 1H), 7.06-6.99 (m, 1H), 5.64 (t, J=4.5 Hz, 1H), 2.50-2.40 (m, 1H), 2.29-2.08 (m, 2H), 1.86-1.79 (m, 2H), 1.74-1.63 (m, 4H), 1.41-1.10 (m, 4H);

Compound 81b:
(16.3 mg, 6.5%, white solid, single stereoisomer) HPLC: 99.9% purity, RT=1.26 min. MS: m/z=346.1 [M+H]$^+$. $^1$H NMR (300 MHz, $CD_3OD$, ppm) δ=7.98 (s, 1H), 7.44-7.41 (m, 2H), 7.20 (s, 1H), 7.07-7.00 (m, 1H), 5.65 (t, J=4.5 Hz, 1H), 2.49-2.39 (m, 1H), 2.32-2.18 (m, 2H), 1.81-1.73 (m, 4H), 1.62-1.21 (m, 6H);

Compound 81c:
(8.6 mg, 3.4%, white solid, single stereoisomer) HPLC: 99.5% purity, RT=1.20 min. MS: m/z=346.1 [M+H]$^+$. $^1$H NMR (300 MHz, $CD_3OD$, ppm) δ=7.93 (s, 1H), 7.44-7.40 (m, 2H), 7.17 (s, 1H), 7.06-6.99 (m, 1H), 5.64 (t, J=4.5 Hz, 1H), 2.50-2.40 (m, 1H), 2.29-2.08 (m, 2H), 1.86-1.79 (m, 2H), 1.74-1.63 (m, 4H), 1.41-1.10 (m, 4H);

Compound 81d:
(12.8 mg, 5.1%, white solid, single stereoisomer) HPLC: 95.0% purity, RT=2.74 min. MS: m/z=346.0 [M+H]$^+$. $^1$H NMR (300 MHz, $CD_3OD$, ppm) δ=7.98 (s, 1H), 7.44-7.41 (m, 2H), 7.20 (s, 1H), 7.07-7.00 (m, 1H), 5.65 (t, J=4.5 Hz, 1H), 2.49-2.39 (m, 1H), 2.32-2.18 (m, 2H), 1.81-1.73 (m, 4H), 1.62-1.21 (m, 6H).

Example 82: Synthesis of 4-fluoro-4-(2-[5H-imidazo[4,3-a]isoindol-5-yl]ethyl)cyclohexane-1-carboxylic acid (82a,b)

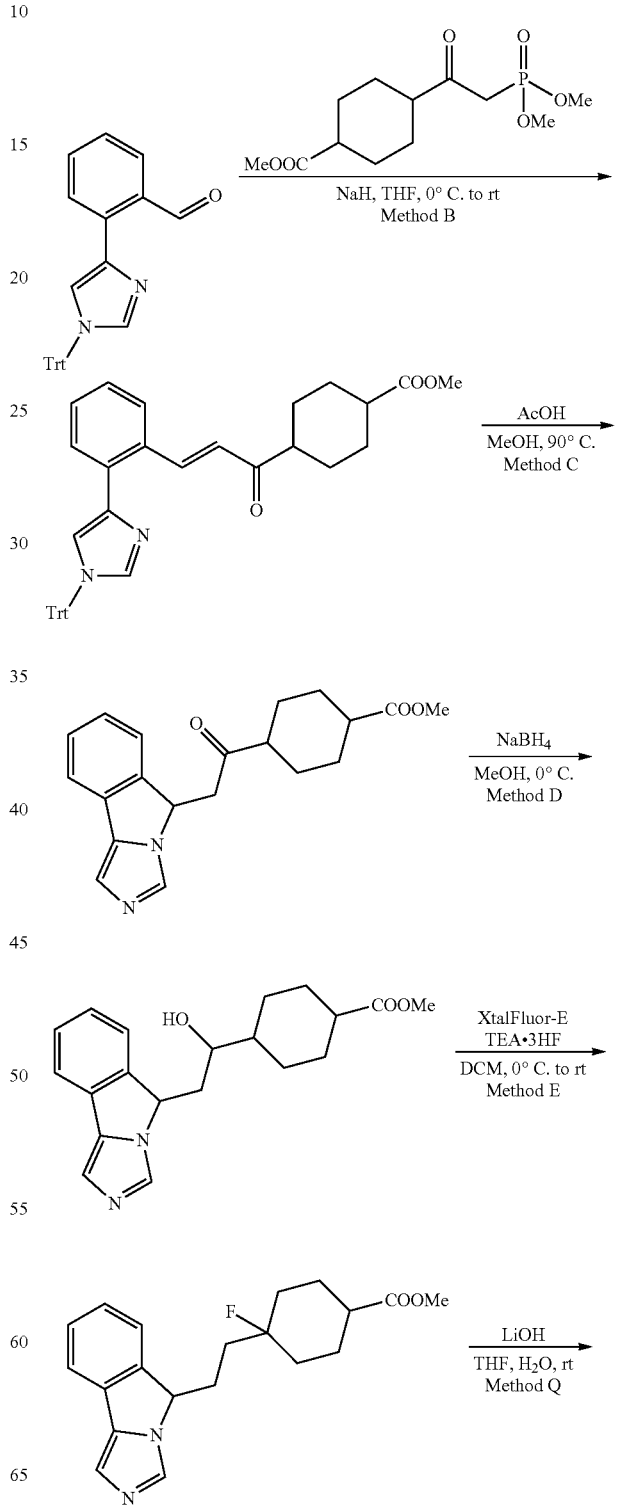

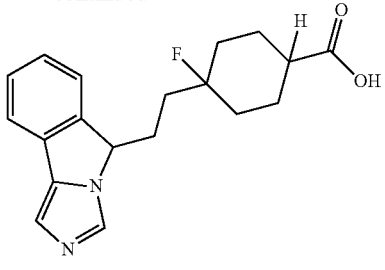

Compounds 82a and 82b

4-Fluoro-4-(2-[5H-imidazo[4,3-a]isoindol-5-yl]ethyl)cyclohexane-1-carboxylic acid 4-Fluoro-4-(2-[5H-imidazo[4,3-a]isoindol-5-yl]ethyl)cyclohexane-1-carboxylic acid was prepared from 2-[1-(triphenylmethyl)-1H-imidazol-4-yl]benzaldehyde and methyl 4-[2-(dimethoxyphosphoryl)acetyl]cyclohexane-1-carboxylate using Method B, C, D, E, and Q. Two pairs of enantiomers were obtained by the separation on prep-HPLC under the following conditions: XBridge C18 OBD Prep Column, 19×250 mm, 5 μm; mobile phase, MeCN in water (with 10 mM NH$_4$HCO$_3$), 46% to 55% gradient in 8 min; Detector, UV 254/220 nm.

Compound 82a:

(12.5 mg, 3.5% for five steps, white solid, mixture of two stereoisomers) HPLC: 99.6% purity, RT=0.89 min. MS: m/z=329.1 [M+H]$^+$. $^1$H NMR (300 MHz, CD$_3$OD, ppm) δ=7.92 (s, 1H), 7.58 (d, J=7.5 Hz, 1H), 7.45 (d, J=7.5 Hz, 1H), 7.38-7.27 (m, 2H), 7.14 (s, 1H), 5.41 (t, J=4.5 Hz, 1H), 2.41-2.31 (m, 1H), 2.20-2.12 (m, 2H), 1.82-1.58 (m, 6H), 1.42-1.14 (m, 4H);

Compound 82b:

(23 mg, 6.4% for five steps, white solid, mixture of two stereoisomers) HPLC: 90.0% purity, RT=3.39 min. MS: m/z=329.05 [M+H]$^+$. $^1$H NMR (300 MHz, CD$_3$OD, ppm) δ=8.68 (s, 1H), 7.72 (d, J=6.3 Hz, 1H), 7.56 (d, J=6.6 Hz, 1H), 7.50-7.41 (m, 3H), 5.63 (t, J=4.5 Hz, 1H), 2.47-2.38 (m, 2H), 2.29-2.20 (m, 1H), 1.83-1.78 (m, 2H), 1.69-1.57 (m, 6H), 1.39-1.26 (m, 2H).

Example 83: Synthesis of 2-[6-chloro-5H-imidazo[4,3-a]isoindol-5-yl]-1-(1-fluorocyclohexyl)ethan-1-ol (83a, b, c, d)

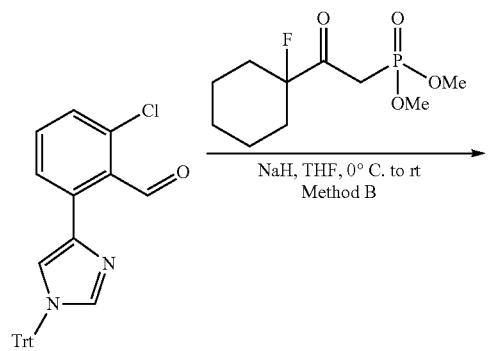

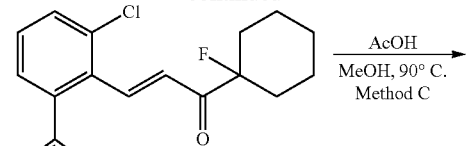

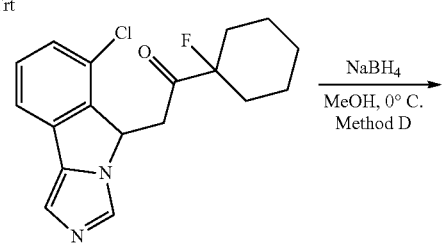

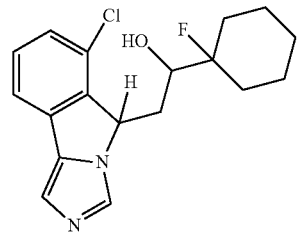

Compound 83 a, b, c, d

2-[6-Chloro-5H-imidazo[4,3-a]isoindol-5-yl]-1-(1-fluorocyclohexyl)ethan-1-ol 2-[6-Chloro-5H-imidazo[4,3-a]isoindol-5-yl]-1-(1-fluorocyclohexyl)ethan-1-ol was prepared from 2-chloro-6-[1-(triphenylmethyl)-1H-imidazol-4-yl]benzaldehyde and dimethyl [2-(1-fluorocyclohexyl)-2-oxoethyl]phosphonate using Method B, C, and D. Four enantiomeric products were obtained by the separation on chiral prep-HPLC under the following conditions: (R,R)-WHELK-O1-Kromasil, 50×250 mm, 5 μm; mobile phase, iPrOH in hexane, 8% isocratic in 26 min; Detector, UV 254/220 nm.

Compound 83a:

(9.9 mg, 5.7% for three steps, white solid, single stereoisomer), HPLC: 99.98% purity, RT=1.46 min. MS: m/z=335.1 [M+H]$^+$. $^1$H NMR (300 MHz, CD$_3$OD, ppm) δ=7.92 (s, 1H), 7.54 (d, J=7.2 Hz, 1H), 7.38 (t, J=7.8 Hz, 1H), 7.27 (d, J=7.8 Hz, 1H), 7.17 (s, 1H), 5.62 (dd, J=9.6, 2.7 Hz, 1H), 3.66-3.57 (m, 1H), 2.81-2.71 (m, 1H), 1.82-1.71 (m, 3H), 1.67-1.49 (m, 6H), 1.39-1.12 (m, 2H);

Compound 83b:

(15.7 mg, 9% for three steps, white solid, single stereoisomer) HPLC: 99.99% purity, RT=1.46 min. MS: m/z=335.05 [M+H]$^+$. $^1$H NMR (300 MHz, CD$_3$OD, ppm) δ=7.92 (s, 1H), 7.54 (d, J=7.2 Hz, 1H), 7.38 (t, J=7.8 Hz, 1H), 7.27 (d, J=7.8 Hz, 1H), 7.17 (s, 1H), 5.62 (dd, J=9.6, 2.7 Hz, 1H), 3.66-3.57 (m, 1H), 2.81-2.71 (m, 1H), 1.82-1.71 (m, 3H), 1.67-1.49 (m, 6H), 1.39-1.12 (m, 2H);

Compound 83c (11.9 mg, 6.8% for three steps, white solid, single stereoisomer), HPLC:

99.3% purity, RT=1.52 min. MS: m/z=335.05 [M+H]$^+$. $^1$H NMR (300 MHz, CD$_3$OD, ppm) δ=8.00 (s, 1H), 7.52 (d, J=7.5 Hz, 1H), 7.36 (t, J=7.8 Hz, 1H), 7.25 (d, J=8.1 Hz, 1H), 7.14 (s, 1H), 5.45 (dd, J=5.7, 2.4 Hz, 1H), 3.55-3.47 (m, 1H), 2.76-2.70 (m, 1H), 2.02-1.93 (m, 1H), 1.79-1.70 (m, 2H), 1.62-1.50 (m, 6H), 1.42-1.32 (m, 1H), 1.28-1.13 (m, 1H);

Compound 83d:

(15.5 mg, 8.9% for three steps, white solid, single stereoisomer) HPLC: 99.8% purity, RT=1.49 min. MS: m/z=335.05 [M+H]+. 1H NMR (300 MHz, CD3OD, ppm) δ=7.99 (s, 1H), 7.52 (d, J=7.5 Hz, 1H), 7.36 (t, J=7.8 Hz, 1H), 7.25 (d, J=8.1 Hz, 1H), 7.13 (s, 1H), 5.45 (dd, J=5.7, 2.4 Hz, 1H), 3.55-3.47 (m, 1H), 2.76-2.70 (m, 1H), 2.02-1.93 (m, 1H), 1.79-1.70 (m, 2H), 1.62-1.50 (m, 6H), 1.42-1.32 (m, 1H), 1.28-1.13 (m, 1H).

Example 84: Synthesis of [4-fluoro-4-[2-[6-fluoro-5H-imidazo[4,3-a]isoindol-5-yl]ethyl]cyclohexyl]methanol (84 a, b, c, d)

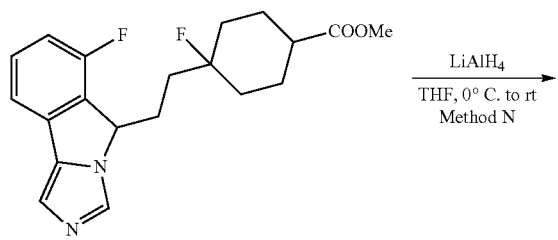

Compounds 84a, b, c, d

[4-Fluoro-4-[2-[6-fluoro-5H-imidazo[4,3-a]isoindol-5-yl]ethyl]cyclohexyl]methanol

[4-Fluoro-4-[2-[6-fluoro-5H-imidazo[4,3-a]isoindol-5-yl]ethyl]cyclohexyl]methanol was prepared from methyl 4-fluoro-4-(2-[6-fluoro-5H-imidazo[4,3-a]isoindol-5-yl]ethyl)cyclohexane-1-carboxylate using Method N. Four enantiomeric products were obtained by the separation on chiral prep-HPLC under the following conditions: CHIRALPAK-AD-H-SL002, 20×250 mm, 5 μm; EtOH in hexane, 30% isocratic in 20 min; Detector, UV 254/220 nm.

Compound 84a:

(10.7 mg, 7%, white solid, single stereoisomer) HPLC: 99.9% purity, RT=0.71 min. MS: m/z=333.0 [M+H]+. 1H NMR (300 MHz, CD3OD, ppm) δ=7.92 (s, 1H), 7.43-7.41 (m, 2H), 7.17 (s, 1H), 7.05-6.99 (m, 1H), 5.64 (t, J=4.5 Hz, 1H), 3.28-3.27 (m, 2H), 2.45-2.35 (m, 1H), 2.29-2.17 (m, 1H), 1.72-1.67 (m, 4H), 1.56-1.43 (m, 3H), 1.38-1.09 (m, 2H), 0.92-0.85 (m, 2H);

Compound 84b:

(5.2 mg, 3.4%, white solid, single stereoisomer) HPLC: 99.9% purity, RT=0.71 min. MS: m/z=333.05 [M+H]+. 1H NMR (300 MHz, CD3OD, ppm) δ=7.97 (s, 1H), 7.44-7.42 (m, 2H), 7.19 (s, 1H), 7.07-7.00 (m, 1H), 5.65 (t, J=4.5 Hz, 1H), 3.33-3.31 (m, 2H), 2.47-2.37 (m, 1H), 2.31-2.20 (m, 1H), 1.81-1.76 (m, 2H), 1.60-1.56 (m, 2H), 1.38-1.09 (m, 7H);

Compound 84c:

(9.9 mg, 6.5%, white solid, single stereoisomer) HPLC: 99.9% purity, RT=0.70 min. MS: m/z=333.0 [M+H]+. 1H NMR (300 MHz, CD3OD, ppm) δ=7.92 (s, 1H), 7.43-7.41 (m, 2H), 7.17 (s, 1H), 7.05-6.99 (m, 1H), 5.64 (t, J=4.5 Hz, 1H), 3.28-3.27 (m, 2H), 2.45-2.35 (m, 1H), 2.29-2.17 (m, 1H), 1.72-1.67 (m, 4H), 1.56-1.43 (m, 3H), 1.38-1.09 (m, 2H), 0.92-0.85 (m, 2H);

Compound 84d:

(4.2 mg, 2.7%, white solid, single stereoisomer) HPLC: 99.9% purity, RT=0.71 min. MS: m/z=333.05 [M+H]+. 1H NMR (300 MHz, CD3OD, ppm) δ=8.01 (br s, 1H), 7.44-7.42 (m, 2H), 7.23 (br s, 1H), 7.07-7.00 (m, 1H), 5.65 (t, J=4.5 Hz, 1H), 3.33-3.31 (m, 2H), 2.47-2.37 (m, 1H), 2.31-2.20 (m, 1H), 1.81-1.76 (m, 2H), 1.60-1.56 (m, 2H), 1.38-1.09 (m, 7H).

Example 85: Synthesis of 1-[4-fluoro-4-(2-[6-fluoro-5H-imidazo[4,3-a]isoindol-5-yl]ethyl)cyclohexyl]cyclopropan-1-ol (85a, b)

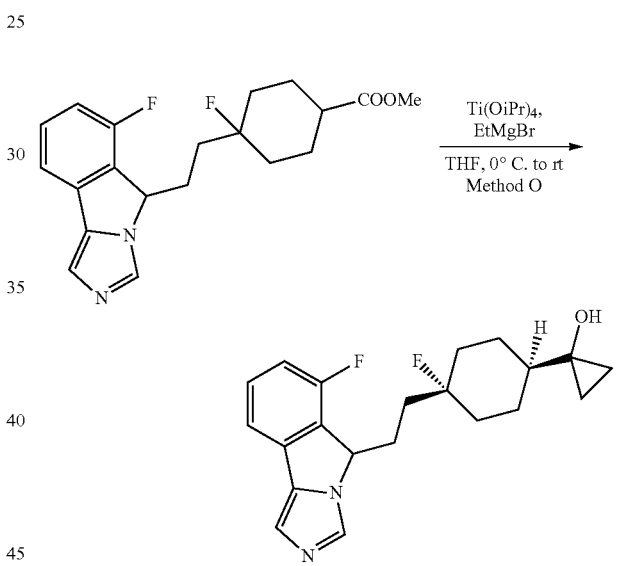

Compounds 85a, b

1-[4-Fluoro-4-(2-[6-fluoro-5H-imidazo[4,3-a]isoindol-5-yl]ethyl)cyclohexyl]cyclopropan-1-ol 1-[4-Fluoro-4-(2-[6-fluoro-5H-imidazo[4,3-a]isoindol-5-yl]ethyl)cyclohexyl]cyclopropan-1-ol was prepared from methyl 4-fluoro-4-(2-[6-fluoro-5H-imidazo[4,3-a]isoindol-5-yl]ethyl)cyclohexane-1-carboxylate using Method O. Two pairs of enantiomeric products were obtained by the separation on prep-HPLC under the following conditions: XBridge BEH C18 OBD Prep Column, 19×250 mm, 5 μm; mobile phase, MeCN in water (with 10 mM NH4HCO3), 45% to 78% gradient in 11 min; Detector, UV 254/220 nm.

Compound 85a:

(15.9 mg, 7.1%, white solid, mixture of two stereoisomers) HPLC: 99.1% purity, RT=1.02 min. MS: m/z=359.15 [M+H]+. 1H NMR (300 MHz, CD3OD, ppm) δ=7.91 (s, 1H), 7.41-7.40 (m, 2H), 7.16 (s, 1H), 7.04-6.99 (m, 1H), 5.63 (t, J=4.5 Hz, 1H), 2.48-2.38 (m, 1H), 2.29-2.18 (m, 1H), 1.82-1.77 (m, 2H), 1.61-1.53 (m, 4H), 1.37-1.07 (m, 4H), 0.90-0.83 (m, 1H), 0.56-0.54 (m, 2H), 0.38-0.35 (m, 2H);

compound 85b:

(20.1 mg, 9%, white solid, mixture of two stereoisomers) HPLC: 99.7% purity, RT=1.05 min. MS: m/z=359.15 [M+H]$^+$. $^1$H NMR (300 MHz, CD$_3$OD, ppm) δ=7.92 (s, 1H), 7.43-7.41 (m, 2H), 7.17 (s, 1H), 7.04-6.99 (m, 1H), 5.65 (br s, 1H), 2.47-2.37 (m, 1H), 2.30-2.19 (m, 1H), 1.85-1.80 (m, 2H), 1.67-1.63 (m, 2H), 1.58-1.04 (m, 6H), 0.93-0.88 (m, 1H), 0.56-0.54 (m, 2H), 0.32-0.29 (m, 2H).

Example 86: Synthesis of 2-[4-fluoro-4-(2-[6-fluoro-5H-imidazo[4,3-a]isoindol-5-yl]ethyl)cyclohexyl]propan-2-ol (86a, b)

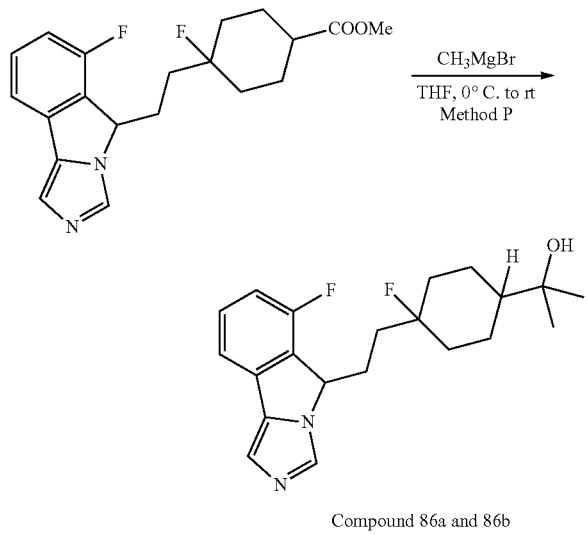

Compound 86a and 86b

2-[4-Fluoro-4-(2-[6-fluoro-5H-imidazo[4,3-a]isoindol-5-yl]ethyl)cyclohexyl]propan-2-ol 2-[4-Fluoro-4-(2-[6-fluoro-5H-imidazo[4,3-a]isoindol-5-yl]ethyl)cyclohexyl]propan-2-ol was prepared from methyl 4-fluoro-4-(2-[6-fluoro-5H-imidazo[4,3-a]isoindol-5-yl]ethyl)cyclohexane-1-carboxylate using Method P. Two pairs of enantiomeric products were obtained by the separation on prep-HPLC under the following conditions: XBridge BEH C18 OBD Prep Column, 19×250 mm, 5 μm; mobile phase, MeCN in water (with 10 mM NH$_4$HCO$_3$), 36% to 41% gradient in 13 min; Detector, UV 254/220 nm.

Compound 86a:

(21 mg, 8.7%, white solid, mixture of two stereoisomers) HPLC: 99.96% purity, RT=1.36 min. MS: m/z=361.15 [M+H]$^+$. $^1$H NMR (300 MHz, CD$_3$OD, ppm) δ=7.94 (s, 1H), 7.43-7.41 (m, 2H), 7.18 (s, 1H), 7.05-6.99 (m, 1H), 5.67 (t, J=4.2 Hz, 1H), 2.47-2.37 (m, 1H), 2.30-2.21 (m, 1H), 1.82-1.78 (m, 2H), 1.72-1.67 (m, 2H), 1.56-1.41 (m, 2H), 1.30-1.09 (m, 3H), 1.00 (s, 6H), 0.85-0.72 (m, 2H);

Compound 86b:

(14.2 mg, 5.9%, white solid, mixture of two stereoisomers) HPLC: 99.8% purity, RT=1.37 min. MS: m/z=361.15 [M+H]$^+$. $^1$H NMR (300 MHz, CD$_3$OD, ppm) δ=7.92 (s, 1H), 7.43-7.40 (m, 2H), 7.17 (s, 1H), 7.05-6.99 (m, 1H), 5.63 (t, J=4.2 Hz, 1H), 2.47-2.37 (m, 1H), 2.29-2.17 (m, 1H), 1.81-1.77 (m, 2H), 1.63-1.60 (m, 2H), 1.35-1.10 (m, 7H), 1.08 (s, 6H).

Example 87: Synthesis of 2-[4,6,9-triazatricyclo[6.4.0.0^[2,6]]dodeca-1(8),2,4,9,11-pentaen-7-yl]-1-(1,4,4-trifluorocyclohexyl)ethan-1-ol (87a, b, c, d)

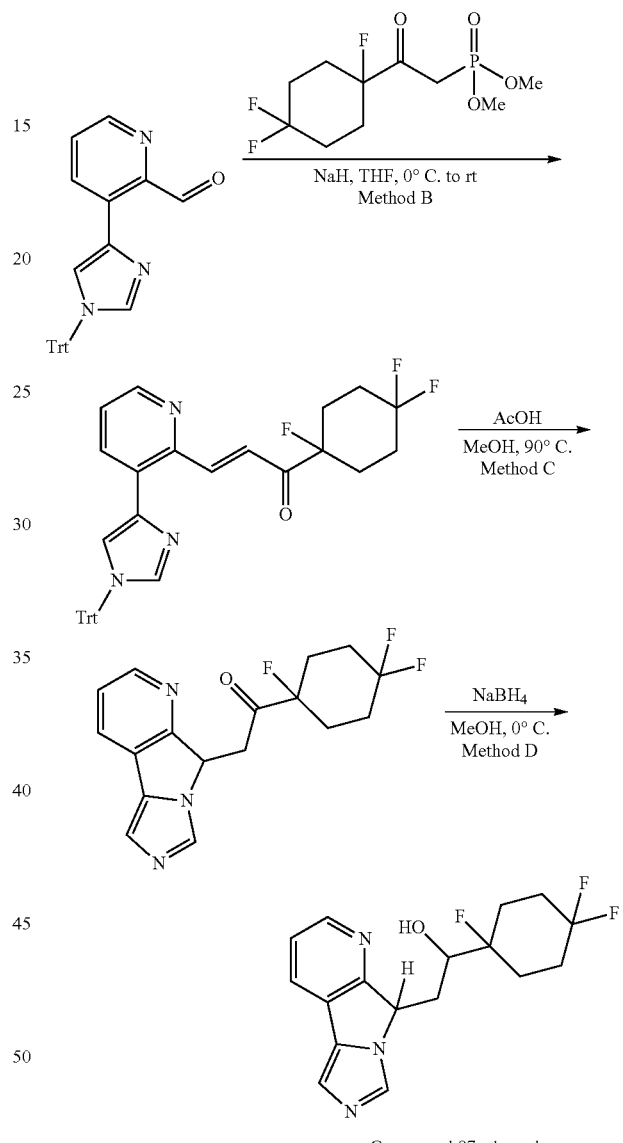

Compound 87a, b, c, d

2-[4,6,9-Triazatricyclo[6.4.0.0^[2,6]]dodeca-1(8),2,4,9,11-pentaen-7-yl]-1-(1,4,4-trifluorocyclohexyl)ethan-1-ol 2-[4,6,9-Triazatricyclo[6.4.0.0^[2,6]]dodeca-1(8),2,4,9,11-pentaen-7-yl]-1-(1,4,4-trifluorocyclohexyl)ethan-1-ol was prepared from 3-[1-(triphenylmethyl)-1H-imidazol-4-yl]pyridine-2-carbaldehyde and dimethyl [2-oxo-2-(1,4,4-trifluorocyclohexyl)ethyl]phosphonate using Method B, C, and D. Four enantiomeric products were obtained by the separation on chiral prep-HPLC under the following conditions: CHIRALPAK-AD-H-SL001, 20×250 mm, 5 μm; mobile phase, EtOH in hexane, 15% isocratic in 27 min; Detector, UV 254/220 nm.

Compound 87a:

(12.5 mg, 5.4% for three steps, white solid, single stereoisomer), HPLC: 99.2% purity, RT=1.22 min. MS: m/z=338.0 [M+H]$^+$. $^1$H NMR (400 MHz, CD$_3$OD, ppm) δ=8.40 (d, J=4.8 Hz, 1H), 8.09 (s, 1H), 8.01 (dd, J=7.6, 1.2 Hz, 1H), 7.40 (dd, J=8.0, 4.8 Hz, 1H), 7.29 (s, 1H), 5.39 (t, J=5.6 Hz, 1H), 4.12-4.06 (m, 1H), 2.48-2.43 (m, 1H), 2.18-2.12 (m, 1H), 2.03-1.77 (m, 8H);

Compound 87b:

(7.2 mg, 3.1% for three steps, white solid, single stereoisomer) HPLC: 85.7% purity, RT=1.98 min. MS: m/z=338.05 [M+H]$^+$. $^1$H NMR (400 MHz, CD$_3$OD, ppm) δ=8.41 (d, J=5.2 Hz, 1H), 8.06-8.03 (m, 2H), 7.43 (dd, J=8.0, 5.2 Hz, 1H), 7.33 (s, 1H), 5.50 (dd, J=10.0, 4.0 Hz, 1H), 3.91-3.84 (m, 1H), 2.57-2.51 (m, 1H), 2.07-1.75 (m, 9H);

Compound 87c:

(7.6 mg, 3.3% for three steps, white solid, single stereoisomer), HPLC: 98.5% purity, RT=1.20 min. MS: m/z=338.0 [M+H]$^+$. $^1$H NMR (400 MHz, CD$_3$OD, ppm) δ=8.41 (d, J=5.2 Hz, 1H), 8.06-8.03 (m, 2H), 7.43 (dd, J=8.0, 5.2 Hz, 1H), 7.33 (s, 1H), 5.50 (dd, J=10.0, 4.0 Hz, 1H), 3.91-3.84 (m, 1H), 2.57-2.51 (m, 1H), 2.07-1.75 (m, 9H);

Compound 87d:

(16.9 mg, 7.3% for three steps, white solid, single stereoisomer) HPLC: 97.0% purity, RT=1.65 min. MS: m/z=338.0 [M+H]$^+$. $^1$H NMR (400 MHz, CD$_3$OD, ppm) δ=8.40 (d, J=4.8 Hz, 1H), 8.09 (s, 1H), 8.01 (dd, J=7.6, 1.2 Hz, 1H), 7.40 (dd, J=8.0, 4.8 Hz, 1H), 7.29 (s, 1H), 5.39 (t, J=5.6 Hz, 1H), 4.12-4.06 (m, 1H), 2.48-2.43 (m, 1H), 2.18-2.12 (m, 1H), 2.03-1.77 (m, 8H).

Example 88: Synthesis of 1-[4-[1-hydroxy-2-[4,6,9-triazatricyclo[6.4.0.0^[2,6]]dodeca-1(8),2,4,9,11-pentaen-7-yl]ethyl]piperidin-1-yl]-2,2-dimethylpropan-1-one (88a, b, c, d)

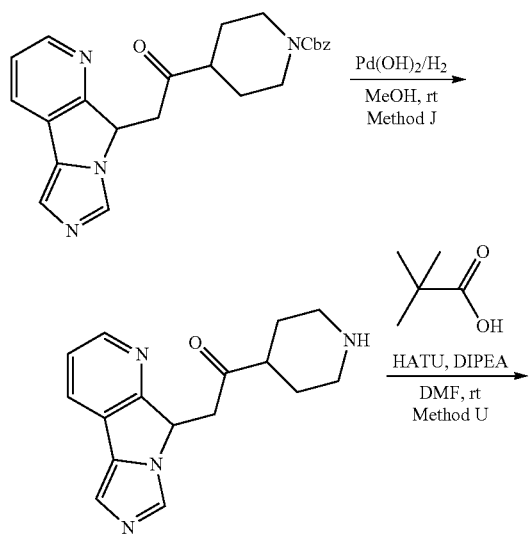

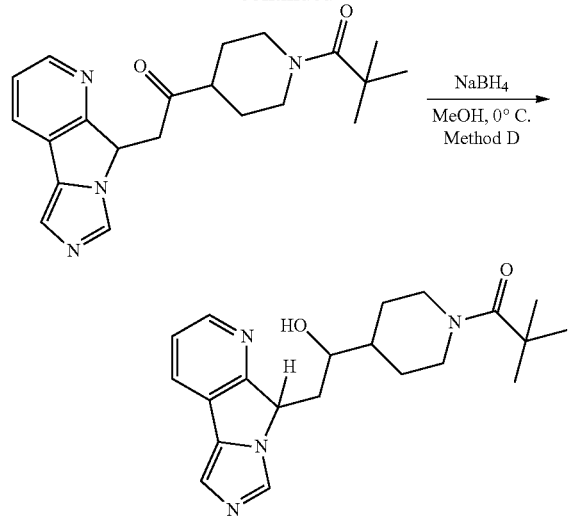

Compounds 88a, b, c, d 1-(Piperidin-4-yl)-2-[4,6,9-triazatricyclo[6.4.0.0^[2,6]]dodeca-1(8),2,4,9,11-pentaen-7-yl]ethan-1-one 1-(Piperidin-4-yl)-2-[4,6,9-triazatricyclo[6.4.0.0^[2,6]]dodeca-1(8),2,4,9,11-pentaen-7-yl]ethan-1-one (450 mg, 73%) was prepared from benzyl 4-(2-[4,6,9-triazatricyclo[6.4.0.0^[2,6]]dodeca-1(8),2,4,9,11-pentaen-7-yl]acetyl)piperidine-1-carboxylate using Method J. MS: m/z=282.95 [M+H]$^+$.

Method U:

2,2-Dimethyl-1-[4-(2-[4,6,9-triazatricyclo[6.4.0.0^[2,6]]dodeca-1(8),2,4,9,11-pentaen-7-yl]acetyl) piperidin-1-yl]propan-1-one At room temperature, to a solution of 1-(piperidin-4-yl)-2-[4,6,9-triazatricyclo[6.4.0.0^[2,6]]dodeca-1(8),2,4,9,11-pentaen-7-yl]ethan-1-one (300 mg, 1.06 mmol) in DMF (8 mL) was added 2,2-dimethylpropanoic acid (119 mg, 1.21 mmol), HATU (485 mg, 1.35 mmol) and DIPEA (165 mg, 1.35 mmol) successively. The resulting mixture was stirred at room temperature for 16 h. Then the reaction mixture was diluted with water (40 mL) and extracted with DCM (40 mL×3). The organic phases were combined, washed with brine and dried over Na$_2$SO$_4$. The solvent was removed under reduced pressure, and the residue was purified by flash chromatography eluting with MeOH in DCM (2% to 8% gradient) to yield 2,2-dimethyl-1-[4-(2-[4,6,9-triazatricyclo[6.4.0.0^[2,6]]dodeca-1(8),2,4,9,11-pentaen-7-yl]acetyl)piperidin-1-yl]propan-1-one (260 mg, 67%) as light yellow solid. MS: m/z=367.0 [M+H]$^+$.

1-[4-[1-Hydroxy-2-[4,6,9-triazatricyclo[6.4.0.0^[2,6]]dodeca-1(8),2,4,9,11-pentaen-7-yl]ethyl]piperidin-1-yl]-2,2-dimethylpropan-1-one 1-[4-[1-Hydroxy-2-[4,6,9-triazatricyclo[6.4.0.0^[2,6]]dodeca-1(8),2,4,9,11-pentaen-7-yl]ethyl]piperidin-1-yl]-2,2-dimethylpropan-1-one was prepared from 2,2-dimethyl-1-[4-(2-[4,6,9-triazatricyclo[6.4.0.0^[2,6]]dodeca-1(8),2,4,9,11-pentaen-7-yl]acetyl)piperidin-1-yl]propan-1-one using Method D. Four enantiomeric products were obtained by the separation on chiral prep-HPLC under the following conditions: CHIRALPAK-AD-H-SL001, 20×250 mm, 5 μm; mobile phase, iPrOH in hexane, 30% isocratic in 16 min; Detector, UV 254/220 nm.

Compound 88a:

(18 mg, 10.4%, light yellow solid, single stereoisomer), HPLC: 99.1% purity, RT=1.14 min. MS: m/z=369.15 [M+H]$^+$. $^1$H NMR (300 MHz, CD$_3$OD, ppm) δ=8.37 (d, J=4.2 Hz, 1H), 8.06 (s, 1H), 7.97 (d, J=7.8 Hz, 1H), 7.37 (dd, J=7.8, 5.1 Hz, 1H), 7.25 (s, 1H), 5.34 (t, J=5.7 Hz, 1H), 4.45-4.40 (m, 2H), 3.87-3.83 (m, 1H), 2.81-2.73 (m, 2H), 2.37-2.30 (m, 1H), 2.11-2.01 (m, 1H), 1.87-1.83 (m, 1H), 1.68-1.58 (m, 2H), 1.30-1.23 (m, 11H);

Compound 88b:

(7.4 mg, 4.3%, light yellow solid, single stereoisomer) HPLC: 98.4% purity, RT=2.01 min. MS: m/z=369.2 [M+H]$^+$. $^1$H NMR (400 MHz, CD$_3$OD, ppm) δ=8.43 (dd, J=5.2, 1.6 Hz, 1H), 8.07-8.05 (m, 2H), 7.44 (dd, J=7.6, 5.2 Hz, 1H), 7.33 (s, 1H), 5.51 (dd, J=9.6, 3.6 Hz, 1H), 4.52-4.44 (m, 2H), 3.76-3.73 (m, 1H), 2.83-2.78 (m, 2H), 2.49-2.43 (m, 1H), 1.98-1.84 (m, 2H), 1.72-1.69 (m, 2H), 1.31-1.28 (m, 11H);

Compound 88c:

(16 mg, 9.2%, light yellow solid, single stereoisomer), HPLC: 97.1% purity, RT=1.49 min. MS: m/z=369.15 [M+H]$^+$. $^1$H NMR (400 MHz, CD$_3$OD, ppm) δ=8.42 (d, J=5.2, 1.2 Hz, 1H), 8.11 (s, 1H), 8.02 (dd, J=7.6, 1.2 Hz, 1H), 7.42 (dd, J=7.6, 5.2 Hz, 1H), 7.30 (s, 1H), 5.39 (t, J=5.6 Hz, 1H), 4.50-4.47 (m, 2H), 3.90-3.87 (m, 1H), 2.82-2.78 (m, 2H), 2.41-2.37 (m, 1H), 2.13-2.07 (m, 1H), 1.92-1.89 (m, 1H), 1.70-1.63 (m, 2H), 1.31-1.27 (m, 11H);

Compound 88d:

(8.1 mg, 4.7%, light yellow solid, single stereoisomer) HPLC: 98.8% purity, RT=1.13 min. MS: m/z=369.15 [M+H]$^+$. $^1$H NMR (300 MHz, CD$_3$OD, ppm) δ=8.37 (dd, J=5.1, 1.2 Hz, 1H), 8.02-8.00 (m, 2H), 7.39 (dd, J=7.8, 5.1 Hz, 1H), 7.28 (s, 1H), 5.46 (dd, J=9.6, 3.9 Hz, 1H), 4.48-4.38 (m, 2H), 3.70-3.67 (m, 1H), 2.80-2.72 (m, 2H), 2.46-2.37 (m, 1H), 1.92-1.79 (m, 2H), 1.66-1.63 (m, 2H), 1.37-1.20 (m, 11H).

Example 89: Synthesis of (2S)-2-amino-1-(4-fluoro-4-[2-[5H-imidazo[4,3-a]isoindol-5-yl]ethyl]piperidin-1-yl)-3-methylbutan-1-one (89a, b)

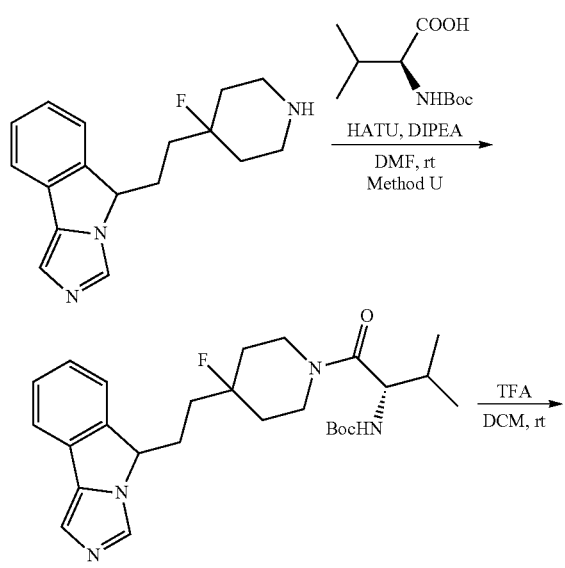

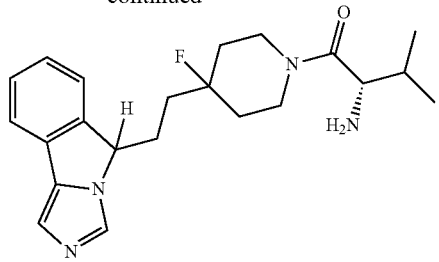

Compound 89a, b tert-Butyl N-[1-[4-fluoro-4-(2-[5H-imidazo[4,3-a]isoindol-5-yl]ethyl)piperidin-1-yl]-3-methyl-1-oxobutan-2-yl]carbamate tert-Butyl N-[1-[4-fluoro-4-(2-[5H-imidazo[4,3-a]isoindol-5-yl]ethyl)piperidin-1-yl]-3-methyl-1-oxobutan-2-yl]carbamate (125 mg, 68%) was prepared from 4-fluoro-4-(2-[5H-imidazo[4,3-a]isoindol-5-yl]ethyl)piperidine and (S)-2-[[(tert-butoxy)carbonyl]amino]-3-methylbutanoic acid using Method U. MS: m/z=485.25 [M+H]$^+$.

(2S)-2-Amino-1-(4-fluoro-4-[2-[5H-imidazo[4,3-a]isoindol-5-yl]ethyl]piperidin-1-yl)-3-methylbutan-1-one At room temperature, to a solution of tert-butyl N-[(2S)-1-[4-fluoro-4-(2-[5H-imidazo[4,3-a]isoindol-5-yl]ethyl)piperidin-1-yl]-3-methyl-1-oxobutan-2-yl]carbamate (100 mg, 0.21 mmol) in DCM (6 mL) was added TFA (2 mL) slowly. The resulting mixture was stirred at room temperature for 1 h. Then the reaction mixture was neutralized with Sat. NaHCO$_3$ solution and extracted with DCM (30 mL×3). The organic phases were combined, washed with brine and dried over Na$_2$SO$_4$. The solvent was removed under reduced pressure and the residue was purified by flash chromatography eluting with MeOH in DCM (2% to 8% gradient). Then two enantiomeric products were obtained by the separation on chiral prep-HPLC under the following conditions: Chiralpak IA, 20×250 mm, 5 μm; mobile phase, EtOH in hexane (with 0.2% DEA), 50% isocratic in 27 min; Detector, UV 254/220 nm.

Compound 89a:

(12 mg, 15%, white solid, single stereoisomer), HPLC: 96.5% purity, RT=2.36 min. MS: m/z=385.25 [M+H]$^+$. $^1$H NMR (400 MHz, CD$_3$OD, ppm) δ=7.95 (s, 1H), 7.63 (d, J=7.6 Hz, 1H), 7.51 (d, J=7.6 Hz, 1H), 7.45-7.41 (m, 1H), 7.36-7.33 (m, 1H), 7.17 (s, 1H), 5.47 (t, J=4.8 Hz, 1H), 4.40-4.29 (m, 1H), 3.84-3.80 (m, 1H), 3.63 (br s, 1H), 3.36-3.32 (m, 1H), 2.99-2.90 (m, 1H), 2.47-2.41 (m, 1H), 2.27-2.20 (m, 1H), 1.88-1.80 (m, 3H), 1.69-1.23 (m, 4H), 0.96 (d, J=6.8 Hz, 3H), 0.90 (d, J=6.8 Hz, 3H);

Compound 89b:

(10 mg, 12%, white solid, single stereoisomer) HPLC: 96.8% purity, RT=2.35 min. MS: m/z=385.25 [M+H]$^+$. $^1$H NMR (400 MHz, CD$_3$OD, ppm) δ=7.95 (s, 1H), 7.63 (d, J=7.6 Hz, 1H), 7.51 (d, J=7.6 Hz, 1H), 7.45-7.41 (m, 1H), 7.36-7.33 (m, 1H), 7.17 (s, 1H), 5.47 (t, J=4.8 Hz, 1H), 4.40-4.29 (m, 1H), 3.84-3.80 (m, 1H), 3.63 (br s, 1H), 3.36-3.32 (m, 1H), 2.99-2.90 (m, 1H), 2.47-2.41 (m, 1H), 2.27-2.20 (m, 1H), 1.88-1.80 (m, 3H), 1.69-1.23 (m, 4H), 0.96 (d, J=6.8 Hz, 3H), 0.90 (d, J=6.8 Hz, 3H).

Example 90: Synthesis of (2S)-2-amino-1-(4-fluoro-4-[2-[6-fluoro-5H-imidazo[4,3-a]isoindol-5-yl]ethyl]piperidin-1-yl)-3-methylbutan-1-one (90 a, b)

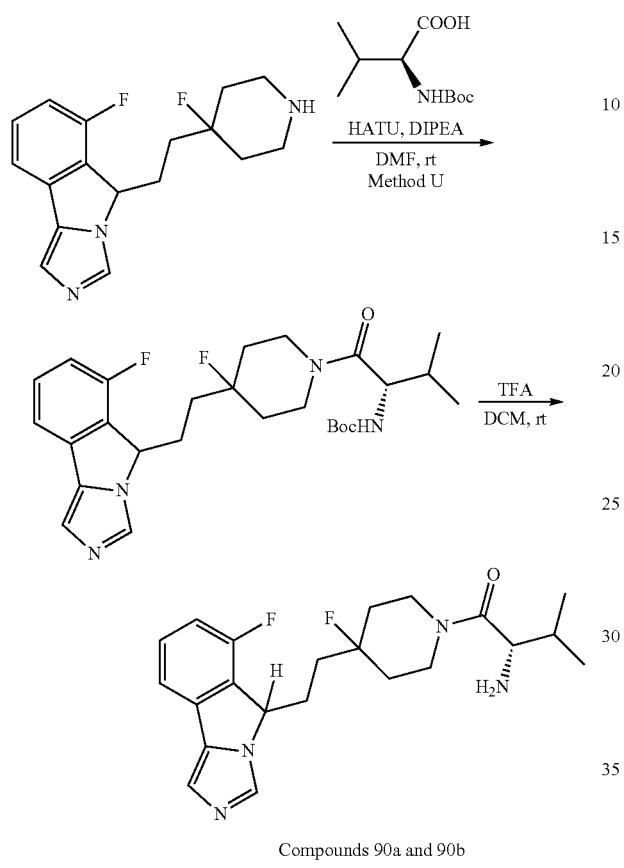

Compounds 90a and 90b tert-Butyl N-[1-[4-fluoro-4-(2-[6-fluoro-5H-imidazo[4,3-a]isoindol-5-yl]ethyl)piperidin-1-yl]-3-methyl-1-oxobutan-2-yl]carbamate tert-Butyl N-[1-[4-fluoro-4-(2-[6-fluoro-5H-imidazo[4,3-a]isoindol-5-yl]ethyl)piperidin-1-yl]-3-methyl-1-oxobutan-2-yl]carbamate (120 mg, 65%) was prepared from 4-fluoro-4-(2-[6-fluoro-5H-imidazo[4,3-a]isoindol-5-yl]ethyl)piperidine and (S)-2-[[(tert-butoxy)carbonyl]amino]-3-methylbutanoic acid using Method U.

(2S)-2-Amino-1-(4-fluoro-4-[2-[6-fluoro-5H-imidazo[4,3-a]isoindol-5-yl]ethyl]piperidin-1-yl)-3-methylbutan-1-one At room temperature, to a solution of tert-butyl N-[(2S)-1-[4-fluoro-4-(2-[6-fluoro-5H-imidazo[4,3-a]isoindol-5-yl]ethyl)piperidin-1-yl]-3-methyl-1-oxobutan-2-yl]carbamate (100 mg, 0.20 mmol) in DCM (6 mL) was added TFA (2 mL) slowly. The resulting mixture was stirred at room temperature for 1 h. Then the reaction mixture was neutralized with sat. NaHCO₃ solution and extracted with DCM (30 mL×3). The organic phases were combined, washed with brine and dried over Na₂SO₄. The solvent was removed under reduced pressure, and the residue was purified by flash chromatography eluting with MeOH in DCM (2% to 8% gradient). Then two enantiomeric products were obtained by the separation on chiral prep-HPLC under the following conditions: Chiralpak IA, 20×250 mm, 5 μm; mobile phase, EtOH in hexane (with 0.2% DEA), 20% isocratic in 32 min; Detector, UV 254/220 nm.

Compound 90a:

(10 mg, 12.5%, white solid, single stereoisomer), HPLC: 99.98% purity, RT=1.06 min. MS: m/z=403.15 [M+H]⁺. ¹H NMR (300 MHz, CD₃OD, ppm) δ=7.97 (s, 1H), 7.46-7.42 (m, 2H), 7.20 (s, 1H), 7.09-7.01 (s, 1H), 5.67 (t, J=4.2 Hz, 1H), 4.38-4.29 (m, 1H), 3.82-3.77 (m, 1H), 3.63 (br s, 1H), 3.38-3.30 (m, 1H), 2.98-2.87 (m, 1H), 2.55-2.44 (m, 1H), 2.35-2.25 (m, 1H), 1.86-1.79 (m, 3H), 1.69-1.20 (m, 4H), 0.88 (d, J=6.6 Hz, 3H), 0.82 (d, J=6.9 Hz, 3H);

Compound 90b:

(9.3 mg, 11.6%, white solid, single stereoisomer) HPLC: 99.6% purity, RT=1.07 min. MS: m/z=403.15 [M+H]⁺. ¹H NMR (300 MHz, CD₃OD, ppm) δ=7.98 (s, 1H), 7.46-7.42 (m, 2H), 7.22 (s, 1H), 7.09-7.01 (s, 1H), 5.67 (t, J=4.2 Hz, 1H), 4.38-4.29 (m, 1H), 3.82-3.77 (m, 1H), 3.63 (br s, 1H), 3.38-3.30 (m, 1H), 2.98-2.87 (m, 1H), 2.55-2.44 (m, 1H), 2.35-2.25 (m, 1H), 1.86-1.79 (m, 3H), 1.69-1.20 (m, 4H), 0.88 (d, J=6.6 Hz, 3H), 0.82 (d, J=6.9 Hz, 3H).

Example 91: Synthesis of 6-chloro-5-(2-[6-fluorospiro[2.5]octan-6-yl]ethyl)-5H-imidazo[4,3-a]isoindole (91a, b)

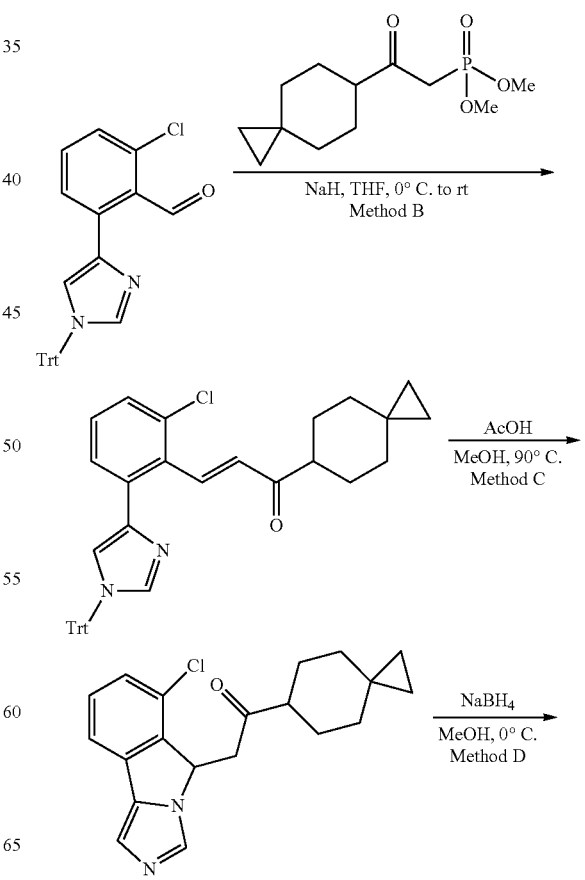

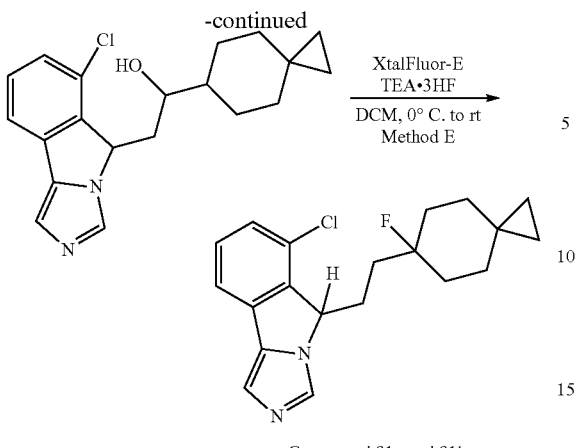

Compound 91a and 91b

6-Chloro-5-(2-[6-fluorospiro[2.5]octan-6-yl]ethyl)-5H-imidazo[4,3-a]isoindole

6-Chloro-5-(2-[6-fluorospiro[2.5]octan-6-yl]ethyl)-5H-imidazo[4,3-a]isoindole was prepared from 2-chloro-6-[1-(triphenylmethyl)-1H-imidazol-4-yl]benzaldehyde and dimethyl (2-oxo-2-[spiro[2.5]octan-6-yl]ethyl)phosphonate using Method B, C, D, and E. Two enantiomeric products were obtained by the separation on chiral prep-HPLC under the following conditions: Phenomenex Lux 5µ Cellulose-4, AXIA Packed, 21.2×250 mm, 5 µm; mobile phase, iPrOH in hexane, 30% isocratic in 13 min; Detector, UV 254/220 nm.

Compound 91a:

(13 mg, 7% for four steps, light yellow oil, single stereoisomer), HPLC: 98.6% purity, RT=1.34 min. MS: m/z=345.05 [M+H]$^+$. $^1$H NMR (400 MHz, CD$_3$OD, ppm) δ=7.99 (s, 1H), 7.60 (d, J=7.6 Hz, 1H), 7.44 (t, J=8.0 Hz, 1H), 7.33 (d, J=8.0 Hz, 1H), 7.24 (s, 1H), 5.63 (t, J=4.0 Hz, 1H), 2.60-2.49 (m, 2H), 1.85-1.73 (m, 4H), 1.56-1.41 (m, 2H), 1.20-0.98 (m, 2H), 0.82-0.79 (m, 2H), 0.30-0.19 (m, 4H);

Compound 91b:

(12 mg, 6.4% for four steps, light yellow oil, single stereoisomer) HPLC: 98.2% purity, RT=1.31 min. MS: m/z=345.05 [M+H]$^+$. $^1$H NMR (400 MHz, CD$_3$OD, ppm) δ=7.99 (s, 1H), 7.60 (d, J=7.6 Hz, 1H), 7.44 (t, J=8.0 Hz, 1H), 7.33 (d, J=8.0 Hz, 1H), 7.24 (s, 1H), 5.63 (t, J=4.0 Hz, 1H), 2.60-2.49 (m, 2H), 1.85-1.73 (m, 4H), 1.56-1.41 (m, 2H), 1.20-0.98 (m, 2H), 0.82-0.79 (m, 2H), 0.30-0.19 (m, 4H).

Example 92: Synthesis of 1-(oxan-4-yl)-2-[4,6,9-triazatricyclo[6.4.0.0ˆ[2,6]]dodeca-1(8),2,4,9,11-pentaen-7-yl]ethan-1-ol (92a, b, c, d)

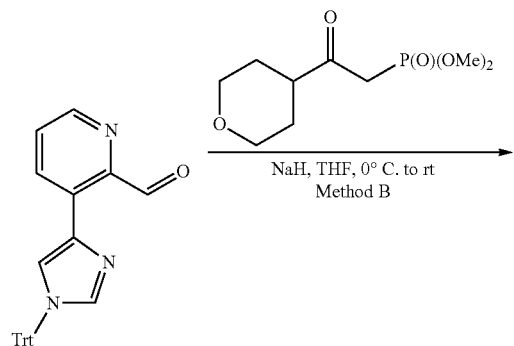

Compounds 92a, b, c, d 1-(Oxan-4-yl)-2-[4,6,9-triazatricyclo[6.4.0.0ˆ[2,6]]dodeca-1(8),2,4,9,11-pentaen-7-yl]ethan-1-ol 1-(Oxan-4-yl)-2-[4,6,9-triazatricyclo[6.4.0.0ˆ[2,6]]dodeca-1(8),2,4,9,11-pentaen-7-yl]ethan-1-ol was prepared from 3-[1-(triphenylmethyl)-1H-imidazol-4-yl]pyridine-2-carbaldehyde and dimethyl [2-(oxan-4-yl)-2-oxoethyl]phosphonate using Method B, C, and D. Four enantiomeric products were obtained by the separation on chiral prep-HPLC under the following conditions: Phenomenex Lux 5µ Cellulose-4, AXIA Packed, 21.2×250 mm, 5 µm; mobile phase, EtOH in hexane, 50% isocratic in 28 min; Detector, UV 254/220 nm.

Compound 92a:

(20 mg, 10% for three steps, light yellow solid, single stereoisomer), HPLC: 99.7% purity, RT=0.62 min. MS: m/z=286.05 [M+H]$^+$. $^1$H NMR (300 MHz, CD$_3$OD, ppm) δ=8.38 (d, J=4.8 Hz, 1H), 8.12 (s, 1H), 7.98 (d, J=7.8 Hz, 1H), 7.37 (dd, J=7.5, 4.8 Hz, 1H), 7.28 (s, 1H), 5.36 (t, J=5.7 Hz, 1H), 3.97-3.89 (m, 2H), 3.80-3.78 (m, 1H), 3.39-3.31 (m, 2H), 2.38-2.32 (m, 1H), 2.09-1.98 (m, 1H), 1.73-1.70 (m, 1H), 1.60-1.33 (m, 4H);

Compound 92b:

(20.9 mg, 10.5% for three steps, light yellow solid, single stereoisomer) HPLC: 99.6% purity, RT=0.62 min. MS: m/z=286.0 [M+H]$^+$. $^1$H NMR (300 MHz, CD$_3$OD, ppm) δ=8.38 (d, J=4.8 Hz, 1H), 8.13 (s, 1H), 7.98 (d, J=7.8 Hz, 1H), 7.37 (dd, J=7.5, 4.8 Hz, 1H), 7.29 (s, 1H), 5.36 (t, J=5.7 Hz, 1H), 3.97-3.89 (m, 2H), 3.80-3.78 (m, 1H), 3.39-3.31 (m, 2H), 2.38-2.32 (m, 1H), 2.09-1.98 (m, 1H), 1.73-1.70 (m, 1H), 1.60-1.33 (m, 4H);

Compound 92c:

(6.4 mg, 3.2% for three steps, light yellow solid, single stereoisomer), HPLC: 98.0% purity, RT=0.85 min. MS: m/z=286.05 [M+H]$^+$. $^1$H NMR (300 MHz, CD$_3$OD, ppm)

δ=8.39 (dd, J=5.1, 1.2 Hz, 1H), 8.09 (s, 1H), 8.02 (dd, J=7.8, 1.2 Hz, 1H), 7.40 (dd, J=7.8, 5.1 Hz, 1H), 7.33 (s, 1H), 5.48 (dd, J=9.3, 3.6 Hz, 1H), 3.97-3.87 (m, 2H), 3.65-3.61 (m, 1H), 3.39-3.31 (m, 2H), 2.42-2.36 (m, 1H), 1.87-1.74 (m, 2H), 1.62-1.32 (m, 4H);

Compound 92d:

(6.4 mg, 3.2% for three steps, light yellow solid, single stereoisomer) HPLC: 98.2% purity, RT=0.61 min. MS: m/z=286.0 [M+H]$^+$. $^1$H NMR (300 MHz, CD$_3$OD, ppm) δ=8.39 (dd, J=5.1, 1.2 Hz, 1H), 8.10 (s, 1H), 8.02 (dd, J=7.8, 1.2 Hz, 1H), 7.40 (dd, J=7.8, 5.1 Hz, 1H), 7.33 (s, 1H), 5.48 (dd, J=9.3, 3.6 Hz, 1H), 3.97-3.87 (m, 2H), 3.65-3.61 (m, 1H), 3.39-3.31 (m, 2H), 2.42-2.36 (m, 1H), 1.87-1.74 (m, 2H), 1.62-1.32 (m, 4H).

Example 93: Synthesis of 7-[2-(4-fluorooxan-4-yl)ethyl]-4,6,9-triazatricyclo[6.4.0.0^[2,6]]dodeca-1(8),2,4,9,11-pentaene (93a, b)

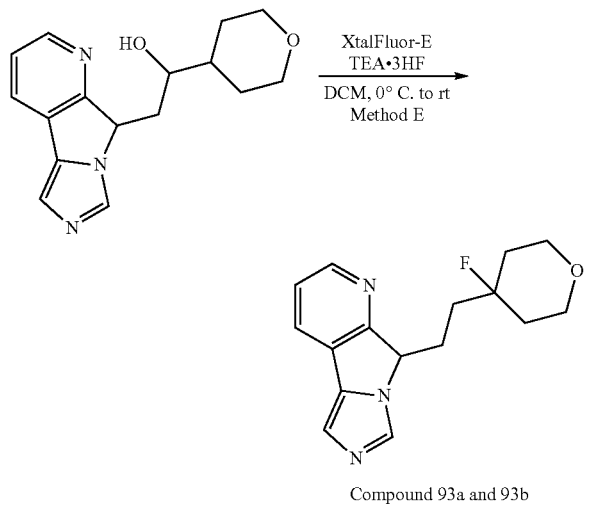

Compound 93a and 93b

7-[2-(4-Fluorooxan-4-yl)ethyl]-4,6,9-triazatricyclo [6.4.0.0^[2,6]]dodeca-1(8),2,4,9,11-pentaene 7-[2-(4-Fluorooxan-4-yl)ethyl]-4,6,9-triazatricyclo [6.4.0.0^[2,6]]dodeca-1(8),2,4,9,11-pentaene was prepared from 1-(oxan-4-yl)-2-[4,6,9-triazatricyclo[6.4.0.0^[2,6]]dodeca-1(8),2,4,9,11-pentaen-7-yl]ethan-1-ol using Method E. Two enantiomeric products were obtained by the separation on chiral prep-HPLC under the following conditions: Phenomenex Lux 5µ Cellulose-4, AXIA Packed, 21.2×250 mm, 5 µm; mobile phase, iPrOH in hexane (with 0.2% DEA), 50% isocratic in 42 min; Detector, UV 254/220 nm.

Compound 93a:

(20 mg, 8.5%, yellow oil, single stereoisomer), HPLC: 99.3% purity, RT=0.70 min. MS: m/z=288.05 [M+H]$^+$. $^1$H NMR (400 MHz, CD$_3$OD, ppm) δ=8.42 (d, J=5.2 Hz, 1H), 8.04-8.02 (m, 2H), 7.42 (dd, J=7.6, 5.2 Hz, 1H), 7.32 (s, 1H), 5.38 (t, J=5.2 Hz, 1H), 3.71-3.60 (m, 4H), 2.51-2.42 (m, 1H), 2.32-2.25 (m, 1H), 1.69-1.55 (m, 4H), 1.48-1.29 (m, 2H);

Compound 93b:

(20.9 mg, 8.9%, yellow oil, single stereoisomer) HPLC: 99.2% purity, RT=0.71 min. MS: m/z=288.05 [M+H]$^+$. $^1$H NMR (400 MHz, CD$_3$OD, ppm) δ=8.42 (d, J=5.2 Hz, 1H), 8.04-8.02 (m, 2H), 7.42 (dd, J=7.6, 5.2 Hz, 1H), 7.32 (s, 1H), 5.38 (t, J=5.2 Hz, 1H), 3.71-3.60 (m, 4H), 2.51-2.42 (m, 1H), 2.32-2.25 (m, 1H), 1.69-1.55 (m, 4H), 1.48-1.29 (m, 2H).

Example 94: Synthesis of 5-[2-(4-fluorooxan-4-yl)ethyl]-5H-imidazo[4,3-a]isoindole (94a, b)

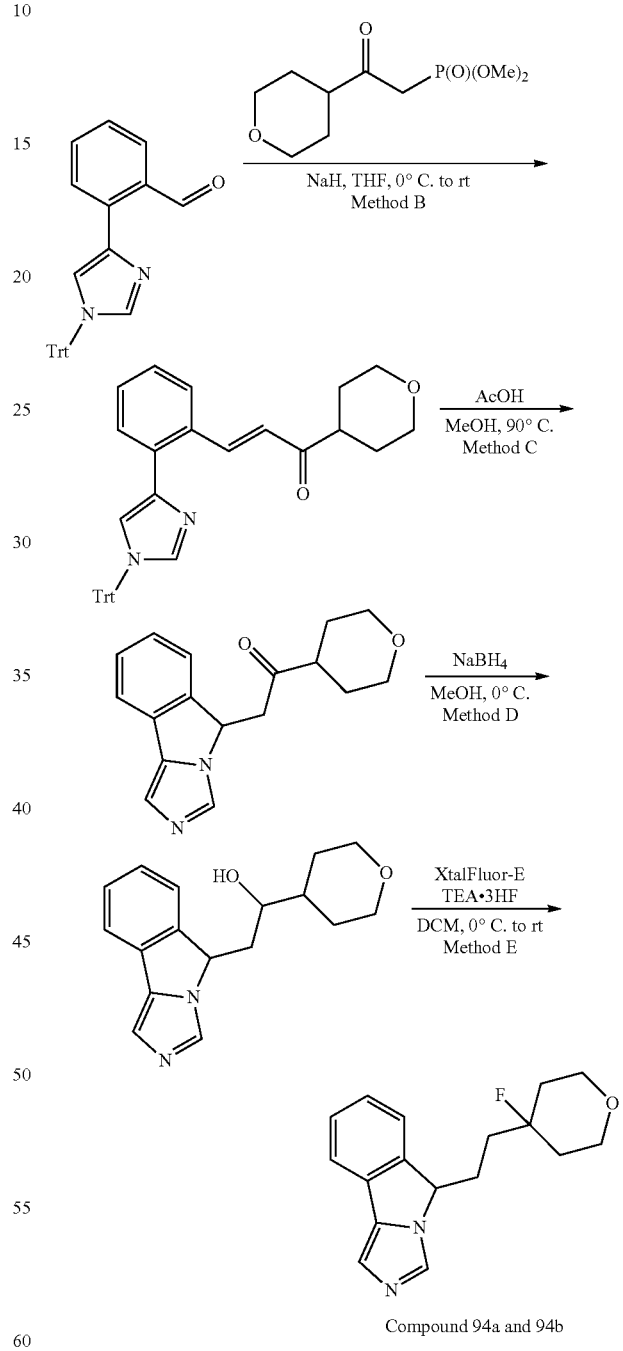

Compound 94a and 94b

5-[2-(4-Fluorooxan-4-yl)ethyl]-5H-imidazo[4,3-a]isoindole

5-[2-(4-Fluorooxan-4-yl)ethyl]-5H-imidazo[4,3-a]isoindole was prepared from 2-[1-(triphenylmethyl)-1H-imidazol-4-yl]benzaldehyde and dimethyl [2-(oxan-4-yl)-2-oxoethyl]phosphonate using Method B, C, D, and E. Two enantiomeric products were obtained by the separation on chiral prep-HPLC under the following conditions: CHIRALPAK-AD-H-SL001, 20×250 mm, 5 μm; mobile phase, iPrOH in hexane (with 0.1% IPA), 30% isocratic in 24 min; Detector, UV 254/220 nm.

Compound 94a:

(21 mg, 10.5%, yellow oil, single stereoisomer), HPLC: 99.97% purity, RT=1.20 min. MS: m/z=287.1 [M+H]$^+$. $^1$H NMR (400 MHz, CD$_3$OD, ppm) δ=7.92 (s, 1H), 7.61 (d, J=7.6 Hz, 1H), 7.49 (d, J=7.6 Hz, 1H), 7.41 (t, J=7.2 Hz, 1H), 7.35-7.31 (m, 1H), 7.16 (s, 1H), 5.44 (t, J=4.8 Hz, 1H), 3.71-3.60 (m, 4H), 2.43-2.36 (m, 1H), 2.22-2.17 (m, 1H), 1.68-1.52 (m, 4H), 1.37-1.20 (m, 2H);

Compound 94b:

(20 mg, 10%, yellow oil, single stereoisomer) HPLC: 99.8% purity, RT=1.21 min. MS: m/z=287.15 [M+H]$^+$. $^1$H NMR (400 MHz, CD$_3$OD, ppm) δ=7.92 (s, 1H), 7.61 (d, J=7.6 Hz, 1H), 7.49 (d, J=7.6 Hz, 1H), 7.41 (t, J=7.2 Hz, 1H), 7.35-7.31 (m, 1H), 7.15 (s, 1H), 5.44 (t, J=4.8 Hz, 1H), 3.71-3.60 (m, 4H), 2.43-2.36 (m, 1H), 2.22-2.17 (m, 1H), 1.68-1.52 (m, 4H), 1.37-1.20 (m, 2H).

Example 95: Synthesis of 6-fluoro-5-[2-(4-fluorooxan-4-yl)ethyl]-5H-imidazo[4,3-a]isoindole (95a, b)

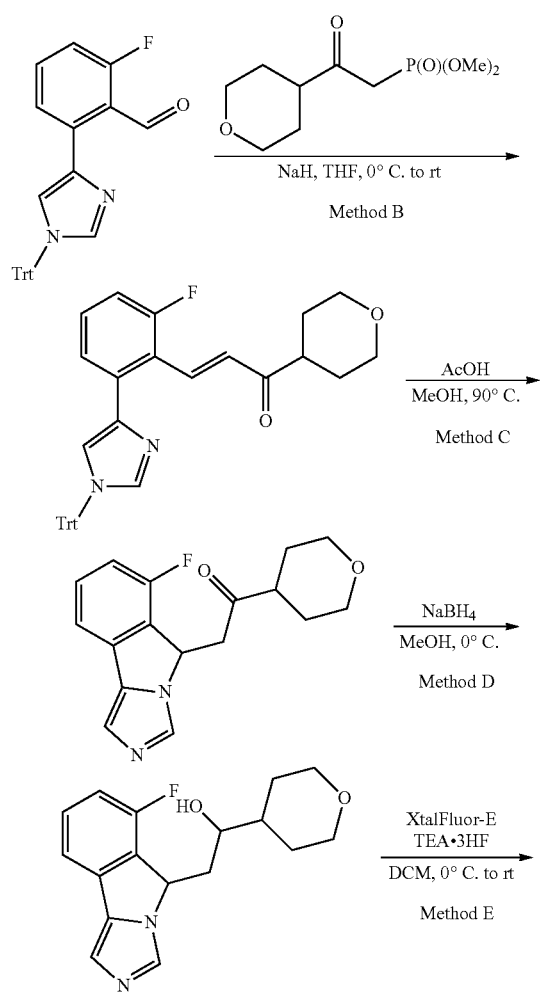

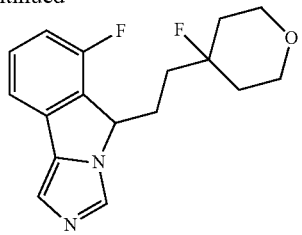

Compound 95a and 95b

6-Fluoro-5-[2-(4-fluorooxan-4-yl)ethyl]-5H-imidazo[4,3-a]isoindole

6-Fluoro-5-[2-(4-fluorooxan-4-yl)ethyl]-5H-imidazo[4,3-a]isoindole was prepared from 2-fluoro-6-[1-(triphenylmethyl)-1H-imidazol-4-yl]benzaldehyde and dimethyl [2-(oxan-4-yl)-2-oxoethyl]phosphonate using Method B, C, D, and E. Two enantiomeric products were obtained by the separation on chiral prep-HPLC under the following conditions: CHIRALPAK-AD-H-SL001, 20×250 mm, 5 μm; mobile phase, EtOH in hexane, 30% isocratic in 23 min; Detector, UV 254/220 nm.

Compound 95a:

(28 mg, 6.4%, yellow oil, single stereoisomer), HPLC: 99.7% purity, RT=0.71 min. MS: m/z=305.1 [M+H]$^+$. $^1$H NMR (400 MHz, CD$_3$OD, ppm) δ=7.94 (s, 1H), 7.45-7.42 (m, 2H), 7.19 (s, 1H), 7.07-7.02 (m, 1H), 5.65 (t, J=4.4 Hz, 1H), 3.70-3.59 (m, 4H), 2.51-2.42 (m, 1H), 2.30-2.23 (m, 1H), 1.66-1.51 (m, 4H), 1.32-1.24 (m, 2H);

Compound 95b:

(25 mg, 5.7%, yellow oil, single stereoisomer) HPLC: 99.9% purity, RT=0.90 min. MS: m/z=305.05 [M+H]$^+$. $^1$H NMR (400 MHz, CD$_3$OD, ppm) δ=7.94 (s, 1H), 7.45-7.42 (m, 2H), 7.20 (s, 1H), 7.07-7.02 (m, 1H), 5.65 (t, J=4.4 Hz, 1H), 3.70-3.59 (m, 4H), 2.51-2.42 (m, 1H), 2.30-2.23 (m, 1H), 1.66-1.51 (m, 4H), 1.32-1.24 (m, 2H).

Example 96: Synthesis of 6-chloro-5-[2-(4-fluorooxan-4-yl)ethyl]-5H-imidazo[4,3-a]isoindole (96a, b)

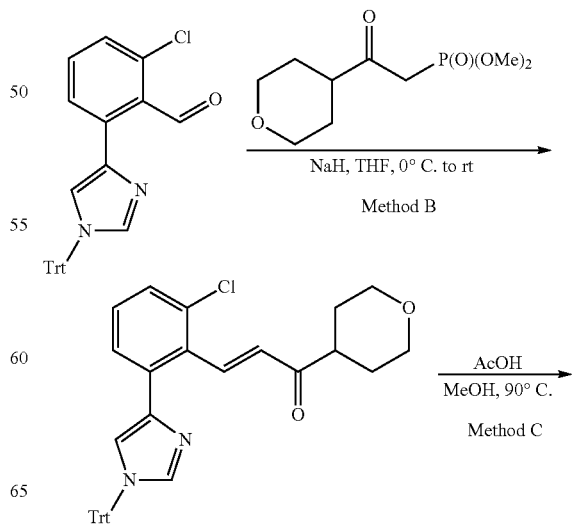

-continued

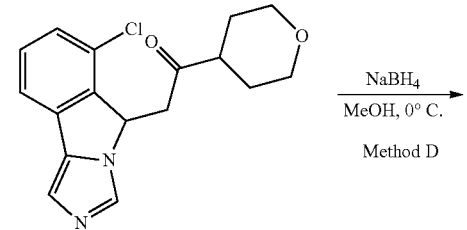

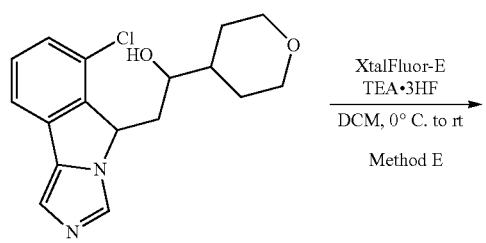

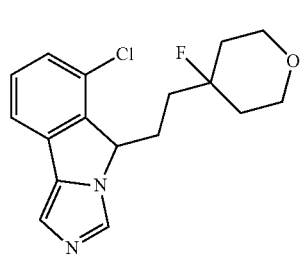

Compounds 96a and 96b

6-Chloro-5-[2-(4-fluorooxan-4-yl)ethyl]-5H-imidazo[4,3-a]isoindole

6-Chloro-5-[2-(4-fluorooxan-4-yl)ethyl]-5H-imidazo[4,3-a]isoindole was prepared from 2-chloro-6-[1-(triphenylmethyl)-1H-imidazol-4-yl]benzaldehyde and dimethyl [2-(oxan-4-yl)-2-oxoethyl]phosphonate using Method B, C, D, and E. Two enantiomeric products were obtained by the separation on chiral prep-HPLC under the following conditions: CHIRALPAK-AD-H-SL001, 20×250 mm, 5 μm; mobile phase, EtOH in hexane, 30% isocratic in 18 min; Detector, UV 254/220 nm.

Compound 96a:

(27 mg, 12%, yellow oil, single stereoisomer), HPLC: 99.8% purity, RT=0.96 min. MS: m/z=321.0 [M+H]$^+$. $^1$H NMR (400 MHz, CD$_3$OD, ppm) δ=7.98 (s, 1H), 7.55 (d, J=7.6 Hz, 1H), 7.40 (t, J=7.6 Hz, 1H), 7.29 (d, J=8.0 Hz, 1H), 7.20 (s, 1H), 5.58 (t, J=4.4 Hz, 1H), 3.69-3.58 (m, 4H), 2.53-2.49 (m, 2H), 1.61-1.47 (m, 4H), 1.19-0.98 (m, 2H);

Compound 96b:

(25 mg, 11.4%, yellow oil, single stereoisomer) HPLC: 99.7% purity, RT=0.95 min. MS: m/z=321.0 [M+H]$^+$. $^1$H NMR (400 MHz, CD$_3$OD, ppm) δ=7.98 (s, 1H), 7.55 (d, J=7.6 Hz, 1H), 7.40 (t, J=7.6 Hz, 1H), 7.29 (d, J=8.0 Hz, 1H), 7.20 (s, 1H), 5.58 (t, J=4.4 Hz, 1H), 3.69-3.58 (m, 4H), 2.53-2.49 (m, 2H), 1.61-1.47 (m, 4H), 1.19-0.98 (m, 2H).

Example 97: Synthesis of 7-[2-cyclohexyl-2-fluoroethyl]-4,6,9-triazatricyclo[6.4.0.0ˆ[2,6]]dodeca-1(8),2,4,9,11-pentaene (97a, b, c, d)

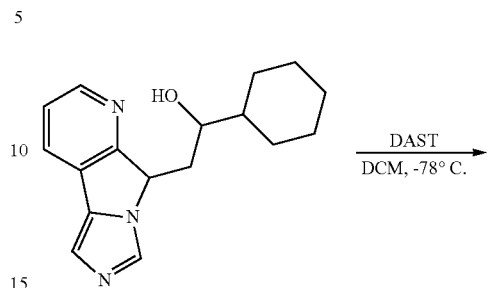

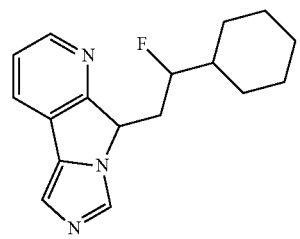

Compound 97a, b, c, d

7-[2-Cyclohexyl-2-fluoroethyl]-4,6,9-triazatricyclo[6.4.0.0ˆ[2,6]]dodeca-1(8),2,4,9,11-pentaene At −78° C., to a solution of 1-cyclohexyl-2-[4,6,9-triazatricyclo[6.4.0.0ˆ[2,6]]dodeca-1(8),2,4,9,11-pentaen-7-yl]ethan-1-ol (200 mg, 0.70 mmol) in DCM (5 mL) was added DAST (171 mg, 1.06 mmol) slowly. The resulting mixture was kept stirring at −78° C. for 30 min. Then the reaction mixture was quenched with H$_2$O (20 mL) and extracted with DCM (20 mL×2). The organic phases were combined, washed with brine and dried over Na$_2$SO$_4$. The solvent was removed under reduced pressure and the residue was purified by flash chromatography eluting with MeOH in DCM (1% to 5% gradient). Four enantiomeric products were obtained by the separation on chiral prep-HPLC under the following conditions: CHIRALPAK-AD-H-SL002, 20×250 mm, 5 μm; mobile phase, EtOH in hexane (with 0.1% DEA), 20% isocratic in 26 min; Detector, UV 254/220 nm.

Compound 97a:

(3.7 mg, 1.9%, yellow oil, single stereoisomer), HPLC: 97.5% purity, RT=2.01 min. MS: m/z=286.05 [M+H]$^+$. $^1$H NMR (400 MHz, CD$_3$OD, ppm) δ=8.42 (d, J=4.8 Hz, 1H), 8.04-8.01 (m, 2H), 7.43 (dd, J=7.6, 5.2 Hz, 1H), 7.31 (s, 1H), 5.45 (t, J=5.6 Hz, 1H), 4.72-4.55 (m, 1H), 2.61-2.47 (m, 1H), 2.40-2.31 (m, 1H), 1.88-1.85 (m, 1H), 1.79-1.76 (m, 2H), 1.70-1.67 (m, 2H), 1.61-1.51 (m, 2H), 1.31-1.06 (m, 5H);

Compound 97b:

(2.8 mg, 1.4%, yellow oil, single stereoisomer) HPLC: 99.7% purity, RT=1.39 min. MS: m/z=286.05 [M+H]$^+$. $^1$H NMR (400 MHz, CD$_3$OD, ppm) δ=8.44 (d, J=5.2 Hz, 1H), 8.07-8.05 (m, 2H), 7.45 (dd, J=7.6, 5.2 Hz, 1H), 7.33 (s, 1H), 5.49 (dd, J=8.8, 3.2 Hz, 1H), 4.53-4.37 (m, 1H), 2.81-2.70 (m, 1H), 2.17-2.02 (m, 1H), 1.93-1.90 (m, 1H), 1.79-1.75 (m, 2H), 1.70-1.58 (m, 3H), 1.31-1.04 (m, 5H);

Compound 97c:

(3.1 mg, 1.5%, yellow oil, single stereoisomer), HPLC: 99.0% purity, RT=2.00 min. MS: m/z=286.05 [M+H]$^+$. $^1$H NMR (400 MHz, CD$_3$OD, ppm) δ=8.42 (d, J=4.8 Hz, 1H), 8.04-8.01 (m, 2H), 7.43 (dd, J=7.6, 5.2 Hz, 1H), 7.31 (s, 1H), 5.45 (t, J=5.6 Hz, 1H), 4.72-4.55 (m, 1H), 2.61-2.47 (m, 1H), 2.40-2.31 (m, 1H), 1.88-1.85 (m, 1H), 1.79-1.76 (m, 2H), 1.70-1.67 (m, 2H), 1.61-1.51 (m, 2H), 1.31-1.06 (m, 5H);

Compound 97d:

(3.7 mg, 1.9%, yellow oil, single stereoisomer) HPLC: 99.9% purity, RT=1.97 min. MS: m/z=286.05 [M+H]⁺. ¹H NMR (400 MHz, CD₃OD, ppm) δ=8.44 (d, J=5.2 Hz, 1H), 8.07-8.05 (m, 2H), 7.45 (dd, J=7.6, 5.2 Hz, 1H), 7.33 (s, 1H), 5.49 (dd, J=8.8, 3.2 Hz, 1H), 4.53-4.37 (m, 1H), 2.81-2.70 (m, 1H), 2.17-2.02 (m, 1H), 1.93-1.90 (m, 1H), 1.79-1.75 (m, 2H), 1.70-1.58 (m, 3H), 1.31-1.04 (m, 5H).

Example 98: Synthesis of 5-[2-cyclohexyl-2-fluoroethyl]-6-fluoro-5H-imidazo[4,3-a]isoindole (98a, b)

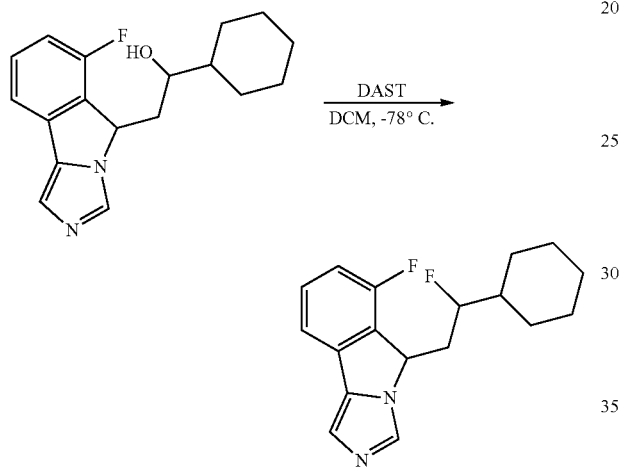

Compounds 98a and 98b

5-[2-Cyclohexyl-2-fluoroethyl]-6-fluoro-5H-imidazo[4,3-a]isoindole

At −78° C., to a solution of 1-cyclohexyl-2-[6-fluoro-5H-imidazo[4,3-a]isoindol-5-yl]ethan-1-ol (180 mg, 0.60 mmol) in DCM (5 mL) was added DAST (193 mg, 1.20 mmol) slowly. The resulting mixture was kept stirring at −78° C. for 30 min. Then the reaction mixture was quenched with H₂O (20 mL) and extracted with DCM (20 mL×2). The organic phases were combined, washed with brine and dried over Na₂SO₄. The solvent was removed under reduced pressure and the residue was purified by flash chromatography eluting with MeOH in DCM (1% to 5% gradient). Four enantiomeric products were obtained by the separation on chiral prep-HPLC under the following conditions: Phenomenex Lux 5µ Cellulose-4, AXIA Packed, 21.2×250 mm, 5 µm; mobile phase, iPrOH in hexane, 10% isocratic in 25 min; Detector, UV 254/220 nm.

Compound 98a:

(3.7 mg, 2.1%, yellow solid, single stereoisomer), HPLC: 99.4% purity, RT=1.23 min. MS: m/z=303.05 [M+H]⁺. ¹H NMR (300 MHz, CD₃OD, ppm) δ=7.92 (s, 1H), 7.44-7.42 (m, 2H), 7.16 (s, 1H), 7.06-7.00 (m, 1H), 5.67 (dd, J=8.1, 2.7 Hz, 1H), 4.41-4.20 (m, 1H), 2.73-2.60 (m, 1H), 2.18-1.98 (m, 1H), 1.83-1.79 (m, 1H), 1.75-1.43 (m, 5H), 1.31-0.97 (m, 5H);

Compound 98b:

(3.5 mg, 1.9%, yellow solid, single stereoisomer) HPLC: 99.9% purity, RT=1.24 min. MS: m/z=303.05 [M+H]⁺. ¹H NMR (300 MHz, CD₃OD, ppm) δ=7.91 (s, 1H), 7.44-7.42 (m, 2H), 7.16 (s, 1H), 7.06-7.00 (m, 1H), 5.67 (dd, J=8.1, 2.7 Hz, 1H), 4.41-4.20 (m, 1H), 2.73-2.60 (m, 1H), 2.18-1.98 (m, 1H), 1.83-1.79 (m, 1H), 1.75-1.43 (m, 5H), 1.31-0.97 (m, 5H).

Example 99: Synthesis of 4-[2-[6-chloro-5H-imidazo[4,3-a]isoindol-5-yl]ethyl]-4-fluorocyclohexane-1-carboxamide (99a, b, c, d)

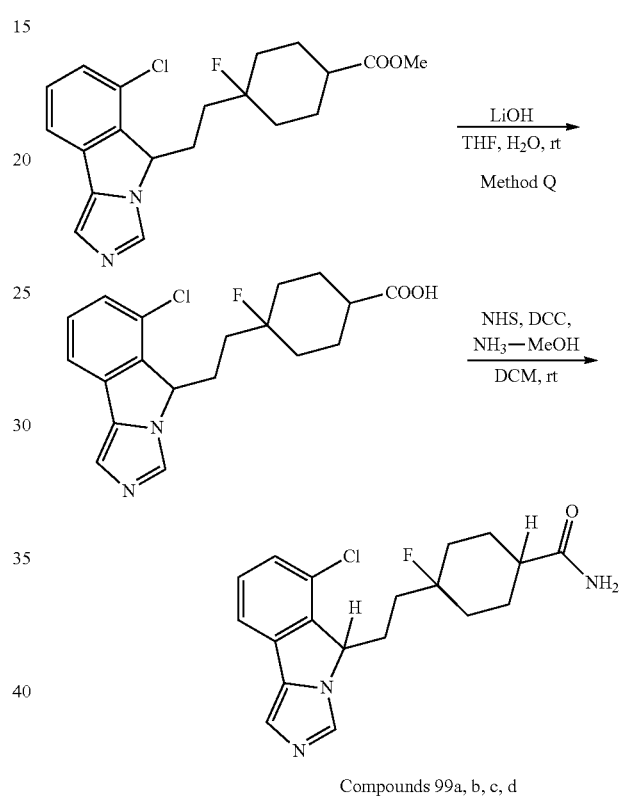

Compounds 99a, b, c, d 4-(2-[6-Chloro-5H-imidazo[4,3-a]isoindol-5-yl]ethyl)-4-fluorocyclohexane-1-carboxylic acid 4-(2-[6-Chloro-5H-imidazo[4,3-a]isoindol-5-yl]ethyl)-4-fluorocyclohexane-1-carboxylic acid (450 mg, 88%) was prepared from methyl 4-(2-[6-chloro-5H-imidazo[4,3-a]isoindol-5-yl]ethyl)-4-fluorocyclohexane-1-carboxylate using Method Q. MS: m/z=363.0 [M+H]⁺.

4-[2-[6-Chloro-5H-imidazo[4,3-a]isoindol-5-yl]ethyl]-4-fluorocyclohexane-1-carboxamide At room temperature, to a solution of 4-(2-[6-chloro-5H-imidazo[4,3-a]isoindol-5-yl]ethyl)-4-fluorocyclohexane-1-carboxylic acid (200 mg, 0.55 mmol) in DCM (5 mL) was added 1-hydroxypyrrolidine-2,5-dione (76 mg, 0.66 mmol) and DCC (142 mg, 0.66 mmol) slowly. The resulting mixture was stirred at room temperature for 30 min, and then was added by NH₃-MeOH (7 M, 0.8 mL) in one batch. The reaction mixture was kept stirring for 16 h at room temperature. Then the reaction mixture was diluted with H₂O (30 mL) and extracted with DCM (40 mL×4). The organic phases were combined, washed with brine and dried over Na$_2$SO$_4$. The solvent was removed under reduced pressure and the residue was purified by flash chromatography eluting with MeOH in DCM (5% to 10% gradient). Four enantiomeric products were obtained by the separation on chiral prep-HPLC under the following conditions: Phenomenex Lux 5μ Cellulose-4 AXIA Packed, 21.2×250 mm, 5 μm; mobile phase, EtOH in hexane, 50% isocratic in 32 min; Detector, UV 254/220 nm.

Compound 99a:

(5.4 mg, 2.7%, white solid, single stereoisomer) HPLC: 99.9% purity, RT=1.70 min. MS: m/z=362.1 [M+H]$^+$. $^1$H NMR (300 MHz, CD$_3$OD, ppm) δ=7.99 (s, 1H), 7.59 (d, J=7.2 Hz, 1H), 7.43 (t, J=7.8 Hz, 1H), 7.32 (d, J=7.8 Hz, 1H), 7.22 (s, 1H), 5.62 (t, J=3.9 Hz, 1H), 2.53-2.48 (m, 2H), 2.34-2.28 (m, 1H), 1.82-1.73 (m, 4H), 1.65-1.41 (m, 4H), 1.32-1.03 (m, 2H);

Compound 99b:

(6 mg, 3%, white solid, single stereoisomer) HPLC: 99.8% purity, RT=1.24 min. MS: m/z=362.05 [M+H]$^+$. $^1$H NMR (300 MHz, CD$_3$OD, ppm) δ=7.98 (s, 1H), 7.59 (d, J=7.2 Hz, 1H), 7.43 (t, J=7.8 Hz, 1H), 7.32 (d, J=7.8 Hz, 1H), 7.22 (s, 1H), 5.62 (t, J=3.9 Hz, 1H), 2.53-2.48 (m, 2H), 2.34-2.28 (m, 1H), 1.82-1.73 (m, 4H), 1.65-1.41 (m, 4H), 1.32-1.03 (m, 2H);

Compound 99c:

(14 mg, 7%, white solid, single stereoisomer) HPLC: 99.8% purity, RT=1.19 min. MS: m/z=362.05 [M+H]$^+$. $^1$H NMR (300 MHz, CD$_3$OD, ppm) δ=7.97 (s, 1H), 7.58 (d, J=7.2 Hz, 1H), 7.43 (t, J=7.8 Hz, 1H), 7.31 (d, J=8.1 Hz, 1H), 7.22 (s, 1H), 5.62 (t, J=4.2 Hz, 1H), 2.57-2.50 (m, 2H), 2.18-2.11 (m, 1H), 1.88-1.67 (m, 6H), 1.41-1.19 (m, 2H), 1.11-0.96 (m, 2H);

Compound 99d:

(19 mg, 9.5%, white solid, single stereoisomer) HPLC: 99.6% purity, RT=1.23 min. MS: m/z=362.2 [M+H]$^+$. $^1$H NMR (400 MHz, CD$_3$OD, ppm) δ=7.97 (s, 1H), 7.57 (d, J=7.6 Hz, 1H), 7.42 (t, J=7.6 Hz, 1H), 7.31 (d, J=8.0 Hz, 1H), 7.21 (s, 1H), 5.61 (t, J=4.0 Hz, 1H), 2.57-2.52 (m, 2H), 2.17-2.12 (m, 1H), 1.87-1.65 (m, 6H), 1.38-1.22 (m, 2H), 1.10-0.96 (m, 2H).

Example 100: Synthesis of 7-[2-[1-fluoro-4-[(piperidin-1-yl)carbonyl]cyclohexyl]ethyl]-4,6,9-triazatricyclo[6.4.0.0^[2,6]]dodeca-1(8),2,4,9,11-pentaene (100a, b)

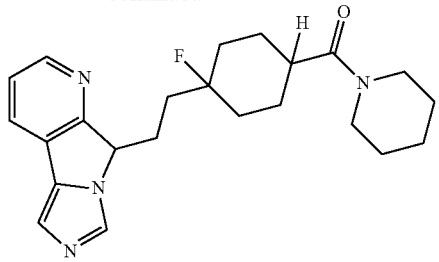

Compound 100a, b

7-[2-[1-Fluoro-4-[(piperidin-1-yl)carbonyl]cyclohexyl]ethyl]-4,6,9-triazatricyclo[6.4.0.0^[2,6]]dodeca-1(8),2,4,9,11-pentaene 7-[2-[1-Fluoro-4-[(piperidin-1-yl)carbonyl]cyclohexyl]ethyl]-4,6,9-triazatricyclo[6.4.0.0^[2,6]]dodeca-1 (8),2,4,9,11-pentaene was prepared from 4-fluoro-4-(2-[4,6,9-triazatricyclo[6.4.0.0^[2,6]]dodeca-1(8),2,4,9,11-pentaen-7-yl]ethyl)cyclohexane-1-carboxylic acid and piperidine using Method U. Two pairs of enantiomeric products were obtained by the separation on prep-HPLC under the following conditions: XBridge C18 OBD Prep Column, 19×250 mm, 5 μm; mobile phase, MeCN in water (with 10 mM NH$_4$HCO$_3$); 30% to 34% gradient in 15 min; Detector, UV 254/220 nm.

Compound 100a:

(16 mg, 4.5%, yellow oil, mixture of two stereoisomers) HPLC: 98.2% purity, RT=1.26 min. MS: m/z=397.15 [M+H]$^+$. $^1$H NMR (400 MHz, CD$_3$OD, ppm) δ=8.42 (d, J=4.8 Hz, 1H), 8.04-8.02 (m, 2H), 7.42 (dd, J=7.6, 5.2 Hz, 1H), 7.31 (s, 1H), 5.39 (t, J=5.2 Hz, 1H), 3.52-3.49 (m, 4H), 2.63-2.59 (m, 1H), 2.49-2.42 (m, 1H), 2.31-2.24 (m, 1H), 1.88-1.64 (m, 6H), 1.59-1.43 (m, 7H), 1.40-1.23 (m, 3H);

Compound 100b (38 mg, 10.7%, yellow oil, mixture of two stereoisomers) HPLC: 99.9% purity, RT=1.33 min. MS: m/z=397.15 [M+H]$^+$. $^1$H NMR (400 MHz, CD$_3$OD, ppm) δ=8.42 (d, J=5.2 Hz, 1H), 8.04-8.02 (m, 2H), 7.43 (dd, J=7.6, 4.8 Hz, 1H), 7.32 (s, 1H), 5.39 (t, J=5.2 Hz, 1H), 3.49-3.46 (m, 4H), 2.74-2.70 (m, 1H), 2.49-2.41 (m, 1H), 2.29-2.20 (m, 1H), 1.91-1.82 (m, 2H), 1.71-1.40 (m, 14H).

Example 101: Synthesis of 1-cyclohexyl-2-[12-fluoro-4,6,9-triazatricyclo[6.4.0.0^[2,6]]dodeca-1(8),2,4,9,11-pentaen-7-yl]ethan-1-ol (101a, b, c, d)

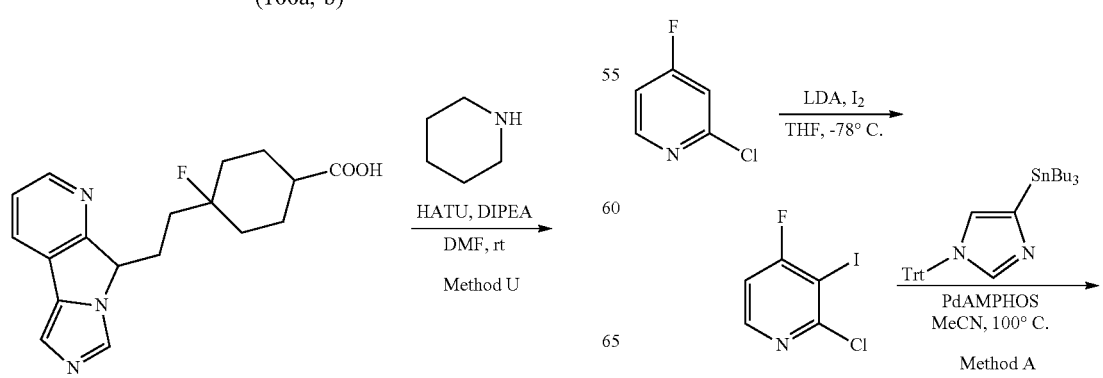

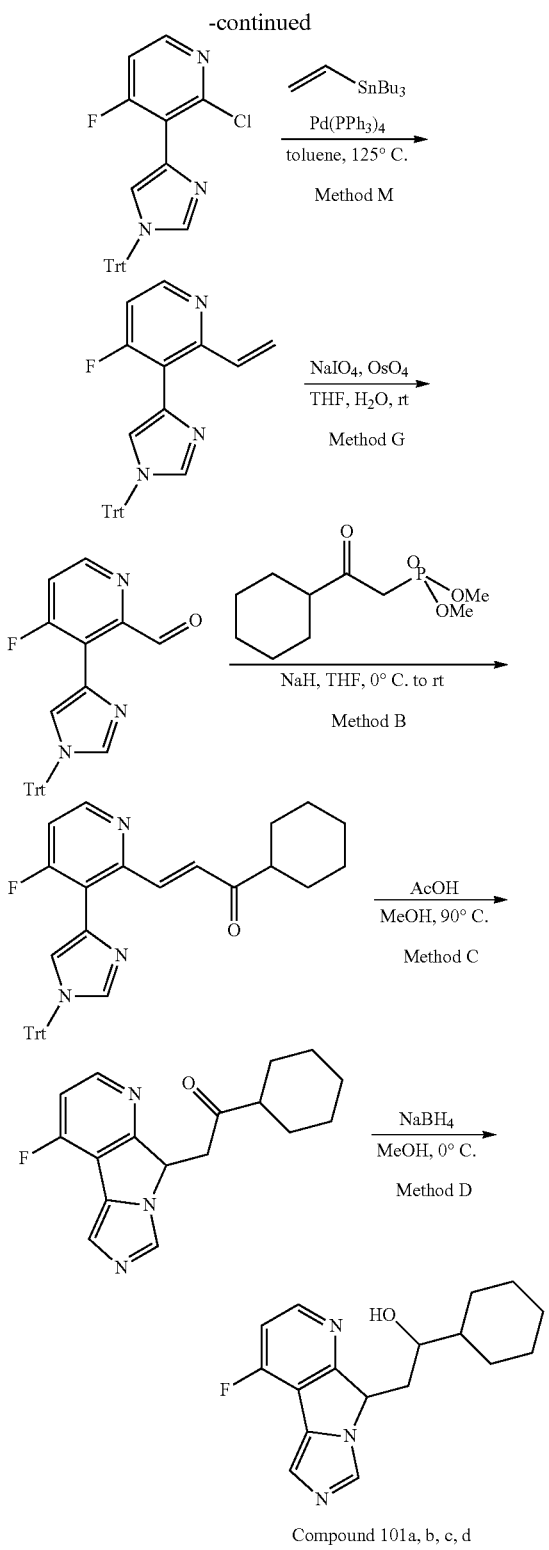

2-Chloro-4-fluoro-3-iodopyridine

At −78° C., to a solution of 2-chloro-4-fluoropyridine (5 g, 38.01 mmol) in anhydrous THF (100 mL) was added LDA (2 M in THF, 28.5 mL) slowly. The resulting mixture was stirred for 30 min at −78° C., and then was added by a solution of $I_2$ (14.6 g, 57.52 mmol) in THF (15 mL) dropwise. The reaction mixture was kept stirring at −78° C. for another 30 min. Then the reaction was quenched by the addition of sat. $Na_2SO_3$ solution (100 mL) and the mixture was extracted with EtOAc (150 mL×2). The organic phases were combined, washed with brine and dried over $Na_2SO_4$. The solvent was removed under reduced pressure and the residue was purified by flash chromatography eluting with EtOAc in petroleum ether (1% to 4% gradient) to yield 2-chloro-4-fluoro-3-iodopyridine (7 g, 72%) as yellow solid. MS: m/z=357.9 [M+H]$^+$.

1-Cyclohexyl-2-[12-fluoro-4,6,9-triazatricyclo [6.4.0.0ˆ[2,6]]dodeca-1(8),2,4,9,11-pentaen-7-yl] ethan-1-ol 1-Cyclohexyl-2-[12-fluoro-4,6,9-triazatricyclo[6.4.0.0ˆ [2,6]]dodeca-1(8),2,4,9,11-pentaen-7-yl]ethan-1-ol was prepared from 2-chloro-4-fluoro-3-iodopyridine, 4-(tributylstannyl)-1-(triphenylmethyl)-1H-imidazole, and dimethyl (2-cyclohexyl-2-oxoethyl)phosphonate using Method A, M, G, B, C, and D. Four enantiomeric products were obtained by the separation on chiral prep-HPLC under the following conditions: Chiralpak IA, 20×250 mm, 5 μm; mobile phase, iPrOH in hexane, 15% isocratic in 15 min; Detector, UV 254/220 nm.

Compound 101a:

(9.6 mg, 2.6% for six steps, white solid, single stereoisomer), HPLC: 99.4% purity, RT=0.71 min. MS: m/z=301.95 [M+H]$^+$. $^1$H NMR (300 MHz, CD$_3$OD, ppm) δ=8.44 (dd, J=7.5, 6.0 Hz, 1H), 8.13 (s, 1H), 7.27-7.25 (m, 2H), 5.45 (t, J=5.7 Hz, 1H), 3.76-3.71 (m, 1H), 2.42-2.37 (m, 1H), 2.13-2.05 (m, 1H), 1.83-1.65 (m, 5H), 1.38-1.02 (m, 6H);

Compound 101b:

(7.1 mg, 1.9% for six steps, white solid, single stereoisomer) HPLC: 97.2% purity, RT=0.71 min. MS: m/z=301.95 [M+H]$^+$. $^1$H NMR (400 MHz, CD$_3$OD, ppm) δ=8.46 (dd, J=7.2, 6.0 Hz, 1H), 8.09 (s, 1H), 7.31-7.27 (m, 2H), 5.57 (dd, J=10.0, 3.6 Hz, 1H), 3.66-3.63 (m, 1H), 2.48-2.41 (m, 1H), 1.92-1.67 (m, 6H), 1.43-1.38 (m, 1H), 1.29-1.02 (m, 5H);

Compound 101c:

(6.7 mg, 1.8% for six steps, white solid, single stereoisomer), HPLC: 99.4% purity, RT=0.71 min. MS: m/z=301.95 [M+H]$^+$. $^1$H NMR (400 MHz, CD$_3$OD, ppm) δ=8.45 (dd, J=7.6, 6.0 Hz, 1H), 8.15 (s, 1H), 7.27-7.25 (m, 2H), 5.46 (t, J=5.6 Hz, 1H), 3.78-3.74 (m, 1H), 2.43-2.38 (m, 1H), 2.13-2.07 (m, 1H), 1.86-1.68 (m, 5H), 1.37-1.03 (m, 6H);

Compound 101d:

(7 mg, 1.9% for six steps, white solid, single stereoisomer) HPLC: 70% purity, RT=0.73 min. MS: m/z=301.95 [M+H]$^+$. $^1$H NMR (400 MHz, CD$_3$OD, ppm) δ=8.46 (dd, J=7.2, 6.0 Hz, 1H), 8.09 (s, 1H), 7.31-7.27 (m, 2H), 5.57 (dd, J=10.0, 3.6 Hz, 1H), 3.66-3.63 (m, 1H), 2.48-2.41 (m, 1H), 1.92-1.67 (m, 6H), 1.43-1.38 (m, 1H), 1.29-1.02 (m, 5H).

Example 102: Synthesis of 12-fluoro-7-[2-(1-fluorocyclohexyl)ethyl]-4,6,9-triazatricyclo[6.4.0.0ˆ[2,6]]dodeca-1(8),2,4,9,11-pentaene (102a, b)

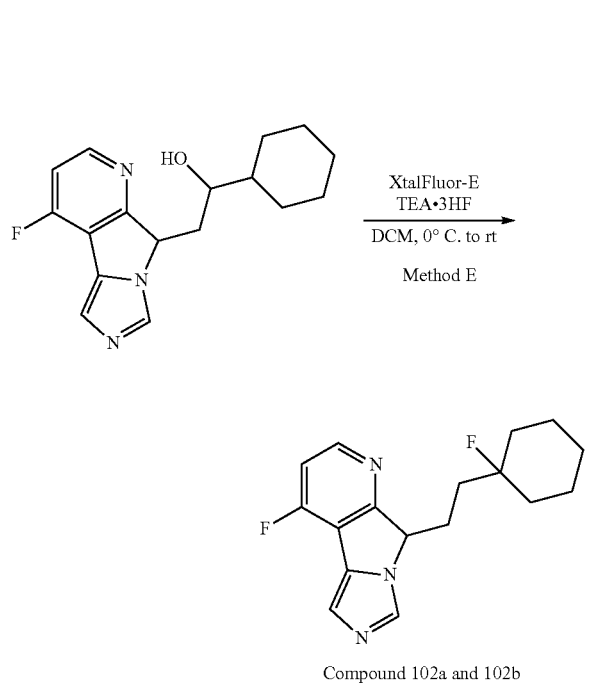 [SMILES: OC(CC1c2nccc(F)c2-c2cncn21)C1CCCCC1 ; Fc1ccnc2c1-c1cncn1C2CCC1(F)CCCCC1]

Compound 102a and 102b

12-Fluoro-7-[2-(1-fluorocyclohexyl)ethyl]-4,6,9-triazatricyclo[6.4.0.0ˆ[2,6]]dodeca-1(8),2,4,9,11-pentaene 12-Fluoro-7-[2-(1-fluorocyclohexyl)ethyl]-4,6,9-triazatricyclo[6.4.0.0ˆ[2,6]]dodeca-1(8),2,4,9,11-pentaene was prepared from 1-cyclohexyl-2-[12-fluoro-4,6,9-triazatricyclo[6.4.0.0ˆ[2,6]]dodeca-1(8),2,4,9,11-pentaen-7-yl]ethan-1-ol using Method E. Two enantiomeric products were obtained by the separation on chiral prep-HPLC under the following conditions: Phenomenex Lux 5μ Cellulose-4, AXIA Packed, 21.2×250 mm, 5 μm; mobile phase, EtOH in hexane, 30% isocratic in 16 min; Detector, UV 254/220 nm.

Compound 102a:

(11.8 mg, 7.8%, clear oil, single stereoisomer), HPLC: 99.3% purity, RT=1.35 min. MS: m/z=304.05 [M+H]$^+$. $^1$H NMR (300 MHz, CD$_3$OD, ppm) δ=8.43 (dd, J=7.5, 6.0 Hz, 1H), 8.06 (s, 1H), 7.28-7.23 (m, 2H), 5.43 (t, J=5.1 Hz, 1H), 2.47-2.39 (m, 1H), 2.31-2.20 (m, 1H), 1.73-1.68 (m, 2H), 1.57-1.20 (m, 10H);

Compound 102b:

(10 mg, 6.6%, clear oil, single stereoisomer) HPLC: 98.0% purity, RT=1.35 min. MS: m/z=304.05 [M+H]$^+$. $^1$H NMR (300 MHz, CD$_3$OD, ppm) δ=8.43 (dd, J=7.5, 6.0 Hz, 1H), 8.06 (s, 1H), 7.28-7.23 (m, 2H), 5.43 (t, J=5.1 Hz, 1H), 2.47-2.39 (m, 1H), 2.31-2.20 (m, 1H), 1.73-1.68 (m, 2H), 1.57-1.20 (m, 10H).

Example 103: Synthesis of 4-fluoro-4-(2-[12-fluoro-4,6,9-triazatricyclo[6.4.0.0ˆ[2,6]]dodeca-1(8),2,4,9,11-pentaen-7-yl]ethyl)cyclohexan-1-ol (103a, b)

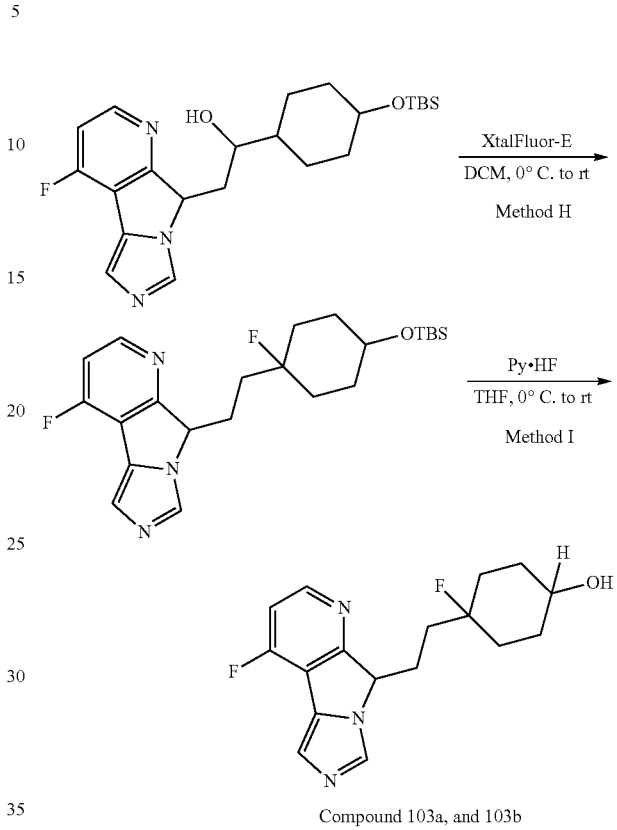

Compound 103a, and 103b

4-Fluoro-4-(2-[12-fluoro-4,6,9-triazatricyclo[6.4.0.0ˆ[2,6]]dodeca-1(8),2,4,9,11-pentaen-7-yl]ethyl)cyclohexan-1-ol 4-Fluoro-4-(2-[12-fluoro-4,6,9-triazatricyclo[6.4.0.0ˆ[2,6]]dodeca-1(8),2,4,9,11-pentaen-7-yl]ethyl)cyclohexan-1-ol was prepared from 1-[4-[(tert-butyldimethylsilyl)oxy]cyclohexyl]-2-[12-fluoro-4,6,9-triazatricyclo[6.4.0.0ˆ[2,6]]dodeca-1(8),2,4,9,11-pentaen-7-yl]ethan-1-ol using Method H and I. Two pairs of enantiomeric products were obtained by the separation on prep-HPLC under the following conditions: XBridge C18 OBD Prep Column, 19×250 mm, 5 μm; mobile phase, MeCN in water (with 10 mM NH$_4$HCO$_3$); 23% to 27% gradient in 11 min; Detector, UV 254/220 nm.

Compound 103a:

(9.2 mg, 3.5% for two steps, white solid, mixture of two stereoisomers), HPLC: 98.8% purity, RT=0.95 min. MS: m/z=320.15 [M+H]$^+$. $^1$H NMR (300 MHz, CD$_3$OD, ppm) δ=8.43 (dd, J=7.5, 6.0 Hz, 1H), 8.05 (s, 1H), 7.29-7.24 (m, 2H), 5.44 (t, J=5.1 Hz, 1H), 3.52-3.44 (m, 1H), 2.47-2.38 (m, 1H), 2.31-2.20 (m, 1H), 1.83-1.68 (m, 4H), 1.53-1.22 (m, 6H);

Compound 103b:

(18.3 mg, 7% for two steps, white solid, mixture of two stereoisomers) HPLC: 99.9% purity, RT=1.04 min. MS: m/z=320.15 [M+H]$^+$. $^1$H NMR (300 MHz, CD$_3$OD, ppm)

δ=8.45 (dd, J=7.5, 6.0 Hz, 1H), 8.13 (s, 1H), 7.31-7.24 (m, 2H), 5.46 (t, J=5.1 Hz, 1H), 3.83 (br s, 1H), 1.75-1.69 (m, 3H), 1.63-1.25 (m, 7H).

Example 104: Synthesis of 4-fluoro-4-(2-[5H-imidazo[4,3-a]isoindol-5-yl]ethyl)cyclohexan-1-amine (104a, b)

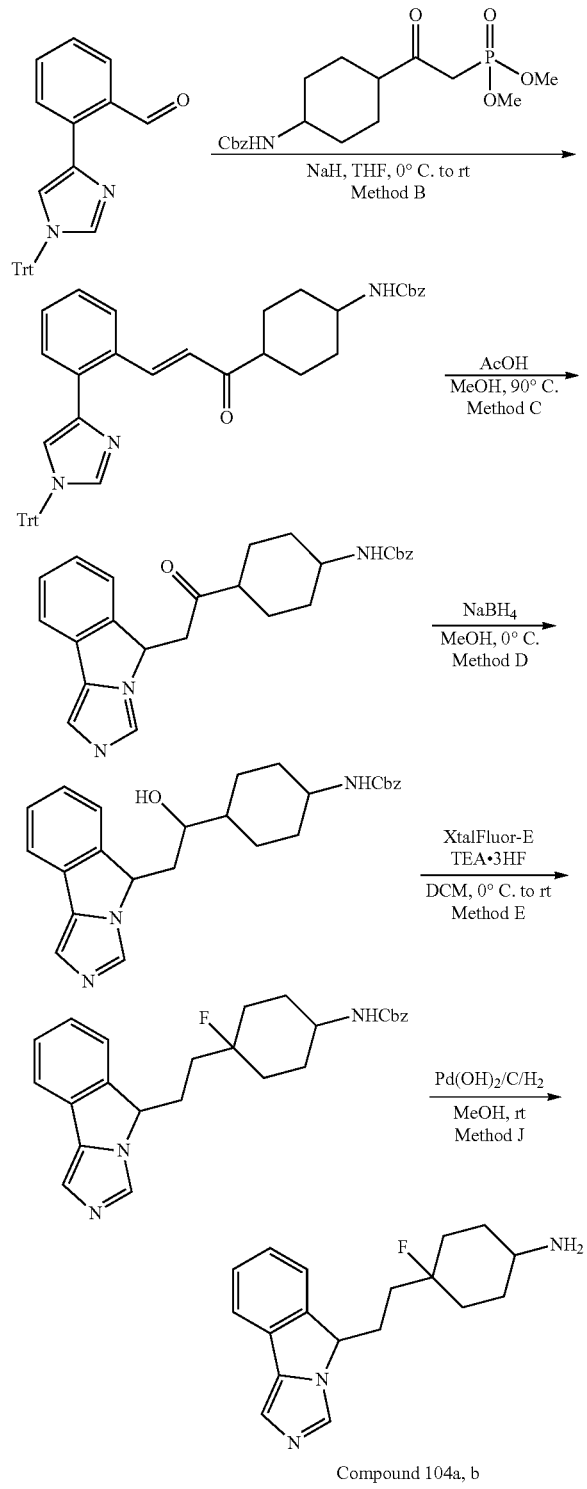

Compound 104a, b

4-Fluoro-4-(2-[5H-imidazo[4,3-a]isoindol-5-yl]ethyl)cyclohexan-1-amine

4-Fluoro-4-(2-[5H-imidazo[4,3-a]isoindol-5-yl]ethyl)cyclohexan-1-amine was prepared from 2-[1-(triphenylmethyl)-1H-imidazol-4-yl]benzaldehyde and benzyl N-[4-[2-(dimethoxyphosphoryl)acetyl]cyclohexyl]carbamate using Method B, C, D, E, and J. Two pairs of enantiomeric products were obtained by the separation on prep-HPLC under the following conditions: XBridge Shield RP18 OBD Column, 19×150 mm, 5 μm; mobile phase, MeCN in water (with 0.05% NH$_3$.H$_2$O); 17% to 30% gradient in 11 min; Detector, UV 254/220 nm.

Compound 104a:
(32.2 mg, 4.5% for five steps, yellow solid, mixture of two stereoisomers), HPLC: 95.6% purity, RT=1.71 min. MS: m/z=300.15 [M+H]$^+$. $^1$H NMR (300 MHz, CD$_3$OD, ppm) δ=7.90 (s, 1H), 7.60 (d, J=7.2 Hz, 1H), 7.47 (d, J=7.5 Hz, 1H), 7.41 (t, J=7.2 Hz, 1H), 7.34-7.29 (m, 1H), 7.14 (s, 1H), 5.43 (t, J=4.8 Hz, 1H), 2.85-2.76 (m, 1H), 2.44-2.33 (m, 1H), 2.22-2.12 (m, 1H), 1.87-1.72 (m, 4H), 1.59-1.43 (m, 3H), 1.40-1.17 (m, 3H);

Compound 104b:
(6.7 mg, 0.9% for five steps, yellow solid, mixture of two stereoisomers) HPLC: 86.9% purity, RT=1.95 min. MS: m/z=300.15 [M+H]$^+$. $^1$H NMR (300 MHz, CD$_3$OD, ppm) δ=7.90 (s, 1H), 7.58 (d, J=7.2 Hz, 1H), 7.46 (d, J=7.5 Hz, 1H), 7.38 (t, J=7.2 Hz, 1H), 7.32-7.27 (m, 1H), 7.12 (s, 1H), 5.43 (t, J=4.8 Hz, 1H), 3.02-2.97 (m, 1H), 2.41-2.32 (m, 1H), 2.24-2.12 (m, 1H), 1.88-1.60 (m, 6H), 1.32-1.21 (m, 4H).

Example 105: Synthesis of [4-[2-[6-chloro-5H-imidazo[4,3-a]isoindol-5-yl]ethyl]-4-fluorocyclohexyl]methanol (105a, b, c)

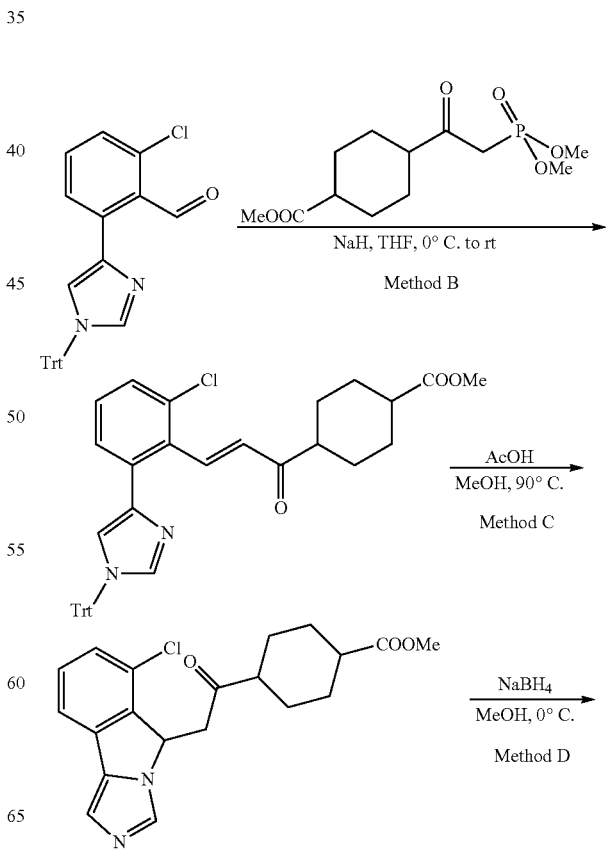

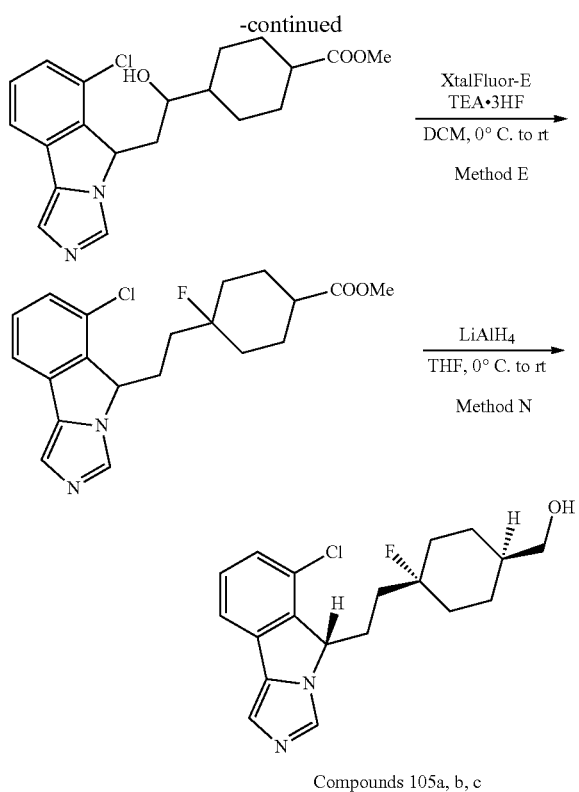

Compounds 105a, b, c

[4-[2-[6-Chloro-5H-imidazo[4,3-a]isoindol-5-yl]ethyl]-4-fluorocyclohexyl]methanol

[4-[2-[6-Chloro-5H-imidazo[4,3-a]isoindol-5-yl]ethyl]-4-fluorocyclohexyl]methanol was prepared from 2-chloro-6-[1-(triphenylmethyl)-1H-imidazol-4-yl]benzaldehyde and methyl 4-[2-(dimethoxyphosphoryl)acetyl]cyclohexane-1-carboxylate using Method B, C, D, E, and N. Two enantiomeric and one pair of enantiomeric products were obtained by the separation on chiral prep-HPLC under the following conditions: Phenomenex Lux 5μ Cellulose-4, AXIA Packed, 21.2×250 mm, 5 μm; mobile phase, EtOH in hexane, 30% isocratic in 18 min; Detector, UV 254/220 nm.

Compound 105a (19 mg, 2.9% for five steps, white solid, single stereoisomer), HPLC: 98.2% purity, RT=1.32 min. MS: m/z=349.05 [M+H]$^+$. $^1$H NMR (300 MHz, CD$_3$OD, ppm) δ=7.94 (s, 1H), 7.55 (d, J=7.5 Hz, 1H), 7.39 (t, J=7.5 Hz, 1H), 7.28 (d, J=7.2 Hz, 1H), 7.19 (s, 1H), 5.59 (t, J=4.2 Hz, 1H), 3.28-3.24 (m, 2H), 2.50-2.42 (m, 2H), 1.70-1.62 (m, 4H), 1.55-1.40 (m, 3H), 1.26-0.79 (m, 4H);

Compound 105b (6.2 mg, 0.9% for five steps, white solid, mixture of two stereoisomers) HPLC: 99.0% purity, RT=1.32 min. MS: m/z=349.0 [M+H]$^+$. $^1$H NMR (300 MHz, CD$_3$OD, ppm) δ=7.92 (s, 1H), 7.54 (d, J=7.5 Hz, 1H), 7.39 (t, J=7.8 Hz, 1H), 7.27 (d, J=8.1 Hz, 1H), 7.17 (s, 1H), 5.57 (t, J=4.2 Hz, 1H), 3.32-3.30 (m, 2H), 2.50-2.42 (m, 2H), 1.80-1.71 (m, 2H), 1.60-1.53 (m, 2H), 1.39-0.89 (m, 7H);

Compound 105c (17.5 mg, 2.6% for five steps, white solid, single stereoisomer) HPLC: 99.7% purity, RT=0.76 min. MS: m/z=349.0 [M+H]$^+$. $^1$H NMR (300 MHz, CD$_3$OD, ppm) δ=7.94 (s, 1H), 7.55 (d, J=7.5 Hz, 1H), 7.39 (t, J=7.5 Hz, 1H), 7.28 (d, J=7.2 Hz, 1H), 7.19 (s, 1H), 5.59 (t, J=4.2 Hz, 1H), 3.28-3.24 (m, 2H), 2.50-2.42 (m, 2H), 1.70-1.62 (m, 4H), 1.55-1.40 (m, 3H), 1.26-0.79 (m, 4H).

Example 106: Synthesis of 1-[4-(2-[6-chloro-5H-imidazo[4,3-a]isoindol-5-yl]ethyl)-4-fluorocyclohexyl]cyclopropan-1-ol (106a, b)

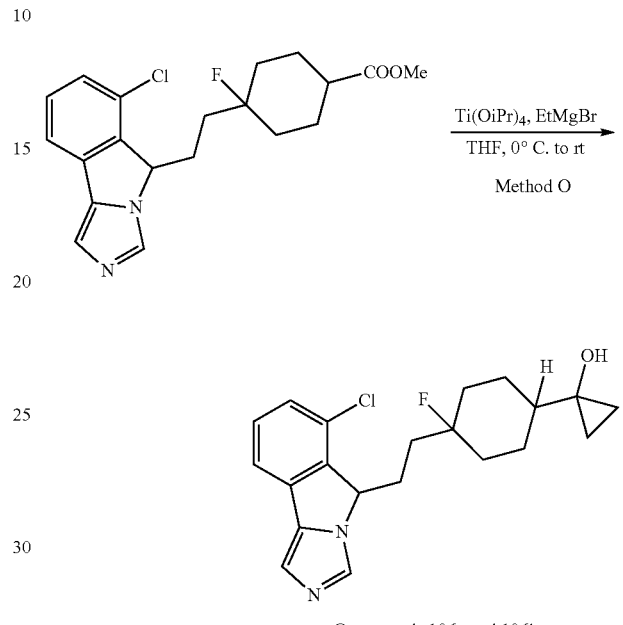

Compounds 106a and 106b

1-[4-(2-[6-Chloro-5H-imidazo[4,3-a]isoindol-5-yl]ethyl)-4-fluorocyclohexyl]cyclopropan-1-ol 1-[4-(2-[6-Chloro-5H-imidazo[4,3-a]isoindol-5-yl]ethyl)-4-fluorocyclohexyl]cyclopropan-1-ol was prepared from methyl 4-(2-[6-chloro-5H-imidazo[4,3-a]isoindol-5-yl]ethyl)-4-fluorocyclohexane-1-carboxylate using Method O. Two pairs of enantiomeric products were obtained by the separation on prep-HPLC under the following conditions: XBridge C18 OBD Prep Column, 19×250 mm, 5 μm; mobile phase, MeCN in water (with 10 mM NH$_4$HCO$_3$); 50% to 51% gradient in 14 min; Detector, UV 254/220 nm.

Compound 106a:

(11 mg, 5.1%, white solid, mixture of two stereoisomers), HPLC: 98.6% purity, RT=2.03 min. MS: m/z=375.05 [M+H]$^+$. $^1$H NMR (300 MHz, CD$_3$OD, ppm) δ=7.92 (s, 1H), 7.54 (d, J=7.5 Hz, 1H), 7.39 (t, J=7.5 Hz, 1H), 7.27 (d, J=7.5 Hz, 1H), 7.18 (s, 1H), 5.57 (t, J=3.9 Hz, 1H), 2.50-2.43 (m, 2H), 1.81-1.72 (m, 2H), 1.60-1.51 (m, 4H), 1.33-0.82 (m, 5H), 0.56-0.54 (m, 2H), 0.37-0.35 (m, 2H);

Compound 106b:

(22.5 mg, 10.4%, white solid, mixture of two stereoisomers) HPLC: 99.7% purity, RT=1.44 min. MS: m/z=375.1 [M+H]$^+$. $^1$H NMR (300 MHz, CD$_3$OD, ppm) δ=7.94 (s, 1H), 7.56 (d, J=7.2 Hz, 1H), 7.39 (t, J=7.8 Hz, 1H), 7.28 (d, J=7.2 Hz, 1H), 7.18 (s, 1H), 5.60 (t, J=4.2 Hz, 1H), 2.50-2.43 (m, 2H), 1.86-1.73 (m, 2H), 1.66-1.42 (m, 4H), 1.36-0.85 (m, 5H), 0.52-0.50 (m, 2H), 0.31-0.29 (m, 2H).

Example 107: Synthesis of 2-[4-(2-[6-chloro-5H-imidazo[4,3-a]isoindol-5-yl]ethyl)-4-fluorocyclohexyl]propan-2-ol (107a, b)

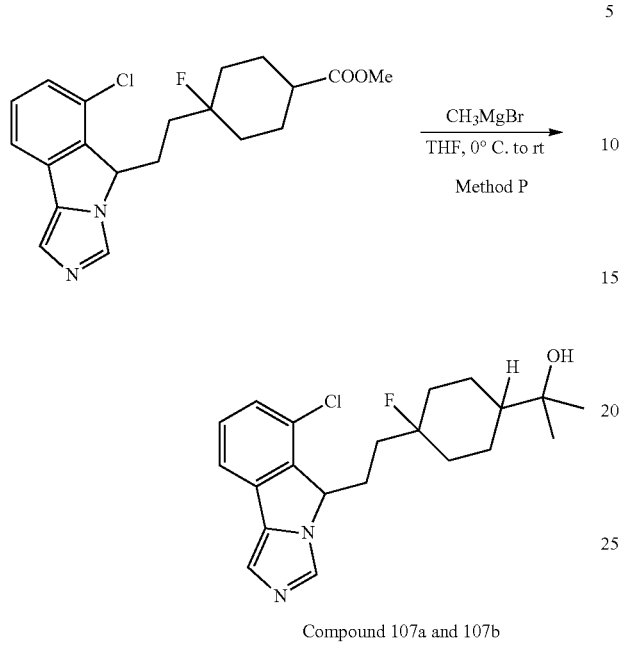

Compound 107a and 107b

2-[4-(2-[6-Chloro-5H-imidazo[4,3-a]isoindol-5-yl]ethyl)-4-fluorocyclohexyl]propan-2-ol 2-[4-(2-[6-Chloro-5H-imidazo[4,3-a]isoindol-5-yl] ethyl)-4-fluorocyclohexyl]propan-2-ol was prepared from methyl 4-(2-[6-chloro-5H-imidazo[4,3-a]isoindol-5-yl] ethyl)-4-fluorocyclohexane-1-carboxylate using Method P. Two pairs of enantiomeric products were obtained by the separation on prep-HPLC under the following conditions: XBridge BEH C18 OBD Prep Column, 19×250 mm, 5 μm; mobile phase, MeCN in water (with 10 mM $NH_4HCO_3$); 41% to 43% gradient in 15 min; Detector, UV 254/220 nm.

Compound 107a:

(22 mg, 10.8%, white solid, mixture of two stereoisomers), HPLC: 99.96% purity, RT=1.42 min. MS: m/z=377.1 $[M+H]^+$. $^1$H NMR (300 MHz, $CD_3OD$, ppm) δ=7.98 (s, 1H), 7.59 (d, J=7.5 Hz, 1H), 7.43 (t, J=7.8 Hz, 1H), 7.31 (d, J=8.1 Hz, 1H), 7.22 (s, 1H), 5.65 (t, J=3.6 Hz, 1H), 2.61-2.42 (m, 2H), 1.88-1.70 (m, 4H), 1.59-1.41 (m, 2H), 1.31-1.04 (m, 3H), 1.01 (s, 6H), 0.83-0.70 (m, 2H);

Compound 107b:

(4.2 mg, 2.1%, white solid, mixture of two stereoisomers) HPLC: 98.5% purity, RT=1.43 min. MS: m/z=377.15 $[M+H]^+$. $^1$H NMR (300 MHz, $CD_3OD$, ppm) δ=7.96 (s, 1H), 7.58 (d, J=7.5 Hz, 1H), 7.43 (t, J=7.8 Hz, 1H), 7.31 (d, J=8.1 Hz, 1H), 7.21 (s, 1H), 5.61 (t, J=3.9 Hz, 1H), 2.57-2.49 (m, 2H), 1.86-1.60 (m, 4H), 1.38-1.12 (m, 6H), 1.10 (s, 6H), 1.07-0.95 (m, 1H).

Example 108: Synthesis of 5-[2-cyclohexyl-2-fluoroethyl]-5H-imidazo[4,3-a]isoindole (108a, b)

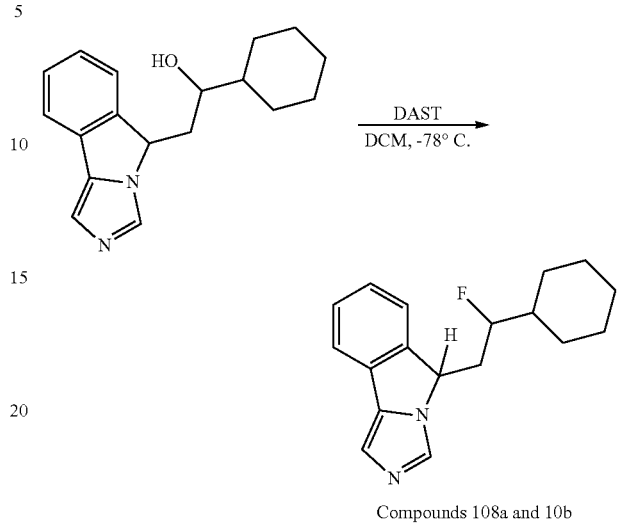

Compounds 108a and 10b

5-[2-Cyclohexyl-2-fluoroethyl]-5H-imidazo[4,3-a]isoindole

At −78° C., to a solution of 1-cyclohexyl-2-[5H-imidazo [4,3-a]isoindol-5-yl]ethan-1-ol (480 mg, 1.70 mmol) in DCM (10 mL) was added DAST (410 mg, 2.54 mmol) slowly. The resulting mixture was stirred at −78° C. for 30 min. Then the reaction mixture was quenched by $H_2O$ (20 mL) and extracted with DCM (30 mL×2). The organic phases were combined, washed with brine and dried over $Na_2SO_4$. The solvent was removed under reduced pressure and the residue was purified by flash chromatography eluting with MeOH in DCM (1% to 5% gradient). Two pairs of enantiomeric products were obtained by the separation on prep-HPLC under the following conditions: XBridge BEH C18 OBD Prep Column, 19×250 mm, 5 μm; mobile phase, MeCN in water (with 10 mM $NH_4HCO_3$); 53% to 56% gradient in 14 min; Detector, UV 254/220 nm.

Compound 108a:

(21.4 mg, 4.5%, yellow solid, mixture of two stereoisomers), HPLC: 99.97% purity, RT=1.57 min. MS: m/z=285.2 $[M+H]^+$. $^1$H NMR (300 MHz, $CD_3OD$, ppm) δ=7.87 (s, 1H), 7.57 (d, J=7.5 Hz, 1H), 7.44 (d, J=7.5 Hz, 1H), 7.37 (t, J=7.5 Hz, 1H), 7.31-7.26 (m, 1H), 7.11 (s, 1H), 5.44 (dd, J=8.4, 3.6 Hz, 1H), 4.48-4.26 (m, 1H), 2.60-2.47 (m, 1H), 2.08-1.80 (m, 2H), 1.74-1.45 (m, 5H), 1.29-0.97 (m, 5H);

Compound 108b:

(2.8 mg, 0.6%, yellow solid, mixture of two stereoisomers) HPLC: 99.9% purity, RT=0.96 min. MS: m/z=285.0 $[M+H]^+$. $^1$H NMR (300 MHz, $CD_3OD$, ppm) δ=7.92 (br s, 1H), 7.61 (d, J=7.5 Hz, 1H), 7.52 (d, J=7.5 Hz, 1H), 7.40 (t, J=7.5 Hz, 1H), 7.34-7.29 (m, 1H), 7.15 (br s, 1H), 5.46 (t, J=5.7 Hz, 1H), 4.66-4.42 (m, 1H), 2.40-2.19 (m, 2H), 1.89-1.43 (m, 6H), 1.31-1.03 (m, 5H).

Example 109: Synthesis of 1-(1-fluorocyclohexyl)-2-[4,6,9-triazatricyclo[6.4.0.0ˆ[2,6]]dodeca-1(8),2,4,9,11-pentaen-7-yl]ethan-1-ol (109a, b, c)

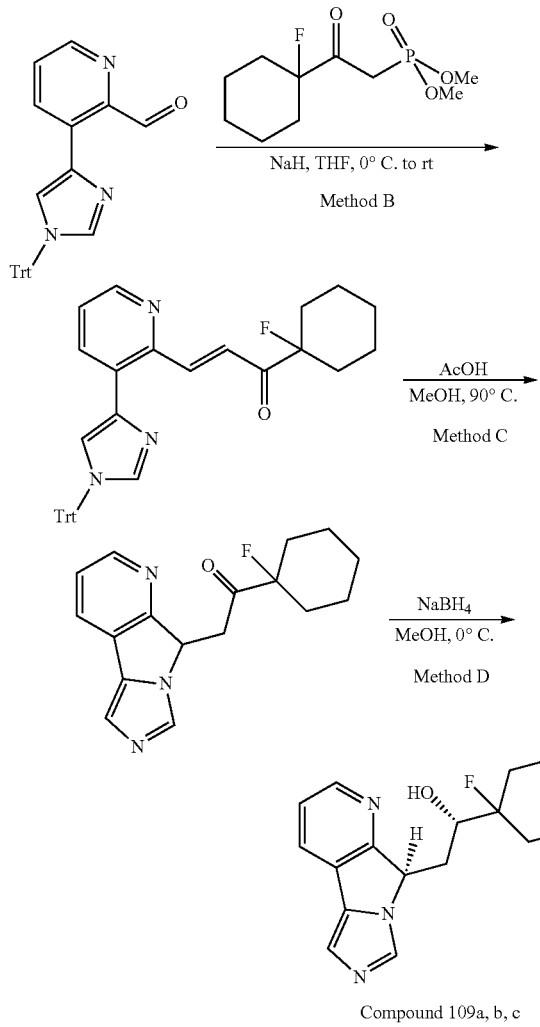

Compound 109a, b, c 1-(1-Fluorocyclohexyl)-2-[4,6,9-triazatricyclo[6.4.0.0ˆ[2,6]]dodeca-1(8),2,4,9,11-pentaen-7-yl]ethan-1-ol 1-(1-Fluorocyclohexyl)-2-[4,6,9-triazatricyclo[6.4.0.0ˆ[2,6]]dodeca-1(8),2,4,9,11-pentaen-7-yl]ethan-1-ol was prepared from 3-[1-(triphenylmethyl)-1H-imidazol-4-yl]pyridine-2-carbaldehyde and dimethyl [2-(1-fluorocyclohexyl)-2-oxoethyl]phosphonate using Method B, C, and D. Two enantiomeric and one pair of enantiomeric products were obtained by the separation on chiral prep-HPLC under the following conditions: CHIRALPAK-AD-H-SL001, 20×250 mm, 5 μm; mobile phase, EtOH in hexane, 30% isocratic in 15 min; Detector, UV 254/220 nm.

Compound 109a:

(23.4 mg, 7% for three steps, white solid, single stereoisomer) HPLC: 98.9% purity, RT=1.25 min. MS: m/z=302.1 [M+H]$^+$. $^1$H NMR (300 MHz, CD$_3$OD, ppm) δ=8.37 (dd, J=5.1, 1.2 Hz, 1H), 8.06 (s, 1H), 7.97 (dd, J=7.8, 1.5 Hz, 1H), 7.37 (dd, J=7.8, 5.1 Hz, 1H), 7.25 (s, 1H), 5.35 (t, J=6.0 Hz, 1H), 4.00-3.89 (m, 1H), 2.43-2.36 (m, 1H), 2.13-2.06 (m, 1H), 1.83-1.72 (m, 2H), 1.64-1.36 (m, 7H), 1.28-1.18 (m, 1H);

Compound 109b:

(13.3 mg, 4% for three steps, white solid, mixture of two stereoisomers) HPLC: 99.4% purity, RT=1.22 min. MS: m/z=302.05 [M+H]$^+$. $^1$H NMR (400 MHz, CD$_3$OD, ppm) δ=8.43 (dd, J=5.2, 1.6 Hz, 1H), 8.07-8.05 (m, 2H), 7.45 (dd, J=8.0, 5.2 Hz, 1H), 7.34 (s, 1H), 5.51 (dd, J=9.6, 3.2 Hz, 1H), 3.81-3.77 (m, 1H), 2.59-2.51 (m, 1H), 1.90-1.79 (m, 3H), 1.69-1.42 (m, 7H), 1.30-1.21 (m, 1H);

Compound 109c:

(19.7 mg, 5.9% for three steps, white solid, single stereoisomer) HPLC: 99.5% purity, RT=1.26 min. MS: m/z=302.05 [M+H]$^+$. $^1$H NMR (300 MHz, CD$_3$OD, ppm) δ=8.37 (dd, J=5.1, 1.2 Hz, 1H), 8.06 (s, 1H), 7.97 (dd, J=7.8, 1.5 Hz, 1H), 7.37 (dd, J=7.8, 5.1 Hz, 1H), 7.25 (s, 1H), 5.35 (t, J=6.0 Hz, 1H), 4.00-3.89 (m, 1H), 2.43-2.36 (m, 1H), 2.13-2.06 (m, 1H), 1.83-1.72 (m, 2H), 1.64-1.36 (m, 7H), 1.28-1.18 (m, 1H).

Example 110: Synthesis of 1-[4-fluoro-4-(2-[6-fluoro-5H-imidazo[4,3-a]isoindol-5-yl]ethyl)cyclohexyl]carbonyl]piperidine (110a, b)

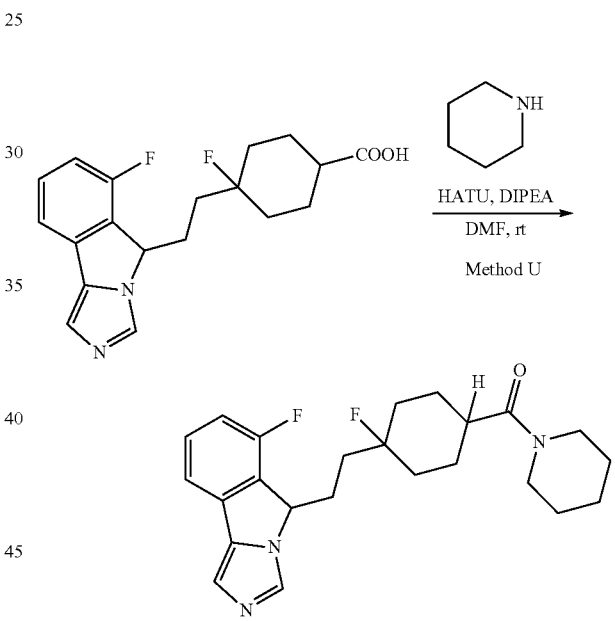

Compounds 110a and 110b

1-[4-Fluoro-4-(2-[6-fluoro-5H-imidazo[4,3-a]isoindol-5-yl]ethyl)cyclohexyl]carbonyl]piperidine 1-[4-Fluoro-4-(2-[6-fluoro-5H-imidazo[4,3-a]isoindol-5-yl]ethyl)cyclohexyl]carbonyl]piperidine was prepared from 4-fluoro-4-(2-[6-fluoro-5H-imidazo[4,3-a]isoindol-5-yl]ethyl)cyclohexane-1-carboxylic acid and piperidine using Method U. Two pairs of enantiomeric products were obtained by the separation on prep-HPLC under the following conditions: XBridge C18 OBD Prep Column, 19×250 mm, 5 μm; mobile phase, MeCN in water (with 10 mM NH$_4$HCO$_3$); 44% to 47% gradient in 14 min; Detector, UV 254/220 nm.

Compound 110a:

(17 mg, 5.7%, white solid, mixture of two stereoisomers) HPLC: 95.4% purity, RT=1.41 min. MS: m/z=414.15

[M+H]+. 1H NMR (300 MHz, CD3OD, ppm) δ=7.96 (s, 1H), 7.47-7.45 (m, 2H), 7.21 (s, 1H), 7.09-7.03 (m, 1H), 5.68 (t, J=4.5 Hz, 1H), 3.52 (br s, 4H), 2.69-2.42 (m, 2H), 2.36-2.22 (m, 1H), 1.89-1.45 (m, 13H), 1.38-1.12 (m, 3H);

Compound 110b:

(25 mg, 8.3%, white solid, mixture of two stereoisomers) HPLC: 99.6% purity, RT=1.49 min. MS: m/z=414.15 [M+H]+. 1H NMR (300 MHz, CD3OD, ppm) δ=7.97 (s, 1H), 7.48-7.46 (m, 2H), 7.21 (s, 1H), 7.09-7.03 (m, 1H), 5.68 (t, J=4.5 Hz, 1H), 3.51-3.48 (m, 4H), 2.78-2.70 (m, 1H), 2.52-2.41 (m, 1H), 2.31-2.20 (m, 1H), 1.91-1.80 (m, 2H), 1.76-1.25 (m, 14H).

Example 111: Synthesis of 4-fluoro-4-(2-[6-fluoro-5H-imidazo[4,3-a]isoindol-5-yl]ethyl)-N,N-dimethylcyclohexane-1-carboxamide (111a, b)

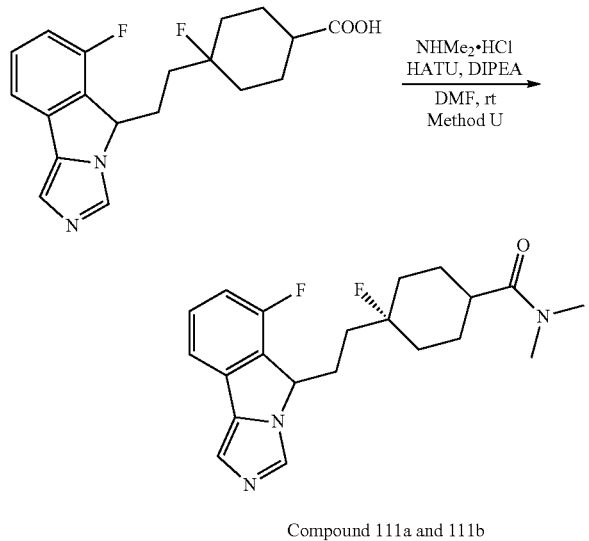

Compound 111a and 111b

4-Fluoro-4-(2-[6-fluoro-5H-imidazo[4,3-a]isoindol-5-yl]ethyl)-N,N-dimethylcyclohexane-1-carboxamide 4-Fluoro-4-(2-[6-fluoro-5H-imidazo[4,3-a]isoindol-5-yl]ethyl)-N,N-dimethylcyclohexane-1-carboxamide was prepared from 4-fluoro-4-(2-[6-fluoro-5H-imidazo[4,3-a]isoindol-5-yl]ethyl)cyclohexane-1-carboxylic acid and NHMe2.HCl using Method U. Two pairs of enantiomeric products were obtained by the separation on prep-HPLC under the following conditions: XBridge Shield RP18 OBD Column, 19×150 mm, 5 μm; mobile phase, MeCN in water (with 10 mM NH4HCO3); 31% isocratic in 10 min; Detector, UV 254/220 nm.

Compound 111a:

(11 mg, 2.2%, white solid, mixture of two stereoisomers) HPLC: 99.0% purity, RT=1.25 min. MS: m/z=374.1 [M+H]+. 1H NMR (300 MHz, CD3OD, ppm) δ=7.96 (s, 1H), 7.47-7.45 (m, 2H), 7.21 (s, 1H), 7.09-7.03 (m, 1H), 5.68 (t, J=4.2 Hz, 1H), 3.08 (s, 3H), 2.91 (s, 3H), 2.68-2.60 (m, 1H), 2.53-2.44 (m, 1H), 2.35-2.23 (m, 1H), 1.89-1.67 (m, 4H), 1.58-1.12 (m, 6H);

Compound 111b:

(50 mg, 10%, white solid, mixture of two stereoisomers) HPLC: 100% purity, RT=1.33 min. MS: m/z=374.1 [M+H]+. 1H NMR (300 MHz, CD3OD, ppm) δ=7.97 (s, 1H), 7.48-7.45 (m, 2H), 7.21 (s, 1H), 7.09-7.03 (m, 1H), 5.68 (t, J=4.5 Hz, 1H), 3.07 (s, 3H), 2.88 (s, 3H), 2.78-2.72 (m, 1H), 2.52-2.42 (m, 1H), 2.31-2.20 (m, 1H), 1.82-1.58 (m, 6H), 1.48-1.24 (m, 4H).

Example 112: Synthesis of 2-[4-fluoro-4-[2-[5H-imidazo[4,3-a]isoindol-5-yl]ethyl]cyclohexyl]acetamide (112a, b, c, d)

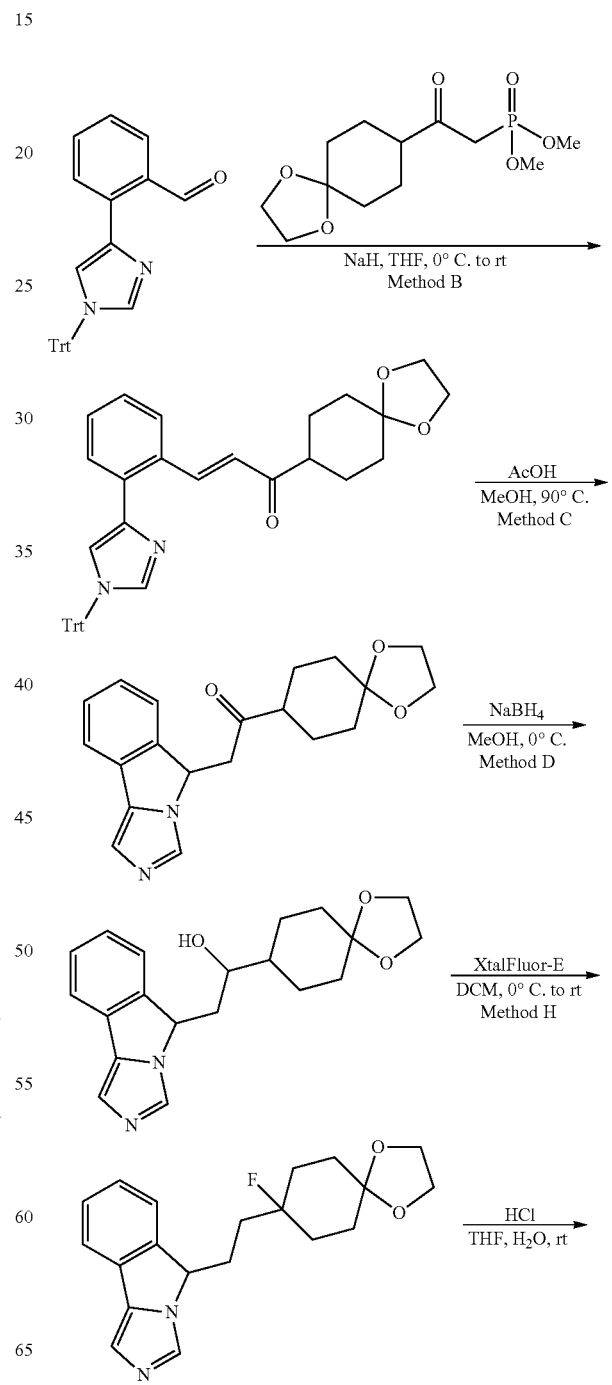

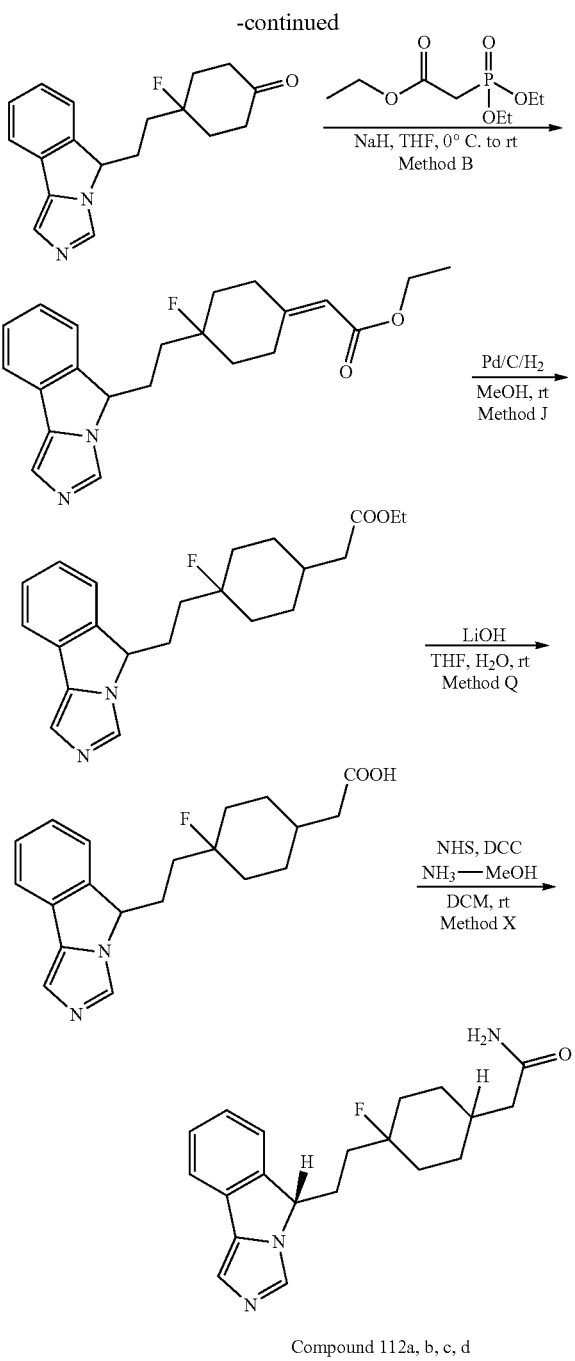

Compound 112a, b, c, d

5-(2-[8-Fluoro-1,4-dioxaspiro[4.5]decan-8-yl]ethyl)-5H-imidazo[4,3-a]isoindole 5-(2-[8-Fluoro-1,4-dioxaspiro[4.5]decan-8-yl]ethyl)-5H-imidazo[4,3-a]isoindole (1.7 g, 33%) was prepared from 2-[1-(triphenylmethyl)-1H-imidazol-4-yl]benzaldehyde and dimethyl (2-[1,4-dioxaspiro[4.5]decan-8-yl]-2-oxoethyl)phosphonate using Method B, C, D, and H. MS: m/z=343.05 [M+H]$^+$.

4-Fluoro-4-(2-[5H-imidazo[4,3-a]isoindol-5-yl]ethyl)cyclohexan-1-one

At room temperature, HCl solution (6 M, 15 mL, 90 mmol) was slowly added to a solution of 5-(2-[8-fluoro-1,4-dioxaspiro[4.5]decan-8-yl]ethyl)-5H-imidazo[4,3-a]isoindole (1.70 g, 4.47 mmol) in THF (10 mL). The resulting mixture was stirred at room temperature for 16 h. Then the reaction mixture was neutralized with sat. NaHCO$_3$ solution and extracted with EtOAc (80 mL×3). The organic phases were combined, washed with brine and dried over Na$_2$SO$_4$. The solvent was removed under reduced pressure, and the residue was purified by flash chromatography eluting with MeOH in DCM (1% to 7% gradient) to yield 4-fluoro-4-(2-[5H-imidazo[4,3-a]isoindol-5-yl]ethyl)cyclohexan-1-one (1 g, 75%) as yellow oil. MS: m/z=298.99 [M+H]$^+$.

2-[4-Fluoro-4-[2-[5H-imidazo[4,3-a]isoindol-5-yl]ethyl]cyclohexyl]acetamide

2-[4-Fluoro-4-[2-[5H-imidazo[4,3-a]isoindol-5-yl]ethyl]cyclohexyl]acetamide was prepared from 4-fluoro-4-(2-[5H-imidazo[4,3-a]isoindol-5-yl]ethyl)cyclohexan-1-one and ethyl 2-(diethoxyphosphoryl)acetate using Method B, J, Q, and X. Four enantiomeric products were obtained by the separation on chiral prep-HPLC under the following conditions: CHIRALPAK-AD-H-SL001, 20×250 mm, 5 μm; mobile phase, EtOH in hexane, 50% isocratic in 29 min; Detector, UV 254/220 nm.

Compound 112a:

(17 mg, 3.5% for four steps, white solid, single stereoisomer), HPLC: 99.3% purity, RT=1.17 min. MS: m/z=342.2 [M+H]$^+$. $^1$H NMR (400 MHz, CD$_3$OD, ppm) δ=7.90 (s, 1H), 7.60 (d, J=7.6 Hz, 1H), 7.47 (d, J=7.6 Hz, 1H), 7.40 (t, J=7.2 Hz, 1H), 7.34-7.30 (m, 1H), 7.14 (s, 1H), 5.42 (t, J=4.8 Hz, 1H), 2.41-2.34 (m, 1H), 2.20-2.12 (m, 1H), 2.07 (d, J=7.2 Hz, 2H), 1.81-1.56 (m, 5H), 1.40-1.17 (m, 6H);

Compound 112b:

(17 mg, 3.5% for four steps, white solid, single stereoisomer) HPLC: 99.3% purity, RT=1.17 min. MS: m/z=342.2 [M+H]$^+$. $^1$H NMR (400 MHz, CD$_3$OD, ppm) δ=7.90 (s, 1H), 7.60 (d, J=7.6 Hz, 1H), 7.47 (d, J=7.6 Hz, 1H), 7.40 (t, J=7.2 Hz, 1H), 7.34-7.30 (m, 1H), 7.15 (s, 1H), 5.42 (t, J=4.8 Hz, 1H), 2.41-2.34 (m, 1H), 2.20-2.12 (m, 1H), 2.07 (d, J=7.2 Hz, 2H), 1.81-1.56 (m, 5H), 1.40-1.17 (m, 6H);

Compound 112c:

(4 mg, 0.8% for four steps, white solid, single stereoisomer), HPLC: 99.9% purity, RT=1.18 min. MS: m/z=342.2 [M+H]$^+$. $^1$H NMR (400 MHz, CD$_3$OD, ppm) δ=7.92 (s, 1H), 7.61 (d, J=7.6 Hz, 1H), 7.48 (d, J=7.6 Hz, 1H), 7.41 (t, J=7.6 Hz, 1H), 7.35-7.31 (m, 1H), 7.15 (s, 1H), 5.45 (t, J=4.4 Hz, 1H), 2.40-2.34 (m, 1H), 2.20-2.13 (m, 1H), 2.05 (d, J=7.2 Hz, 2H), 1.87-1.55 (m, 7H), 1.29-1.20 (m, 2H), 1.02-0.91 (m, 2H);

Compound 112d:

(3.8 mg, 0.8% for four steps, white solid, single stereoisomer) HPLC: 99.95% purity, RT=1.18 min. MS: m/z=342.2 [M+H]$^+$. $^1$H NMR (400 MHz, CD$_3$OD, ppm) δ=7.92 (s, 1H), 7.61 (d, J=7.6 Hz, 1H), 7.48 (d, J=7.6 Hz, 1H), 7.41 (t, J=7.6 Hz, 1H), 7.35-7.31 (m, 1H), 7.15 (s, 1H), 5.45 (t, J=4.4 Hz, 1H), 2.40-2.34 (m, 1H), 2.20-2.13 (m, 1H), 2.05 (d, J=7.2 Hz, 2H), 1.87-1.55 (m, 7H), 1.29-1.20 (m, 2H), 1.02-0.91 (m, 2H).

Example 113: Synthesis of 2-[4-[2-[6-chloro-5H-imidazo[4,3-a]isoindol-5-yl]ethyl]-4-fluorocyclohexyl]acetamide((113a, b, c, d)

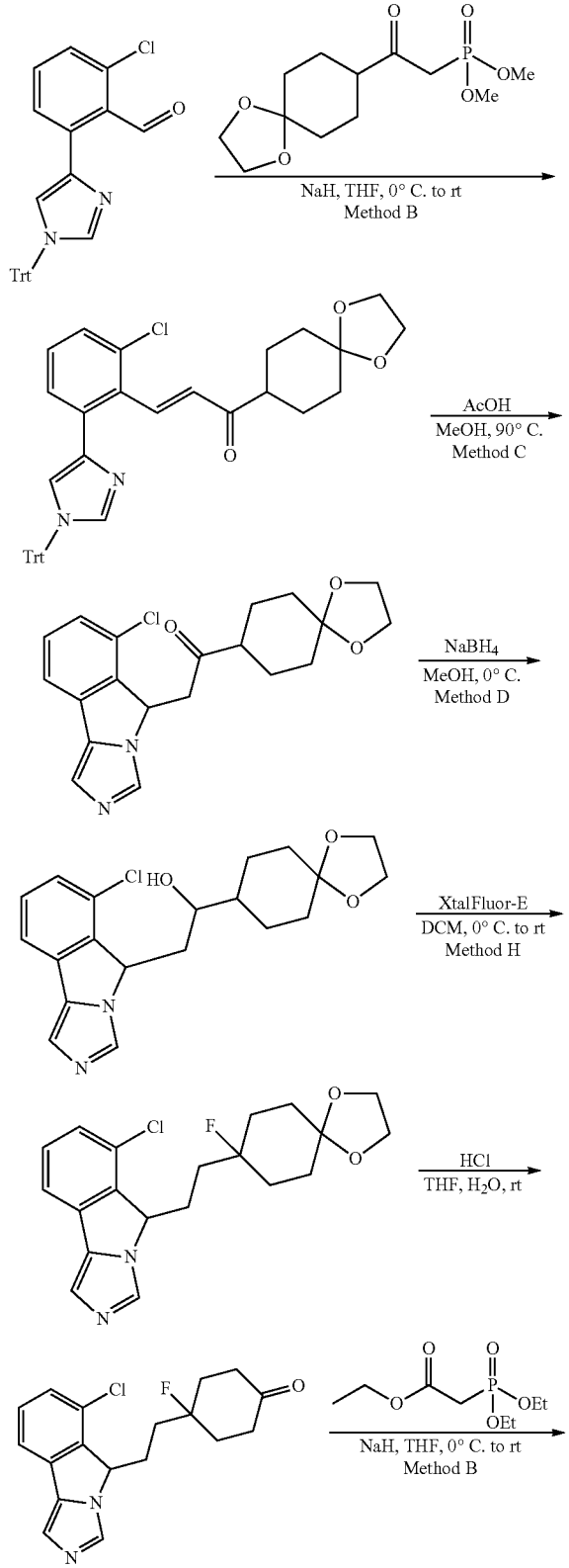

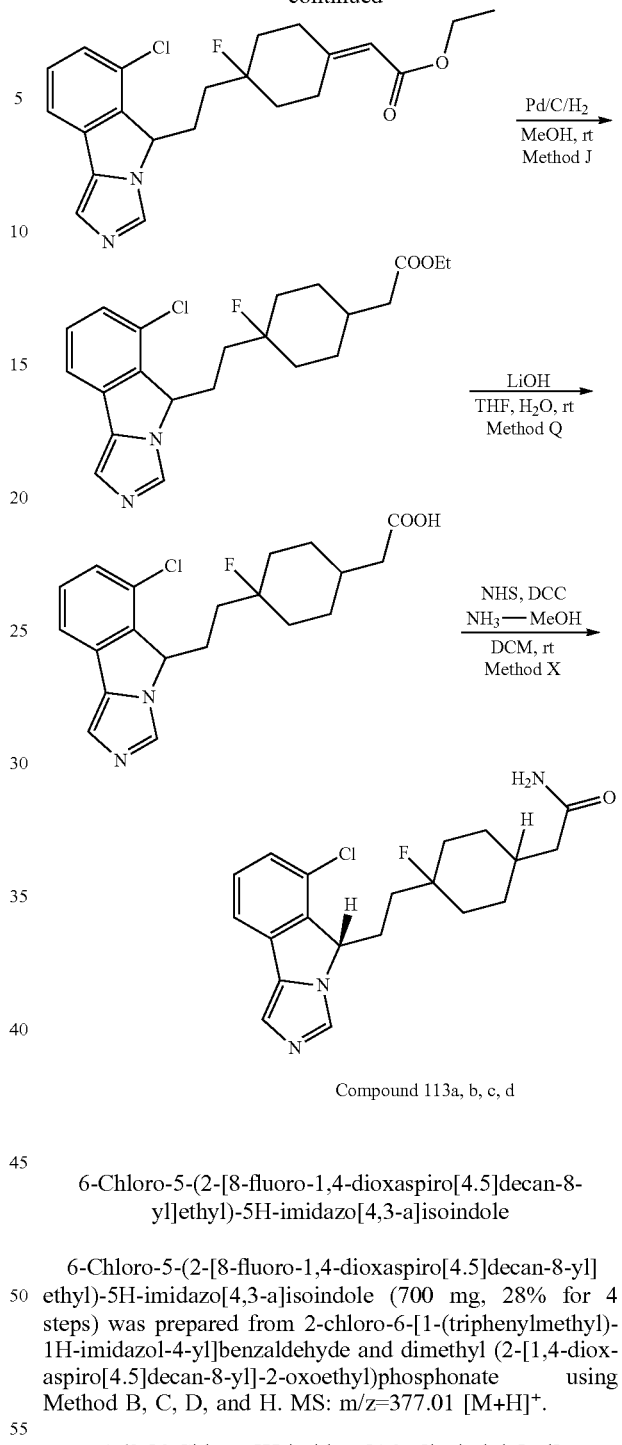

Compound 113a, b, c, d

6-Chloro-5-(2-[8-fluoro-1,4-dioxaspiro[4.5]decan-8-yl]ethyl)-5H-imidazo[4,3-a]isoindole 6-Chloro-5-(2-[8-fluoro-1,4-dioxaspiro[4.5]decan-8-yl]ethyl)-5H-imidazo[4,3-a]isoindole (700 mg, 28% for 4 steps) was prepared from 2-chloro-6-[1-(triphenylmethyl)-1H-imidazol-4-yl]benzaldehyde and dimethyl (2-[1,4-dioxaspiro[4.5]decan-8-yl]-2-oxoethyl)phosphonate using Method B, C, D, and H. MS: m/z=377.01 [M+H]$^+$.

4-(2-[6-Chloro-5H-imidazo[4,3-a]isoindol-5-yl]ethyl)-4-fluorocyclohexan-1-one

At room temperature, HCl solution (6 M, 12 mL, 72 mmol) was slowly added to a solution of 6-chloro-5-(2-[8-fluoro-1,4-dioxaspiro[4.5]decan-8-yl]ethyl)-5H-imidazo[4,3-a]isoindole (700 mg, 1.86 mmol) in THF (8 mL). The resulting mixture was stirred at room temperature for 16 h. Then the reaction mixture was neutralized with sat. NaHCO$_3$ solution and extracted with EtOAc (70 mL×3). The organic phases were combined, washed with brine and dried over Na$_2$SO$_4$. The solvent was removed under reduced pressure, and the residue was purified by flash chromatography eluting with MeOH in DCM (1% to 7% gradient) to yield 4-(2-[6-chloro-5H-imidazo[4,3-a]isoindol-5-yl]ethyl)-4-fluorocyclohexan-1-one (500 mg, 81%) as yellow oil. MS: m/z=332.97 [M+H]$^+$.

2-[4-[2-[6-Chloro-5H-imidazo[4,3-a]isoindol-5-yl]ethyl]-4-fluorocyclohexyl]acetamide 2-[4-[2-[6-Chloro-5H-imidazo[4,3-a]isoindol-5-yl]ethyl]-4-fluorocyclohexyl]acetamide was prepared from 4-(2-[6-chloro-5H-imidazo[4,3-a]isoindol-5-yl]ethyl)-4-fluorocyclohexan-1-one and ethyl 2-(diethoxyphosphoryl)acetate using Method B, J, Q, and X. Four enantiomeric products were obtained by the separation on chiral prep-HPLC under the following conditions: Phenomenex Lux 5μ Cellulose-4, AXIA Packed, 21.2×250 mm, 5 μm; mobile phase, EtOH in hexane, 50% isocratic in 25 min; Detector, UV 254/220 nm.

Compound 113a:

(19.5 mg, 3.5% for four steps, white solid, single stereoisomer), HPLC: 97.7% purity, RT=1.28 min. MS: m/z=376.15 [M+H]$^+$. $^1$H NMR (400 MHz, CD$_3$OD, ppm) δ=7.97 (s, 1H), 7.57 (d, J=7.6 Hz, 1H), 7.42 (t, J=8.0 Hz, 1H), 7.30 (d, J=8.0 Hz, 1H), 7.21 (s, 1H), 5.60 (t, J=4.0 Hz, 1H), 2.54-2.47 (m, 2H), 2.07 (d, J=7.2 Hz, 2H), 1.79-1.62 (m, 3H), 1.60-1.54 (m, 2H), 1.36-1.23 (m, 4H), 1.11-0.90 (m, 2H);

Compound 113b:

(19 mg, 3.4% for four steps, white solid, single stereoisomer) HPLC: 99.8% purity, RT=1.29 min. MS: m/z=376.15 [M+H]$^+$. $^1$H NMR (400 MHz, CD$_3$OD, ppm) δ=7.97 (s, 1H), 7.57 (d, J=7.6 Hz, 1H), 7.42 (t, J=8.0 Hz, 1H), 7.30 (d, J=8.0 Hz, 1H), 7.21 (s, 1H), 5.60 (t, J=4.0 Hz, 1H), 2.54-2.47 (m, 2H), 2.07 (d, J=7.2 Hz, 2H), 1.79-1.62 (m, 3H), 1.60-1.54 (m, 2H), 1.36-1.23 (m, 4H), 1.11-0.90 (m, 2H);

Compound 113c:

(6 mg, 1% for four steps, white solid, single stereoisomer), HPLC: 99.8% purity, RT=1.29 min. MS: m/z=376.15 [M+H]$^+$. $^1$H NMR (400 MHz, CD$_3$OD, ppm) δ=7.99 (s, 1H), 7.58 (d, J=7.2 Hz, 1H), 7.43 (t, J=8.0 Hz, 1H), 7.31 (d, J=8.0 Hz, 1H), 7.22 (s, 1H), 5.62 (t, J=4.0 Hz, 1H), 2.59-2.44 (m, 2H), 2.03 (d, J=7.6 Hz, 2H), 1.87-1.81 (m, 1H), 1.72-1.65 (m, 4H), 1.62-1.52 (m, 2H), 1.31-0.89 (m, 4H);

Compound 113d:

(5 mg, 0.9% for four steps, white solid, single stereoisomer) HPLC: 99.9% purity, RT=1.29 min. MS: m/z=376.2 [M+H]$^+$. $^1$H NMR (400 MHz, CD$_3$OD, ppm) δ=7.99 (s, 1H), 7.58 (d, J=7.2 Hz, 1H), 7.43 (t, J=8.0 Hz, 1H), 7.31 (d, J=8.0 Hz, 1H), 7.22 (s, 1H), 5.62 (t, J=4.0 Hz, 1H), 2.59-2.44 (m, 2H), 2.03 (d, J=7.6 Hz, 2H), 1.87-1.81 (m, 1H), 1.72-1.65 (m, 4H), 1.62-1.52 (m, 2H), 1.31-0.89 (m, 4H).

Example 114: Synthesis of 4-[2-[6-chloro-5H-imidazo[4,3-a]isoindol-5-yl]ethyl]-4-fluoro-N,N-dimethylcyclohexane-1-carboxamide (114a, b, c, d)

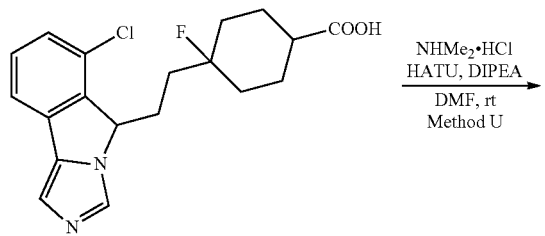

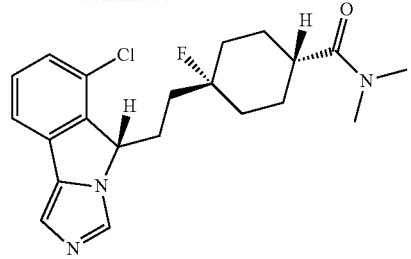

Compounds 114a, b, c, d

4-[2-[6-Chloro-5H-imidazo[4,3-a]isoindol-5-yl]ethyl]-4-fluoro-N,N-dimethylcyclohexane-1-carboxamide 4-[2-[6-Chloro-5H-imidazo[4,3-a]isoindol-5-yl]ethyl]-4-fluoro-N,N-dimethylcyclohexane-1-carboxamide was prepared from 4-(2-[6-chloro-5H-imidazo[4,3-a]isoindol-5-yl]ethyl)-4-fluorocyclohexane-1-carboxylic acid and NHMe$_2$·HCl using Method U. Four enantiomeric products were obtained by the separation on chiral prep-HPLC under the following conditions: Phenomenex Lux 5μ Cellulose-4, AXIA Packed, 21.2×250 mm, 5 μm; mobile phase, EtOH in hexane, 50% isocratic in 30 min; Detector, UV 254/220 nm.

Compound 114a:

(13.5 mg, 4.8%, white solid, single stereoisomer), HPLC: 99.7% purity, RT=1.37 min. MS: m/z=390.15 [M+H]$^+$. $^1$H NMR (300 MHz, CD$_3$OD, ppm) δ=7.93 (s, 1H), 7.54 (d, J=7.5 Hz, 1H), 7.39 (t, J=7.8 Hz, 1H), 7.27 (d, J=8.1 Hz, 1H), 7.18 (s, 1H), 5.58 (t, J=3.9 Hz, 1H), 3.04 (s, 3H), 2.87 (s, 3H), 2.62-2.46 (m, 3H), 1.82-1.63 (m, 4H), 1.53-1.48 (m, 2H), 1.45-1.20 (m, 2H), 1.12-0.88 (m, 2H);

Compound 114b:

(15 mg, 5.3%, white solid, single stereoisomer) HPLC: 98.7% purity, RT=1.36 min. MS: m/z=390.2 [M+H]$^+$. $^1$H NMR (300 MHz, CD$_3$OD, ppm) δ=7.93 (s, 1H), 7.54 (d, J=7.5 Hz, 1H), 7.39 (t, J=7.8 Hz, 1H), 7.27 (d, J=8.1 Hz, 1H), 7.18 (s, 1H), 5.58 (t, J=3.9 Hz, 1H), 3.04 (s, 3H), 2.87 (s, 3H), 2.62-2.46 (m, 3H), 1.82-1.63 (m, 4H), 1.53-1.48 (m, 2H), 1.45-1.20 (m, 2H), 1.12-0.88 (m, 2H);

Compound 114c:

(6 mg, 2.1%, white solid, single stereoisomer), HPLC: 99.9% purity, RT=1.44 min. MS: m/z=390.2 [M+H]$^+$. $^1$H NMR (300 MHz, CD$_3$OD, ppm) δ=7.94 (s, 1H), 7.55 (d, J=7.5 Hz, 1H), 7.39 (t, J=7.8 Hz, 1H), 7.28 (d, J=8.1 Hz, 1H), 7.18 (s, 1H), 5.58 (t, J=4.2 Hz, 1H), 3.03 (s, 3H), 2.84 (s, 3H), 2.72-2.66 (m, 1H), 2.50-2.44 (m, 2H), 1.89-1.52 (m, 6H), 1.40-1.00 (m, 4H);

Compound 114d:

(7.3 mg, 2.6%, white solid, single stereoisomer) HPLC: 88% purity, RT=1.45 min. MS: m/z=390.2 [M+H]$^+$. $^1$H NMR (300 MHz, CD$_3$OD, ppm) δ=7.94 (s, 1H), 7.55 (d, J=7.5 Hz, 1H), 7.39 (t, J=7.8 Hz, 1H), 7.28 (d, J=8.1 Hz, 1H), 7.18 (s, 1H), 5.58 (t, J=4.2 Hz, 1H), 3.03 (s, 3H), 2.84 (s, 3H), 2.72-2.66 (m, 1H), 2.50-2.44 (m, 2H), 1.89-1.52 (m, 6H), 1.40-1.00 (m, 4H).

Example 115: Synthesis of 1-[4-[2-[6-chloro-5H-imidazo[4,3-a]isoindol-5-yl]ethyl]-4-fluorocyclohexyl]carbonyl]piperidine (115a, b, c, d)

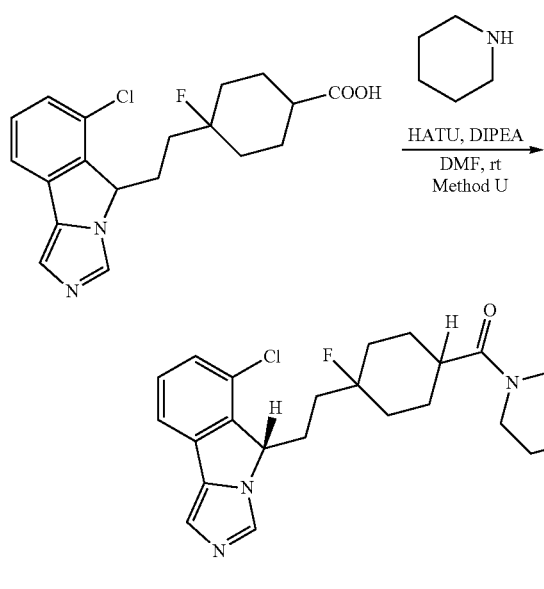

Compound 115a, b, c, d

1-[4-[2-[6-Chloro-5H-imidazo[4,3-a]isoindol-5-yl]ethyl]-4-fluorocyclohexyl]carbonyl]piperidine 1-[4-[2-[6-Chloro-5H-imidazo[4,3-a]isoindol-5-yl]ethyl]-4-fluorocyclohexyl]carbonyl]piperidine was prepared from 4-(2-[6-chloro-5H-imidazo[4,3-a]isoindol-5-yl]ethyl)-4-fluorocyclohexane-1-carboxylic acid and piperidine using Method U. Four enantiomeric products were obtained by the separation on chiral prep-HPLC under the following conditions: Phenomenex Lux 5μ Cellulose-4, AXIA Packed, 21.2×250 mm, 5 μm; mobile phase, EtOH in hexane, 50% isocratic in 30 min; Detector, UV 254/220 nm.

Compound 115a:
(22 mg, 5.6%, white solid, single stereoisomer), HPLC: 99.8% purity, RT=1.59 min. MS: m/z=430.25 [M+H]$^+$. $^1$H NMR (300 MHz, CD$_3$OD, ppm) δ=7.93 (s, 1H), 7.54 (d, J=7.5 Hz, 1H), 7.39 (t, J=7.8 Hz, 1H), 7.27 (d, J=7.8 Hz, 1H), 7.18 (s, 1H), 5.58 (t, J=4.2 Hz, 1H), 3.50-3.46 (m, 4H), 2.60-2.46 (m, 3H), 1.81-1.60 (m, 6H), 1.52-1.44 (m, 6H), 1.41-1.20 (m, 2H), 1.13-0.91 (m, 2H);

Compound 115b:
(21 mg, 5.3%, white solid, single stereoisomer) HPLC: 99.7% purity, RT=1.59 min. MS: m/z=430.25 [M+H]$^+$. $^1$H NMR (300 MHz, CD$_3$OD, ppm) δ=7.93 (s, 1H), 7.54 (d, J=7.5 Hz, 1H), 7.39 (t, J=7.8 Hz, 1H), 7.27 (d, J=7.8 Hz, 1H), 7.18 (s, 1H), 5.58 (t, J=4.2 Hz, 1H), 3.50-3.46 (m, 4H), 2.60-2.46 (m, 3H), 1.81-1.60 (m, 6H), 1.52-1.44 (m, 6H), 1.41-1.20 (m, 2H), 1.13-0.91 (m, 2H);

Compound 115c:
(7 mg, 1.8%, white solid, single stereoisomer), HPLC: 99.4% purity, RT=1.67 min. MS: m/z=430.2 [M+H]$^+$. $^1$H NMR (300 MHz, CD$_3$OD, ppm) δ=7.94 (s, 1H), 7.55 (d, J=7.2 Hz, 1H), 7.39 (t, J=7.8 Hz, 1H), 7.28 (d, J=7.8 Hz, 1H), 7.18 (s, 1H), 5.58 (t, J=3.9 Hz, 1H), 3.46-3.43 (m, 4H), 2.72-2.66 (m, 1H), 2.51-2.44 (m, 2H), 1.89-1.42 (m, 12H), 1.39-1.00 (m, 4H);

Compound 115d:
(10.5 mg, 2.6%, white solid, single stereoisomer) HPLC: 80% purity, RT=1.67 min. MS: m/z=430.2 [M+H]$^+$. $^1$H NMR (300 MHz, CD$_3$OD, ppm) δ=7.94 (s, 1H), 7.55 (d, J=7.2 Hz, 1H), 7.39 (t, J=7.8 Hz, 1H), 7.28 (d, J=7.8 Hz, 1H), 7.18 (s, 1H), 5.58 (t, J=3.9 Hz, 1H), 3.46-3.43 (m, 4H), 2.72-2.66 (m, 1H), 2.51-2.44 (m, 2H), 1.89-1.42 (m, 12H), 1.39-1.00 (m, 4H).

Example 116: Synthesis of 2-[4-fluoro-4-[2-[6-fluoro-5H-imidazo[4,3-a]isoindol-5-yl]ethyl]cyclohexyl]acetamide (116a, b, c, d)

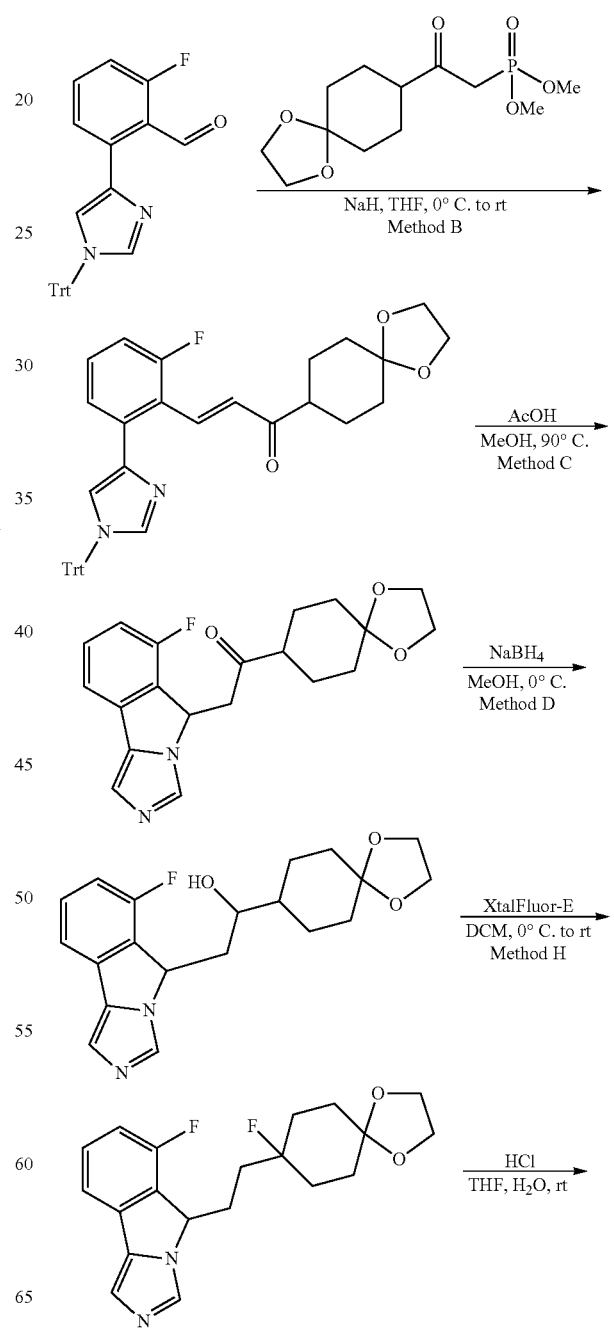

-continued

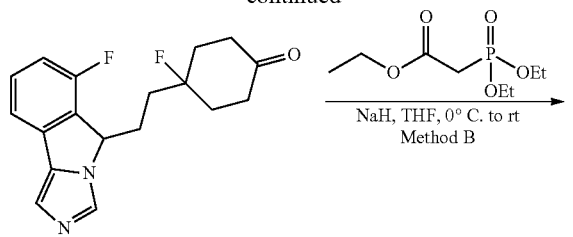

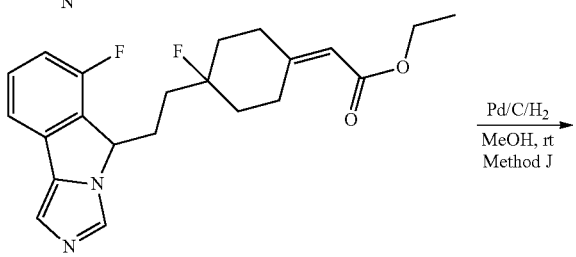

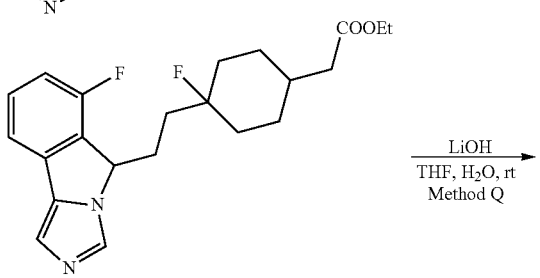

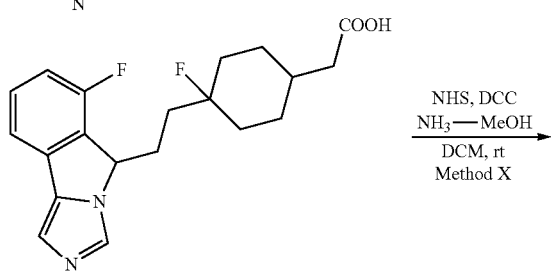

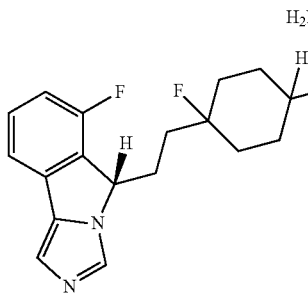

Compound 116a, b, c, d

6-Fluoro-5-(2-[8-fluoro-1,4-dioxaspiro[4.5]decan-8-yl]ethyl)-5H-imidazo[4,3-a]isoindole 6-Fluoro-5-(2-[8-fluoro-1,4-dioxaspiro[4.5]decan-8-yl]ethyl)-5H-imidazo[4,3-a]isoindole (900 mg, 31% for 4 steps) was prepared from 2-fluoro-6-[1-(triphenylmethyl)-1H-imidazol-4-yl]benzaldehyde and dimethyl (2-[1,4-dioxaspiro[4.5]decan-8-yl]-2-oxoethyl)phosphonate using Method B, C, D, and H. MS: m/z=361.05 [M+H]⁺.

4-Fluoro-4-(2-[6-fluoro-5H-imidazo[4,3-a]isoindol-5-yl]ethyl)cyclohexan-1-one

At room temperature, HCl solution (6 M, 12 mL, 72 mmol) was slowly added to a solution of 6-fluoro-5-(2-[8-fluoro-1,4-dioxaspiro[4.5]decan-8-yl]ethyl)-5H-imidazo[4,3-a]isoindole (900 mg, 2.50 mmol) in THF (8 mL). The resulting mixture was stirred at room temperature for 16 h. Then the reaction mixture was neutralized with sat. NaHCO₃ solution and extracted with EtOAc (70 mL×3). The organic phases were combined, washed with brine and dried over Na₂SO₄. The solvent was removed under reduced pressure and the residue was purified by flash chromatography eluting with MeOH in DCM (1% to 5% gradient) to yield 4-fluoro-4-(2-[6-fluoro-5H-imidazo[4,3-a]isoindol-5-yl]ethyl)cyclohexan-1-one (527 mg, 67%) as yellow oil. MS: m/z=317.0 [M+H]⁺.

2-[4-Fluoro-4-[2-[6-fluoro-5H-imidazo[4,3-a]isoindol-5-yl]ethyl]cyclohexyl]acetamide 2-[4-Fluoro-4-[2-[6-fluoro-5H-imidazo[4,3-a]isoindol-5-yl]ethyl]cyclohexyl]acetamide was prepared from 4-fluoro-4-(2-[6-fluoro-5H-imidazo[4,3-a]isoindol-5-yl]ethyl)cyclohexan-1-one and ethyl 2-(diethoxyphosphoryl)acetate using Method B, J, Q, and X. Four enantiomeric products were obtained by the separation on chiral prep-HPLC under the following conditions: Phenomenex Lux 5µ Cellulose-4, AXIA Packed, 21.2×250 mm, 5 µm; mobile phase, EtOH in hexane, 50% isocratic in 25 min; Detector, UV 254/220 nm.

Compound 116a:

(9.2 mg, 1.5% for four steps, white solid, single stereoisomer), HPLC: 95.1% purity, RT=1.19 min. MS: m/z=360.05 [M+H]⁺. ¹H NMR (400 MHz, CD₃OD, ppm) δ=7.97 (s, 1H), 7.46-7.44 (m, 2H), 7.21 (s, 1H), 7.08-7.03 (m, 1H), 5.68 (t, J=4.4 Hz, 1H), 2.48-2.41 (m, 1H), 2.30-2.23 (m, 1H), 2.05 (d, J=7.6 Hz, 2H), 1.87-1.81 (m, 1H), 1.75-1.65 (m, 4H), 1.62-1.52 (m, 2H), 1.35-1.23 (m, 2H), 1.00-0.90 (m, 2H);

Compound 116b:

(9.3 mg, 1.5% for four steps, white solid, single stereoisomer) HPLC: 99.1% purity, RT=1.19 min. MS: m/z=360.05 [M+H]⁺. ¹H NMR (400 MHz, CD₃OD, ppm) δ=7.97 (s, 1H), 7.46-7.44 (m, 2H), 7.21 (s, 1H), 7.08-7.03 (m, 1H), 5.68 (t, J=4.4 Hz, 1H), 2.48-2.41 (m, 1H), 2.30-2.23 (m, 1H), 2.05 (d, J=7.6 Hz, 2H), 1.87-1.81 (m, 1H), 1.75-1.65 (m, 4H), 1.62-1.52 (m, 2H), 1.35-1.23 (m, 2H), 1.00-0.90 (m, 2H);

Compound 116c:

(25 mg, 4.2% for four steps, white solid, single stereoisomer), HPLC: 93.8% purity, RT=1.20 min. MS: m/z=360.05 [M+H]⁺. ¹H NMR (400 MHz, CD₃OD, ppm) δ=7.94 (s, 1H), 7.46-7.44 (m, 2H), 7.19 (s, 1H), 7.07-7.03 (m, 1H), 5.66 (t, J=4.4 Hz, 1H), 2.50-2.40 (m, 1H), 2.31-2.21 (m, 1H), 2.08 (d, J=7.2 Hz, 2H), 1.81-1.62 (m, 3H), 1.59-1.56 (m, 2H), 1.40-1.08 (m, 6H);

Compound 116d:

(27.7 mg, 4.6% for four steps, white solid, single stereoisomer) HPLC: 97.5% purity, RT=1.21 min. MS: m/z=360.05 [M+H]⁺. ¹H NMR (400 MHz, CD₃OD, ppm) δ=7.94 (s, 1H), 7.46-7.44 (m, 2H), 7.19 (s, 1H), 7.07-7.03 (m, 1H), 5.66 (t, J=4.4 Hz, 1H), 2.50-2.40 (m, 1H), 2.31-2.21 (m, 1H), 2.08 (d, J=7.2 Hz, 2H), 1.81-1.62 (m, 3H), 1.59-1.56 (m, 2H), 1.40-1.08 (m, 6H).

Example 117: Synthesis of 1-[4-[1-hydroxy-2-[4,6, 9-triazatricyclo[6.4.0.0^[2,6]]dodeca-1(8),2,4,9,11-pentaen-7-yl]ethyl]cyclohexyl]cyclopropan-1-ol (117a, b, c, d)

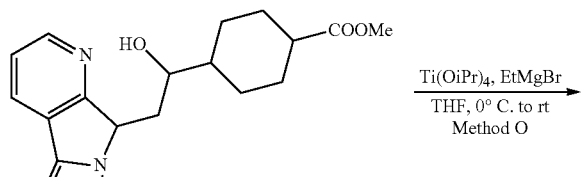

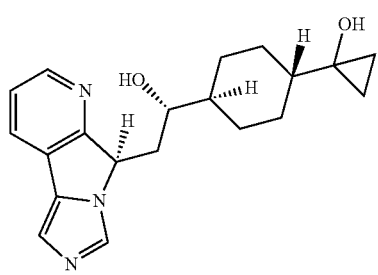

Compound 117a, b, c, d

1-[4-[1-Hydroxy-2-[4,6,9-triazatricyclo[6.4.0.0^[2,6]]dodeca-1(8),2,4,9,11-pentaen-7-yl]ethyl]cyclohexyl]cyclopropan-1-ol 1-[4-[1-Hydroxy-2-[4,6,9-triazatricyclo[6.4.0.0^[2,6]]dodeca-1(8),2,4,9,11-pentaen-7-yl]ethyl]cyclohexyl]cyclopropan-1-ol was prepared from methyl 4-(1-hydroxy-2-[4,6,9-triazatricyclo[6.4.0.0^[2,6]]dodeca-1(8),2,4,9,11-pentaen-7-yl]ethyl)cyclohexane-1-carboxylate using Method O. Four pairs of enantiomeric products were obtained by the separation on prep-HPLC under the following conditions: XBridge C18 OBD Prep Column, 19×250 mm, 5 μm; mobile phase, MeCN in water (with 10 mM NH$_4$HCO$_3$); 27% to 37% gradient in 12 min; Detector, UV 254/220 nm.

Compound 117a:

(6 mg, 1.5%, white solid, mixture of two stereoisomers) HPLC: 99.8% purity, RT=1.10 min. MS: m/z=340.05 [M+H]$^+$. $^1$H NMR (400 MHz, CD$_3$OD, ppm) δ=8.43 (dd, J=5.2, 1.2 Hz, 1H), 8.07-8.04 (m, 2H), 7.44 (dd, J=8.0, 5.2 Hz, 1H), 7.33 (s, 1H), 5.50 (dd, J=9.6, 3.6 Hz, 1H), 3.71-3.67 (m, 1H), 2.50-2.41 (m, 1H), 2.04-2.00 (m, 1H), 1.89-1.77 (m, 4H), 1.41-1.29 (m, 3H), 1.13-1.05 (m, 2H), 0.92-0.88 (m, 1H), 0.63-0.60 (m, 2H), 0.44-0.41 (m, 2H);

Compound 117b:

(8.8 mg, 2.2%, white solid, mixture of two stereoisomers) HPLC: 99.3% purity, RT=1.12 min. MS: m/z=340.1 [M+H]$^+$. $^1$H NMR (400 MHz, CD$_3$OD, ppm) δ=8.42 (dd, J=4.8, 1.2 Hz, 1H), 8.11 (s, 1H), 8.02 (dd, J=8.0, 1.2 Hz, 1H), 7.42 (dd, J=7.6, 5.2 Hz, 1H), 7.30 (s, 1H), 5.38 (t, J=5.6 Hz, 1H), 3.86-3.83 (m, 1H), 2.42-2.37 (m, 1H), 2.11-2.03 (m, 1H), 1.99-1.95 (m, 1H), 1.86-1.78 (m, 3H), 1.38-1.30 (m, 3H), 1.19-1.03 (m, 2H), 0.91-0.86 (m, 1H), 0.63-0.60 (m, 2H), 0.45-0.42 (m, 2H);

Compound 117c:

(23 mg, 5.7%, white solid, mixture of two stereoisomers) HPLC: 99.5% purity, RT=1.18 min. MS: m/z=340.05 [M+H]$^+$. $^1$H NMR (400 MHz, CD$_3$OD, ppm) δ=8.43 (dd, J=5.2, 1.2 Hz, 1H), 8.12 (s, 1H), 8.03 (dd, J=7.6, 1.2 Hz, 1H), 7.42 (dd, J=7.6, 5.2 Hz, 1H), 7.31 (s, 1H), 5.43 (t, J=6.0 Hz, 1H), 4.35-4.30 (m, 1H), 2.53-2.48 (m, 1H), 2.21-2.17 (m, 1H), 2.01-1.96 (m, 1H), 1.80-1.75 (m, 1H), 1.61-1.39 (m, 7H), 1.10-1.06 (m, 1H), 0.64-0.61 (m, 2H), 0.48-0.45 (m, 2H);

Compound 117d:

(20 mg, 5%, white solid, mixture of two stereoisomers) HPLC: 98.6% purity, RT=1.16 min. MS: m/z=340.05 [M+H]$^+$. $^1$H NMR (400 MHz, CD$_3$OD, ppm) δ=8.43 (d, J=4.8 Hz, 1H), 8.07-8.05 (m, 2H), 7.44 (dd, J=7.6, 5.2 Hz, 1H), 7.34 (s, 1H), 5.54 (dd, J=10.0, 2.8 Hz, 1H), 4.14-4.09 (m, 1H), 2.40-2.32 (m, 1H), 2.27-2.22 (m, 1H), 1.99-1.92 (m, 1H), 1.76-1.58 (m, 4H), 1.55-1.43 (m, 3H), 1.31-1.21 (m, 1H), 1.03-0.98 (m, 1H), 0.63-0.59 (m, 2H), 0.43-0.39 (m, 2H).

Example 118: Synthesis of 1-cyclohexyl-2-[10-methoxy-4,6,9-triazatricyclo[6.4.0.0^[2,6]]dodeca-1(8),2,4,9,11-pentaen-7-yl]ethan-1-amine (118a, b, c)

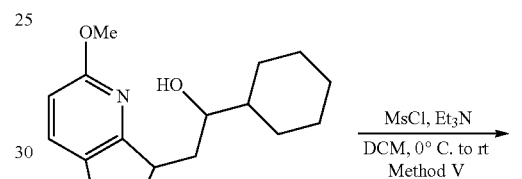

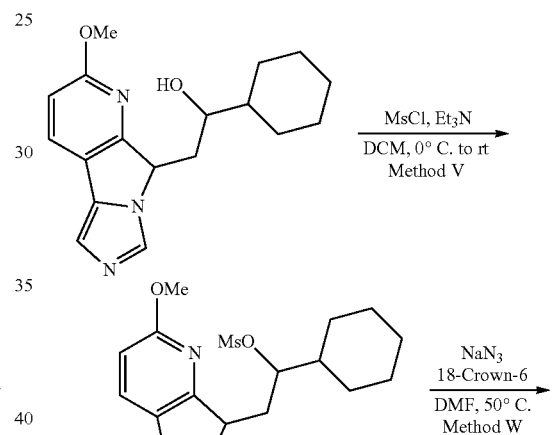

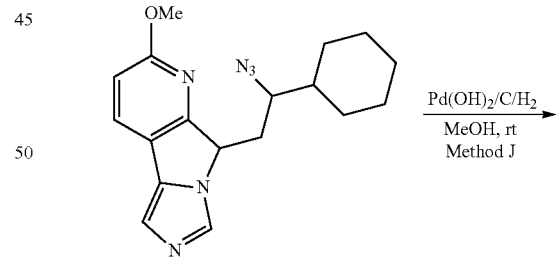

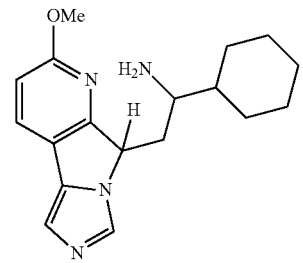

Compound 118a, b, c

1-Cyclohexyl-2-[10-methoxy-4,6,9-triazatricyclo[6.4.0.0^[2,6]]dodeca-1(8),2,4,9,11-pentaen-7-yl]ethan-1-amine 1-Cyclohexyl-2-[10-methoxy-4,6,9-triazatricyclo[6.4.0.0^[2,6]]dodeca-1(8),2,4,9,11-pentaen-7-yl]ethan-1-amine was prepared from 1-cyclohexyl-2-[10-methoxy-4,6,9-triazatricyclo[6.4.0.0^[2,6]]dodeca-1(8),2,4,9,11-pentaen-7-yl]ethan-1-ol using Method V, W, and J. One pair of enantiomeric and two enantiomeric products were obtained by the separation on chiral prep-HPLC under the following conditions: Phenomenex Lux 5μ Cellulose-4, AXIA Packed, 21.2×250 mm, 5 μm; mobile phase, EtOH in hexane, 30% isocratic in 23 min; Detector, UV 254/220 nm.

Compound 118a:

(6 mg, 1.5% for three steps, yellow oil, mixture of two stereoisomers) HPLC: 89.3% purity, RT=1.06 min. MS: m/z=313.1 [M+H]$^+$. $^1$H NMR (400 MHz, CD$_3$OD, ppm) δ=7.99 (s, 1H), 7.93 (d, J=8.4 Hz, 1H), 7.13 (s, 1H), 6.83 (d, J=8.4 Hz, 1H), 5.37 (dd, J=8.0, 4.8 Hz, 1H), 3.98 (s, 3H), 3.05-3.01 (m, 1H), 2.22-2.18 (m, 1H), 2.02-1.96 (m, 1H), 1.80-1.67 (m, 5H), 1.38-1.07 (m, 6H);

Compound 118b:

(8.8 mg, 2.2% for three steps, yellow oil, single stereoisomer) HPLC: 91.7% purity, RT=1.11 min. MS: m/z=313.1 [M+H]$^+$. $^1$H NMR (400 MHz, CD$_3$OD, ppm) δ=7.95-7.92 (m, 2H), 7.11 (s, 1H), 6.82 (d, J=8.4 Hz, 1H), 5.32 (dd, J=8.4, 4.8 Hz, 1H), 3.99 (s, 3H), 3.27-3.22 (m, 1H), 2.19-2.05 (m, 2H), 1.80-1.67 (m, 5H), 1.39-1.04 (m, 6H);

Compound 118c:

(23 mg, 5.7% for three steps, yellow oil, single stereoisomer) HPLC: 92.0% purity, RT=1.10 min. MS: m/z=313.1 [M+H]$^+$. $^1$H NMR (400 MHz, CD$_3$OD, ppm) δ=7.95-7.92 (m, 2H), 7.11 (s, 1H), 6.82 (d, J=8.4 Hz, 1H), 5.32 (dd, J=8.4, 4.8 Hz, 1H), 3.99 (s, 3H), 3.27-3.22 (m, 1H), 2.19-2.05 (m, 2H), 1.80-1.67 (m, 5H), 1.39-1.04 (m, 6H).

Example 119: Synthesis of 1-(4,4-dimethylcyclohexyl)-2-[10-methoxy-4,6,9-triazatricyclo[6.4.0.0^[2,6]]dodeca-1(8),2,4,9,11-pentaen-7-yl]ethan-1-amine (119a, b, c, d)

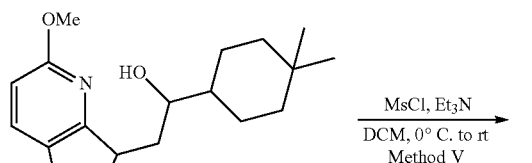

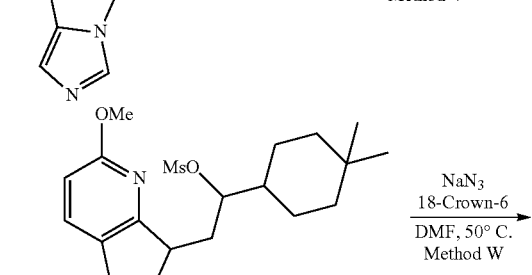

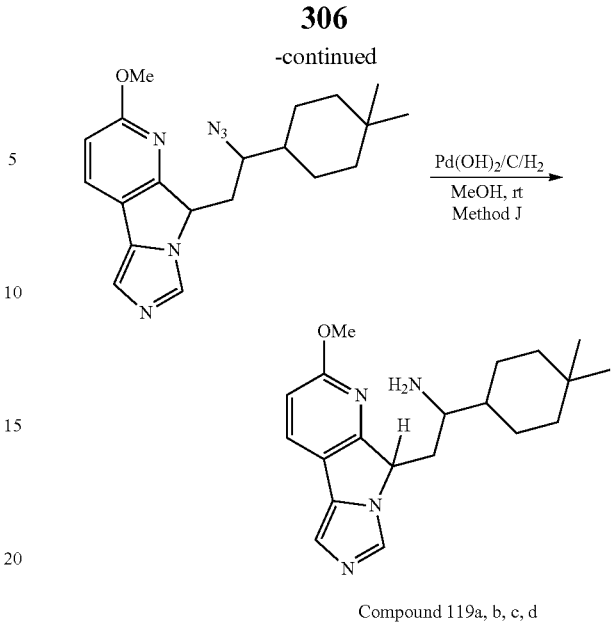

Compound 119a, b, c, d

1-(4,4-Dimethylcyclohexyl)-2-[10-methoxy-4,6,9-triazatricyclo[6.4.0.0^[2,6]]dodeca-1(8),2,4,9,11-pentaen-7-yl]ethan-1-amine 1-(4,4-Dimethylcyclohexyl)-2-[10-methoxy-4,6,9-triazatricyclo[6.4.0.0^[2,6]]dodeca-1(8),2,4,9,11-pentaen-7-yl]ethan-1-amine was prepared from 1-(4,4-dimethylcyclohexyl)-2-[10-methoxy-4,6,9-triazatricyclo[6.4.0.0^[2,6]]dodeca-1(8),2,4,9,11-pentaen-7-yl]ethan-1-ol using Method V, W, and J. Four enantiomeric products were obtained by the separation on chiral prep-HPLC under the following conditions: CHIRALPAK-AD-H-SL001, 20×250 mm, 5 μm; mobile phase, EtOH in hexane, 20% isocratic in 15 min; Detector, UV 254/220 nm.

Compound 119a:

(7.8 mg, 1.8% for three steps, yellow oil, single stereoisomer) HPLC: 98.6% purity, RT=0.93 min. MS: m/z=341.2 [M+H]$^+$. $^1$H NMR (400 MHz, CD$_3$OD, ppm) δ=7.92 (s, 1H), 7.89 (d, J=8.8 Hz, 1H), 7.09 (s, 1H), 6.80 (d, J=8.4 Hz, 1H), 5.30 (dd, J=8.0, 4.8 Hz, 1H), 3.97 (s, 3H), 3.24-3.21 (m, 1H), 2.18-2.05 (m, 2H), 1.57-1.38 (m, 4H), 1.31-1.15 (m, 5H), 0.88 (s, 6H);

Compound 119b:

(13.8 mg, 3.2% for three steps, yellow oil, single stereoisomer) HPLC: 99.2% purity, RT=0.88 min. MS: m/z=341.15 [M+H]$^+$. $^1$H NMR (400 MHz, CD$_3$OD, ppm) δ=7.97 (s, 1H), 7.91 (d, J=8.4 Hz, 1H), 7.11 (s, 1H), 6.82 (d, J=8.4 Hz, 1H), 5.35 (dd, J=8.0, 5.2 Hz, 1H), 3.96 (s, 3H), 3.07-3.05 (m, 1H), 2.21-2.15 (m, 1H), 2.04-1.98 (m, 1H), 1.60-1.57 (m, 1H), 1.52-1.39 (m, 3H), 1.32-1.13 (m, 5H), 0.88 (s, 6H);

Compound 119c:

(14.1 mg, 3.2% for three steps, yellow oil, single stereoisomer) HPLC: 96.5% purity, RT=0.88 min. MS: m/z=341.15 [M+H]$^+$. $^1$H NMR (400 MHz, CD$_3$OD, ppm) δ=7.97 (s, 1H), 7.91 (d, J=8.4 Hz, 1H), 7.11 (s, 1H), 6.82 (d, J=8.4 Hz, 1H), 5.35 (dd, J=8.0, 5.2 Hz, 1H), 3.96 (s, 3H), 3.07-3.05 (m, 1H), 2.21-2.15 (m, 1H), 2.04-1.98 (m, 1H), 1.60-1.57 (m, 1H), 1.52-1.39 (m, 3H), 1.32-1.13 (m, 5H), 0.88 (s, 6H);

Compound 119d:

(14.1 mg, 3.2% for three steps, yellow oil, single stereoisomer) HPLC: 91.6% purity, RT=1.88 min. MS: m/z=341.15 [M+H]$^+$. $^1$H NMR (400 MHz, CD$_3$OD, ppm) δ=7.92 (s, 1H), 7.89 (d, J=8.8 Hz, 1H), 7.09 (s, 1H), 6.80 (d, J=8.4 Hz, 1H), 5.30 (dd, J=8.0, 4.8 Hz, 1H), 3.97 (s, 3H), 3.24-3.21 (m, 1H), 2.18-2.05 (m, 2H), 1.57-1.38 (m, 4H), 1.31-1.15 (m, 5H), 0.88 (s, 6H).

Example 120: Synthesis of 1-(4,4-difluorocyclohexyl)-2-[10-methoxy-4,6,9-triazatricyclo[6.4.0.0^[2,6]]dodeca-1(8),2,4,9,11-pentaen-7-yl]ethan-1-amine (120a, b, c, d)

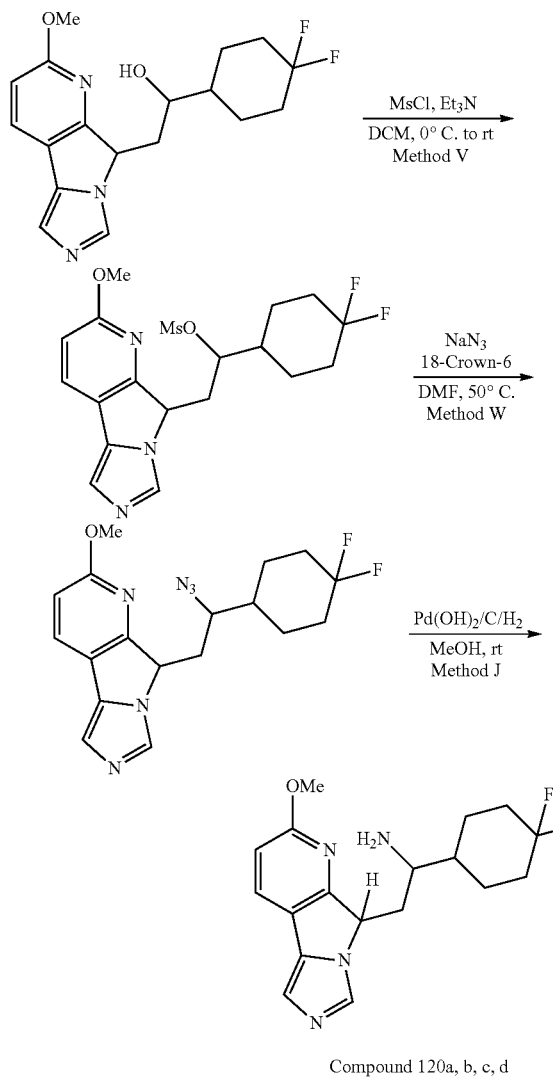

Compound 120a, b, c, d 1-(4,4-Difluorocyclohexyl)-2-[10-methoxy-4,6,9-triazatricyclo[6.4.0.0^[2,6]]dodeca-1(8),2,4,9,11-pentaen-7-yl]ethan-1-amine 1-(4,4-Difluorocyclohexyl)-2-[10-methoxy-4,6,9-triazatricyclo[6.4.0.0^[2,6]]dodeca-1(8),2,4,9,11-pentaen-7-yl]ethan-1-amine was prepared from 1-(4,4-difluorocyclohexyl)-2-[10-methoxy-4,6,9-triazatricyclo[6.4.0.0^[2,6]] dodeca-1(8),2,4,9,11-pentaen-7-yl]ethan-1-ol using Method V, W, and J. Four enantiomeric products were obtained by the separation on chiral prep-HPLC under the following conditions: CHIRALPAK-AD-H-SL001, 20×250 mm, 5 μm; mobile phase, EtOH in hexane, 20% isocratic in 21 min; Detector, UV 254/220 nm.

Compound 120a:

(15 mg, 3.5% for three steps, yellow oil, single stereoisomer) HPLC: 93.8% purity, RT=0.78 min. MS: m/z=349.15 [M+H]$^+$. $^1$H NMR (400 MHz, CD$_3$OD, ppm) δ=7.93 (s, 1H), 7.88 (d, J=8.4 Hz, 1H), 7.08 (s, 1H), 6.79 (d, J=8.4 Hz, 1H), 5.31 (dd, J=8.8, 4.8 Hz, 1H), 3.93 (s, 3H), 3.31-3.29 (m, 1H), 2.18-2.12 (m, 1H), 2.09-2.01 (m, 3H), 1.81-1.64 (m, 4H), 1.41-1.34 (m, 3H);

Compound 120b:

(14 mg, 3.3% for three steps, yellow oil, single stereoisomer) HPLC: 97.3% purity, RT=0.73 min. MS: m/z=349.15 [M+H]$^+$. $^1$H NMR (400 MHz, CD$_3$OD, ppm) δ=7.99 (s, 1H), 7.88 (d, J=8.8 Hz, 1H), 7.10 (s, 1H), 6.80 (d, J=8.4 Hz, 1H), 5.36 (dd, J=8.4, 4.8 Hz, 1H), 3.94 (s, 3H), 3.10-3.06 (m, 1H), 2.22-2.17 (m, 1H), 2.09-2.01 (m, 1H), 1.95-1.89 (m, 1H), 1.84-1.61 (m, 4H), 1.45-1.33 (m, 3H);

Compound 120c:

(15 mg, 3.5% for three steps, yellow oil, single stereoisomer) HPLC: 97.2% purity, RT=0.78 min. MS: m/z=349.1 [M+H]$^+$. $^1$H NMR (400 MHz, CD$_3$OD, ppm) δ=7.93 (s, 1H), 7.88 (d, J=8.4 Hz, 1H), 7.08 (s, 1H), 6.79 (d, J=8.4 Hz, 1H), 5.31 (dd, J=8.8, 4.8 Hz, 1H), 3.93 (s, 3H), 3.31-3.29 (m, 1H), 2.18-2.12 (m, 1H), 2.09-2.01 (m, 3H), 1.81-1.64 (m, 4H), 1.41-1.34 (m, 3H);

Compound 120d:

(16 mg, 3.7% for three steps, yellow oil, single stereoisomer) HPLC: 95.4% purity, RT=0.72 min. MS: m/z=349.1 [M+H]$^+$. $^1$H NMR (400 MHz, CD$_3$OD, ppm) δ=7.99 (s, 1H), 7.88 (d, J=8.8 Hz, 1H), 7.10 (s, 1H), 6.80 (d, J=8.4 Hz, 1H), 5.36 (dd, J=8.4, 4.8 Hz, 1H), 3.94 (s, 3H), 3.10-3.06 (m, 1H), 2.22-2.17 (m, 1H), 2.09-2.01 (m, 1H), 1.95-1.89 (m, 1H), 1.84-1.61 (m, 4H), 1.45-1.33 (m, 3H).

Example 121: Synthesis of 4-fluoro-4-[2-[5H-imidazo[4,3-a]isoindol-5-yl]ethyl]cyclohexane-1-sulfonamide (121a, b, c, d)

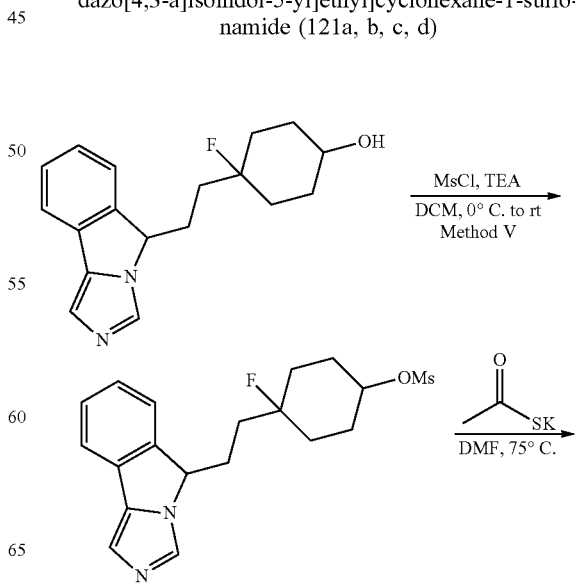

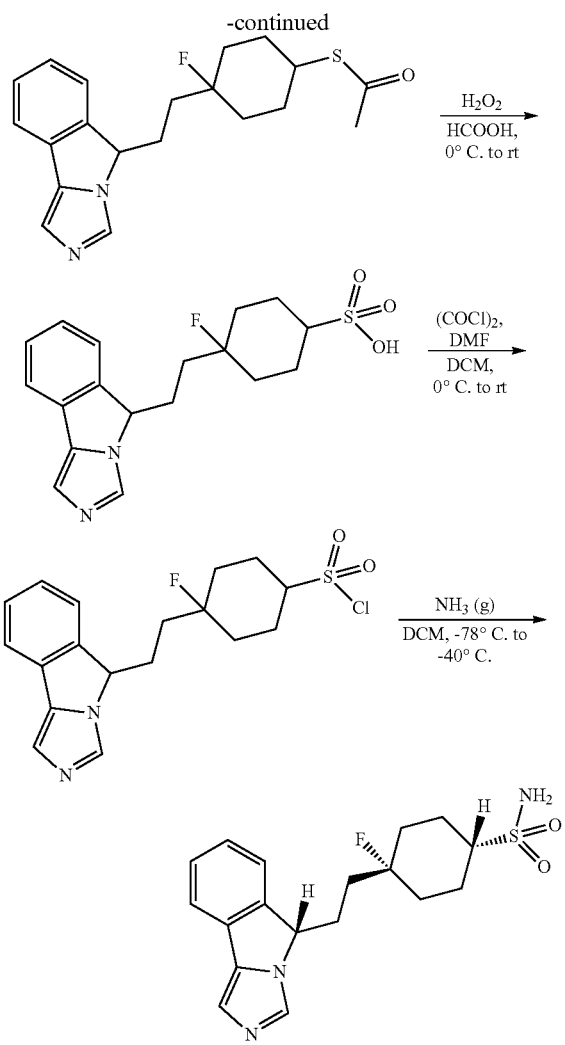

Compound 121a, b, c, d

4-Fluoro-4-(2-[5H-imidazo[4,3-a]isoindol-5-yl]ethyl)cyclohexyl methanesulfonate 4-Fluoro-4-(2-[5H-imidazo[4,3-a]isoindol-5-yl]ethyl)cyclohexyl methanesulfonate (1.6 g, 85%) was prepared from 4-fluoro-4-(2-[5H-imidazo[4,3-a]isoindol-5-yl]ethyl)cyclohexan-1-ol using Method V. MS: m/z=379.0 [M+H]$^+$.

1-[[4-Fluoro-4-(2-[5H-imidazo[4,3-a]isoindol-5-yl]ethyl)cyclohexyl]sulfanyl]ethan-1-one At room temperature, to a solution of 4-fluoro-4-(2-[5H-imidazo[4,3-a]isoindol-5-yl]ethyl)cyclohexyl methanesulfonate (1.6 g, 4.23 mmol) in DMF (20 mL) was added 1-(potassiosulfanyl)ethan-1-one (1.45 g, 12.72 mmol). The resulting mixture was stirred at 75° C. for 4 h. Then the reaction mixture was diluted with water (80 mL) and extracted with EtOAc (100 mL×2). The organic phases were combined, washed with brine and dried over Na$_2$SO$_4$. The solvent was removed under reduced pressure and the residue was purified by flash chromatography eluting with MeOH in DCM (1% to 5% gradient) to yield 1-[[4-fluoro-4-(2-[5H-imidazo[4,3-a]isoindol-5-yl]ethyl)cyclohexyl]sulfanyl] ethan-1-one (1.45 g, 81%) as light brown oil. MS: m/z=359.05 [M+H]$^+$.

4-Fluoro-4-(2-[5H-imidazo[4,3-a]isoindol-5-yl]ethyl)cyclohexane-1-sulfonic acid At 0° C., to a solution of 1-[[4-fluoro-4-(2-[5H-imidazo[4,3-a]isoindol-5-yl]ethyl)cyclohexyl]sulfanyl] ethan-1-one (1.45 g, 4.05 mmol) in HCOOH (20 mL) was added H$_2$O$_2$ (30%, 4 mL) dropwise. The resulting mixture was stirred at room temperature for 2 h. Then the reaction mixture was concentrated under reduced pressure and the residue was purified by reverse phase chromatography eluting with MeCN in water (5% to 30% gradient) to yield 4-fluoro-4-(2-[5H-imidazo[4,3-a]isoindol-5-yl]ethyl)cyclohexane-1-sulfonic acid (300 mg, 20%) as light yellow solid. MS: m/z=365.0 [M+H]$^+$.

4-Fluoro-4-(2-[5H-imidazo[4,3-a]isoindol-5-yl]ethyl)cyclohexane-1-sulfonyl chloride At 0° C., to a solution of 4-fluoro-4-(2-[5H-imidazo[4,3-a]isoindol-5-yl]ethyl)cyclohexane-1-sulfonic acid (300 mg, 0.82 mmol) in DCM (10 mL) was added (COCl)$_2$ (0.35 mL, 4.11 mmol) slowly, followed by the addition of one drop of anhydrous DMF. The resulting mixture was then stirred at room temperature for 1 h. After the reaction was done, the reaction mixture was concentrated under reduced pressure to yield 4-fluoro-4-(2-[5H-imidazo[4,3-a]isoindol-5-yl]ethyl)cyclohexane-1-sulfonyl chloride (310 mg, 98%) as light yellow solid which was used in the next step without further purification. MS: m/z=383.0 [M+H]$^+$.

4-Fluoro-4-[2-[5H-imidazo[4,3-a]isoindol-5-yl]ethyl]cyclohexane-1-sulfonamide At −78° C., a solution of 4-fluoro-4-(2-[5H-imidazo[4,3-a]isoindol-5-yl]ethyl)cyclohexane-1-sulfonyl chloride (310 mg, 0.81 mmol) in DCM (10 mL) was stirring while NH$_3$ gas was bubbled through it for 5 min. The resulting mixture was kept stirring while slowly warmed up to −40° C. over 20 min period. Then the reaction mixture was concentrated under reduced pressure and the residue was purified by prep-HPLC to give two pairs of enantiomeric products under the following conditions: XBridge BEH130 Prep C18 OBD Column, 19×150 mm, 5 µm; mobile phase, MeCN in water (with 0.05% TFA); 6% to 20% gradient in 20 min; Detector, UV 254/220 nm. Then four enantiomeric products were obtained by the further separation on chiral prep-HPLC under the following conditions: Phenomenex Lux 5µ Cellulose-4, AXIA Packed, 21.2×250 mm, 5 µm; mobile phase, EtOH in hexane, 50% isocratic in 60 min; Detector, UV 254/220 nm.

Compound 121a:
(25 mg, 8.4%, white solid, single stereoisomer), HPLC: 99.95% purity, RT=0.86 min. MS: m/z=364.15 [M+H]$^+$. $^1$H NMR (300 MHz, CD$_3$OD, ppm) δ=7.89 (s, 1H), 7.58 (d, J=7.5 Hz, 1H), 7.45 (d, J=7.5 Hz, 1H), 7.38 (t, J=7.2 Hz, 1H), 7.32-7.27 (m, 1H), 7.12 (s, 1H), 5.41 (t, J=4.8 Hz, 1H), 2.89-2.79 (m, 1H), 2.42-2.32 (m, 1H), 2.23-2.10 (m, 1H), 2.02-1.87 (m, 4H), 1.83-1.68 (m, 2H), 1.50-1.15 (m, 4H);

Compound 121b:
(21 mg, 7.1%, white solid, single stereoisomer) HPLC: 97.9% purity, RT=0.88 min. MS: m/z=364.15 [M+H]$^+$. $^1$H NMR (300 MHz, CD$_3$OD, ppm) δ=7.95 (s, 1H), 7.59 (d, J=7.5 Hz, 1H), 7.47 (d, J=7.2 Hz, 1H), 7.39 (t, J=7.2 Hz, 1H), 7.33-7.28 (m, 1H), 7.15 (s, 1H), 5.43 (t, J=4.8 Hz, 1H), 2.98-2.92 (m, 1H), 2.40-2.28 (m, 1H), 2.21-1.86 (m, 5H), 1.70-1.55 (m, 4H), 1.40-1.23 (m, 2H);

Compound 121c:

(26 mg, 8.8%, white solid, single stereoisomer), HPLC: 99.7% purity, RT=0.85 min. MS: m/z=364.1 [M+H]$^+$. $^1$H NMR (300 MHz, CD$_3$OD, ppm) δ=7.89 (s, 1H), 7.58 (d, J=7.5 Hz, 1H), 7.45 (d, J=7.5 Hz, 1H), 7.38 (t, J=7.2 Hz, 1H), 7.32-7.27 (m, 1H), 7.12 (s, 1H), 5.41 (t, J=4.8 Hz, 1H), 2.89-2.79 (m, 1H), 2.42-2.32 (m, 1H), 2.23-2.10 (m, 1H), 2.02-1.87 (m, 4H), 1.83-1.68 (m, 2H), 1.50-1.15 (m, 4H);

Compound 121d:

(22 mg, 7.4%, white solid, single stereoisomer) HPLC: 99.0% purity, RT=1.66 min. MS: m/z=364.15 [M+H]$^+$. $^1$H NMR (300 MHz, CD$_3$OD, ppm) δ=7.95 (s, 1H), 7.59 (d, J=7.5 Hz, 1H), 7.47 (d, J=7.2 Hz, 1H), 7.39 (t, J=7.2 Hz, 1H), 7.33-7.28 (m, 1H), 7.15 (s, 1H), 5.43 (t, J=4.8 Hz, 1H), 2.98-2.92 (m, 1H), 2.40-2.28 (m, 1H), 2.21-1.86 (m, 5H), 1.70-1.55 (m, 4H), 1.40-1.23 (m, 2H).

Example 122: Biological Assays

Measurement of human IDO-1 inhibition was performed in 384-well format using the BRIDGE-IT® tryptophan Fluorescence Assay (Mediomics, LLC, St. Louis, Mo., U.S.A.). The assay was adapted from published protocol; Meininger et al., *Biochimica et Biophysica Acta* 2011. Recombinant human IDO in assay buffer (50 mM potassium phosphate buffer pH 6.5, 20 mM Ascorbic acid (Sigma), 10 mM Methylen Blue (Sigma) and 0.1 ug/ml catalase (Sigma)) was added to a range of compounds concentration previously serial diluted in DMSO (range of concentrations from 10 μM to 38 pM) or controls (1% DMSO). The concentration of enzyme in all the reaction wells was 7.5 nM. After 30 minutes of pre-incubation at 25° C., the reaction was initiated by the addition of L-Tryptophan (Sigma) at a final concentration of 50 μM in assay buffer. After 60 minutes of incubation at 25° C., the reaction is stopped by transferring 1 μl of the reaction mixture to 9 μl of Bridge-IT assay solution A. After 30 min of incubation at 30° C., the fluorescence intensity was measured at $\lambda_{ex}$=485 nm and $\lambda_{em}$=665 nm using Perkin Elmer ENVISION® Multilabel Reader.

The data is interpreted according to the following:

| Compound number | Bridge-it |
|---|---|
| 1a | C |
| 1b | B |
| 8a | B |
| 8b | C |
| 9a | C |
| 9b | C |
| 11a | C |
| 12a | C |
| 12b | C |
| 11b | C |
| 14a | C |
| 14b | A |
| 5a | B |
| 5b | C |
| 6a | C |
| 6b | C |
| 6c | C |
| 6d | C |
| 15a | C |
| 15b | C |
| 17 | B |
| 18a | B |
| 18b | C |
| 3a | C |
| 3b | C |
| 2a | C |
| 2b | C |
| 10a | C |
| 10b | C |
| 4a | C |
| 22a | B |
| 4b | C |
| 22b | C |
| 22c | C |
| 22d | C |
| 7a | C |
| 20a | C |
| 19a | C |
| 7b | C |
| 19b | A |
| 20b | B |
| 13a | C |
| 16b | B |
| 21a | C |
| 13b | A |
| 21b | C |
| 21c | C |
| 21d | C |
| 16a | A |
| 23a | C |
| 24a | C |
| 24b | C |
| 24c | A |
| 24d | A |
| 25a | C |
| 25b | C |
| 25c | C |
| 25d | C |
| 26a | C |
| 26b | B |
| 27a | C |
| 27b | B |
| 28a | C |
| 28b | C |
| 28c | C |
| 28d | C |
| 29a | B |
| 29b | C |
| 29c | B |
| 29d | C |
| 30a | B |
| 30b | C |
| 31a | B |
| 31b | B |
| 32a | C |
| 32b | B |
| 33a | B |
| 33b | B |
| 34a | A |
| 34b | C |
| 35a | C |
| 35b | B |
| 35c | A |
| 35d | C |
| 36a | C |
| 36b | C |
| 37a | C |
| 37b | B |
| 38a | C |
| 38b | B |
| 38c | C |
| 38d | A |
| 39a | A |
| 39b | B |
| 40a | C |
| 40b | B |
| 41a | C |
| 41b | C |

-continued

| Compound number | Bridge-it |
|---|---|
| 42a | C |
| 42b | B |
| 43a | C |
| 43b | A |
| 44a | B |
| 44b | B |
| 45a | C |
| 45b | C |
| 46 | C |
| 47 | C |
| 48a | C |
| 48b | C |
| 49 | B |
| 50 | B |
| 51 | C |
| 52a | B |
| 52b | B |
| 52c | C |
| 53a | B |
| 53b | A |
| 53c | C |
| 54a | A |
| 54b | C |
| 55a | B |
| 55b | C |
| 55c | C |
| 55d | B |
| 56a | A |
| 56b | A |
| 56c | C |
| 57a | C |
| 57b | B |
| 57c | B |
| 58a | C |
| 58c | C |
| 58d | C |
| 59a | C |
| 59b | A |
| 59c | A |
| 59d | C |
| 60a | A |
| 60b | C |
| 60c | C |
| 60d | A |
| 61a | C |
| 61b | C |
| 61c | A |
| 61d | A |
| 62a | B |
| 62c | C |
| 62c | C |
| 62d | C |
| 63a | C |
| 63b | C |
| 63c | C |
| 63d | C |
| 64 | B |
| 65 | B |
| 66a | C |
| 66b | C |
| 67a | C |
| 67b | C |
| 67c | C |
| 67d | C |
| 67a | B |
| 67b | C |
| 67c | C |
| 68a | B |
| 68b | C |
| 68c | C |
| 69a | B |
| 69b | C |
| 69c | C |
| 69d | C |
| 70a | C |
| 70b | B |

-continued

| Compound number | Bridge-it |
|---|---|
| 71a | B |
| 71b | B |
| 71c | C |
| 71d | A |
| 72a | C |
| 72b | B |
| 73a | C |
| 73b | C |
| 73c | C |
| 73d | C |
| 74a | A |
| 74b | B |
| 75a | A |
| 75b | B |
| 76a | C |
| 76b | C |
| 77a | C |
| 77b | C |
| 77b | C |
| 77c | C |
| 78a | B |
| 78b | C |
| 79a | C |
| 79b | C |
| 79c | A |
| 79d | A |
| 80a | A |
| 80b | B |
| 81a | B |
| 81b | C |
| 81c | A |
| 81d | A |
| 82a | A |
| 82b | B |
| 83a | C |
| 83b | B |
| 83c | C |
| 83d | A |
| 84a | C |
| 84b | C |
| 84c | A |
| 84d | A |
| 85a | A |
| 85b | B |
| 86a | B |
| 86b | A |
| 87a | C |
| 87b | C |
| 87c | C |
| 87d | B |
| 88a | C |
| 88b | C |
| 88c | C |
| 88d | C |
| 89a | C |
| 89b | C |
| 90a | C |
| 90b | C |
| 91a | C |
| 91b | C |
| 92a | C |
| 92b | C |
| 92c | C |
| 92d | C |
| 93a | C |
| 93b | C |
| 94a | C |
| 94b | A |
| 95a | C |
| 95b | B |
| 96a | C |
| 96b | B |
| 97a | C |
| 97b | B |
| 97c | B |
| 97d | C |

| Compound number | Bridge-it |
|---|---|
| 98a | B |
| 98b | A |
| 99a | C |
| 99b | B |
| 99c | A |
| 99d | C |
| 100a | B |
| 100b | C |
| 101a | C |
| 101b | C |
| 101c | C |
| 101d | C |
| 102a | C |
| 102b | C |
| 103a | C |
| 103b | C |
| 104a | C |
| 104b | B |
| 105a | C |
| 105b | C |
| 105c | A |
| 106a | A |
| 106b | B |
| 107a | C |
| 107b | B |
| 108a | B |
| 108b | B |
| 109a | C |
| 109b | B |
| 109c | B |
| 110a | A |
| 110b | B |
| 111a | A |
| 111b | B |
| 112a | C |
| 112b | A |
| 112c | C |
| 112d | A |
| 113a | A |
| 113b | C |
| 113c | C |
| 113d | A |
| 114a | A |
| 114b | A |
| 114c | C |
| 114d | C |
| 115a | A |
| 115b | A |
| 115c | B |
| 115d | C |
| 116a | C |
| 116b | A |
| 116c | C |
| 116d | A |
| 117a | C |
| 117b | B |
| 117c | C |
| 117d | C |
| 118a | C |
| 118b | B |
| 118c | C |
| 119a | C |
| 119b | C |
| 119c | B |
| 119d | C |
| 120a | C |
| 120b | C |
| 120c | B |
| 120d | C |
| 121a | A |
| 121b | C |
| 121c | C |
| 121d | A |

C >1 μM;
B 100 nM-1 μM;
A <100 nM.

Example 122. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

I claim:

1. A compound of formula II,

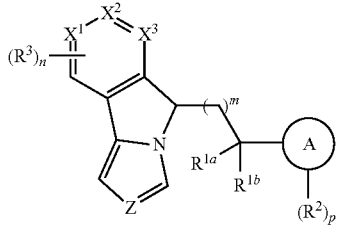

or a pharmaceutically acceptable salt thereof, wherein:
$R^{1a}$ is —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
$R^{1b}$ is —R, halogen, -haloalkyl, -hydroxyalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or
$R^{1a}$ and $R^{1b}$, together with the atom to which each is attached, may form a fused or spiro ring selected from $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
Ring A is cyclohexyl, piperidinyl, tetrahydropyranyl or phenyl;
each $R^2$ is independently R, halogen, —OR, —C(O)R, or —C(O)N(R)$_2$,
$X^1$, $X^2$, or $X^3$, are each, independently, selected from carbon, nitrogen, oxygen, or sulfur provided that at least one of $X^1$, $X^2$ or $X^3$ is not carbon;
each $R^3$ is independently —R, halogen, -haloalkyl, -hydroxyalkyl, —OR, —SR, —CN, —NO$_2$, —SO$_2$R, —SOR, —CO$_2$R, —C(O)N(R)$_2$, —NRC(O)R, —NRC(O)N(R)$_2$, —NRSO$_2$R, or —N(R)$_2$;
Z is selected from nitrogen, oxygen, or sulfur;
each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
m is 1 or 2;
n is 0, 1, 2, or 3; and
p is 0, 1 or 2.

2. The compound of claim 1, wherein $R^{1a}$ is —H; or $R^{1a}$ is halogen, —OR, —NRSO$_2$R, or —N(R)$_2$.

3. The compound of claim 2, wherein $R^{1a}$ is —H; or $R^{1a}$ is

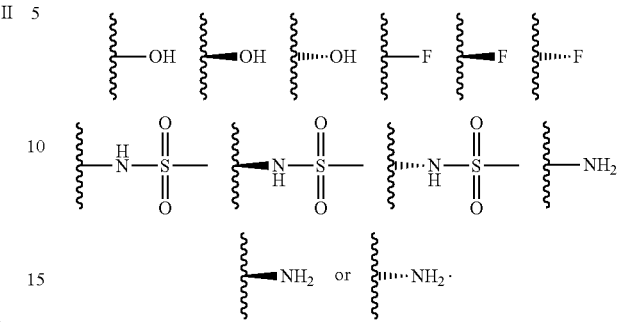

4. The compound of claim 1, wherein $R^{1b}$ is —H; or $R^{1b}$ is halogen, —OR, —NRSO$_2$R, or —N(R)$_2$.

5. The compound of claim 4, wherein $R^{1b}$ is —H; or $R^{1b}$ is

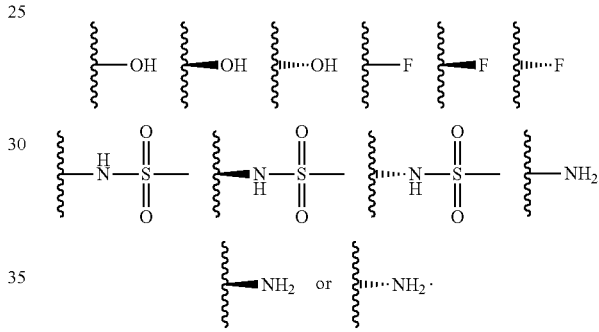

6. The compound of claim 1, wherein the ring with the $X^1$, $X^2$ and $X^3$ groups, together with the optional $R^3$ substituents, is selected from:

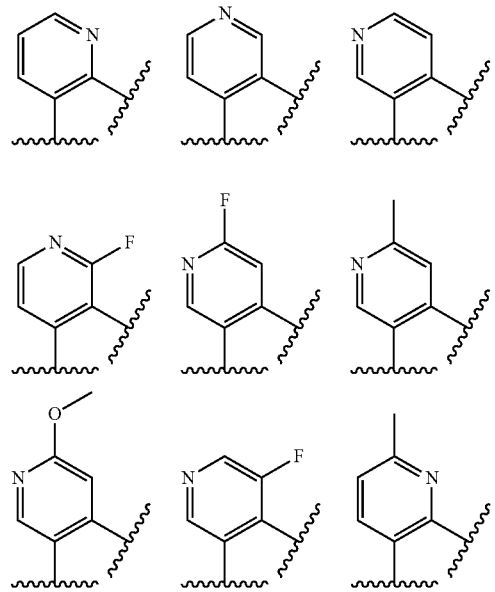

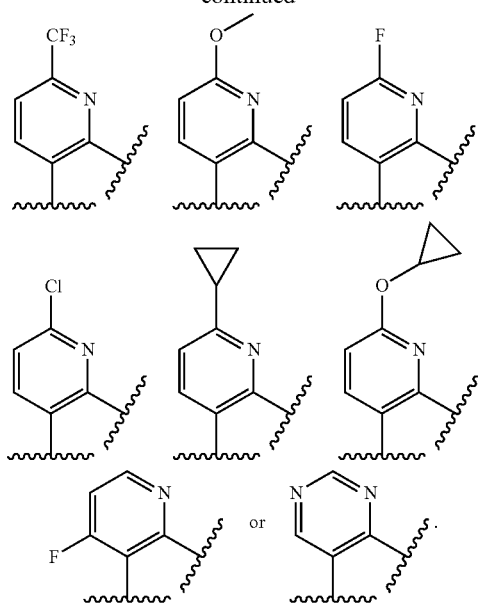
7. The compound of claim 1, selected from Table 1
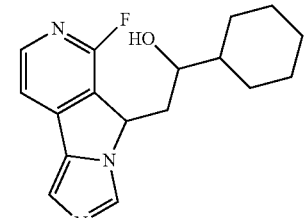
(2 stereoisomers)
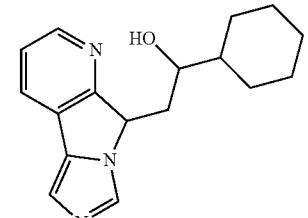
(2 stereoisomers)
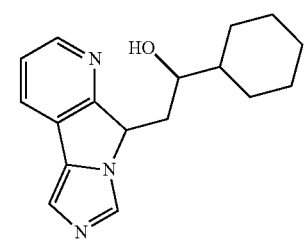
(2 stereoisomers)
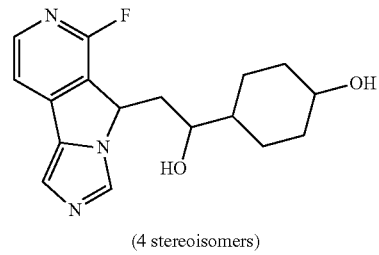
(2 stereoisomers)
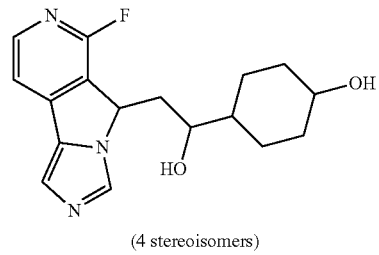
(4 stereoisomers)
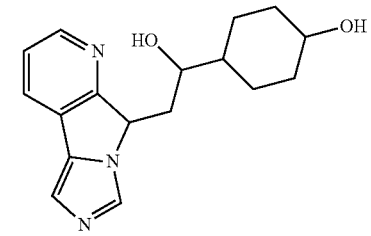
(4 stereoisomers)
(2 stereoisomers)
(2 stereoisomers)
(2 stereoisomers)

321
-continued
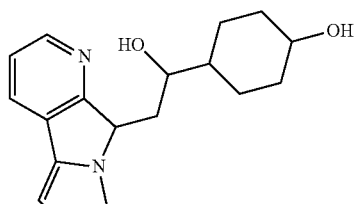
6b
(2 stereoisomers)
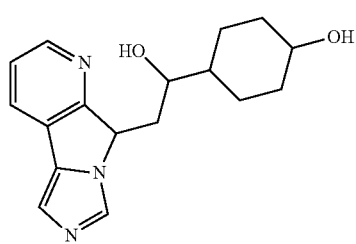
6c
(2 stereoisomers)
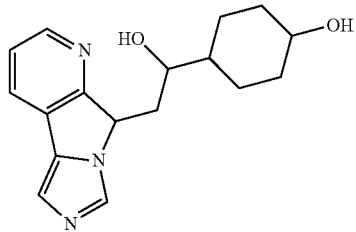
6d
(2 stereoisomers)
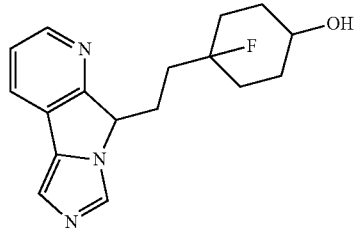
7a
(2 stereoisomers)
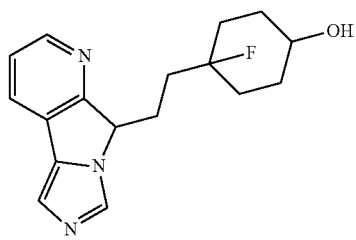
7b
(2 stereoisomers)
322
-continued
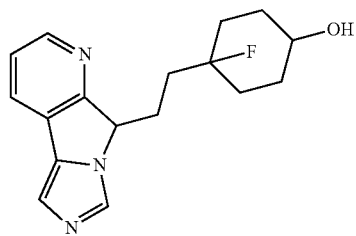
8a
(1 stereoisomers)
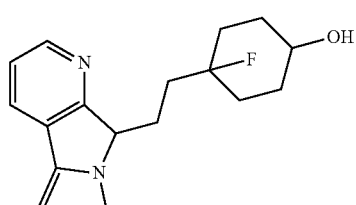
8b
(1 stereoisomers)
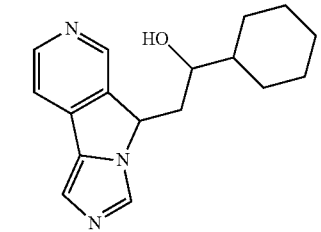
9a
(2 stereoisomers)
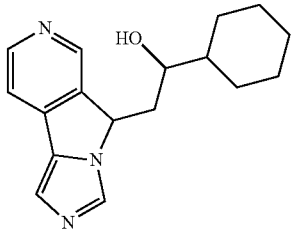
9b
(2 stereoisomers)
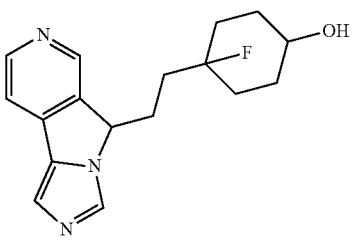
10a
(1 stereoisomers)

| | |
|---|---|
| 10b 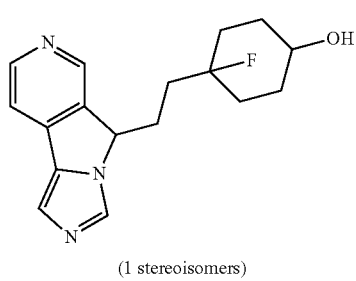
(1 stereoisomers) | 15a 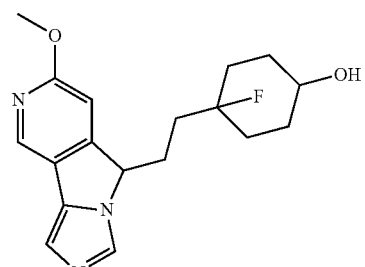
(1 stereoisomer) |
| 11a 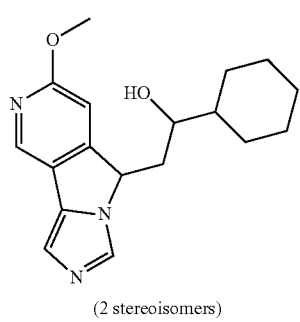
(2 stereoisomers) | 15b 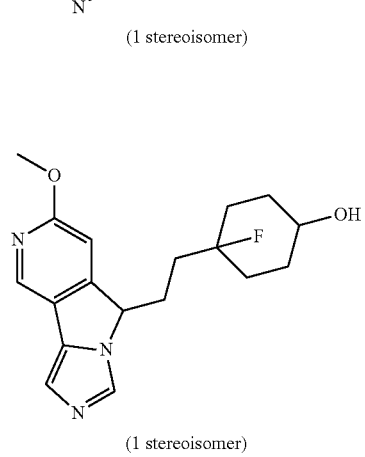
(1 stereoisomer) |
| 11b 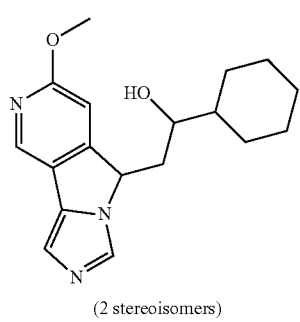
(2 stereoisomers) | 17 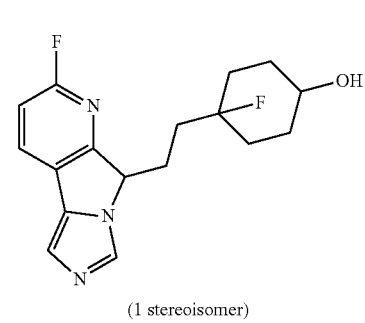
(1 stereoisomer) |
| 12a 
(2 stereoisomers) | 18a 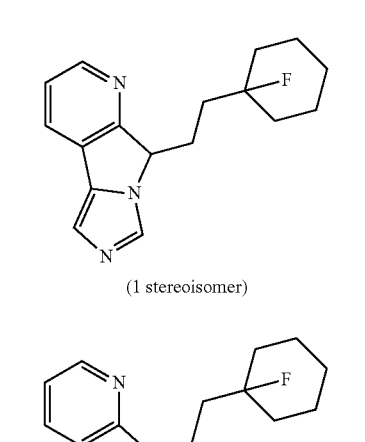
(1 stereoisomer) |
| 12b 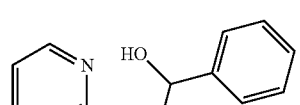
(2 stereoisomers) | 18b 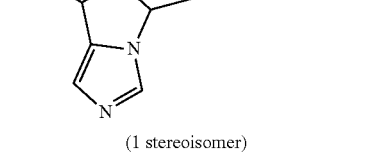
(1 stereoisomer) |

325

-continued

21a
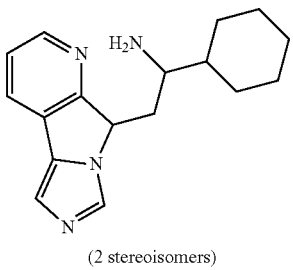
(2 stereoisomers)

21b
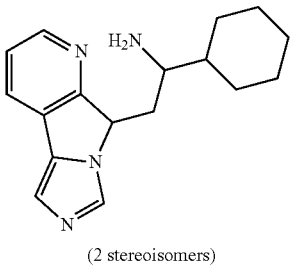
(2 stereoisomers)

21c
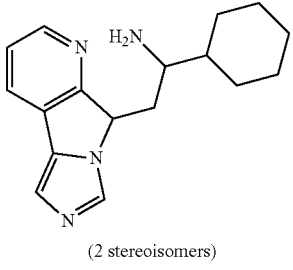
(2 stereoisomers)

21d
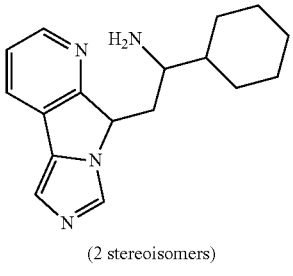
(2 stereoisomers)

22a
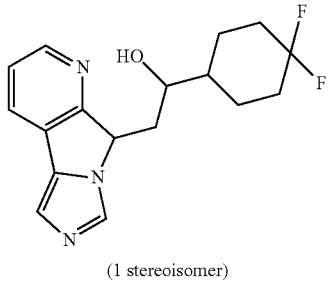
(1 stereoisomer)

326

-continued

22b
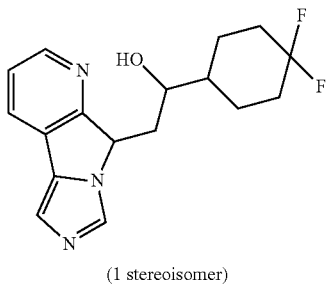
(1 stereoisomer)

22c
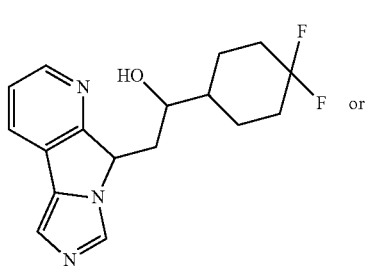
or (1 stereoisomer)

22d
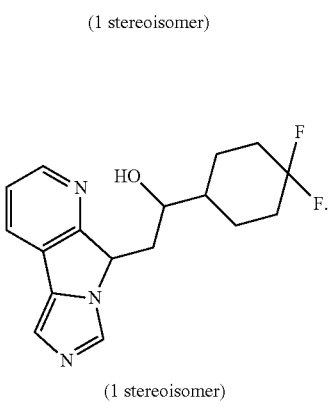
(1 stereoisomer)

8. A pharmaceutical composition comprising a compound of claim 1, and a pharmaceutically acceptable adjuvant, carrier, or vehicle.

9. A method for treating a IDO-mediated disease or disorder in a subject in need thereof, comprising the step of administering to said subject a compound of claim 1.

10. The method of claim 9, wherein the disease or disorder is selected from cancer, proliferative disorder, viral disease, sepsis, pneumonia, bacteremia, trauma, tuberculosis, parasitic disease, neuroinflammation, schizophrenia, depression, neurodegenerative disease, and pain.

11. The compound of claim 1, wherein Z is nitrogen.

12. The compound of claim 1, wherein one of $X^1$, $X^2$ and $X^3$ is nitrogen and the other two of $X^1$, $X^2$ and $X^3$ are carbon.

* * * * *